United States Patent
Liu et al.

(10) Patent No.: US 11,845,730 B2
(45) Date of Patent: Dec. 19, 2023

(54) 1,3-SUBSTITUTED CYCLOBUTYL DERIVATIVES AND USES THEREOF

(71) Applicant: Novartis AG, Basel (CH)

(72) Inventors: Donglei Liu, Dover, MA (US); Julien Papillon, Somerville, MA (US); Stefan Peukert, Arlington, MA (US); James J. Powers, Waltham, MA (US)

(*) Notice: Subject to any disclaimer, the term of this patent is extended or adjusted under 35 U.S.C. 154(b) by 0 days.

(21) Appl. No.: 17/656,313

(22) Filed: Mar. 24, 2022

(65) Prior Publication Data
US 2022/0324811 A1    Oct. 13, 2022

Related U.S. Application Data

(60) Provisional application No. 63/166,289, filed on Mar. 26, 2021.

(51) Int. Cl.
| | | |
|---|---|---|
| C07D 217/02 | (2006.01) | |
| C07D 401/12 | (2006.01) | |
| C07D 405/12 | (2006.01) | |
| C07D 417/12 | (2006.01) | |

(52) U.S. Cl.
CPC ......... C07D 217/02 (2013.01); C07D 401/12 (2013.01); C07D 405/12 (2013.01); C07D 417/12 (2013.01)

(58) Field of Classification Search
CPC .. C07D 217/02; C07D 401/12; C07D 405/12; C07D 417/12
See application file for complete search history.

(56) References Cited

U.S. PATENT DOCUMENTS

2012/0245163 A1    9/2012 Gomtsyan et al.

FOREIGN PATENT DOCUMENTS

| | | |
|---|---|---|
| EP | 2050734 A1 | 4/2009 |
| WO | 2008077551 A1 | 7/2008 |
| WO | 2012/072152 A1 | 6/2012 |
| WO | 2012/139963 A1 | 10/2012 |
| WO | 2018/151678 * | 8/2018 |
| WO | 2018/226976 A1 | 12/2018 |
| WO | 2020/118194 A1 | 6/2020 |

OTHER PUBLICATIONS

International Search Report and Written Opinion for International Application No. PCT/IB2022/052720, dated May 13, 2022 (16 pages).
Voight et al., "Transient receptor potential vanilloid-1 antagonists: a survey of recent patent literature," Expert Opin Ther Pat. 20(9):1107-22 (2010).

* cited by examiner

*Primary Examiner* — D Margaret M Seaman

(57) ABSTRACT

Provided herein are compounds and pharmaceutical compositions useful for treating diseases or disorders mediated by the TRPV1 receptor. The present invention also provides methods for treating ocular diseases or disorders by administering to a subject in need thereof a therapeutically effective amount of a compound of Formula (I) or a pharmaceutical composition described herein.

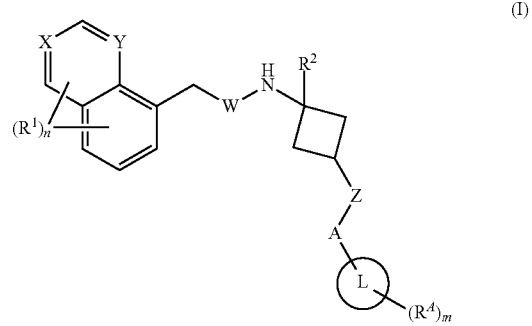

30 Claims, No Drawings

1,3-SUBSTITUTED CYCLOBUTYL DERIVATIVES AND USES THEREOF

FIELD OF THE DISCLOSURE

The present disclosure relates to 1,3-substituted cyclobutyl compounds and pharmaceutical compositions and their use in antagonizing TRPV1 activity, and in the treatment of ocular diseases or disorders (e.g., ocular surface disorder) such as dry eye disease.

BACKGROUND OF THE DISCLOSURE

Transient receptor potential cation channel, subfamily V, member 1 (TRPV1), also known as capsaicin receptor and vanilloid receptor 1 (VR1), is an ion channel belonging to the transient receptor potential (TRP) family. TRPV1 is a non-selective cation channel that can be activated by heat, protons, and vanilloid compounds (e.g., capsaicin). Activation of TRPV1 leads to the release of neurotransmitters, and results in pain and inflammation. TRPV1 antagonists, which can alleviate inflammation and pain caused by TRPV1 activation, fall into two major categories, those that inhibit both capsaicin and proton activation, and those that inhibit capsaicin but not proton activation. Several such TRPV1 antagonists are known, as described by Roberts and Connor (2006, Recent Patents on CNS Drug Discovery 1:65-76). As discussed herein, TRPV1 antagonists can effectively reduce ocular pain and reduce symptoms of dry eye without causing anesthesia effects on the ocular surface.

The role of TRPV1 has been well established in pain models. TRPV1 has also been implicated in other diseases where symptoms are potentially driven wholly or in part by neuronal hypersensitivity or hyperactivity, because of its role in sensory signalling in peripheral nerves. Such diseases include asthma, rhinitis, cough, overactive bladder, reflux oesophagitis, irritable bowel syndrome and migraine. TRPV1 has been implicated to have a role in the afferent sensory loop of the cough reflex and the heightened cough sensitivity seen in disease (Grace, Dubuis, Birrell, Belvisi (2012), TRP Channel Antagonists as Potential Antitussives, Lung 190: 11-15, and Gu and Lee (2011), Airway irritation and cough evoked by acid: from human to ion channel, Current Opinion in Pharmacology 11: 238-247). TRPV1 has been implicated in inflammatory responses occurring in dry eye syndrome (Pan, Wang, Yang, Zhang & Reinach (2010), TRPV1 Activation is Required for Hypertonicity Stimulated Inflammatory Cytokine Release in Human Corneal Epithelial Cells, Manuscript IOVS, 10-5801). TRPV1 is also implicated to play a role in metabolic diseases such as diabetes and obesity (Motter A L & Ahern G P (2008) FEBS Letters 582, 2257-2262; Suri & Szallasi A (2007), The emerging role of TRPV1 in diabetes and obesity, Trends in Pharm Sci, Rasavi et al (2006) Cell 127, 1123-1135.

The ocular surface, particularly the cornea, is densely innervated by sensory nerves. The activity of corneal nerves can be modified by inflammation caused by a number of factors, such as osmotic stress and tissue damage, as well as nerve injuries of the ocular surface. Ocular surface symptoms are the alarm system to indicate an imbalanced ocular surface homeostasis resulting in chronic ocular surface pain due to continuous stimuli causing stress and sensitization of the ocular surface.

Patients suffering from ocular surface pain, particularly chronic ocular surface pain have a significant decline in quality of life. In utility studies to date, the burden of severe chronic ocular surface pain has been likened to moderate to severe angina, dialysis, or disabling hip fracture. Severe chronic ocular surface pain has also been associated with depression and suicidal ideation. In many patients, the ocular surface pain remains unresolved despite treatment of the underlying pathology (e.g., recent trauma or surgery, infection, or inflammation). Moreover, treatments that are used for short term management of ocular pain (e.g., non-steroidal anti-inflammatory drugs, steroids) cannot be used for long term therapy. Thus, there is a long-felt and unmet need for safe, effective treatments for the treatment of ocular surface pain, particularly chronic ocular surface pain, when there are no other options to improve patients' quality of life, or to supplement current treatments.

Other approaches to treating ocular pain, such as local topical ocular application of anesthetics, NSAIDS, or topical corticosteroids are undesirable due to side effects upon chronic administration. Ocular pain manifests in a number of conditions including Dry eye disease, Sjogren's Syndrome, lacrimal gland dysfunction due autoimmune diseases such as Sjögren's syndrome or Systemic Lupus Erythymatus, organ transplantation such as graft versus host disease, or simply as a result of aging, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, meibomitis, meibomian gland dysfunction, glaucoma, conjunctivochalasis, keratopathies, corneal infections etc. In such patients, there is a need for more effective therapies to address the ocular pain.

The present disclosure provides compounds for treating or alleviating pain in general, and ocular surface pain, in particular.

SUMMARY OF THE DISCLOSURE

The disclosure relates to compounds effective as TRPV1 antagonists, pharmaceutically acceptable salts thereof, compositions thereof, and their use in therapies for the conditions and purposes detailed herein.

The disclosure provides, in a first aspect, a compound of Formula (I), or a pharmaceutically acceptable salt thereof,

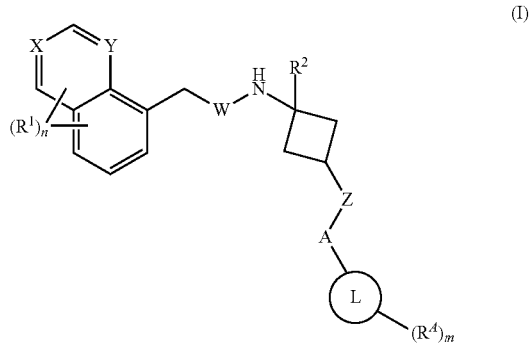

wherein:
W is C(=O) or absent;
X is N or N oxide;
Y is N or CH;
Z is NH, O or S;
A is $CH_2$ or absent;
L is selected from 5- to 10-membered heteroaryl having 1-3 heteroatoms independently selected from N, O, and S, $C_6$-$C_{10}$aryl and 6- to 10-membered partially saturated heterocyclyl having 1-3 heteroatoms independently selected from N, O, and S;

$R^A$ is at each occurrence independently selected from halo, —CN, $C_1$-$C_6$haloalkyl, $C_1$-$C_6$alkyl, $SF_5$, $C_3$-$C_6$cycloalkyl, $C_1$-$C_6$alkoxyl, $C_1$-$C_6$haloalkoxyl, 4- to 6-membered heterocyclyl having 1-2 heteroatoms independently selected from N, O, and S, —$(CH_2)_p$—$NR^3R^4$ and —C(=O)—O—($C_1$-$C_6$alkyl), wherein the $C_3$-$C_6$cycloalkyl and 4- to 6-membered heterocyclyl are each independently substituted with 0-4 $R^{A1}$;

$R^{A1}$ is at each occurrence independently selected from halo and $C_1$-$C_6$haloalkyl;

$R^1$ is at each occurrence independently selected from hydroxyl, $C_1$-$C_6$alkyl, $C_1$-$C_6$alkoxyl, halo, $C_1$-$C_6$haloalkyl and $NR^3R^4$, wherein the $C_1$-$C_6$alkyl and $C_1$-$C_6$haloalkyl are each independently substituted with 0-4 $R^{1a}$;

$R^{1a}$ is at each occurrence independently selected from hydroxyl, $NR^3R^4$ and —C(=O)—OH;

$R^2$ is selected from hydrogen and $C_1$-$C_6$alkyl;

$R^3$ is at each occurrence independently selected from hydrogen and $C_1$-$C_6$alkyl;

$R^4$ is at each occurrence independently selected from —$SO_2R^5$, hydrogen, —C(=O)—($C_1$-$C_6$alkyl) and $C_1$-$C_6$alkyl;

$R^5$ is at each occurrence independently selected from $NH_2$ and $C_1$-$C_6$alkyl;

n is 0, 1, 2, 3 or 4;

m is 0, 1, 2, 3, 4 or 5;

p is 0, 1 or 2.

In a second aspect, there is provided a pharmaceutical composition comprising a therapeutically effective amount of a compound of Formula (I), or a pharmaceutically acceptable salt thereof, and a pharmaceutically acceptable carrier or excipient.

In a third aspect, there is provided a method of treating or preventing a disease or disorder in a subject in need thereof, the method comprising administering to the subject a therapeutically effective amount of a compound of Formula (I), or a pharmaceutically acceptable salt thereof.

In a further aspect, there is provided a method of treating or preventing a disease or disorder mediated by TRPV1 in a subject in need thereof, the method comprising administering to the subject a therapeutically effective amount of a compound of Formula (I), or a pharmaceutically acceptable salt thereof.

In a further aspect, there is provided a method of treating an ocular disease or disorder in a subject in need thereof, the method comprising administering to the subject a therapeutically effective amount of a compound of Formula (I), or a pharmaceutically acceptable salt thereof, wherein the ocular disease or disorder is mediated by TRPV1.

In a further aspect, there is provided a method of treating an ocular surface disorder in a subject in need thereof, the method comprising administering to the subject a therapeutically effective amount of a compound of Formula (I), or a pharmaceutically acceptable salt thereof.

In a further aspect, there is provided a method of treating ocular surface pain (e.g., corneal induced pain) in a subject in need thereof, the method comprising administering to the subject a therapeutically effective amount of a compound of Formula (I), or a pharmaceutically acceptable salt thereof.

In a further aspect, there is provided a method of treating ocular hyperemia in a subject in need thereof, the method comprising administering to the subject a therapeutically effective amount of a compound of Formula (I), or a pharmaceutically acceptable salt thereof.

In a further aspect, there is provided a compound of Formula (I), or a pharmaceutically acceptable salt thereof, for use in the treatment of ocular surface pain (e.g., corneal induced pain).

In a further aspect, there is provided a compound of Formula (I), or a pharmaceutically acceptable salt thereof, for use in the treatment of ocular hyperemia.

In a further aspect, there is provided a compound of Formula (I), or a pharmaceutically acceptable salt thereof, for use in the treatment of an ocular surface disorder.

In a further aspect, there is provided the use of a compound of Formula (I), or a pharmaceutically acceptable salt thereof, in the manufacture of a medicament for treating an ocular disease or disorder that is mediated by TRPV1.

In a further aspect, there is provided the use of a compound of Formula (I), or a pharmaceutically acceptable salt thereof, in the treatment of an ocular disease or disorder that is mediated by TRPV1.

In a further aspect, there is provided a pharmaceutical combination comprising a compound of Formula (I), or a pharmaceutically acceptable salt thereof, and one or more additional therapeutic agent(s).

DETAILED DESCRIPTION OF THE DISCLOSURE

The compounds disclosed herein are effective as TRPV1 antagonists. Without wishing to be bound by any theory, it is believed that the disclosed compounds may treat disorders associated with TRPV1, including the treatment of pain or discomfort associated with such disorders. In particular examples, the pain is ocular surface pain, particularly corneal or ocular surface induced pain and chronic ocular surface pain.

Definitions

Unless specified otherwise, the terms "compounds of the present disclosure," "compounds of the disclosure," or "compound of the disclosure" refer to compounds of formulae (I), (Ia), (Ib), (Ic), (Id), (Ie), (If), (Ig), (Ih), (Ii), (I-i), (I-ii), exemplified compounds, salts thereof, particularly pharmaceutically acceptable salts thereof, hydrates, solvates, prodrugs, as well as all stereoisomers (including diastereoisomers and enantiomers), rotamers, tautomers, and isotopically labeled compounds (including deuterium substitutions), as well as inherently formed moieties.

In the groups, radicals, or moieties defined below, the number of carbon atoms is often specified preceding the group, for example, $C_1$-$C_{10}$alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-.

Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The terms $C_1$-$C_3$alkyl and $C_1$-$C_5$alkyl are to be construed accordingly. Examples of $C_1$-$C_6$alkyl include, but are not limited to, methyl, ethyl, n-propyl, 1-methylethyl (iso-propyl), n-butyl, 1-methylpropyl (sec-butyl), 2-methylpropyl (iso-butyl), 1,1-dimethylethyl (t-butyl), n-pentyl and n-hexyl.

As used herein, the term "$C_1$-$C_6$alkoxyl" refers to a radical of the formula —$OR_a$ where $R_a$ is a $C_1$-$C_6$alkyl radical as generally defined above. Examples of $C_1$-$C_6$alkoxyl include, but are not limited to, methoxy, ethoxy, propoxy, iso-propoxy, butoxy, iso-butoxy, tert-butoxy, sec-butoxy, pentoxy, and hexoxy.

As used herein, the term "$C_1$-$C_6$haloalkyl" refers to $C_1$-$C_6$alkyl radical, as defined above, substituted by one or more halo radicals, as defined herein. Examples of $C_1$-$C_6$haloalkyl include, but are not limited to, trifluoromethyl, difluoromethyl, fluoromethyl, trichloromethyl, 1,1-difluoroethyl, 2,2-difluoroethyl, 2,2,2-trifluoroethyl, 2-fluoropropyl, 3,3-difluoropropyl and 1-fluoromethyl-2-fluoroethyl, 1,3-dibromopropan-2-yl, 3-bromo-2-fluoropropyl and 1,4,4-trifluorobutan-2-yl.

As used herein, the term "$C_1$-$C_6$haloalkoxyl" means a $C_1$-$C_6$alkoxyl group as defined herein substituted with one or more halo radicals. Examples of $C_1$-$C_6$haloalkoxyl groups include, but are not limited to, trifluoromethoxy, difluoromethoxy, fluoromethoxy, trichloromethoxy, 1,1-difluoroethoxy, 2,2-difluoroethoxy, 2,2,2-trifluoroethoxy, 1-fluoromethyl-2-fluoroethoxy, pentafluoroethoxy, 2-fluoropropoxy, 3,3-difluoropropoxy and 3-dibromopropoxy. Preferably, the one or more halo radicals of $C_1$-$C_6$haloalkoxyl is fluoro. Preferably, $C_1$-$C_6$haloalkoxyl is selected from trifluoromethoxy, difluoromethoxy, fluoromethoxy, 1,1-difluoroethoxy, 2,2-difluoroethoxy, 2,2,2-trifluoroethoxy, 1-fluoromethyl-2-fluoroethoxy, and pentafluoroethoxy.

The term "halogen" or "halo" means fluorine, chlorine, bromine or iodine.

As used herein, the term "cycloalkyl" means a monocyclic or polycyclic saturated or partially unsaturated carbon ring containing 3-18 carbon atoms wherein there are no delocalized pi electrons (aromaticity) shared among the ring carbon. The term "$C_3$-$C_6$cycloalkyl" is to be construed accordingly. The term polycyclic encompasses bridged (e.g., norbornane), fused (e.g., decalin) and spirocyclic cycloalkyl. Preferably, cycloalkyl, e.g., $C_3$-$C_6$cycloalkyl, is a monocyclic or bridged hydrocarbon group of 3 to 6 carbon atoms.

Examples of cycloalkyl groups include, without limitations, cyclopropenyl, cyclopropyl cyclobutyl, cyclobutenyl, cyclopentyl, cyclohexyl, cycloheptanyl, cyclooctanyl, norboranyl, norborenyl, bicyclo[2.2.2]octanyl, bicyclo[2.2.2]octenyl, bicyclo[1.1.1]pentanyl and derivatives thereof.

Examples of $C_3$-$C_6$cycloalkyl include, but are not limited to, cyclopropyl, cyclobutyl, cyclopentyl, cyclohexyl.

"Heterocyclyl" means a saturated or partially saturated monocyclic or polycyclic ring containing carbon and at least one heteroatom selected from oxygen, nitrogen, and sulfur (O, N, and S) and wherein there are no delocalized pi electrons (aromaticity) shared among the ring carbon or heteroatoms. The term "4- to 6-membered heterocyclyl" is to be construed accordingly. The heterocyclyl ring structure may be substituted by one or more substituents. The substituents can themselves be optionally substituted. The heterocyclyl may be bonded via a carbon atom or heteroatom. The term polycyclic encompasses bridged, fused and spirocyclic heterocyclyl.

Examples of heterocyclyl rings include, but are not limited to, oxetanyl, azetidinyl, tetrahydrofuranyl, tetrahydropyranyl, pyrrolidinyl, oxazolinyl, isoxazolinyl, oxazolidinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, dihydroisoxazolinyl, pyrrolinyl, pyrazolinyl, oxazepinyl, dithiolanyl, homotropanyl, dihydropyranyl (e.g., 3,6-dihydro-2H-pyranyl), oxaspiroheptanyl (e.g., 2-oxaspiro[3.3]heptan-6-yl) and the like.

Examples of 4- to 6-membered heterocyclyl include, without limitations, azetidinyl, pyrrolidinyl, tetrahydrofuranyl, tetrahydrothienyl, piperidinyl, piperazinyl, dihydroisoxazolinyl, tetrahydropyranyl, morpholinyl, dihydropyranyl (e.g., 3,6-dihydro-2H-pyranyl) and oxaspiroheptanyl (e.g., 2-oxaspiro[3.3]heptan-6-yl).

As used herein, the term "aryl" as used herein means monocyclic, bicyclic or polycyclic carbocyclic aromatic rings. Examples of aryl include, but are not limited to, phenyl, naphthyl (e.g., naphth-1-yl, naphth-2-yl), anthryl (e.g., anthr-1-yl, anthr-9-yl), phenanthryl (e.g., phenanthr-1-yl, phenanthr-9-yl), and the like. Aryl is also intended to include monocyclic, bicyclic or polycyclic carbocyclic aromatic rings substituted with carbocyclic aromatic rings. Representative examples are biphenyl (e.g., biphenyl-2-yl, biphenyl-3-yl, biphenyl-4-yl), phenylnaphthyl (e.g., 1-phenylnaphth-2-yl, 2-phenylnaphth-1-yl), and the like. Aryl is also intended to include partially saturated bicyclic or polycyclic carbocyclic rings with at least one unsaturated moiety (e.g., a benzo moiety). Representative examples are, indanyl (e.g., indan-1-yl, indan-5-yl), indenyl (e.g., inden-1-yl, inden-5-yl), 1,2,3,4-tetrahydronaphthyl (e.g., 1,2,3,4-tetrahydronaphth-1-yl, 1,2,3,4-tetrahydronaphth-2-yl, 1,2,3,4-tetrahydronaphth-6-yl), 1,2-dihydronaphthyl (e.g., 1,2-dihydronaphth-1-yl, 1,2-dihydronaphth-4-yl, 1,2-dihydronaphth-6-yl), fluorenyl (e.g., fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (e.g., benzonorborn-3-yl, benzonorborn-6-yl), 1,4-ethano-1,2,3,4-tetrahydronapthyl (e.g., 1,4-ethano-1,2,3,4-tetrahydronapth-2-yl, 1,4-ethano-1,2,3,4-tetrahydronapth-10-yl), and the like. The term "$C_6$-$C_{10}$aryl" is to be construed accordingly.

Examples of aryl include, but are not limited to, indenyl, (e.g., inden-1-yl, inden-5-yl) phenyl ($C_6H_5$), naphthyl ($C_{10}H_7$) (e.g., naphth-1-yl, naphth-2-yl), indanyl (e.g., indan-1-yl, indan-5-yl), and tetrahydronaphthalenyl (e.g., 1,2,3,4-tetrahydronaphthalenyl). The term $C_6$-$C_{10}$aryl is to be construed accordingly. Examples of $C_6$-$C_{10}$aryl include a monocyclic or bicyclic carbocyclic aromatic ring.

Examples of $C_6$-$C_{10}$aryl include, but are not limited to, phenyl and naphthyl. In an embodiment, $C_6$-$C_{10}$aryl is phenyl.

As used herein, the term "heteroaryl" is intended to include monocyclic heterocyclic aromatic rings containing one or more heteroatoms selected from oxygen, nitrogen, and sulfur (O, N, and S). Representative examples are pyrrolyl, furanyl, thienyl, oxazolyl, thiazolyl, imidazolyl, pyrazolyl, isothiazolyl, isooxazolyl, triazolyl, (e.g., 1,2,4-triazolyl), oxadiazolyl, (e.g., 1,2,3-oxadiazolyl, 1,2,4-oxadiazolyl, 1,2,5-oxadiazolyl, 1,3,4-oxadiazolyl), thiadiazolyl (e.g., 1,2,3-thiadiazolyl, 1,2,4-thiadiazolyl, 1,2,5-thiadiazolyl, 1,3,4-thiadiazolyl), tetrazolyl, pyranyl, pyridinyl, pyridazinyl, pyrimidinyl, pyrazinyl, 1,2,3-triazinyl, 1,2,4-triazinyl, 1,3,5-triazinyl, thiadiazinyl, azepinyl, azecinyl, and the like.

Heteroaryl is also intended to include bicyclic heterocyclic aromatic rings containing one or more heteroatoms selected from oxygen, nitrogen, and sulfur (O, N, and S). Representative examples are indolyl, isoindolyl, benzofuranyl, benzothiophenyl, indazolyl, benzopyranyl, benzimidazolyl, benzothiazolyl, benzisothiazolyl, benzoxazolyl, benzisoxazolyl, benzoxazinyl, benzotriazolyl, naphthyridinyl, phthalazinyl, pteridinyl, purinyl, quinazolinyl, cinnolinyl, quinolinyl, isoquinolinyl, quinoxalinyl, oxazolopyridinyl, isooxazolopyridinyl, pyrrolopyridinyl, furopyridinyl, thienopyridinyl, imidazopyridinyl, imidazopyrimidinyl, pyrazolopyridinyl, pyrazolopyrimidinyl, pyrazolotriazinyl, thiazolopyridinyl, thiazolopyrimidinyl, imdazothiazolyl, triazolopyridinyl, triazolopyrimidinyl, and the like.

Heteroaryl is also intended to include polycyclic heterocyclic aromatic rings containing one or more heteroatoms selected from oxygen, nitrogen, and sulfur (O, N, and S). Representative examples are carbazolyl, phenoxazinyl, phenazinyl, acridinyl, phenothiazinyl, carbolinyl, phenanthrolinyl, and the like.

The heteroaryl ring structure may be substituted by one or more substituents. The substituents can themselves be optionally substituted. The heteroaryl ring may be bonded via a carbon atom or heteroatom.

The term "5-10 membered heteroaryl" is to be construed accordingly.

Examples of 5-10 membered heteroaryl include, but are not limited to, indolyl, imidazopyridyl, isoquinolinyl, benzooxazolonyl, pyridinyl, pyrimidinyl, pyridinonyl, benzotriazolyl, pyridazinyl, pyrazolotriazinyl, indazolyl, benzimidazolyl, quinolinyl, triazolyl, (e.g., 1,2,4-triazolyl), pyrazolyl, thiazolyl, oxazolyl, isooxazolyl, pyrrolyl, oxadiazolyl, (e.g., 1,2,3-oxadiazolyl, 1,2,4-oxadiazolyl, 1,2,5-oxadiazolyl, 1,3,4-oxadiazolyl), imidazolyl, pyrrolopyridinyl, tetrahydroindazolyl, quinoxalinyl, thiadiazolyl (e.g., 1,2,3-thiadiazolyl, 1,2,4-thiadiazolyl, 1,2,5-thiadiazolyl, 1,3,4-thiadiazolyl), pyrazinyl, oxazolopyridinyl, pyrazolopyrimidinyl, benzoxazolyl, indolinyl, isooxazolopyridinyl, dihydropyridooxazinyl and tetrazolyl.

The term "partially saturated heterocyclyl" is intended to include partially saturated monocyclic, bicyclic or polycyclic heterocyclyls containing one or more heteroatoms selected oxygen, nitrogen, and sulfur (O, N, and S). Representative examples are imidazolinyl, indolinyl, dihydrobenzofuranyl, dihydrobenzothienyl, dihydrobenzopyranyl, dihydropyridooxazinyl, dihydrobenzodioxinyl (e.g., 2,3-dihydrobenzo[b][1,4]dioxinyl), benzodioxolyl (e.g., benzo[d][1,3]dioxole), dihydrobenzooxazinyl (e.g., 3,4-dihydro-2H-benzo[b][1,4]oxazine), tetrahydroindazolyl, tetrahydrobenzimidazolyl, tetrahydroimidazo[4,5-c]pyridyl, tetrahydroquinolinyl, tetrahydroisoquinolinyl, tetrahydroquinoxalinyl, and the like.

The term "6- to 10-membered partially saturated heterocyclyl" is to be construed accordingly.

Examples of 6- to 10-membered partially saturated heterocyclyl include, but are not limited to, indolinyl, dihydrobenzofuranyl, dihydrobenzothienyl, dihydrobenzopyranyl, dihydropyridooxazinyl, dihydrobenzodioxinyl (e.g., 2,3-dihydrobenzo[b][1,4]dioxinyl), benzodioxolyl (e.g., benzo[d][1,3]dioxole), dihydrobenzooxazinyl (e.g., 3,4-dihydro-2H-benzo[b][1,4]oxazine), tetrahydroindazolyl, tetrahydrobenzimidazolyl, tetrahydroimidazo[4,5-c]pyridyl, tetrahydroquinolinyl, tetrahydroisoquinolinyl and tetrahydroquinoxalinyl.

"TRPV1 receptor" refers to the Transient Receptor Potential Vanilloid 1 that has been characterized through molecular cloning and pharmacology. See, e.g., Caterina M J, et al., Nature 1997; 389:816-824. TRPV1 receptor activity is measured as described in WO2005/120510, hereby incorporated by reference in its entirety.

The term "TRPV1 antagonist" and "TRPV1 inhibitor" includes any agent that can inhibit the activity of TRPV1 (e.g., block TRPV1-mediated signaling cascade).

The language "effective amount" of the compounds described herein, refers to that amount of a therapeutic compound necessary or sufficient to perform its intended function within a mammal. An effective amount of the therapeutic compound can vary according to factors such as the amount of the causative agent already present in the mammal, the age, sex, and weight of the mammal, and the ability of the therapeutic compounds of the present disclosure to treat the conditions wherein TRPV1 plays a role.

The phrase "ophthalmically compatible" refers to formulations, polymers and other materials and/or dosage forms which are suitable for use in contact with the ocular tissues of human beings and animals without excessive toxicity, irritation, allergic response, or other problem or As used herein, "ocular surface" refers to the outer surface of the eye, which anatomically comprises the cornea (with epithelium, bowman layer, stroma, descement membrane, endothelium), conjunctiva, cul de sac, and the corneo-scleral junction, i.e., limbus.

As used herein, the term "treat", "treating" or "treatment" in connection to a disease or disorder refers in some embodiments, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those, which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder or a symptom thereof.

As used herein, the term "subject" or "patient" refers to human and non-human mammals, including but, not limited to, primates, rabbits, pigs, horses, dogs, cats, sheep, and cows. In particular embodiments, a subject or patient is a human. In some embodiments, the term "patient" or "subject" refers to a human being who is diseased with the condition (i.e., disease or disorder) described herein and who would benefit from the treatment. As used herein, a subject is "in need of" a treatment if such subject (patient) would benefit biologically, medically or in quality of life from such treatment. In particular embodiments, the subject is an adult human at least about 18 years of age. In particular embodiments, the subject is an adult human from about 18 to about 75 years of age. In some embodiments, the subject is a human child up to about 18 years of age.

As used herein, "ocular surface" refers to the outer surface of the eye, which anatomically comprises the cornea (with epithelium, bowman layer, stroma, descement membrane, endothelium), conjunctiva, cul de sac, and the corneo-scleral junction, i.e., limbus.

As used herein, ocular administration includes administration to all parts of the eye including all parts of the ocular surface such as the cornea, conjunctiva, the cul de sac and the corneo-scleral junction, i.e., limbus.

As used herein, "pain" refers to constant or intermittent sensation of actual pain described as but not limited to stabbing, dull, sharp, or ache. Pain may also refer to similar related descriptors such as but not limited to discomfort, burning, stinging, grittiness, foreign body sensation, dryness, sandy, tired, itchy, irritated, sensitivity to light.

As used herein, "ocular surface pain" refers to pain on the surface of the eye, e.g., cornea. Ocular pain may be nociceptive pain, which is generally caused by external physical or chemical damaging stimuli such as corneal surgery, inflammation, or other damage to the corneal surface. Ocular pain may also result from neuropathic pain, which may occur due to direct damage to the neurons of the body, resulting in messages of pain being sent to the central nervous system and brain regardless of the presence of noxious stimuli. As used herein "ocular surface pain" includes both nociceptive pain and neuropathic pain.

Ocular surface pain may be measured using different scales. For example, the "visual analog scale" (VAS) is a measure of pain intensity where a subject typically marks a place on a scale that aligns with their level of pain. The pain is marked in a range of "no pain" (score of 0) and "pain as bad as it could be" or "worst imaginable pain" (score of 100). See e.g., Hawker, et al., *Arthritis Care & Research* 63 (11), pp. S240-S252 (November 2011). There are several other well-designed pain scales that may be used to help assess the extent of pain. The numerical rating scale (NRS) is often used, in which subjects use numbers to rate pain. The number scale may be from 1-10, or 1-100. The Wong-Baker FACES Pain Scale combines pictures and numbers for pain ratings. It can be used in children over the age of 3 and in adults. Six faces depict different expressions, ranging from happy to extremely upset. Each is assigned a numerical rating between 0 (smiling) and 10 (crying). The Verbal Pain Intensity Scale uses wordings on a scale to rate pain intensity: No Pain/Mild Pain/Moderate Pain/Severe Pain Very Severe Pain/Worst Possible Pain.

The Eye Sensation Scale is a specific pain scale was developed to measure ophthalmic pain severity. See Caudle L. E. et al., *Optom Vis Sci.* 2007 August; 84(8):752-62. In this scale, pain, discomfort or light sensitivity is typically measured by 5 category labels of "extreme," "severe," "moderate," "mild," or "none."

The Ocular Pain Assessment Survey (OPAS) is a quantitative, multidimensional questionnaire, specifically designed for assessment of corneal and ocular surface pain and Quality of Life (QoL) changes. The OPAS assesses pain intensity, frequency of eye and non-eye pain, QoL changes, aggravating factors, associated factors, and symptomatic relief quantitative, allowing for monitoring of treatment responses. See Qazi et al., *Ophthalmology* July 123(7):1458-1468 (2016).

As used herein, "ocular hyperemia" refers to redness of the ocular surface. Ocular hyperemia may be a clinical marker for inflammation and/or ocular irritation. Ocular hyperemia may be measured using a visual scale such as the McMonnies scale, at values from 0 to 5, based on standard photographs or using photographs taken under standardized lighting conditions that can be analyzed digitally in an semi- or fully automated fashion for an reading or any relevant method.

The term "ocular surface disease" or "ocular surface disorder" encompasses disease entities as well as related symptoms that result from a variety of abnormalities, including abnormal lid anatomy or function, abnormal or altered tear production or composition, and related subclinical or clinical signs. Many diseases can cause ocular surface disorders. Patients with ocular surface disorders may exhibit clinical signs common to several diseases, and include but not limited to chronic punctate keratopathy, filamentary keratopathy, recurrent corneal erosion, bacterial conjunctivitis, culture-negative conjunctivitis, cicatrising (scarring) conjunctivitis, persistent epithelial defect, infectious keratitis, corneal melt and ocular surface failure. The most common ocular surface disorders stem from tear-film abnormalities and/or meibomian gland dysfuntion or blepharitis.

As used herein, the term "about" refers to a range of values+/−10% of a specified value.

As used herein, a pharmaceutical composition is a composition suitable for pharmaceutical use. A composition suitable for pharmaceutical use may be sterile, homogeneous and/or isotonic. Pharmaceutical compositions may be prepared in certain embodiments in an aqueous form, for example in a pre-filled syringe or other single- or multi-dose container. In certain embodiments of the invention, the pharmaceutical composition is ophthalmically compatible and suitable for ophthalmic administration to a human subject by, for example, topical or other known methods of delivery. These methods include but are not limited to incorporating the compounds disclosed herein into an ocular insert or ocular film that dissolves and releases the compounds over extended periods of time.

As used herein, the term "a," "an," "the" and similar terms used in the context of the disclosure (especially in the context of the claims) are to be construed to cover both the singular and plural unless otherwise indicated herein or clearly contradicted by the context.

Various enumerated embodiments of the disclosure are described herein. It will be recognized that features specified in each embodiment may be combined with other specified features to provide further embodiments of the disclosure.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22nd Ed. Pharmaceutical Press, 2013, pp. 1049-1070).

ENUMERATED EMBODIMENTS

Embodiment 1. A compound of Formula (I), or a pharmaceutically acceptable salt thereof,

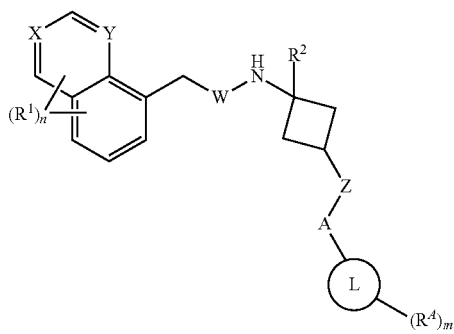

(I)

wherein:
W is C(=O) or absent;
X is N or N oxide;
Y is N or CH;
Z is NH, O or S;
A is CH$_2$ or absent;
L is selected from 5- to 10-membered heteroaryl having 1-3 heteroatoms independently selected from N, O, and S, C$_6$-C$_{10}$aryl and 6- to 10-membered partially saturated heterocyclyl having 1-3 heteroatoms independently selected from N, O, and S;
R$^A$ is at each occurrence independently selected from halo, —CN, C$_1$-C$_6$haloalkyl, C$_1$-C$_6$alkyl, SF$_5$, C$_3$-C$_6$cycloalkyl, C$_1$-C$_6$alkoxyl, C$_1$-C$_6$haloalkoxyl, 4- to 6-membered heterocyclyl having 1-2 heteroatoms independently selected from N, O, and S, —(CH$_2$)$_p$—NR$^3$R$^4$ and —C(=O)—O—(C$_1$-C$_6$alkyl),
wherein the C$_3$-C$_6$cycloalkyl and 4- to 6-membered heterocyclyl are each independently substituted with 0-4 R$^{A1}$.
R$^{A1}$ is at each occurrence independently selected from halo and C$_1$-C$_6$haloalkyl;
R$^1$ is at each occurrence independently selected from hydroxyl, C$_1$-C$_6$alkyl, C$_1$-C$_6$alkoxyl, halo, C$_1$-C$_6$haloalkyl and NR$^3$R$^4$,
wherein the C$_1$-C$_6$alkyl and C$_1$-C$_6$haloalkyl are each independently substituted with 0-4 R$^{1a}$;
R$^{1a}$ is at each occurrence independently selected from hydroxyl, NR$^3$R$^4$ and —C(=O)—OH;
R$^2$ is selected from hydrogen and C$_1$-C$_6$alkyl;
R$^3$ is at each occurrence independently selected from hydrogen and C$_1$-C$_6$alkyl;
R$^4$ is at each occurrence independently selected from —SO$_2$R$^5$, hydrogen, —C(=O)—(C$_1$-C$_6$alkyl) and C$_1$-C$_6$alkyl;
R$^5$ is at each occurrence independently selected from NH$_2$ and C$_1$-C$_6$alkyl;
n is 0, 1, 2, 3 or 4;
m is 0, 1, 2, 3, 4 or 5;
p is 0, 1 or 2.
Embodiment 2. The compound of Embodiment 1 or a pharmaceutically acceptable salt thereof,
wherein
W is C(=O) or absent;
X is N or N oxide;
Y is CH;
Z is NH, O or S;
A is CH$_2$ or absent;
L is selected from 5- to 10-membered heteroaryl having 1-3 heteroatoms independently selected from N, O, and S, C$_6$-C$_{10}$aryl and 6- to 10-membered partially saturated heterocyclyl having 1-3 heteroatoms independently selected from N, O, and S;
R$^A$ is at each occurrence independently selected from halo, —CN, C$_1$-C$_6$haloalkyl, C$_1$-C$_6$alkyl, SF$_5$, C$_3$-C$_6$cycloalkyl, C$_1$-C$_6$alkoxyl, C$_1$-C$_6$haloalkoxyl, 4- to 6-membered heterocyclyl having 1-2 heteroatoms independently selected from N, O, and S and —(CH$_2$)$_p$—NR$^3$R$^4$,
wherein the C$_3$-C$_6$cycloalkyl and 4- to 6-membered heterocyclyl are each independently substituted with 0-4 R$^{A1}$.
R$^{A1}$ is at each occurrence independently selected from halo and C$_1$-C$_6$haloalkyl;
R$^1$ is at each occurrence independently selected from C$_1$-C$_6$alkyl, halo, C$_1$-C$_6$haloalkyl and NR$^3$R$^4$,
wherein the C$_1$-C$_6$alkyl and C$_1$-C$_6$haloalkyl are each independently substituted with 0-4 R$^{1a}$;
R$^{1a}$ is at each occurrence independently selected from hydroxyl, NR$^3$R$^4$ and —C(=O)—OH;
R$^2$ is selected from hydrogen and C$_1$-C$_6$alkyl;
R$^3$ is at each occurrence independently selected from hydrogen and C$_1$-C$_6$alkyl;
R$^4$ is at each occurrence independently selected from —SO$_2$R$^5$, hydrogen, —C(=O)—(C$_1$-C$_6$alkyl) and C$_1$-C$_6$alkyl;
R$^5$ is at each occurrence independently selected from NH$_2$ and C$_1$-C$_6$alkyl;
n is 0, 1, 2, 3, 4;
m is 0, 1, 2, 3, 4 or 5;
p is 0, 1 or 2.
Embodiment 3. The compound of Embodiment 1 or 2 or a pharmaceutically acceptable salt thereof,
wherein
W is C(=O) or absent;
X is N or N oxide;
Y is CH;
Z is NH, O or S;
A is CH$_2$ or absent;
L is selected from 5- to 10-membered heteroaryl having 1-3 heteroatoms independently selected from N, O, and S, C$_6$-C$_{10}$aryl and 6- to 10-membered partially saturated heterocyclyl having 1-3 heteroatoms independently selected from N, O, and S;
R$^A$ is at each occurrence independently selected from halo, —CN, C$_1$-C$_6$haloalkyl, C$_1$-C$_6$alkyl, C$_3$-C$_6$cycloalkyl, C$_1$-C$_6$alkoxyl, C$_1$-C$_6$haloalkoxyl, 4- to 6-membered heterocyclyl having 1-2 heteroatoms independently selected from N, O, and S and —(CH$_2$)$_p$—NR$^3$R$^4$,
wherein the C$_3$-C$_6$cycloalkyl and 4- to 6-membered heterocyclyl are each independently substituted with 0-4 R$^{A1}$;
R$^{A1}$ is at each occurrence independently selected from halo and C$_1$-C$_6$haloalkyl;
R$^1$ is at each occurrence independently selected from C$_1$-C$_6$alkyl, halo, C$_1$-C$_6$haloalkyl and NH$_2$,
wherein the C$_1$-C$_6$alkyl and C$_1$-C$_6$haloalkyl are each independently substituted with 0-4 R$^{1a}$;
R$^{1a}$ is at each occurrence independently selected from hydroxyl, NR$^3$R$^4$ and —C(=O)—OH;
R$^2$ is selected from hydrogen and C$_1$-C$_3$alkyl;
R$^3$ is at each occurrence independently selected from hydrogen and C$_1$-C$_6$alkyl;
R$^4$ is at each occurrence independently selected from —SO$_2$R$^5$, hydrogen, —C(=O)—(C$_1$-C$_6$alkyl) and C$_1$-C$_6$alkyl;

$R^5$ is at each occurrence independently selected from $NH_2$ and $C_1$-$C_6$alkyl;

n is 0, 1, 2 or 3;

m is 0, 1, 2, 3 or 4;

p is 0, 1 or 2.

Embodiment 4. The compound of any of the preceding Embodiments or a pharmaceutically acceptable salt thereof, wherein W is absent;

X is N;

Y is CH;

Z is NH, O or S;

A is absent;

L is selected from 5- to 10-membered heteroaryl having 1-3 heteroatoms independently selected from N, O, and S, $C_6$-$C_{10}$aryl and 6- to 10-membered partially saturated heterocyclyl having 1-3 heteroatoms independently selected from N, O, and S;

$R^4$ is at each occurrence independently selected from halo, —CN, $C_1$-$C_6$haloalkyl, $C_1$-$C_6$alkyl, $C_3$-$C_6$cycloalkyl, $C_1$-$C_6$haloalkoxyl, 4- to 6-membered heterocyclyl having 1-2 heteroatoms independently selected from N, O, and S and —$(CH_2)_p$—$NR^3R^4$, wherein the $C_3$-$C_6$cycloalkyl and 4- to 6-membered heterocyclyl are each independently substituted with 0-4 $R^{41}$.

$R^{41}$ is at each occurrence independently selected from halo and $C_1$-$C_6$haloalkyl;

$R^1$ is at each occurrence independently selected from $C_1$-$C_6$alkyl, halo, $C_1$-$C_6$haloalkyl, wherein the $C_1$-$C_6$alkyl and $C_1$-$C_6$haloalkyl are each independently substituted with 0-4 $R^{1a}$;

$R^{1a}$ is at each occurrence independently selected from hydroxyl, $NR^3R^4$ and —C(=O)—OH;

$R^2$ is selected from hydrogen and $C_1$-$C_3$alkyl;

$R^3$ is at each occurrence independently selected from hydrogen and $C_1$-$C_6$alkyl;

$R^4$ is at each occurrence independently selected from —$SO_2R^5$, hydrogen, —C(=O)—($C_1$-$C_6$alkyl) and $C_1$-$C_6$alkyl;

$R^5$ is at each occurrence independently selected from $NH_2$ and $C_1$-$C_6$alkyl;

n is 0, 1, 2 or 3;

m is 0, 1, 2, 3 or 4;

p is 0, 1 or 2.

Embodiment 5. The compound of any of the preceding Embodiments or a pharmaceutically acceptable salt thereof, wherein $R^4$ is selected from fluoro, —CN, —$CF_3$, —$CHF_2$, —$CHFCH_2F$, —$CH_2F$, $C_1$-$C_4$alkyl, $C_3$-$C_6$cycloalkyl, —$OCF_3$, —$OCHF_2$, —$OCH_2F$, —$OCHFCH_2F$ and 4-membered heterocyclyl having 1 oxygen atom wherein the $C_3$-$C_6$cycloalkyl and the 4-membered O containing heterocyclyl are each independently substituted with 0-2 $R^{41}$, and wherein $R^{41}$ is at each occurrence independently selected from fluoro and $C_1$-$C_6$fluoroalkyl.

Embodiment 6. The compound of any of the preceding Embodiments or a pharmaceutically acceptable salt thereof, wherein $R^4$ is selected from fluoro, —CN, —$CF_3$, —$CHF_2$, —$CHFCH_2F$, —$CH_2F$, $C_1$-$C_4$alkyl, $C_3$-$C_6$cycloalkyl, —$OCF_3$, —$OCHF_2$, —$OCH_2F$, —$OCHFCH_2F$ and 4-membered heterocyclyl having 1 oxygen atom wherein the $C_3$-$C_6$cycloalkyl and the 4-membered O containing heterocyclyl are each independently substituted with 0-2 $R^{41}$, and wherein $R^{41}$ is at each occurrence independently selected from fluoro and $C_1$-$C_6$fluoroalkyl.

Embodiment 7. The compound of any of the preceding Embodiments or a pharmaceutically acceptable salt thereof, wherein $R^4$ is selected from fluoro, —CN, —$CF_3$, —$CHF_2$, —$CHFCH_2F$ and —$CH_2F$.

Embodiment 8. The compound of any of the preceding Embodiments or a pharmaceutically acceptable salt thereof, wherein L is selected from $C_6$-$C_{10}$aryl, 6- to 10-membered partially saturated heterocyclyl having 1-3 heteroatoms independently selected from N, O, and S, and 5- to 10-membered heteroaryl having 1-3 heteroatoms independently selected from N, O, and S selected from

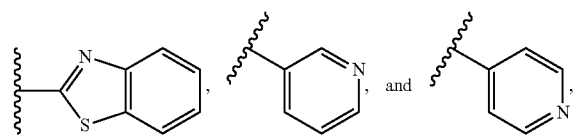

wherein the $C_6$-$C_{10}$aryl, 6- to 10-membered partially saturated heterocyclyl and 5- to 10-membered heteroaryl are each independently substituted with 0-4 $R^4$, and wherein $R^4$ is defined according to any of the preceding Embodiments.

Embodiment 9. The compound of any of the preceding Embodiments or a pharmaceutically acceptable salt thereof, wherein L is selected from $C_6$-$C_{10}$aryl, 6- to 10-membered partially saturated heterocyclyl having 1-3 heteroatoms independently selected from N, O, and S, and 5- to 10-membered heteroaryl having 1-3 heteroatoms independently selected from N, O, and S selected from

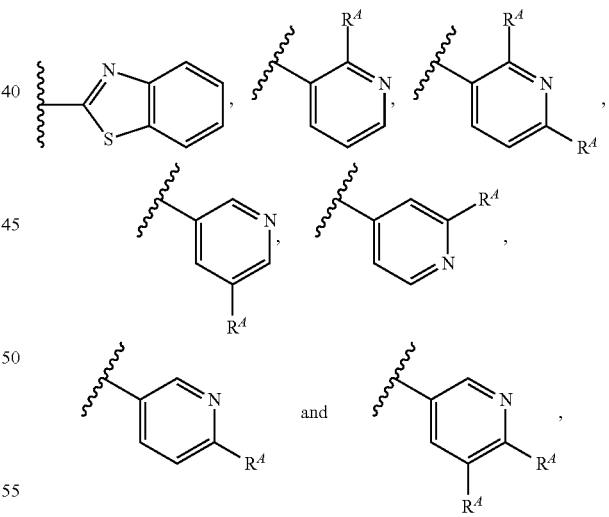

wherein the $C_6$-$C_{10}$aryl and 6- to 10-membered partially saturated heterocyclyl are each independently substituted with 0-2 $R^4$, and wherein $R^4$ is defined according to any of the preceding Embodiments.

Embodiment 10. The compound of any of the preceding Embodiments or a pharmaceutically acceptable salt thereof, wherein L is selected from $C_6$-$C_{10}$aryl, 6- to 10-membered partially saturated heterocyclyl having 1-3 heteroatoms independently selected from N, O, and S, and 5- to 10-membered heteroaryl having 1-3 heteroatoms independently selected from N, O, and S selected from

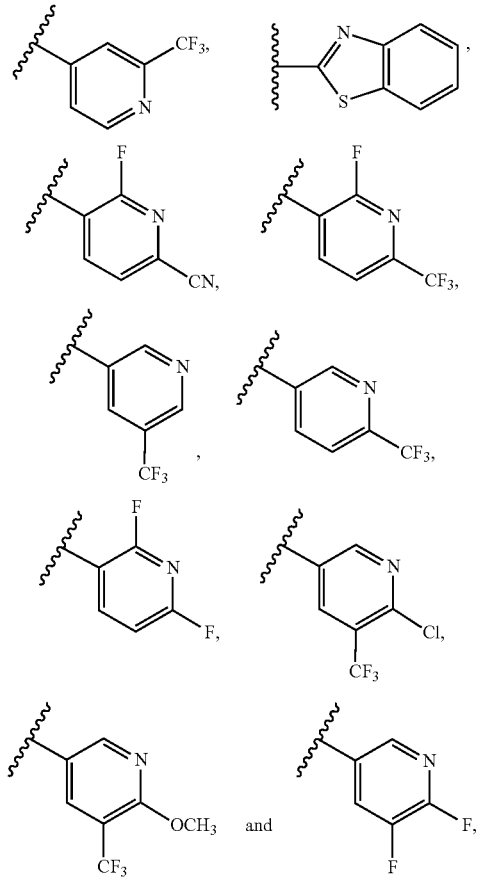

wherein the $C_6$-$C_{10}$aryl and 6- to 10-membered partially saturated heterocyclyl are each independently substituted with 0-2 $R^A$, and wherein $R^A$ is defined according to any of the preceding Embodiments.

Embodiment 11. The compound of any of Embodiments 1 to 7, or a pharmaceutically acceptable salt thereof, wherein L is selected from 6- to 10-membered partially saturated heterocyclyl having 1-3 heteroatoms independently selected from N, O, and S, 5- to 10-membered heteroaryl having 1-3 heteroatoms independently selected from N, O, and S, and $C_6$-$C_{10}$aryl selected from phenyl and naphthyl, wherein the 6- to 10-membered partially saturated heterocyclyl, 5- to 10-membered heteroaryl, phenyl and naphthyl are each independently substituted with 0-4 $R^A$, and wherein $R^A$ is defined according to any of the preceding Embodiments.

Embodiment 12. The compound of any of Embodiments 1 to 7, 11, or a pharmaceutically acceptable salt thereof, wherein L is selected from 6- to 10-membered partially saturated heterocyclyl having 1-3 heteroatoms independently selected from N, O, and S, 5- to 10-membered heteroaryl having 1-3 heteroatoms independently selected from N, O, and S, and $C_6$-$C_{10}$aryl selected from

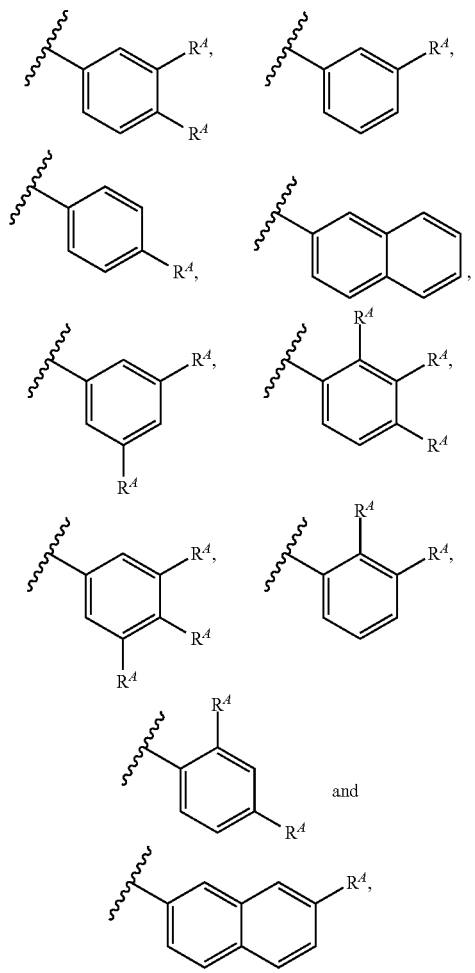

wherein the 6- to 10-membered partially saturated heterocyclyl and 5- to 10-membered heteroaryl are each independently substituted with 0-3 $R^A$, and wherein $R^A$ is defined according to any of the preceding Embodiments.

Embodiment 13. The compound of any of Embodiments 1 to 7, 11, 12, or a pharmaceutically acceptable salt thereof, wherein L is selected from 6- to 10-membered partially saturated heterocyclyl having 1-3 heteroatoms independently selected from N, O, and S, 5- to 10-membered heteroaryl having 1-3 heteroatoms independently selected from N, O, and S, and $C_6$-$C_{10}$aryl selected from

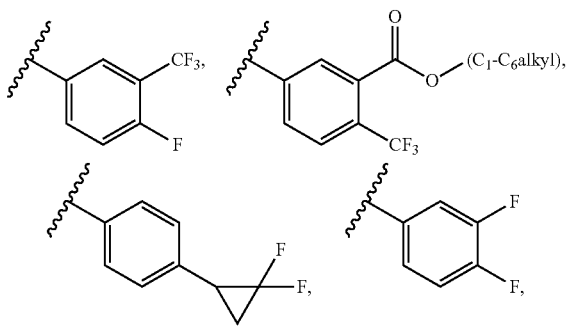

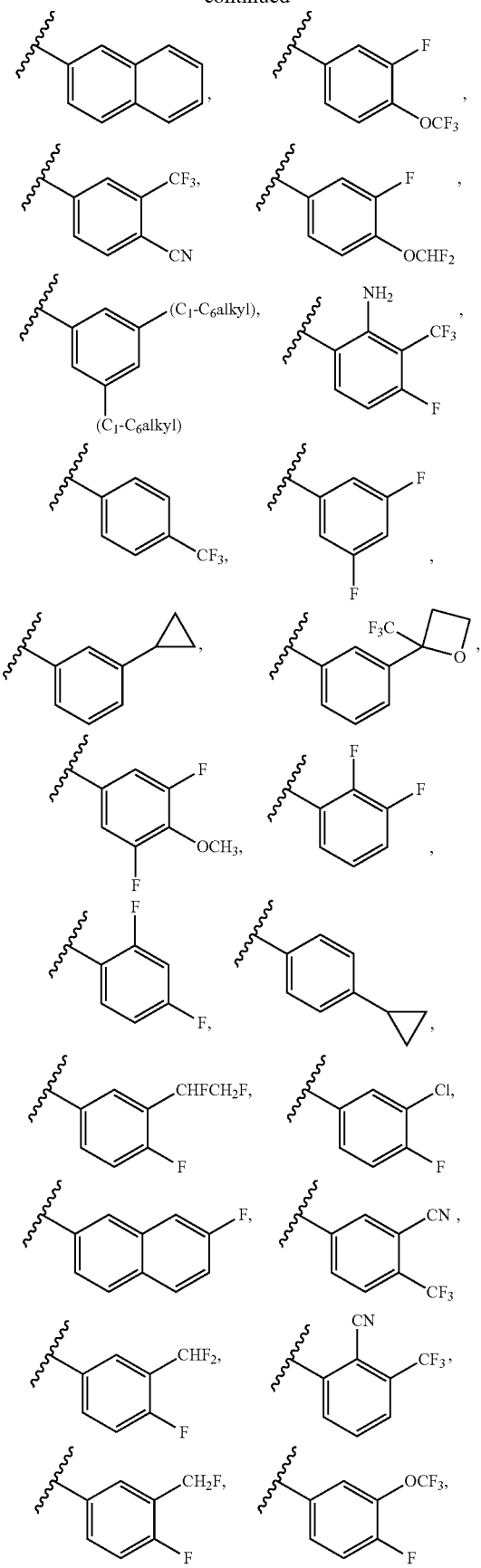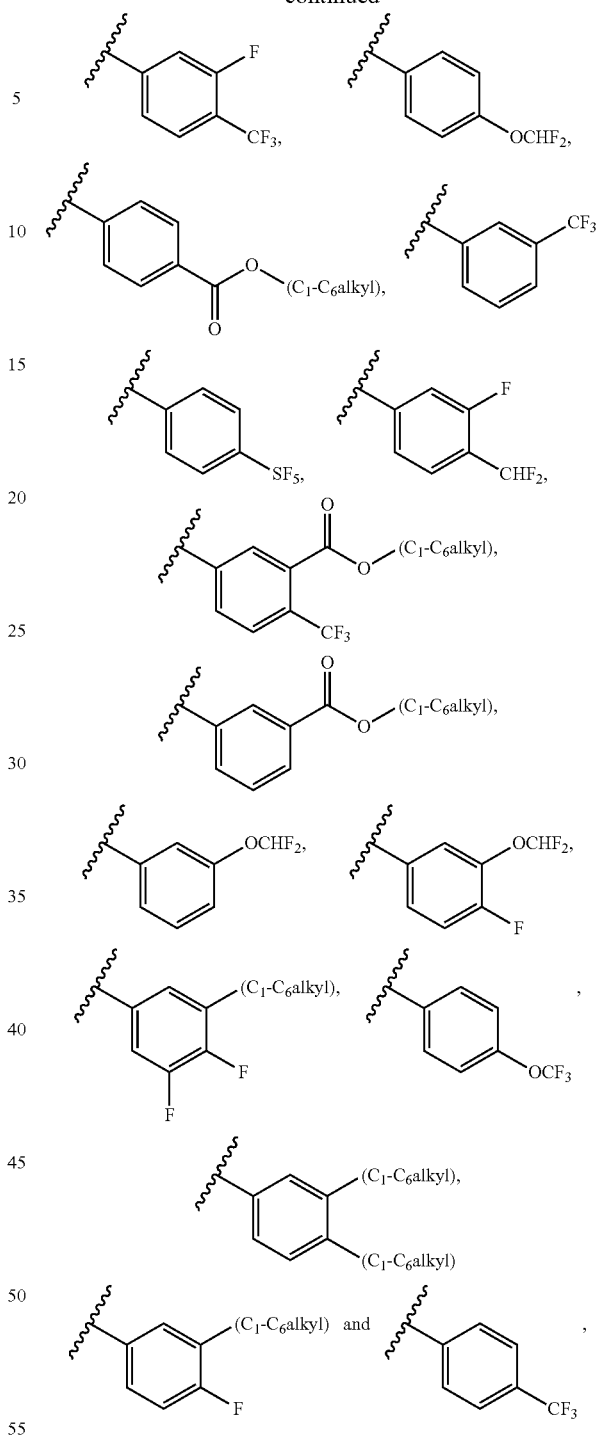

wherein the 6- to 10-membered partially saturated heterocyclyl and 5- to 10-membered heteroaryl are each independently substituted with 0-3 $R^A$ and wherein $R^A$ is defined according to any of the preceding Embodiments.

Embodiment 14. The compound of any of Embodiments 1 to 7, or a pharmaceutically acceptable salt thereof, wherein L is selected from 5- to 10-membered heteroaryl having 1-3 heteroatoms independently selected from N, O, and S, $C_6$-$C_{10}$aryl and 6- to 10-membered partially saturated heterocyclyl selected from

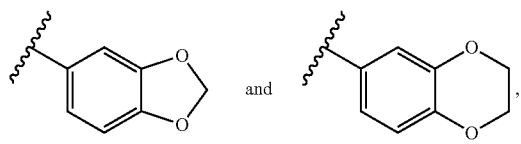 [SMILES: *c1ccc2c(c1)OCO2 ; *c1ccc2c(c1)OCCO2]

wherein the 5- to 10-membered heteroaryl, $C_6$-$C_{10}$aryl and 6- to 10-membered partially saturated heterocyclyl are each independently substituted with 0-4 $R^A$, and wherein $R^A$ is defined according to any of the preceding Embodiments.

Embodiment 15. The compound of any of Embodiments 1 to 7, 14, or a pharmaceutically acceptable salt thereof, wherein L is selected from 5- to 10-membered heteroaryl having 1-3 heteroatoms independently selected from N, O, and S, $C_6$-$C_{10}$aryl and 6- to 10-membered partially saturated heterocyclyl selected from

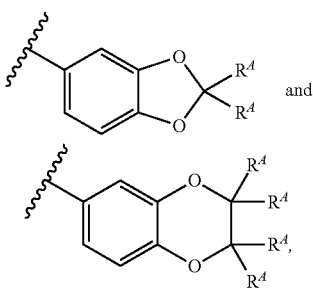

wherein the 5- to 10-membered heteroaryl and $C_6$-$C_{10}$aryl are each independently substituted with 0-4 $R^A$, and wherein $R^A$ is defined according to any of the preceding Embodiments.

Embodiment 16. The compound of any of Embodiments 1 to 7, 14, 15, or a pharmaceutically acceptable salt thereof, wherein L is selected from 5- to 10-membered heteroaryl having 1-3 heteroatoms independently selected from N, O, and S, $C_6$-$C_{10}$aryl and 6- to 10-membered partially saturated heterocyclyl selected from

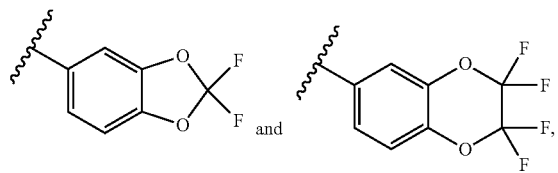 [SMILES: *c1ccc2c(c1)OC(F)(F)O2 ; *c1ccc2c(c1)OC(F)(F)C(F)(F)O2]

wherein the 5- to 10-membered heteroaryl and $C_6$-$C_{10}$aryl are each independently substituted with 0-4 $R^A$, and wherein $R^A$ is defined according to any of the preceding Embodiments.

Embodiment 17. The compound of any of the preceding Embodiments or a pharmaceutically acceptable salt thereof, wherein $R^1$ is at each occurrence is independently selected from $C_1$-$C_6$alkyl, halo, $C_1$-$C_6$haloalkyl and $NH_2$, wherein the $C_1$-$C_6$alkyl and $C_1$-$C_6$haloalkyl are each independently substituted with 0-4 $R^{1a}$, wherein $R^{1a}$ is at each occurrence independently selected from hydroxyl and $NR^3R^4$.

Embodiment 18. The compound of any of the preceding Embodiments or a pharmaceutically acceptable salt thereof, wherein $R^1$ is at each occurrence is independently selected from $C_1$-$C_6$alkyl, fluoro, $NH_2$, —$N(C_1$-$C_6$alkyl)$_2$ and chloro, wherein the $C_1$-$C_6$alkyl is at each occurrence independently substituted with 0-4 hydroxyl.

Embodiment 19. The compound of any of the preceding Embodiments or a pharmaceutically acceptable salt thereof, wherein $R^1$ is at each occurrence is independently selected from $C_1$-$C_6$alkyl and fluoro, wherein the $C_1$-$C_6$alkyl is each occurrence independently substituted with 0-4 hydroxyl.

Embodiment 20. The compound of any of the preceding Embodiments or a pharmaceutically acceptable salt thereof, wherein n is 1, 2 or 3.

Embodiment 21. The compound of any of the preceding Embodiments or a pharmaceutically acceptable salt thereof, wherein m is 1, 2 or 3.

Embodiment 22. The compound of any of the preceding Embodiments or a pharmaceutically acceptable salt thereof, wherein $R^2$ is hydrogen.

Embodiment 23. The compound of any of the preceding Embodiments or a pharmaceutically acceptable salt thereof, wherein Y is CH.

Embodiment 24. The compound of any of the preceding Embodiments or a pharmaceutically acceptable salt thereof, wherein W is absent.

Embodiment 25. The compound of any of the preceding Embodiments or a pharmaceutically acceptable salt thereof, wherein Z is O.

Embodiment 26. The compound of any of the preceding Embodiments or a pharmaceutically acceptable salt thereof, wherein
W is absent;
X is N;
Y is CH;
Z is O;
A is absent;
L is $C_6$-$C_{10}$aryl;
$R^A$ is at each occurrence independently selected from halo, —CN, $C_1$-$C_6$haloalkyl, $C_1$-$C_6$alkyl;
$R^1$ is at each occurrence independently selected from $C_1$-$C_6$alkyl, halo and $C_1$-$C_6$haloalkyl,
wherein the $C_1$-$C_6$alkyl and $C_1$-$C_6$haloalkyl are each independently substituted with 0-4 $R^{1a}$;
$R^{1a}$ is at each occurrence independently selected from hydroxyl and $NR^3R^4$;
$R^2$ is selected from hydrogen and $C_1$-$C_3$alkyl;
$R^3$ is at each occurrence independently selected from hydrogen and $C_1$-$C_6$alkyl;
$R^4$ is at each occurrence independently selected from —$SO_2R^5$, hydrogen and $C_1$-$C_6$alkyl;
$R^5$ is at each occurrence independently selected from $NH_2$ and $C_1$-$C_6$alkyl;
n is 1, 2 or 3;
m is 0, 1, 2 or 3.

Embodiment 27. The compound of any of the preceding Embodiments or a pharmaceutically acceptable salt thereof, wherein
W is absent;
X is N;
Y is CH;
Z is O;
A is absent;
L is $C_6$-$C_{10}$aryl;
$R^A$ is at each occurrence independently selected from halo (e.g., fluoro), $C_1$-$C_6$haloalkyl (e.g., $C_1$-$C_6$fluoroalkyl) and $C_1$-$C_6$alkyl;

R¹ is at each occurrence independently selected from C$_1$-C$_6$alkyl and halo (e.g., fluoro),
wherein the C$_1$-C$_6$alkyl is substituted with 0-4 hydroxyl;
R² is hydrogen;
n is 1, 2 or 3;
m is 1, 2 or 3.

Embodiment 28. The compound of any of the preceding Embodiments or a pharmaceutically acceptable salt thereof, wherein R¹ is at each occurrence independently selected from

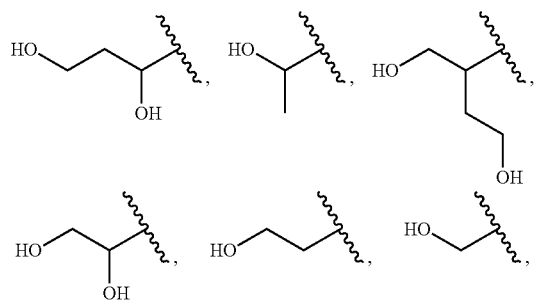

fluoro and NH$_2$.

Embodiment 29. The compound of any of the preceding Embodiments or a pharmaceutically acceptable salt thereof, wherein R¹ is at each occurrence independently selected from

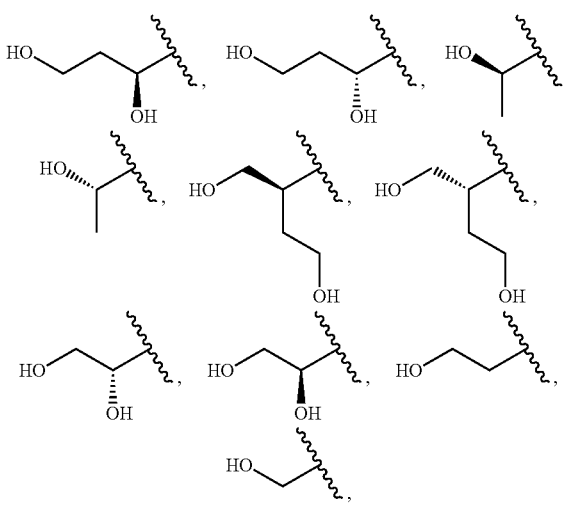

fluoro and NH$_2$.

Embodiment 30. The compound of any of the preceding Embodiments or a pharmaceutically acceptable salt thereof, wherein R¹ is at each occurrence independently selected from

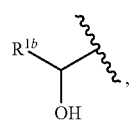

fluoro and NH$_2$,
wherein R$^{1b}$ is hydrogen or C$_1$-C$_5$alkyl,
wherein the C$_1$-C$_5$alkyl is substituted with 0-3 hydroxyl.

Embodiment 31. The compound of any of the preceding Embodiments or a pharmaceutically acceptable salt thereof, of Formula (Ia)

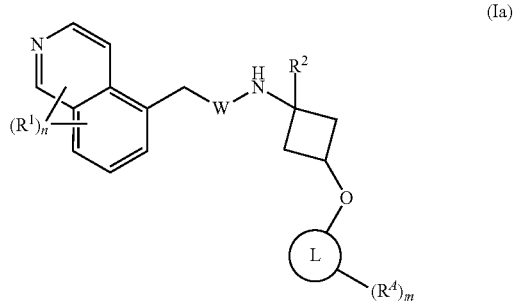

wherein W, L, R¹, R², R⁴, n and m are defined according to any of the preceding Embodiments.

Embodiment 32. The compound of any of the preceding Embodiments or a pharmaceutically acceptable salt thereof, of Formula (Ib)

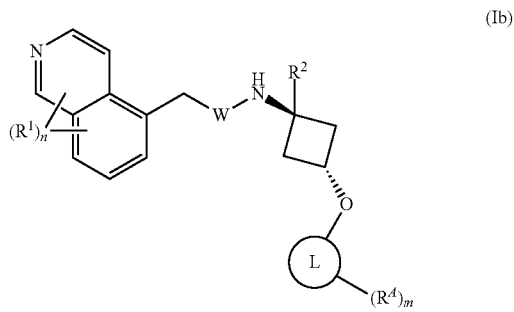

wherein W, L, R¹, R², R⁴, n and m are defined according to any of the preceding Embodiments.

Embodiment 33. The compound of any of the preceding Embodiments or a pharmaceutically acceptable salt thereof, of Formula (Ig)

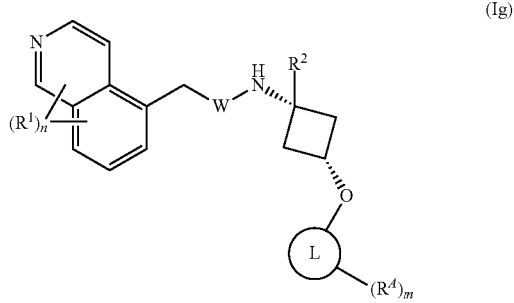

wherein W, L, R¹, R², R⁴, n and m are defined according to any of the preceding Embodiments.

Embodiment 34. The compound of any of the preceding Embodiments or a pharmaceutically acceptable salt thereof, of Formula (Ic)

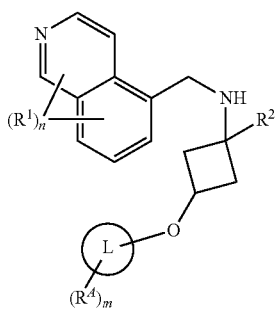

(Ic)

wherein L, $R^1$, $R^2$, $R^A$, n and m are defined according to any of the preceding Embodiments.

Embodiment 35. The compound of any of the preceding Embodiments or a pharmaceutically acceptable salt thereof, of Formula (Id)

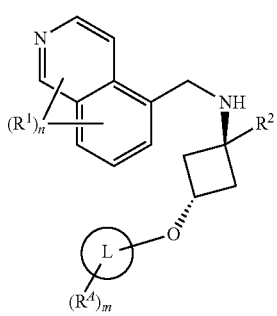

(Id)

wherein L, $R^1$, $R^2$, $R^A$, n and m are defined according to any of the preceding Embodiments.

Embodiment 36. The compound of any of the preceding Embodiments or a pharmaceutically acceptable salt thereof, of Formula (Ih)

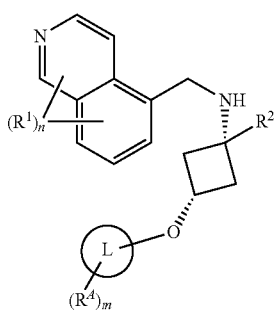

(Ih)

wherein L, $R^1$, $R^2$, $R^A$, n and m are defined according to any of the preceding Embodiments.

Embodiment 37. The compound of any of the preceding Embodiments or a pharmaceutically acceptable salt thereof, of Formula (Ie)

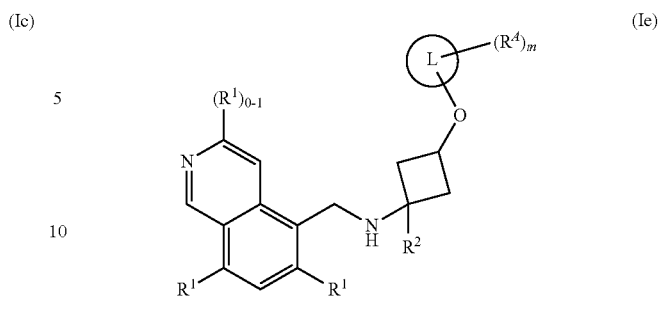

(Ie)

wherein L, $R^1$, $R^2$, $R^A$ and m are defined according to any of the preceding Embodiments.

Embodiment 38. The compound of any of the preceding Embodiments or a pharmaceutically acceptable salt thereof, of Formula (If)

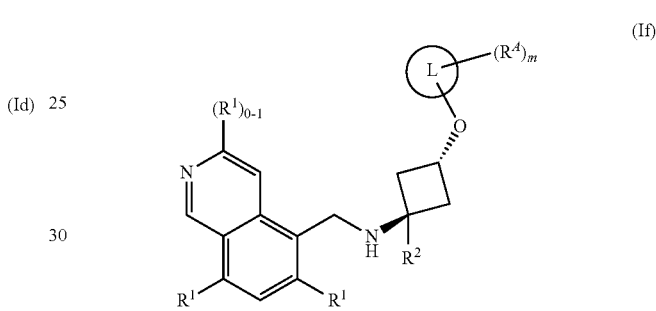

(If)

wherein L, $R^1$, $R^2$, $R^A$ and m are defined according to any of the preceding Embodiments.

Embodiment 39. The compound of any of the preceding Embodiments or a pharmaceutically acceptable salt thereof, of Formula (Ii)

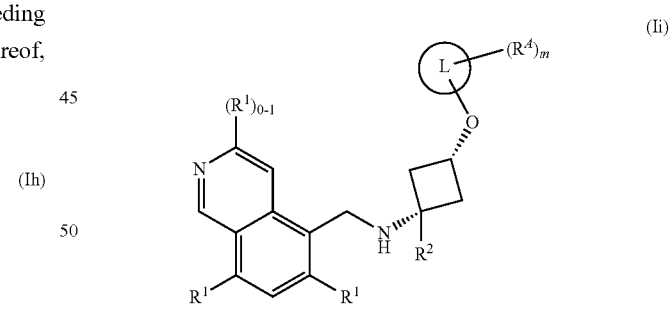

(Ii)

wherein L, $R^1$, $R^2$, $R^A$ and m are defined according to any of the preceding Embodiments.

Embodiment 40. The compound of any of Embodiments 1 to 31, 34, 37 or a pharmaceutically acceptable salt thereof, wherein the substituents at the 1- and 3-positions of the cyclobutyl ring have a trans configuration.

Embodiment 41. The compound of any of Embodiments 1 to 31, 34, 37 or a pharmaceutically acceptable salt thereof, wherein the substituents at the 1- and 3-positions of the cyclobutyl ring have a cis configuration.

Embodiment 42. The compound of Embodiment 1 or a pharmaceutically acceptable salt thereof, selected from:

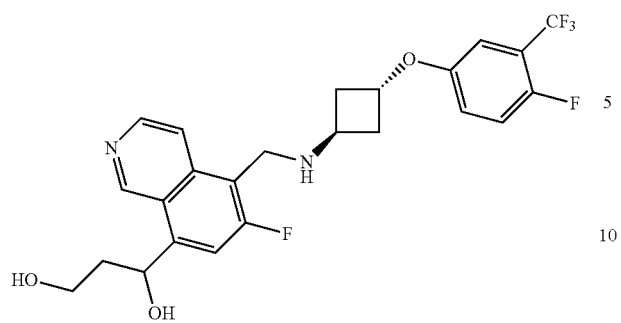

1-(6-fluoro-5-((((1r,3r)-3-(4-fluoro-3-(trifluoromethyl)phenoxy)cyclobutyl)amino)methyl)isoquinolin-8-yl)propane-1,3-diol

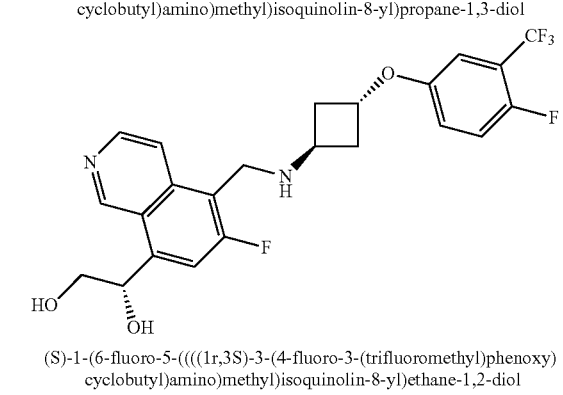

(S)-1-(6-fluoro-5-((((1r,3S)-3-(4-fluoro-3-(trifluoromethyl)phenoxy)cyclobutyl)amino)methyl)isoquinolin-8-yl)ethane-1,2-diol

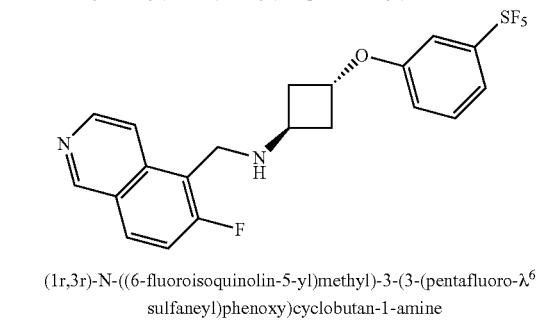

(1r,3r)-N-((6-fluoroisoquinolin-5-yl)methyl)-3-(3-(pentafluoro-$\lambda^6$–sulfaneyl)phenoxy)cyclobutan-1-amine

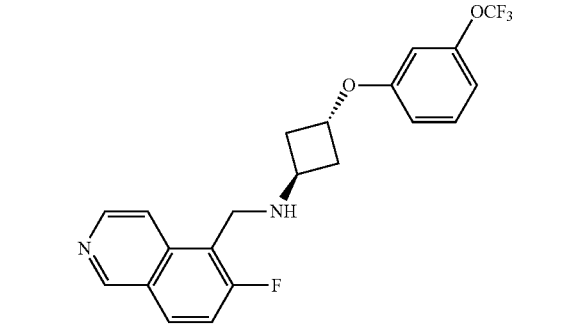

(1r,3r)-N-((6-fluoroisoquinolin-5-yl)methyl)-3-(3-(trifluoromethoxy)phenoxy)cyclobutan-1-amine

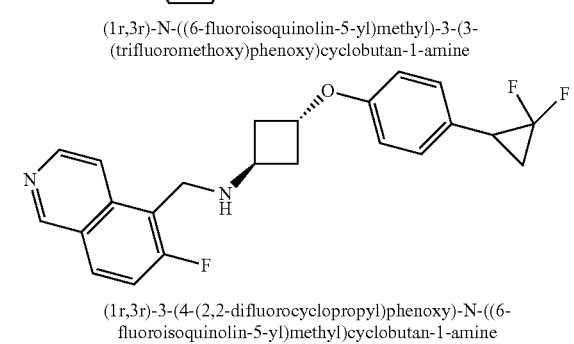

(1r,3r)-3-(4-(2,2-difluorocyclopropyl)phenoxy)-N-((6-fluoroisoquinolin-5-yl)methyl)cyclobutan-1-amine -continued

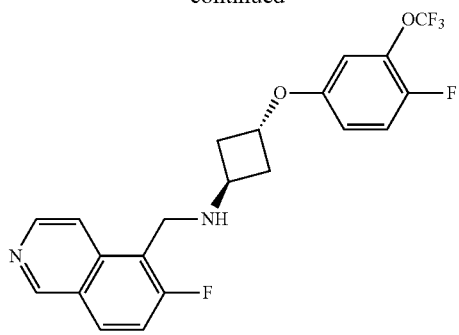

(1r,3r)-3-((3-fluoro-4-(trifluoromethyl)benzyl)oxy)-N-((6-fluoroisoquinolin-5-yl)methyl)cyclobutan-1-amine

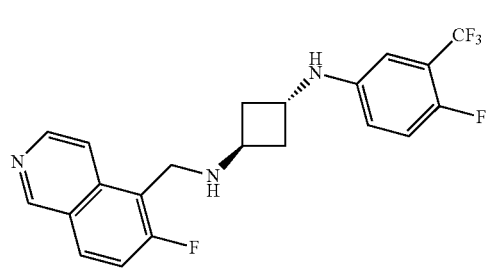

(1r,3r)-N1-(4-fluoro-3-(trifluoromethyl)phenyl)-N3-((6-fluoroisoquinolin-5-yl)methyl)cyclobutane-1,3-diamine

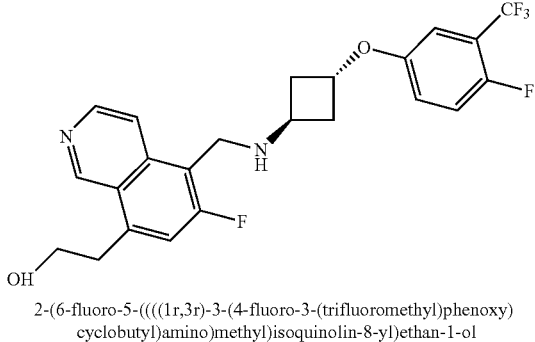

2-(6-fluoro-5-((((1r,3r)-3-(4-fluoro-3-(trifluoromethyl)phenoxy)cyclobutyl)amino)methyl)isoquinolin-8-yl)ethan-1-ol

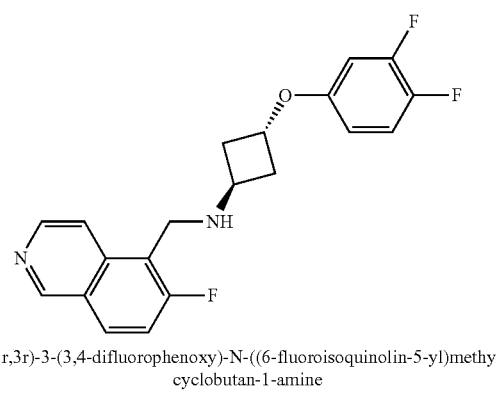

(1r,3r)-3-(3,4-difluorophenoxy)-N-((6-fluoroisoquinolin-5-yl)methyl)cyclobutan-1-amine

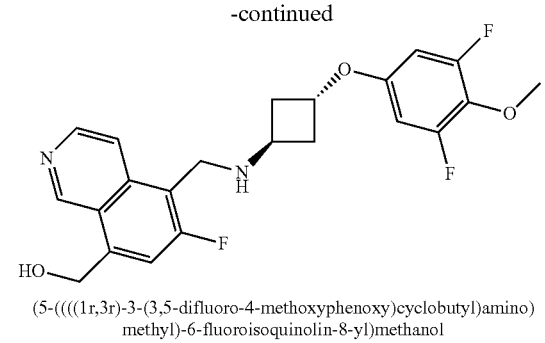

(5-((((1r,3r)-3-(3,5-difluoro-4-methoxyphenoxy)cyclobutyl)amino)methyl)-6-fluoroisoquinolin-8-yl)methanol

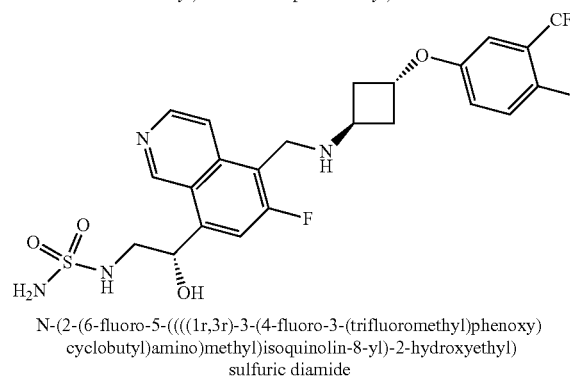

N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl)sulfuric diamide

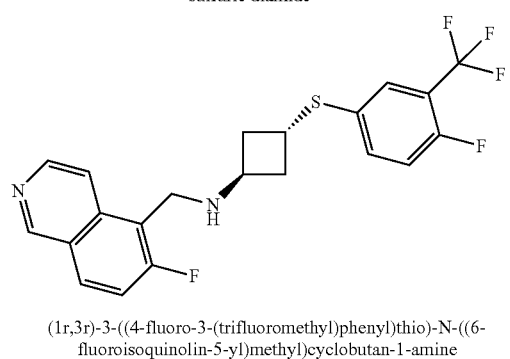

(1r,3r)-3-((4-fluoro-3-(trifluoromethyl)phenyl)thio)-N-((6-fluoroisoquinolin-5-yl)methyl)cyclobutan-1-amine

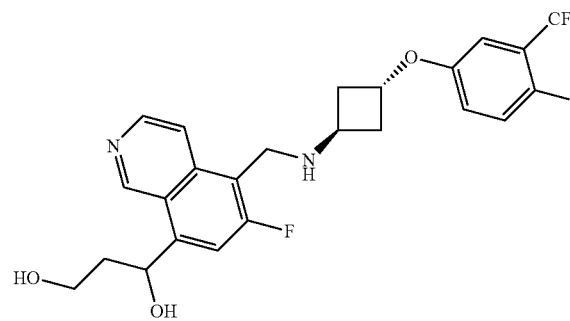

1-(6-fluoro-5-((((1r,3r)-3-(4-fluoro-3-(trifluoromethyl)phenoxy)cyclobutyl)amino)methyl)isoquinolin-8-yl)propane-1,3-diol

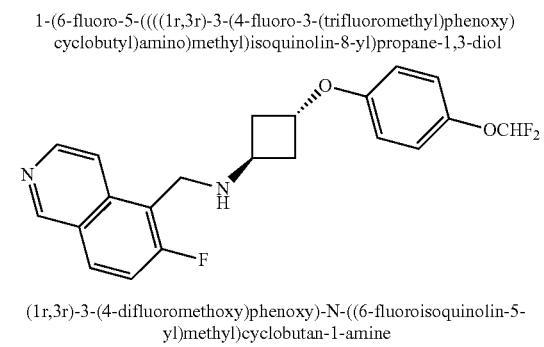

(1r,3r)-3-(4-(difluoromethoxy)phenoxy)-N-((6-fluoroisoquinolin-5-yl)methyl)cyclobutan-1-amine

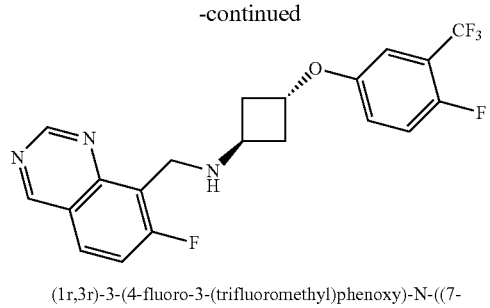

(1r,3r)-3-(4-fluoro-3-(trifluoromethyl)phenoxy)-N-((7-fluoroquinazolin-8-yl)methyl)cyclobutan-1-amine

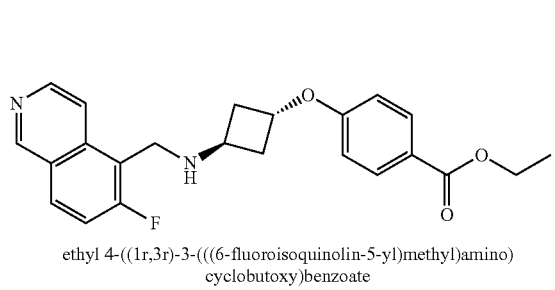

ethyl 4-((1r,3r)-3-(((6-fluoroisoquinolin-5-yl)methyl)amino)cyclobutoxy)benzoate

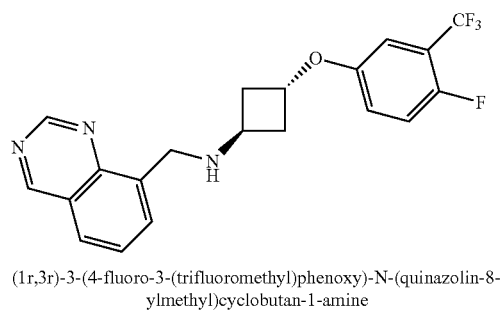

(1r,3r)-3-(4-fluoro-3-(trifluoromethyl)phenoxy)-N-(quinazolin-8-ylmethyl)cyclobutan-1-amine

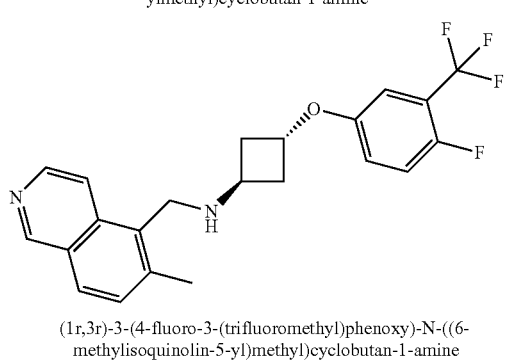

(1r,3r)-3-(4-fluoro-3-(trifluoromethyl)phenoxy)-N-((6-methylisoquinolin-5-yl)methyl)cyclobutan-1-amine

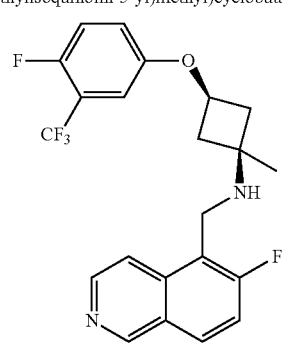

(1s,3s)-3-(4-fluoro-3-(trifluoromethyl)phenoxy)-N-((6-fluoroisoquinolin-5-yl)methyl)-1-methylcyclobutan-1-amine

29

-continued

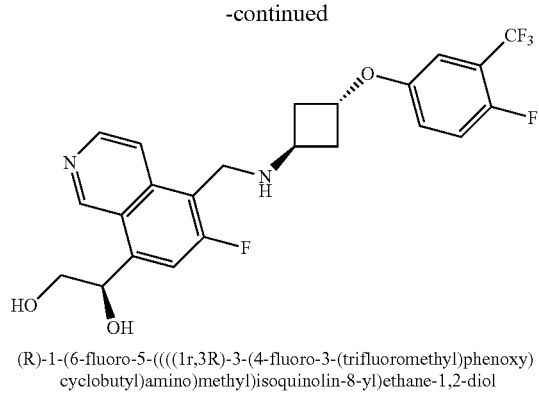

(R)-1-(6-fluoro-5-((((1r,3R)-3-(4-fluoro-3-(trifluoromethyl)phenoxy)
cyclobutyl)amino)methyl)isoquinolin-8-yl)ethane-1,2-diol

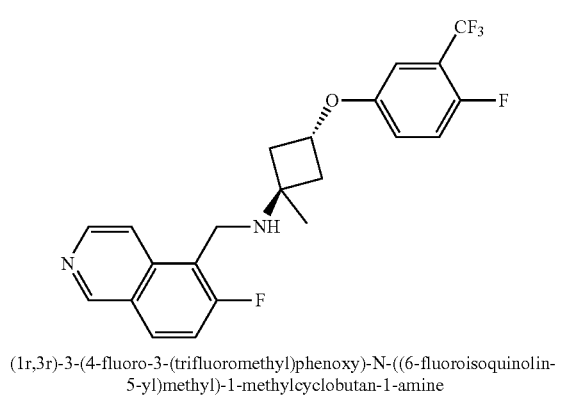

(1r,3r)-3-(4-fluoro-3-(trifluoromethyl)phenoxy)-N-((6-fluoroisoquinolin-
5-yl)methyl)-1-methylcyclobutan-1-amine

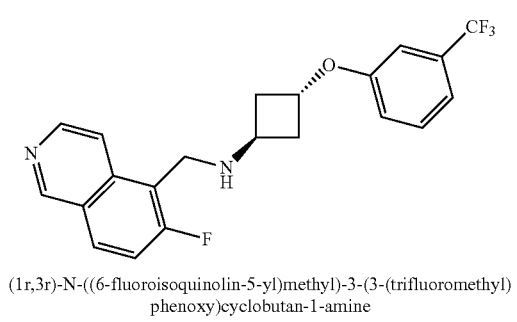

(1r,3r)-N-((6-fluoroisoquinolin-5-yl)methyl)-3-(3-(trifluoromethyl)
phenoxy)cyclobutan-1-amine

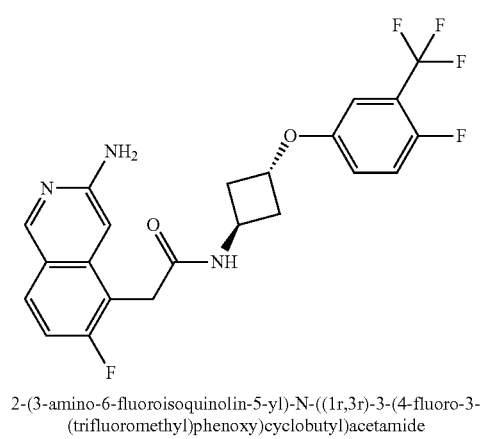

2-(3-amino-6-fluoroisoquinolin-5-yl)-N-((1r,3r)-3-(4-fluoro-3-
(trifluoromethyl)phenoxy)cyclobutyl)acetamide

30

-continued

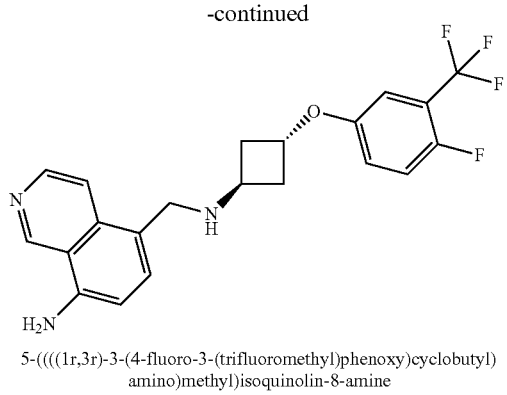

5-((((1r,3r)-3-(4-fluoro-3-(trifluoromethyl)phenoxy)cyclobutyl)
amino)methyl)isoquinolin-8-amine

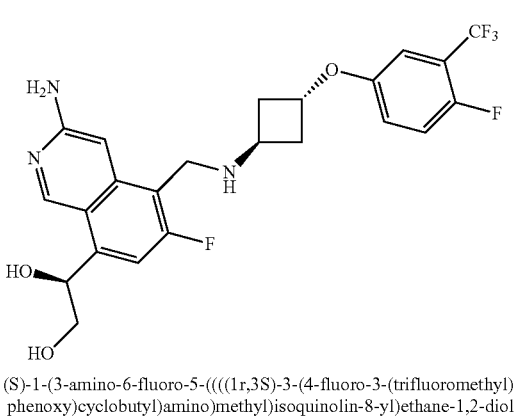

(S)-1-(3-amino-6-fluoro-5-((((1r,3S)-3-(4-fluoro-3-(trifluoromethyl)
phenoxy)cyclobutyl)amino)methyl)isoquinolin-8-yl)ethane-1,2-diol

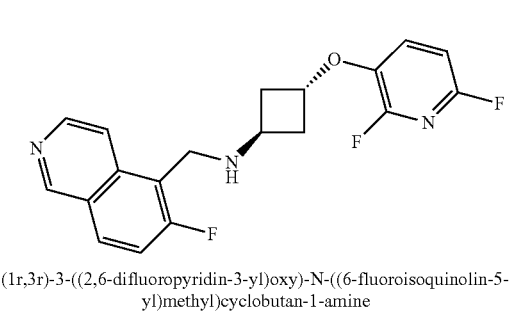

(1r,3r)-3-((2,6-difluoropyridin-3-yl)oxy)-N-((6-fluoroisoquinolin-5-
yl)methyl)cyclobutan-1-amine

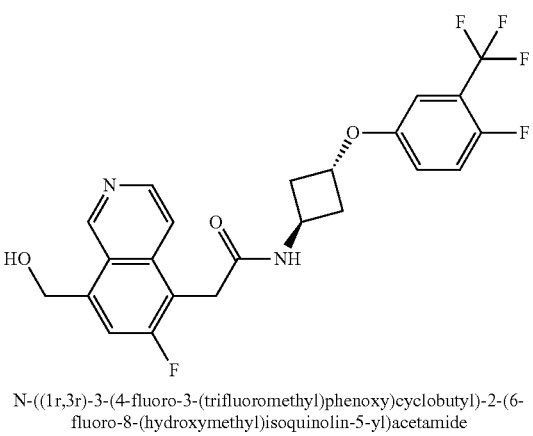

N-((1r,3r)-3-(4-fluoro-3-(trifluoromethyl)phenoxy)cyclobutyl)-2-(6-
fluoro-8-(hydroxymethyl)isoquinolin-5-yl)acetamide

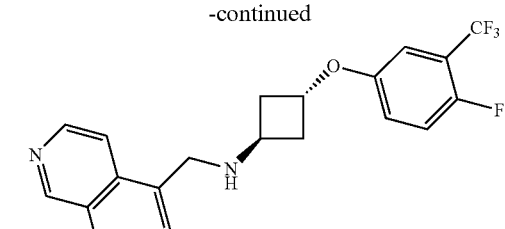

(5-((((1r,3r)-3-(4-fluoro-3-(trifluoromethyl)phenoxy)cyclobutyl)amino)methyl)isoquinolin-8-yl)methanol

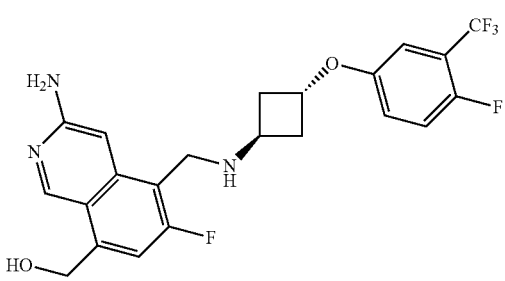

(3-amino-6-fluoro-5-((((1r,3r)-3-(4-fluoro-3-(trifluoromethyl)phenoxy)cyclobutyl)amino)methyl)isoquinolin-8-yl)methanol

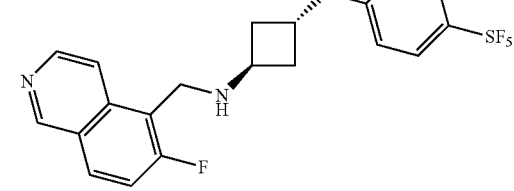

(1r,3r)-N-((6-fluoroisoquinolin-5-yl)methyl)-3-(4-(pentafluoro-λ⁶-sulfaneyl)phenoxy)cyclobutan-1-amine

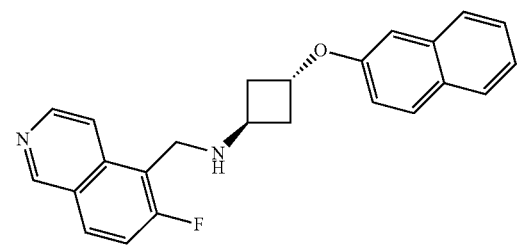

(1r,3r)-N-((6-fluoroisoquinolin-5-yl)methyl)-3-(naphthalen-2-yloxy)cyclobutan-1-amine

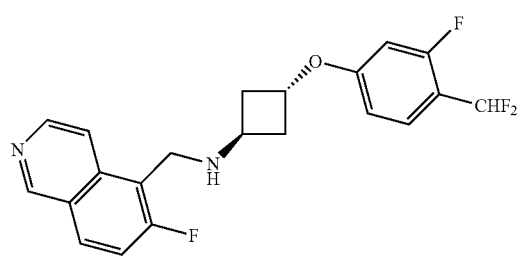

(1r,3r)-3-(4-difluoromethyl)-3-fluorophenoxy)-N-((6-fluoroisoquinolin-5-yl)methyl)cyclobutan-1-amine

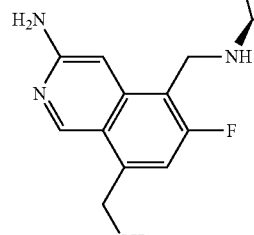

(3-amino-6-fluoro-5-((((1r,3r)-3-((2-(trifluoromethyl)pyridin-4-yl)oxy)cyclobutyl)amino)methyl)isoquinolin-8-yl)methanol

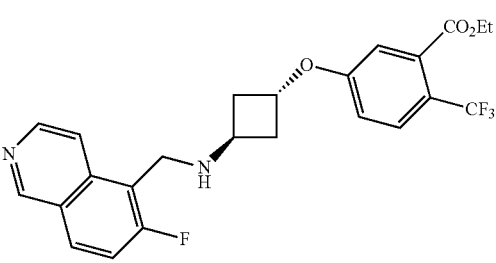

ethyl 5-((1r,3r)-3-(((6-fluoroisoquinolin-5-yl)methyl)amino)cyclobutoxy)-2-(trifluoromethyl)benzoate

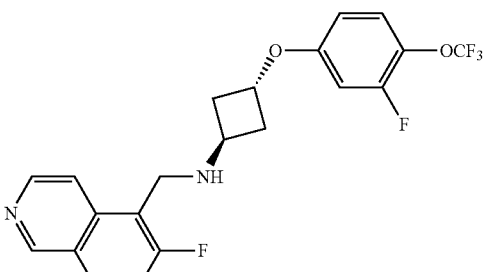

(1r,3r)-3-(3-fluoro-4-(trifluoromethoxy)phenoxy)-N-((6-fluoroisoquinolin-5-yl)methyl)cyclobutan-1-amine

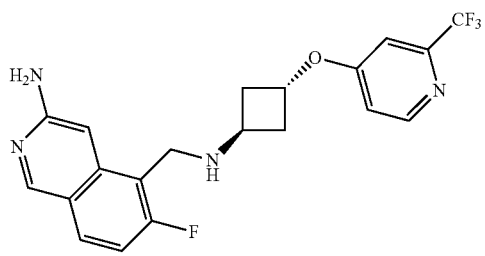

6-fluoro-5-((((1r,3r)-3-((2-(trifluoromethyl)pyridin-4-yl)oxy)cyclobutyl)amino)methyl)isoquinolin-3-amine

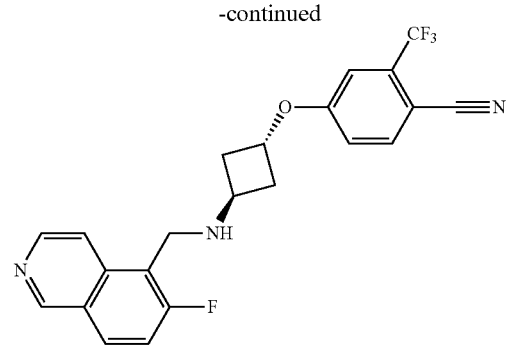

4-((1r,3r)-3-(((6-fluoroisoquinolin-5-yl)methyl)amino)cyclobutoxy)-2-(trifluoromethyl)benzonitrile

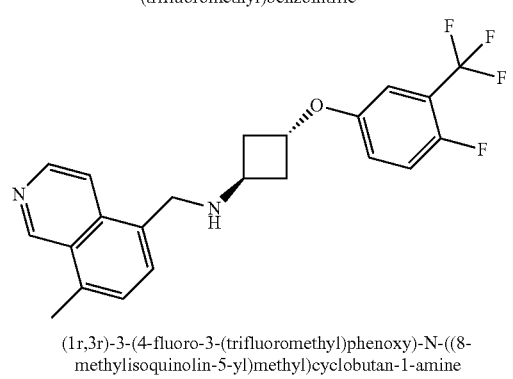

(1r,3r)-3-(4-fluoro-3-(trifluoromethyl)phenoxy)-N-((8-methylisoquinolin-5-yl)methyl)cyclobutan-1-amine

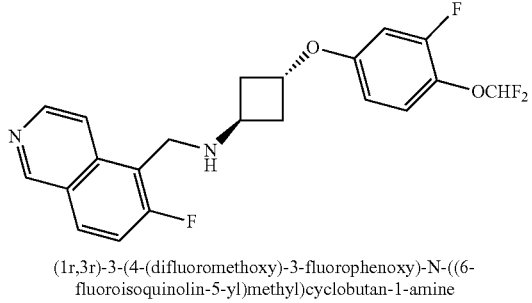

(1r,3r)-3-(4-(difluoromethoxy)-3-fluorophenoxy)-N-((6-fluoroisoquinolin-5-yl)methyl)cyclobutan-1-amine

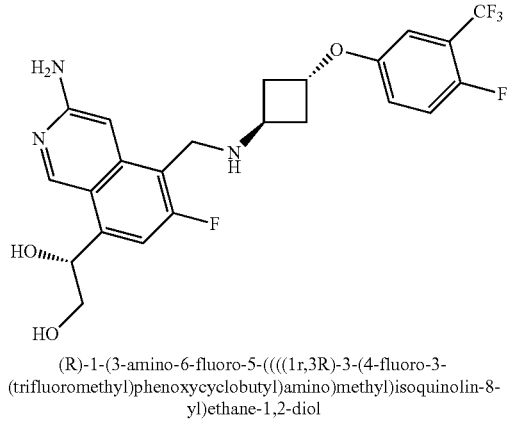

(R)-1-(3-amino-6-fluoro-5-((((1r,3R)-3-(4-fluoro-3-(trifluoromethyl)phenoxycyclobutyl)amino)methyl)isoquinolin-8-yl)ethane-1,2-diol

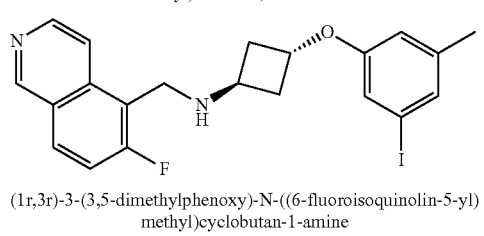

(1r,3r)-3-(3,5-dimethylphenoxy)-N-((6-fluoroisoquinolin-5-yl)methyl)cyclobutan-1-amine

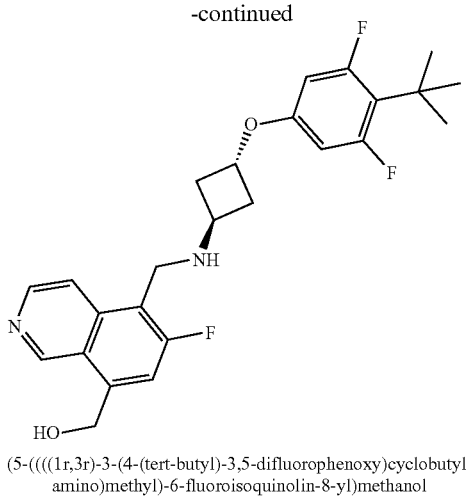

(5-(((((1r,3r)-3-(4-(tert-butyl)-3,5-difluorophenoxy)cyclobutyl)amino)methyl)-6-fluoroisoquinolin-8-yl)methanol

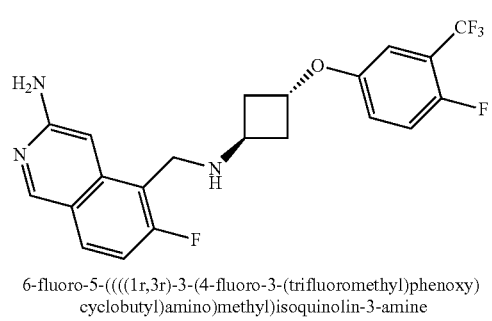

6-fluoro-5-(((((1r,3r)-3-(4-fluoro-3-(trifluoromethyl)phenoxy)cyclobutyl)amino)methyl)isoquinolin-3-amine

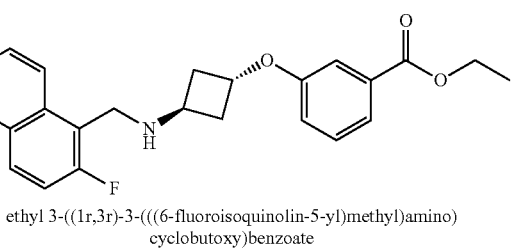

ethyl 3-((1r,3r)-3-(((6-fluoroisoquinolin-5-yl)methyl)amino)cyclobutoxy)benzoate

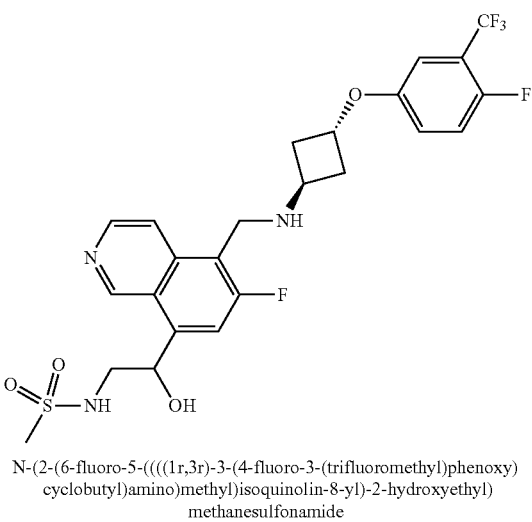

N-(2-(6-fluoro-5-(((((1r,3r)-3-(4-fluoro-3-(trifluoromethyl)phenoxy)cyclobutyl)amino)methyl)isoquinolin-8-yl)-2-hydroxyethyl)methanesulfonamide

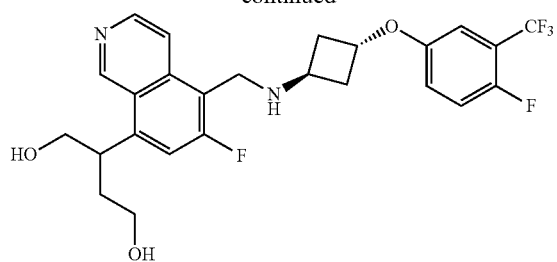

2-(6-fluoro-5-((((1r,3r)-3-(4-fluoro-3-(trifluoromethyl)phenoxy)
cyclobutyl)amino)methyl)isoquinolin-8-yl)butane-1,4-diol

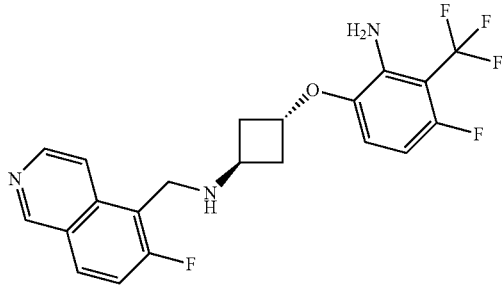

3-fluoro-6-((1r,3r)-3-(((6-fluoroisoquinolin-5-yl)methyl)amino)
cyclobutoxy)-2-(trifluoromethyl)aniline

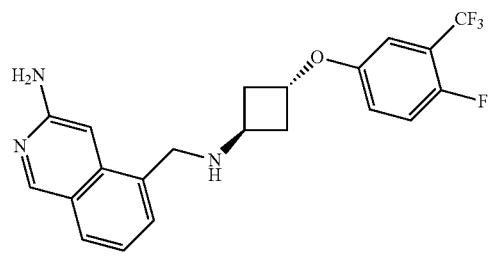

5-((((1r,3r)-3-(4-fluoro-3-(trifluoromethyl)phenoxy)cyclobutyl)amino)
methyl)isoquinolin-3-amine

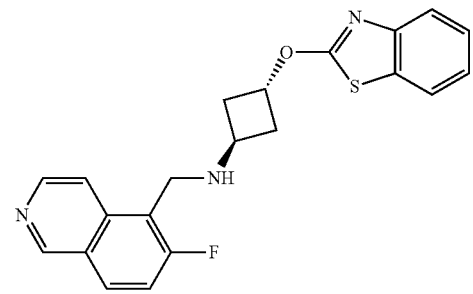

(1r,3r)-3-(benzo[d]thiazol-2-yloxy)-N-((6-fluoroisoquinolin-5-yl)
methyl)cyclobutan-1-amine

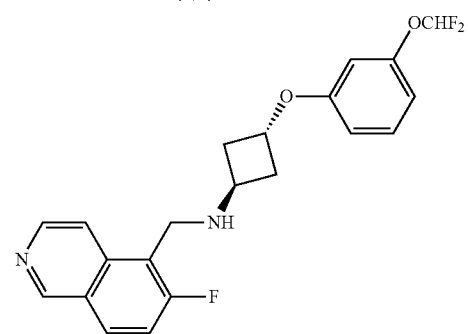

(1r,3r)-3-(3-difluoromethoxy)phenoxy)-N-((6-fluoroisoquinolin-
5-yl)methyl)cyclobutan-1-amine

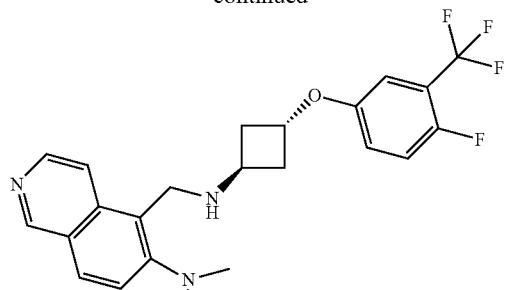

5-((((1r,3r)-3-(4-fluoro-3-(trifluoromethyl)ohenoxy)cyclobutyl)
amino)methyl)-N,N-dimethylisoquinolin-6-amine

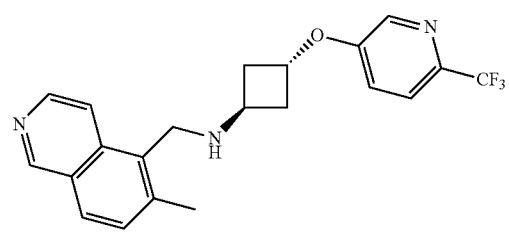

(1r,3r)-N-((6-methylisoquinolin-5-yl)methyl)-3-((6-(trifluoromethyl)
pyridin-3-yl)oxy)cyclobutan-1-amine

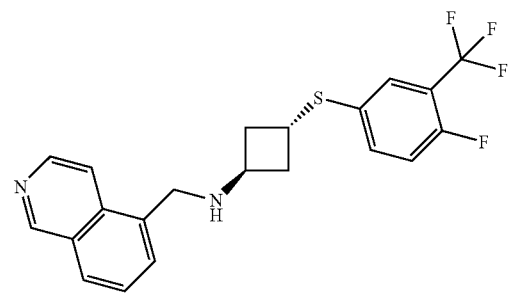

(1r,3r)-3-((4-fluoro-3-(trifluoromethyl)phenyl)thio)-N-(isoquinolin-
5-ylmethyl)cyclobutan-1-amine

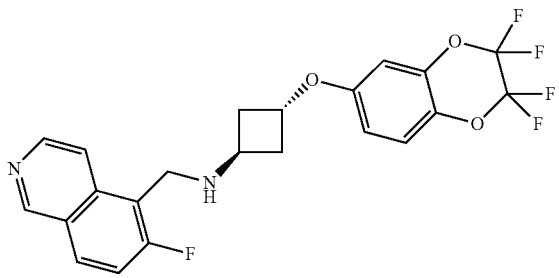

(1r,3r)-N-((6-fluoroisoquinolin-5-yl)methyl)-3-((2,2,3,3-
tetrafluoro-2,3-dihydrobenzo[b][1,4]dioxin-6-yl)oxy)cyclobutan-
1-amine

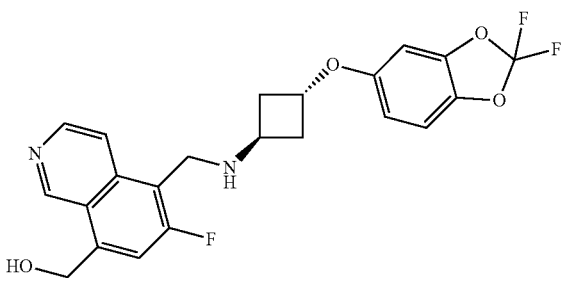

(5-((((1r,3r)-3-((2,2-difluorobenzo[d][1,3]dioxol-5-yl)oxy)
cyclobutyl)amino)methyl)-6-fluoroisoquinolin-8-yl)methanol

37
-continued

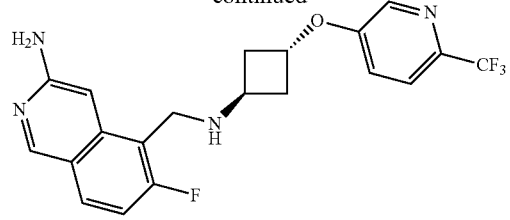

6-fluoro-5-((((1r,3r)-3-((6-(trifluoromethyl)pyridin-3-yl)oxy)cyclobutyl)
amino)methyl)isoquinolin-3-amine

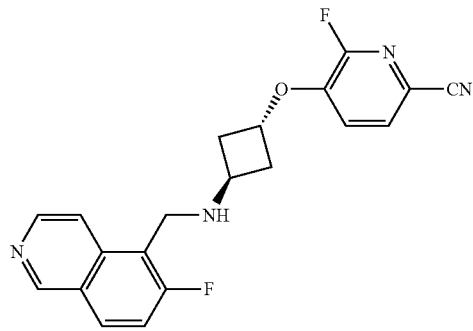

6-fluoro-5-(((1r,3r)-3-(((6-fluoroisoquinolin-5-yl)methyl)
amino)cyclobutoxy)picolinonitrile

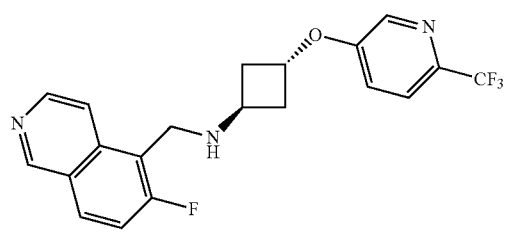

(1r,3r)-N-((6-fluoroisoquinolin-5-yl)methyl)-3-((6-
(trifluoromethyl)pyridin-3-yl)ooxy)cyclobutan-1-amine

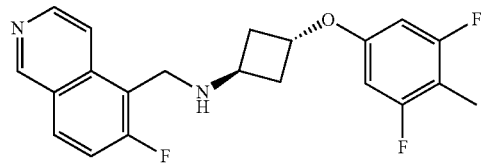

(1r,3r)-3-(3,5-difluoro-4-methylphenoxy)-N-((6-
fluoroisoquinolin-5-yl)methyl)cyclobutan-1-amine

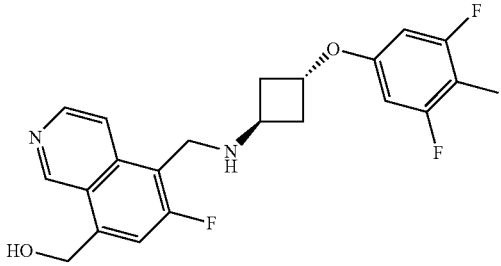

(5-((((1r,3r)-3-(3,5-difluoro-4-methylphenoxy)cyclobutyl)amino)
methyl)-6-fluoroisoquinolin-8-yl)methanol

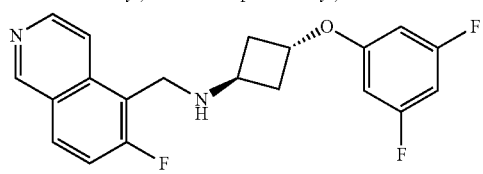

(1r,3r)-3-(3,5-difluorophenoxy)-N-((6-fluoroisoquinolin-5-yl)
methyl)cyclobutan-1-amine

38
-continued

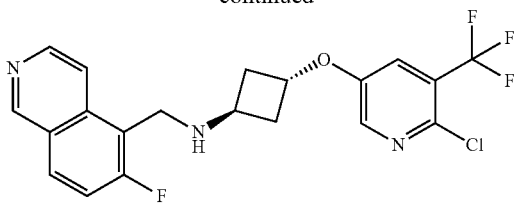

(1r,3r)-3-((6-chloro-5-(trifluoromethyl)pyridin-3-yl)oxy)-N-
((6-fluoroisoquinolin-5-yl)methyl)cyclobutan-1-amine

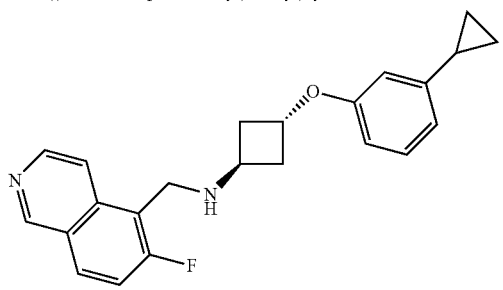

(1r,3r)-3-(3-cyclopropylphenoxy)-N-((6-fluoroisoquinolin-5-yl)
methyl)cyclobutan-1-amine

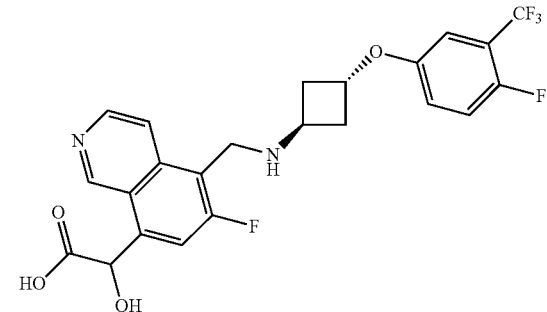

2-(6-fluoro-5-((((1r,3r)-3-(4-fluoro-3-(trifluoromethyl)phenoxy)
cyclobutyl)amino)methyl)isoquinolin-8-yl)-2-hydroxyacetic acid

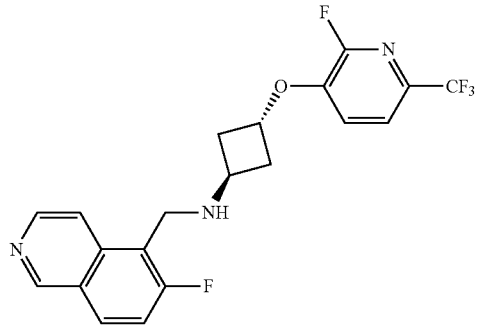

(1r,3r)-3-((2-fluoro-6-(trifluoromethyl)pyridin-3-yl)oxy)-N-
((6-fluoroisoquinolin-5-yl)methyl)cyclobutan-1-amine

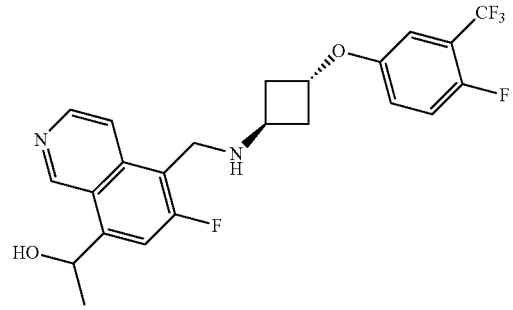

1-(6-fluoro-5-((((1r,3r)-3-(4-fluoro-3-(trifluoromethyl)phenoxy)
cyclobutyl)amino)methyl)isoquinolin-8-yl)ethan-1-ol -continued

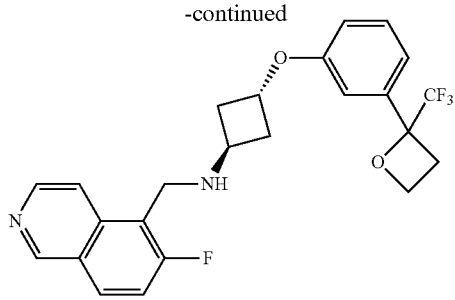

(1r,3r)-N-((6-fluoroisoquinolin-5-yl)methyl)-3-(3-(2-(trifluoromethyl)oxetan-2-yl)phenoxy)cyclobutan-1-amine

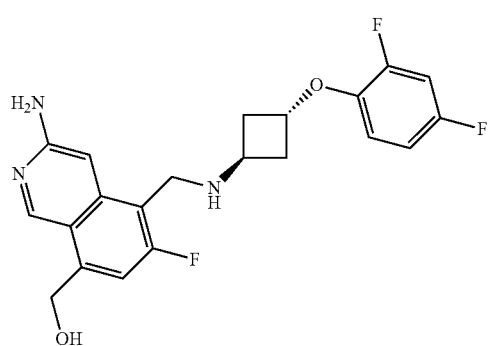

(3-amino-5-(((((1r,3r)-3-(2,4-difluorophenoxy)cyclobutyl)amino)methyl)-6-fluoroisoquinolin-8-yl)methanol

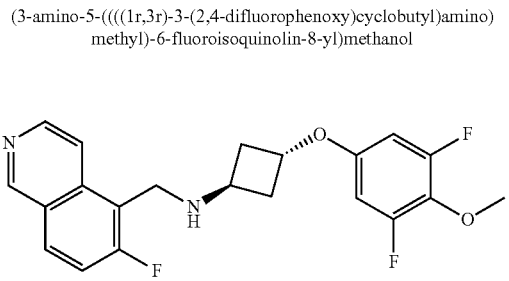

(1r,3r)-3-(3,5-difluoro-4-methoxyphenoxy)-N-((6-fluoroisoquinolin-5-yl)methyl)cyclobutan-1-amine

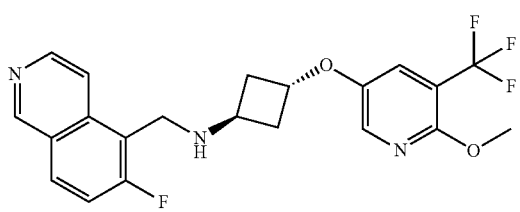

(1r,3r)-N-((6-fluoroisoquinolin-5-yl)methyl)-3-((6-methoxy-5-(trifluoromethyl)pyridin-3-yl)oxy)cyclobutan-1-amine

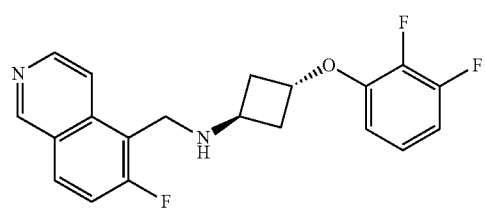

(1r,3r)-3-(2,3-difluorophenoxy)-N-((6-fluoroisoquinolin-5-yl)methyl)cyclobutan-1-amine

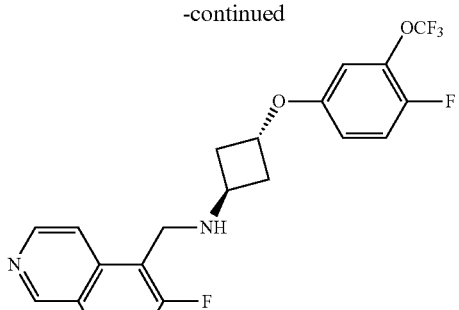

(1r,3r)-3-(4-fluoro-3-(trifluoromethoxy)phenoxy)-N-((6-fluoroisoquinolin-5-yl)methyl)cyclobutan-1-amine

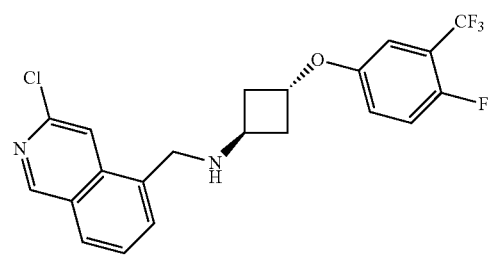

(1r,3r)-N-((3-chloroisoquinolin-5-yl)methyl)3-3(4-fluoro-3-(trifluoromethyl)phenoxy)cyclobutan-1-amine

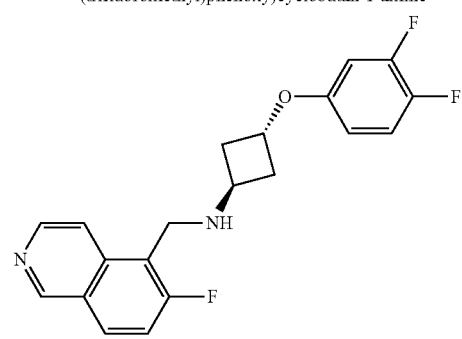

(1r,3r)-3-((3,4-difluorobenzyl)oxy)-N-((6-fluoroisoquinolin-5-yl)methyl)cyclobutan-1-amine

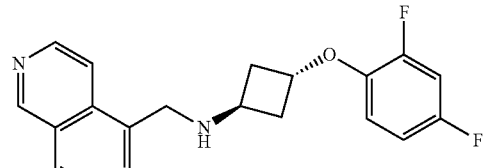

(1r,3r)-3-(2,4-difluorophenoxy)-N-((6-fluoroisoquinolin-5-yl)methyl)cyclobutan-1-amine

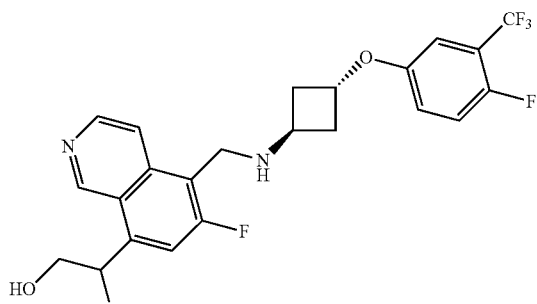

1-(6-fluoro-5-(((((1r,3r)-3-(4-fluoro-3-(trifluoromethyl)phenoxy)cyclobutyl)amino)methyl)isoquinolin-8-yl)ethane-1,2-diol

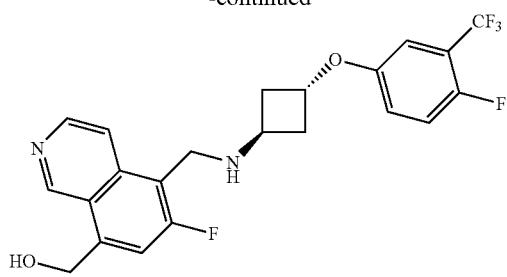

(6-fluoro-5-((((1r,3r)-3-(4-fluoro-3-(trifluoromethyl)phenoxy)
cyclobutyl)amino)methyl)isoquinolin-8-yl)methanol

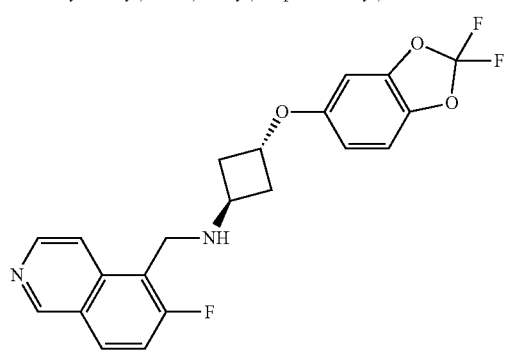

(1r,3r)-3-((2,2-difluorobenzo[d][1,3]dioxol-5-yl)oxy)-N-((6-
fluoroisoquinolin-5-yl)methyl)cyclobutan-1-amine

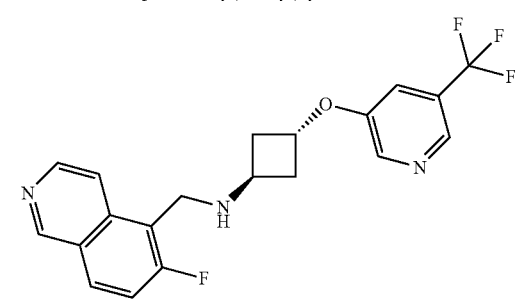

(1r,3r)-N-((6-fluoroisoquinolin-5-yl)methyl)-3-((5-
(trifluoromethyl)pyridin-3-yl)oxy)cyclobutan-1-amine

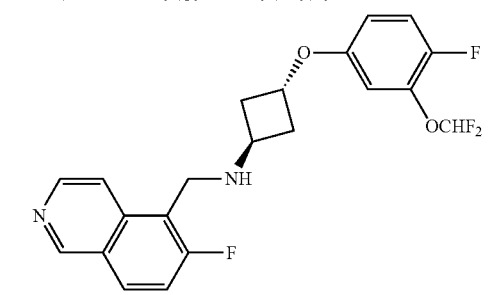

(1r,3r)-3-(3-(difluoromethoxy)-4-fluorophenoxy)-N-
((6-fluoroisoquinolin-5-yl)methyl)cyclobutan-1-amine

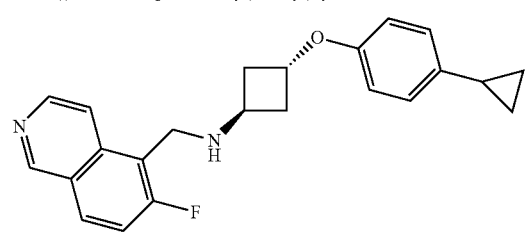

(1r,3r)-3-(4-cyclopropylphenoxy)-N-((6-
fluoroisoquinolin-5-yl)methyl)cyclobutan-1-amine

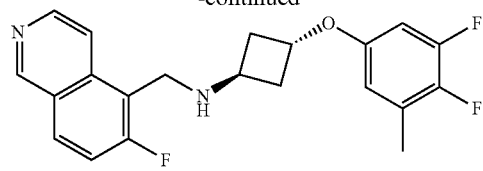

(1r,3r)-3-(3,4-difluoro-5-methylphenoxy)-N-((6-
fluoroisoquinolin-5-yl)methyl)cyclobutan-1-amine

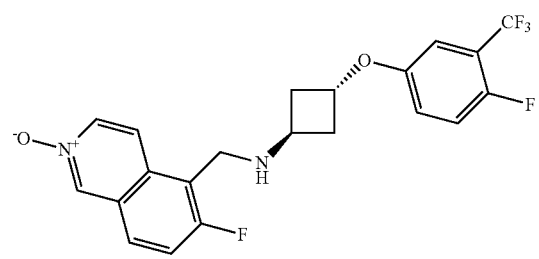

6-fluoro-5-((((1r,3r)-3-(4-fluoro-3-(trifluoromethyl)phenoxy)
cyclobutyl)amino)methyl)isoquinoline 2-oxide

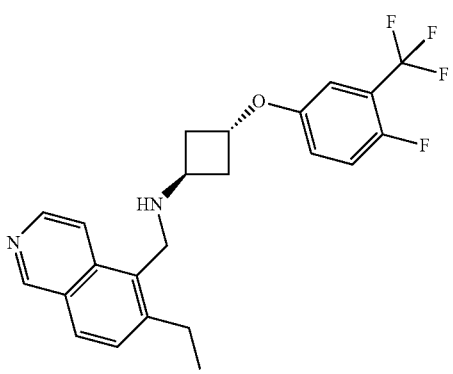

(1r,3r)-N-((6-ethylisoquinolin-5-yl)methyl)-3-(4-fluoro-
3-(trifluoromethyl)phenoxy)cyclobutan-1-amine

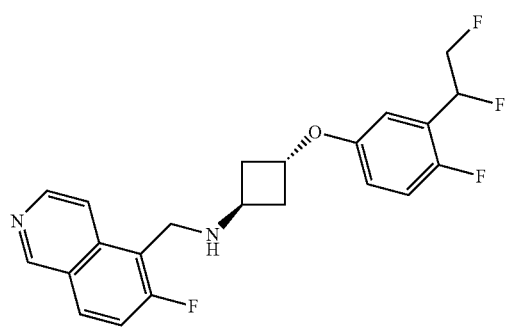

(1r,3r)-3-(3-(1,2-difluoroethyl)-4-fluorophenoxy)-N-
((6-fluoroisoquinolin-5-yl)methyl)cyclobutan-1-amine

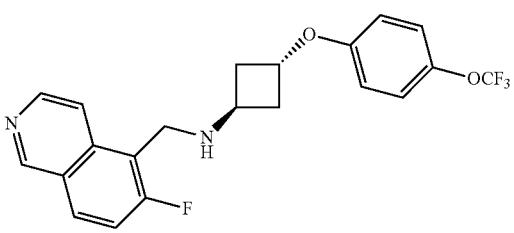

(1r,3r)-N-((6-fluoroisoquinolin-5-yl)methyl)-3-(4-
(trifluoromethoxy)phenoxy)cyclobutan-1-amine -continued

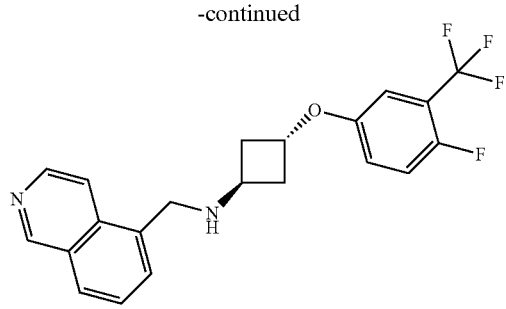

(1r,3r)-3-(4-fluoro-3-(trifluoromethyl)phenoxy)-N-
(isoquinolin-5-ylmethyl)cyclobutan-1-amine

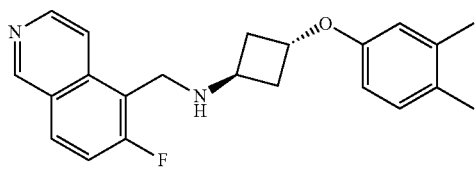

(1r,3r)-3-(3,4-dimethylphenoxy)-N-((6-fluoroisoquinolin-5-yl)
methyl)cyclobutan-1-amine

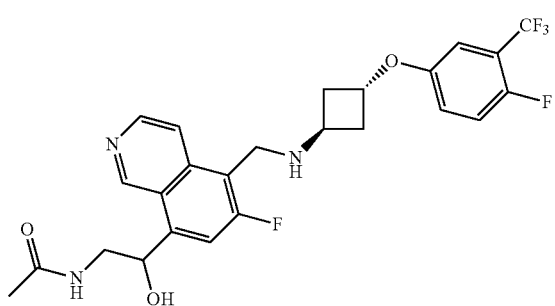

N-(2-(6-fluoro-5-((((1r,3r)-3-(4-fluoro-3-(trifluoromethyl)phenoxy)
cyclobutyl)amino)methyl)isoquinolin-8-yl)-2-hydroxyethyl)acetamide

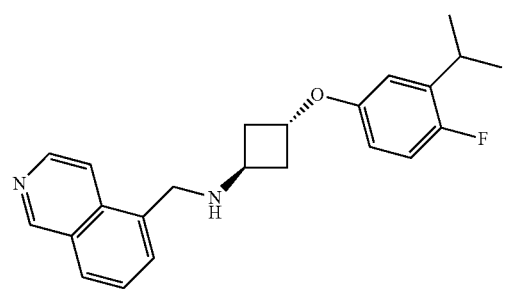

(1r,3r)-3-(4-fluoro-3-isopropylphenoxy)-N-(isoquinolin-
5-ylmethyl)cyclobutan-1-amine

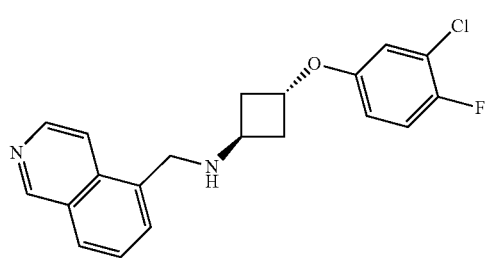

(1r,3r)-3-(3-chloro-4-fluorophenoxy)-N-(isoquinolin-5-
ylmethyl)cyclobutan-1-amine -continued

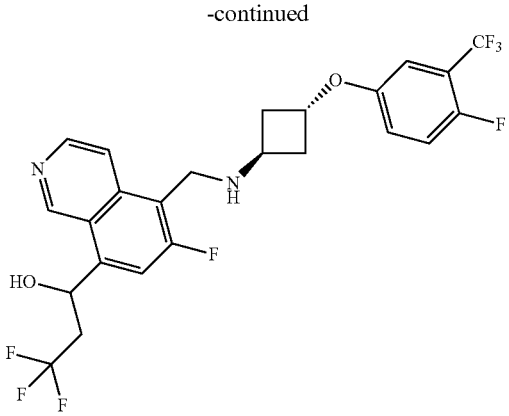

3,3,3-trifluoro-1-(6-fluoro-5-((((1r,3r)-3-(4-fluoro-3-
(trifluoromethyl)phenoxy)cyclobutyl)amino)methyl)
isoquinolin-8-yl)propan-1-ol

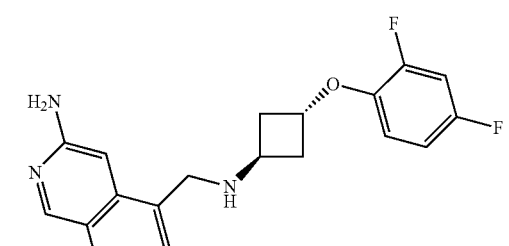

5-((((1r,3r)-3-(2,4-diffluorophenoxy)cyclobutyl)amino)methyl)-
6-fluoroisoquinolin-3-amine

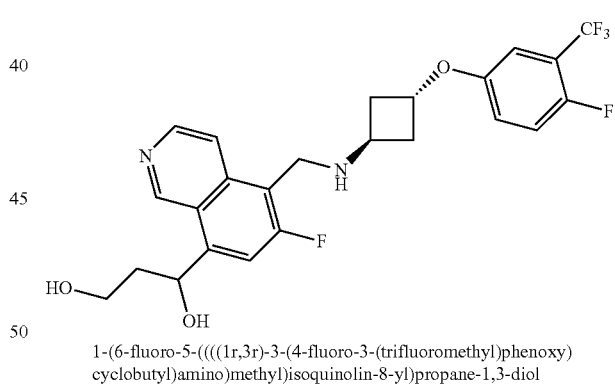

1-(6-fluoro-5-((((1r,3r)-3-(4-fluoro-3-(trifluoromethyl)phenoxy)
cyclobutyl)amino)methyl)isoquinolin-8-yl)propane-1,3-diol

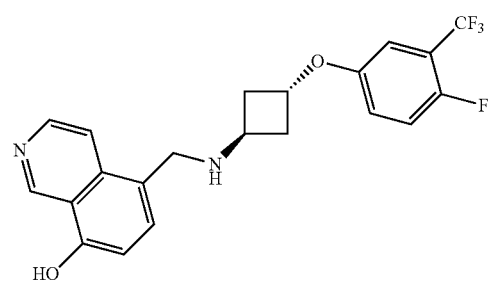

5-((((1r,3r)-3-(4-fluoro-3-(trifluoromethyl)phenoxy)
cyclobutyl)amino)methyl)isoquinolin-8-ol -continued

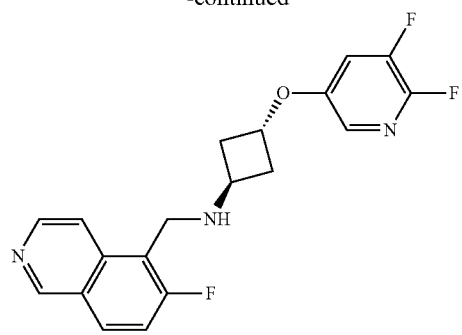

(1r,3r)-3-((5,6-difluoropyridin-3-yl)oxy)-N-((6-fluoroisoquinolin-5-yl)methyl)cyclobutan-1-amine

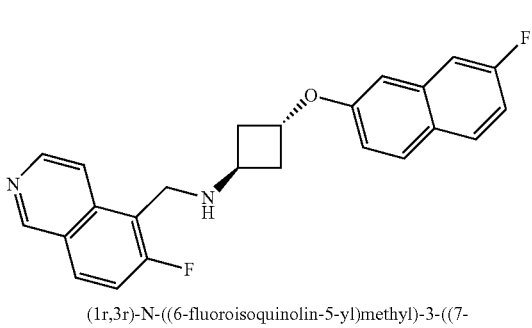

(1r,3r)-N-((6-fluoroisoquinolin-5-yl)methyl)-3-((7-fluoronaphthalen-2-yl)oxy)cyclobutan-1-amine

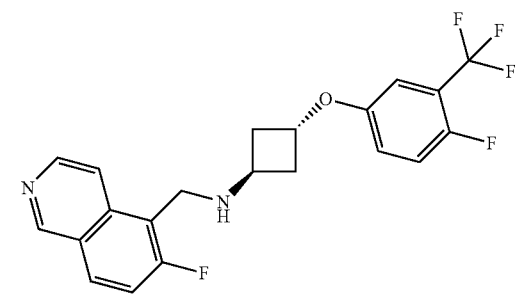

(1r,3r)-3-(4-fluoro-3-(trifluoromethyl)phenoxy)-N-((6-fluoroisoquinolin-5-yl)methyl)cyclobutan-1-amine

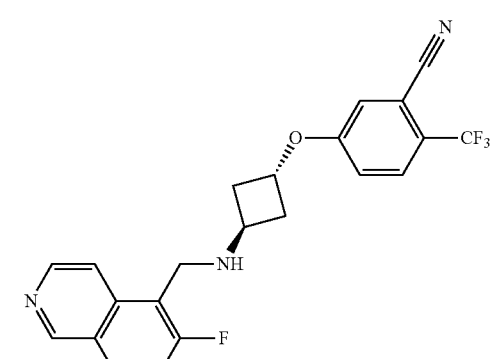

5-((1r,3r)-3-(((6-fluoroisoquinolin-5-yl)methyl)amino)cyclobutoxy)-2-(trifluoromethyl)benzonitrile -continued

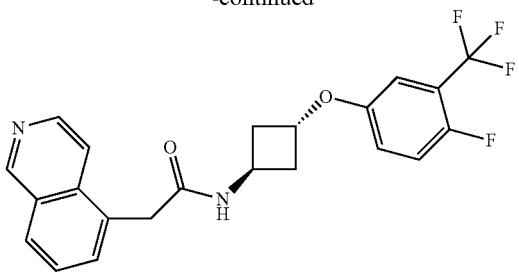

N-((1r,3r)-3-(4-fluoro-3-(trifluoromethyl)phenoxy)cyclobutyl)-2-(isoquinolin-5-yl)acetamide

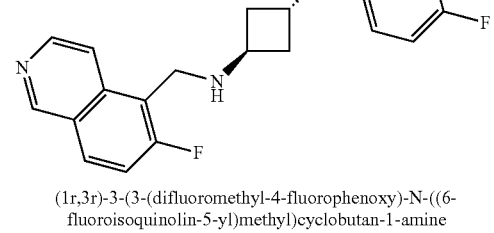

(1r,3r)-3-(3-(difluoromethyl-4-fluorophenoxy)-N-((6-fluoroisoquinolin-5-yl)methyl)cyclobutan-1-amine

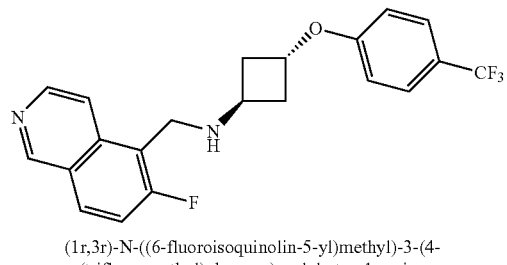

(1r,3r)-N-((6-fluoroisoquinolin-5-yl)methyl)-3-(4-(trifluoromethyl)phenoxy)cyclobutan-1-amine

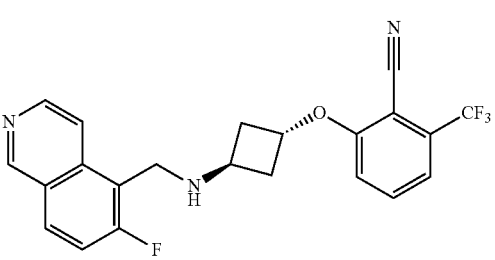

2-((1r,3r)-3-(((6-fluoroisoquinolin-5-yl)methyl)amino)cyclobutoxy)-6-(trifluoromethyl)benzonitrile

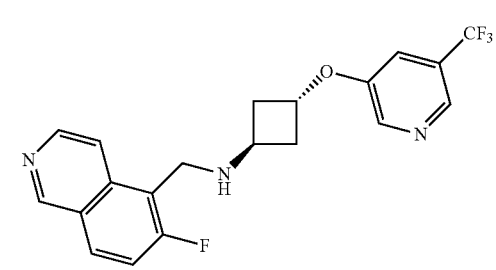

(1r,3r)-N-((6-fluoroisoquinolin-5-yl)methyl)-3-((2-(trifluoromethyl)pyridin-4-yl)oxy)cyclobutan-1-amine -continued

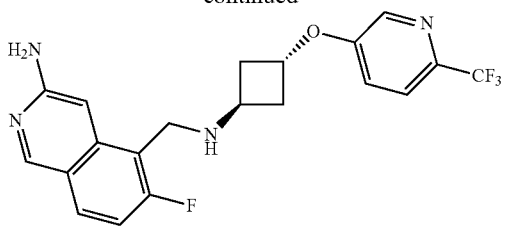

5-((((1r,3r)-3-((6-(trifluoromethyl)pyridin-3-yl)oxy)cyclobutyl)amino)methyl)isoquinolin-3-amine

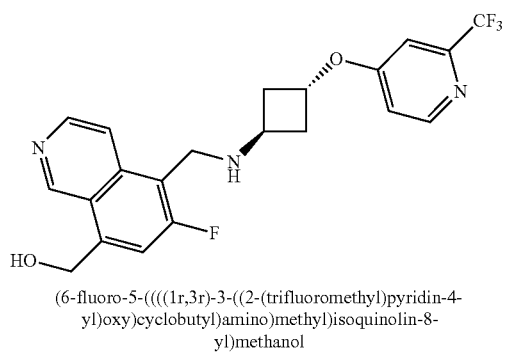

(6-fluoro-5-((((1r,3r)-3-((2-(trifluoromethyl)pyridin-4-yl)oxy)cyclobutyl)amino)methyl)isoquinolin-8-yl)methanol

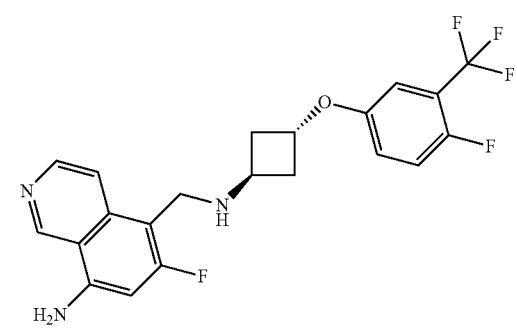

6-fluoro-5-((((1r,3r)-3-(4-fluoro-3-(trifluoromethyl)phenoxy)cyclobutyl)amino)methyl)isoquinolin-8-amine

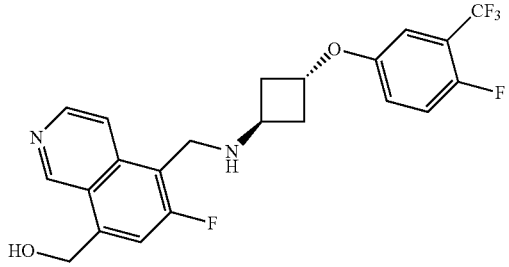

(6-fluoro-5-((((1s,3s)-3-(4-fluoro-3-(trifluoromethyl)phenoxy)cyclobutyl)amino)methyl)isoquinolin-8-yl)methanol

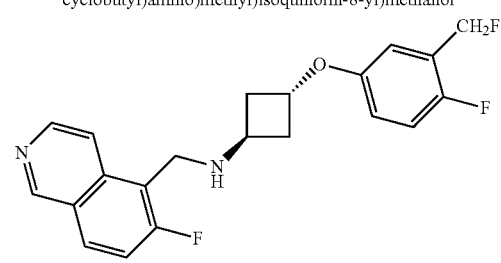

(1r,3r)-3-(4-fluoro-3-(fluoromethyl)phenoxy)-N-((6-fluoroisoquinolin-5-yl)methyl)cyclobutan-1-amine Embodiment 43. The compound of any of the preceding Embodiments, or a pharmaceutically acceptable salt thereof, wherein the pharmaceutically acceptable salt is an acid addition salt.

Embodiment 44. A pharmaceutical composition comprising a therapeutically effective amount of a compound of any one of Embodiments 1 to 43, or a pharmaceutically acceptable salt thereof, and a pharmaceutically acceptable carrier or excipient.

Embodiment 45. A method of treating or preventing a disease or disorder in a subject in need thereof, the method comprising administering to the subject a therapeutically effective amount of a compound of any one of Embodiments 1 to 43, or a pharmaceutically acceptable salt thereof.

Embodiment 46. A method of treating or preventing a disease or disorder mediated by TRPV1 in a subject in need thereof, the method comprising administering to the subject a therapeutically effective amount of a compound of any one of Embodiments 1 to 43, or a pharmaceutically acceptable salt thereof.

Embodiment 47. A method of treating or preventing pain in a subject in need thereof, the method comprising administering to the subject a therapeutically effective amount of a compound of any one of Embodiments 1 to 43, or a pharmaceutically acceptable salt thereof. The pain may be acute, such as pain caused after injury or surgery, or chronic. Examples of pain include, in particular, pain, e.g., bone and joint pain (osteoarthritis), cancer pain, myofascial pain (muscular injury, fibromyalgia) and perioperative pain (general surgery, gynecologic surgery). Other examples include chronic pain, especially inflammatory, e.g., chronic inflammatory pain. Additional examples of pain include pain in which TRPV1 activation plays a role or is implicated, and therefore susceptible to treatment by the compounds disclosed herein. Such conditions include chronic pain with an inflammatory component such as rheumatoid arthritis; bone and joint pain (osteoarthritis); post-surgical pain; musculoskeletal pain such as fibromyalgia; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, migraine, abdominal pain, gynaecological pain, such as dysmenorrhoea, and labour pain; pain associated with the urogenital tract such as cystitis and vulvadynia; inflammatory skin disorders, for example psoriasis and eczema, or itch of non-specific origin; chronic pain associated with nerve injury and/or diseases affecting the nervous system, such as neuropathic pain associated with post-herpetic neuralgia, diabetic neuropathy, chemotherapy-induced neuropathy, amputations ("phantom limb pain"), nerve entrapment and brachial plexus avulsions, low back pain, sciatica and ankylosing spondylitis, reflex sympathetic dystrophy and other chronic nerve injuries; complex regional pain syndromes; central nervous system pain, such as pain due to spinal cord or brain stem damage, or stroke; gout; scar pain; pain associated with carcinoma, often referred to as cancer pain.

Embodiment 48. A method of treating or preventing inflammatory diseases in a subject in need thereof, the method comprising administering to the subject a therapeutically effective amount of a compound of any one of Embodiments 1 to 43, or a pharmaceutically acceptable salt thereof. Exemplary inflammatory diseases include inflammatory airways disease, e.g., chronic obstructive pulmonary disease (COPD), or asthma; cough; urinary incontinence;

migraine; visceral disorders, e.g., inflammatory bowel disease; rhinitis; cystitis, e.g. interstitial cystitis; pancreatitis; uveitis; inflammatory skin disorders such as eczema and psoriasis; rheumatoid arthritis; inflammatory disorders of the gut, e.g., irritable bowel syndrome; Crohn's disease; ulcerative colitis; and cystitis, e.g., interstitial cystitis, nephritis and uveitis.

Embodiment 49. A method of relaxing smooth muscle in a subject in need thereof, the method comprising administering to the subject a therapeutically effective amount of a compound of any one of Embodiments 1 to 43, or a pharmaceutically acceptable salt thereof. Examples of diseases or conditions requiring smooth muscle relaxants include, e.g., treatment of spasm of the gastrointestinal tract or uterus, e.g., in the therapy of Crohn's disease, ulcerative colitis or pancreatitis.

Embodiment 50. A method of treating or preventing airway hyperreactivity or treating or preventing inflammatory events associated with airways disease, the method comprising administering to the subject a therapeutically effective amount of a compound of any one of Embodiments 1 to 43, or a pharmaceutically acceptable salt thereof. Exemplary conditions include asthma, restriction or reversal of airways hyperreactivity in asthma. Other conditions include both intrinsic and, especially, extrinsic asthma, such as allergic asthma, as well as, e.g., exercise induced asthma, occupational asthma, asthma induced following bacterial infection, other non-allergic asthmas and "wheezy-infant syndrome". Efficacy in the treatment of asthma will be evidenced by reduced frequency or severity of symptomatic attack, e.g., of acute asthmatic or bronchoconstrictor attack and by reduced requirement for other, symptomatic therapy, e.g., anti-inflammatory, e.g., corticosteroid; or bronchodilator, e.g., β2 adrenergic, therapy. Other inflammatory or obstructive airways diseases include pneumoconiosis (an inflammatory, commonly occupational, disease of the lungs, frequently accompanied by repeated inhalation of dusts) of whatever type or genesis including, e.g., aluminosis, anthracosis, asbestosis, chalicosis, ptilosis, siderosis, silicosis, tabacosis and, in particular, byssinosis. Further inflammatory or obstructive airways diseases and conditions include adult respiratory distress syndrome (ARDS), chronic obstructive pulmonary or airways disease (COPD or COAD), and bronchitis, allergic and vasomotor rhinitis.

Embodiment 51. A method of treating or preventing septic shock in a subject in need thereof, the method comprising administering to the subject a therapeutically effective amount of a compound of any one of Embodiments 1 to 43, or a pharmaceutically acceptable salt thereof. Exemplary conditions include septic shock, e.g., as anti-hypovolaemic and/or anti-hypotensive agents; in the treatment of inflammatory bowel disease; cerebral oedema; headache;

Embodiment 52. A method of treating an ocular disease or disorder in a subject in need thereof, the method comprising administering to the subject a therapeutically effective amount of a compound of any one of Embodiments 1 to 43, or a pharmaceutically acceptable salt thereof.

Embodiment 53. A method of treating an ocular surface disorder in a subject in need thereof, the method comprising administering to the subject a therapeutically effective amount of a compound of any one of Embodiments 1 to 43, or a pharmaceutically acceptable salt thereof.

Embodiment 54. The method of Embodiment 53, wherein the ocular surface disorder is selected from chronic ocular surface pain (COSP), dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathies (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, and patients recovering from neurotrophic keratitis.

Embodiment 55. The method of Embodiment 54, wherein the ocular surface disorder is dry eye disease.

Embodiment 56. A method of treating or reducing ocular surface pain (e.g., corneal induced pain) in a subject in need thereof, the method comprising administering to the subject a therapeutically effective amount of a compound of any one of Embodiments 1 to 43, or a pharmaceutically acceptable salt thereof.

Embodiment 57. The method of Embodiment 56, wherein the administration of a compound of any one of Embodiments 1 to 43, or a pharmaceutically acceptable salt thereof results in a reduction in the subject's ocular pain, compared to a placebo. In some embodiments, the reduction in the subjects ocular pain is at least about 10%, at least about 15%, at least about 20%, or at least about 25%, compared to a placebo, when measured on a pain scale, for example, the VAS or the OPAS.

Embodiment 58. A method of treating or reducing corneal induced pain in a subject in need thereof, the method comprising administering to the subject a therapeutically effective amount of a compound of any one of Embodiments 1 to 43, or a pharmaceutically acceptable salt thereof.

Embodiment 59. The method of Embodiment 58, wherein the administration of a compound of any one of Embodiments 1 to 43, or a pharmaceutically acceptable salt thereof results in a reduction in the subject's ocular pain, compared to a placebo. In some embodiments, the reduction in the subjects ocular pain is at least about 10%, at least about 15%, at least about 20%, or at least about 25%, compared to a placebo, when measured on a pain scale, for example, the VAS or the OPAS.

Embodiment 60. The method of Embodiments 56 to 59, wherein the ocular surface pain or corneal induced pain is episodic, i.e., acute.

Embodiment 61. The method of Embodiments 56 to 59, wherein the ocular surface pain or corneal induced pain is chronic.

Embodiment 62. The method according to any of Embodiments 56 to 61, wherein the ocular surface pain or corneal induced pain is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

Embodiment 63. The method according to any of Embodiments 56 to 62, wherein the ocular surface pain or corneal induced pain is associated with dry eye disease or Sjogren's Syndrome.

Embodiment 64. The method according to any of Embodiments 56 to 63, wherein the subject suffers from ocular pain persisting for at least three months after photorefractive keratectomy (PRK) surgery or laser-assisted in situ keratomileusis (LASIK) surgery.

Embodiment 65. The method according to any of Embodiments 56 to 63, wherein the subject suffers from conjunctivitis, subconjunctival hemorrhage, subconjunctival scarring, conjunctival membranes, conjunctival ulceration, superficial punctate epithelial erosions, epithelial defects, lid margin ulceration, lid margin keratinization, symblepharon, ankyloblepharon, trichiasis, anterior blepharitis, punctal auto-occlusion, meibomian gland disease, corneal opacification, dry eye, districhiasis, limbal stem cell failure, or corneal vascularization.

Embodiment 66. A method of treating ocular hyperemia in a subject in need thereof, the method comprising administering to the subject a therapeutically effective amount of a compound of any one of Embodiments 1 to 43, or a pharmaceutically acceptable salt thereof.

Embodiment 67. The method of Embodiment 66, wherein the ocular hyperemia is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

Embodiment 68. The method of Embodiment 66 or 67, wherein the ocular hyperemia is associated with dry eye disease.

Embodiment 69. The method of any of Embodiments 66 to 68, wherein the ocular hyperemia persists for at least three months after photorefractive keratectomy (PRK) surgery or laser-assisted in situ keratomileusis (LASIK) surgery.

Embodiment 70. A compound of any of Embodiments 1 to 43 or a pharmaceutically acceptable salt thereof, for use in the treatment or reduction of ocular surface pain (e.g., corneal induced pain).

Embodiment 71. The compound for use according to Embodiment 70, wherein the compound of any one of Embodiments 1 to 43, or a pharmaceutically acceptable salt thereof results in a reduction in the subject's ocular pain, compared to a placebo. In some embodiments, the reduction in the subjects ocular pain is at least about 10%, at least about 15%, at least about 20%, or at least about 25%, compared to a placebo, when measured on a pain scale, for example, the VAS or the OPAS.

Embodiment 72. The compound for use according to Embodiments 70 or 71, or a pharmaceutically acceptable salt thereof, wherein the ocular surface pain is episodic, i.e., acute.

Embodiment 73. The compound for use according to Embodiments 70 or 71, or a pharmaceutically acceptable salt thereof, wherein the ocular surface pain is chronic. For example, the pain persists for at least 12 weeks, or at least 3 months, or at least 2 months, or at least 1 month.

Embodiment 74. The compound for use according to any of Embodiments 70 to 73, or a pharmaceutically acceptable salt thereof, wherein the ocular surface pain is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

Embodiment 75. The compound for use according to any of Embodiments 70 to 74, or a pharmaceutically acceptable salt thereof, wherein the ocular surface pain is associated with dry eye disease or Sjogren's Syndrome.

Embodiment 76. A compound of any of Embodiments 1 to 43 or a pharmaceutically acceptable salt thereof, for use in the treatment or reduction of ocular hyperemia.

Embodiment 77. The compound for use according to any one of Embodiments 1 to 43, or a pharmaceutically acceptable salt, wherein the administration of the compound results in reduced grade 1, grade 2, grade 3, or grade 4 hyperemia compared to placebo. In some embodiments, the administration results in a reduction in ocular hyperemia score of at least about 1, at least about 2, at least about 3, at least about 4, or at least about 5, on the McMonnies scale.

Embodiment 78. The compound for use according to Embodiment 76 or 77, or a pharmaceutically acceptable salt thereof, wherein the ocular hyperemia is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

Embodiment 79. The compound for use according to Embodiment 76 or 77, or a pharmaceutically acceptable salt thereof, wherein the ocular hyperemia is associated with dry eye disease.

Embodiment 80. The compound for use according to any of Embodiments 76 to 78, wherein the ocular hyperemia persists for at least three months after photorefractive keratectomy (PRK) surgery or laser-assisted in situ keratomileusis (LASIK) surgery.

Embodiment 81. A compound of any of Embodiments 1 to 43 or a pharmaceutically acceptable salt thereof, for use in the treatment of an ocular surface disorder.

Embodiment 82. The compound for use according to Embodiment 81, or a pharmaceutically acceptable salt thereof, wherein the ocular surface disorder is selected from chronic ocular surface pain (COSP), dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

Embodiment 83. The compound for use according to any of Embodiments 68 to 72, 77, 78, or a pharmaceutically acceptable salt thereof, wherein the subject suffers from ocular pain persisting for at least three months after photorefractive keratectomy (PRK) surgery or laser-assisted in situ keratomileusis (LASIK) surgery.

Embodiment 84. The compound for use according to any of Embodiments 70 to 75, 81, 82, or a pharmaceutically acceptable salt thereof, wherein the subject suffers from conjunctivitis, subconjunctival hemorrhage, subconjunctival scarring, conjunctival membranes, conjunctival ulceration, superficial punctate epithelial erosions, epithelial defects, lid margin ulceration, lid margin keratinization, symblepharon, ankyloblepharon, trichiasis, anterior blepharitis, punctal auto-occlusion, meibomian gland disease, corneal opacification, dry eye, districhiasis, limbal stem cell failure, or corneal vascularization.

Embodiment 85. Use of a compound of any one of Embodiments 1 to 43, or a pharmaceutically acceptable salt thereof, in the manufacture of a medicament for treating an ocular disease or disorder that is mediated by TRPV1.

Embodiment 86. Use according to Embodiment 85, wherein the ocular disease or disorder is selected from ocular surface disorder, ocular surface pain (e.g., corneal induced pain) and ocular hyperemia.

Embodiment 87. Use according to Embodiment 85 or 86, wherein the ocular surface disorder is selected from chronic ocular surface pain (COSP), dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, and patients recovering from neurotrophic keratitis.

Embodiment 88. Use according to Embodiments 86 or 87, wherein the ocular surface disorder is dry eye disease.

Embodiment 89. Use according to Embodiment 86, wherein ocular surface pain is pain is episodic, i.e., acute.

Embodiment 90. Use according to Embodiment 86, wherein ocular surface pain is pain is chronic.

Embodiment 91. Use according to any of Embodiments 86, 89 or 90, wherein the ocular surface pain is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

Embodiment 92. Use according to any of Embodiments 86, 89 to 91, wherein the ocular surface pain is associated with dry eye disease or Sjogren's Syndrome.

Embodiment 93. Use according to Embodiment 86, wherein the ocular hyperemia is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In particular embodiments, the ocular hyperemia is associated with dry eye disease. In some embodiments of the methods described herein, the ocular hyperemia persists for at least three months after photorefractive keratectomy (PRK) surgery or laser-assisted in situ keratomileusis (LASIK) surgery.

Embodiment 94. Use of a compound of any of Embodiments 1 to 43 or a pharmaceutically acceptable salt thereof, in the treatment of an ocular disease or disorder, e.g., mediated by TRPV1.

Embodiment 95. Use according to Embodiment 94, wherein the ocular disease or disorder is selected from ocular surface disorder, ocular surface pain (e.g., corneal induced pain) and ocular hyperemia.

Embodiment 96. Use according to Embodiment 94 or 95, wherein the ocular surface disorder is selected from chronic ocular surface pain (COSP), dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia and patients recovering from neurotrophic keratitis.

Embodiment 97. Use according to any of Embodiments 94 to 96, wherein the ocular surface disorder is dry eye disease.

Embodiment 98. Use according to Embodiment 95, wherein ocular surface pain is pain is episodic, i.e., acute.

Embodiment 99. Use according to Embodiment 95, wherein ocular surface pain is pain is chronic.

Embodiment 100. Use according to any of Embodiments 95, 98 or 99, wherein the ocular surface pain is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

Embodiment 101. Use according to any of Embodiments 95, 98 to 100, wherein the ocular surface pain is associated with dry eye disease or Sjogren's Syndrome.

Embodiment 102. Use according to Embodiment 95, wherein the ocular hyperemia is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

Embodiment 103. Use according to Embodiment 95 or 102, wherein the ocular hyperemia is associated with dry eye disease.

Embodiment 104. Use according to any of Embodiments 95, 102 or 103, wherein the ocular hyperemia persists for at least three months after photorefractive keratectomy (PRK) surgery or laser-assisted in situ keratomileusis (LASIK) surgery.

Embodiment 105. A pharmaceutical combination comprising a compound of any of Embodiments 1 to 43, or a pharmaceutically acceptable salt thereof, and one or more additional therapeutic agent(s).

Depending on the choice of the starting materials and procedures, the compounds can be present in the form of one of the possible isomers or as mixtures thereof, for example as pure optical isomers, or as isomer mixtures, such as racemates and diastereomeric mixtures, depending on the number of asymmetric centres. The disclosure is meant to include all such possible isomers, including racemic mixtures, enantiomerically enriched mixtures, diastereomeric mixtures and optically pure forms. Optically active (R)- and (S)-isomers may be prepared using chiral synthons or chiral reagents, or resolved using conventional techniques. If the compound contains a disubstituted or trisubstituted cycloalkyl, the cycloalkyl substituent(s) may have a cis- or trans-configuration. The disclosure includes cis and trans configurations of substituted cycloalkyl groups, e.g., cyclobutyl group, as well as mixtures thereof. All tautomeric forms are also intended to be included. In particular, where a heteroaryl ring containing N as a ring atom is 2-pyridone, for example, tautomers where the carbonyl is depicted as a hydroxy (e.g., 2-hydroxypyridine) are included.

Thus, it will be appreciated that in compounds of Formula (I), the cyclobutyl ring portion of the molecule can be in the cis or trans configuration. Using Formula (Ib) for illustrative purposes whereby the substituents at the 1- and 3-positions of the cyclobutyl ring have a trans configuration, it will be appreciated by the skilled person in the art that (Ib*) and (Ib**) are equivalent ways of drawing a molecule of Formula (Ib):

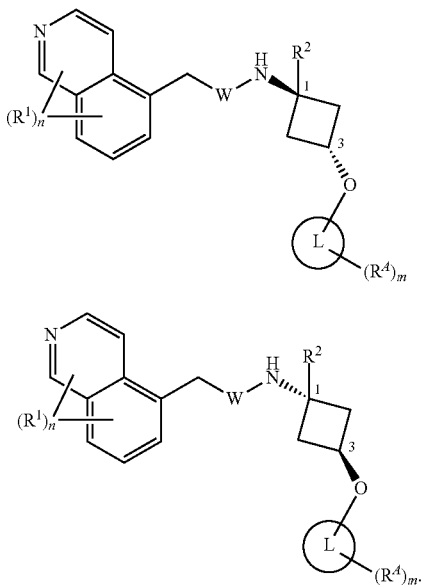

Separation of cis and trans isomers can be achieved according to methods known to a person of skill in the art, such as chromatographic methods, with tools such as HPLC (High Performance Liquid Chromatography), Thin Layer Chromatography, SFC (Supercritical Fluid Chromatography), GC (Gas Chromatography), or recrystallization techniques.

Pharmaceutically Acceptable Salts

As used herein, the terms "salt" or "salts" refers to an acid addition or base addition salt of a compound of the disclosure. "Salts" include in particular "pharmaceutically acceptable salts". The term "pharmaceutically acceptable salts" refers to salts that retain the biological effectiveness and properties of the compounds of this disclosure and, which typically are not biologically or otherwise undesirable. The compounds of the disclosure may be capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, formic acid, trifluoroacetic acid, and the like. In an embodiment, the compounds of Formula (I) are in HCl or formic acid salt form.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the disclosure provides compounds in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the disclosure provides compounds in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Isotopically Labelled Compounds

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, sulfur, fluorine, chlorine and iodine, such as $^{2}H$, $^{3}H$, $^{11}C$, $^{13}C$, $^{14}C$, $^{18}O$, $^{15}N$, $^{18}F$, $^{17}O$, $^{18}O$, $^{35}S$, $^{36}Cl$, $^{123}I$, $^{124}I$, $^{125}I$ respectively. The disclosure includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ compound may be particularly desirable for PET or SPECT studies. Isotopically-labeled compounds of formula (I), or sub-formulae thereof, can generally be prepared by conventional techniques known to those skilled in the art or by processes analogous to those described in the accompanying Examples and General Schemes using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I), or any of the sub-formulae thereof. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the disclosure include those wherein the solvent of crystallization may be isotopically substituted, e.g., $D_2O$, $d_6$-acetone, $d_6$-DMSO.

Compounds of the disclosure, i.e. compounds of formulae (I), (Ia), (Ib), (Ic), (Id), (Ie), (If), (Ig), (Ih), (Ii), (I-i), (I-ii), that contain groups capable of acting as donors and/or acceptors for hydrogen bonds may be capable of forming co-crystals with suitable co-crystal formers. These co-crystals may be prepared from compounds of formula (I), or sub-formulae thereof, by known co-crystal forming procedures. Such procedures include grinding, heating, co-subliming, co-melting, or contacting in solution compounds of (I), (Ia), (Ib), (Ic), (Id), (Ie), (If), (Ig), (Ih), (Ii), (I-i), (I-i), with the co-crystal former under crystallization conditions and isolating co-crystals thereby formed. Suitable co-crystal formers include those described in WO 2004/078163.

All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed.

Any asymmetric center (e.g., carbon or the like) of the compound(s) of the disclosure can be present in racemic or enantiomerically enriched, for example the (R)-, (S)- or (R,S)-configuration. In certain embodiments, for example, as a mixture of enantiomers, each asymmetric center is present in at least 10% enantiomeric excess, at least 20% enantiomeric excess, at least 30% enantiomeric excess, at least 40% enantiomeric excess, at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. In certain embodiments, for example, in enantiomerically enriched form, each asymmetric center is present in at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. Thus, compounds of the disclosure can be present in a racemic mixture or in enantiomerically enriched form or in an enantiopure form or as a mixture of diastereoisomers.

In an embodiment, there is provided a compound of formula (I), or a pharmaceutically acceptable salt thereof, present in at least 90% enantiomeric excess, at least 95% enantiomeric excess, or at least 99% enantiomeric excess.

In an embodiment, there is provided a compound of formula (I), or a pharmaceutically acceptable salt thereof, present in at least 90% diastereomeric excess, at least 95% diastereomeric excess, or at least 99% diastereomeric excess.

In one embodiment, the compound of formula (I) is a compound of formulae (I-i):

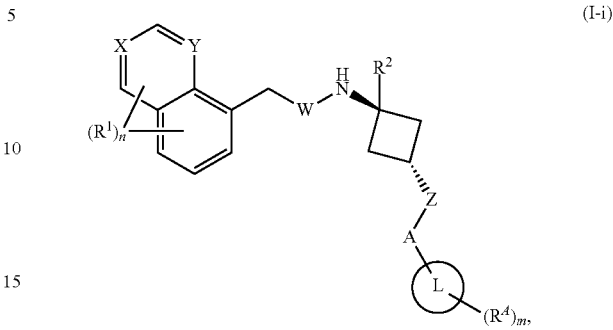

(I-i)

or a pharmaceutically acceptable salt thereof, wherein A, L, W, X, Y, Z, $R^1$, $R^2$, $R^4$, n and m are defined according to Embodiment 1. In particular, A, L, W, X, Y, Z, $R^1$, $R^2$, $R^4$, n and m may be defined according to any of Embodiments 2 to 39.

In another embodiment, the compound of formula (I) is a compound of formulae (I-i):

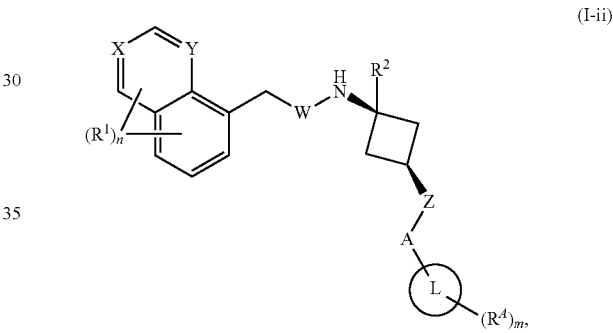

(I-ii)

or a pharmaceutically acceptable salt thereof, wherein A, L, W, X, Y, Z, $R^1$, $R^2$, $R^4$, n and m are defined according to Embodiment 1. In particular, A, L, W, X, Y, Z, $R^1$, $R^2$, $R^4$, n and m may be defined according to any of Embodiments 2 to 39.

In the formulae of the present application the term "⬈" on a C-sp³ indicates the absolute stereochemistry, either (R) or (S). In the formulae of the present application the term "⬈" on a C-sp³ indicates the absolute stereochemistry, either (R) or (S). In the formulae of the present application the term "╱" on a C-sp³ represents a covalent bond wherein the stereochemistry of the bond is not defined. This means that the term "╱" on a C-s comprises an (S) configuration or an (R) configuration of the respective chiral centre. Furthermore, mixtures may also be present. Therefore, mixtures of stereoisomers, e.g., mixtures of enantiomers, such as racemates, and/or mixtures of diastereoisomers are encompassed by the present disclosure.

For the avoidance of doubt, where compound structures are drawn with undefined stereochemistry with respect to any R group, as represented by a bond (╱), this means the asymmetric center has either a (R)- or (S)-configuration, or exists as a mixture thereof and stated as such.

For the avoidance of doubt, in any of the formulae of the present application when the $R^1$ group is shown with attachment to both rings, this means that the R¹ group(s) can be attached to either ring, or multiple R¹ groups attached to either ring.

Accordingly, as used herein a compound of the disclosure can be in the form of one of the possible stereoisomers, rotamers, atropisomers, tautomers or mixtures thereof, for example, as substantially pure geometric (cis or trans) stereoisomers, diastereomers, optical isomers, racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the disclosure or of intermediates can be resolved into the optical isomers (enantiomers) by known methods, e.g., by separation of the diastereomeric salts thereof, obtained with an optically active acid or base, and liberating the optically active acidic or basic compound. In particular, a basic moiety may thus be employed to resolve the compounds of the disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the disclosure or racemic intermediates can also be resolved by chiral chromatography, e.g., high pressure liquid chromatography (HPLC) using a chiral adsorbent.

Furthermore, the compounds of the disclosure, including their salts, can also be obtained in the form of their hydrates, or include other solvents used for their crystallization. The compounds of the disclosure may inherently or by design form solvates with pharmaceutically acceptable solvents (including water); therefore, it is intended that the disclosure embrace both solvated and unsolvated forms. The term "solvate" refers to a molecular complex of a compound of the disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The presence of solvates can be identified by a person of skill in the art with tools such as NMR.

The compounds of the disclosure, including salts, hydrates and solvates thereof, may inherently or by design form polymorphs.

Methods of Making

The compounds of the disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art.

Generally, the compounds of formula (I) can be prepared according to the Schemes provided infra.

Compounds provided herein can be prepared according to the following Examples. In the following Schemes, Y, R¹, L, R⁴, n and m are defined according to enumerated Embodiment 1. In an embodiment, Y, R¹, L, R⁴, n and m are defined according to any of enumerated Embodiments 2 to 21, 23, 26 to 30.

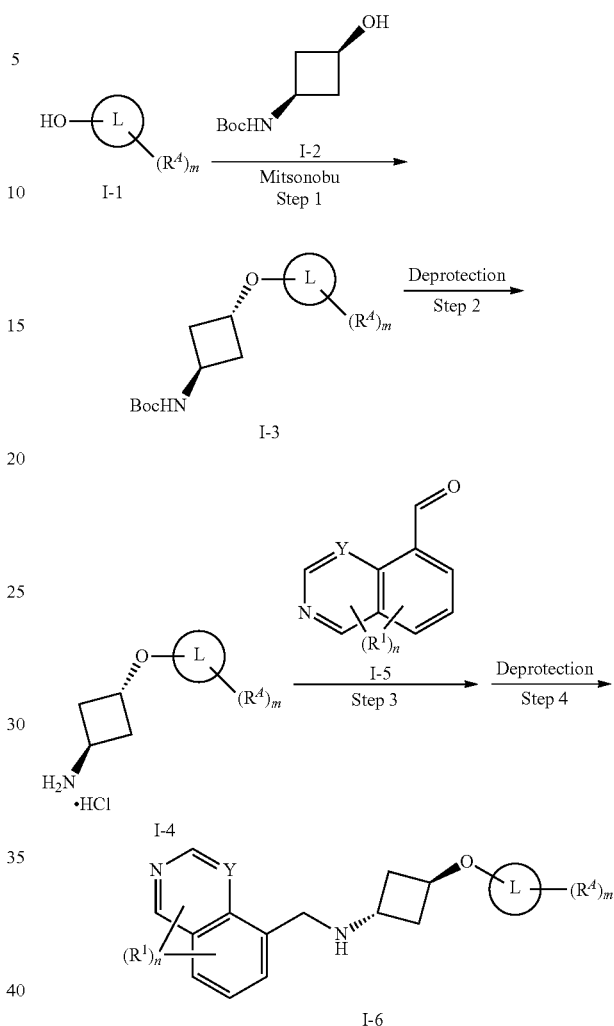

General Scheme 1

Condition 1:
NaBH₄, TEA, AcOH
MeOH, rt
Condition 2:
DIPEA, NaBH(OAc)₃, DCM, rt
Condition 3:
1. TEA/benzene, heat
2. NaBH₄ or Na(CN)BH₃, MeOH Starting material I-1 is either commercially available or can be made according to standard chemical transformations as described in the individual procedures or known in the art. I-1 is reacted with commercially available cyclobutyl alcohol I-2 under Mitsonobu type conditions, e.g., PPh₃, DIAD, in a solvent such as THF, to provide I-3, which is subsequently treated under acidic conditions, e.g., HCl/dioxane, to provide amine derivative I-4. The resultant amine product I-4 can undergo a reductive amination with the corresponding aldehyde I-5 to provide final compound I-6 after deprotection of any protected functional groups, e.g., present as a substituent of R¹ and/or R⁴, e.g., under acidic conditions with hydrochloric acid in dioxane or with a fluoride source such as tetra-n-butylammonium fluoride in THF.

Alternatively, compounds can be produced as shown in General Scheme 2 below.

General Scheme 2

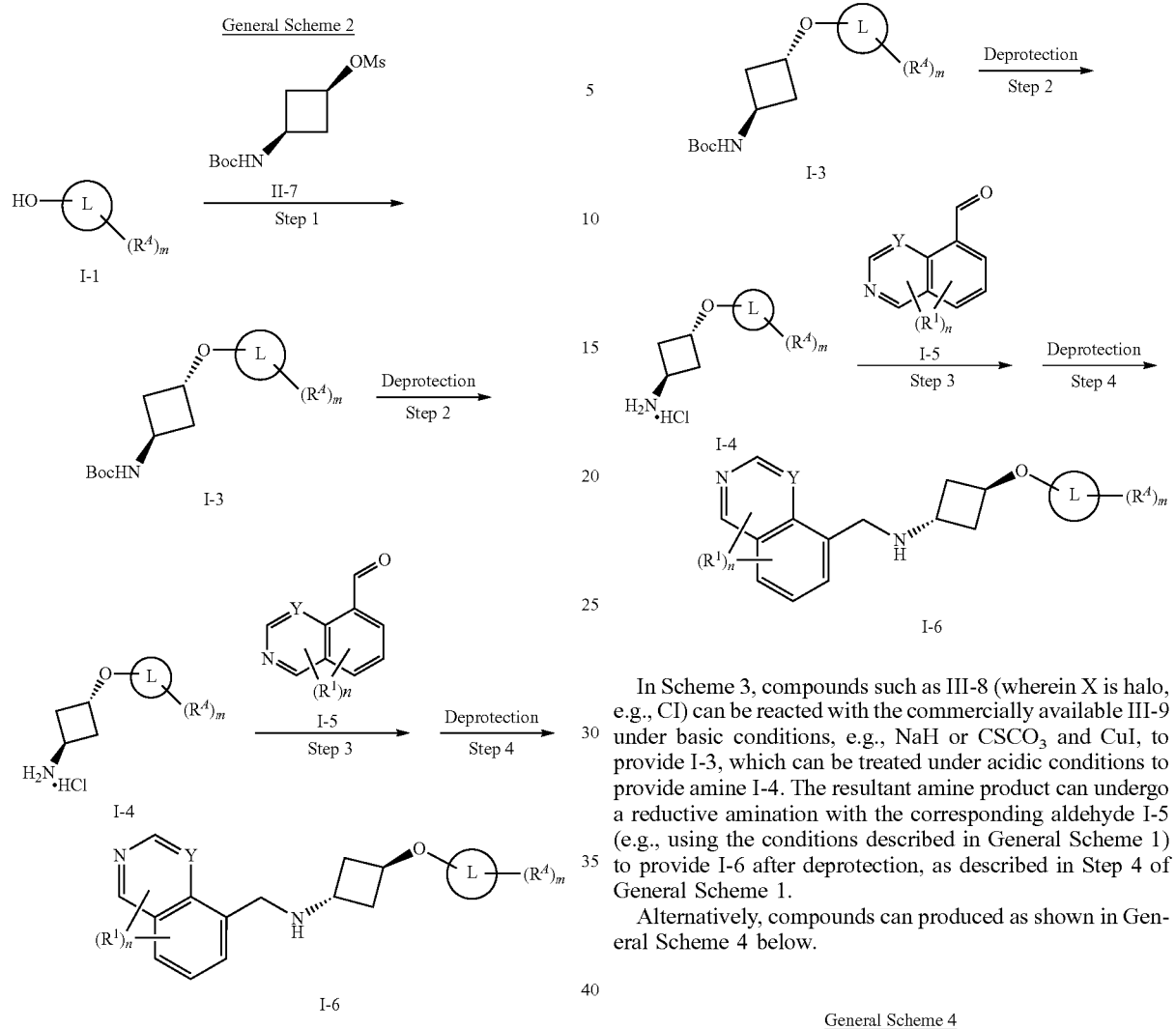

In Scheme 2, compounds such as I-1 can be reacted with II-7 under basic conditions, e.g., CsCO₃, to provide I-3, which can be treated under acidic conditions to provide amine I-4. The resultant amine can undergo a reductive amination with the corresponding aldehyde I-5 (e.g., using the conditions described in General Scheme 1) to provide I-6 after deprotection, as described in Step 4 of General scheme 1.

Alternatively, compounds can produced as shown in General Scheme 3 below.

General Scheme 3

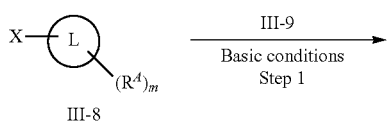

In Scheme 3, compounds such as III-8 (wherein X is halo, e.g., Cl) can be reacted with the commercially available III-9 under basic conditions, e.g., NaH or CSCO₃ and CuI, to provide I-3, which can be treated under acidic conditions to provide amine I-4. The resultant amine product can undergo a reductive amination with the corresponding aldehyde I-5 (e.g., using the conditions described in General Scheme 1) to provide I-6 after deprotection, as described in Step 4 of General Scheme 1.

Alternatively, compounds can produced as shown in General Scheme 4 below.

General Scheme 4

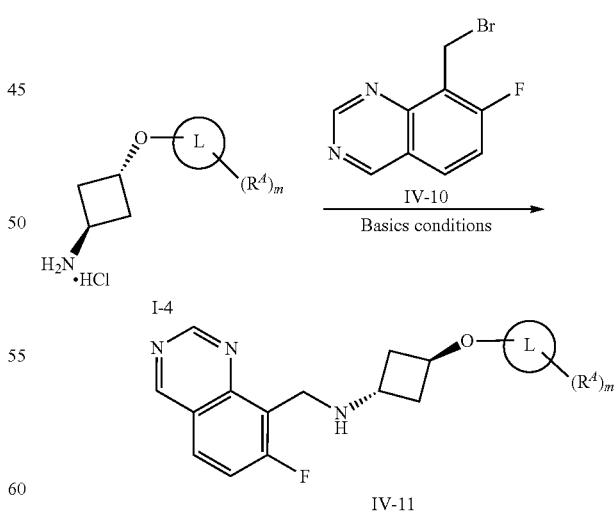

In Scheme 4, compounds such as I-4 are reacted with the corresponding bromide IV-10 under basic conditions, e.g., triethylamine, to provide IV-11.

Alternatively, compounds can produced as shown in General Scheme 5 below.

General Scheme 5

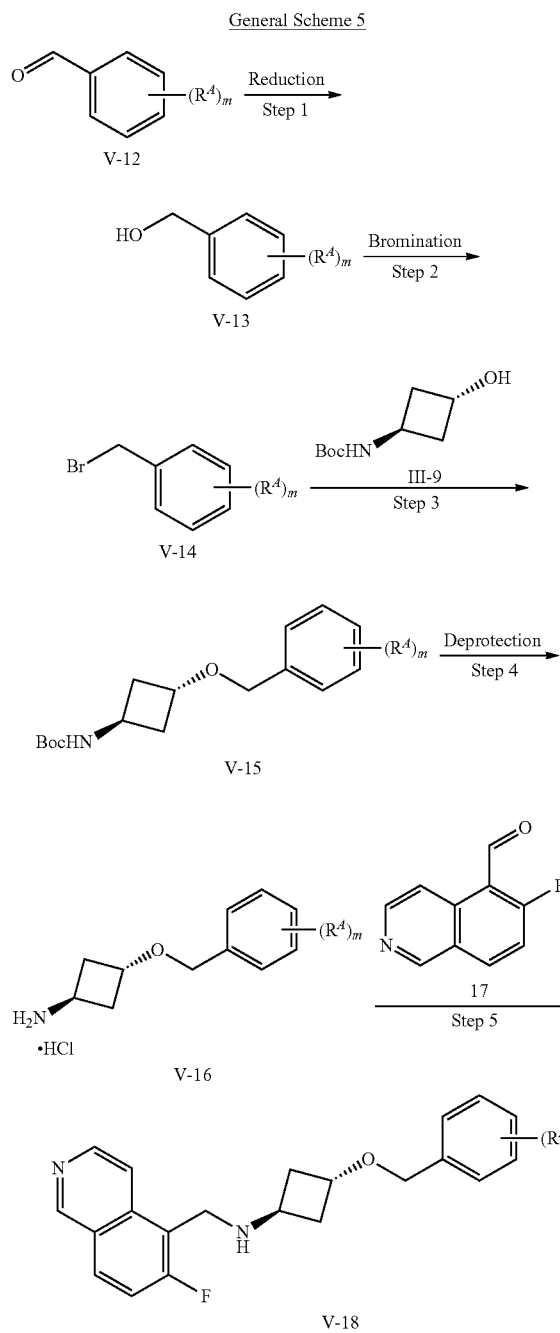

General Scheme 6

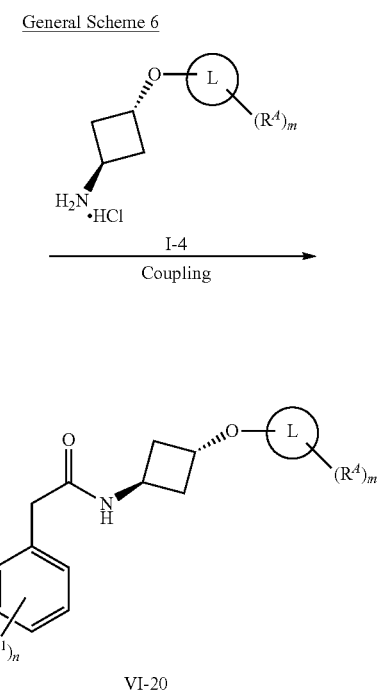

In Scheme 6, an acid such as VI-19 can react with I-4 under peptide coupling conditions, e.g., HATU, DIPEA, and using a solvent such as DMF. Any protected functional groups may subsequently undergo deprotection as described in Step 4 of General Scheme 1, to provide amide VI-20.

Alternatively, compounds can be produced as shown in General Scheme 7 below.

General Scheme 7

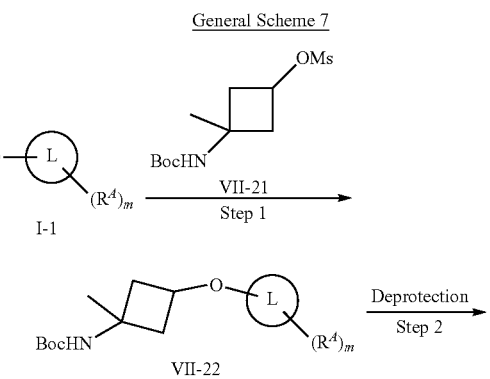

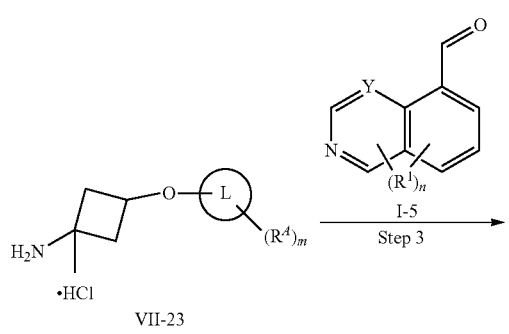

In Scheme 5, an aldehyde such as V-12 can be treated with a reducing agent, such as sodium borohydride, to provide V-13. Bromination of V-13 provides V-14 using a suitable brominating reagent, such as phosphorus tribromide. Nucleophilic displacement with III-9 in the presence of a base, such as sodium hydride, provides V-15. Removal of the Boc protecting group under acidic conditions, e.g., HCl/dioxane, provides amine V-16. Subsequent reductive amination with the corresponding aldehyde V-17 (e.g., using the conditions described in General Scheme 1, suitably Condition 3) provides V-18.

Alternatively, compounds can be produced as shown in General Scheme 6 below.

-continued

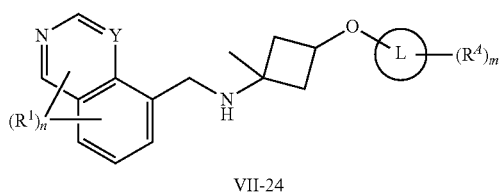

VII-24

Mesylate VII-21 undergoes nucleophilic displacement with alcohol I-1 (e.g., L is $C_6$-$C_{10}$ aryl) under basic conditions, e.g., $CsCO_3$, to provide VII-22. Deprotection of under acidic conditions, e.g., HCl/dioxane, provides amine VII-23. VII-23 can undergo reductive amination with the corresponding aldehyde I-5 (e.g., using the conditions described in General Scheme 1, suitably Condition 3) to provide VII-24. The cyclobutyl cis and trans isomers are then separated.

Alternatively, compounds can be produced as shown in General Scheme 8 below.

General Scheme 8

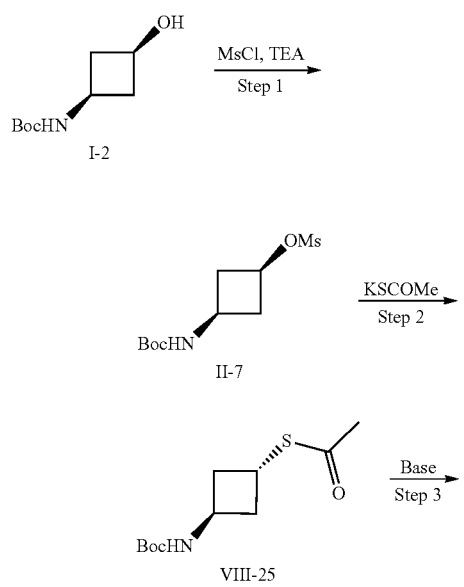

-continued

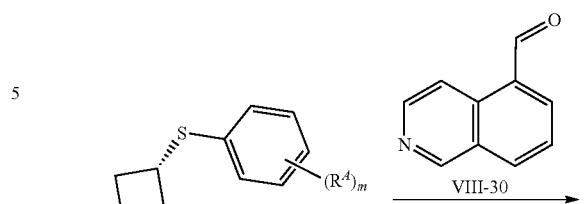

In Scheme 8, commercially available alcohol I-2 can react with mesyl chloride under basic conditions, e.g., triethylamine, to provide II-7. Thio ester product VIII-25 can be formed by treatment of II-7 under nucleophilic conditions, e.g., with KSCOMe. Deprotection under basic conditions, e.g., NaOH, affords VIII-26, which can then react with the corresponding aryl bromide VIII-27 under Buchwald type conditions using a Pd catalyst, e.g., $Pd_2(dba)_3$, and phosphine ligand, e.g., Xanthphos, and base, e.g., DIPEA, in a solvent such as dioxane, to provide VIII-28. Deprotection of VIII-28 with acid, e.g., HCl, provides amine VIII-29, which can undergo reductive amination with the corresponding aldehyde VIII-30 (e.g., using the conditions described in General Scheme 1, suitably Condition 1) to provide VIII-31.

Alternatively, compounds can be produced as shown in General Scheme 9 below.

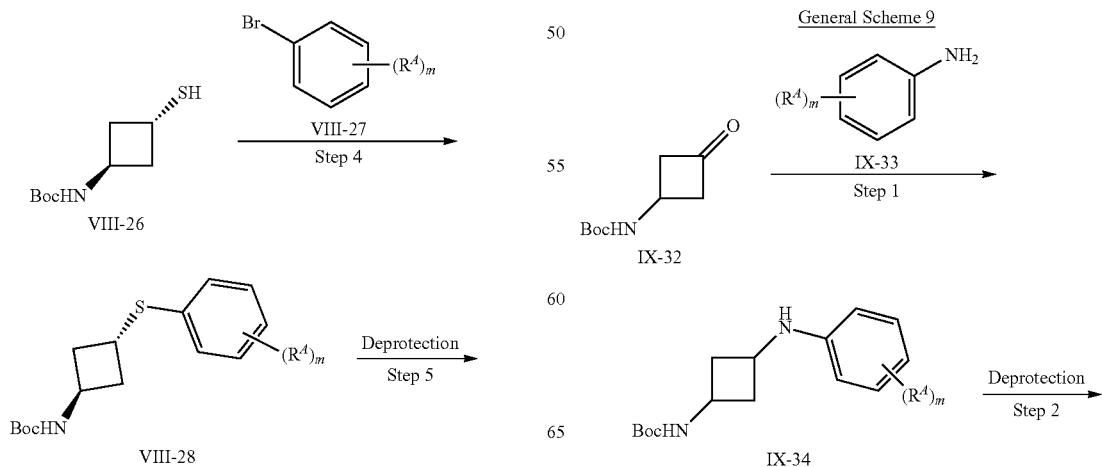

-continued

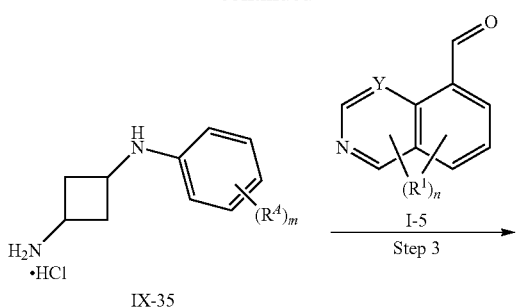

IX-35

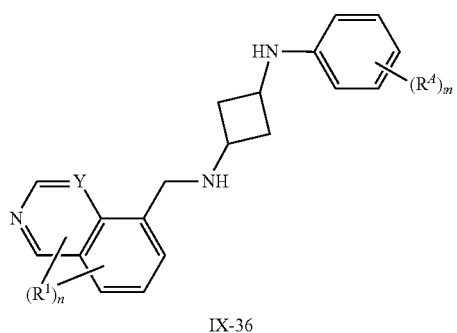

IX-36

Commercially available IX-32 reacts with aniline IX-33 under reductive amination conditions to provide IX-34, which is subsequently deprotected under acidic conditions, e.g., HCl/dioxane, to provide amine IX-35. Reaction with aldehyde I-5 under reductive amination conditions (e.g., using the conditions described in General Scheme 1, suitably Condition 1) provides IX-36.

Alternatively, compounds can be produced as shown in General Scheme 10 below.

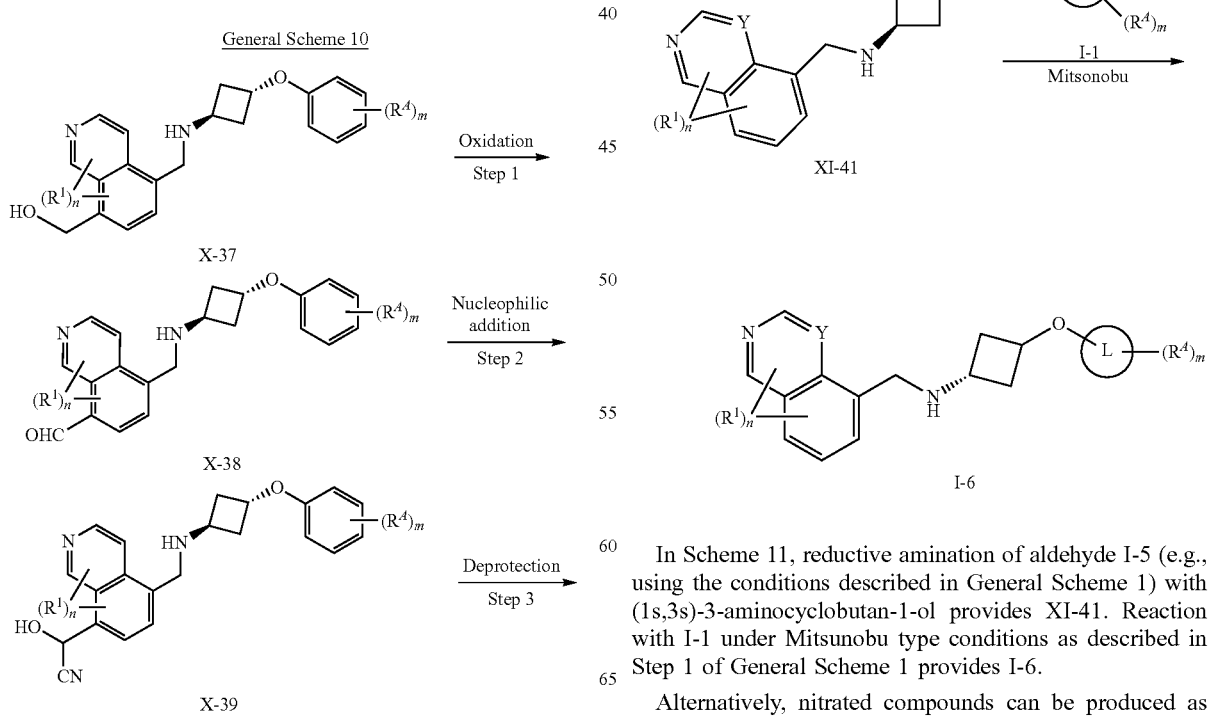

-continued

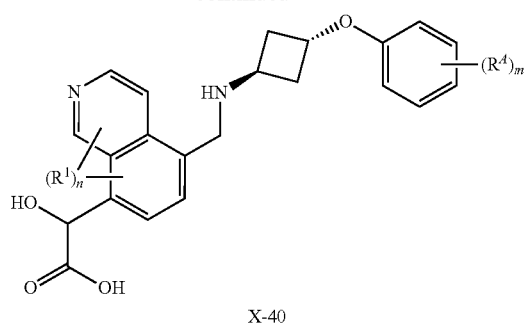

X-40

In Scheme 10, oxidation of compound X-37, e.g., with $MnO_2$, affords X-38. Nucleophilic addition to aldehyde X-38 with a cyano source, e.g., TMSCN, gives X-39. Deprotection of X-39 under acidic conditions, e.g., HCl, provides acid X-40.

Alternatively, compounds can be produced as shown in General Scheme 11 below.

General Scheme 11

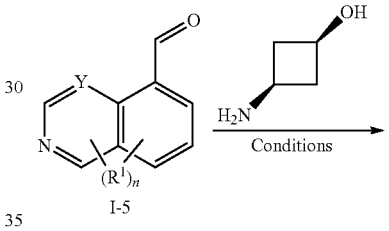

In Scheme 11, reductive amination of aldehyde I-5 (e.g., using the conditions described in General Scheme 1) with (1s,3s)-3-aminocyclobutan-1-ol provides XI-41. Reaction with I-1 under Mitsunobu type conditions as described in Step 1 of General Scheme 1 provides I-6.

Alternatively, nitrated compounds can be produced as shown in General Scheme 12 below.

General Scheme 12

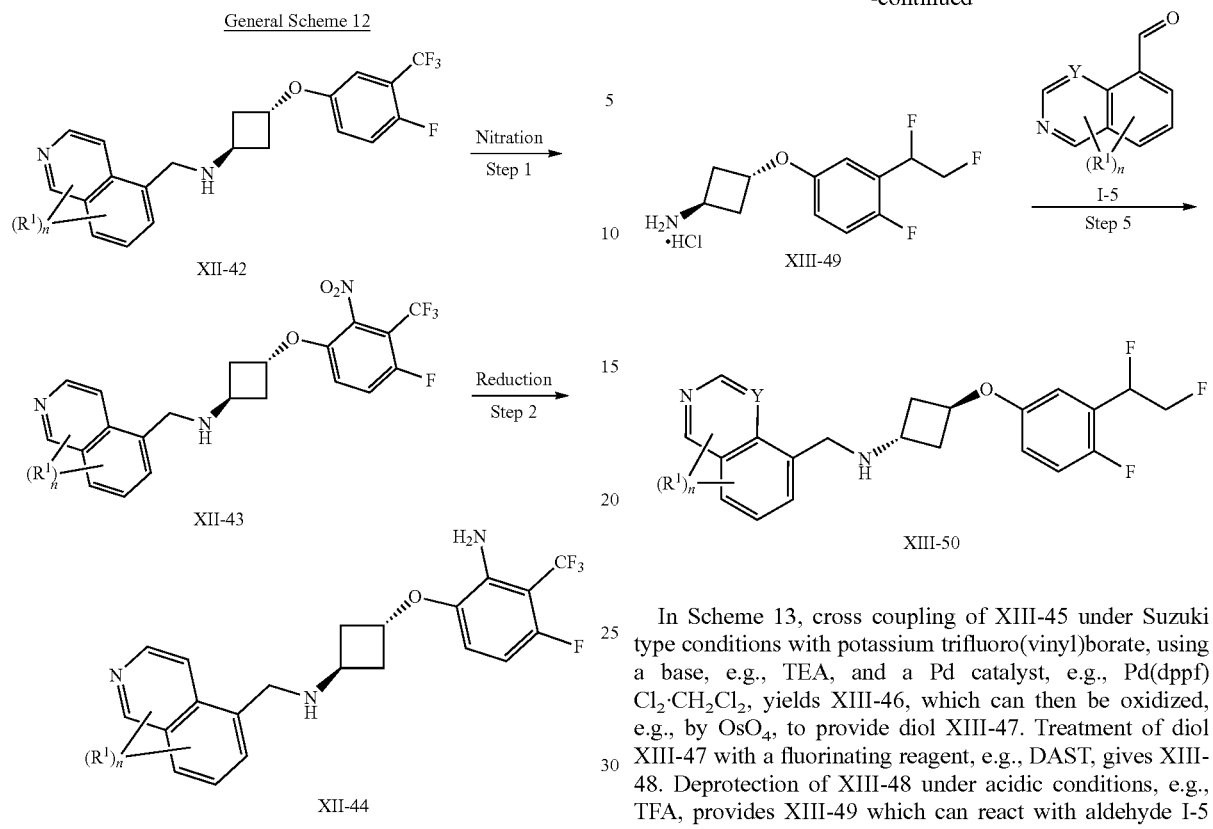

In Scheme 12, nitration of XII-42, e.g., using $H_2SO_4$ and $HNO_3$, gives XII-43, which is then reduced, e.g., Zn and AcOH, to provide XII-44, after separation of the regioisomers.

Alternatively, compounds can be produced as shown in General Scheme 13 below.

In Scheme 13, cross coupling of XIII-45 under Suzuki type conditions with potassium trifluoro(vinyl)borate, using a base, e.g., TEA, and a Pd catalyst, e.g., Pd(dppf)$Cl_2 \cdot CH_2Cl_2$, yields XIII-46, which can then be oxidized, e.g., by $OsO_4$, to provide diol XIII-47. Treatment of diol XIII-47 with a fluorinating reagent, e.g., DAST, gives XIII-48. Deprotection of XIII-48 under acidic conditions, e.g., TFA, provides XIII-49 which can react with aldehyde I-5 under reductive amination conditions (as described in Step 4 of General Scheme 1) to provide XIII-50.

Alternatively, compounds can be produced as shown in General Scheme 14 below.

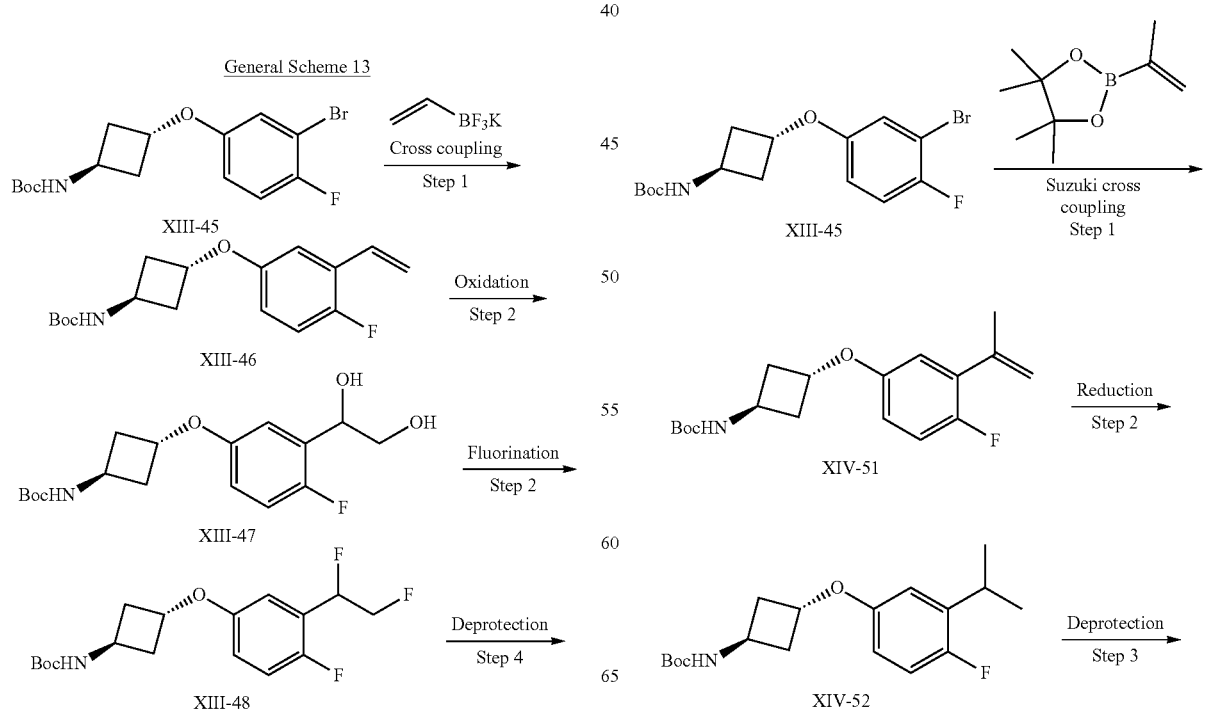

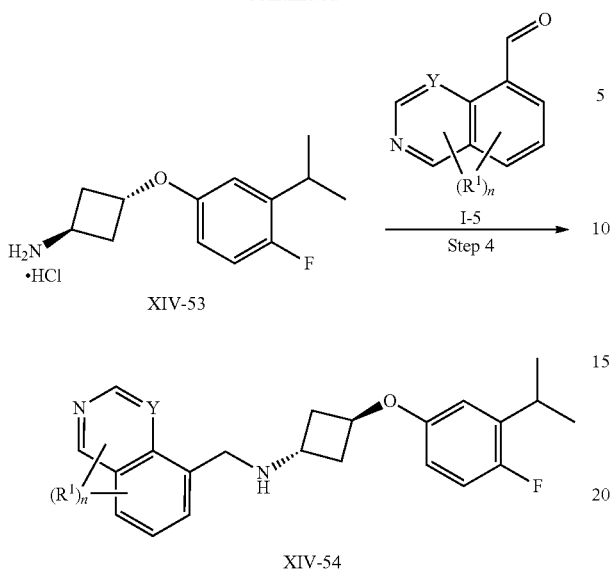

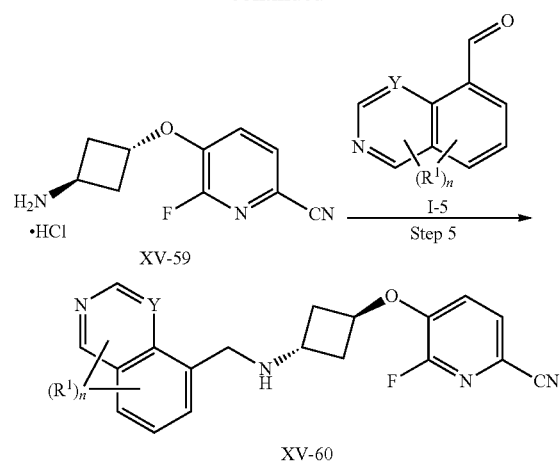

Cross coupling of XIII-45 with the corresponding boronic ester, e.g., 4,4,5,5-tetramethyl-2-(prop-1-en-2-yl)-1,3,2-dioxaborolane, under Suzuki type conditions, e.g., base such as K$_3$PO$_4$, Pd catalyst such as Pd(dppf)Cl$_2$·CH$_2$Cl$_2$, in a suitable solvent, e.g., 1,4-dioxane, gives XIV-51. Reduction, e.g., under hydrogenation conditions, e.g., Pd/C and H$_2$, of alkene XIV-51 gives XIV-52. Subsequent deprotection of XIV-52 under acidic conditions provides XIV-53 which undergoes a reductive amination with corresponding aldehyde I-5 (as described in Step 4 of General Scheme 1) to provide XIV-54.

Alternatively, compounds can be produced as shown in General Scheme 15 below.

General Scheme 15

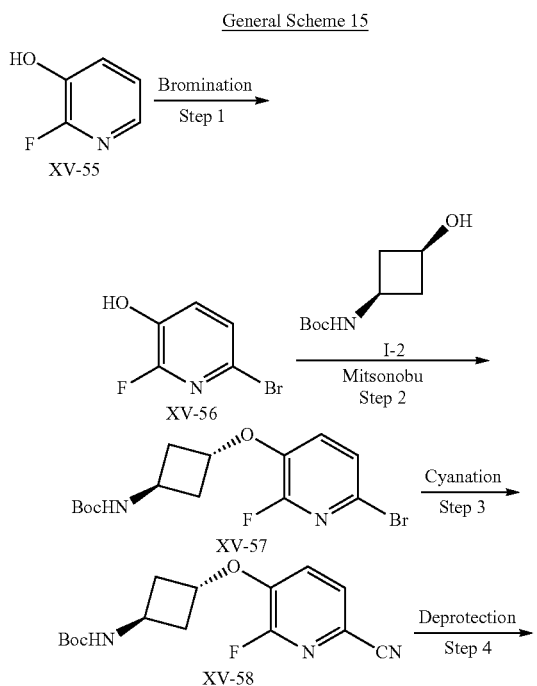

In Scheme 15, commercially available XV-55 can be brominated, e.g., using bromine/acetic acid, to provide XV-56. Subsequent reaction with I-2 under Mitsunobu type conditions (e.g., as described in Step 1 of General Scheme 1) provides XV-57. Pd catalysed cyanation of XV-57 using Zn(CN)$_2$ and a Pd catalyst such as Pd$_2$(dba)$_3$ and a ligand such as dppf, gives XV-58, which is then deprotected under acidic conditions to provide XV-59. Reaction with aldehyde I-5 under reductive amination conditions (as described in Step 4 of General Scheme 1) provides XV-60.

Alternatively, compounds can be produced as shown in General Scheme 16 below.

General Scheme 16

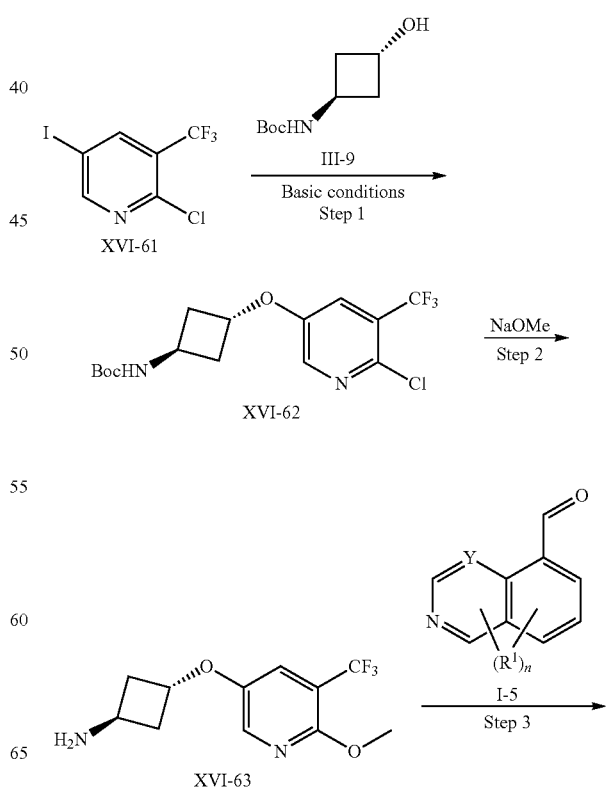

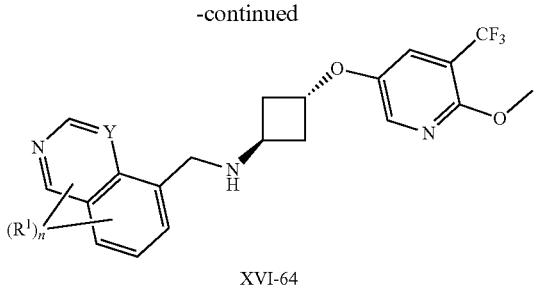

XVI-64

In Scheme 16, commercially available XVI-61 is reacted with III-9 under basic conditions, e.g., NaH or Cs$_2$CO$_3$ and CuI, to provide XVI-62. XVI-62 is then reacted with NaOMe to provide XVI-63. Subsequent reaction with aldehyde I-5 under reductive amination conditions (as described in Step 4 of General Scheme 1) provides XVI-64.

Alternatively, compounds can be produced as shown in General Scheme 17 below.

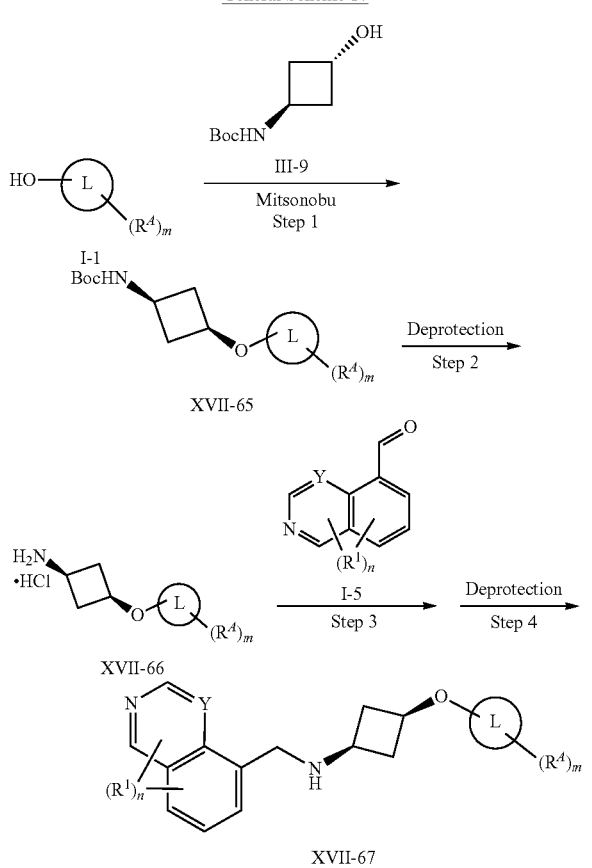

In Scheme 17, a Mitsonobu reaction of I-1 (e.g., as described in Step 1 of General Scheme 1) with commercially available III-9 provides XVII-65, which can be subsequently treated under acidic conditions to provide amine XVII-66. Further reaction with aldehyde I-5 under reductive amination conditions (as described in Step 4 of General Scheme 1) provides XVII-67 after deprotection of any protected functional groups, e.g., present as a substituent of R$^1$ and/or R$^A$ e.g., under acidic conditions with hydrochloric acid in dioxane or with a fluoride source such as tetra-n-butylammonium fluoride in THF.

In a further embodiment, provided herein is a compound of formula (X) or a salt thereof,

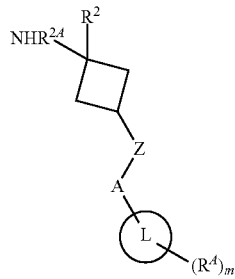

(X)

wherein:
Z is NH, O or S;
A is CH$_2$ or absent;
L is selected from 5- to 10-membered heteroaryl having 1-3 heteroatoms independently selected from N, O, and S, C$_6$-C$_{10}$aryl and 6- to 10-membered partially saturated heterocyclyl having 1-3 heteroatoms independently selected from N, O, and S;
R$^A$ is at each occurrence independently selected from halo, —CN, C$_1$-C$_6$haloalkyl, C$_1$-C$_6$alkyl, SF$_5$, C$_3$-C$_6$cycloalkyl, C$_1$-C$_6$alkoxyl, C$_1$-C$_6$haloalkoxyl, 4- to 6-membered heterocyclyl having 1-2 heteroatoms independently selected from N, O, and S, —(CH$_2$)$_p$—NR$^3$R$^4$ and —C(=O)—O—(C$_1$-C$_6$alkyl),
wherein the C$_3$-C$_6$cycloalkyl and 4- to 6-membered heterocyclyl are each independently substituted with 0-4 R$^{A1}$;
R$^{A1}$ is at each occurrence independently selected from halo and C$_1$-C$_6$haloalkyl;
R$^2$ is selected from hydrogen and C$_1$-C$_6$alkyl;
R$^{2A}$ is selected from hydrogen and a nitrogen protecting group (PG) (suitably, tert-butyl carbamate (Boc));
R$^3$ is at each occurrence independently selected from hydrogen and C$_1$-C$_6$alkyl;
R$^4$ is at each occurrence independently selected from —SO$_2$R$^5$, hydrogen, —C(=O)—(C$_1$-C$_6$alkyl) and C$_1$-C$_6$alkyl;
R$^5$ is at each occurrence independently selected from NH$_2$ and C$_1$-C$_6$alkyl;
m is 0, 1, 2, 3, 4 or 5.

In a further embodiment, the compound of Formula (X) is of Formula (X-a):

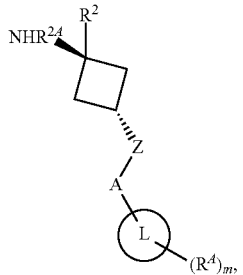

(X-a)

wherein A, L, Z, $R^A$, $R^2$, $R^{2A}$ and m are as defined for Formula (X).

In a further aspect, the disclosure provides a process for the preparation of a compound of formula (I), in free form or in pharmaceutically acceptable salt form, comprising the step of:

1) Reacting a compound of formula (X) (e.g., when $R^{2A}$ is hydrogen) or a salt thereof, e.g., HCl, with a compound of formula (I-5):

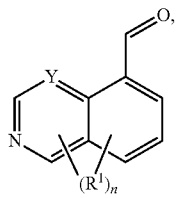

(I-5)

wherein:
Y is selected from N and CH;
$R^1$ is at each occurrence independently selected from hydroxyl, $C_1$-$C_6$alkyl, $C_1$-$C_6$alkoxyl, halo, $C_1$-$C_6$haloalkyl and $NR^3R^4$,
wherein the $C_1$-$C_6$alkyl and $C_1$-$C_6$haloalkyl are each independently substituted with 0-4 $R^{1a}$;
$R^{1a}$ is at each occurrence independently selected from hydroxyl, $NR^3R^4$ and —C(=O)—OH;
$R^3$ is at each occurrence independently selected from hydrogen and $C_1$-$C_6$alkyl;
$R^4$ is at each occurrence independently selected from —$SO_2R^5$, hydrogen, —C(=O)—($C_1$-$C_6$alkyl) and $C_1$-$C_6$alkyl;
$R^5$ is at each occurrence independently selected from $NH_2$ and $C_1$-$C_6$alkyl;
n is 0, 1, 2, 3 or 4;
under reductive amination conditions, optionally followed by 2) Deprotection of any protected protected functional groups, e.g., present as a substituent of $R^1$ and/or $R^4$, to give a compound of formula (I).

Reductive amination reactions can be carried out as described in the procedures in the Examples section or known in the art.

In an embodiment, the reductive amination conditions are selected from:

1) $NaBH_4$, $NEt_3$, AcOH, solvent, such as methanol, and the reaction conducted at room temperature or heated to a suitable temperature (e.g., up to reflux temperature);
2) $NaBH(OAc)_3$, i-$Pr_2NEt$, solvent, such as DCM, and the reaction conducted at room temperature or heated to a suitable temperature (e.g., up to reflux temperature); and
3) $NEt_3$ and a solvent, such as benzene, and heated to a suitable temperature (e.g., up to reflux temperature), followed by addition of $NaBH_4$ or $Na(CN)BH_3$, and a solvent, such as methanol, and the reaction conducted at room temperature or heated to a suitable temperature (e.g., up to reflux temperature).

Deprotection, e.g., of protected amine or hydroxyl functional groups, can be carried out as described in the procedures in the Examples section or known in the art.

In an embodiment, the deprotection conditions are selected from:

1) Acidic conditions, e.g., with neat hydrochloric acid or hydrochloric in dioxane or trifluoroacetic acid;
2) Fluoride source, such as tetra-n-butylammonium fluoride, in a solvent such as THF; and
3) Mixture of conditions 1 and 2.

Pharmaceutical Compositions

In another aspect, the disclosure provides a pharmaceutical composition comprising one or more compounds of described herein or a pharmaceutically acceptable salt thereof, and one or more pharmaceutically acceptable carriers.

In a further embodiment, the composition comprises at least two pharmaceutically acceptable carriers, such as those described herein. For purposes of the disclosure, unless designated otherwise, solvates and hydrates are generally considered compositions.

The compounds of Formula (I), and subformulae thereof, described herein may be administered alone or as an active ingredient of a pharmaceutical composition. Accordingly, provided herein are pharmaceutical compositions comprising a compounds of Formula (I), or subformulae thereof, or a pharmaceutically acceptable salt thereof, and one or more pharmaceutically acceptable carriers.

Methods of preparing various pharmaceutical compositions are known to those of skill in the art and may be described in, for example, in the Handbook of Pharmaceutical Excipients, American Pharmaceutical Association (current edition); Pharmaceutical Dosage Forms Tablets (Lieberman, Lachman and Schwartz, editors) current edition, published by Marcel Dekker, Inc., as well as Remington's Pharmaceutical Sciences (Arthur Osol, editor), 1553-1593 (current edition).

The pharmaceutical composition can be formulated for particular routes of administration such as oral administration, topical administration, parenteral administration, and rectal administration, etc. In addition, the pharmaceutical compositions of the disclosure can be made up in a solid form (including without limitation capsules, tablets, pills, granules, powders or suppositories), or in a liquid form (including without limitation solutions, gels, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol;
c) binders, e.g., magnesium aluminum silicate, starch paste, gelatin, tragacanth, methylcellulose, sodium carboxymethylcellulose and/or polyvinylpyrrolidone;
d) disintegrants, e.g., starches, agar, alginic acid or its sodium salt, or effervescent mixtures; and
e) absorbents, colorants, flavors and sweeteners.

In an embodiment, the pharmaceutical compositions are capsules comprising the active ingredient only.

Tablets may be either film coated or enteric coated according to methods known in the art.

The mode of administration and pharmaceutical composition are closely related to the therapeutic amounts of the compounds or compositions which are desirable and efficacious for the given treatment application. Pharmaceutical compositions provided herein can be formulated for ophthalmic, ocular, topical, and transdermal administration. In particular embodiments, the pharmaceutical compositions provided herein are suitable for ocular administration. To prepare pharmaceutical compositions, the active ingredient may be mixed with one or more pharmaceutically acceptable carrier(s) according to conventional pharmaceutical compounding techniques. The carrier(s) may take a wide variety of forms depending on the form of preparation desired for administration.

Suitable compositions for oral administration include an effective amount of a compound of the disclosure in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients, which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the disclosure with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

In certain embodiments, the pharmaceutical compositions provided herein are formulated as solutions, suspensions, gels, creams, ointments, liposomes, ocular inserts or other pharmaceutical compositions suitable, in particular embodiments, for topical administration to the ocular surface, the cornea, the eyelid, margins of the eye, eyelashes and/or eye lid margin in order to deliver the composition to the eye. In some embodiments, liquid (aqueous or non-aqeuous) solutions may be used. In certain embodiments the pharmaceutical compositions are formulated as eye drops for topical administration to the ocular surface, the cornea, the eyelid, eye lid margins, eyelashes and/or margins of the eye in order to deliver the composition to the eye. Application of the pharmaceutical composition may be performed with an applicator, such as the subject's finger, a Weck-Cel®, Q-tip®, or other device capable of delivering a formulation to the eyelid, eyelashes and/or eyelid margin in order to deliver the formulation to the eye. The pharmaceutical compositions provided herein may be viscous or semi-viscous; liquid, solid, or semi-solid; aqueous or non-aqueous, depending on the site of application, dose, solubility of drug, and a variety of other factors that are considered by those of skill in the art.

Any of a variety of carriers may be used in a pharmaceutical composition provided herein. In one embodiment, the pharmaceutically acceptable carrier is a non-aqueous carrier (e.g., oil, or oil mixture) having a viscosity in a range from about 50 cps to about 1000 cps, about 50 cps to about 500 cps, about 50 cps to about 200 cps, or about 60 cps to about 120 cps. In certain embodiments, the non-aqueous carrier comprises an oil, e.g., vegetable oils, silicone oils, mineral oil or any combination thereof. In some embodiments, the carrier may be liquid paraffin, white petrolatum, purified lanolin, gelation hydrocarbon, polyethylene glycol, hydrophilic ointment base, white ointment base, absorptive ointment base, Macrogol ointment base, simple ointment base, and the like. In certain embodiments, the pharmaceutical composition may include a monomeric polyol such as, glycerol, propylene glycol, and ethylene glycol, polymeric polyols such as polyethylene glycol, cellulose esters such hydroxypropylmethyl cellulose, carboxy methylcellulose sodium and hydroxy propylcellulose; dextrans such as dextran 70; water soluble proteins such as gelatin, polymers such as polyvinyl alcohol, polyvinylpyrrolidone, and povidone; carbomers, such as carbomer 934P. carbomer 941, carbomer 940 and carbomer 974P; and gums such as HP-guar.

Additional excipients may optionally be included in the pharmaceutical compositions provided herein. Examples of additional excipients include, for example, tonicity enhancers, preservatives, solubilizers, non-toxic excipients, demulcents, sequestering agents, pH adjusting agents, co-solvents, viscosity building agents, and combinations thereof.

For the adjustment of the pH, e.g., to a physiological pH, buffers may be used. In certain embodiments, the pH of the pharmaceutical composition is maintained within the range of about 4.0 to about 8.0, such as, about 4.0 to about 6.0, for example, about 6.5 to about 7.8. Suitable buffers may be added, such as, e.g., boric acid, sodium borate, potassium citrate, citric acid, sodium bicarbonate, tris(hydroxymethyl) aminomethane (TRIS), and various mixed phosphate buffers (including combinations of $Na_2HPO_4$, $NaH_2PO_4$ and $KH_2PO_4$) and mixtures thereof. Generally, buffers may be used in amounts ranging from about 0.05 to about 2.5 percent by weight, such as, from about 0.1 to about 1.5 percent by weight.

Tonicity may be adjusted, if needed, by the use of tonicity enhancing agents. Such agents may, for example, be of ionic and/or non-ionic type. Examples of ionic tonicity enhancers include, for example, alkali metal or earth metal halides such as, e.g., $CaCl_2$, KBr, KCl, LiCl, NaI, NaBr or NaCl, $Na_2SO_4$ or boric acid. Non-ionic tonicity enhancing agents include, e.g., urea, glycerol, sorbitol, mannitol, propylene glycol, or dextrose. In one embodiment, the pharmaceutical compositions provided herein may have an osmolality of about 225 to about 400 milliosmoles per kilogram (mOsm/kg). In one embodiment, an osmolality of about 280 to about 320 mOsm is obtained.

In further embodiments, the pharmaceutical compositions provided herein, such as topical compositions, may additionally comprise a preservative. A preservative may typically be selected from a quaternary ammonium compound such as benzalkonium chloride, benzoxonium chloride (e.g., N-benzyl-N—($C_8$-$C_{18}$ dimethylammonium chloride) or the like. Examples of preservatives different from quaternary ammonium salts include, e.g., alkyl-mercury salts of thiosalicylic acid, such as, for example, thiomersal, phenylmercuric nitrate, phenylmercuric acetate or phenylmercuric borate, sodium perborate, sodium chlorite, parabens, such as, for example, methylparaben or propylparaben, alcohols, such as, for example, chlorobutanol, benzyl alcohol or phenylethanol, guanidine derivatives, such as, for example, chlorohexidine or polyhexamethylene biguanide, sodium perborate, or sorbic acid. Where appropriate, a sufficient amount of preservative may be added to the pharmaceutical composition provided herein to ensure protection against secondary-contaminations during use caused by bacteria and fungi. In certain embodiments the pharmaceutical compositions provided herein, such as topical compositions, may additionally comprise Polyquad®. In another embodiment, the pharmaceutical compositions provided herein do not comprise a preservative.

The pharmaceutical compositions provided herein may additionally comprise a solubilizer. Suitable solubilizers include, but are not limited to, tyloxapol, fatty acid glycerol polyethylene glycol esters, fatty acid polyethylene glycol esters, polyethylene glycols, glycerol ethers, or cyclodextrins.

The pharmaceutical compositions provided herein may further comprise non-toxic excipients, such as emulsifiers, wetting agents or fillers, by way of example, polyethylene glycols designated 200, 300, 400 and 600, or Carbowax designated 1000, 1500, 4000, 6000 and 10000. The amount and type of excipient added is in accordance with the particular requirements and is generally in the range of from approximately 0.0001 to approximately 90% by weight. Other compounds may also be added to the pharmaceutical compositions provided herein to adjust (e.g., increase) the viscosity of the carrier. Examples of viscosity enhancing agents include, but are not limited to, polysaccharides, such as hyaluronic acid and its salts, chondroitin sulfate and its salts, dextrans, various polymers of the cellulose family, vinyl polymers, and acrylic acid polymers.

The pharmaceutical composition of the disclosure may be in the form of an aqueous suspension or an aqueous solution. In one embodiment, the aqueous pharmaceutical composition of the disclosure is in the form of an aqueous suspension.

Aqueous pharmaceutical compositions according to the disclosure can be prepared using standard procedures that are familiar to the person skilled in the art, e.g., by admixture of the various components, suitably at ambient temperature and atmospheric pressure. In one embodiment, the aqueous pharmaceutical compositions of the disclosure are suitable for ocular administration.

In a further embodiment, the pharmaceutical composition of the disclosure is in the form of eye ointment, eye gel, eye cream, or eye drops.

In a further embodiment, the pharmaceutical composition of the disclosure is administered to the subject topically in the eyes.

The compounds of formula (I), in free form or in pharmaceutically acceptable salt form, exhibit valuable pharmacological properties, e.g., TRPV1 antagonizing properties e.g., as indicated in the in vitro tests as provided in the examples, and are therefore indicated for therapy or for use as research chemicals, e.g., as tool compounds.

Additional properties of the disclosed compounds include having good potency in the biological assays described herein, favorable safety profile, and possess favorable pharmacokinetic properties Diseases and Disorders and Methods of Use In a further aspect, the invention provides a compound of formula (I), or a pharmaceutically acceptable salt thereof, for use in therapy.

In a further aspect, the invention provides a compound of formula (I), or a pharmaceutically acceptable salt thereof, for use in the treatment of a disease or disorder for which a TRPV1 antagonist is indicated. In one embodiment, the disease or disorder is affected by the inhibition of TRPV1 activity.

Compounds of formula (I) and their pharmaceutically acceptable salts have TRPV1 antagonist activity and are believed to be of potential use for the treatment or prophylaxis of certain diseases or disorders, or treatment of the pain associated with these, such as respiratory diseases, asthma, cough, chronic obstructive pulmonary disease (COPD), bronchoconstriction, rhinitis, inflammatory disorders, pain, such as acute pain, chronic pain, neuropathic pain, postoperative pain, postrheumatoid arthritic pain, osteoarthritic pain, back pain, visceral pain, cancer pain, algesia, neuralgia, dental pain, headache, migraine, neuropathies, carpal tunnel syndrome, diabetic neuropathy, HIV-related neuropathy, post-herpetic neuralgia, fibromyalgia, neuritis, sciatica, nerve injury, ischaemia, neurodegeneration, stroke, post stroke pain, multiple sclerosis, oesophagitis, heart burn, Barrett's metaplasia, dysphagia, gastroeosophageal reflux disorder (GERD), stomach and duodenal ulcers, functional dyspepsia, irritable bowel syndrome, inflammatory bowel disease, colitis, Crohn's disease, pelvic hypersensitivity, pelvic pain, menstrual pain, renal colic, urinary incontinence, cystitis, burns, itch, psoriasis, pruritis andemesis, ocular diseases or disorders.

In an embodiment, the ocular disease or disorder is an ocular surface disorder. In a further embodiment, the ocular surface disorder is selected from chronic ocular surface pain (COSP), dry eye disease (including dry eye symptoms, including symptoms of dry eye associated with refractive surgery such as LASIK surgery), Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

In an embodiment, the ocular ocular disease or disorder is ocular surface pain. In some embodiments, the ocular surface pain is acute or episodic ocular surface pain. In some embodiments, the ocular surface pain is chronic ocular surface pain, e.g., lasting for at least 3 months.

In an embodiment, the ocular ocular disease or disorder is ocular hyperemia.

Having regard to their activity as TRPV1 inhibitors, compounds of formula (I) and sub-formulae thereof, in free or pharmaceutically acceptable salt form, are useful in the treatment of conditions which may be treated by inhibition of TRPV1 activity. In one aspect, the disclosure provides a method of treating or preventing a disease or disorder in a subject in need thereof, the method comprising administering to the subject a therapeutically effective amount of a compound of formula (I) or sub-formula thereof, or a pharmaceutically acceptable salt thereof.

In another aspect, the disclosure provides a method of treating or preventing a disease or disorder that is affected by the inhibition of TRPV1 activity, in a subject in need thereof, the method comprising administering to the subject a therapeutically effective amount of a compound of formula (I) or sub-formula thereof, or a pharmaceutically acceptable salt thereof.

In another aspect, the disclosure provides a method of inhibiting TRPV1 activity in a subject in need thereof, the method comprising administering to the subject a therapeutically effective amount of a compound of formula (I) or sub-formula thereof, or a pharmaceutically acceptable salt thereof.

In another aspect, the disclosure provides a method of antagonizing TRPV1 activity in a subject in need thereof, the method comprising administering to the subject a therapeutically effective amount of a compound of formula (I) or sub-formula thereof, or a pharmaceutically acceptable salt thereof.

In another aspect, the disclosure provides a method of treating or preventing a disease or disorder mediated by TRPV1 in a subject in need thereof, the method comprising administering to the subject a therapeutically effective amount of a compound of formula (I) or sub-formula thereof, or a pharmaceutically acceptable salt thereof.

In another aspect, the disclosure provides a method of treating, reducing, or preventing pain in a subject in need thereof, the method comprising administering to the subject a therapeutically effective amount of a compound of formula (I) or sub-formula thereof, or a pharmaceutically acceptable salt thereof. The pain may be acute, such as pain caused after injury or surgery, or chronic. Examples of pain include, in particular, pain, e.g., bone and joint pain (osteoarthritis), cancer pain, myofascial pain (muscular injury, fibromyalgia) and perioperative pain (general surgery, gynecologic surgery). Other examples include chronic pain, especially inflammatory, e.g., chronic inflammatory pain. Additional examples of pain include pain in which TRPV1 activation plays a role or is implicated, and therefore susceptible to treatment by the compounds disclosed herein. Such conditions include chronic pain with an inflammatory component such as rheumatoid arthritis; bone and joint pain (osteoarthritis); post-surgical pain; musculo-skeletal pain such as fibromyalgia; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, migraine, abdominal pain, gynaecological pain, such as dysmenorrhoea, and labour pain; pain associated with the urogenital tract such as cystitis and vulvadynia; inflammatory skin disorders, for example psoriasis and eczema, or itch of non-specific origin; chronic pain associated with nerve injury and/or diseases affecting the nervous system, such as neuropathic pain associated with post-herpetic neuralgia, diabetic neuropathy, chemotherapy-induced neuropathy, amputations ("phantom limb pain"), nerve entrapment and brachial plexus avulsions, low back pain, sciatica and ankylosing spondylitis, reflex sympathetic dystrophy and other chronic nerve injuries; complex regional pain syndromes; central nervous system pain, such as pain due to spinal cord or brain stem damage, or stroke; gout; scar pain; pain associated with carcinoma, often referred to as cancer pain.

In another aspect, the disclosure provides a method of treating or preventing inflammatory diseases in a subject in need thereof, the method comprising administering to the subject a therapeutically effective amount of a compound of formula (I) or sub-formula thereof, or a pharmaceutically acceptable salt thereof. Exemplary inflammatory diseases include inflammatory airways disease, e.g., chronic obstructive pulmonary disease (COPD), or asthma; cough; urinary incontinence; migraine; visceral disorders, e.g., inflammatory bowel disease; rhinitis; cystitis, e.g. interstitial cystitis; pancreatitis; uveitis; inflammatory skin disorders such as eczema and psoriasis; rheumatoid arthritis; inflammatory disorders of the gut, e.g., irritable bowel syndrome; Crohn's disease; ulcerative colitis; and cystitis, e.g., interstitial cystitis, nephritis and uveitis.

In another aspect, the disclosure provides a method of relaxing smooth muscle in a subject in need thereof, the method comprising administering to the subject a therapeutically effective amount of a compound of formula (I) or sub-formula thereof, or a pharmaceutically acceptable salt thereof. Examples of diseases or conditions requiring smooth muscle relaxants include, e.g., treatment of spasm of the gastrointestinal tract or uterus, e.g., in the therapy of Crohn's disease, ulcerative colitis or pancreatitis.

In another aspect, the disclosure provides a method of treating or preventing airway hyperreactivity or treating or preventing inflammatory events associated with airways disease, the method comprising administering to the subject a therapeutically effective amount of a compound of formula (I) or sub-formula thereof, or a pharmaceutically acceptable salt thereof. Exemplary conditions include asthma, restriction or reversal of airways hyperreactivity in asthma. Other conditions include both intrinsic and, especially, extrinsic asthma, such as allergic asthma, as well as, e.g., exercise induced asthma, occupational asthma, asthma induced following bacterial infection, other non-allergic asthmas and "wheezy-infant syndrome". Efficacy in the treatment of asthma will be evidenced by reduced frequency or severity of symptomatic attack, e.g., of acute asthmatic or bronchoconstrictor attack and by reduced requirement for other, symptomatic therapy, e.g., anti-inflammatory, e.g., corticosteroid; or bronchodilator, e.g., β2 adrenergic, therapy. Other inflammatory or obstructive airways diseases include pneumoconiosis (an inflammatory, commonly occupational, disease of the lungs, frequently accompanied by repeated inhalation of dusts) of whatever type or genesis including, e.g., aluminosis, anthracosis, asbestosis, chalicosis, ptilosis, siderosis, silicosis, tabacosis and, in particular, byssinosis. Further inflammatory or obstructive airways diseases and conditions include adult respiratory distress syndrome (ARDS), chronic obstructive pulmonary or airways disease (COPD or COAD), and bronchitis, allergic and vasomotor rhinitis.

In another aspect, the disclosure provides a method of treating or preventing septic shock in a subject in need thereof, the method comprising administering to the subject a therapeutically effective amount of a compound of formula (I) or sub-formula thereof, or a pharmaceutically acceptable salt thereof. Exemplary conditions include septic shock, e.g., as anti-hypovolaemic and/or anti-hypotensive agents; in the treatment of inflammatory bowel disease; cerebral oedema; headache;

In another aspect, the disclosure provides a method of treating an ocular surface disorder in a subject in need thereof, the method comprising administering to the subject a therapeutically effective amount of a compound of formula (I) or sub-formula thereof, or a pharmaceutically acceptable salt thereof. In some embodiments, In some embodiments, the disclosure relates to a method of treating dry eye disease in a subject in need thereof, comprising administering to the subject an effective amount of a compound of formula (I) or sub-formula thereof, or a pharmaceutically acceptable salt thereof.

In another aspect, the disclosure provides a method of treating or reducing ocular surface pain in a subject in need thereof, the method comprising administering to the subject a therapeutically effective amount of a compound of formula (I) or sub-formula thereof, or a pharmaceutically acceptable salt thereof. In some embodiments, the ocular surface pain is acute or episodic ocular surface pain. In some embodiments, the ocular surface pain is chronic ocular surface pain, e.g., lasting for at least 3 months. In an embodiment, the ocular surface pain or the chronic ocular surface pain is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

In a particular embodiment, the ocular surface pain or the chronic ocular surface pain is associated with dry eye disease or Sjogren's Syndrome. In some embodiments of the methods described herein, the subject suffers from ocular pain persisting for at least three months after photorefractive keratectomy (PRK) surgery or laser-assisted in situ keratomileusis (LASIK) surgery. In some embodiments, the subject suffers from conjunctivitis, subconjunctival hemorrhage, subconjunctival scarring, conjunctival membranes, conjunctival ulceration, superficial punctate epithelial erosions, epithelial defects, lid margin ulceration, lid margin keratinization, symblepharon, ankyloblepharon, trichiasis, anterior blepharitis, punctal auto-occlusion, meibomian gland disease, corneal opacification, dry eye, districhiasis, limbal stem cell failure, or corneal vascularization.

In another aspect, the disclosure provides a method of treating or reducing ocular hyperemia in a subject in need thereof, the method comprising administering to the subject a therapeutically effective amount of a compound formula (I) or sub-formula thereof, or a pharmaceutically acceptable salt thereof. In an embodiment, the ocular hyperemia is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In a particular embodiment, the ocular hyperemia is associated with dry eye disease. In an embodiment of the methods described herein, the ocular hyperemia persists for at least three months after photorefractive keratectomy (PRK) surgery or laser-assisted in situ keratomileusis (LASIK) surgery.

All the aforementioned embodiments relating to the methods of treatment of the aforementioned diseases are equally applicable to:

a compound of formula (I) or sub-formula thereof, or a pharmaceutically acceptable salt thereof, for use in the treatment of the aforementioned diseases according to the present disclosure; use of a compound of formula (I) or sub-formula thereof, or a pharmaceutically acceptable salt thereof, in the manufacture of a medicament for the treatment of the aforementioned diseases according to the present disclosure;

use of a compound of formula (I) or sub-formula thereof, or a pharmaceutically acceptable salt thereof, for the treatment of the aforementioned diseases according to the present disclosure; and a pharmaceutical composition comprising a compound of formula (I) or sub-formula thereof, or a pharmaceutically acceptable salt thereof, and one or more pharmaceutically acceptable carriers, for use in the treatment of the aforementioned diseases according to the present disclosure.

Dosage

The pharmaceutical composition or combination of the disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated.

The above-cited dosage properties are demonstrable in vitro and in vivo tests using advantageously mammals, e.g., mice, rats, dogs, monkeys or isolated organs, tissues and preparations thereof. The compounds of the disclosure can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

In certain embodiments, the disclosure provides for administration of a compound of Formula (I), or subformulae thereof, or a pharmaceutically acceptable salt thereof, to a subject in need thereof in an ophthalmically compatible pharmaceutical composition, wherein said compound is present at a concentration of about 0.01% w/v to about 10.0% w/v. In some embodiments, the compound of formula I is administered, e.g., to the surface of the eye, to the subject one to six times a day, e.g., one, two, three, or four times a day. In some embodiments, the compound of formula (I) is administered to the subject for a period of at least about one month, at least about two months, or at least about three months. The therapeutically effective dosage of a compound, the pharmaceutical composition, or the combinations thereof, is dependent on the species of the subject, the body weight, age and individual condition, the disorder or disease or the severity thereof being treated.

The preferred compositions of the present invention are intended for administration to a human patient suffering from an ocular disease or disorder. Preferably, such compositions will be administered topically.

The activity of a compound according to the disclosure can be assessed by the in vitro methods described in the Examples.

Combination Therapy

In another aspect, the disclosure provides a pharmaceutical combination comprising a compound of formula (I), or subformulae thereof, or a pharmaceutically acceptable salt thereof, and one or more additional therapeutic agent(s) for simultaneous, separate or sequential use in therapy.

The compound of the disclosure may be administered either simultaneously with, or before or after, one or more other therapeutic agent. The compound of the disclosure may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the disclosure. Thus, in one embodiment, the disclosure provides a combination comprising a therapeutically effective amount of a compound of formula or subformulae thereof, or a pharmaceutically acceptable salt thereof, and one or more therapeutically active agents.

In certain embodiments, a compound of Formula (I), or subformulae thereof, or a pharmaceutically acceptable salt thereof, may be administered with an additional therapeutic agent. A non-limiting list of such agents incudes pharmaceutical agents effective in the treatment of diseases and conditions in which vanilloid receptor activation plays a role or is implicated, including cyclooxygenase-2 (COX-2) inhibitors, such as specific COX-2 inhibitors, e.g., celecoxib and rofecoxib; and non-steroidal anti-inflammatory drugs (NSAIDs), e.g., acetylsalicylic acid and propionic acid derivatives; tricyclic anti-depressants, e.g., Anafranil®, Asendin®, Aventyl®, Elavil®, Endep®, Norfranil®, Norpramin®, Pamelor®, Sinequan®, Surmontil®, Tipramine®, Tofranil®, Vivactil®, Tofranil-PM®; anti-convulsants, e.g., carbamazepine, oxcarbazepine and gabapentin; bradykinin B1 or B2 antagonists; and $GABA_B$ agonists, e.g., L-baclofen.

In certain embodiments, further therapeutic agents may include, for instance, other compounds and antibodies useful for treating ocular disorders. A non-limiting list of such agents incudes retinoid X receptor agonists, such as vitamin A, retinoic acid, phytanic acid, lithocholic acid, bexarotene, docosahexaenoic acid, or flurobexarotene. Other additional therapeutic agents include ophthalmic steroids such as, dexamethasone, fluocinolone, loteprednol, difluprednate, fluorometholone, prednisolone, prednisone, medrysone, triamcinolone, betamethasone, rimexolone, or pharmaceutically acceptable salts thereof. In addition, other additional therapeutic agents include those used to target ocular surface disease disorders, such as dry eye disease. Non-limiting example of such additional therapeutic agents include Xildra® (lifitegrast), Restasis® (cyclosporine), minocycline, doxycycline, or other tetracycline antibiotics. Other examples include keratolytic agents such as selenium disulfide, salicylic acid, glycolic acid etc., or pharmaceutically acceptable salts thereof.

In certain embodiments, further therapeutic agents may include, for instance, other compounds useful in the treatment of pain. In an embodiment, a compound of Formula (I), or subformula thereof, or a pharmaceutically acceptable salt thereof, may be administered with an additional analgesic agent. Such analgesic agent may be an NSAID (e.g., acetylsalicylic acid and propionic acid derivatives, e.g., Aleve®), opioid or steroid.

In one embodiment, the disclosure provides a product comprising a compound of formula (I), or subformula thereof, or a pharmaceutically acceptable salt thereof, and at least one other therapeutic agent as a combined preparation for simultaneous, separate or sequential use in therapy. In one embodiment, the therapy is the treatment of a disease or condition modulated by TRPV1. Products provided as a combined preparation include a composition comprising the compound of formula (I), or subformula thereof, or a pharmaceutically acceptable salt thereof, and the other therapeutic agent(s) together in the same pharmaceutical composition, or the compound of formula (I), or subformula thereof, or a pharmaceutically acceptable salt thereof, and the other therapeutic agent(s) in separate form, e.g., in the form of a kit.

In one embodiment, the disclosure provides a pharmaceutical composition comprising a compound of formula (I), or subformula thereof, or a pharmaceutically acceptable salt thereof, and another therapeutic agent(s). Optionally, the pharmaceutical composition may comprise a pharmaceutically acceptable carrier, as described above.

In one embodiment, the disclosure provides a kit comprising two or more separate pharmaceutical compositions, at least one of which contains a compound of formula (I), or subformula thereof, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

In the combination therapies of the disclosure, the compound of the disclosure and the other therapeutic agent may be manufactured and/or formulated by the same or different manufacturers. Moreover, the compound of the disclosure and the other therapeutic may be brought together into a combination therapy: (i) prior to release of the combination product to physicians (e.g., in the case of a kit comprising the compound of the disclosure and the other therapeutic agent); (ii) by the physician themselves (or under the guidance of the physician) shortly before administration; (iii) in the patient themselves, e.g., during sequential administration of the compound of the disclosure and the other therapeutic agent.

Preparation of Compounds

It is understood that in the following description, combinations of substituents and/or variables of the depicted formulae are permissible only if such combinations result in stable compounds.

It will also be appreciated by those skilled in the art that in the processes described below, the functional groups of intermediate compounds may need to be protected by suitable protecting groups. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; P. J. Kocienski, "Protecting Groups", Third Edition, Georg Thieme Verlag, Stuttgart and New York 2005; and in "Methoden der organischen Chemie" (Methods of Organic Chemistry), Houben Weyl, 4th edition, Volume 15/I, Georg Thieme Verlag, Stuttgart 1974.

The protecting group may also be a polymer resin, such as a Wang resin or a 2-chlorotrityl-chloride resin.

The following reaction Examples illustrate methods to make compounds of this disclosure.

It is understood that one skilled in the art would be able to make these compounds by similar methods or by methods known to one skilled in the art. In general, starting components and reagents may be obtained from sources such as Sigma Aldrich, Lancaster Synthesis, Inc., Maybridge, Matrix Scientific, TCI, and Fluorochem USA, Strem, other commercial vendors, or synthesized according to sources known to those skilled in the art, or prepared as described in this disclosure.

Analytical Methods, Materials, and Instrumentation

Unless otherwise noted, reagents and solvents were used as received from commercial suppliers. Proton nuclear magnetic resonance (NMR) spectra were obtained on either Bruker Avance spectrometer or Varian Oxford 400 MHz spectrometer unless otherwise noted. Spectra are given in ppm ($\delta$) and coupling constants, J, are reported in Hertz. Tetramethylsilane (TMS) was used as an internal standard. Chemical shifts are reported in ppm relative to dimethyl sulfoxide ($\delta$ 2.50), methanol ($\delta$ 3.31), chloroform ($\delta$ 7.26) or other solvent as indicated in NMR spectral data. A small amount of the dry sample (2-5 mg) is dissolved in an appropriate deuterated solvent (1 mL). The chemical names were generated using ChemBioDraw Ultra v12 from CambridgeSoft.

Mass spectra (ESI-MS) were collected using a Waters System (Acquity UPLC and a Micromass ZQ mass spectrometer) or Agilent-1260 Infinity (6120 Quadrupole); all masses reported are the m/z of the protonated parent ions unless recorded otherwise. The sample was dissolved in a suitable solvent such as MeCN, DMSO, or MeOH and was injected directly into the column using an automated sample handler. The analysis is performed on Waters Acquity UPLC system (Column: Waters Acquity UPLC BEH C18 1.7 µm, 2.1×30 mm; Flow rate: 1 mL/min; 55° C. (column temperature); Solvent A: 0.05% formic acid in water, Solvent B: 0.04% formic acid in MeOH; gradient 95% Solvent A from 0 to 0.10 min; 95% Solvent A to 20% Solvent A from 0.10 to 0.50 min; 20% Solvent A to 5% Solvent A from 0.50 to 0.60 min; hold at 5% Solvent A from 0.6 min to 0.8 min; 5% Solvent A to 95% Solvent A from 0.80 to 0.90 min; and hold 95% Solvent A from 0.90 to 1.15 min.

LIST OF ABBREVIATIONS

P(OEt)$_3$ triethyl phosphite
rt room temperature
h hour(s)
aq aqueous
LCMS liquid chromatography mass spectrometry
MS mass spectrometry
m/z mass to charge ratio
NMR nuclear magnetic resonance
br broad
d; dd doublet; doublet of doublets
m multiplet
MHz megahertz
q quartet
t triplet
NBS N-bromosuccinimide
EtOAc ethyl acetate
THF tetrahydrofuran
DMF dimethylformamide
TEA triethylamine
MeOH methanol
MeCN acetonitrile
AcOH acetic acid
Pd(PPh$_3$)$_2$Cl$_2$ Bis(triphenylphosphine)palladium(II) dichloride
DMAP 4-dimethylaminopyridine
p-TsCl p-toluenesulfonyl chloride
IPA isopropyl alcohol
t-BuOH t-butanol
g grams mL milliliters
mmol millimoles
mg milligrams
min minutes
TBDMS-Cl tert-butyldimethylsilyl chloride
M molar
HPLC high performance liquid chromatography
Et$_2$O ethyl ether
DMSO dimethyl sulfoxide
LDA lithium diisopropylamide
TBAF tetra-n-butylammonium fluoride
MeMgBr methylmagnesium bromide
DIBAL-H diisobutylaluminum hydride
TBDMS-OTf tert-butyldimethylsilyl trifluoromethyl sulfonate
Rt retention time
CF$_3$TMS trifluoromethyltrimethylsilane
NaOMe sodium methoxide
Boc$_2$O di-tert-butyl dicarbonate
PPh$_3$ triphenylphosphine
n-BuLi n-butyllithium
DAST diethylaminosulfur trifluoride
TFA trifluoroacetic acid
HATU Hexafluorophosphate Azabenzotriazole Tetramethyl Uronium
DIPEA N,N-diisopropylethylamine
MeNO$_2$ nitromethane
Ms$_2$O methanesulfonic anhydride
PTSA p-toluenesulfonic acid
MsCl methanesulfonyl chloride
Ac$_2$O acetic anhydride
Cu(OTf)$_2$ copper II trifluoromethane sulfonate
TMSCN trimethylsilyl cyanide
m-CPBA meta-chloroperoxybenzoic acid
Pd(dppf)(Cl$_2$·CH$_2$Cl$_2$) [1,1'-Bis(diphenylphosphino)ferrocene]dichloropalladium(II) dichloromethane LCMS Conditions:

LCMS Method 1A: Instrument: API 2000, Triple Quad, ESI. Column: Mercury MS Synergi 2µ (20×4.0 mm), C12; Gradient: A—0.1% formic acid in water, B— acetonitrile; Time/% B: 0.0/30, 0.5/30, 1.5/95, 2.0/95, 2.5/30, 3.0/30; Flow: 2.0 mL/min; UV detection array 190-400; Mass detection 100-1000 (electrospray ionization); column temperature 30° C.

LCMS Method 2A: Instrument: API3000, column: Synergi 2.5µ (50×4.6 mm), MAX-RP 100 A; Gradient: A—0.1% formic acid in water, B— acetonitrile; Time/% B: 0.0/20, 0.2/50, 1.0/95, 2.5/95, 2.9/50, 3.2/20, 4/20; Flow: 1.2 mL/min; UV detection array 190-400 (Total Wavelength Chromatogram), Mass detection 100-1000 (electrospray ionization); column temperature 30° C.

LCMS Method 3A: Instrument: API 3200 Q Trap, Triple Quad, ESI. Column: Synergi 2.5µ (50×4.6 mm), MAX-RP 100 A; Gradient: A—0.1% formic acid in water, B— acetonitrile; Time/% B: 0.0/20, 0.2/50, 1.0/95, 2.7/95, 2.8/50, 4.0/20; Flow: 1.2 mL/min; UV detection array 190-400 (Total Wavelength Chromatogram); Mass detection 100-1000 (electrospray ionization); Column temperature: 30° C.

LCMS Method 4A: Instrument: Agilent 1100 series with Single Quad, Dual Mode mass spectrometer. Column: Zorbax XBD C18 (50×4.6 mm) 1.8µ; Gradient: A—0.1% formic acid in water, B— acetonitrile; Time/% B: 0.0/10, 0.5/10, 1.0/95.0, 2.0/95, 2.1/10, 3.5/10; Flow: 1.2 mL/min; UV detection array 200-400; Mass detection 100-1000 (electrospray ionization); Column temperature 40° C.

LCMS Method 4B: Instrument: Agilent 1100 series with Single Quad, Dual Mode mass spectrometer. Column: Synergi 2.5p MAX-RP 100 A Mercury; Gradient: A—0.1% formic acid in water, B—acetonitrile; Time/% B: 0.0/10, 0.5/10, 1/95.0, 2.0/10, 3.0/10; Flow: 2.0 mL/min; UV detection array 200-400; Mass detection 100-1000 (electrospray ionization); Column temperature 40° C.

LCMS Method 5A: Instrument: Agilent 1290-Infinity II. Column: Kinetex EVO 2.6µ (50×4.6 mm); gradient: A—0.1% formic acid in water, B—acetonitrile; Time/% B: 0.0/20, 0.25/20, 01.0/95.0, 2.5/95, 3.0/20, 4/20, flow 1.5 mL/min; UV detection array 200-400, Mass detection 100-1000 (electrospray ionization); Column temperature 40° C.

LCMS Method 6A: Instrument: Shimadzu Nexera LCMS-2020 with Single Quad. Column: Synergi 2.5µ (20×4.0 mm), MAX-RP 100 A Mercury; Gradient: A—0.1% formic acid in water, B—acetonitrile; Time/% B: 0.1/5, 0.5/5, 1.0/95, 1.5/95, 2.0/5, 3.0/5; Flow: 2.0 mL/min; UV detection array 200-400; Mass detection 100-1000 (electrospray ionization); Column temperature: 40° C.

LCMS Method 7A: Instrument: Agilent 1290 Infinity RRLC attached with Agilent 6120 Mass detector and Diode array Detector had a mobile phase (A) 2 mM ammonium acetate followed by 0.1% Formic acid in water (B) 0.1% Formic Acid in Acetonitrile, BEH C18 (50*21. mm) 1.7 µm, column oven temperature was
22° C., with flow rate 0.55 ml/min and runtime was 3.0 min LCMS Method 7B: Instrument: Waters H-class Acquity UPLC attached with SQ detector and Photo diode Array detector had a mobile phase (A) 2 mM ammonium acetate followed by 0.1% Formic acid in water (B) 0.1% Formic Acid in Acetonitrile, BEH C18 (50*21. mm) 1.7 µm column and column oven temperature was 22° C., with flow rate 0.55 ml/min and runtime was 3.0 min LCMS Method 7C: Instrument: Waters AcQuity UPLC attached with Waters AcQuity UPLC PDA and Waters AcQuity UPLC ELSD. Mass spec: Waters Qda. Mobile phase 0.1% Formic Acid in Water followed by 0.1% Formic Acid in Acetonitrile, AcQuity UPLC BEH C18 1.7 µm 2.1×30 mm, column temperature
50° C., with a flow rate of 1 mL/min and runtime was 5.20 min NMR Instrument details: Nuclear magnetic resonance spectroscopy was performed using any of the following instrumental conditions NMR-300: VARIAN 300 (Mercury) equipped with ASW Probe (Proton, Carbon, Fluorine, Phosphorous) and Z-gradient, operating VnmrJ 2.2

NMR-400: VARIAN 400 equipped with ATB Probe (Proton, Carbon, Fluorine) and Z-gradient, operating VnmrJ 3.2

NMR-600: INOVA 600 equipped with HCN Probe (Proton, Carbon, Nitrogen) and Z-gradient, operating VnmrJ 2.2

NMR-400-b: Bruker 400 equipped with BBFO Cryo-Probe (proton, carbon, fluorine and broadband) and Z-gradient, operated by TOPSPIN 3.5

NMR-400-c: Bruker NMR 400 MHz Avance III HD equipped with 5 mm PABBO BB/19F-1H/D Z-GRD

EXPERIMENTAL PROCEDURES

Example 1: Synthesis of (1r,3r)-3-(4-fluoro-3-(trifluoromethyl)phenoxy)-N-((6-methylisoquinolin-5-yl)methyl)cyclobutan-1-amine, HCl

Step 1.1: Synthesis of 6-methylisoquinoline-5-carbaldehyde

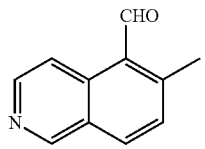

To the solution of 5-bromo-6-methylisoquinoline [CAS No. 1146298-61-4] (0.4 g, 1.80 mmol) in dry THF (10 mL), n-BuLi (2.5M in THF) (1.1 mL, 2.70 mmol) was added dropwise at −78° C. and stirred for 30 min under argon atmosphere. DMF (0.27 mL, 3.60 mmol) was added dropwise at −78° C., temperature was raised to rt gradually and stirred for 1 h. Reaction mixture was quenched with 10% NH$_4$Cl solution and extracted with EtOAc 3×'s. The combined organic portion was washed with brine solution, dried over anhydrous Na$_2$SO$_4$, filtered and concentrated in vacuo to yield the crude product. The crude was purified by flash chromatography (12 g SiliCycle column, 0-50% EtOAc in Hexane elution) to provide 6-methylisoquinoline-5-carbaldehyde (0.16 g, 52%). MS (ESI+) [Method 1A]: m/z 172.0 (M+H); Rt 0.14 min. $^1$H NMR (400 MHz, CD$_3$OD) δ 10.89 (s, 1H), 9.22 (s, 1H), 8.88 (d, J=6.4 Hz, 1H), 8.51 (d, J=6.0 Hz, 1H), 8.23 (d, J=8.0 Hz, 1H), 7.63 (d, J=8.0 Hz, 1H), 2.89 (s, 3H).

Step 1.2: Synthesis of tert-butyl ((1r,3r)-3-(4-fluoro-3 (trifluoromethyl)phenoxy)cyclobutyl)carbamate

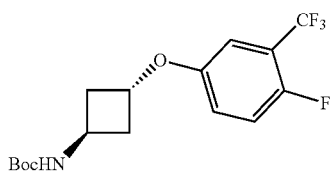 [SMILES: CC(C)(C)OC(=O)N[C@H]1C[C@H](Oc2ccc(F)c(C(F)(F)F)c2)C1]

To the solution of tert-butyl ((1s,3s)-3-hydroxycyclobutyl)carbamate (6.0 g, 32.04 mmol) in THF (60 mL), 4-fluoro-3-(trifluoromethyl)phenol [CAS No. 61721-07-1] (6.3 g, 35.25 mmol), PPh$_3$ (12.6 g, 48.07 mmol) and diisopropyl azodicarboxylate (9.4 mL, 48.07 mmol) were added at rt. The reaction mixture was stirred at 50° C. for 16 h under N$_2$ atmosphere. The reaction mixture was concentrated and the residue was purified by flash chromatography (40 g SiliCycle column, 0-30% EtOAc in Hexane elution) to provide tert-butyl ((1r,3r)-3-(4-fluoro-3-(trifluoromethyl)phenoxy)cyclobutyl)carbamate (8.4 g, 75%). $^1$H NMR (300 MHz, CDCl$_3$) δ 7.12-7.08 (m, 1H), 6.95-6.87 (m, 2H), 4.79-4.72 (m, 1H), 4.31-4.27 (m, 1H), 2.59-2.50 (m, 2H), 2.43-2.37 (m, 2H), 1.45 (s, 9H).

Step 1.3: Synthesis of (1r,3r)-3-(4-fluoro-3-(trifluoromethyl)phenoxy)cyclobutan-1-amine, HCl

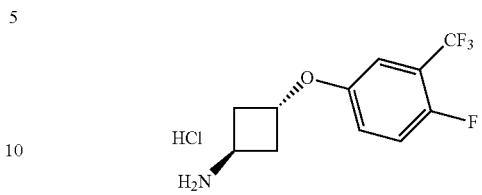

A round bottom flask was charged with tert-butyl ((1r,3r)-3-(4-fluoro-3-(trifluoromethyl)phenoxy)cyclobutyl)carbamate (8.4 g, 28.05 mmol) and HCl solution (20% in 1,4-dioxane) (80 mL), and stirred at rt for 16 h. Then the reaction mixture was concentrated in vacuo. The residue was triturated with pentane, the solid appeared was filtered and dried to yield (1r,3r)-3-(4-fluoro-3-(trifluoromethyl)phenoxy)cyclobutan-1-amine, HCl (5.1 g crude). LCMS [Method 6A]: m/z 250.1 [M+H]$^+$; Rt 1.29 min.

Step 1.4: Synthesis of (1r,3r)-3-(4-fluoro-3-(trifluoromethyl)phenoxy)-N-((6-methylisoquinolin-5-yl)methyl)cyclobutan-1-amine, HCl

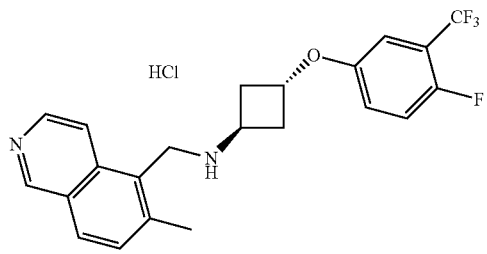 [SMILES: Cc1ccc2cnccc2c1CN[C@H]1C[C@H](Oc2ccc(F)c(C(F)(F)F)c2)C1 ; Cl]

The solution of (1r,3r)-3-(4-fluoro-3-(trifluoromethyl)phenoxy)cyclobutan-1-amine, HCl (80 mg, 0.28 mmol) and TEA (40 mg, 0.28 mmol) in MeOH (2 mL) was stirred at rt for 15 min; then 6-methylisoquinoline-5-carbaldehyde (43 mg, 0.25 mmol) and AcOH (0.01 mL) were added, and stirred at rt for 16 h under argon. Then NaBH$_4$ (22 mg, 0.56 mmol) was added at 0° C. and stirred at rt for further 1 h. Reaction mixture was concentrated in vacuo, residue was diluted with water and extracted 3× with EtOAc. The combined organic portion was washed with brine solution, dried over anhydrous Na$_2$SO$_4$, filtered and concentrated in vacuo. Prep-HPLC (Column: XBRIDGE C18, (150 mm×19 mm), 5.0µ; Mobile Phase: 0.1% NH$_4$OH in water and Acetonitrile) of the crude afforded (1r,3r)-3-(4-fluoro-3-(trifluoromethyl)phenoxy)-N-((6-methylisoquinolin-5-yl)methyl)cyclobutan-1-amine. To the solution of the isolated product in 1,4-dioxane (1 mL), was added HCl solution (4M in 1,4-dioxane) (2 mL) at 10° C., stirred at rt for 4 h, and then concentrated in vacuo to afford (1r,3r)-3-(4-fluoro-3-(trifluoromethyl)phenoxy)-N-((6-methylisoquinolin-5-yl)methyl)cyclobutan-1-amine, HCl (80 mg, 93%). MS (ESI+) [Method 5A]: m/z 405.1 (M+H); Rt 1.32 min. $^1$H NMR (400 MHz, CD$_3$OD) δ 9.78 (s, 1H), 8.72 (s, 2H), 8.52 (d, J=8.8 Hz, 1H), 8.04 (d, J=8.0 Hz, 1H), 7.30 (t, J=9.6 Hz, 1H), 7.16-7.10 (m, 2H), 5.06-5.04 (m, 1H), 4.84 (s, 2H), 4.41-4.38 (m, 1H), 2.94-2.90 (m, 2H), 2.88 (s, 3H), 2.78-2.72 (m, 2H).

Example 2: Synthesis of (1r,3r)-N-((6-methylisoqui-nolin-5-yl)methyl)-3-((6-(trifluoromethyl)pyridin-3-yl)oxy)cyclobutan-1-amine, HCl Step 2.1: Synthesis of tert-butyl ((1r,3r)-3-((6-(trifluoromethyl)pyridin-3-yl)oxy)cyclobutyl)carbamate

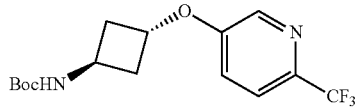

To the solution of tert-butyl ((1s,3s)-3-hydroxycyclobutyl)carbamate (200 mg, 1.07 mmol) in THF (5 mL), 6-(trifluoromethyl)pyridin-3-ol [CAS No. 216766-12-0] (191 mg, 1.17 mmol), PPh$_3$ (420 mg, 1.60 mmol) and diisopropyl azodicarboxylate (0.25 mL, 1.60 mmol) were added at rt. The reaction mixture was stirred at 50° C. for 16 h under N$_2$ atmosphere. Reaction mixture was diluted with water and extracted 3× with EtOAc. The combined organic portion was washed with brine solution, dried over anhydrous Na$_2$SO$_4$, filtered and concentrated in vacuo. The residue was purified by flash chromatography (12 g SiliCycle column, 0-20% EtOAc in Hexane elution) to provide tert-butyl ((1r,3r)-3-((6-(trifluoromethyl)pyridin-3-yl)oxy)cyclobutyl)carbamate (300 mg, 71%). $^1$H NMR (300 MHz, CDCl$_3$) δ 8.26 (d, J=2.8 Hz, 1H), 7.60 (s, 1H), 7.14 (dd, J=8.8, 3.2 Hz, 1H), 4.90-4.85 (m, 1H), 4.78 (br, 1H), 4.33-4.29 (m, 1H), 2.62-2.56 (m, 2H), 2.50-2.46 (m, 2H), 1.45 (s, 9H).

Step 2.2: Synthesis of (1r,3r)-3-((6-(trifluoromethyl)pyridin-3-yl)oxy)cyclobutan-1-amine, HCl [C-07838-037]

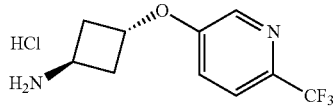

To the solution of with tert-butyl ((1r,3r)-3-((6-(trifluoromethyl)pyridin-3-yl)oxy)cyclobutyl)carbamate (300 mg, 0.90 mmol) in CH$_2$Cl$_2$, HCl solution (4M in 1,4-dioxane) (3 mL) was added, and stirred at rt for 16 h. Then the reaction mixture was concentrated in vacuo to afford crude (1r,3r)-3-((6-(trifluoromethyl)pyridin-3-yl)oxy)cyclobutan-1-amine, HCl (300 mg, 109%). LCMS [Method 6A]: m/z 233.1 [M+H]$^+$; Rt 1.22 min.

Step 2.3: Synthesis of (1r,3r)-N-((6-methylisoquinolin-5-yl)methyl)-3-((6-(trifluoromethyl)pyridin-3-yl)oxy)cyclobutan-1-amine, HCl

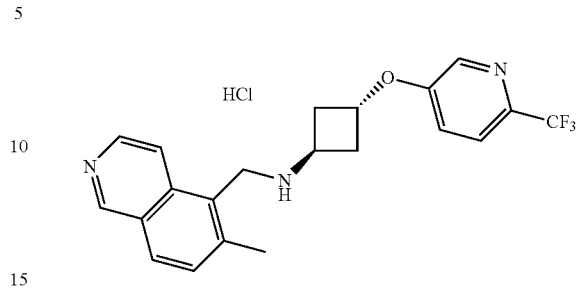

The title compound was synthesized in a similar manner as described in Step 1.4, using (1r,3r)-3-((6-(trifluoromethyl)pyridin-3-yl)oxy)cyclobutan-1-amine, HCl (100 mg, 0.37 mmol) and 6-methylisoquinoline-5-carbaldehyde (Example, 1, Step 1.1, 55 mg, 0.34 mmol). Purification of the crude by flash chromatography (12 g SiliCycle column, 0-8% MeOH in CH$_2$Cl$_2$ elution), followed by treatment with HCl solution (4M in 1,4-dioxane) afforded (1r,3r)-N-((6-methylisoquinolin-5-yl)methyl)-3-((6-(trifluoromethyl)pyridin-3-yl)oxy)cyclobutan-1-amine, HCl (40 mg, 34%). MS (ESI+) [Method 6A]: m/z 388.3 (M+H); Rt 1.24 min. $^1$H NMR (400 MHz, CD$_3$OD) δ 9.76 (s, 1H), 8.71 (s, 2H), 8.51 (d, J=8.4 Hz, 1H), 8.34 (d, J=2.8 Hz, 1H), 8.02 (d, J=8.8 Hz, 1H), 7.78 (d, J=8.4 Hz, 1H), 7.48-7.46 (m, 1H), 5.21-5.17 (m, 1H), 4.85 (s, 2H), 4.43-4.39 (m, 1H), 3.02-2.97 (m, 2H), 2.88 (s, 3H), 2.81-2.77 (m, 2H).

Example 3: Synthesis of (1r,3r)-3-(4-fluoro-3-(trifluoromethyl)phenoxy)-N-((6-fluoroisoquinolin-5-yl)methyl)cyclobutan-1-amine, HCl Step 3.1: Synthesis of 6-fluoroisoquinoline-5-carbaldehyde

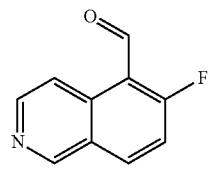 [SMILES: O=Cc1c(F)ccc2cnccc12]

To the solution of 6-fluoroisoquinoline [CAS No. 1075-11-2] (0.4 g, 2.72 mmol) in anhydrous THF (10 mL), LDA (2M in THF) (2.04 mL, 4.08 mmol) was added dropwise at −78° C. and stirred for 2.5 h under N$_2$ atmosphere. Piperidine-1-carbaldehyde [CAS No. 2591-86-8] (0.92 g, 8.15 mmol) dissolved in THF (5 mL) was added dropwise at −78° C. over a period of 0.5 h and stirred for 1 h, while temperature was raised slowly to 0° C. Then the reaction was quenched with saturated NH$_4$Cl solution and extracted with EtOAc twice. The combined organic portion was washed with brine, dried over anhydrous Na$_2$SO$_4$, filtered and concentrated in vacuo to yield the crude product. The crude was purified by flash chromatography (12 g SiliCycle column, 0-20% EtOAc in Hexane elution) to provide 6-fluoroisoquinoline-5-carbaldehyde (0.17 g, 35%). MS (ESI+) [Method 6A]: m/z 175.9 (M+H); Rt 0.86 min.

Step 3.2: Synthesis of (1r,3r)-3-(4-fluoro-3-(trifluoromethyl)phenoxy)-N-((6-fluoroisoquinolin-5-yl)methyl)cyclobutan-1-amine, HCl

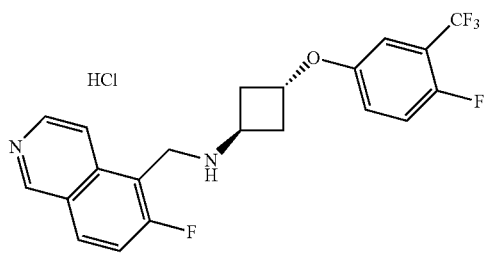 [SMILES: Fc1ccc(O[C@H]2C[C@H](NCc3c(F)ccc4cnccc34)C2)cc1C(F)(F)F ; Cl]

(1r,3r)-3-(4-fluoro-3-(trifluoromethyl)phenoxy)-N-((6-fluoroisoquinolin-5-yl)methyl)cyclobutan-1-amine, HCl was prepared in a similar manner as described in Step 1.4, using (1r,3r)-3-(4-fluoro-3-(trifluoromethyl)phenoxy)cyclobutan-1-amine, HCl (Step 1.3, 200 mg, 0.70 mmol) and 6-fluoroisoquinoline-5-carbaldehyde (111 mg, 0.63 mmol). The residue was purified by prep-HPLC (Column: LUNA Phenomenex (150 mm×21.2 mm), 5.0μ; Mobile Phase: 0.1% HCO$_2$H in water and acetonitrile) to afford the product. To the isolated product, HCl solution (4M in 1,4-dioxane) (4 mL) was added at 10° C., stirred at rt for 2 h, concentrated in vacuo, then lyophilized to afford (1r,3r)-3-(4-fluoro-3-(trifluoromethyl)phenoxy)-N-((6-fluoroisoquinolin-5-yl)methyl)cyclobutan-1-amine, HCl (139 mg, 44%). MS (ESI+) [Method 6A]: m/z 409.1 (M+H); Rt 1.31 min. $^1$H NMR (400 MHz, CD$_3$OD) δ 9.90 (s, 1H), 8.87-8.85 (m, 1H), 8.81-8.77 (m, 2H), 8.02 (t, J=9.2 Hz, 1H), 7.28 (t, J=9.6 Hz, 1H), 7.15-7.09 (m, 2H), 5.09-5.05 (m, 1H), 4.84 (s, 2H), 4.31-4.27 (m, 1H), 2.97-2.90 (m, 2H), 2.73-2.68 (m, 2H).

Example 4: Synthesis of 3-fluoro-6-((1r,3r)-3-(((6-fluoroisoquinolin-5-yl)methyl)amino)cyclobutoxy)-2-(trifluoromethyl)aniline, HCl and 5-fluoro-2-((1r,3r)-3-(((6-fluoroisoquinolin-5-yl)methyl)amino)cyclobutoxy)-4-(trifluoromethyl)aniline, HCl Step 4.1: Synthesis of (1r,3r)-3-(4-fluoro-2-nitro-3-(trifluoromethyl)phenoxy)-N-((6-fluoroisoquinolin-5-yl)methyl)cyclobutan-1-amine

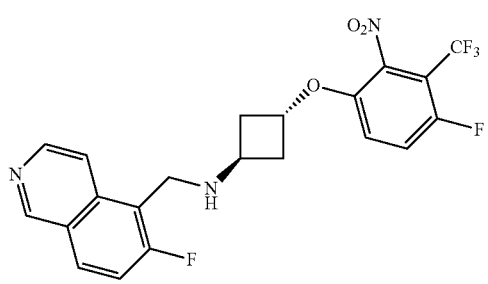 [SMILES: O=[N+]([O-])c1c(O[C@H]2C[C@H](NCc3c(F)ccc4cnccc34)C2)ccc(F)c1C(F)(F)F]

To a round bottom flask, charged with concentrated H$_2$SO$_4$ (2 mL), KNO$_3$ (68 mg, 0.68 mmol) was added at 0° C. Then (1r,3r)-3-(4-fluoro-3-(trifluoromethyl)phenoxy)-N-((6-fluoroisoquinolin-5-yl)methyl)cyclobutan-1-amine (Step 3.2, 230 mg, 0.56 mmol), dissolved in H$_2$SO$_4$ (2 mL), was added dropwise at 0° C. and stirred at rt for 16 h.

Reaction mixture was poured dropwise onto ice, basified with aqueous NH$_4$OH (30%) and extracted 3× with EtOAc. The combined organic portion was washed with brine, dried over anhydrous Na$_2$SO$_4$, filtered and concentrated in vacuo to afford mixture of (1r,3r)-3-(4-fluoro-2-nitro-3-(trifluoromethyl)phenoxy)-N-((6-fluoroisoquinolin-5-yl)methyl)cyclobutan-1-amine and (1r,3r)-3-(4-fluoro-2-nitro-5-(trifluoromethyl)phenoxy)-N-((6-fluoroisoquinolin-5-yl)methyl)cyclobutan-1-amine (200 mg crude). MS (ESI+) [Method 6A]: m/z 454.1 (M+H); Rt 1.32 min.

Step 4.2: Synthesis of 5-fluoro-2-((1r,3r)-3-(((6-fluoroisoquinolin-5-yl)methyl)amino)cyclobutoxy)-4-(trifluoromethyl)aniline, HCl

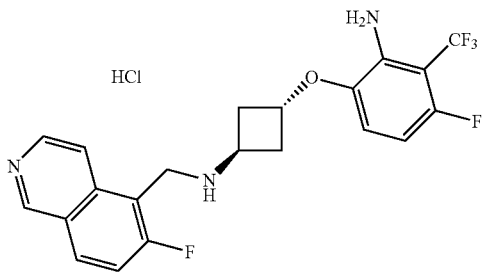 [SMILES: Nc1c(O[C@H]2C[C@H](NCc3c(F)ccc4cnccc34)C2)ccc(F)c1C(F)(F)F ; Cl]

To the solution of (1r,3r)-3-(4-fluoro-2-nitro-5-(trifluoromethyl)phenoxy)-N-((6-fluoroisoquinolin-5-yl)methyl)cyclobutan-1-amine and (1r,3r)-3-(4-fluoro-2-nitro-3-(trifluoromethyl)phenoxy)-N-((6-fluoroisoquinolin-5-yl)methyl)cyclobutan-1-amine (200 mg, 0.44 mmol) in AcOH (2 mL), Zn-dust (50 mg, 0.75 mmol) was added at 0° C. and stirred at rt for 4 h. The reaction mixture was basified with 2N NaOH solution and extracted 3× with EtOAc. The combined organic portion was washed with brine, dried over anhydrous Na$_2$SO$_4$, filtered and concentrated in vacuo. The residue was purified by prep-HPLC (Column: XBRIDGE (150 mm×21.20 mm), 5.0μ; Mobile Phase: 0.02% NH$_4$OH in water and acetonitrile) to afford the products, 5-fluoro-2-((1r,3r)-3-(((6-fluoroisoquinolin-5-yl)methyl)amino)cyclobutoxy)-4-(trifluoromethyl)aniline and 3-fluoro-6-((1r,3r)-3-(((6-fluoroisoquinolin-5-yl)methyl)amino)cyclobutoxy)-2-(trifluoromethyl)aniline. To the isolated products, HCl solution (4M in 1,4-dioxane) (2 mL) was added at 10° C., stirred at rt for 2 h, concentrated, the residue was washed with Et$_2$O-Pentane and in vacuo to afford the HCl salts. 3-fluoro-6-((1r,3r)-3-(((6-fluoroisoquinolin-5-yl)methyl)amino)cyclobutoxy)-2-(trifluoromethyl)aniline, HCl (15 mg, 7%): Rf 11.684 min(Column: WATERS XBRIDGE C18 (150 mm×4.6 mm) 5.0μ; Mobile phase: 0.05% NH$_4$OH in water and acetonitrile). MS (ESI+) [Method 6A]: m/z 424.2 (M+H); Rt 1.31 min. $^1$H NMR (400 MHz, CD$_3$OD) δ 9.92 (s, 1H), 8.92-8.90 (m, 1H), 8.83-8.78 (m, 2H), 8.04 (t, J=9.2 Hz, 1H), 6.95-6.92 (m, 2H), 5.15-5.12 (m, 1H), 4.85 (s, 2H), 4.37-4.41 (m, 1H), 2.95-2.92 (m, 2H), 2.79-2.76 (m, 2H).

Example 5: Synthesis of (1r,3r)-3-(4-fluoro-3-(trifluoromethyl)phenoxy)-N-((6-fluoroisoquinolin-5-yl)methyl)cyclobutan-1-amine, HCl

Step 5.1: Synthesis of 8-nitro-5-vinylisoquinoline

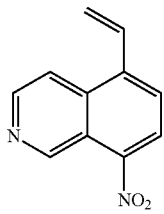

The stirred solution of 5-bromo-8-nitroisoquinoline [CAS No. 63927-23-1] (0.50 g, 1.98 mmol) and tributyl(vinyl)stannane (0.72 g, 2.37 mmol) in toluene (10 mL) was degassed with argon for 10 min. Then Pd(PPh$_3$)$_2$Cl$_2$ (0.13 g, 0.19 mmol) was added, degassed and heated at 100° C. for 13 h under argon atmosphere. Reaction mixture was cooled to rt, filtered through a celite bed and the bed was washed with EtOAc. The combined filtrate was washed with water, brine, dried over anhydrous Na$_2$SO$_4$, filtered and concentrated in vacuo. The residue was purified by flash chromatography (12 g SiliCycle column, 0-20% EtOAc in Hexane elution) to provide 8-nitro-5-vinylisoquinoline (0.10 g, 25%). MS (ESI+) [Method 6A]: m/z 201.0 (M+H); Rt 1.47 min.

Step 5.2: Synthesis of 8-nitroisoquinoline-5-carbaldehyde

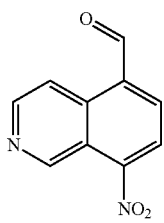

To the solution of 8-nitro-5-vinylisoquinoline (0.15 g, 0.75 mmol) in t-BuOH-1,4-dioxane (15 mL, 1:2 v/v), OsO$_4$ (6 mg, 0.02 mmol) was added at rt and stirred for 15 min. Then NaIO$_4$ (0.8 g, 3.76 mmol) dissolved in water (3 mL) was added dropwise and stirred at rt for 16 h. Reaction mixture was diluted with water and extracted with EtOAc twice. The combined organic portion was washed with brine, dried over anhydrous Na$_2$SO$_4$, filtered and concentrated in vacuo. The residue was purified by flash chromatography (12 g SiliCycle column, 0-25% EtOAc in Hexane elution) to provide 8-nitroisoquinoline-5-carbaldehyde (60 mg, 40%). MS (ESI+) [Method 6A]: m/z 202.9 (M+H); Rt 0.40 min.

Step 5.3: Synthesis of (1r,3r)-3-(4-fluoro-3-(trifluoromethyl)phenoxy)-N-((8-nitroisoquinolin-5-yl)methyl)cyclobutan-1-amine

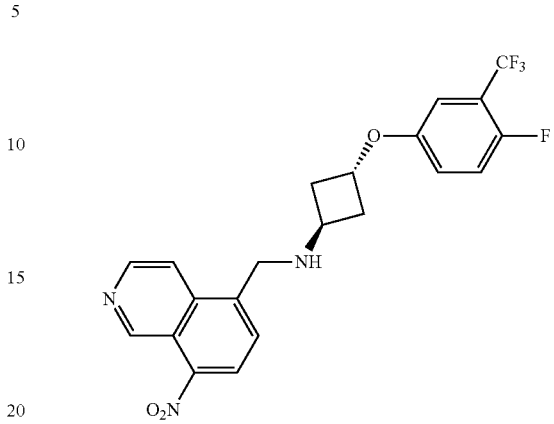

The title compound was synthesized following the procedure as described in step 1.4, using (1r,3r)-3-(4-fluoro-3-(trifluoromethyl)phenoxy)cyclobutan-1-amine, HCl (Step 1.3, 85 mg, 0.30 mmol) and 8-nitroisoquinoline-5-carbaldehyde (54 mg, 0.27 mmol). MS (ESI+) [Method 1A]: m/z 435.6 (M+H); Rt 0.45 min.

Step 5.4: Synthesis of 5-((((1r,3r)-3-(4-fluoro-3-(trifluoromethyl)phenoxy)cyclobutyl)amino)methyl)isoquinolin-8-amine, HCl [C-07482-074]

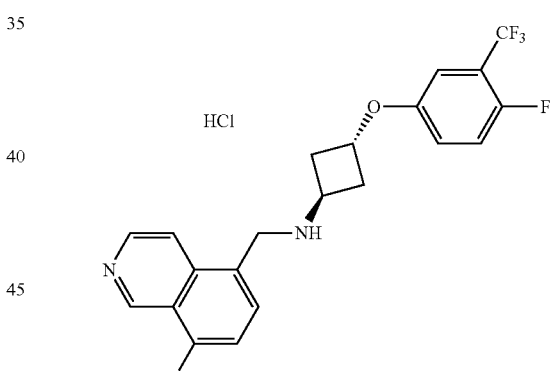

To the solution of (1r,3r)-3-(4-fluoro-3-(trifluoromethyl)phenoxy)-N-((8-nitroisoquinolin-5-yl)methyl)cyclobutan-1-amine (70 mg, 0.16 mmol) in AcOH (5 mL), was added Zn dust (53 mg, 0.80 mmol) at rt and stirred for 2 h. The reaction mixture was filtered through celite bed, bed was washed with AcOH. The combined filtrate was concentrated in vacuo. The residue was basified with saturated NaHCO$_3$ solution and extracted with CH$_2$Cl$_2$ twice. The combined organic portion was washed with brine solution, dried over anhydrous Na$_2$SO$_4$, filtered and concentrated in vacuo. The residue was purified by prep-HPLC (Column: GEMINI-NX-C18 (150 mm×21.20 mm), 5.0µ; Mobile Phase: 0.01% NH$_4$OH in water and acetonitrile-MeOH (1:1)). To the isolated product, HCl solution (4M in 1,4-dioxane) (1 mL) was added at 10° C., stirred at rt for 1 h, concentrated in vacuo, triturated with Et$_2$O-Pentane, collected solid was dried to provide 5-((((1r,3r)-3-(4-fluoro-3-(trifluoromethyl)

phenoxy)cyclobutyl)amino)methyl)isoquinolin-8-amine, HCl (8 mg, 11%). MS (ESI+) [Method 6A]: m/z 406.3 (M+H); Rt 1.29 min. $^1$H NMR (400 MHz, CD$_3$OD) δ 9.73 (s, 1H), 8.43 (d, J=7.2 Hz, 1H), 8.33 (d, J=7.2 Hz, 1H), 8.00 (d, J=8.4 Hz, 1H), 7.28 (d, J=7.2 Hz, 1H), 7.12-7.08 (m, 3H), 5.02-4.98 (m, 1H), 4.55 (s, 2H), 4.20-4.18 (m, 1H), 2.86-2.80 (m, 2H), 2.67-2.61 (m, 2H).

Example 6: Synthesis of (6-fluoro-5-(((((1r,3r)-3-(4-fluoro-3-(trifluoromethyl)phenoxy)cyclobutyl) amino)methyl)isoquinolin-8-yl)methanol, HCl (or trans-(6-fluoro-5-(((3-(4-fluoro-3-(trifluoromethyl) phenoxy)cyclobutyl)amino)methyl)isoquinolin-8-yl) methanol)

Step 6.1: Synthesis of 1-(2-bromo-4-fluorophenyl)-N-(2,2-dimethoxyethyl)methanimine

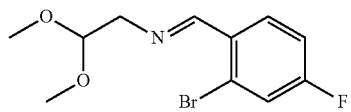 [SMILES: COC(C/N=C/c1ccc(F)cc1Br)OC]

A two necked round bottom flask, fitted with Dean Stark apparatus, was charged with 2-bromo-4-fluorobenzaldehyde [CAS No. 59142-68-6] (250.0 g, 1231.47 mmol), 2,2-dimethoxyethan-1-amine (268 mL, 2459.77 mmol) and toluene (1000 mL). The reaction mixture was stirred at 130° C. for 16 h, during azeotropic removal of H$_2$O. Then the reaction mixture was concentrated in vacuo to afford crude 1-(2-bromo-4-fluorophenyl)-N-(2,2-dimethoxyethyl)methanimine. $^1$H NMR (300 MHz, CDCl$_3$) δ 8.58 (s, 1H), 8.04 (dd, J=8.7, 6.3 Hz, 1H), 7.30 (dd, J=8.1, 2.4 Hz, 1H), 7.05 (td, J=8.7, 2.4 Hz, 1H), 4.68 (t, J=5.4 Hz, 1H), 3.81 (d, J=5.4 Hz, 1H), 3.42 (s, 6H).

Step 6.2: Synthesis of N-(2-bromo-4-fluorobenzyl)-2,2-dimethoxyethan-1-amine

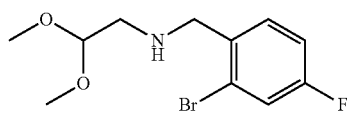 [SMILES: COC(CNCc1ccc(F)cc1Br)OC]

To the stirred solution of 1-(2-bromo-4-fluorophenyl)-N-(2,2-dimethoxyethyl)methanimine (404.0 g, 1392.4 mmol) in MeOH (2000 mL), NaBH$_4$ (105.3 g, 2784.9 mmol) was added portion wise at 0° C. The reaction mixture was stirred at rt for 16 h. Then the reaction mixture was concentrated in vacuo, residue was diluted with water and extracted 3× with EtOAc. The combined organic portion was washed with brine, dried over anhydrous Na$_2$SO$_4$, filtered and concentrated in vacuo to afford crude N-(2-bromo-4-fluorobenzyl)-2,2-dimethoxyethan-1-amine (378.0 g, 92%). MS (ESI+) [Method 6A]: m/z 292.1 (M+H); Rt 1.25 min. $^1$H NMR (400 MHz, CDCl$_3$) δ 7.36 (dd, J=8.4, 2.0 Hz, 1H), 7.27 (dd, J=8.4, 2.8 Hz, 1H), 7.01-6.98 (m, 1H), 4.48 (t, J=5.6 Hz, 1H), 3.84 (s, 2H), 3.36 (s, 6H), 2.72 (d, J=5.2 Hz, 2H).

Step 6.3: Synthesis of N-(2-bromo-4-fluorobenzyl)-N-(2,2-dimethoxyethyl)-4-methylbenzenesulfonamide

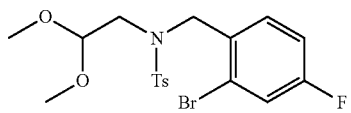 [SMILES: COC(CN(Cc1ccc(F)cc1Br)S(=O)(=O)c1ccc(C)cc1)OC]

To the solution of N-(2-bromo-4-fluorobenzyl)-2,2-dimethoxyethan-1-amine (378.0 g, 1293.8 mmol), TEA (541 mL, 1940.7 mmol) and DMAP (15.8 g, 129.4 mmol) in CH$_2$Cl$_2$ (2000 mL), p-TsCl was added portion wise at 0° C., and the reaction mixture was stirred at rt for 16 h. Then the reaction mixture was diluted with water and extracted with CH$_2$Cl$_2$ twice. The combined organic portion was washed with brine, dried over anhydrous Na$_2$SO$_4$, filtered and concentrated in vacuo. The residue was purified by column chromatography (Silica-gel 60-120 mesh size, 0-30% EtOAc in Hexane elution) to provide N-(2-bromo-4-fluorobenzyl)-N-(2,2-dimethoxyethyl)-4-methylbenzenesulfonamide (568 g, 98%). MS (ESI+) [Method 6A]: m/z 414.0 (M+H); Rt 1.67 min. $^1$H NMR (600 MHz, CDCl$_3$) δ 7.72 (d, J=8.4 Hz, 2H), 7.50 (dd, J=9.0, 6.0 Hz, 1H), 7.33 (d, J=8.4 Hz, 2H), 7.26-7.24 (m, 1H), 7.03 (td, J=9.0, 3.0 Hz, 1H), 4.48 (s, 2H), 4.36 (t, J=5.4, 1H), 3.29 (d, J=5.4 Hz, 2H), 3.23 (s, 6H), 2.45 (s, 3H), Step 6.4: Synthesis of 8-bromo-6-fluoroisoquinoline

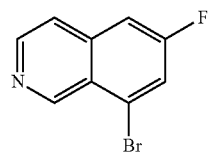 [SMILES: Fc1cc(Br)c2cnccc2c1]

To the stirred solution of AlCl$_3$ (836.0 g, 6269.68 mmol) in anhydrous CH$_2$Cl$_2$ (2200 mL), N-(2-bromo-4-fluorobenzyl)-N-(2,2-dimethoxyethyl)-4-methylbenzenesulfonamide (560.0 g, 1254.68 mmol) dissolved in CH$_2$Cl$_2$ (800 mL) was added dropwise at −10° C. Then the reaction mixture was stirred at rt for 16 h under N$_2$. The reaction mixture was poured onto ice, basified with 30% NaOH solution. The solid formed was filtered through a celite bed, and the bed was washed with CH$_2$Cl$_2$. The organic portion was separated and the aqueous layer was extracted with CH$_2$Cl$_2$ twice. The combined organic layer was washed with brine, anhydrous Na$_2$SO$_4$, filtered and concentrated in vacuo to afford crude 8-bromo-6-fluoroisoquinoline (300 g, 106%). MS (ESI+) [Method 6A]: m/z 226.0, 228.0 (M+H); Rt 1.41 min. H NMR (600 MHz, CDCl$_3$) δ 9.56 (s, 1H), 8.60 (d, J=6.0 Hz, 1H), 7.66 (dd, J=7.8, 1.6 Hz, 1H), 7.59 (d, J=6.0 Hz, 1H), 7.42 (dd, J=8.4, 1.8 Hz, 1H).

Step 6.5: Synthesis of 6-fluoro-8-vinylisoquinoline

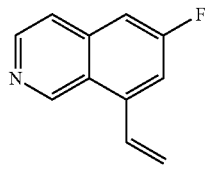

The stirred solution of 8-bromo-6-fluoroisoquinoline [CAS No. 1258833-77-0] (25.0 g, 110.5 mmol), potassium trifluoro(vinyl)borate (29.6 g, 221.1 mmol) and TEA (61.6 mL, 442.3 mmol) in IPA (400 mL), was degassed with $N_2$ for 10 min. Then Pd(dppf)Cl$_2$·CH$_2$Cl$_2$ (9.03 g, 11.05 mmol) was added, degassed and heated at 100° C. for 2 h under $N_2$ atmosphere. Reaction mixture was cooled to rt, diluted with water and extracted with EtOAc twice. The combined organic portion was washed with brine, dried over anhydrous Na$_2$SO$_4$, filtered and concentrated in vacuo to yield the crude product. The crude was purified by flash chromatography (80 g SiliCycle column, 0-20% EtOAc in Hexane elution) to provide 6-fluoro-8-vinylisoquinoline (15.0 g, 78%). MS (ESI+) [Method 8]: m/z 174.1 (M+H); Rt 1.186 min.

Step 6.6: Synthesis of 6-fluoroisoquinoline-8-carbaldehyde

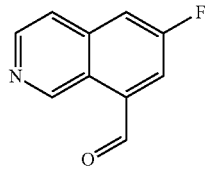 [SMILES: O=Cc1cc(F)cc2ccncc12]

The title compound was prepared according to the procedure in Step 5.2. The residue was purified by flash chromatography (80 g SiliCycle column, 0-25% EtOAc in Hexane elution) to provide 6-fluoroisoquinoline-8-carbaldehyde (11.0 g, 72%). MS (ESI+) [Method 1A]: m/z 176.1 (M+H); Rt 0.17 min.

Step 6.7: Synthesis of (6-fluoroisoquinolin-8-yl)methanol

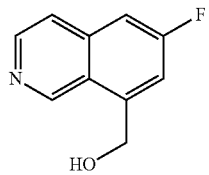 [SMILES: OCc1cc(F)cc2ccncc12]

To the stirred solution of 6-fluoroisoquinoline-8-carbaldehyde (11.0 g, 62.79 mmol) in MeOH (220 mL), NaBH$_4$ (3.56 g, 94.19 mmol) was added portion wise at 0° C. The reaction mixture was stirred at 0° C. for 1 h. Then the reaction mixture was concentrated in vacuo, residue was diluted with water and extracted with EtOAc twice. The combined organic portion was washed with brine, dried over anhydrous Na$_2$SO$_4$, filtered and concentrated in vacuo to afford crude (6-fluoroisoquinolin-8-yl)methanol (11.0 g, 99%). MS (ESI+) [Method 1A]: m/z 178.2 (M+H); Rt 0.12 min.

Step 6.8: Synthesis of 8-(((tert-butyldimethylsilyl)oxy)methyl)-6-fluoroisoquinoline

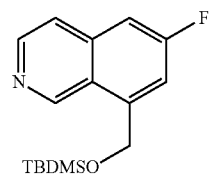 [SMILES: CC(C)(C)[Si](C)(C)OCc1cc(F)cc2ccncc12]

To the stirred solution of (6-fluoroisoquinolin-8-yl)methanol (11.0 g, 62.08 mmol) and imidazole (21.1 g, 309.98 mmol) in DMF (110 mL), TBDMS-Cl (28.0 g, 185.77 mmol) was added portion wise at 0° C. The reaction mixture was stirred at rt for 16 h. Then the reaction mixture was diluted with water and extracted with CH$_2$Cl$_2$ twice. The combined organic portion was washed with brine, dried over anhydrous Na$_2$SO$_4$, filtered and concentrated in vacuo. The residue was purified by flash chromatography (80 g SiliCycle column, 0-15% EtOAc in Hexane elution) to afford 8-(((tert-butyldimethylsilyl)oxy)methyl)-6-fluoroisoquinoline (11.0 g, 61%). MS (ESI+) [Method 1A]: m/z 292.2 (M+H); Rt 1.78 min.

Step 6.9: Synthesis of 8-(((tert-butyldimethylsilyl)oxy)methyl)-6-fluoroisoquinoline-5-carbaldehyde

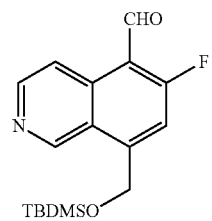 [SMILES: CC(C)(C)[Si](C)(C)OCc1cc(F)c(C=O)c2ccncc12]

To the stirred solution of 8-(((tert-butyldimethylsilyl)oxy)methyl)-6-fluoroisoquinoline (5.0 g, 17.16 mmol) in anhydrous THF (50 mL), LDA (2M in THF) (25.7 mL, 51.46 mmol) was added dropwise at −78° C. under $N_2$ atmosphere. After 2.5 h, ethyl formate (6.35 g, 85.78 mmol) dissolved in THF (25 mL) was added dropwise at −78° C., and stirred for another 1 h. The reaction was quenched with saturated NH$_4$Cl solution and extracted with EtOAc twice. The combined organic portion was washed with brine, dried over anhydrous Na$_2$SO$_4$, filtered and concentrated in vacuo. The residue was purified by flash chromatography (40 g SiliCycle column, 0-10% EtOAc in Hexane elution) to provide 8-(((tert-butyldimethylsilyl)oxy)methyl)-6-fluoroisoquinoline-5-carbaldehyde (3.4 g, 62%). MS (ESI+) [Method 4A]: m/z 320.2 (M+H); Rt 2.30 min.

Step 6.10: Synthesis of (1r,3r)-N-((8-(((tert-butyldimethylsilyl)oxy)methyl)-6-fluoroisoquinolin-5-yl)methyl)-3-(4-fluoro-3-(trifluoromethyl)phenoxy)cyclobutan-1-amine

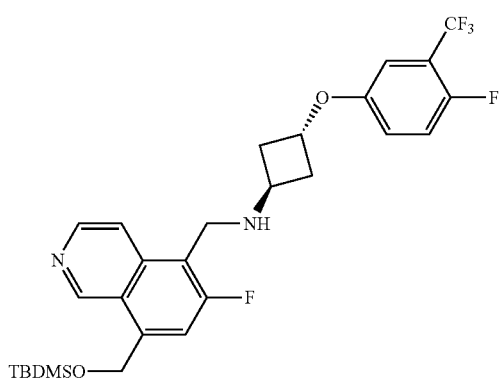 [SMILES: CC(C)(C)[Si](C)(C)OCc1cc(F)c(CN[C@H]2C[C@H](Oc3ccc(F)c(C(F)(F)F)c3)C2)c2ccncc12]

The title compound was synthesized following the procedure as described in step 1.4, using (1r,3r)-3-(4-fluoro-3-(trifluoromethyl)phenoxy)cyclobutan-1-amine, HCl (Step 1.3, 500 mg, 1.75 mmol) and 8-(((tert-butyldimethylsilyl)oxy)methyl)-6-fluoroisoquinoline-5-carbaldehyde (830 mg, 2.63 mmol). The crude was purified by flash chromatography (12 g SiliCycle column, 0-25% EtOAc in Hexane elution) to provide (1r,3r)-N-((8-(((tert-butyldimethylsilyl)oxy)methyl)-6-fluoroisoquinolin-5-yl)methyl)-3-(4-fluoro-3-(trifluoromethyl)phenoxy)cyclobutan-1-amine (920 mg, 95%). MS (ESI+) [Method 6A]: m/z 553.4 (M+H); Rt 1.42 min.

Step 6.11: Synthesis of (6-fluoro-5-((((1r,3r)-3-(4-fluoro-3-(trifluoromethyl)phenoxy)cyclobutyl)amino)methyl)isoquinolin-8-yl)methanol, HCl

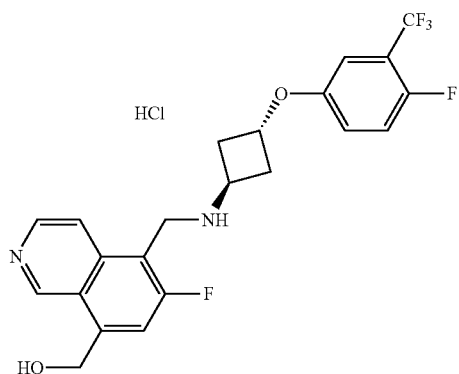 [SMILES: OCc1cc(F)c(CN[C@H]2C[C@H](Oc3ccc(F)c(C(F)(F)F)c3)C2)c2ccncc12 ; Cl]

To the solution of (1r,3r)-N-((8-(((tert-butyldimethylsilyl)oxy)methyl)-6-fluoroisoquinolin-5-yl)methyl)-3-(4-fluoro-3-(trifluoromethyl)phenoxy)cyclobutan-1-amine (920 mg, 1.66 mmol) in THF (15 mL), TBAF solution (1M in THF) (1.6 mL, 1.66 mmol) was added dropwise as 0° C. and stirred for 1 h. Reaction mixture was diluted with water and extracted with EtOAc twice. The combined organic portion was washed with brine solution, dried over anhydrous Na₂SO₄, filtered and concentrated in vacuo. The residue was purified by prep-HPLC (Column: EPIC (150 mm×21.2 mm), 5.0µ; Mobile Phase: 0.02% NH₄OH in water and acetonitrile). To the isolated product, HCl solution (4M in 1,4-dioxane) (4 mL) was added at 10° C., stirred at rt for 2 h, concentrated in vacuo, triturated with Et₂O-Pentane, collected solid was dried to provide (6-fluoro-5-((((1r,3r)-3-(4-fluoro-3-(trifluoromethyl)phenoxy)cyclobutyl)amino)methyl)isoquinolin-8-yl)methanol, HCl (260 mg, 35%). MS (ESI+) [Method 6A]: m/z 439.2 (M+H); Rt 1.30 min. ¹H NMR (400 MHz, CD₃OD) δ 9.96 (s, 1H), 8.84 (d, J=7.2 Hz, 1H), 8.79 (d, J=7.2 Hz, 1H), 8.04 (d, J=10.4 Hz, 1H), 7.29 (t, J=9.6 Hz, 1H), 7.15-7.09 (m, 2H), 5.31 (s, 2H), 5.07-5.04 (m, 1H), 4.81 (d, J=1.2 Hz, 2H), 4.31-4.26 (m, 1H), 2.95-2.88 (m, 2H), 2.74-2.67 (m, 2H).

Example 7: Synthesis of (S)-1-(6-fluoro-5-((((1r,3S)-3-(4-fluoro-3-(trifluoromethyl)phenoxy)cyclobutyl)amino)methyl)isoquinolin-8-yl)ethane-1,2-diol (or trans-(S)-1-(6-fluoro-5-(((3-(4-fluoro-3-(trifluoromethyl)phenoxy)cyclobutyl)amino)methyl)isoquinolin-8-yl)ethane-1,2-diol) and (R)-1-(6-fluoro-5-((((1r,3R)-3-(4-fluoro-3-(trifluoromethyl)phenoxy)cyclobutyl)amino)methyl)isoquinolin-8-yl)ethane-1,2-diol (or trans-(R)-1-(6-fluoro-5-(((3-(4-fluoro-3-(trifluoromethyl)phenoxy)cyclobutyl)amino)methyl)isoquinolin-8-yl)ethane-1,2-diol)

Step 7.1: Synthesis of 6-fluoro-8-(oxiran-2-yl)isoquinoline

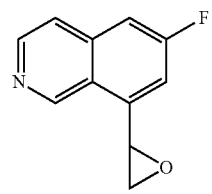 [SMILES: Fc1cc(C2CO2)c2cnccc2c1]

To the solution of NaH (1.0 g, 41.45 mmol) and anhydrous DMSO (40 mL), trimethylsulfoxonium iodide (8.3 g, 37.68 mmol) was added at rt and stirred for 30 min. Then 6-fluoroisoquinoline-8-carbaldehyde (Step 6.5, 3.3 g, 18.84 mmol), dissolved in DMSO (20 mL), was added dropwise at rt. After 5 min, the reaction was quenched with ice-water and extracted with EtOAc 3×'s. The combined organic portion was washed with brine, dried over anhydrous Na₂SO₄, filtered and concentrated in vacuo. The residue was purified by flash chromatography (12 g SiliCycle column, 0-20% EtOAc in Hexane elution) to provide 6-fluoro-8-(oxiran-2-yl)isoquinoline (2.3 g, 64%). MS (ESI+) [Method 6A]: m/z 190.1 (M+H); Rt 0.79 min. ¹H NMR (600 MHz, CDCl₃) δ 9.55 (s, 1H), 8.58 (d, J=5.4 Hz, 1H), 7.65 (d, J=5.4 Hz, 1H), 7.37 (d, J=9.0 Hz, 2H), 4.60-4.59 (m, 1H), 3.37-3.35 (m, 1H), 2.82-2.80 (m, 1H).

Step 7.2: Synthesis of 1-(6-fluoroisoquinolin-8-yl)ethane-1,2-diol

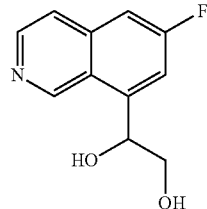 [SMILES: OCC(O)c1cc(F)cc2ccncc12]

To the solution of 6-fluoro-8-(oxiran-2-yl)isoquinoline (2.1 g, 11.11 mmol) in THF-H₂O (12 mL, 2:1 v/v), H₂SO₄ (5 mL) was added dropwise at rt and stirred at 60° C. for 16 h. The reaction mixture was basified with saturated NaHCO₃ solution and extracted with EtOAc twice. The combined organic portion was washed with brine, dried over anhydrous Na₂SO₄, filtered and concentrated in vacuo. The residue was purified by flash chromatography (12 g SiliCycle column, 0-5% MeOH in CH₂Cl₂ elution) to provide 1-(6-fluoroisoquinolin-8-yl)ethane-1,2-diol (1.6 g, 69%). MS (ESI+) [Method 4A]: m/z 208.3 (M+H); Rt 0.40 min. ¹H NMR (600 MHz, CDCl₃) δ 9.49 (s, 1H), 8.49 (d, J=6.0 Hz, 1H), 7.67-7.63 (m, 2H), 7.35 (dd, J=8.4, 1.8 Hz, 1H), 4.13-4.10 (m, 1H), 4.06 (dd, J=12.6, 3.6 Hz, 1H), 3.76 (dd, J=11.4, 3.6 Hz, 1H).

Step 7.3: Synthesis of 6-fluoro-8-(2,2,3,3,8,8,9,9-octamethyl-4,7-dioxa-3,8-disiladecan-5-yl)isoquinoline

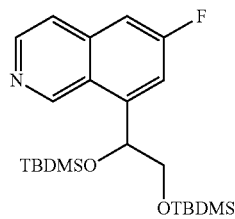 [SMILES: CC(C)(C)[Si](C)(C)OCC(O[Si](C)(C)C(C)(C)C)c1cc(F)cc2ccncc12]

To the solution of 1-(6-fluoroisoquinolin-8-yl)ethane-1,2-diol (1.5 g, 7.24 mmol) and imidazole (3.4 g, 50.68 mmol) in DMF (15 mL), TBDMS-Cl (5.4 g, 36.17 mmol) was added portion wise at 0° C. and stirred at rt for 16 h. Then the reaction mixture was diluted with water and extracted 3× with EtOAc. The combined organic portion was washed with brine, dried over anhydrous Na₂SO₄, filtered and concentrated in vacuo. The residue was purified by flash chromatography (12 g SiliCycle column, 0-10% EtOAc in Hexane elution) to afford 6-fluoro-8-(2,2,3,3,8,8,9,9-octamethyl-4,7-dioxa-3,8-disiladecan-5-yl)isoquinoline (2.7 g, 85%). MS (ESI+) [Method 6A]: m/z 436.3 (M+H); Rt 2.15 min. ¹H NMR (600 MHz, CDCl₃) δ 9.59 (s, 1H), 8.52 (d, J=4.8 Hz, 1H), 7.61 (d, J=5.4 Hz, 1H), 7.55 (dd, J=10.2, 1.8 Hz, 1H), 7.33 (dd, J=9.0, 2.4 Hz, 1H), 5.54 (d, J=6.0 Hz, 1H), 3.87-3.85 (m, 1H), 3.77-3.74 (m, 1H), 0.92 (s, 9H), 0.90 (s, 9H), 0.13 (s, 6H), 0.09 (s, 6H).

Step 7.4: Synthesis of 6-fluoro-8-(2,2,3,3,8,8,9,9-octamethyl-4,7-dioxa-3,8-disiladecan-5-yl)isoquinoline-5-carbaldehyde

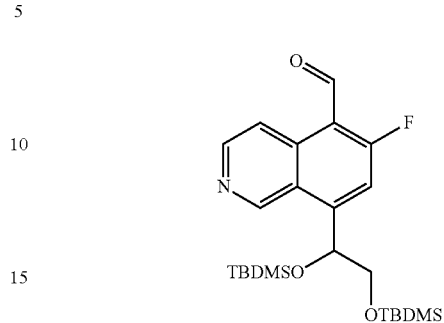

The title compound was prepared according to the procedure in Step 6.8. The residue was purified by flash chromatography (40 g SiliCycle column, 0-15% EtOAc in Hexane elution) to provide 6-fluoro-8-(2,2,3,3,8,8,9,9-octamethyl-4,7-dioxa-3,8-disiladecan-5-yl)isoquinoline-5-carbaldehyde (2.0 g, 62%). MS (ESI+) [Method 4A]: m/z 464.4 (M+H); Rt 1.77 min. ¹H NMR (600 MHz, CDCl₃) δ 9.57 (s, 1H), 8.50 (d, J=5.4 Hz, 1H), 7.60 (d, J=5.4 Hz, 1H), 7.54 (dd, J=7.8, 2.4 Hz, 1H), 7.32 (dd, J=9.0, 2.4 Hz, 1H), 5.53 (d, J=6.0 Hz, 1H), 3.87-3.84 (m, 1H), 3.76-3.73 (m, 1H), 0.89 (s, 9H), 0.75 (s, 9H), 0.12 (s, 6H), −0.05 (s, 6H).

Step 7.5: Synthesis of (1r,3r)-3-(4-fluoro-3-(trifluoromethyl)phenoxy)-N-((6-fluoro-8-(2,2,3,3,8,8,9,9-octamethyl-4,7-dioxa-3,8-disiladecan-5-yl)isoquinolin-5-yl)methyl)cyclobutan-1-amine

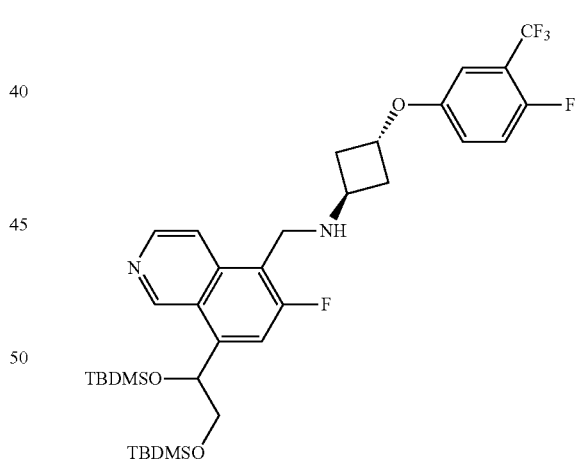

The title compound was synthesized following the procedure as described in step 1.4, using (1r,3r)-3-(4-fluoro-3-(trifluoromethyl)phenoxy)cyclobutan-1-amine, HCl (Step 1.3, 1.0 g, 3.50 mmol) and 6-fluoro-8-(2,2,3,3,8,8,9,9-octamethyl-4,7-dioxa-3,8-disiladecan-5-yl)isoquinoline-5-carbaldehyde (1.46 g, 3.15 mmol). The crude was purified by flash chromatography (24 g SiliCycle column, 0-5% MeOH in CHCl₃ elution) to provide (1r,3r)-3-(4-fluoro-3-(trifluoromethyl)phenoxy)-N-((6-fluoro-8-(2,2,3,3,8,8,9,9-octamethyl-4,7-dioxa-3,8-disiladecan-5-yl)isoquinolin-5-yl)methyl)cyclobutan-1-amine_(1.5 g, 62%). MS (ESI+) [Method 6A]: m/z 697.3 (M+H); Rt 1.63 min.

Step 7.6: Synthesis of (S)-1-(6-fluoro-5-((((1r,3S)-3-(4-fluoro-3-(trifluoromethyl)phenoxy)cyclobutyl)amino)methyl)isoquinolin-8-yl)ethane-1,2-diol and (R)-1-(6-fluoro-5-((((1r,3R)-3-(4-fluoro-3-(trifluoromethyl)phenoxy)cyclobutyl)amino)methyl)isoquinolin-8-yl)ethane-1,2-diol

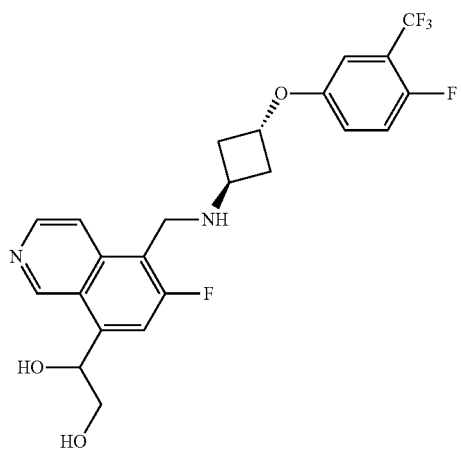 [SMILES: OCC(O)c1cc(F)c(CN[C@H]2C[C@H](Oc3ccc(F)c(C(F)(F)F)c3)C2)c2ccncc12]

To the solution (1r,3r)-3-(4-fluoro-3-(trifluoromethyl)phenoxy)-N-((6-fluoro-8-(2,2,3,3,8,8,9,9-octamethyl-4,7-dioxa-3,8-disiladecan-5-yl)isoquinolin-5-yl)methyl)cyclobutan-1-amine (1.5 g, 2.15 mmol) in THF (25 mL), TBAF solution (1M in THF) (5.4 mL, 5.38 mmol) was added dropwise as 0° C. and stirred for 2 h. Reaction mixture was diluted with water and extracted with EtOAc twice. The combined organic portion was washed with a brine solution, dried over anhydrous Na$_2$SO$_4$, filtered and concentrated in vacuo. The residue was purified by flash chromatography (24 g SiliCycle column, 0-10% MeOH in CH$_2$Cl$_2$ elution) to afford 1-(6-fluoro-5-((((1r,3r)-3-(4-fluoro-3-(trifluoromethyl)phenoxy)cyclobutyl)amino)methyl)isoquinolin-8-yl)ethane-1,2-diol (1.0 g, 98%). MS (ESI+) [Method 6A]: m/z 469.2 (M+H); Rt 1.29 min. $^1$H NMR (400 MHz, CD$_3$OD) δ 9.57 (s, 1H), 8.52 (d, J=6.0 Hz, 1H), 8.12 (d, J=5.6 Hz, 1H), 7.67 (d, J=10.6 Hz, 1H), 7.22 (t, J=9.6 Hz, 1H), 7.05-7.01 (m, 2H), 5.58-5.56 (m, 1H), 4.85-4.82 (m, 1H), 4.17 (d, J=1.6 Hz, 2H), 3.86-3.82 (m, 1H), 3.78-3.74 (m, 1H), 3.60-3.57 (m, 1H), 2.36-2.33 (m, 4H).

Chiral prep-HPLC (Column: CHIRALPAK IG (250 mm×20 mm); Mobile Phase: Hexane and IPA:MeOH (1:1); Isocratic: 60/40; Flow: 15 mL/min) of the racemate provided (S)-1-(6-fluoro-5-((((1r,3S)-3-(4-fluoro-3-(trifluoromethyl)phenoxy)cyclobutyl)amino)methyl)isoquinolin-8-yl)ethane-1,2-diol as a white solid Peak 1 (395 mg, 40%): Chiral HPLC: 99% (Rf 7.840 min; Column: CHIRALPAK-IG (150 mm×4.6 mm), 5.0μ; Mobile phase: n-Hexane and EtOH; Isocratic: 80/20; Flow: 1 mL/min). MS (ESI+) [Method 1A]: m/z 469.2 (M+H); Rt 1.29 min. $^1$H NMR (400 MHz, CD$_3$OD) δ 9.57 (s, 1H), 8.53 (d, J=6.0 Hz, 1H), 8.13 (d, J=5.6 Hz, 1H), 7.68 (d, J=10.6 Hz, 1H), 7.23 (t, J=9.6 Hz, 1H), 7.06-7.01 (m, 2H), 5.59-5.56 (m, 1H), 4.85-4.82 (m, 1H), 4.19 (s, 2H), 3.87-3.83 (m, 1H), 3.78-3.74 (m, 1H), 3.60-3.57 (m, 1H), 2.37-2.34 (m, 4H); and (R)-1-(6-fluoro-5-((((1r,3R)-3-(4-fluoro-3-(trifluoromethyl)phenoxy)cyclobutyl)amino)methyl)isoquinolin-8-yl)ethane-1,2-diol as a white solid Peak 2 (345 mg, 35%) Chiral HPLC: 97% (Rf 17.481 min; Column: CHIRALPAK-IG (150 mm×4.6 mm), 5.0μ; Mobile phase: n-Hexane and EtOH; Isocratic: 80/20; Flow: 1 mL/min). MS (ESI+) [Method 3A]: m/z 469.0 (M+H); Rt 1.25 min. $^1$H NMR (400 MHz, CD$_3$OD) δ 9.57 (s, 1H), 8.53 (d, J=6.0 Hz, 1H), 8.13 (d, J=5.6 Hz, 1H), 7.68 (d, J=10.6 Hz, 1H), 7.23 (t, J=9.6 Hz, 1H), 7.06-7.01 (m, 2H), 5.59-5.56 (m, 1H), 4.85-4.82 (m, 1H), 4.18 (d, J=1.2 Hz, 2H), 3.87-3.83 (m, 1H), 3.78-3.74 (m, 1H), 3.60-3.57 (m, 1H), 2.37-2.34 (m, 4H).

Example 8: Synthesis of 1-(6-fluoro-5-((((1r,3r)-3-(4-fluoro-3-(trifluoromethyl)phenoxy)cyclobutyl)amino)methyl)isoquinolin-8-yl)ethan-1-ol, HCl Step 8.1: Synthesis of 1-(6-fluoroisoquinolin-8-yl)ethan-1-ol

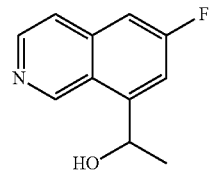

To the stirred solution of 6-fluoroisoquinoline-8-carbaldehyde (Step 6.5, 0.7 g, 4.0 mmol) in anhydrous THF (10 mL), MeMgBr (3M in Et$_2$O) (4.0 mL, 11.98 mmol) was added dropwise at 0° C. under N$_2$ atmosphere. The reaction mixture was stirred at 0° C. for 2 h, before quenching with saturated NH$_4$Cl solution. Then the reaction mixture was extracted with EtOAc twice. The combined organic portion was washed with brine, dried over anhydrous Na$_2$SO$_4$, filtered and concentrated in vacuo to provide 1-(6-fluoroisoquinolin-8-yl)ethan-1-ol (0.8 g crude). MS (ESI+) [Method 4B]: m/z 192.0 (M+H); Rt 0.20 min.

Step 8.2: Synthesis of 8-(1-((tert-butyldimethylsilyl)oxy)ethyl)-6-fluoroisoquinoline

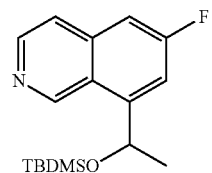 [SMILES: CC(O[Si](C)(C)C(C)(C)C)c1cc(F)cc2ccncc12]

The title compound was prepared according to Step 6.7. The residue was purified by flash chromatography (12 g SiliCycle column, 0-15% EtOAc in Hexane elution) to afford 8-(1-((tert-butyldimethylsilyl)oxy)ethyl)-6-fluoroisoquinoline (0.9 g, 70%). MS (ESI+) [Method 6A]: m/z 306.2 (M+H); Rt 1.72 min. $^1$H NMR (300 MHz, CDCl$_3$) δ 9.49 (s, 1H), 8.51 (d, J=5.4 Hz, 1H), 7.62 (d, J=4.5 Hz, 1H), 7.55 (dd, J=10.5, 2.7 Hz, 1H), 7.29 (dd, J=9.3, 2.7 Hz, 1H), 5.66-5.62 (m, 1H), 1.60 (d, J=6.6 Hz, 3H), 0.93 (s, 9H), 0.11 (s, 3H), 0.00 (s, 3H).

Step 8.3: Synthesis of 8-(1-((tert-butyldimethylsilyl) oxy)ethyl)-6-fluoroisoquinoline-5-carbaldehyde

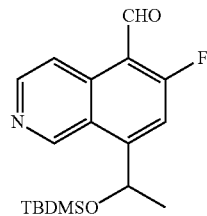 [SMILES: CC(O[Si](C)(C)C(C)(C)C)c1cc(F)c(C=O)c2ccncc12]

The title compound was prepared according to Step 3.1 except that after addition of piperidine-1-carbaldehyde, the reaction mixture was stirred for a further 1 h at −78° C. The residue was purified by flash chromatography (40 g SiliCycle column, 0-10% EtOAc in Hexane elution) to provide 8-(1-((tert-butyldimethylsilyl)oxy)ethyl)-6-fluoroisoquinoline-5-carbaldehyde (0.7 g, 71%). MS (ESI+) [Method 6A]: m/z 334.1 (M+H); Rt 1.79 min.

Step 8.4: Synthesis of (1r,3r)-N-((8-(1-((tert-butyldimethylsilyl)oxy)ethyl)-6-fluoroisoquinolin-5-yl)methyl)-3-(4-fluoro-3-(trifluoromethyl)phenoxy)cyclobutan-1-amine

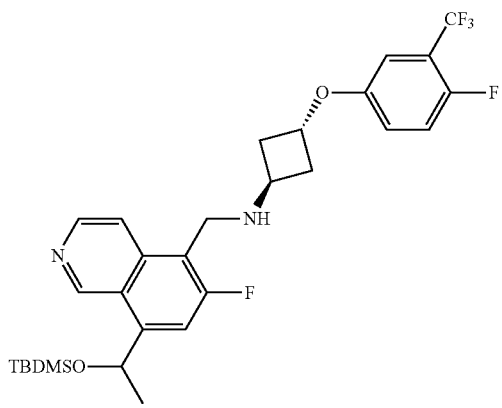 [SMILES: CC(O[Si](C)(C)C(C)(C)C)c1cc(F)c(CN[C@H]2C[C@H](Oc3ccc(F)c(C(F)(F)F)c3)C2)c2ccncc12]

The title compound was synthesized following the procedure as described in step 1.4, using (1r,3r)-3-(4-fluoro-3-(trifluoromethyl)phenoxy)cyclobutan-1-amine, HCl (Step 1.3, 0.3 g, 1.05 mmol) and 8-(1-((tert-butyldimethylsilyl)oxy)ethyl)-6-fluoroisoquinoline-5-carbaldehyde (0.42 g, 1.26 mmol). The crude product was purified by flash chromatography (12 g SiliCycle column, 0-5% MeOH in CHCl$_3$ elution) to provide (1r,3r)-N-((8-(1-((tert-butyldimethylsilyl)oxy)ethyl)-6-fluoroisoquinolin-5-yl)methyl)-3-(4-fluoro-3-(trifluoromethyl)phenoxy)cyclobutan-1-amine (0.5 g, 84%). MS (ESI+) [Method 6A]: m/z 567.2 (M+H); Rt 1.49 min.

Step 8.5: Synthesis of 1-(6-fluoro-5-((((1r,3r)-3-(4-fluoro-3-(trifluoromethyl)phenoxy)cyclobutyl)amino)methyl)isoquinolin-8-yl)ethan-1-ol, HCl

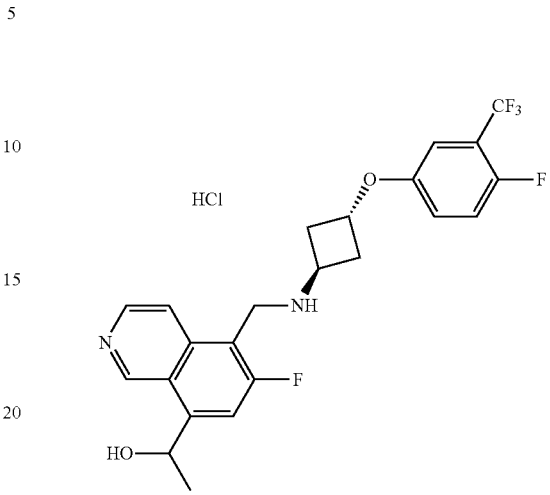

To the solution of (1r,3r)-N-((8-(1-((tert-butyldimethylsilyl)oxy)ethyl)-6-fluoroisoquinolin-5-yl)methyl)-3-(4-fluoro-3-(trifluoromethyl)phenoxy)cyclobutan-1-amine (0.5 g, 0.88 mmol) in THF (10 mL), TBAF solution (1M in THF) (1.06 mL, 1.06 mmol) was added dropwise as 0° C. and stirred at rt for 2 h. Reaction mixture was diluted with water and extracted with EtOAc twice. The combined organic portion was washed with brine solution, dried over anhydrous Na$_2$SO$_4$, filtered and concentrated in vacuo. The residue was purified by flash chromatography (12 g SiliCycle column, 0-5% MeOH in CH$_2$Cl$_2$ elution) to provide 1-(6-fluoro-5-((((1r,3r)-3-(4-fluoro-3-(trifluoromethyl)phenoxy)cyclobutyl)amino)methyl)isoquinolin-8-yl)ethan-1-ol (0.4 g, quantitative). MS (ESI+) [Method 6A]: m/z 453.1 (M+H); Rt 1.33 min. 100 mg product was re-purified by prep-HPLC (Column: GEMINI NX (150 mm×21.2 mm), 5.0μ; Mobile Phase: 0.02% NH$_4$OH in water and acetonitrile); to the isolated product, HCl solution (4M in 1,4-dioxane) (2 mL) was added at 10° C., stirred at rt for 1 h, concentrated in vacuo, triturated with Et$_2$O, collected solid was dried in vacuo to provide 1-(6-fluoro-5-((((1r,3r)-3-(4-fluoro-3-(trifluoromethyl)phenoxy)cyclobutyl)amino)methyl)isoquinolin-8-yl)ethan-1-ol, HCl as white solid (33 mg, 33%). MS (ESI+) [Method 4A]: m/z 453.2 (M+H); Rt 1.47 min. $^1$H NMR (400 MHz, CD$_3$OD) δ 10.20 (s, 1H), 8.90 (d, J=6.8 Hz, 1H), 8.78 (d, J=6.8 Hz, 1H), 8.06 (d, J=10.8 Hz, 1H), 7.30 (t, J=9.6 Hz, 1H), 7.15-7.09 (m, 2H), 5.73-5.70 (m, 1H), 5.09-5.05 (m, 1H), 4.82 (s, 2H), 4.31-4.27 (m, 1H), 2.97-2.90 (m, 2H), 2.73-2.67 (m, 2H), 1.68 (d, J=6.8 Hz, 3H).

Example 9: Synthesis of 1-(6-fluoro-5-((((1r,3r)-3-(4-fluoro-3-(trifluoromethyl)phenoxy)cyclobutyl)amino)methyl)isoquinolin-8-yl)propane-1,3-diol, (S)-1-(6-fluoro-5-((((1r,3S)-3-(4-fluoro-3-(trifluoromethyl)phenoxy)cyclobutyl)amino)methyl)isoquinolin-8-yl)propane-1,3-diol and (R)-1-(6-fluoro-5-((((1r,3R)-3-(4-fluoro-3-(trifluoromethyl)phenoxy)cyclobutyl)amino)methyl)isoquinolin-8-yl)propane-1,3-diol Step 9.1: Synthesis of ethyl 3-(6-fluoroisoquinolin-8-yl)-3-hydroxypropanoate

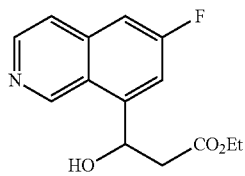

A two necked round bottom flask was charged with EtOAc (1.51 mL, 15.41 mmol) and anhydrous THF (25 mL). Then LDA (2M in Hexane) (8.6 mL, 17.12 mol) was added drop wise at −78° C. and stirred for 30 min under argon. Finally 6-fluoroisoquinoline-8-carbaldehyde (Step 6.5, 1.5 g, 8.56 mmol), dissolved in THF (5 mL) was added dropwise at −78° C. and stirred for 2.5 h. The reaction was quenched with saturated NH$_4$Cl solution and extracted with EtOAc 3×'s. The combined organic portion was washed with brine, dried over anhydrous Na$_2$SO$_4$, filtered and concentrated in vacuo. The residue was purified by flash chromatography (24 g SiliCycle column, 0-20% EtOAc in Hexane elution) to provide ethyl 3-(6-fluoroisoquinolin-8-yl)-3-hydroxypropanoate (2.0 g, 88%). MS (ESI+) [Method 6A]: m/z 264.1 (M+H); Rt 1.24 min.

Step 9.2: Synthesis of 1-(6-fluoroisoquinolin-8-yl)propane-1,3-diol

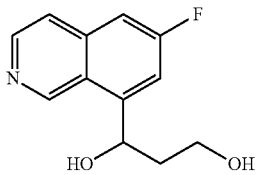

To the solution of ethyl 3-(6-fluoroisoquinolin-8-yl)-3-hydroxypropanoate (2.0 g, 7.59 mmol) in anhydrous THF (40 mL), DIBAL-H (1M in toluene) (19.0 mL, 18.99 mmol) was added drop wise at −78° C. and stirred for 1 h, before warming the reaction mixture to rt over 30 min. Then the reaction mixture was quenched with saturated NH$_4$Cl solution and extracted with EtOAc 3×'s. The combined organic portion was washed with brine, dried over anhydrous Na$_2$SO$_4$, filtered and concentrated in vacuo to provide crude 1-(6-fluoroisoquinolin-8-yl)propane-1,3-diol (1.8 g crude). MS (ESI+) [Method 6A]: m/z 222.1 (M+H); Rt 0.29 min.

Step 9.3: Synthesis of 6-fluoro-8-(2,2,3,3,9,9,10,10-octamethyl-4,8-dioxa-3,9-disilaundecan-5-yl)isoquinoline

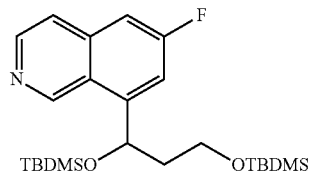 [SMILES: CC(C)(C)[Si](C)(C)OCCC(O[Si](C)(C)C(C)(C)C)c1cc(F)cc2ccncc12]

To the stirred solution of 1-(6-fluoroisoquinolin-8-yl)propane-1,3-diol (1.8 g, 8.14 mmol), imidazole (2.7 g, 40.68 mmol) and DMAP (0.5 g, 4.07 mmol) in anhydrous DMF (35 mL), TBDMS-Cl (3.6 g, 24.4 mmol) was added at 0° C. and stirred at rt for 16 h under N$_2$ atmosphere. The reaction was diluted with water and extracted with CH$_2$Cl$_2$ twice. The combined organic portion was washed with brine, dried over anhydrous Na$_2$SO$_4$, filtered and concentrated in vacuo. The residue was purified by flash chromatography (24 g SiliCycle column, 0-10% EtOAc in Hexane elution) to provide 6-fluoro-8-(2,2,3,3,9,9,10,10-octamethyl-4,8-dioxa-3,9-disilaundecan-5-yl)isoquinoline (1.2 g, 30%). MS (ESI+) [Method 6A]: m/z 450.5 (M+H); Rt 2.44 min.

Step 9.4: Synthesis of 6-fluoro-8-(2,2,3,3,9,9,10,10-octamethyl-4,8-dioxa-3,9-disilaundecan-5-yl)isoquinoline-5-carbaldehyde

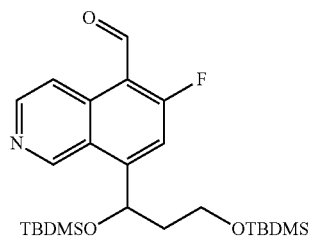 [SMILES: CC(C)(C)[Si](C)(C)OCCC(O[Si](C)(C)C(C)(C)C)c1cc(F)c(C=O)c2ccncc12]

The title compound was prepared according to the procedure in Step 6.8. The residue was purified by flash chromatography (24 g SiliCycle column, 0-15% EtOAc in Hexane elution) to provide 6-fluoro-8-(2,2,3,3,9,9,10,10-octamethyl-4,8-dioxa-3,9-disilaundecan-5-yl)isoquinoline-5-carbaldehyde (0.8 g, 75%). MS (ESI+) [Method 1A]: m/z 478.3 (M+H); Rt 2.41 min.

Step 9.5: Synthesis of (1r,3r)-3-(4-fluoro-3-(trifluoromethyl)phenoxy)-N-((6-fluoro-8-(2,2,3,3,9,9,10,10-octamethyl-4,8-dioxa-3,9-disilaundecan-5-yl)isoquinolin-5-yl)methyl)cyclobutan-1-amine

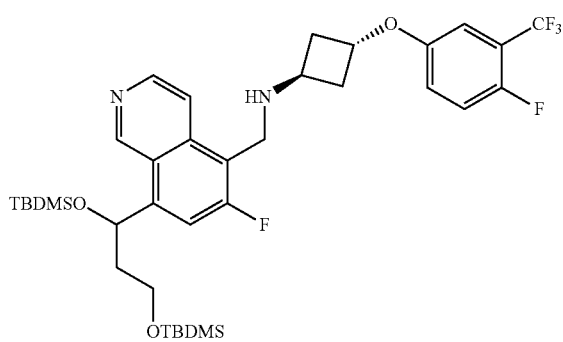 [SMILES: CC(C)(C)[Si](C)(C)OCCC(O[Si](C)(C)C(C)(C)C)c1cc(F)c(CN[C@H]2C[C@H](Oc3ccc(F)c(C(F)(F)F)c3)C2)c2ccncc12]

The title compound was synthesized following the procedure as described in step 1.4, using (1r,3r)-3-(4-fluoro-3-(trifluoromethyl)phenoxy)cyclobutan-1-amine, HCl (Step 1.3, 0.4 g, 1.40 mmol) and 6-fluoro-8-(2,2,3,3,9,9,10,10-octamethyl-4,8-dioxa-3,9-disilaundecan-5-yl)isoquinoline-5-carbaldehyde (0.8 g, 1.68 mmol). The crude was purified by flash chromatography (24 g SiliCycle column, 0-5% MeOH in $CH_2Cl_2$ elution) to provide (1r,3r)-3-(4-fluoro-3-(trifluoromethyl)phenoxy)-N-((6-fluoro-8-(2,2,3,3,9,9,10,10-octamethyl-4,8-dioxa-3,9-disilaundecan-5-yl)isoquinolin-5-yl)methyl)cyclobutan-1-amine (0.97 g, 97%). MS (ESI+) [Method 6A]: m/z 711.3 (M+H); Rt 1.64 min.

Step 9.6: Synthesis of 1-(6-fluoro-5-((((1r,3r)-3-(4-fluoro-3-(trifluoromethyl)phenoxy)cyclobutyl)amino)methyl)isoquinolin-8-yl)propane-1,3-diol, (S)-1-(6-fluoro-5-((((1r,3S)-3-(4-fluoro-3-(trifluoromethyl)phenoxy)cyclobutyl)amino)methyl)isoquinolin-8-yl)propane-1,3-diol and (R)-1-(6-fluoro-5-((((1r,3R)-3-(4-fluoro-3-(trifluoromethyl)phenoxy)cyclobutyl)amino)methyl)isoquinolin-8-yl)propane-1,3-diol

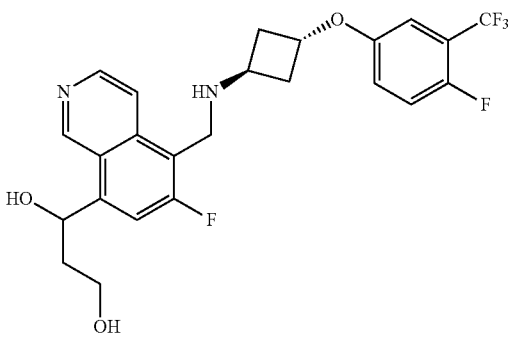 [SMILES: OCCC(O)c1cc(F)c(CN[C@H]2C[C@H](Oc3ccc(F)c(C(F)(F)F)c3)C2)c2ccncc12]

The title compound was prepared according to the procedure in Step 7.6. Prep-HPLC (Column: WATERS X BRIDGE C18 (150 mm×19.0 mm), 5.0μ; Mobile Phase: 0.02% $NH_4OH$ in water and acetonitrile) of the residue provided 1-(6-fluoro-5-((((1r,3r)-3-(4-fluoro-3-(trifluoromethyl)phenoxy)cyclobutyl)amino)methyl)isoquinolin-8-yl)propane-1,3-diol (335 mg, 51%). MS (ESI+) [Method 6A]: m/z 483.2 (M+H); Rt 1.30 min. $^1$H NMR (400 MHz, $CD_3OD$) δ 9.64 (s, 1H), 8.59 (d, J=6.0 Hz, 1H), 8.13 (d, J=6.0 Hz, 1H), 7.72 (d, J=11.6 Hz, 1H), 7.25 (t, J=9.2 Hz, 1H), 7.10-7.04 (m, 2H), 5.76 (dd, J=8.8, 2.8 Hz, 1H), 4.92-4.89 (m, 1H), 4.17 (s, 2H), 3.92-3.86 (m, 2H), 3.75-3.70 (m, 1H), 2.56-2.47 (m, 4H), 2.10-2.05 (m, 1H), 2.02-1.95 (m, 1H).

Chiral prep-HPLC (Column: LUX AMYLOSE-1 (250 mm×21.2 mm); Mobile Phase: Hexane and EtOH:MeOH (1:1); Isocratic: 75/25; Flow: 15 mL/min) of the racemate (300 mg) provided (S)-1-(6-fluoro-5-((((1r,3S)-3-(4-fluoro-3-(trifluoromethyl) phenoxy)cyclobutyl)amino)methyl)isoquinolin-8-yl) propane-1,3-diol and (R)-1-(6-fluoro-5-((((1r,3R)-3-(4-fluoro-3-(trifluoromethyl)phenoxy)cyclobutyl)amino)methyl)isoquinolin-8-yl)propane-1,3-diol as white solids (Peak 1: 130 mg, 43% and Peak 2: 130 mg, 43%). Peak 1: Chiral HPLC: 98% (Rf 2.508 min; Column: LUX AMYLOSE-1 (150 mm×4.6 mm), 5.0μ; Mobile phase: n-Hexane and 0.1% DEA in EtOH:MeOH (70:30); Isocratic: 50/50; Flow: 1 mL/min). MS (ESI+) [Method 5A]: m/z 483.2 (M+H); Rt 0.97 min. $^1$H NMR (400 MHz, $CD_3OD$) δ 9.59 (s, 1H), 8.53 (d, J=5.6 Hz, 1H), 8.12 (d, J=5.6 Hz, 1H), 7.65 (d, J=11.2 Hz, 1H), 7.22 (t, J=9.2 Hz, 1H), 7.06-7.01 (m, 2H), 5.73 (dd, J=8.8, 3.2 Hz, 1H), 4.85-4.82 (m, 1H), 4.17 (d, J=1.6 Hz, 2H), 3.91-3.85 (m, 1H), 3.74-3.69 (m, 1H), 3.61-3.57 (m, 1H), 2.45-2.35 (m, 4H), 2.10-2.04 (m, 1H), 2.02-1.95 (m, 1H).

Peak 2: Chiral HPLC: 99% (Rf 3.035 min; Column: LUX, AMYLOSE-1 (150 mm×4.6 mm), 5.0μ; Mobile phase: n-Hexane and 0.1% DEA in EtOH:MeOH (70:30); Isocratic: 50/50; Flow: 1 mL/min). MS (ESI+) [Method 6A]: m/z 483.2 (M+H); Rt 1.32 min. $^1$H NMR (400 MHz, $CD_3OD$) δ 9.59 (s, 1H), 8.53 (d, J=6.0 Hz, 1H), 8.12 (d, J=6.0 Hz, 1H), 7.65 (d, J=11.6 Hz, 1H), 7.22 (t, J=10.0 Hz, 1H), 7.06-7.01 (m, 2H), 5.73 (dd, J=8.8, 3.6 Hz, 1H), 4.85-4.82 (m, 1H), 4.17 (d, J=2.0 Hz, 2H), 3.91-3.85 (m, 1H), 3.74-3.69 (m, 1H), 3.61-3.58 (m, 1H), 2.36-2.33 (m, 4H), 2.08-2.06 (m, 1H), 2.02-1.95 (m, 1H).

Example 10: Synthesis of 2-(6-fluoro-5-((((1r,3r)-3-(4-fluoro-3-(trifluoromethyl)phenoxy)cyclobutyl)amino)methyl)isoquinolin-8-yl)ethan-1-ol, HCl Step 10.1: Synthesis of (E)-8-(2-ethoxyvinyl)-6-fluoroisoquinoline

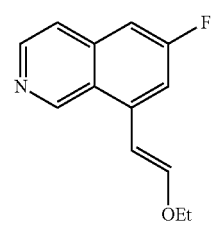 [SMILES: CCO/C=C/c1cc(F)cc2ccncc12]

To the stirred solution of 8-bromo-6-fluoroisoquinoline (Step 6.5, 1.0 g, 4.42 mmol) and (E)-2-(2-ethoxyvinyl)-4,4,5,5-tetra methyl-1,3,2-dioxaborolane (1.05 g, 5.31 mmol) in 1,4-dioxane-water (20 mL, 3:1 v/v), $K_3PO_4$ (2.81 g, 13.27 mmol) was added, and degassed with $N_2$ for 10 min. Then $Pd(dppf)Cl_2·CH_2Cl_2$ (0.36 g, 0.44 mmol) was added, degassed and heated at 90° C. for 16 h under $N_2$ atmosphere. Reaction mixture was cooled to rt, diluted with water and extracted with EtOAc twice. The combined organic portion was washed with brine, dried over anhydrous Na₂SO₄, filtered and concentrated in vacuo to yield the crude product. The crude product was purified by flash chromatography (12 g SiliCycle column, 0-20% EtOAc in Hexane elution) to provide (E)-8-(2-ethoxyvinyl)-6-fluoroisoquinoline (1.0 g, 108%). MS (ESI+) [Method 6A]: m/z 218.0 (M+H); Rt 1.34 min. ¹H NMR (400 MHz, CDCl₃) δ 9.43 (s, 1H), 8.49 (d, J=5.6 Hz, 1H), 7.55 (d, J=5.6 Hz, 1H), 7.26-7.22 (m, 2H), 7.04 (d, J=12.4 Hz, 1H), 6.52 (d, J=12.8 Hz, 1H), 4.04 (q, J=7.2 Hz, 2H), 1.41 (t, J=7.2 Hz, 3H).

Step 10.2: Synthesis of 2-(6-fluoroisoquinolin-8-yl)acetaldehyde

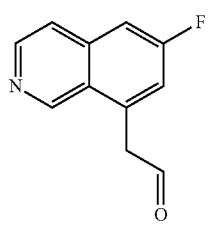 [SMILES: O=CCc1cc(F)cc2ccncc12]

To the stirred solution of (E)-8-(2-ethoxyvinyl)-6-fluoroisoquinoline (0.5 g, 2.30 mmol) in THF (5 mL), aqueous 2N HCl (5 mL) was added and heated at 70° C. for 2 h. Reaction mixture was cooled to rt, quenched with saturated NaHCO₃ solution and extracted with EtOAc twice. The combined organic portion was washed with brine, dried over anhydrous Na₂SO₄, filtered and concentrated in vacuo to yield the crude 2-(6-fluoroisoquinolin-8-yl)acetaldehyde (0.5 g, 87%). MS (ESI+) [Method 6A]: m/z 190.0 (M+H); Rt 1.37 min.

Step 10.3: Synthesis of 2-(6-fluoroisoquinolin-8-yl)ethan-1-ol

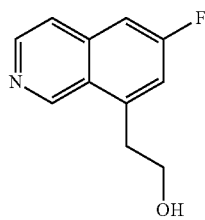 [SMILES: OCCc1cc(F)cc2ccncc12]

To the solution of 2-(6-fluoroisoquinolin-8-yl)acetaldehyde (0.5 g, 2.64 mmol) in MeOH (5 mL), NaBH₄ (0.15 g, 3.96 mmol) was added portion wise at 0° C. and stirred for 1 h. Then the reaction mixture was concentrated in vacuo, residue was diluted with water and extracted with EtOAc 3×'s. The combined organic portion was washed with brine, dried over anhydrous Na₂SO₄, filtered and concentrated in vacuo to afford crude 2-(6-fluoroisoquinolin-8-yl)ethan-1-ol (0.5 g, 99%). MS (ESI+) [Method 6A]: m/z 192.2 (M+H); Rt 1.34 min.

Step 10.4: Synthesis of 8-(2-((tert-butyldimethylsilyl)oxy)ethyl)-6-fluoroisoquinoline

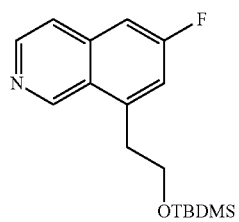 [SMILES: CC(C)(C)[Si](C)(C)OCCc1cc(F)cc2ccncc12]

The title compound was prepared according to Step 6.7. The residue was purified by flash chromatography (12 g SiliCycle column, 0-15% EtOAc in Hexane elution) to afford 8-(2-((tert-butyldimethylsilyl)oxy)ethyl)-6-fluoroisoquinoline (0.11 g, 13%). MS (ESI+) [Method 6A]: m/z 306.0 (M+H); Rt 1.60 min.

Step 10.5: Synthesis of 8-(2-((tert-butyldimethylsilyl)oxy)ethyl)-6-fluoroisoquinoline-5-carbaldehyde

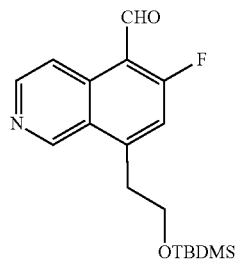 [SMILES: CC(C)(C)[Si](C)(C)OCCc1cc(F)c(C=O)c2ccncc12]

To the stirred solution of 8-(2-((tert-butyldimethylsilyl)oxy)ethyl)-6-fluoroisoquinoline (0.11 g, 0.36 mmol) in anhydrous THF (1.5 mL), LDA (2M in THF) (0.36 mL, 0.72 mmol) was added dropwise at −78° C. under N₂ atmosphere. After 2.5 h, piperidine-1-carbaldehyde (0.12 g, 1.08 mmol) dissolved in THF (0.5 mL) was added dropwise at −78° C., and stirred for another 1 h, while temperature was slowly raised to 0° C. The reaction was quenched with saturated NH₄Cl solution and extracted with EtOAc twice. The combined organic portion was washed with brine, dried over anhydrous Na₂SO₄, filtered and concentrated in vacuo. The residue was purified by flash chromatography (12 g SiliCycle column, 0-10% EtOAc in Hexane elution) to provide 8-(2-((tert-butyldimethylsilyl)oxy)ethyl)-6-fluoroisoquinoline-5-carbaldehyde (70 mg, 58%). MS (ESI+) [Method 6A]: m/z 334.1 (M+H); Rt 1.70 min.

Step 10.6: Synthesis of (1r,3r)-N-((8-(2-((tert-butyldimethylsilyl)oxy)ethyl)-6-fluoroisoquinolin-5-yl)methyl)-3-(4-fluoro-3-(trifluoromethyl)phenoxy)cyclobutan-1-amine

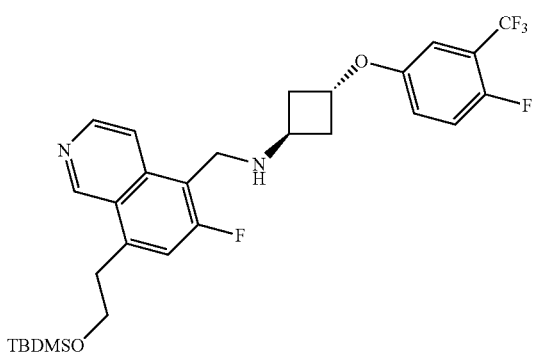 [SMILES: CC(C)(C)[Si](C)(C)OCCc1cc(F)c(CN[C@H]2C[C@H](Oc3ccc(F)c(C(F)(F)F)c3)C2)c2ccncc12]

The title compound was synthesized following the procedure as described in step 1.4, using (1r,3r)-3-(4-fluoro-3-(trifluoromethyl)phenoxy)cyclobutan-1-amine, HCl (Step 1.3, 70 mg, 0.25 mmol) and 8-(2-((tert-butyldimethylsilyl)oxy)ethyl)-6-fluoroisoquinoline-5-carbaldehyde (65 mg, 0.20 mmol). The crude was purified by flash chromatography (12 g SiliCycle column, 0-5% MeOH in CHCl$_3$ elution) to provide (1r,3r)-N-((8-(2-((tert-butyldimethylsilyl)oxy)ethyl)-6-fluoroisoquinolin-5-yl)methyl)-3-(4-fluoro-3-(trifluoromethyl)phenoxy)cyclobutan-1-amine (100 mg, 72%). MS (ESI+) [Method 6A]: m/z 567.2 (M+H); Rt 1.45 min.

Step 10.7: Synthesis of 2-(6-fluoro-5-((((1r,3r)-3-(4-fluoro-3-(trifluoromethyl)phenoxy)cyclobutyl)amino)methyl)isoquinolin-8-yl)ethan-1-ol, HCl

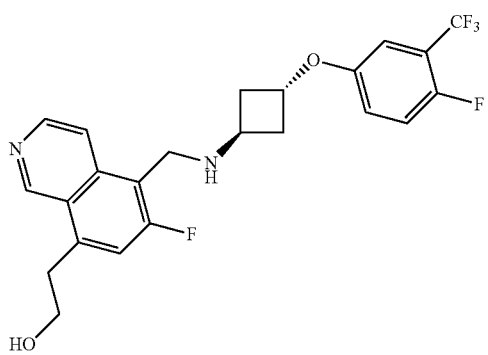 [SMILES: OCCc1cc(F)c(CN[C@H]2C[C@H](Oc3ccc(F)c(C(F)(F)F)c3)C2)c2ccncc12]

Deprotection was carried out using the procedure of Step 8.5. The residue was purified by prep-HPLC (Column: X BRIDGE (150 mm×19 mm), 5.0µ; Mobile Phase: 0.02% NH$_4$OH in water and acetonitrile). To the isolated product, HCl solution (4M in 1,4-dioxane) (2 mL) was added at 10° C., stirred at rt for 1 h, concentrated in vacuo, triturated with Et$_2$O, collected solid was dried in vacuo to provide 2-(6-fluoro-5-((((1r,3r)-3-(4-fluoro-3-(trifluoromethyl)phenoxy)cyclobutyl)amino)methyl)isoquinolin-8-yl)ethan-1-ol, HCl (22 mg, 25%). MS (ESI+) [Method 6A]: m/z 453.1 (M+H); Rt 1.33 min. $^1$H NMR (400 MHz, CD$_3$OD) δ 10.01 (s, 1H), 8.82 (d, J=6.8 Hz, 1H), 8.76 (d, J=6.8 Hz, 1H), 7.95 (d, J=10.4 Hz, 1H), 7.28 (t, J=9.2 Hz, 1H), 7.14-7.09 (m, 2H), 5.06-5.03 (m, 1H), 4.81 (d, J=1.6 Hz, 2H), 4.27-4.23 (m, 1H), 3.99 (t, J=6.0 Hz, 2H), 3.55 (t, J=6.0 Hz, 2H), 2.93-2.87 (m, 2H), 2.73-2.67 (m, 2H).

Example 11: Synthesis of 3,3,3-trifluoro-1-(6-fluoro-5-((((1r,3r)-3-(4-fluoro-3-(trifluoromethyl)phenoxy)cyclobutyl)amino)methyl)isoquinolin-8-yl)propan-1-ol Step 11.1: Synthesis of 3,3,3-trifluoro-1-(6-fluoroisoquinolin-8-yl)propan-1-ol

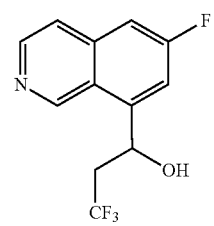 [SMILES: OC(CC(F)(F)F)c1cc(F)cc2ccncc12]

A round bottom flask charge with AgF (1.09 g, 8.66 mmol), was degassed and flushed with oxygen (3×'s). Then 6-fluoro-8-vinylisoquinoline (Step 6.5, 1.0 g, 5.77 mmol) and CF$_3$TMS (0.85 mL, 5.77 mmol), dissolved in anhydrous DMF (10 mL), was added at a time at 0° C. The reaction mixture was stirred at 0° C. under oxygen atmosphere. After 1 h, once again CF$_3$TMS (0.85 mL, 5.77 mmol) was added and stirred for 2 h, under same condition. The reaction mixture was diluted with Et$_2$O, filtered through celite bed. The celite bed was thoroughly washed with Et$_2$O. The filtrate was collected, washed with water (twice), brine, dried over anhydrous Na$_2$SO$_4$, filtered and concentrated in vacuo. The crude was purified by flash chromatography (12 g SiliCycle column, 0-20% EtOAc in Hexane elution) to provide 3,3,3-trifluoro-1-(6-fluoroisoquinolin-8-yl)propan-1-ol (0.3 g, 20%). MS (ESI+) [Method 1A]: m/z 259.9 (M+H); Rt 0.17 min.

Step 11.2: Synthesis of 8-(1-((tert-butyldimethylsilyl)oxy)-3,3,3-trifluoropropyl)-6-fluoroisoquinoline [C-08422-047]

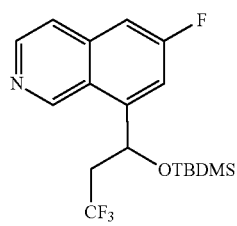 [SMILES: CC(C)(C)[Si](C)(C)OC(CC(F)(F)F)c1cc(F)cc2ccncc12]

To the solution of 3,3,3-trifluoro-1-(6-fluoroisoquinolin-8-yl)propan-1-ol (0.24 g, 0.93 mmol) and imidazole (0.31 g, 2.78 mmol) in DMF (5 mL), TBDMS-OTf (0.63 mL, 2.78 mmol) was added drop wise at 0° C. and stirred at rt. After 16 h, once again imidazole (0.31 g, 2.78 mmol) and TBDMS-OTf (0.63 mL, 2.78 mmol) were added at 0° C. and stirred at rt for 20 h. The reaction mixture was diluted with water and extracted with EtOAc twice. The combined organic portion was washed with brine, dried over anhydrous Na$_2$SO$_4$, filtered and concentrated in vacuo. The residue was purified by flash chromatography (12 g SiliCycle column, 0-10% EtOAc in Hexane elution) to afford 8-(1-((tert-butyldimethylsilyl)oxy)-3,3,3-trifluoropropyl)-6-fluoroisoquinoline (0.25 g, 72%). MS (ESI+) [Method 1A]: m/z 374.3 (M+H); Rt 2.03 min.

Step 11.3: Synthesis of 8-(1-((tert-butyldimethylsilyl)oxy)-3,3,3-trifluoropropyl)-6-fluoroisoquinoline-5-carbaldehyde

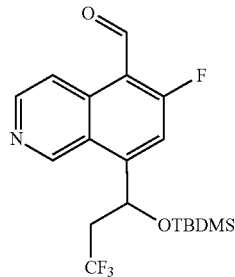 [SMILES: CC(C)(C)[Si](C)(C)OC(CC(F)(F)F)c1cc(F)c(C=O)c2ccncc12]

The title compound was prepared according to the procedure in Step 10.5. The residue was purified by flash chromatography (12 g SiliCycle column, 0-20% EtOAc in Hexane elution) to provide 8-(1-((tert-butyldimethylsilyl)oxy)-3,3,3-trifluoropropyl)-6-fluoroisoquinoline-5-carbaldehyde (0.15 g, 70%). MS (ESI+) [Method 1A]: m/z 402.5 (M+H); Rt 2.08 min.

Step 11.4: Synthesis of (1r,3r)-N-((8-(1-((tert-butyldimethylsilyl)oxy)-3,3,3-trifluoropropyl)-6-fluoroisoquinolin-5-yl)methyl)-3-(4-fluoro-3-(trifluoromethyl)phenoxy)cyclobutan-1-amine

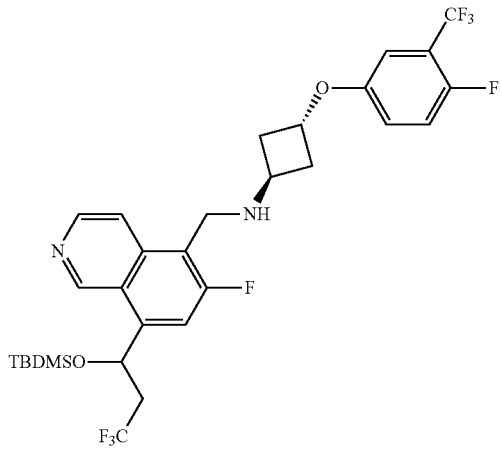 [SMILES: CC(C)(C)[Si](C)(C)OC(CC(F)(F)F)c1cc(F)c(CN[C@H]2C[C@H](Oc3ccc(F)c(C(F)(F)F)c3)C2)c2ccncc12]

The title compound was synthesized following the procedure as described in step 1.4, using (1r,3r)-3-(4-fluoro-3-(trifluoromethyl)phenoxy)cyclobutan-1-amine, HCl (Step 1.3, 120 mg, 0.42 mmol) and 8-(1-((tert-butyldimethylsilyl)oxy)-3,3,3-trifluoropropyl)-6-fluoroisoquinoline-5-carbaldehyde (150 mg, 0.38 mmol). The crude was purified by flash chromatography (12 g SiliCycle column, 0-5% MeOH in CHCl$_3$ elution) to provide (1r,3r)-N-((8-(1-((tert-butyldimethylsilyl)oxy)-3,3,3-trifluoropropyl)-6-fluoroisoquinolin-5-yl)methyl)-3-(4-fluoro-3-(trifluoromethyl)phenoxy)cyclobutan-1-amine (130 mg, 48%). MS (ESI+) [Method 1A]: m/z 635.1 (M+H); Rt 1.65 min.

Step 11.5: Synthesis of 3,3,3-trifluoro-1-(6-fluoro-5-((((1r,3r)-3-(4-fluoro-3-(trifluoromethyl)phenoxy)cyclobutyl)amino)methyl)isoquinolin-8-yl)propan-1-ol [C-08422-059]

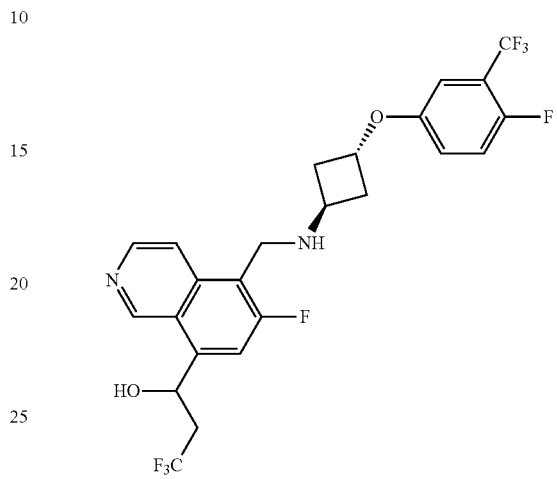

Deprotection was carried out using the procedure of Step 8.5. The residue was purified by flash chromatography (12 g SiliCycle column, 0-5% MeOH in CHCl$_3$ elution). The isolated product was re-purified by reverse phase MPLC (C18 Gold column, 0-100% MeCN in H$_2$O elution) to provide 3,3,3-trifluoro-1-(6-fluoro-5-((((1r,3r)-3-(4-fluoro-3-(trifluoromethyl)phenoxy)cyclobutyl)amino)methyl)isoquinolin-8-yl)propan-1-ol (44 mg, 41%). MS (ESI+) [Method 5A]: m/z 521.2 (M+H); Rt 1.10 min. 1H NMR (400 MHz, CD$_3$OD) δ 9.53 (s, 1H), 8.56 (d, J=6.0 Hz, 1H), 8.13 (d, J=6.0 Hz, 1H), 7.67 (d, J=11.6 Hz, 1H), 7.22 (t, J=10.0 Hz, 1H), 7.06-6.99 (m, 2H), 5.86-5.82 (m, 1H), 4.87-4.82 (m, 1H), 4.19 (d, J=1.6 Hz, 2H), 3.51-3.55 (m, 1H), 2.82-2.73 (m, 2H), 2.34 (t, J=6.0 Hz, 4H).

Example 12: Synthesis of 6-fluoro-5-((((1r,3r)-3-(4-fluoro-3-(trifluoromethyl)phenoxy)cyclobutyl)amino)methyl)isoquinolin-8-amine Step 12.1: Synthesis of N-(6-fluoroisoquinolin-8-yl)-1,1-diphenylmethanimine

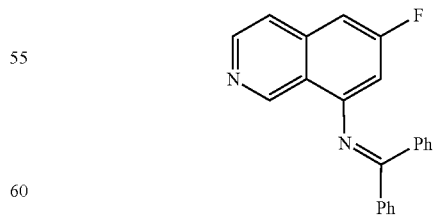

To a stirred solution of 8-bromo-6-fluoroisoquinoline (Step 6.4, 0.5 g, 2.23 mmol), diphenylmethanimine (0.6 g, 3.31 mmol) in 1,4-dioxane (30 mL), Cs$_2$CO$_3$ (1.7 g, 5.22 mmol) was added, and purged with N$_2$ for 10 min. Then Pd$_2$(dba)$_3$ (0.18 g, 0.20 mmol) and Xantphos (0.23 g, 0.40 mmol) were added and the reaction mixture was heated at 90° C. for 16 h under N₂. The reaction mixture was cooled to rt, filtered through a celite bed and washed with ethyl acetate. The filtrate was concentrated in vacuo and the crude was purified by flash chromatography (24 g SiliCycle column, 0-20% EtOAc in Hexane elution) to provide N-(6-fluoroisoquinolin-8-yl)-1,1-diphenylmethanimine (0.8 g, quantitative). MS (ESI+) [Method 6A]: m/z 327.2 (M+H); Rt 1.48 min. ¹H NMR (300 MHz, CDCl₃) δ 9.37 (s, 1H), 8.49 (d, J=6.0 Hz, 1H), 7.89-7.86 (m, 2H), 7.57-7.47 (m, 4H), 7.26-7.18 (m, 3H), 7.10-7.06 (m, 2H), 6.99 (dd, J=9.0, 1.8 Hz, 1H), 6.36 (dd, J=10.2, 1.2 Hz, 1H).

Step 12.2: Synthesis of N-(5-bromo-6-fluoroisoquinolin-8-yl)-1,1-diphenylmethanimine

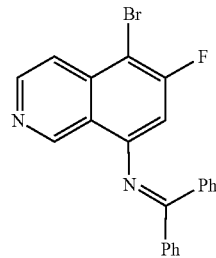 [SMILES: Fc1cc(N=C(c2ccccc2)c2ccccc2)c2cnccc2c1Br]

To a stirred solution of N-(6-fluoroisoquinolin-8-yl)-1,1-diphenylmethanimine (0.5 g, 1.53 mmol), in MeCN (10 mL), NBS (0.4 g, 2.25 mmol) was added at 0° C., and stirred for 1 h under N₂, while temperature was raised slowly to rt. Reaction mixture was diluted with water and extracted with EtOAc twice. The combined organic portion was washed with brine, dried over anhydrous Na₂SO₄, filtered and concentrated in vacuo. The residue was purified by flash chromatography (12 g SiliCycle column, 0-10% EtOAc in Hexane elution) to provide N-(5-bromo-6-fluoroisoquinolin-8-yl)-1,1-diphenylmethanimine (0.5 g, 82%). MS (ESI+) [Method 6A]: m/z 405.1 (M+H); Rt 1.74 min.

Step 12.3: Synthesis of N-(6-fluoro-5-vinylisoquinolin-8-yl)-1,1-diphenylmethanimine

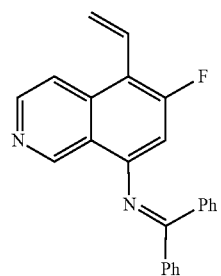 [SMILES: C=Cc1c(F)cc(N=C(c2ccccc2)c2ccccc2)c2cnccc12]

The stirred solution of N-(5-bromo-6-fluoroisoquinolin-8-yl)-1,1-diphenylmethanimine (0.3 g, 0.74 mmol), Vinyl-SnBu₃ (0.25 g, 0.79 mmol) in 1,4-dioxane (20 mL), was degassed with argon for 10 min. Then Pd(PPh₃)₄ (80 mg, 0.07 mmol) was added, degassed and heated at 100° C. for 16 h under argon atmosphere. Reaction mixture was cooled to rt, diluted with water and extracted with EtOAc 3×'s. The combined organic portion was washed with brine, dried over anhydrous Na₂SO₄, filtered and concentrated in vacuo to yield the crude product. The crude was purified by flash chromatography (24 g SiliCycle column, 0-15% EtOAc in Hexane elution) to provide N-(6-fluoro-5-vinylisoquinolin-8-yl)-1,1-diphenylmethanimine (0.3 g, 100%). MS (ESI+) [Method 6A]: m/z 353.2 (M+H); Rt 1.59 min.

Step 12.4: Synthesis of 8-((diphenylmethylene)amino)-6-fluoroisoquinoline-5-carbaldehyde

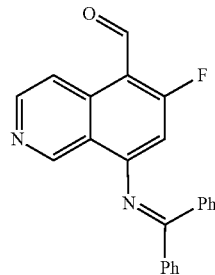 [SMILES: O=Cc1c(F)cc(N=C(c2ccccc2)c2ccccc2)c2cnccc12]

To the solution of N-(6-fluoro-5-vinylisoquinolin-8-yl)-1,1-diphenylmethanimine (0.2 g, 0.57 mmol) in t-BuOH-1,4-dioxane (15 mL, 1:2 v/v), OsO₄ (10% in t-BuOH) (0.1 mL, 0.04 mmol) was added at rt and stirred for 15 min. Then NaIC₄ (0.5 g, 2.35 mmol) dissolved in water (5 mL) was added dropwise and stirred at rt for 1 h. Reaction mixture was diluted with water and extracted with EtOAc 3×'s. The combined organic portion was washed with brine, dried over anhydrous Na₂SO₄, filtered and concentrated in vacuo. The residue was purified by flash chromatography (12 g SiliCycle column, 0-15% EtOAc in Hexane elution) to provide 8-((diphenylmethylene)amino)-6-fluoroisoquinoline-5-carbaldehyde (90 mg, 47%). MS (ESI+) [Method 4A]: m/z 355.1 (M+H); Rt 1.28 min.

Step 12.5: Synthesis of (1r,3r)-N-((8-((diphenylmethylene)amino)-6-fluoroisoquinolin-5-yl)methyl)-3-(4-fluoro-3-(trifluoromethyl)phenoxy)cyclobutan-1-amine

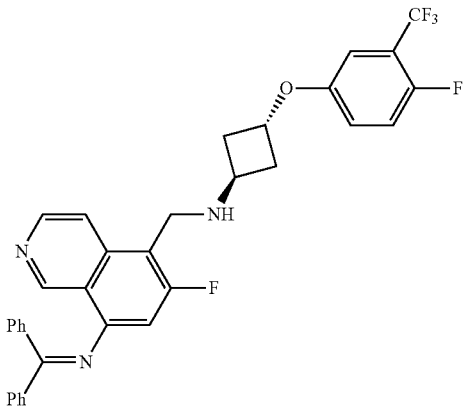 [SMILES: Fc1ccc(O[C@H]2C[C@H](NCc3c(F)cc(N=C(c4ccccc4)c4ccccc4)c4cnccc34)C2)cc1C(F)(F)F]

The title compound was synthesized following the procedure as described in step 1.4, using (1r,3r)-3-(4-fluoro-3-(trifluoromethyl)phenoxy)cyclobutan-1-amine, HCl (65 mg, 0.22 mmol) and 8-((diphenylmethylene)amino)-6-fluoroisoquinoline-5-carbaldehyde (90 mg, 0.25 mmol). The crude (1r,3r)-N-((8-((diphenylmethylene)amino)-6-fluoroisoquinolin-5-yl)methyl)-3-(4-fluoro-3-(trifluoromethyl)phenoxy)cyclobutan-1-amine (100 mg, 77%) was used in next step without purification. MS (ESI+) [Method 6A]: m/z 588.3 (M+H); Rt 1.40 min.

Step 12.6: Synthesis of 6-fluoro-5-((((1r,3r)-3-(4-fluoro-3-(trifluoromethyl)phenoxy)cyclobutyl)amino)methyl)isoquinolin-8-amine

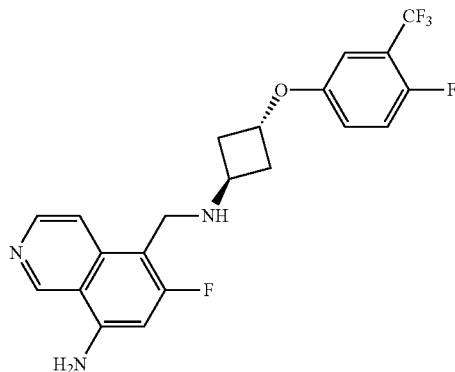

The solution of (1r,3r)-N-((8-((diphenylmethylene)amino)-6-fluoroisoquinolin-5-yl)methyl)-3-(4-fluoro-3-(trifluoromethyl)phenoxy)cyclobutan-1-amine (100 mg, 0.17 mmol) and HCl solution (4M in 1,4-dioxane) (2 mL) was stirred at rt for 1 h. Then the reaction mixture was concentrated in vacuo and purified by prep-HPLC (Column: LUNA Phenomenex (250 mm×21.2 mm), 5.0μ; Mobile Phase: 0.01% NH$_4$OH in water and acetonitrile) to provide 6-fluoro-5-((((1r,3r)-3-(4-fluoro-3-(trifluoromethyl)phenoxy)cyclobutyl)amino)methyl)isoquinolin-8-amine (6 mg, 8%). MS (ESI+) [Method 6A]: m/z 424.1 (M+H); Rt 1.30 min. $^1$H NMR (400 MHz, CD$_3$OD) δ 9.41 (s, 1H), 8.49-8.47 (m, 2H), 7.92 (d, J=10.0 Hz, 1H), 7.89 (t, J=11.6 Hz, 1H), 7.13-7.08 (m, 2H), 6.68 (d, J=13.2 Hz, 1H), 4.96-4.92 (m, 1H), 4.40 (s, 2H), 4.04-3.99 (m, 1H), 2.70-2.64 (m, 2H), 2.62-2.57 (m, 2H).

Example 13: Synthesis of 5-((((1r,3r)-3-(4-fluoro-3-(trifluoromethyl)phenoxy)cyclobutyl)amino)methyl)isoquinolin-3-amine Step 13.1: Synthesis of tert-butyl (5-bromoisoquinolin-3-yl)(tert-butoxycarbonyl)carbamate

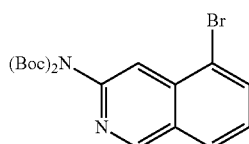

The stirred solution of 5-bromoisoquinolin-3-amine [CAS No. 1192815-01-2] (2.0 g, 8.97 mmol) in THF (20 mL) was cooled to 0° C. Then DMAP (2.19 g, 17.93 mmol) and Boc$_2$O (3.9 g, 17.93 mmol) were added and stirred at rt for 16 h. Reaction mixture was diluted with water and extracted with EtOAc twice. The combined organic portion was washed with brine, dried over anhydrous Na$_2$SO$_4$, filtered and concentrated in vacuo. The crude was purified by flash chromatography (12 g SiliCycle column, 0-8% EtOAc in Hexane elution) to provide tert-butyl (5-bromoisoquinolin-3-yl)(tert-butoxycarbonyl)carbamate (1.2 g, 30%). MS (ESI+) [Method 6A]: m/z 423.2, 425.2 (M+H); Rt 1.70 min. $^1$H NMR (600 MHz, CDCl$_3$) δ 9.09 (S, 1H), 8.16 (s, 1H), 7.78-7.76 (m, 1H), 7.72 (d, J=9.0 Hz, 1H), 7.59 (s, 1H), 1.44 (s, 18H).

Step 13.2: Synthesis of tert-butyl (tert-butoxycarbonyl)(5-vinylisoquinolin-3-yl)carbamate

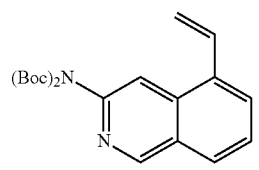

The stirred solution of tert-butyl (5-bromoisoquinolin-3-yl)(tert-butoxycarbonyl)carbamate (1.2 g, 2.83 mmol), potassium trifluoro(vinyl)borate (0.76 g, 5.67 mmol) and TEA (0.79 mL, 5.67 mmol) in IPA (20 mL) was degassed with argon for 10 min. Then Pd(dppf)Cl$_2$·CH$_2$Cl$_2$ (185 mg, 0.23 mmol) was added, degassed and heated at 80° C. for 16 h under argon atmosphere. Reaction mixture was cooled to rt, diluted with water and extracted with EtOAc twice. The combined organic portion was washed with brine, dried over anhydrous Na$_2$SO$_4$, filtered and concentrated in vacuo to yield the crude product. The crude was purified by flash chromatography (12 g SiliCycle column, 0-10% EtOAc in Hexane elution) to provide tert-butyl (tert-butoxycarbonyl)(5-vinylisoquinolin-3-yl)carbamate (0.8 g, 80%). MS (ESI+) [Method 6A]: m/z 370.9 (M+H); Rt 1.67 min. $^1$H NMR (300 MHz, CDCl$_3$) δ 9.12 (s, 1H), 7.88-7.77 (m, 3H), 7.55 (s, 1H), 6.89 (dd, J=17.4, 10.5 Hz, 1H), 5.92 (d, J=17.7 Hz, 1H), 5.43 (d, J=11.1 Hz, 1H), 1.44 (s, 18H).

Step 13.3: Synthesis of tert-butyl (tert-butoxycarbonyl)(5-formylisoquinolin-3-yl)carbamate

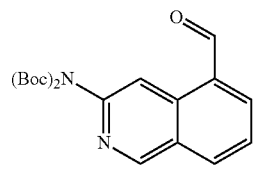

To the solution of tert-butyl (tert-butoxycarbonyl)(5-vinylisoquinolin-3-yl)carbamate (0.8 g, 2.16 mmol) in t-BuOH-1,4-dioxane (18 mL, 1:2 v/v), OsO$_4$ (16 mg, 0.06 mmol) was added at 0° C. and stirred at rt for 20 min. Then NaIC$_4$ (1.38 g, 6.48 mmol) dissolved in water (4 mL) was added dropwise and stirred at rt for 1 h. Reaction mixture was diluted with water and extracted with EtOAc 3×'s. The combined organic portion was washed with brine, dried over anhydrous Na$_2$SO$_4$, filtered and concentrated in vacuo. The residue was purified by flash chromatography (12 g SiliCycle column, 0-15% EtOAc in Hexane elution) to provide tert-butyl (tert-butoxycarbonyl)(5-formylisoquinolin-3-yl)carbamate (0.6 g, 62%). MS (ESI+) [Method 6A]: m/z 373.2

(M+H); Rt 1.60 min. ¹H NMR (400 MHz, CDCl₃) δ 10.19 (s, 1H), 9.30 (s, 1H), 8.48 (d, J=0.8 Hz, 1H), 8.16 (dd, J=8.8, 1.6 Hz, 1H), 7.94 (d, J=8.8 Hz, 1H), 7.74 (s, 1H), 1.48 (s, 18H).

Step 13.4: Synthesis of tert-butyl (tert-butoxycarbonyl)(5-((((1r,3r)-3-(4-fluoro-3-(trifluoromethyl)phenoxy)cyclobutyl)amino)methyl)isoquinolin-3-yl)carbamate

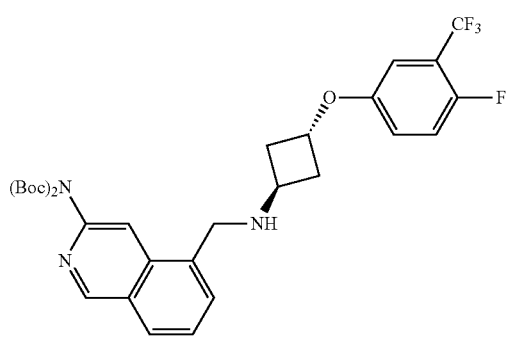

The title compound was synthesized following the procedure as described in step 1.4, using (1r,3r)-3-(4-fluoro-3-(trifluoromethyl)phenoxy)cyclobutan-1-amine, HCl (Step 1.3, 200 mg, 0.70 mmol) and tert-butyl (tert-butoxycarbonyl)(5-formylisoquinolin-3-yl)carbamate (260 mg, 0.70 mmol). The crude tert-butyl (tert-butoxycarbonyl)(5-((((1r,3r)-3-(4-fluoro-3-(trifluoromethyl)phenoxy)cyclobutyl)amino)methyl)isoquinolin-3-yl)carbamate (250 mg, 59%) was used in next step without purification. MS (ESI+) [Method 1A]: m/z 606.0 (M+H); Rt 1.36 min.

Step 13.5: Synthesis of 5-((((1r,3r)-3-(4-fluoro-3-(trifluoromethyl)phenoxy)cyclobutyl)amino)methyl)isoquinolin-3-amine

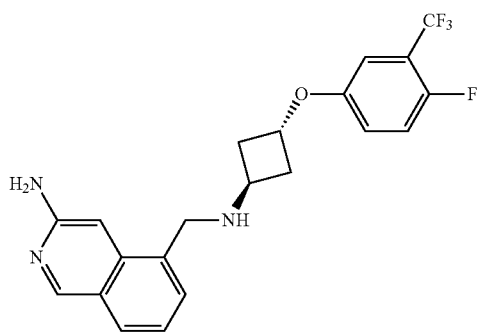 [SMILES: Nc1cc2c(CN[C@H]3C[C@H](Oc4ccc(F)c(C(F)(F)F)c4)C3)cccc2cn1]

The solution of tert-butyl (tert-butoxycarbonyl)(5-((((1r,3r)-3-(4-fluoro-3-(trifluoromethyl)phenoxy)cyclobutyl)amino)methyl)isoquinolin-3-yl)carbamate (250 mg, 0.41 mmol) and HCl solution (4M in 1,4-dioxane) (5 mL) was stirred at rt for 16 h. Then the reaction mixture was concentrated in vacuo and purified by prep-HPLC (Column: KINETEX EVO C18 (150 mm×21.0 mm), 5.0μ; Mobile Phase: 0.02% NH₄OH in water and acetonitrile) to provide 5-((((1r,3r)-3-(4-fluoro-3-(trifluoromethyl)phenoxy)cyclobutyl)amino)methyl)isoquinolin-3-amine (100 mg, 59%). MS (ESI+) [Method 6A]: m/z 406.2 (M+H); Rt 1.30 min. ¹H NMR (400 MHz, CD₃OD) δ 9.23 (s, 1H), 8.13 (d, J=8.8 Hz, 1H), 8.00 (d, J=6.8 Hz, 1H), 7.53-7.50 (m, 2H), 7.30 (t, J=10.2 Hz, 1H), 7.17-7.11 (m, 2H), 5.08-5.04 (m, 1H), 4.58 (s, 2H), 4.27-4.23 (m, 1H), 2.94-2.89 (m, 2H), 2.72-2.67 (m, 2H).

Example 14: Synthesis of 6-fluoro-5-((((1r,3r)-3-(4-fluoro-3-(trifluoromethyl)phenoxy)cyclobutyl)amino)methyl)isoquinolin-3-amine, HCl Step 14.1: Synthesis of tert-butyl (tert-butoxycarbonyl)(6-fluoroisoquinolin-3-yl)carbamate

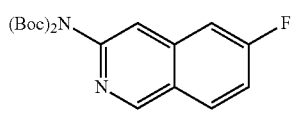

The stirred solution of 6-fluoroisoquinolin-3-amine [CAS No. 1260760-86-8] (17.0 g, 104.43 mmol) in THF (100 mL) was cooled to 0° C. Then DMAP (51.2 g, 419.09 mmol) and Boc₂O (120.0 mL, 522.34 mmol) were added and stirred at rt for 24 h. Reaction mixture was diluted with water and extracted with EtOAc 3×'s. The combined organic portion was washed with brine, dried over anhydrous Na₂SO₄, filtered and concentrated in vacuo. The crude was purified by flash chromatography (80 g SiliCycle column, 0-15% EtOAc in Hexane elution) to provide tert-butyl (tert-butoxycarbonyl)(6-fluoroisoquinolin-3-yl)carbamate (15.0 g, 39%). MS (ESI+) [Method 6A]: m/z 363.2 (M+H); Rt 1.64 min.

Step 14.2: Synthesis of tert-butyl (tert-butoxycarbonyl)(6-fluoro-5-formylisoquinolin-3-yl)carbamate

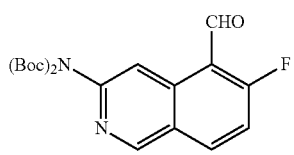

To the stirred solution of tert-butyl (tert-butoxycarbonyl)(6-fluoroisoquinolin-3-yl)carbamate (4.0 g, 11.03 mmol) in anhydrous THF (40 mL), LDA (2M in THF) (13.8 mL, 27.59 mmol) was added dropwise at −78° C. under N₂ atmosphere. After 2.5 h, piperidine-1-carbaldehyde (2.7 mL g, 33.11 mmol) dissolved in THF (10 mL) was added dropwise at −78° C., and stirred for another 1 h. The reaction was quenched with saturated NH₄Cl solution and extracted with EtOAc 3×'s. The combined organic portion was washed with brine, dried over anhydrous Na₂SO₄, filtered and concentrated in vacuo. The residue was purified by flash chromatography (24 g SiliCycle column, 0-20% EtOAc in Hexane elution) to provide tert-butyl (tert-butoxycarbonyl)(6-fluoro-5-formylisoquinolin-3-yl)carbamate (2.5 g, 58%). MS (ESI+) [Method 6A]: m/z 391.2 (M+H); Rt 1.63 min.

Step 14.3: Synthesis of tert-butyl (tert-butoxycarbonyl)(6-fluoro-5-((((1r,3r)-3-(4-fluoro-3-(trifluoromethyl)phenoxy)cyclobutyl)amino)methyl)isoquinolin-3-yl)carbamate

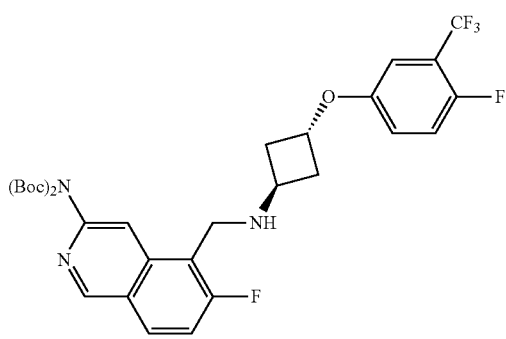

The title compound was synthesized following the procedure as described in step 1.4, using (1r,3r)-3-(4-fluoro-3-(trifluoromethyl)phenoxy)cyclobutan-1-amine, HCl (Step 1.3, 1.1 g, 3.85 mmol) and tert-butyl (tert-butoxycarbonyl)(6-fluoro-5-formylisoquinolin-3-yl)carbamate (2.1 g, 5.39 mmol). The crude was purified by flash chromatography (24 g SiliCycle column, 0-2% MeOH in CH₂Cl₂ elution) to provide tert-butyl (tert-butoxycarbonyl)(6-fluoro-5-((((1r,3r)-3-(4-fluoro-3-(trifluoromethyl)phenoxy)cyclobutyl)amino)methyl)isoquinolin-3-yl)carbamate (2.0 g, 82%). MS (ESI+) [Method 6A]: m/z 624.3 (M+H); Rt 1.43 min.

Step 14.4: Synthesis of 6-fluoro-5-((((1r,3r)-3-(4-fluoro-3-(trifluoromethyl)phenoxy)cyclobutyl)amino)methyl)isoquinolin-3-amine, HCl

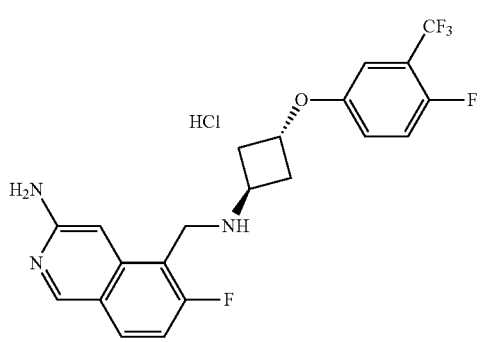 [SMILES: Nc1cc2c(CN[C@H]3C[C@H](Oc4ccc(F)c(C(F)(F)F)c4)C3)c(F)ccc2cn1 ; Cl]

Deprotection was carried out according to Step 13.5. The reaction mixture was concentrated in vacuo and purified by prep-HPLC (Column: WATERS XBRIDGE C18 (150 mm×20.0 mm), 5.0µ; Mobile Phase: 0.02% NH₄OH in water and acetonitrile). To the isolated product, HCl solution (4M in 1,4-dioxane) (5 mL) was added, stirred at rt for 1 h, concentrated in vacuo, triturated with Et₂O, collected solid was dried in vacuo to provide 6-fluoro-5-((((1r,3r)-3-(4-fluoro-3-(trifluoromethyl)phenoxy)cyclobutyl)amino)methyl)isoquinolin-3-amine, HCl (360 mg, 24%). MS (ESI+) [Method 5A]: m/z 424.3 (M+H); Rt 0.30 min. ¹H NMR (400 MHz, CD₃OD) δ 9.10 (s, 1H), 8.26-8.22 (m, 1H), 7.45 (s, 1H), 7.37 (t, J=10.0 Hz, 1H), 7.31 (t, J=9.6 Hz, 1H), 7.15-7.08 (m, 2H), 5.05-5.01 (m, 1H), 4.56 (d, J=1.6 Hz, 2H), 4.26-4.21 (m, 1H), 2.91-2.84 (m, 2H), 2.73-2.66 (m, 2H).

Example 15: Synthesis of 5-((((1r,3r)-3-(2,4-difluorophenoxy)cyclobutyl)amino)methyl)-6-fluoroisoquinolin-3-amine, HCl Step 15.1: Synthesis of tert-butyl ((1r,3r)-3-(2,4-difluorophenoxy)cyclobutyl)carbamate

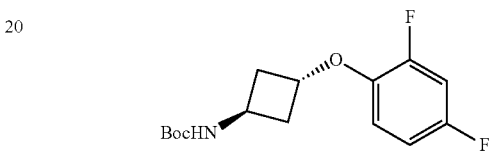

The title compound was synthesized following the procedure as described in step 1.2, using tert-butyl ((1s,3s)-3-hydroxycyclobutyl)carbamate (1.0 g, 5.34 mmol) and 2,4-difluorophenol [CAS No. 367-27-1] (0.7 g, 5.34 mmol). The residue was purified by flash chromatography (24 g SiliCycle column, 0-20% EtOAc in Hexane elution) to provide tert-butyl ((1r,3r)-3-(2,4-difluorophenoxy)cyclobutyl)carbamate (2.0 g, 124%). ¹H NMR (300 MHz, CDCl₃) δ 6.88-6.81 (m, 1H), 6.75-6.65 (m, 2H), 4.99-4.94 (m, 1H), 4.30-4.26 (m, 1H), 2.63-2.54 (m, 2H), 2.40-2.33 (m, 2H), 1.44 (s, 9H).

Step 15.2: Synthesis of (1r,3r)-3-(2,4-difluorophenoxy)cyclobutan-1-amine, HCl

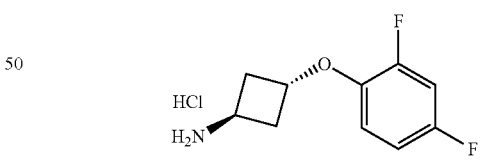

A round bottom flask was charge with tert-butyl ((1r,3r)-3-(2,4-difluorophenoxy)cyclobutyl)carbamate (2.0 g, 6.69 mmol) and HCl solution (20% in 1,4-dioxane) (10 mL), and stirred at rt for 16 h. Then the reaction mixture was concentrated in vacuo. The residue was triturated with pentane, the solid appeared was filtered and dried to yield (1r,3r)-3-(2,4-difluorophenoxy)cyclobutan-1-amine, HCl (1.3 g, 103%). ¹H NMR (300 MHz, CDCl₃) δ 7.04-6.97 (m, 1H), 6.92-6.86 (m, 2H), 4.97-4.92 (m, 1H), 4.01-3.96 (m, 1H), 2.64-2.60 (m, 4H).

Step 15.3: Synthesis of tert-butyl (tert-butoxycarbonyl)(5-((((1r,3r)-3-(2,4-difluorophenoxy)cyclobutyl)amino)methyl)-6-fluoroisoquinolin-3-yl)carbamate

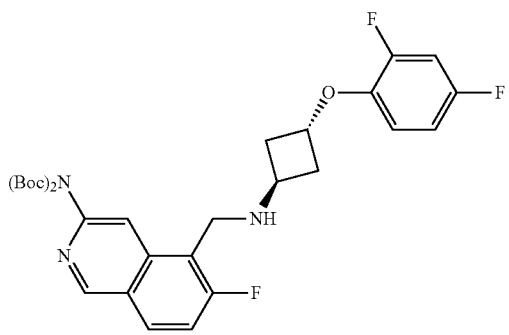

The title compound was synthesized following the procedure as described in step 1.4, using (1r,3r)-3-(2,4-difluorophenoxy)cyclobutan-1-amine, HCl (120 mg, 0.51 mmol) and tert-butyl (tert-butoxycarbonyl)(6-fluoro-5-formylisoquinolin-3-yl)carbamate (Step 14.2, 240 mg, 0.61 mmol). The crude was purified by flash chromatography (12 g SiliCycle column, 0-4% MeOH in CHCl$_3$ elution) to provide tert-butyl (tert-butoxycarbonyl)(5-((((1r,3r)-3-(2,4-difluorophenoxy)cyclobutyl)amino)methyl)-6-fluoroisoquinolin-3-yl)carbamate (200 mg, 68%). MS (ESI+) [Method 6A]: m/z 574.4 (M+H); Rt 1.38 min.

Step 15.4: Synthesis of 5-((((1r,3r)-3-(2,4-difluorophenoxy)cyclobutyl)amino)methyl)-6-fluoroisoquinolin-3-amine, HCl

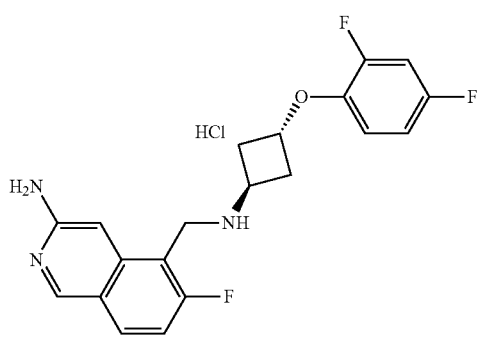 [SMILES: Nc1cc2c(CN[C@H]3C[C@H](Oc4ccc(F)cc4F)C3)c(F)ccc2cn1 ; Cl]

Deprotection was carried out according to Step 13.5. The reaction mixture was concentrated in vacuo and purified by prep-HPLC (Column: GEMINI NX (150 mm×21.2 mm), 5.0μ; Mobile Phase: 0.02% NH$_4$OH in water and acetonitrile). To the isolated product, HCl solution (4M in 1,4-dioxane) (1 mL) was added and stirred at rt for 1 h. Solvent was evaporated, and the residue was triturated with Et$_2$O. The solid formed was collected by filtration and dried in vacuo to provide 5-((((1r,3r)-3-(2,4-difluorophenoxy)cyclobutyl)amino)methyl)-6-fluoroisoquinolin-3-amine, HCl (33 mg, 23%). MS (ESI+) [Method 6A]: m/z 374.2 (M+H); Rt 1.29 min. $^1$H NMR (400 MHz, CD$_3$OD) δ 9.11 (s, 1H), 8.28-8.23 (m, 1H), 7.43 (s, 1H), 7.38 (t, J=10.0 Hz, 1H), 7.08-6.90 (m, 3H), 5.05-5.01 (m, 1H), 4.56 (s, 2H), 4.28-4.23 (m, 1H), 2.88-2.83 (m, 2H), 2.77-2.72 (m, 2H).

Example 16: Synthesis of 6-fluoro-5-(((((1r,3r)-3-((2-(trifluoromethyl)pyridin-4-yl)oxy)cyclobutyl)amino)methyl)isoquinolin-3-amine, HCl

Step 16.1: Synthesis of tert-butyl ((1r,3r)-3-((2-(trifluoromethyl)pyridin-4-yl)oxy)cyclobutyl)carbamate

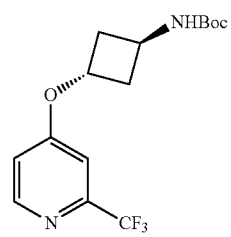 [SMILES: CC(C)(C)OC(=O)N[C@H]1C[C@H](Oc2ccnc(C(F)(F)F)c2)C1]

To the solution of NaH (60% on mineral oil) (66 mg, 1.65 mmol) in DMF (2 mL), was added 4-chloro-2-(trifluoromethyl)pyridine [CAS No. 131748-14-6] (200 mg, 1.10 mmol), followed by tert-butyl ((1r,3r)-3-hydroxycyclobutyl)carbamate [CAS No. 389890-42-0] (207 mg, 1.10 mmol) at 0° C. and stirred at rt for 16 h. The reaction was quenched with ice-water, extracted with EtOAc 3×'s. The combined organic portion was washed with brine, dried over anhydrous Na$_2$SO$_4$, filtered and concentrated in vacuo. The residue was purified by flash chromatography (12 g SiliCycle column, 0-6% EtOAc in Hexane elution) to provide tert-butyl ((1r,3r)-3-((2-(trifluoromethyl)pyridin-4-yl)oxy)cyclobutyl)carbamate (250 mg, 68%). MS (ESI+) [Method 6A]: m/z 333.1 (M+H); Rt 1.57 min.

Step 16.2: Synthesis of (1r,3r)-3-((2-(trifluoromethyl)pyridin-4-yl)oxy)cyclobutan-1-amine

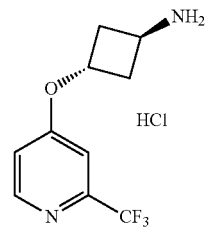 [SMILES: N[C@H]1C[C@H](Oc2ccnc(C(F)(F)F)c2)C1 ; Cl]

A round bottom flask was charge with tert-butyl ((1r,3r)-3-((2-(trifluoromethyl)pyridin-4-yl)oxy)cyclobutyl)carbamate (250 mg, 1.14 mmol) and HCl solution (4M in 1,4-dioxane) (5 mL), and stirred at rt for 16 h. Then the reaction mixture was concentrated in vacuo. The residue was triturated with pentane, the solid appeared was filtered and dried to yield (1r,3r)-3-((2-(trifluoromethyl)pyridin-4-yl)oxy)cyclobutan-1-amine, HCl (300 mg crude). LCMS [Method 6A]: m/z 233.1 [M+H]$^+$; Rt 0.70 min.

Step 16.3: Synthesis of tert-butyl (tert-butoxycarbonyl)(6-fluoro-5-((((1r,3r)-3-((2-(trifluoromethyl)pyridin-4-yl)oxy)cyclobutyl)amino)methyl)isoquinolin-3-yl)carbamate [C-07860-048]

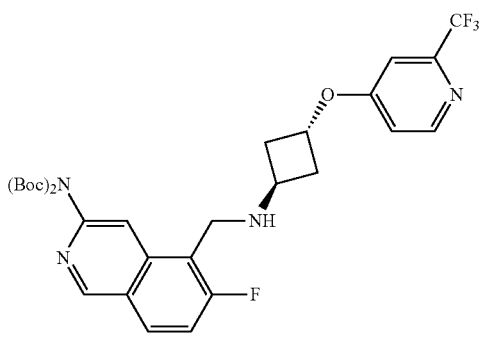

The title compound was synthesized following the procedure as described in step 1.4, using (1r,3r)-3-((2-(trifluoromethyl)pyridin-4-yl)oxy)cyclobutan-1-amine, HCl (130 mg, 0.48 mmol) and tert-butyl (tert-butoxycarbonyl)(6-fluoro-5-formylisoquinolin-3-yl)carbamate (Step 14.2, 220 mg, 0.58 mmol). The crude was purified by flash chromatography (12 g SiliCycle column, 0-4% MeOH in CHCl₃ elution) to provide tert-butyl (tert-butoxycarbonyl)(6-fluoro-5-((((1r,3r)-3-((2-(trifluoromethyl)pyridin-4-yl)oxy)cyclobutyl)amino)methyl)isoquinolin-3-yl)carbamate (200 mg, 68%). MS (ESI+) [Method 6A]: m/z 607.4 (M+H); Rt 1.36 min.

Step 16.4: Synthesis of 6-fluoro-5-((((1r,3r)-3-((2-(trifluoromethyl)pyridin-4-yl)oxy)cyclobutyl)amino)methyl)isoquinolin-3-amine, HCl [C-07860-054]

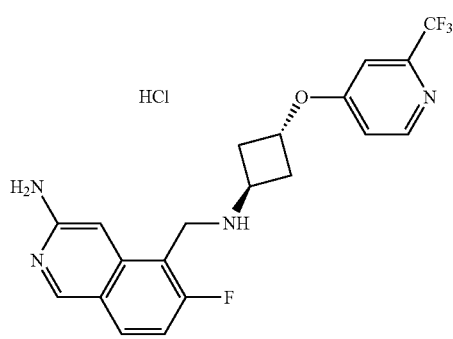 [SMILES: Nc1cc2c(CN[C@H]3C[C@H](Oc4ccnc(C(F)(F)F)c4)C3)c(F)ccc2cn1 ; Cl]

Deprotection was carried out according to Step 13.5. Then the reaction mixture was concentrated in vacuo and purified by prep-HPLC (Column: KINETEX EVO C18, (150 mm×21.2 mm), 5.0µ; Mobile Phase: 0.05% NH₄OH in water and acetonitrile). To the isolated product, HCl solution (4M in 1,4-dioxane) (1 mL) was added and stirred at rt for 1 h. Solvent was evaporated, and the residue was triturated with Et₂O. The solid formed was collected by filtration and dried in vacuo to provide 6-fluoro-5-((((1r,3r)-3-((2-(trifluoromethyl)pyridin-4-yl)oxy)cyclobutyl)amino)methyl)isoquinolin-3-amine, HCl (30 mg, 20%). MS (ESI+) [Method 6A]: m/z 407.2 (M+H); Rt 1.26 min. ¹H NMR (400 MHz, CD₃OD) δ 9.15 (s, 1H), 8.58 (d, J=6.0 Hz, 1H), 8.31-8.27 (m, 1H), 7.54 (s, 1H), 7.42 (t, J=9.6 Hz, 1H), 7.34 (d, J=2.4 Hz, 1H), 7.17-7.15 (m, 1H), 5.26-5.22 (m, 1H), 4.60 (d, J=2.0 Hz, 2H), 4.32-4.28 (m, 1H), 3.02-2.96 (m, 2H), 2.82-2.75 (m, 2H).

Example 17: Synthesis of 6-fluoro-5-((((1r,3r)-3-((6-(trifluoromethyl)pyridin-3-yl)oxy)cyclobutyl)amino)methyl)isoquinolin-3-amine, HCl Step 17.1: Synthesis of tert-butyl (tert-butoxycarbonyl)(6-fluoro-5-((((1r,3r)-3-((6-(trifluoromethyl)pyridin-3-yl)oxy)cyclobutyl)amino)methyl)isoquinolin-3-yl)carbamate

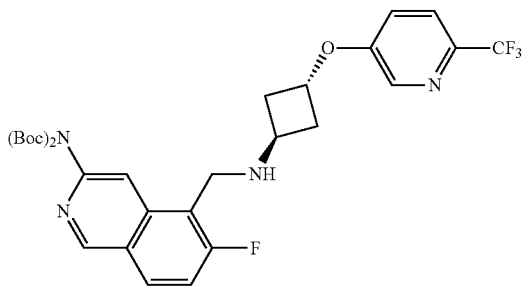

The title compound was synthesized following the procedure as described in step 1.4, using (1r,3r)-3-((6-(trifluoromethyl)pyridin-3-yl)oxy)cyclobutan-1-amine, HCl (Step 2.2, 130 mg, 0.48 mmol) and tert-butyl (tert-butoxycarbonyl)(6-fluoro-5-formylisoquinolin-3-yl)carbamate (Step 14.2, 220 mg, 0.58 mmol). The crude was purified by flash chromatography (12 g SiliCycle column, 0-4% MeOH in CHCl₃ elution) to provide tert-butyl (tert-butoxycarbonyl)(6-fluoro-5-((((1r,3r)-3-((6-(trifluoromethyl)pyridin-3-yl)oxy)cyclobutyl)amino)methyl)isoquinolin-3-yl)carbamate (200 mg, 68%). MS (ESI+) [Method 6A]: m/z 607.4 (M+H); Rt 1.38 min.

Step 17.2: Synthesis of 6-fluoro-5-((((1r,3r)-3-((6-(trifluoromethyl)pyridin-3-yl)oxy)cyclobutyl)amino)methyl)isoquinolin-3-amine, HCl

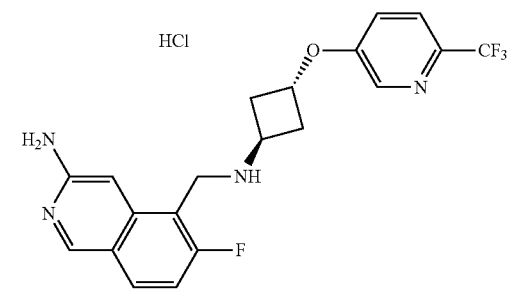 [SMILES: Nc1cc2c(CN[C@H]3C[C@H](Oc4ccc(C(F)(F)F)nc4)C3)c(F)ccc2cn1 ; Cl]

Deprotection was carried out according to Step 13.5. The reaction mixture was concentrated in vacuo and purified by prep-HPLC (Column: KINETEX EVO C18 (150 mm×21.2 mm), 5.0µ; Mobile Phase: 0.02% NH₄OH in water and acetonitrile). To the isolated product, HCl solution (4M in 1,4-dioxane) (1 mL) was added and stirred at rt for 1 h. Solvent was evaporated, and the residue was triturated with Et₂O. The solid formed was collected by filtration and dried in vacuo to provide 6-fluoro-5-(((((1r,3r)-3-((6-(trifluoromethyl)pyridin-3-yl)oxy)cyclobutyl)amino)methyl)isoquinolin-3-amine, HCl (35 mg, 24%). MS (ESI+) [Method 4B]: m/z 407.2 (M+H); Rt 0.97 min. ¹H NMR (400 MHz, CD₃OD) δ 9.10 (s, 1H), 8.32 (d, J=2.8 Hz, 1H), 8.26-8.22 (m, 1H), 7.77 (d, J=8.8, 1H), 7.46-7.43 (m, 2H), 7.37 (t, J=9.6 Hz, 1H), 5.19-5.15 (m, 1H), 4.57 (d, J=2.0 Hz, 2H), 4.28-4.23 (m, 1H), 2.98-2.91 (m, 2H), 2.78-2.72 (m, 2H).

Example 18: Synthesis of (3-amino-6-fluoro-5-(((((1r,3r)-3-(4-fluoro-3-(trifluoromethyl)phenoxy)cyclobutyl)amino)methyl)isoquinolin-8-yl)methanol, HCl Step 18.1: Synthesis of 2-bromo-4-fluorobenzaldehyde oxime

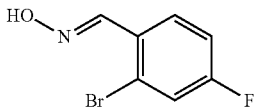 [SMILES: O/N=C/c1ccc(F)cc1Br]

To the solution of 2-bromo-4-fluorobenzaldehyde [59142-68-6] (50.0 g, 246.29 mmol) in EtOH (600 mL), a solution of NaHCO₃ (41.4 g, 492.58 mmol) and hydroxylamine hydrochloride (25.7 g, 369.44 mmol) in water (600 mL), was added at rt and stirred for 16 h. Reaction mixture was concentrated in vacuo to remove EtOH, diluted with water and extracted with EtOAc 3×'s. The combined organic portion was washed with brine, dried over anhydrous Na₂SO₄, filtered and concentrated in vacuo to afford crude 2-bromo-4-fluorobenzaldehyde oxime (53.0 g, 98%). MS (ESI+) [Method 6A]: m/z 217.9 (M+H); Rt 1.50 min. ¹H NMR (300 MHz, CDCl₃) δ 8.47 (s, 1H), 7.89 (brs, 1H), 7.84-7.80 (m, 1H), 7.34-7.32 (m, 1H), 7.08-7.03 (m, 1H).

Step 18.2: Synthesis of (2-bromo-4-fluorophenyl)methanamine

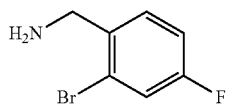

To the stirred solution of 2-bromo-4-fluorobenzaldehyde oxime (48.0 g, 220.15 mmol) in EtOH (480 mL), concentrated HCl (240 mL) was added at 0° C. Then Zn-dust was added portion wise at 0° C. and stirred at rt for 4 h. Reaction mixture was concentrated in vacuo to remove EtOH, diluted with water, basified with aqueous NH₄OH and extracted with EtOAc 3×'s. The combined organic layer was washed with brine and dried over Na₂SO₄, filtered and concentrated in vacuo to afford crude (2-bromo-4-fluorophenyl)methanamine (33.0 g, 73%). MS (ESI+) [Method 6A]: m/z 203.9 (M+H); Rt 0.29 min.

Step 18.3: Synthesis of N-(2-bromo-4-fluorobenzyl)-2,2-diethoxyacetimidamide

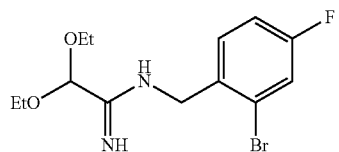 [SMILES: CCOC(OCC)C(=N)NCc1ccc(F)cc1Br]

To the solution of (2-bromo-4-fluorophenyl)methanamine (33.0 g, 161.73 mmol) in MeOH (350 mL), methyl 2,2-diethoxyacetimidate (31.3 g, 194.07 mmol) was added drop wise at rt and stirred at 70° C. for 16 h. Reaction mixture was concentrated in vacuo to provide crude N-(2-bromo-4-fluorobenzyl)-2,2-diethoxyacetimidamide (54.8 g, 101%). MS (ESI+) [Method 6A]: m/z 333.1 (M+H); Rt 1.29 min. ¹H NMR (300 MHz, CDCl₃) δ 7.46-7.42 (m, 1H), 7.30-7.27 (m, 1H), 7.02-6.99 (m, 1H), 4.93 (s, 1H), 4.48 (s, 2H), 3.64-3.54 (m, 4H), 1.25-1.20 (m, 6H).

Step 18.4: Synthesis of 8-bromo-6-fluoroisoquinolin-3-amine

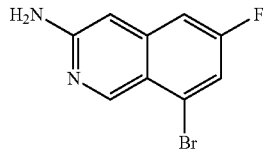 [SMILES: Nc1cc2cc(F)cc(Br)c2cn1]

To a round bottomed flask, charged with N-(2-bromo-4-fluorobenzyl)-2,2-diethoxyacetimidamide (54.8 g, 164.61 mmol), concentrated H₂SO₄ (351 mL, 6458.40 mmol) was added dropwise at 0° C. The reaction mixture was stirred at 80° C. for 3 h. Then the reaction mixture was cooled to 0° C. and poured into ice-water. The resulting solution was basified with 50% NaOH solution, extracted with EtOAc twice. The combined organic layer was washed with brine and dried over Na₂SO₄, filtered and concentrated in vacuo. The residue was purified by column chromatography (Silica gel, 60-120 mesh size, 35% EtOAc in Hexane elution) to provide 8-bromo-6-fluoroisoquinolin-3-amine (14.0 g, 32%). MS (ESI+) [Method 6A]: m/z 240.9, 242.9 (M+H); Rt 1.42 min. ¹H NMR (300 MHz, CDCl₃) δ 9.12 (s, 1H), 7.29-7.26 (m, 1H), 7.09 (d, J=9.3 Hz, 1H), 6.61 (s, 1H), 2.62 (brs, 2H).

Step 18.5: Synthesis of tert-butyl (8-bromo-6-fluoroisoquinolin-3-yl)(tert-butoxycarbonyl)carbamate

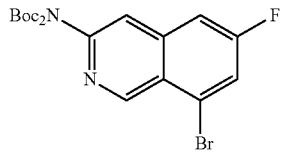

The stirred solution of 8-bromo-6-fluoroisoquinolin-3-amine (13.0 g, 53.93 mmol) and DMAP (9.9 g, 80.89 mmol) in THF (150 mL), Boc₂O (35.3 g, 161.78 mmol) was added at 0° C., then stirred at rt for 16 h. Reaction mixture was diluted with water and extracted with EtOAc 3×'s. The combined organic portion was washed with brine, dried over anhydrous Na$_2$SO$_4$, filtered and concentrated in vacuo. The crude product was purified by column chromatography (Silica gel, 60-120 mesh size, 20% EtOAc in Hexane elution) to provide tert-butyl (8-bromo-6-fluoroisoquinolin-3-yl)(tert-butoxycarbonyl)carbamate (12.0 g, 50%). MS (ESI+) [Method 6A]: m/z 443.0 (M+H); Rt 1.74 min. $^1$H NMR (300 MHz, CDCl$_3$) δ 9.43 (s, 1H), 7.64 (dd, J=8.1, 2.1 Hz, 1H), 7.59 (s, 1H), 7.42 (dd, J=9.0, 2.1 Hz, 1H), 1.47 (s, 18H).

Step 18.6: Synthesis of tert-butyl (tert-butoxycarbonyl)(6-fluoro-8-vinylisoquinolin-3-yl)carbamate

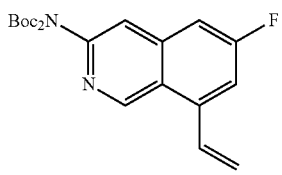

The stirred solution of tert-butyl (8-bromo-6-fluoroisoquinolin-3-yl)(tert-butoxycarbonyl)carbamate (8.0 g, 18.13 mmol), potassium trifluoro(vinyl)borate (4.05 g, 36.26 mmol) and TEA (5.05 mL, 36.26 mmol) in IPA (80 mL) was degassed with N$_2$ for 10 min. Then Pd(dppf)Cl$_2$·CH$_2$Cl$_2$ (1.48 g, 1.81 mmol) was added, degassed and heated at 100° C. for 2 h under N$_2$. Reaction mixture was cooled to rt, diluted with water and extracted with EtOAc twice. The combined organic portion was washed with brine, dried over anhydrous Na$_2$SO$_4$, filtered and concentrated in vacuo to yield the crude product. The crude product was purified by flash chromatography (40 g SiliCycle column, 0-10% EtOAc in Hexane elution) to provide tert-butyl (tert-butoxycarbonyl)(6-fluoro-8-vinylisoquinolin-3-yl)carbamate (3.7 g, 51%). MS (ESI+) [Method 5A]: m/z 389.2 (M+H); Rt 1.83 min. $^1$H NMR (300 MHz, CDCl$_3$) δ 9.39 (s, 1H), 7.56 (s, 1H), 7.49-7.41 (m, 2H), 7.37-7.34 (m, 1H), 5.91 (d, J=17.1 Hz, 1H), 5.67 (d, J=10.8 Hz, 1H), 1.45 (s, 18H).

Step 18.7: Synthesis of tert-butyl (tert-butoxycarbonyl)(6-fluoro-8-formylisoquinolin-3-yl)carbamate

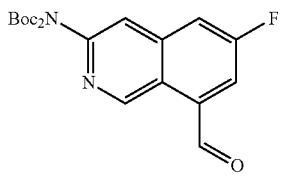

To the solution of tert-butyl (tert-butoxycarbonyl)(6-fluoro-8-vinylisoquinolin-3-yl)carbamate (2.8 g, 7.21 mmol) in t-BuOH-1,4-dioxane (45 mL, 1:2 v/v), OsO$_4$ (55 mg, 0.22 mmol) was added and stirred at rt for 15 min. Then NaIO$_4$ (7.7 g, 36.04 mmol) dissolved in water (30 mL) was added dropwise and stirred at rt for 16 h. Reaction mixture was diluted with water and extracted with EtOAc 3×'s. The combined organic portion was washed with brine, dried over anhydrous Na$_2$SO$_4$, filtered and concentrated in vacuo. The residue was purified by flash chromatography (12 g SiliCycle column, 0-15% EtOAc in Hexane elution) to provide tert-butyl (tert-butoxycarbonyl)(6-fluoro-8-formylisoquinolin-3-yl)carbamate (1.9 g, 67%). MS (ESI+) [Method 6A]: m/z 391.1 (M+H); Rt 1.64 min.

Step 18.8: Synthesis of tert-butyl (tert-butoxycarbonyl)(6-fluoro-8-(hydroxymethyl)isoquinolin-3-yl)carbamate

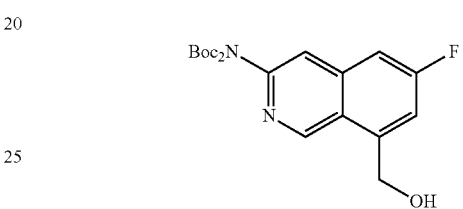

The solution of tert-butyl (tert-butoxycarbonyl)(6-fluoro-8-formylisoquinolin-3-yl)carbamate (1.9 g, 4.87 mmol) in MeOH (30 mL) was cooled to 0° C. Then NaBH$_4$ (0.27 g, 7.30 mmol) was added portion wise and stirred for 1 h. The reaction mixture was concentrated in vacuo, residue was diluted with water and extracted with EtOAc 3×'s. The combined organic portion was washed with brine, dried over anhydrous Na$_2$SO$_4$, filtered and concentrated in vacuo to afford crude tert-butyl (tert-butoxycarbonyl)(6-fluoro-8-(hydroxymethyl)isoquinolin-3-yl)carbamate (1.9 g, 99%). MS (ESI+) [Method 1A]: m/z 393.1 (M+H); Rt 1.68 min.

Step 18.9: Synthesis of tert-butyl (tert-butoxycarbonyl)(8-(((tert-butyldimethylsilyl)oxy)methyl)-6-fluoroisoquinolin-3-yl)carbamate

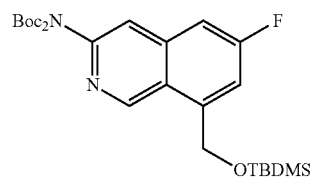

The title compound was prepared according to Step 6.7. The residue was purified by flash chromatography (12 g SiliCycle column, 0-15% EtOAc in Hexane elution) to afford tert-butyl (tert-butoxycarbonyl)(8-(((tert-butyldimethylsilyl)oxy)methyl)-6-fluoroisoquinolin-3-yl)carbamate (2.0 g, 81%). MS (ESI+) [Method 1A]: m/z 507.4 (M+H); Rt 2.03 min. $^1$H NMR (300 MHz, CDCl$_3$) δ 9.25 (s, 1H), 7.57 (s, 1H), 7.46 (dd, J=9.3, 2.4 Hz, 1H), 7.31 (dd, J=9.3, 2.4 Hz, 1H), 5.26 (s, 2H), 1.44 (s, 18H), 0.96 (s, 9H), 0.16 (s, 6H).

Step 18.10: Synthesis of tert-butyl (tert-butoxycarbonyl)(8-(((tert-butyldimethylsilyl)oxy)methyl)-6-fluoro-5-formylisoquinolin-3-yl)carbamate

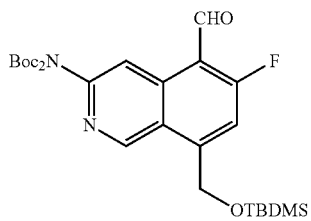

The title compound was prepared according to Step 14.2. The residue was purified by flash chromatography (12 g SiliCycle column, 0-10% EtOAc in Hexane elution) to provide tert-butyl (tert-butoxycarbonyl)(8-(((tert-butyldimethylsilyl)oxy)methyl)-6-fluoro-5-formylisoquinolin-3-yl)carbamate (0.5 g, 47%). MS (ESI+) [Method 6A]: m/z 535.4 (M+H); Rt 2.02 min.

Step 18.11: Synthesis of tert-butyl (tert-butoxycarbonyl)(8-(((tert-butyldimethylsilyl)oxy)methyl)-6-fluoro-5-((((1r,3r)-3-(4-fluoro-3-(trifluoromethyl)phenoxy)cyclobutyl)amino)methyl)isoquinolin-3-yl)carbamate

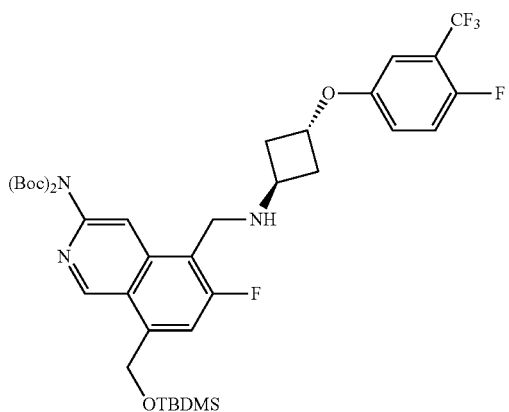

The title compound was synthesized following the procedure as described in step 1.4, using (1r,3r)-3-(4-fluoro-3-(trifluoromethyl)phenoxy)cyclobutan-1-amine, HCl (Step 1.3, 300 mg, 1.05 mmol) and tert-butyl (tert-butoxycarbonyl)(8-(((tert-butyldimethylsilyl)oxy)methyl)-6-fluoro-5-formylisoquinolin-3-yl)carbamate (560 mg, 1.05 mmol). The crude was purified by flash chromatography (12 g SiliCycle column, 0-4% MeOH in CHCl$_3$ elution) to provide tert-butyl (tert-butoxycarbonyl)(8-(((tert-butyldimethylsilyl)oxy)methyl)-6-fluoro-5-((((1r,3r)-3-(4-fluoro-3-(trifluoromethyl)phenoxy)cyclobutyl)amino)methyl)isoquinolin-3-yl)carbamate (550 mg, 68%). MS (ESI+) [Method 6A]: m/z 768.5 (M+H); Rt 1.55 min.

Step 18.12: Synthesis of tert-butyl (tert-butoxycarbonyl)(6-fluoro-5-((((1r,3r)-3-(4-fluoro-3-(trifluoromethyl)phenoxy)cyclobutyl)amino)methyl)-8-(hydroxymethyl)isoquinolin-3-yl)carbamate

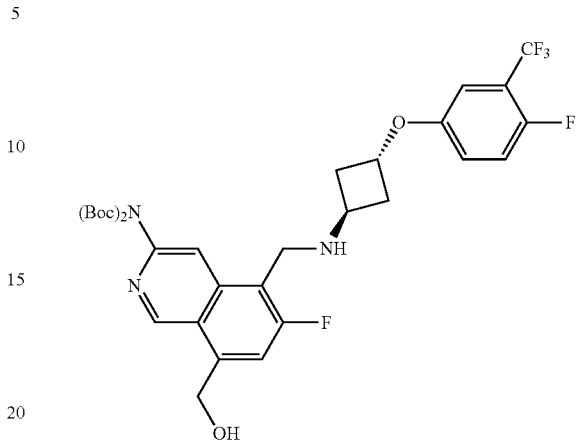

Deprotection was carried out according to Step 8.5. The residue was purified by flash chromatography (12 g SiliCycle column, 0-5% MeOH in CH$_2$Cl$_2$ elution) to provide tert-butyl (tert-butoxycarbonyl)(6-fluoro-5-((((1r,3r)-3-(4-fluoro-3-(trifluoromethyl)phenoxy)cyclobutyl)amino)methyl)-8-(hydroxymethyl)isoquinolin-3-yl)carbamate (450 mg, 96%). MS (ESI+) [Method 4B]: m/z 654.2 (M+H); Rt 1.10 min.

Step 18.13: Synthesis of (3-amino-6-fluoro-5-((((1r,3r)-3-(4-fluoro-3-(trifluoromethyl)phenoxy)cyclobutyl)amino)methyl)isoquinolin-8-yl)methanol, HCl

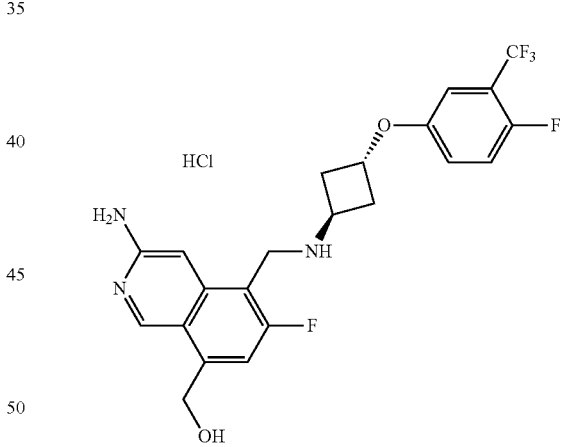

Deprotection was carried out according to Step 13.5. The product was purified by prep-HPLC (Column: WATERS X BRIDGE C18 (150 mm×19.0 mm), 5.0μ; Mobile Phase: 0.02% NH$_4$OH in water and acetonitrile). To the isolated product, HCl solution (4M in 1,4-dioxane) (2 mL) was added and stirred at rt for 1 h. Solvent was evaporated, and the residue was triturated with Et$_2$O. The solid formed was collected by filtration and dried in vacuo to provide (3-amino-6-fluoro-5-((((1r,3r)-3-(4-fluoro-3-(trifluoromethyl)phenoxy)cyclobutyl)amino)methyl)isoquinolin-8-yl)methanol, HCl (130 mg, 38%). MS (ESI+) [Method 4B]: m/z 454.2 (M+H); Rt 0.99 min. $^1$H NMR (400 MHz, CD$_3$OD) δ 9.14 (s, 1H), 7.49 (s, 1H), 7.40 (d, J=10.8 Hz, 1H), 7.29 (t, J=9.6 Hz, 1H), 7.15-7.09 (m, 2H), 5.06-5.02 (m, 3H), 4.54 (d, J=1.6 Hz, 2H), 4.25-4.22 (m, 1H), 2.90-2.85 (m, 2H), 2.73-2.66 (m, 2H).

Example 19: Synthesis of (3-amino-5-((((1r,3r)-3-(2,4-difluorophenoxy)cyclobutyl)amino)methyl)-6-fluoroisoquinolin-8-yl)methanol, HCl Step 19.1: Synthesis of tert-butyl (tert-butoxycarbonyl)(8-(((tert-butyldimethylsilyl)oxy)methyl)-5-((((1r,3r)-3-(2,4-difluorophenoxy)cyclobutyl)amino)methyl)-6-fluoroisoquinolin-3-yl)carbamate

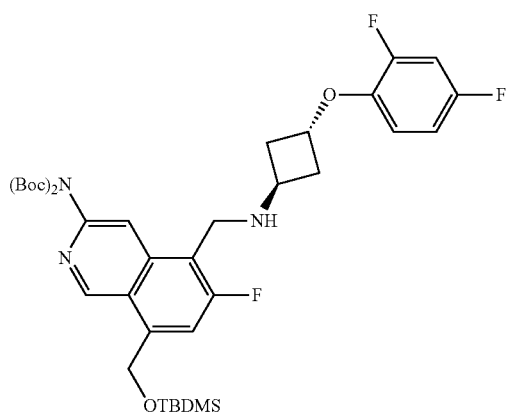

The title compound was synthesized following the procedure as described in step 1.4, using (1r,3r)-3-(2,4-difluorophenoxy)cyclobutan-1-amine, HCl (Step 15.2, 120 mg, 0.51 mmol) and tert-butyl (tert-butoxycarbonyl)(8-(((tert-butyldimethylsilyl)oxy)methyl)-6-fluoro-5-formylisoquinolin-3-yl)carbamate (Step 18.10, 240 mg, 0.46 mmol). The crude was purified by flash chromatography (12 g SiliCycle column, 0-4% MeOH in CHCl$_3$ elution) to provide tert-butyl (tert-butoxycarbonyl)(8-(((tert-butyldimethylsilyl)oxy)methyl)-5-((((1r,3r)-3-(2,4-difluorophenoxy)cyclobutyl)amino)methyl)-6-fluoroisoquinolin-3-yl)carbamate (200 mg, 54%). MS (ESI+) [Method 6A]: m/z 718.3 (M+H); Rt 1.53 min.

Step 19.2: Synthesis of tert-butyl (tert-butoxycarbonyl)(5-((((1r,3r)-3-(2,4-difluorophenoxy)cyclobutyl)amino)methyl)-6-fluoro-8-(hydroxymethyl)isoquinolin-3-yl)carbamate

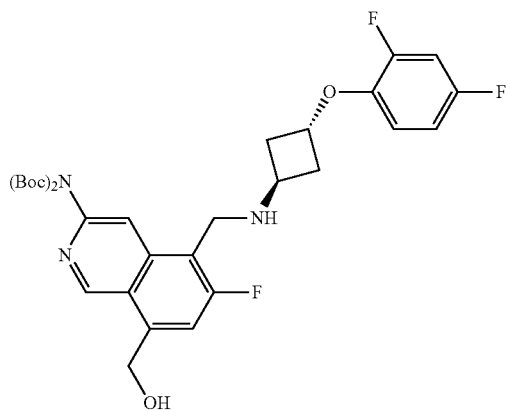

Deprotection was carried out according to Step 8.5. The residue was purified by flash chromatography (12 g SiliCycle column, 0-5% MeOH in CH$_2$Cl$_2$ elution) to provide tert-butyl (tert-butoxycarbonyl)(5-((((1r,3r)-3-(2,4-difluorophenoxy)cyclobutyl)amino)methyl)-6-fluoro-8-(hydroxymethyl)isoquinolin-3-yl)carbamate (120 mg, 71%). MS (ESI+) [Method 6A]: m/z 604.4 (M+H); Rt 1.38 min.

Step 19.3: Synthesis of (3-amino-5-((((1r,3r)-3-(2,4-difluorophenoxy)cyclobutyl)amino)methyl)-6-fluoroisoquinolin-8-yl)methanol, HCl [C-07860-067]

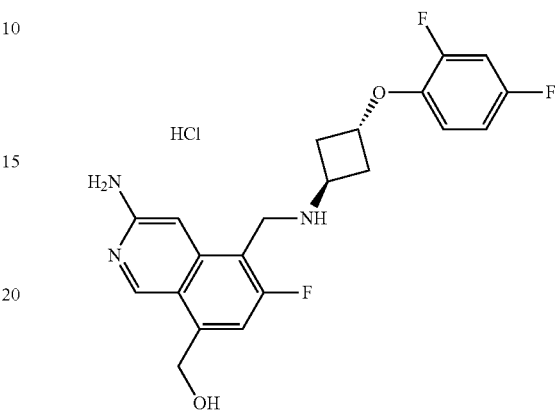

Deprotection was carried out according to Step 13.5. The product was purified by prep-HPLC (Column: GEMINI NX C18 (150 mm×21.0 mm), 5.0μ; Mobile Phase: 0.02% NH$_4$OH in water and acetonitrile). To the isolated product, HCl solution (4M in 1,4-dioxane) (1 mL) was added and stirred at rt for 1 h. Solvent was evaporated, and the residue was triturated with Et$_2$O. The solid formed was collected by filtration and dried in vacuo to provide (3-amino-5-((((1r,3r)-3-(2,4-difluorophenoxy)cyclobutyl)amino)methyl)-6-fluoroisoquinolin-8-yl)methanol, HCl (18 mg, 20%). MS (ESI+) [Method 6A]: m/z 404.2 (M+H); Rt 1.27 min. $^1$H NMR (400 MHz, CD$_3$OD) δ 9.14 (s, 1H), 7.43 (s, 1H), 7.39 (d, J=10.8 Hz, 1H), 7.03-6.87 (m, 3H), 5.05 (s, 2H), 5.01-4.97 (m, 1H), 4.53 (s, 2H), 4.23-4.20 (m, 1H), 2.83-2.78 (m, 2H), 2.73-2.68 (m, 2H).

Example 20: Synthesis of (3-amino-6-fluoro-5-((((1r,3r)-3-((2-(trifluoromethyl)pyridin-4-yl)oxy)cyclobutyl)amino)methyl)isoquinolin-8-yl)methanol, HCl Step 20.1: Synthesis of tert-butyl (tert-butoxycarbonyl)(8-(((tert-butyldimethylsilyl)oxy)methyl)-6-fluoro-5-((((1r,3r)-3-((2-(trifluoromethyl)pyridin-4-yl)oxy)cyclobutyl)amino)methyl)isoquinolin-3-yl)carbamate

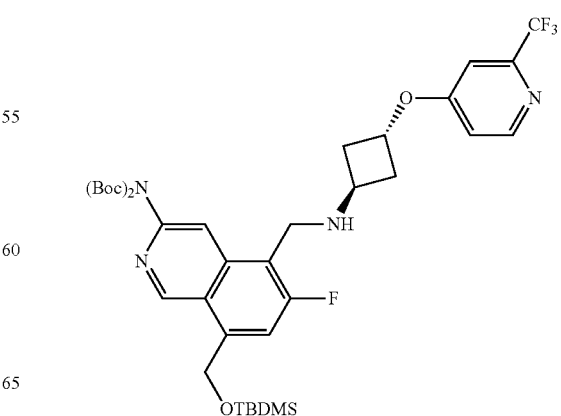

The title compound was synthesized following the procedure as described in step 1.4, using (1r,3r)-3-((2-(trifluoromethyl)pyridin-4-yl)oxy)cyclobutan-1-amine, HCl (Step 16.2, 70 mg, 0.26 mmol) and tert-butyl (tert-butoxycarbonyl)(8-(((tert-butyldimethylsilyl)oxy)methyl)-6-fluoro-5-formylisoquinolin-3-yl)carbamate (Step 18.10, 98 mg, 0.18 mmol). The crude was purified by flash chromatography (12 g SiliCycle column, 0-4% MeOH in CHCl₃ elution) to provide tert-butyl (tert-butoxycarbonyl)(8-(((tert-butyldimethylsilyl)oxy)methyl)-6-fluoro-5-((((1r,3r)-3-((2-(trifluoromethyl)pyridin-4-yl)oxy)cyclobutyl)amino)methyl)isoquinolin-3-yl)carbamate (100 mg, 51%). MS (ESI+) [Method 6A]: m/z 751.5 (M+H), Rt 1.49 min; 651.4 (M−Boc+H), Rt 1.44 min.

Step 20.2: Synthesis of tert-butyl (tert-butoxycarbonyl)(6-fluoro-8-(hydroxymethyl)-5-((((1r,3r)-3-((2-(trifluoromethyl)pyridin-4-yl)oxy)cyclobutyl)amino)methyl)isoquinolin-3-yl)carbamate

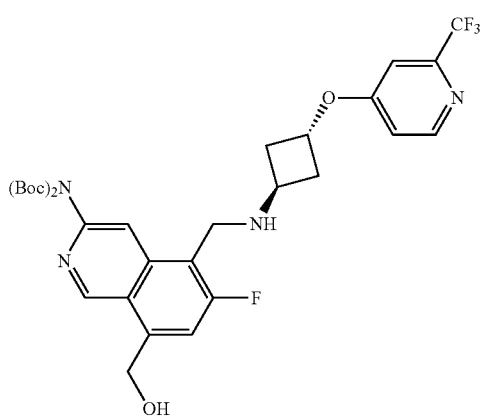

Deprotection was carried out according to Step 8.5. The residue was purified by flash chromatography (12 g SiliCycle column, 0-5% MeOH in CH₂Cl₂ elution) to provide tert-butyl (tert-butoxycarbonyl)(6-fluoro-8-(hydroxymethyl)-5-((((1r,3r)-3-((2-(trifluoromethyl)pyridin-4-yl)oxy)cyclobutyl)amino)methyl)isoquinolin-3-yl)carbamate (60 mg, 71%). MS (ESI+) [Method 6A]: m/z 637.4 (M+H), Rt 1.36 min; 535.2 (M−Boc+H), Rt 1.33 min.

Step 20.3: Synthesis of (3-amino-6-fluoro-5-((((1r,3r)-3-((2-(trifluoromethyl)pyridin-4-yl)oxy)cyclobutyl)amino)methyl)isoquinolin-8-yl)methanol, HCl

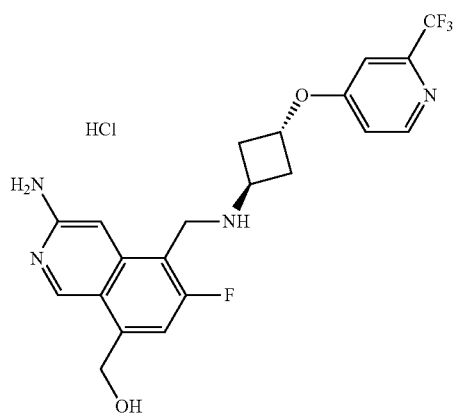 [SMILES: Nc1cc2c(CN[C@H]3C[C@H](Oc4ccnc(C(F)(F)F)c4)C3)c(F)cc(CO)c2cn1 ; Cl]

Deprotection was carried out according to Step 13.5. Then the reaction mixture was concentrated in vacuo and purified by prep-HPLC (Column: WATERS X BRIDGE C18 (150 mm×19.0 mm), 5.0µ; Mobile Phase: 0.02% NH₄OH in water and acetonitrile). To the isolated product, HCl solution (4M in 1,4-dioxane) (1 mL) was added and stirred at rt for 1 h. Solvent was evaporated, and the residue was triturated with Et₂O. The solid formed was collected by filtration and dried in vacuo to provide (3-amino-6-fluoro-5-((((1r,3r)-3-((2-(trifluoromethyl)pyridin-4-yl)oxy)cyclobutyl)amino)methyl)isoquinolin-8-yl)methanol, HCl (14 mg, 31%). MS (ESI+) [Method 6A]: m/z 437.0 (M+H); Rt 1.27 min. ¹H NMR (400 MHz, CD₃OD) δ 9.18 (s, 1H), 8.57 (d, J=9.0 Hz, 1H), 7.56 (s, 1H), 7.44 (d, J=9.0 Hz, 1H), 7.34 (d, J=2.4 Hz, 1H), 7.17-7.14 (m, 1H), 5.26-5.21 (m, 1H), 5.08 (s, 2H), 4.58 (s, 2H), 4.32-4.28 (m, 1H), 3.02-2.97 (m, 2H), 2.80-2.75 (m, 2H).

Example 21: Synthesis of 1-(3-amino-6-fluoro-5-(((((1r,3r)-3-(4-fluoro-3-(trifluoromethyl)phenoxy)cyclobutyl)amino)methyl)isoquinolin-8-yl)ethane-1,2-diol Step 21.1: Synthesis of tert-butyl (tert-butoxycarbonyl)(8-(1,2-dihydroxyethyl)-6-fluoroisoquinolin-3-yl)carbamate

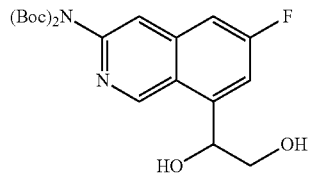

To the solution of tert-butyl (tert-butoxycarbonyl)(6-fluoro-8-vinylisoquinolin-3-yl)carbamate (Step 18.6, 3.7 g, 9.53 mmol) in acetone (40 mL), 4-methylmorpholine N-oxide (2.8 g, 23.82 mmol), dissolved in water (4 mL), was added at rt, followed by OsO₄ (0.12 g, 0.48 mmol). Then the reaction mixture was stirred at rt for 16 h. The reaction mixture was concentrated in vacuo, residue was diluted with water and extracted 20% MeOH in CH$_2$Cl$_2$ 3×'s. The combined organic portion was washed with brine, dried over anhydrous Na$_2$SO$_4$, filtered and concentrated in vacuo. The residue was purified by flash chromatography (12 g SiliCycle column, 0-8% MeOH in CH$_2$Cl$_2$ elution) to provide tert-butyl (tert-butoxycarbonyl)(8-(1,2-dihydroxyethyl)-6-fluoroisoquinolin-3-yl)carbamate (2.9 g, 72%). MS (ESI+) [Method 6A]: m/z 423.2 (M+H); Rt 1.48 min.

Step 21.2: Synthesis of tert-butyl (tert-butoxycarbonyl)(6-fluoro-8-(2,2,3,3,8,8,9,9-octamethyl-4,7-dioxa-3,8-disiladecan-5-yl)isoquinolin-3-yl)carbamate

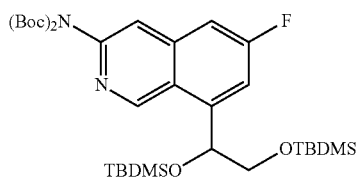

To the stirred solution of tert-butyl (tert-butoxycarbonyl)(8-(1,2-dihydroxyethyl)-6-fluoroisoquinolin-3-yl)carbamate (2.9 g, 6.87 mmol) and imidazole (2.8 g, 41.21 mmol) in DMF-DCM (35 mL, 1:6 v/v), TBDMS-Cl (5.43 g, 34.34 mmol) was added portion wise at 0° C. The reaction mixture was stirred at rt for 16 h. Then the reaction mixture was diluted with water and extracted with CH$_2$Cl$_2$ twice. The combined organic portion was washed with brine, dried over anhydrous Na$_2$SO$_4$, filtered and concentrated in vacuo. The residue was purified by flash chromatography (24 g SiliCycle column, 0-15% EtOAc in Hexane elution) to afford tert-butyl (tert-butoxycarbonyl)(6-fluoro-8-(2,2,3,3,8,8,9,9-octamethyl-4,7-dioxa-3,8-disiladecan-5-yl)isoquinolin-3-yl)carbamate (3.6 g, 80%). MS (ESI+) [Method 1A]: m/z 651.4 (M+H); Rt 2.54 min. $^1$H NMR (600 MHz, CDCl$_3$) δ 9.50 (s, 1H), 7.56 (s, 1H), 7.48 (d, J=9.0 Hz, 1H), 7.31 (d, J=9.0 Hz, 1H), 4.12-4.09 (m, 1H), 3.87-3.84 (m, 1H), 3.79-3.77 (m, 1H), 1.43 (s, 18H), 0.86 (s, 9H), 0.78 (s, 9H), 0.10 (s, 6H), −0.08 (s, 6H).

Step 21.3: Synthesis of tert-butyl (tert-butoxycarbonyl)(6-fluoro-5-formyl-8-(2,2,3,3,8,8,9,9-octamethyl-4,7-dioxa-3,8-disiladecan-5-yl)isoquinolin-3-yl)carbamate

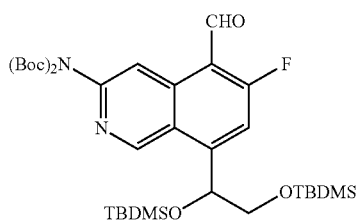

The title compound was prepared according to Step 14.2. The residue was purified by flash chromatography (40 g SiliCycle column, 0-15% EtOAc in Hexane elution) to provide tert-butyl (tert-butoxycarbonyl)(6-fluoro-5-formyl-8-(2,2,3,3,8,8,9,9-octamethyl-4,7-dioxa-3,8-disiladecan-5-yl)isoquinolin-3-yl)carbamate (0.74 g, 39%). MS (ESI+) [Method 1A]: m/z 679.6 (M+H); Rt 2.89 min. 1H NMR (300 MHz, CDCl3) δ 10.72 (s, 1H), 9.50 (s, 1H), 9.10 (s, 1H), 7.58 (d, J=9.0 Hz, 1H), 5.53-5.50 (m, 1H), 3.87-3.79 (m, 2H), 1.46 (s, 18H), 0.90 (s, 9H), 0.78 (s, 9H), 0.14 (s, 3H), −0.03 (s, 3H), −0.09 (s, 3H), −0.14 (s, 3H).

Step 21.4: Synthesis of tert-butyl (tert-butoxycarbonyl)(6-fluoro-5-((((1r,3r)-3-(4-fluoro-3-(trifluoromethyl)phenoxy)cyclobutyl)amino)methyl)-8-(2,2,3,3,8,8,9,9-octamethyl-4,7-dioxa-3,8-disiladecan-5-yl)isoquinolin-3-yl)carbamate

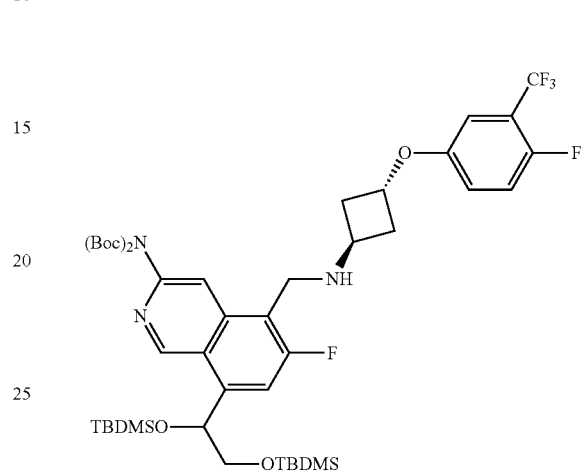

The title compound was synthesized following the procedure as described in step 1.4, using (1r,3r)-3-(4-fluoro-3-(trifluoromethyl)phenoxy)cyclobutan-1-amine, HCl (Step 1.3, 0.59 g, 2.07 mmol) and tert-butyl (tert-butoxycarbonyl)(6-fluoro-5-formyl-8-(2,2,3,3,8,8,9,9-octamethyl-4,7-dioxa-3,8-disiladecan-5-yl)isoquinolin-3-yl)carbamate (1.4 g, 2.07 mmol). The crude was purified by flash chromatography (12 g SiliCycle column, 0-10% MeOH in CH$_2$Cl$_3$ elution) to provide tert-butyl (tert-butoxycarbonyl)(6-fluoro-5-((((1r,3r)-3-(4-fluoro-3-(trifluoromethyl)phenoxy)cyclobutyl)amino)methyl)-8-(2,2,3,3,8,8,9,9-octamethyl-4,7-dioxa-3,8-disiladecan-5-yl)isoquinolin-3-yl)carbamate (1.16 g, 61%). MS (ESI+) [Method 1A]: m/z 912.3 (M+H), Rt 2.10 min.

Step 21.5: Synthesis of tert-butyl (tert-butoxycarbonyl)(8-(1,2-dihydroxyethyl)-6-fluoro-5-((((1r,3r)-3-(4-fluoro-3-(trifluoromethyl)phenoxy)cyclobutyl)amino)methyl)isoquinolin-3-yl)carbamate

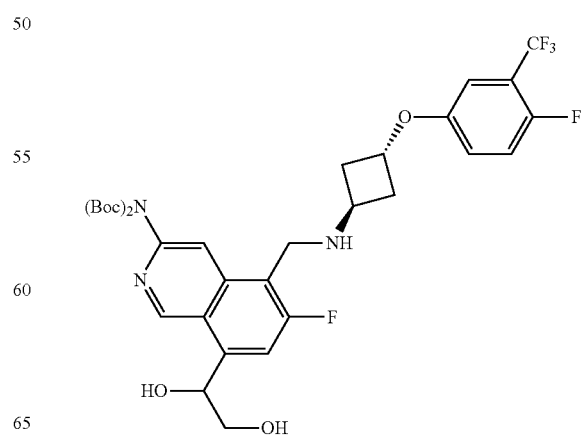

The title compound was prepared according to the procedure in Step 7.6 to provide the title compound. MS (ESI+) [Method 1A]: m/z 684.4 (M+H), Rt 1.39 min.

Step 21.6: Synthesis of 1-(3-amino-6-fluoro-5-((((1r,3r)-3-(4-fluoro-3-(trifluoromethyl)phenoxy)cyclobutyl)amino)methyl)isoquinolin-8-yl)ethane-1,2-diol

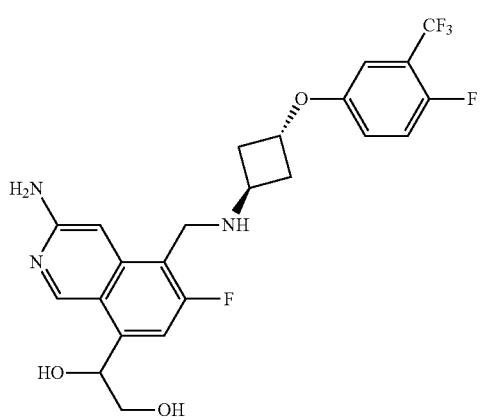 [SMILES: Nc1cc2c(CN[C@H]3C[C@H](Oc4ccc(F)c(C(F)(F)F)c4)C3)c(F)cc(C(O)CO)c2cn1]

Deprotection was carried out according to Step 13.5 to afford racemic 1-(3-amino-6-fluoro-5-((((1r,3r)-3-(4-fluoro-3-(trifluoromethyl)phenoxy)cyclobutyl)amino)methyl)isoquinolin-8-yl)ethane-1,2-diol, HCl (0.65 g, 85%). MS (ESI+) [Method 1A]: m/z 484.3 (M+H); Rt 0.10 min. Chiral prep-HPLC (Column: CHIRALPAK IG (250 mm×20 mm); Mobile Phase: Hexane and 0.1% DEA in EtOH:MeOH (1:1); Isocratic: 60/40; Flow: 16 mL/min) of the racemate (650 mg) provided (R)-1-(3-amino-6-fluoro-5-((((1r,3R)-3-(4-fluoro-3-(trifluoromethyl)phenoxy)cyclobutyl)amino)methyl)isoquinolin-8-yl)ethane-1,2-diol and (S)-1-(3-amino-6-fluoro-5-((((1r,3S)-3-(4-fluoro-3-(trifluoromethyl)phenoxy)cyclobutyl)amino)methyl)isoquinolin-8-yl)ethane-1,2-diol as white solids (Peak 1: 155 mg, 24% and Peak 2: 180 mg, 27%). Peak 1: Chiral HPLC: 99% (Rf 5.315 min; Column: CHIRAL PAK IG (150 mm×4.6 mm), 5.0μ; Mobile phase: n-Hexane and 0.1% DEA in EtOH:MeOH (70:30); Isocratic: 70/30; Flow: 1 mL/min). MS (ESI+) [Method 6A]: m/z 484.1 (M+H); Rt 1.32 min. $^1$H NMR (400 MHz, CD$_3$OD) δ 9.11 (s, 1H), 7.25-7.22 (m, 2H), 7.09-7.04 (m, 2H), 6.95 (s, 1H), 5.45-5.42 (m, 1H), 4.92-4.89 (m, 1H), 4.24 (d, J=1.6 Hz, 2H), 3.87-3.79 (m, 2H), 3.72-3.68 (m, 1H), 2.57-2.48 (m, 4H).

Peak 2: Chiral HPLC: 98% (Rf 7.812 min; Column: CHIRAL PAK IG (150 mm×4.6 mm), 5.0μ; Mobile phase: n-Hexane and 0.1% DEA in EtOH:MeOH (70:30); Isocratic: 70/30; Flow: 1 mL/min). MS (ESI+) [Method 6A]: m/z 484.2 (M+H); Rt 1.32 min. $^1$H NMR (400 MHz, CD$_3$OD) δ 9.12 (s, 1H), 7.26-7.23 (m, 2H), 7.09-7.05 (m, 2H), 6.95 (s, 1H), 5.47-5.43 (m, 1H), 4.92-4.89 (m, 1H), 4.29 (s, 2H), 3.93-3.88 (m, 1H), 3.82-3.79 (m, 1H), 3.73-3.69 (m, 1H), 2.61-2.52 (m, 4H).

Example 22: Synthesis of (1r,3r)-3-(4-fluoro-3-(trifluoromethyl)phenoxy)-N-(isoquinolin-5-ylmethyl)cyclobutan-1-amine, HCl

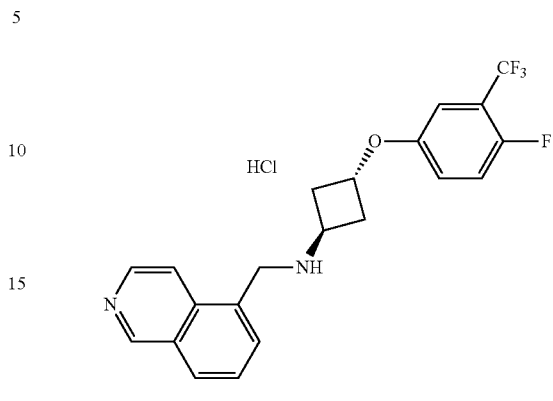

The title compound was synthesized following the procedure as described in step 1.4, using (1r,3r)-3-(4-fluoro-3-(trifluoromethyl)phenoxy)cyclobutan-1-amine, HCl (Step 1.3, 300 mg, 1.05 mmol) and isoquinoline-5-carbaldehyde (150 mg, 0.96 mmol). Prep-HPLC (Column: XBRIDGE C18 (150 mm×21.2 mm), 5.0μ; Mobile Phase: 0.01% NH$_4$OH in water and acetonitrile) of the crude, followed by treatment with HCl solution (4M in 1,4-dioxane) afforded (1r,3r)-3-(4-fluoro-3-(trifluoromethyl)phenoxy)-N-(isoquinolin-5-ylmethyl)cyclobutan-1-amine, HCl (250 mg, 55%). MS (ESI+) [Method 6A]: m/z 391.1 (M+H); Rt 1.32 min. $^1$H NMR (400 MHz, CD$_3$OD) δ 9.92 (s, 1H), 8.85-8.83 (m, 1H), 8.79-8.77 (m, 1H), 8.67 (d, J=8.0 Hz, 1H), 8.51 (d, J=7.6 Hz, 1H), 8.16 (t, J=8.0 Hz, 1H), 7.31 (t, J=9.6 Hz, 1H), 7.17-7.11 (m, 2H), 5.11-5.06 (m, 1H), 4.87 (s, 2H), 4.33-4.29 (m, 1H), 3.00-2.92 (m, 2H), 2.74-2.68 (m, 2H).

Example 23: Synthesis of 5-((((1r,3r)-3-(4-fluoro-3-(trifluoromethyl)phenoxy)cyclobutyl)amino)methyl)isoquinolin-8-ol, HCl Step 23.1: Synthesis of 1-(5-bromo-2-methoxyphenyl)-N-(2,2-dimethoxyethyl)methanimine

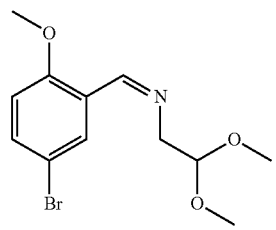 [SMILES: COc1ccc(Br)cc1/C=N\CC(OC)OC]

A two necked round bottom flask, fitted with Dean Stark apparatus, was charged with 5-bromo-2-methoxybenzaldehyde [CAS No. 25016-01-7] (3.0 g, 13.95 mmol), 2,2-dimethoxyethan-1-amine (1.5 mL, 13.95 mmol) and toluene (50 mL). The reaction mixture was stirred at 140° C. for 16 h, while azeotropic removal of H$_2$O. Then the reaction mixture was concentrated in vacuo to afford crude 1-(5-bromo-2-methoxyphenyl)-N-(2,2-dimethoxyethyl)methanimine (5.4 g, 128%). $^1$H NMR (300 MHz, CDCl$_3$) δ 8.63 (d, J=1.2 Hz, 1H), 8.07 (d, J=3.0 Hz, 1H), 7.46 (dd, J=8.7, 3.0 Hz, 1H), 6.79 (d, J=8.7 Hz, 1H), 4.68 (t, J=5.4 Hz, 1H), 3.85 (s, 3H), 3.78 (dd, J=5.4, 1.2 Hz, 2H), 3.42 (s, 6H).

Step 23.2: Synthesis of 5-bromo-8-methoxyisoquinoline

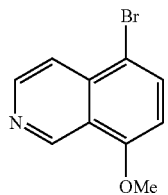 [SMILES: COc1ccc(Br)c2ccncc12]

To the solution of 1-(5-bromo-2-methoxyphenyl)-N-(2,2-dimethoxyethyl)methanimine (5.4 g, 17.87 mmol) in CHCl$_3$ (50 mL), ethyl carbonochloridate (1.7 mL, 17.87 mmol) and P(OEt)$_3$ (2.5 mL, 21.45 mmol) were added at 0° C. and stirred at 60° C. for 16 h. The reaction mixture was cooled to rt, poured into ice water and the organic portion was separated. The aqueous portion was washed with CH$_2$Cl$_2$ twice and basified with aqueous NH$_4$OH, then extracted with CH$_2$Cl$_2$ twice. The combined organic portion was washed with brine, dried over anhydrous Na$_2$SO$_4$, filtered and concentrated in vacuo. The residue was purified by flash chromatography (12 g SiliCycle column, 0-30% EtOAc in Hexane elution) to provide 5-bromo-8-methoxyisoquinoline (1.0 g, 28%). $^1$H NMR (600 MHz, CDCl$_3$) δ 9.61 (s, 1H), 8.65 (d, J=6.0 Hz, 1H), 7.89 (d, J=6.0 Hz, 1H), 7.84 (d, J=8.4 Hz, 1H), 6.78 (d, J=8.4 Hz, 1H), 4.03 (s, 3H).

Step 23.3: Synthesis of 8-methoxy-5-vinylisoquinoline

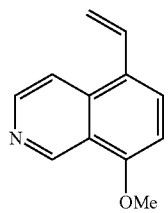

The stirred solution of 5-bromo-8-methoxyisoquinoline (1.0 g, 4.20 mmol), potassium trifluoro(vinyl)borate (1.12 g, 8.40 mmol) and TEA (1.2 mL, 8.40 mmol) in IPA (10 mL), was degassed with N$_2$ for 10 min. Then Pd(dppf)Cl$_2$·CH$_2$Cl$_2$ (343 mg, 0.04 mmol) was added, degassed and heated at 90° C. for 3 h under N$_2$. Reaction mixture was cooled to rt, diluted with water and extracted with EtOAc twice. The combined organic portion was washed with brine, dried over anhydrous Na$_2$SO$_4$, filtered and concentrated in vacuo to yield the crude product. The crude was purified by flash chromatography (12 g SiliCycle column, 0-30% EtOAc in Hexane elution) to provide 8-methoxy-5-vinylisoquinoline (0.56 g, 71%). MS (ESI+) [Method 6A]: m/z 185.9 (M+H); Rt 1.28 min.

Step 23.4: Synthesis of 8-methoxyisoquinoline-5-carbaldehyde

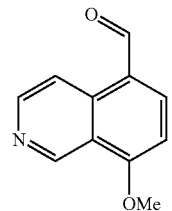 [SMILES: COc1ccc(C=O)c2ccncc12]

The compound was prepared by analogy to Step 5.2 from 8-methoxy-5-vinylisoquinoline (560 mg, 3.02 mmol) The residue was purified by flash chromatography (12 g SiliCycle column, 0-50% EtOAc in Hexane elution) to provide 8-methoxyisoquinoline-5-carbaldehyde (188 mg, 33%). MS (ESI+) [Method 6A]: m/z 187.9 (M+H); Rt 0.62 min.

Step 23.5: Synthesis of 8-hydroxyisoquinoline-5-carbaldehyde

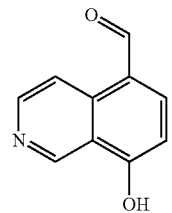 [SMILES: O=Cc1ccc(O)c2cnccc12]

To the solution of 8-methoxyisoquinoline-5-carbaldehyde (188 mg, 1.00 mmol) in CH$_2$Cl$_2$ (5 mL), BBr$_3$ (1M in heptane) (5.0 mL, 5.02 mmol) was added at 0° C. and stirred at rt for 16 h. To the reaction mixture MeOH was added, stirred for 15 min and then concentrated in vacuo to provide crude 8-hydroxyisoquinoline-5-carbaldehyde (230 mg, 132%). MS (ESI+) [Method 6A]: m/z 174.2 (M+H); Rt 0.38 min.

Step 23.6: Synthesis of 5-((((1r,3r)-3-(4-fluoro-3-(trifluoromethyl)phenoxy)cyclobutyl)amino)methyl)isoquinolin-8-ol, HCl

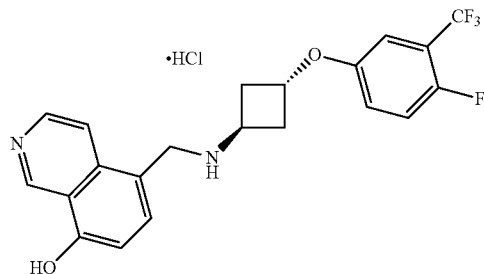 [SMILES: Oc1ccc(CN[C@H]2C[C@H](Oc3ccc(F)c(C(F)(F)F)c3)C2)c2ccncc12 ; Cl]

The title compound was synthesized following the procedure as described in step 1.4. The solution of (1r,3r)-3-(4-fluoro-3-(trifluoromethyl)phenoxy)cyclobutan-1-amine, HCl (Step 1.3, 350 mg, 1.23 mmol) and TEA (0.2 mL, 1.47 mmol) in MeOH (5 mL) was stirred for 15 min, then 8-hydroxyisoquinoline-5-carbaldehyde (191 mg, 1.10 mmol) and AcOH (0.01 mL) were added, and stirred at rt for 16 h under argon. Then NaBH₄ (232 mg, 6.13 mmol) was added at 0° C. and stirred at rt for further 2 h. The reaction mixture was quenched with water and extracted with EtOAc twice. The combined organic portion was acidified with HCl solution (4M in 1,4-dioxane) (5.0 mL), washed with brine and dried over Na₂SO₄, filtered and concentrated in vacuo. Prep-HPLC (Column: KINETEX EVO (150 mm×21.2 mm), 5.0µ; Mobile Phase: 0.1% HCO₂H in water and acetonitrile) of the crude, followed by treatment with HCl solution (4M in 1,4-dioxane) of the isolated product afforded 5-((((1r,3r)-3-(4-fluoro-3-(trifluoromethyl)phenoxy)cyclobutyl)amino)methyl)isoquinolin-8-ol, HCl. MS (ESI+) [Method 6A]: m/z 407.2 (M+H); Rt 1.28 min. ¹H NMR (400 MHz, CD₃OD) δ 9.84 (brs, 1H), 8.63 (brs, 2H), 8.29 (d, J=8.4 Hz, 1H), 7.34 (d, J=8.0 Hz, 1H), 7.28 (t, J=9.2 Hz, 1H), 7.14-7.08 (m, 2H), 5.06-5.02 (m, 1H), 4.68 (s, 2H), 4.25-4.21 (m, 1H), 2.91-2.85 (m, 2H), 2.70-2.63 (m, 2H).

Example 24: Synthesis of (1r,3r)-3-(4-fluoro-3-(trifluoromethyl)phenoxy)-N-((8-methylisoquinolin-5-yl)methyl)cyclobutan-1-amine, HCl Step 24.1: Synthesis of 8-methylisoquinoline

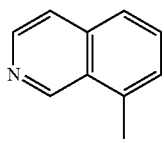

A sealed tube was charged with 8-bromoisoquinoline [CAS No. 63927-22-0] (1.5 g, 7.20 mmol), methylboronic acid (0.86 g, 14.40 mmol), K₃PO₄ (6.1 g, 28.74 mmol) and toluene (20 mL), degassed (argon) for 10 min. Then Pd₂(dba)₃ (0.65 g, 0.72 mmol) and S-PHOS (0.59 g, 1.44 mmol) were added, degassed, sealed tube was closed and heated at 125° C. for 20 h. Reaction mixture was cooled to rt, diluted with water and extracted with EtOAc 3×'s. The combined organic portion was washed with brine, dried over anhydrous Na₂SO₄, filtered and concentrated in vacuo to yield the crude product. The crude was purified by flash chromatography (24 g SiliCycle column, 0-20% EtOAc in Hexane elution) to provide 8-methylisoquinoline (1.0 g, 95%). MS (ESI+) [Method 2A]: m/z 143.6 (M+H); Rt 0.46 min. ¹H NMR (300 MHz, CDCl₃) δ 9.47 (s, 1H), 8.55 (d, J=5.7 Hz, 1H), 7.89-7.55 (m, 3H), 7.40 (d, J=6.9 Hz, 1H), 2.80 (s, 3H).

Step 24.2: Synthesis of 5-bromo-8-methylisoquinoline

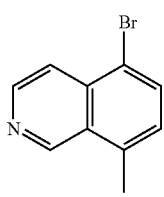

To the solution of 8-methylisoquinoline (0.5 g, 3.49 mmol) in concentrated H₂SO₄ (5 mL), NBS (0.62 g, 3.49 mmol) was added at −10° C., and stirred at rt for 16 h. The reaction mixture was poured dropwise onto ice, extracted with CH₂Cl₂ 3×'s. The combined organic portion was washed with brine, dried over anhydrous Na₂SO₄, filtered and concentrated in vacuo to yield the crude product. The crude was purified by flash chromatography (12 g SiliCycle column, 0-20% EtOAc in Hexane elution) to provide 5-bromo-8-methylisoquinoline (0.55 g, 71%). MS (ESI+) [Method 1A]: m/z 221.8 (M+H); Rt 0.40 min. ¹H NMR (400 MHz, CD₃OD) δ 9.38 (s, 1H), 8.56 (d, J=6.0 Hz, 1H), 8.03 (d, J=6.0 Hz, 1H), 7.92 (d, J=8.0 Hz, 1H), 7.36 (d, J=7.2 Hz, 1H), 2.75 (s, 3H).

Step 24.3: Synthesis of 8-methylisoquinoline-5-carbaldehyde

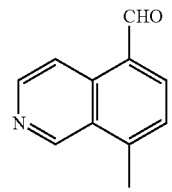

To the solution of 5-bromo-8-methylisoquinoline (0.25 g, 1.12 mmol) in dry THF (5 mL), n-BuLi (2.5M in THF) (0.65 mL, 1.68 mmol) was added dropwise at −78° C. and stirred for 30 min under argon atmosphere. Then anhydrous DMF (0.17 mL, 2.25 mmol) was added dropwise at −78° C., temperature was raised to rt gradually and stirred for 1 h. Reaction mixture was quenched with 10% NH₄Cl solution and extracted with EtOAc 3×'s. The combined organic portion was washed with brine solution, dried over anhydrous Na₂SO₄, filtered and concentrated in vacuo to yield the crude product. The crude was purified by flash chromatography (12 g SiliCycle column, 0-30% EtOAc in Hexane elution) to provide 8-methylisoquinoline-5-carbaldehyde (80 mg, 41%). MS (ESI+) [Method 1A]: m/z 172.1 (M+H); Rt 0.15 min. ¹H NMR (300 MHz, CD₃OD) δ 10.30 (s, 1H), 9.53 (s, 1H), 9.11 (dd, J=6.9, 1.2 Hz, 1H), 8.63 (d, J=6.0 Hz, 1H), 8.26 (d, J=7.2 Hz, 1H), 7.70 (dd, J=7.8, 1.2 Hz, 1H), 2.90 (s, 3H).

Step 24.4: Synthesis of (1r,3r)-3-(4-fluoro-3-(trifluoromethyl)phenoxy)-N-((8-methylisoquinolin-5-yl)methyl)cyclobutan-1-amine, HCl

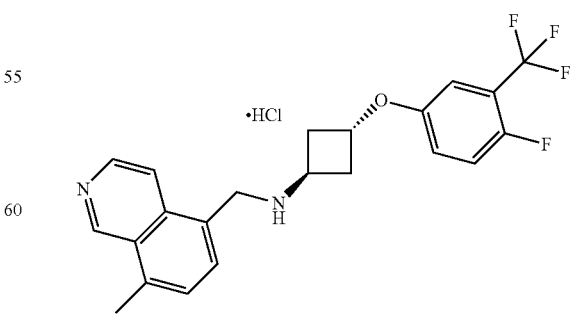

The title compound was synthesized following the procedure as described in step 1.4, using (1r,3r)-3-(4-fluoro-3-

(trifluoromethyl)phenoxy)cyclobutan-1-amine, HCl (Step 1.3, 70 mg, 0.24 mmol) and 8-methylisoquinoline-5-carbaldehyde (42 mg, 0.24 mmol). Prep-HPLC (Column: KINETEX EVO C18 (150 mm×21.2 mm), 5.0µ; Mobile Phase: 0.02% NH$_4$OH in water and acetonitrile) of the crude, followed by treatment with HCl solution (4M in 1,4-dioxane) afforded (1r,3r)-3-(4-fluoro-3-(trifluoromethyl)phenoxy)-N-((8-methylisoquinolin-5-yl)methyl)cyclobutan-1-amine, HCl as brown solid (40 mg, 41%). MS (ESI+) [Method 1A]: m/z 404.8 (M+H); Rt 0.19 min. $^1$H NMR (400 MHz, CD$_3$OD) δ 9.92 (brs, 1H), 8.75 (brs, 2H), 8.30 (d, J=7.6 Hz, 1H), 7.94 (dd, J=7.6, 0.8 Hz, 1H), 7.28 (t, J=9.6 Hz, 1H), 7.15-7.08 (m, 2H), 5.06-5.01 (m, 1H), 4.79 (s, 2H), 4.28-4.24 (m, 1H), 2.96 (s, 3H), 2.94-2.87 (m, 2H), 2.71-2.63 (m, 2H).

Example 25: Synthesis of (5-((((1r,3r)-3-(4-fluoro-3-(trifluoromethyl)phenoxy)cyclobutyl)amino) methyl)isoquinolin-8-yl)methanol, HCl Step 25.1: Synthesis of 5,8-dibromoisoquinoline

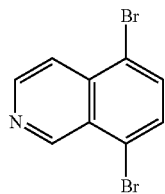 [SMILES: Brc1ccc(Br)c2cnccc12]

To the solution of isoquinoline [CAS No. 119-65-3] (2.0 g, 15.48 mmol) in concentrated H$_2$SO$_4$ (20 mL), NBS (8.26 g, 46.45 mmol) was added at −15° C., and stirred for 2 h. The reaction mixture was poured dropwise onto ice, basified with aqueous NH$_4$OH solution, extracted with EtOAc twice. The combined organic portion was washed with brine, dried over anhydrous Na$_2$SO$_4$, filtered and concentrated in vacuo to yield the crude product. The crude was purified by flash chromatography (24 g SiliCycle column, 0-10% EtOAc in Hexane elution) to provide 5,8-dibromoisoquinoline (4.0 g, 90%). MS (ESI+) [Method 1A]: m/z 285.8, 287.8, 289.8 (M+H); Rt 1.55 min. $^1$H NMR (600 MHz, CDCl$_3$) δ 9.61 (s, 1H), 8.73 (d, J=4.8 Hz, 1H), 7.99 (d, J=4.8 Hz, 1H), 7.82 (d, J=7.8 Hz, 1H), 7.22 (d, J=7.8 Hz, 1H).

Step 25.2: Synthesis of 5-bromoisoquinoline-8-carbaldehyde

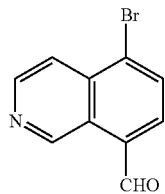 [SMILES: O=Cc1ccc(Br)c2ccncc12]

The title compound was synthesized following the protocol reported in the patent WO2017/79162. To the solution of 5,8-dibromoisoquinoline (2.0 g, 6.97 mmol) in dry THF (20 mL), n-BuLi (2.5M in THF) (3.6 mL, 9.06 mmol) was added dropwise at −78° C. and stirred for 30 min under N$_2$ atmosphere. Then anhydrous DMF (1.88 mL, 2.36 mmol) was added dropwise at −78° C., and stirred for 1 h. Reaction mixture was quenched with saturated NH$_4$Cl solution and extracted with EtOAc twice. The combined organic portion was washed with brine solution, dried over anhydrous Na$_2$SO$_4$, filtered and concentrated in vacuo to yield the crude product. The crude was purified by flash chromatography (24 g SiliCycle column, 0-20% EtOAc in Hexane elution) to provide 5-bromoisoquinoline-8-carbaldehyde (300 mg, 18%) (30 mg 8-bromoisoquinoline-5-carbaldehyde was isolated as byproduct). MS (ESI+) [Method 1A]: m/z 235.8, 237.8 (M+H); Rt 1.69 min. $^1$H NMR (400 MHz, CDCl$_3$) δ 10.57 (d, J=1.6 Hz, 1H), 10.40 (s, 1H), 8.81 (d, J=8.0 Hz, 1H), 8.17 (d, J=10.4 Hz, 1H), 8.11 (dd, J=7.6, 1.6 Hz, 1H), 7.94 (d, J=10.4 Hz, 1H).

Step 25.3: Synthesis of (5-bromoisoquinolin-8-yl)methanol

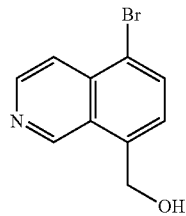 [SMILES: OCc1ccc(Br)c2ccncc12]

To the stirred solution of 5-bromoisoquinoline-8-carbaldehyde (300 mg, 1.27 mmol) in anhydrous THF (5 mL), NaBH$_4$ (72 mg, 1.91 mmol) was added portion wise at 0° C. Then MeOH (5 mL) was added dropwise and stirred at 0° C. for 2 h. Reaction was quenched with water and extracted with EtOAc twice. The combined organic portion was washed with brine, dried over anhydrous Na$_2$SO$_4$, filtered and concentrated in vacuo. The crude product obtained from two batches was combined and purified by flash chromatography (12 g SiliCycle column, 0-30% EtOAc in Hexane elution) to provide (5-bromoisoquinolin-8-yl)methanol (360 mg, 59%). MS (ESI+) [Method 1A]: m/z 238.0, 240.0 (M+H); Rt 0.16 min. $^1$H NMR (300 MHz, CDCl$_3$) δ 9.54 (s, 1H), 8.67 (d, J=5.7 Hz, 1H), 8.03 (dd, J=6.0, 0.9 Hz, 1H), 7.95 (d, J=7.8 Hz, 1H), 7.51 (d, J=7.8 Hz, 1H), 5.24 (s, 2H).

Step 25.4: Synthesis of (5-vinylisoquinolin-8-yl)methanol

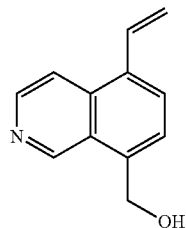

The stirred solution of (5-bromoisoquinolin-8-yl)methanol (300 mg, 1.26 mmol), potassium trifluoro(vinyl)borate (330 mg, 2.52 mmol) and TEA (0.35 mL, 2.52 mmol) in IPA (10 mL), was degassed with N$_2$ for 10 min. Then Pd(dppf)Cl$_2$·CH$_2$Cl$_2$ (100 mg, 0.13 mmol) was added, degassed and heated at 100° C. for 3 h under N$_2$. Reaction mixture was cooled to rt, diluted with water and extracted with EtOAc twice. The combined organic portion was washed with brine, dried over anhydrous Na$_2$SO$_4$, filtered and concentrated in vacuo to yield the crude product. The crude was purified by flash chromatography (12 g SiliCycle column, 0-30% EtOAc in Hexane elution) to provide (5-vinylisoquinolin-8-yl)methanol (200 mg, 85%). MS (ESI+) [Method 6A]: m/z 185.9 (M+H); Rt 0.69 min.

Step 25.5: Synthesis of 8-(hydroxymethyl)isoquinoline-5-carbaldehyde

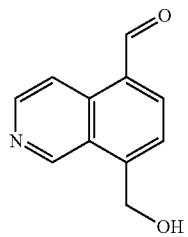 [SMILES: O=Cc1ccc(CO)c2cnccc12]

The title compound was prepared according to Step 5.2. The residue was purified by flash chromatography (12 g SiliCycle column, 0-30% EtOAc in Hexane elution) to provide 8-(hydroxymethyl)isoquinoline-5-carbaldehyde (120 mg, 59%). MS (ESI+) [Method 2A]: m/z 188.0 (M+H); Rt 0.56 min. $^1$H NMR (400 MHz, DMSO-d6) δ 10.38 (s, 1H), 9.59 (s, 1H), 8.95 (d, J=6.0 Hz, 1H), 8.72 (d, J=6.0 Hz, 1H), 8.42 (d, J=7.6 Hz, 1H), 7.94 (d, J=7.6 Hz, 1H), 5.73 (t, J=5.6 Hz, 1H), 5.20 (d, J=5.2 Hz, 2H).

Step 25.6: Synthesis of (5-((((1r,3r)-3-(4-fluoro-3-(trifluoromethyl)phenoxy)cyclobutyl)amino)methyl)isoquinolin-8-yl)methanol, HCl

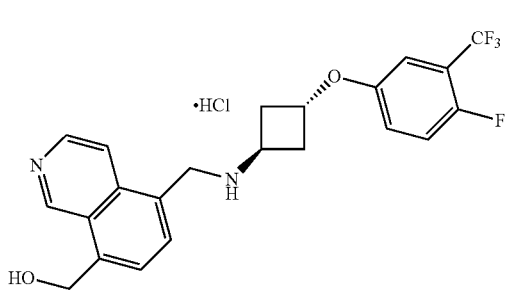 [SMILES: OCc1ccc(CN[C@H]2C[C@H](Oc3ccc(F)c(C(F)(F)F)c3)C2)c2ccncc12 ; Cl]

A solution of (1r,3r)-3-(4-fluoro-3-(trifluoromethyl)phenoxy)cyclobutan-1-amine, HCl (Step 1.3, 60 mg, 0.21 mmol) and TEA (0.03 mL, 0.21 mmol) in MeOH (3 mL) was stirred at rt for 10 min. Then 8-(hydroxymethyl)isoquinoline-5-carbaldehyde (36 mg, 0.19 mmol) was added and stirred for 2 h. Finally NaBH$_4$ (16 mg, 0.42 mmol) was added at 0° C. and stirred at rt for further 3 h. The reaction mixture was diluted with water and extracted with EtOAc twice. The combined organic portion was washed with brine solution, dried over anhydrous Na$_2$SO$_4$, filtered and concentrated in vacuo. The residue was purified by prep-HPLC (Column: KINETEX C18 (150 mm×21.2 mm), 5.0μ; Mobile Phase: 0.02% NH$_4$OH in water and acetonitrile). The isolated product was stirred with HCl solution (4M in 1,4-dioxane) (1 mL) at rt for 1 h; then concentrated to dryness to afford (5-((((1r,3r)-3-(4-fluoro-3-(trifluoromethyl)phenoxy)cyclobutyl)amino)methyl)isoquinolin-8-yl)methanol, HCl (23 mg, 26%). MS (ESI+) [Method 6A]: m/z 421.30 (M+H); Rt 1.303 min. $^1$H NMR (400 MHz, CD$_3$OD) δ 10.01 (s, 1H), 8.78 (s, 2H), 8.38 (d, J=7.6 Hz, 1H), 8.10 (d, J=7.6 Hz, 1H), 7.28 (t, J=9.6 Hz, 1H), 7.14-7.08 (m, 2H), 5.27 (s, 2H), 5.07-5.03 (m, 1H), 4.82 (s, 2H), 4.29-4.26 (m, 1H), 2.93-2.89 (m, 2H), 2.72-2.66 (m, 2H).

Example 26: Synthesis of (1r,3r)-3-(2,4-difluorophenoxy)-N-((6-fluoroisoquinolin-5-yl)methyl)cyclobutan-1-amine

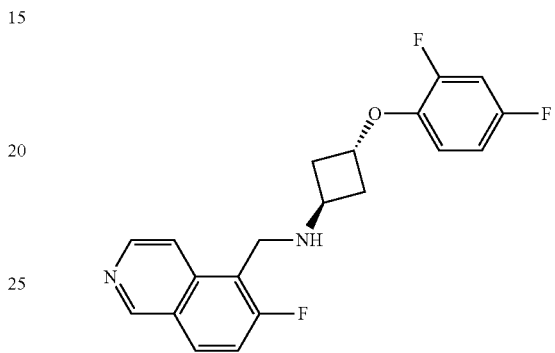

The title compound was synthesized following the procedure as described in Step 25.6, using (1r,3r)-3-(2,4-difluorophenoxy)cyclobutan-1-amine, HCl (Step 15.2, 80 mg, 0.40 mmol) and 6-fluoroisoquinoline-5-carbaldehyde (Step 3.1, 70 mg, 0.40 mmol). The residue was purified by prep-HPLC (Column: LUNA (250 mm×21.20 mm), 5.0μ; Mobile Phase: 0.1% HCO$_2$H in water and acetonitrile) to afford (1r,3r)-3-(2,4-difluorophenoxy)-N-((6-fluoroisoquinolin-5-yl)methyl)cyclobutan-1-amine (40 mg, 28%). MS (ESI+) [Method 6A]: m/z 359.2 (M+H); Rt 1.28 min. $^1$H NMR (400 MHz, CD$_3$OD) δ 9.30 (s, 1H), 8.58 (d, J=6.4 Hz, 1H), 8.26 (dd, J=9.2, 5.6 Hz, 1H), 8.13 (d, J=6.0 Hz, 1H), 7.60 (t, J=9.2 Hz, 1H), 7.02-6.98 (m, 1H), 6.90-6.85 (m, 2H), 4.91-4.87 (m, 1H), 4.40 (d, J=2.0 Hz, 2H), 3.87-3.83 (m, 1H), 2.51-2.48 (m, 4H).

Example 27: Synthesis of (1r,3r)-3-(3,4-difluorophenoxy)-N-((6-fluoroisoquinolin-5-yl)methyl)cyclobutan-1-amine, HCl Step 27.1: Synthesis of tert-butyl ((1r,3r)-3-(3,4-difluorophenoxy)cyclobutyl)

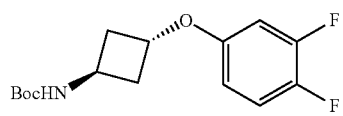 [SMILES: CC(C)(C)OC(=O)N[C@H]1C[C@H](Oc2ccc(F)c(F)c2)C1]

To the solution of tert-butyl ((1s,3s)-3-hydroxycyclobutyl)carbamate (0.4 g, 2.08 mmol) in THF (10 mL), 3,4-difluorophenol [CAS No. 2713-33-9] (0.27 g, 2.08 mmol), PPh$_3$ (0.8 g, 3.12 mmol) and diisopropyl azodicarboxylate (0.61 g, 3.12 mmol) were added at rt. The reaction mixture was stirred at 50° C. for 16 h under N$_2$ atmosphere. Reaction mixture was diluted with water and extracted with EtOAc 3×'s. The combined organic portion was washed with brine solution, dried over anhydrous Na$_2$SO$_4$, filtered and concentrated in vacuo. The residue was purified by flash chromatography (8 g SiliCycle column, 0-20% EtOAc in Hexane elution) to provide tert-butyl ((1r,3r)-3-(3,4-difluorophenoxy)cyclobutyl)carbamate (0.5 g, 96%). $^1$H NMR (300 MHz, CDCl$_3$) δ 7.08-6.96 (m, 1H), 6.71-6.43 (m, 2H), 4.72-4.67 (m, 1H), 4.31-4.26 (m, 1H), 2.58-2.49 (m, 2H), 2.40-2.34 (m, 2H), 1.45 (s, 9H).

Step 27.2: Synthesis of (1r,3r)-3-(3,4-difluorophenoxy)cyclobutan-1-amine, HCl

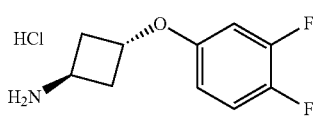 [SMILES: Cl ; N[C@H]1C[C@H](Oc2ccc(F)c(F)c2)C1]

The solution of tert-butyl ((1r,3r)-3-(3,4-difluorophenoxy)cyclobutyl)carbamate (0.5 g, 1.67 mmol) and HCl (20% in 1,4-dioxane) (2.0 mL) was stirred at rt for 1 h. The reaction mixture was concentrated in vacuo and the residue was triturated with pentane, the solid appeared was filtered and dried to yield (1r,3r)-3-(3,4-difluorophenoxy)cyclobutan-1-amine, HCl (0.3 g, 75%). $^1$H NMR (400 MHz, CD$_3$OD) δ 7.19-7.15 (m, 1H), 6.77-6.73 (m, 1H), 6.61-6.58 (M, 1H), 4.91-4.88 (m, 1H), 3.98-3.93 (m, 1H), 2.62-2.56 (m, 4H).

Step 27.3: Synthesis of (1r,3r)-3-(3,4-difluorophenoxy)-N-((6-fluoroisoquinolin-5-yl)methyl)cyclobutan-1-amine, HCl

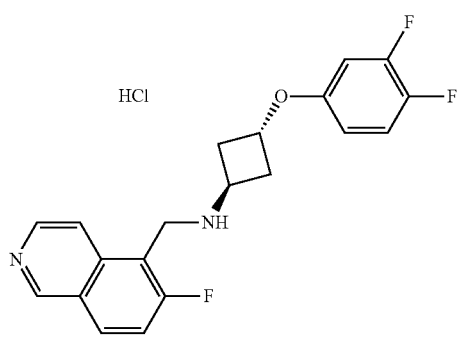 [SMILES: Fc1ccc(O[C@H]2C[C@H](NCc3c(F)ccc4cnccc34)C2)cc1F ; Cl]

The title compound was synthesized following procedure as described in step 1.4, using (1r,3r)-3-(3,4-difluorophenoxy)cyclobutan-1-amine, HCl (70 mg, 0.14 mmol) and 6-fluoroisoquinoline-5-carbaldehyde (Step 3.1, 45 mg, 0.12 mmol). Prep-HPLC (Column: YMC-ACTUS TRIART C$_{18}$ (150 mm×21.2 mm), 5.0µ; Mobile Phase: 0.02% NH$_4$OH in water and acetonitrile) of the crude, followed by treatment with HCl solution (4M in 1,4-dioxane) afforded (1r,3r)-3-(3,4-difluorophenoxy)-N-((6-fluoroisoquinolin-5-yl) methyl)cyclobutan-1-amine, HCl (10 mg, 18%). MS (ESI+) [Method 6A]: m/z 359.2 (M+H); Rt 1.30 min. $^1$H NMR (400 MHz, CD$_3$OD) δ 9.88 (s, 1H), 8.80-8.76 (m, 3H), 8.03 (t, J=9.6 Hz, 1H), 7.25-7.18 (m, 1H), 6.84-6.79 (m, 1H), 6.68-6.63 (m, 1H), 5.01-4.97 (m, 1H), 4.84 (d, J=2.0 Hz, 2H), 4.32-4.27 (m, 1H), 2.92-2.85 (m, 2H), 2.74-2.67 (m, 2H).

Example 28: Synthesis of (1r,3r)-3-(3-chloro-4-fluorophenoxy)-N-(isoquinolin-5-ylmethyl)cyclobutan-1-amine, HCl Step 28.1: Synthesis of tert-butyl ((1r,3r)-3-(3-chloro-4-fluorophenoxy)cyclobutyl)carbamate

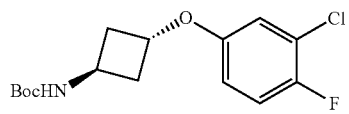

The following compound was synthesized following the procedure as described in Step 1.2, using tert-butyl ((1s,3s)-3-hydroxycyclobutyl)carbamate (0.6 g, 3.20 mmol) and 3-chloro-4-fluorophenol [CAS No. 2613-23-2] (0.46 g, 3.20 mmol). Reaction mixture was concentrated in vacuo and the residue was purified by flash chromatography (12 g Sili-Cycle column, 0-10% EtOAc in Hexane elution) to provide tert-butyl ((1r,3r)-3-(3-chloro-4-fluorophenoxy)cyclobutyl) carbamate (0.8 g, 79%). $^1$H NMR (600 MHz, CDCl$_3$) δ 7.02-7.00 (m, 1H), 6.77-6.76 (m, 2H), 6.63-6.61 (m, 1H), 4.71-4.69 (m, 1H), 4.30-4.27 (m, 1H), 2.55-2.51 (m, 2H), 2.39-2.35 (m, 2H), 1.45 (s, 9H).

Step 28.2: Synthesis of (1r,3r)-3-(3-chloro-4-fluorophenoxy)cyclobutan-1-amine, HCl

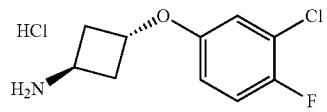 [SMILES: Cl ; N[C@H]1C[C@H](Oc2ccc(F)c(Cl)c2)C1]

A round bottom flask was charge with tert-butyl ((1r,3r)-3-(3-chloro-4-fluorophenoxy)cyclobutyl)carbamate (0.8 g, 2.53 mmol) and HCl solution (20% in 1,4-dioxane) (10 mL), and stirred at rt for 16 h. Then the reaction mixture was concentrated in vacuo. To the residue Et$_2$O was added, stirred for 10 min, the solid was collected by filtration and dried to yield (1r,3r)-3-(3-chloro-4-fluorophenoxy)cyclobutan-1-amine, HCl (0.5 g, 78%). MS (ESI+) [Method 6A]: m/z 216.1 (M+H); Rt 1.29 min. $^1$H NMR (300 MHz, DMSO-d6) δ 8.38 (brs, 3H), 7.33 (t, J=9.6 Hz, 1H), 7.01-6.98 (m, 1H), 6.84-6.78 (m, 1H), 5.02-4.96 (m, 1H), 3.81-3.77 (m, 1H), 2.64-2.55 (m, 2H), 2.42-2.35 (m, 2H).

Step 28.3: Synthesis of (1r,3r)-3-(3-chloro-4-fluorophenoxy)-N-(isoquinolin-5-ylmethyl)cyclobutan-1-amine, HCl

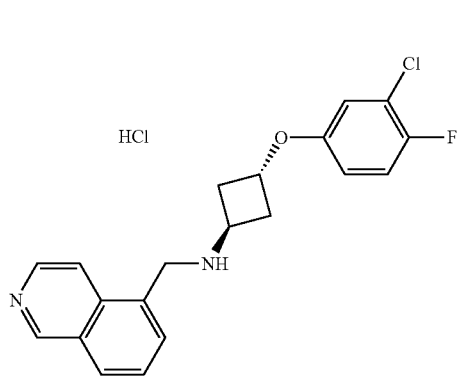 [SMILES: Fc1ccc(O[C@H]2C[C@H](NCc3cccc4cnccc34)C2)cc1Cl ; Cl]

The title compound was synthesized following the procedure as described in step 1.4, using (1r,3r)-3-(3-chloro-4-fluorophenoxy)cyclobutan-1-amine, HCl (80 mg, 0.32 mmol) and isoquinoline-5-carbaldehyde (45 mg, 0.29 mmol). Prep-HPLC (Column: KINETEX C18 (150 mm×21.2 mm), 5.0μ; Mobile Phase: 0.02% NH$_4$OH in water and acetonitrile) of the crude, followed by treatment with HCl solution (4M in 1,4-dioxane) afforded (1r,3r)-3-(3-chloro-4-fluorophenoxy)-N-(isoquinolin-5-ylmethyl)cyclobutan-1-amine, HCl (110 mg, 88%). MS (ESI+) [Method 6A]: m/z 357.3 (M+H); Rt 0.14 min. $^1$H NMR (400 MHz, CD$_3$OD) δ 9.91 (s, 1H), 8.83 (d, J=6.8 Hz, 1H), 8.75 (d, J=6.8 Hz, 1H), 8.64 (d, J=8.0 Hz, 1H), 8.48 (d, J=7.2 Hz, 1H), 8.14 (dd, J=8.4, 7.6 Hz, 1H), 7.17 (d, J=8.8 Hz, 1H), 6.97-6.95 (m, 1H), 6.83-6.79 (m, 1H), 5.02-4.98 (m, 1H), 4.85 (s, 2H), 4.29-4.25 (m, 1H), 2.95-2.88 (m, 2H), 2.70-2.63 (m, 2H).

Example 29: Synthesis of (1r,3r)-3-(3-(difluoromethoxy)phenoxy)-N-((6-fluoroisoquinolin-5-yl)methyl)cyclobutan-1-amine, HCl

Step 29.1: Synthesis of tert-butyl ((1r,3r)-3-(3-(difluoromethoxy)phenoxy)cyclobutyl)carbamate

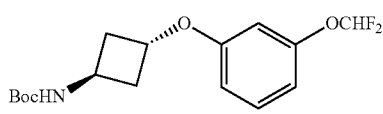 [SMILES: CC(C)(C)OC(=O)N[C@H]1C[C@H](Oc2cccc(OC(F)F)c2)C1]

The title compound was synthesized following the procedure as described in Step 1.2, using tert-butyl ((1s,3s)-3-hydroxycyclobutyl)carbamate (0.4 g, 2.14 mmol) and 3-(difluoromethoxy)phenol [CAS No. 88798-13-4] (0.35 g, 2.14 mmol). tert-butyl ((1r,3r)-3-(3-(difluoromethoxy)phenoxy)cyclobutyl)carbamate was isolated (0.6 g, 84%). $^1$H NMR (600 MHz, CDCl3) δ 7.23-7.18 (m, 2H), 6.68-6.61 (m, 1H), 6.61-6.59 (m, 1H), 6.51 (t, J=95.4 Hz, 1H), 4.75-4.73 (m, 1H), 4.30-4.27 (m, 1H), 2.55-2.53 (m, 2H), 2.39-2.35 (m, 2H), 1.44 (s, 9H).

Step 29.2: Synthesis of (1r,3r)-3-(3-(difluoromethoxy)phenoxy)cyclobutan-1-amine, HCl A round bottom flask was charged with tert-butyl ((1r,3r)-3-(3-(difluoromethoxy)phenoxy)cyclobutyl)carbamate (0.6 g, 1.81 mmol) and HCl solution (20% in 1,4-dioxane) (5 mL), and stirred at rt for 1 h. Then the reaction mixture was concentrated in vacuo. The residue was triturated with Et$_2$O, solid was collected by filtration and dried to yield (1r,3r)-3-(3-(difluoromethoxy)phenoxy)cyclobutan-1-amine, HCl (0.35 g, 72%). $^1$H NMR (300 MHz, DMSO-d6) δ 8.24 (brs, 3H), 7.34 (t, J=8.4 Hz, 1H), 7.25 (t, J=74.4 Hz, 1H), 6.78-6.75 (m, 1H), 6.71-6.68 (m, 1H), 6.62-6.60 (m, 1H), 5.02-4.97 (m, 1H), 3.84-3.79 (m, 1H), 2.63-2.57 (m, 2H), 2.46-2.41 (m, 2H).

Step 29.3: Synthesis of (1r,3r)-3-(3-(difluoromethoxy)phenoxy)-N-((6-fluoroisoquinolin-5-yl)methyl)cyclobutan-1-amine, HCl

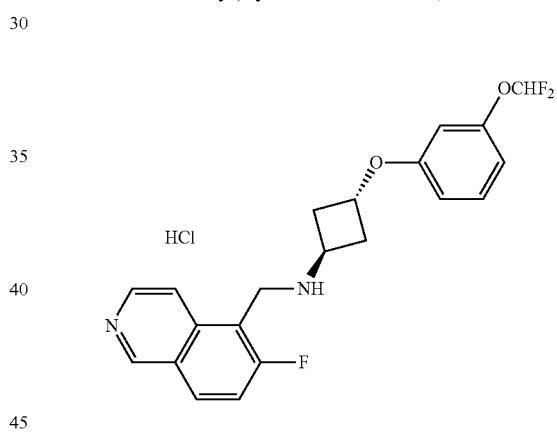

The title compound was synthesized following the procedure as described in Step 25.6, using (1r,3r)-3-(3-(difluoromethoxy)phenoxy)cyclobutan-1-amine, HCl (300 mg, 1.13 mmol) and 6-fluoroisoquinoline-5-carbaldehyde (Step 3.1, 176 mg, 1.01 mmol). Prep-HPLC (Column: LUNA Phenomenex (250 mm×21.2 mm), 5.0μ; Mobile Phase: 0.01% HCO$_2$H in water and acetonitrile-MeOH) of the crude, followed by treatment with HCl solution (4M in 1,4-dioxane) afforded (1r,3r)-3-(3-(difluoromethoxy)phenoxy)-N-((6-fluoroisoquinolin-5-yl)methyl)cyclobutan-1-amine, HCl (140 mg, 30%). MS (ESI+) [Method 6A]: m/z 389.1 (M+H); Rt 1.29 min. $^1$H NMR (400 MHz, CD$_3$OD) δ 9.83 (s, 1H), 8.80-8.71 (m, 3H), 8.00 (t, J=9.2 Hz, 1H), 7.33 (d, J=8.0 Hz, 1H), 6.84 (t, J=74.0 Hz, 1H), 6.78 (dd, J=8.0, 2.0 Hz, 1H), 6.74-6.71 (m, 1H), 6.64-6.62 (m, 1H), 5.05-4.99 (m, 1H), 4.83 (d, J=2.0 Hz, 2H), 4.31-4.26 (m, 1H), 2.91-2.84 (m, 2H), 2.75-2.68 (m, 2H).

Example 30: Synthesis of (1r,3r)-3-(4-(difluoromethoxy)phenoxy)-N-((6-fluoroisoquinolin-5-yl)methyl)cyclobutan-1-amine, HCl Step 30.1: Synthesis of 1-(benzyloxy)-4-(difluoromethoxy)benzene

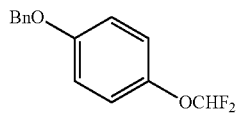

To the solution of 4-(benzyloxy)phenol [CAS No. 103-16-2] (1.0 g, 4.99 mmol) in DMF-water (8.2 mL, 40:1 v/v), sodium 2-chloro-2,2-difluoroacetate (1.14 g, 7.49 mmol) and NaOH (0.24 g, 5.99 mmol) were added and the reaction mixture was heated as 130° C. for 2 h under $N_2$. Reaction mixture was diluted with water and extracted with EtOAc twice. The combined organic portion was washed with brine, dried over anhydrous $Na_2SO_4$, filtered and concentrated in vacuo. The residue was purified by flash chromatography (12 g SiliCycle column, Hexane elution) to provide 1-(benzyloxy)-4-(difluoromethoxy)benzene (0.15 g, 12%). MS (ESI+) [Method 6A]: m/z 249.1 (M−H); Rt 1.63 min.

Step 30.2: Synthesis of 4-(difluoromethoxy)phenol

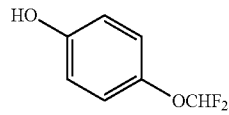

To the solution of 1-(benzyloxy)-4-(difluoromethoxy)benzene (300 mg, 1.20 mmol) in THF (10 mL), Pd/C (10% w/w) (50 mg) was added under argon. Reaction mixture was degassed, connected with $H_2$ balloon and stirred at rt for 2 h. Reaction mixture was filtered through celite bed, the bed was washed with EtOAc. The combined filtrate was concentrated in vacuo to afford 4-(difluoromethoxy)phenol (200 mg, 104%). MS (ESI+) [Method 6A]: m/z 159.1 (M−H); Rt 1.44 min. $^1$H NMR (300 MHz, CDCl$_3$) δ 7.02 (d, J=8.7 Hz, 2H), 6.80 (dd, J=6.6, 2.1 Hz, 2H), 6.41 (t, J=74.1 Hz, 1H).

Step 30.3: Synthesis of tert-butyl ((1r,3r)-3-(4-(difluoromethoxy)phenoxy)cyclobutyl)carbamate

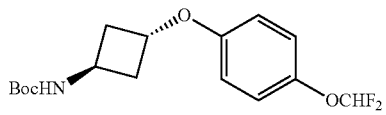 [SMILES: CC(C)(C)OC(=O)N[C@H]1C[C@H](Oc2ccc(OC(F)F)cc2)C1]

The title compound was synthesized following the procedure as described in Step 1.2, using tert-butyl ((1s,3s)-3-hydroxycyclobutyl)carbamate (230 mg, 1.25 mmol) and 4-(difluoromethoxy)phenol (200 mg, 1.25 mmol). The crude product was purified by flash chromatography (12 g SiliCycle column, 0-10% EtOAc in Hexane elution) to provide tert-butyl ((1r,3r)-3-(4-(difluoromethoxy)phenoxy)cyclobutyl)carbamate (200 mg, 48%). MS (ESI+) [Method 6A]: m/z 659.2 (2M+H); Rt 1.44 min. $^1$H NMR (300 MHz, CDCl$_3$) δ 7.04 (d, J=8.7 Hz, 2H), 6.73 (d, J=9.3 Hz, 2H), 6.41 (t, J=74.1 Hz, 1H), 4.77-4.71 (m, 1H), 4.32-4.28 (m, 1H), 2.59-2.50 (m, 2H), 2.41-2.35 (m, 2H), 1.45 (s, 9H).

Step 30.4: Synthesis of (1r,3r)-3-(4-(difluoromethoxy)phenoxy)cyclobutan-1-amine, HCl

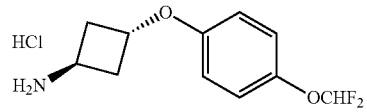 [SMILES: Cl ; N[C@H]1C[C@H](Oc2ccc(OC(F)F)cc2)C1]

The solution of tert-butyl ((1r,3r)-3-(4-(difluoromethoxy)phenoxy)cyclobutyl)carbamate (0.2 g, 0.61 mmol) and HCl solution (20% in 1,4-dioxane) (4 mL) was stirred at rt for 4 h. Then the reaction mixture was concentrated in vacuo to yield crude (1r,3r)-3-(4-(difluoromethoxy)phenoxy)cyclobutan-1-amine, HCl (0.2 g, 124%). MS (ESI+) [Method 6A]: m/z 230.7 (M−H); Rt 1.28 min.

Step 30.5: Synthesis of (1r,3r)-3-(4-(difluoromethoxy)phenoxy)-N-((6-fluoroisoquinolin-5-yl)methyl)cyclobutan-1-amine, HCl

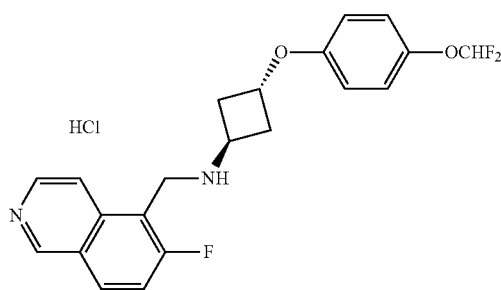 [SMILES: Fc1ccc2cnccc2c1CN[C@H]1C[C@H](Oc2ccc(OC(F)F)cc2)C1 ; Cl]

The title compound was synthesized following the procedure as described in Step 25.6, using (1r,3r)-3-(4-(difluoromethoxy)phenoxy)cyclobutan-1-amine, HCl (200 mg, 0.87 mmol) and 6-fluoroisoquinoline-5-carbaldehyde (Step 3.1, 152 mg, 0.87 mmol). Prep-HPLC (Column: LUNA C18 (250 mm×21.2 mm), 5.0μ; Mobile Phase: 0.01% HCO$_2$H in water and acetonitrile-MeOH (1:1)) of the crude, followed by treatment with HCl solution (4M in 1,4-dioxane) afforded (1r,3r)-3-(4-(difluoromethoxy)phenoxy)-N-((6-fluoroisoquinolin-5-yl)methyl)cyclobutan-1-amine, HCl (120 mg, 36%). MS (ESI+) [Method 6A]: m/z 389.2 (M+H); Rt 1.28 min. $^1$H NMR (400 MHz, CD$_3$OD) δ 9.91 (s, 1H), 8.86-8.78 (m, 3H), 8.04 (t, J=9.6 Hz, 1H), 7.09 (dd, J=6.8, 1.6 Hz, 2H), 6.87-6.85 (m, 2H), 6.69 (t, J=74.4 Hz, 1H), 5.01-4.98 (m, 1H), 4.83 (d, J=2.0 Hz, 2H), 4.28-4.24 (m, 1H), 2.89-2.84 (m, 2H), 2.72-2.65 (m, 2H).

Example 31: Synthesis of (1r,3r)-N-((6-fluoroisoquinolin-5-yl)methyl)-3-(naphthalen-2-yloxy)cyclobutan-1-amine, HCl

Step 31.1: Synthesis of tert-butyl ((1r,3r)-3-(naphthalen-2-yloxy)cyclobutyl)carbamate

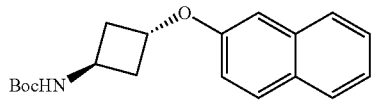 [SMILES: CC(C)(C)OC(=O)N[C@H]1C[C@H](Oc2ccc3ccccc3c2)C1]

The title compound was synthesized following the procedure as described in Step 1.2, using tert-butyl ((1s,3s)-3-hydroxycyclobutyl)carbamate (250 mg, 1.34 mmol) and naphthalen-2-ol [CAS No. 135-19-3] (212 mg, 1.47 mmol). Product was purified by flash chromatography (12 g Sili-Cycle column, 0-30% EtOAc in Hexane elution) to provide tert-butyl ((1r,3r)-3-(naphthalen-2-yloxy)cyclobutyl)carbamate (220 mg, 52%). $^1$H NMR (400 MHz, CDCl$_3$) δ 7.78-7.72 (m, 2H), 7.70-7.66 (m, 1H), 7.44-7.39 (m, 1H), 7.34-7.29 (m, 1H), 7.15-7.08 (m, 2H), 4.95-4.90 (m, 1H), 4.34-4.29 (m, 1H), 2.67-2.58 (m, 2H), 2.49-2.42 (m, 2H), 1.46 (s, 9H).

Step 31.2: Synthesis of (1r,3r)-3-(naphthalen-2-yloxy)cyclobutan-1-amine, HCl

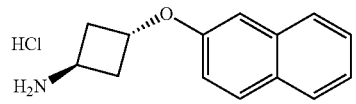 [SMILES: Cl ; N[C@H]1C[C@H](Oc2ccc3ccccc3c2)C1]

The solution of tert-butyl ((1r,3r)-3-(naphthalen-2-yloxy)cyclobutyl)carbamate (220 mg, 0.70 mmol) and HCl solution (20% in 1,4-dioxane) (3 mL) was stirred at rt for 3 h. Then the reaction mixture was concentrated in vacuo, and triturated with Et$_2$O to yield (1r,3r)-3-(naphthalen-2-yloxy)cyclobutan-1-amine, HCl (90 mg, 51%). MS (ESI+) [Method 6A]: m/z 214.0 (M+H); Rt 1.32 min.

Step 31.3: Synthesis of (1r,3r)-N-((6-fluoroisoquinolin-5-yl)methyl)-3-(naphthalen-2-yloxy)cyclobutan-1-amine, HCl

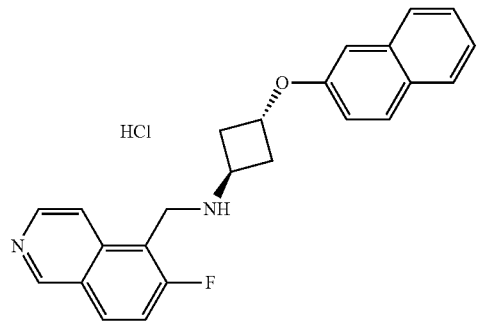 [SMILES: Fc1ccc2cnccc2c1CN[C@H]1C[C@H](Oc2ccc3ccccc3c2)C1 ; Cl]

The title compound was synthesized following the procedure as described in Step 1.4, using (1r,3r)-3-(naphthalen-2-yloxy)cyclobutan-1-amine, HCl (90 mg, 0.36 mmol) and 6-fluoroisoquinoline-5-carbaldehyde (Step 3.1, 64 mg, 0.36 mmol). Prep-HPLC (Column: GEMINI NX C18 (150 mm×21.2 mm), 5.0µ; Mobile Phase: 0.02% NH$_4$OH in water and acetonitrile) of the crude, followed by treatment with HCl solution (4M in 1,4-dioxane) afforded (1r,3r)-N-((6-fluoroisoquinolin-5-yl)methyl)-3-(naphthalen-2-yloxy)cyclobutan-1-amine, HCl (90 mg, 63%). MS (ESI+) [Method 6A]: m/z 373.2 (M+H); Rt 1.30 min. $^1$H NMR (400 MHz, CD$_3$OD) δ 9.85 (s, 1H), 8.78-8.73 (m, 3H), 8.01 (t, J=9.6 Hz, 1H), 7.80-7.73 (m, 3H), 7.43 (td, J=6.8, 1.2 Hz, 1H), 7.33 (td, J=6.8, 1.2 Hz, 1H), 7.12 (dd, J=8.8, 2.4 Hz, 1H), 7.05-7.04 (m, 1H), 5.16-5.12 (m, 1H), 4.84 (d, J=2.0 Hz, 2H), 4.32-4.29 (m, 1H), 2.98-2.92 (m, 2H), 2.80-2.73 (m, 2H).

Example 32: Synthesis of (1r,3r)-N-((6-fluoroisoquinolin-5-yl)methyl)-3-((7-fluoronaphthalen-2-yl)oxy)cyclobutan-1-amine, HCl

Step 32.1: Synthesis of tert-butyl ((1r,3r)-3-((7-fluoronaphthalen-2-yl)oxy)cyclobutyl)carbamate

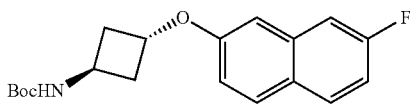 [SMILES: CC(C)(C)OC(=O)N[C@H]1C[C@H](Oc2ccc3ccc(F)cc3c2)C1]

The title compound was synthesized following the procedure as described in Step 1.2, using tert-butyl ((1s,3s)-3-hydroxycyclobutyl)carbamate (200 g, 1.23 mmol) and 7-fluoronaphthalen-2-ol [CAS No. 889884-94-0] (231 g, 1.23 mmol). The crude product was purified by flash chromatography (12 g SiliCycle column, 0-30% EtOAc in Hexane elution) to provide tert-butyl ((1r,3r)-3-((7-fluoronaphthalen-2-yl)oxy)cyclobutyl)carbamate (240 g, 58%). $^1$H NMR (300 MHz, CDCl$_3$) δ 7.75-7.70 (m, 2H), 7.32-7.28 (m, 1H), 7.12-7.02 (m, 2H), 6.83 (d, J=3.0 Hz, 1H), 4.94-4.87 (m, 1H), 4.36-4.30 (m, 1H), 2.67-2.59 (m, 2H), 2.49-2.42 (m, 2H), 1.46 (s, 9H).

Step 32.2: Synthesis of (1r,3r)-3-((7-fluoronaphthalen-2-yl)oxy)cyclobutan-1-amine, HCl

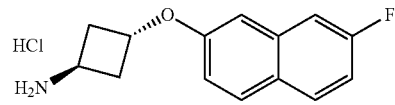 [SMILES: Cl ; N[C@H]1C[C@H](Oc2ccc3ccc(F)cc3c2)C1]

The solution of tert-butyl ((1r,3r)-3-((7-fluoronaphthalen-2-yl)oxy)cyclobutyl)carbamate (240 mg, 0.72 mmol) and HCl solution (20% in 1,4-dioxane) (6 mL) was stirred at rt for 1 h. Then the reaction mixture was concentrated in vacuo, and triturated with Et$_2$O to yield (1r,3r)-3-((7-fluoronaphthalen-2-yl)oxy)cyclobutan-1-amine, HCl (170 mg, 87%). MS (ESI+) [Method 6A]: m/z 232.2 (M+H); Rt 1.29 min.

Step 32.3: Synthesis of (1r,3r)-N-((6-fluoroisoquinolin-5-yl)methyl)-3-((7-fluoronaphthalen-2-yl)oxy)cyclobutan-1-amine, HCl

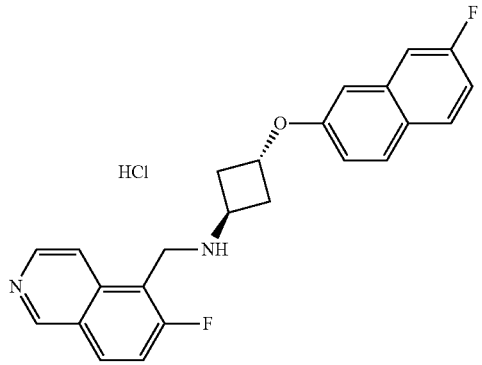 [SMILES: Fc1ccc2ccc(O[C@H]3C[C@H](NCc4c(F)ccc5cnccc45)C3)cc2c1 ; Cl]

The title compound was synthesized following the procedure as described in Step 1.4, using (1r,3r)-3-((7-fluoronaphthalen-2-yl)oxy)cyclobutan-1-amine, HCl (170 mg, 0.64 mmol) and 6-fluoroisoquinoline-5-carbaldehyde (Step 3.1, 100 mg, 0.57 mmol). Crude product was purified by prep-HPLC (Column: LUNA Phenomenex (250 mm×21.2 mm), 5.0μ; Mobile Phase: 0.1% HCO$_2$H in water and acetonitrile). The isolated product was stirred with HCl solution (4M in 1,4-dioxane) (3 mL) at rt for 1 h. Then concentrated and the residue was triturated with Et$_2$O to provide (1r,3r)-N-((6-fluoroisoquinolin-5-yl)methyl)-3-((7-fluoronaphthalen-2-yl)oxy)cyclobutan-1-amine, HCl (90 mg, 33%). MS (ESI+) [Method 6A]: m/z 391.0 (M+H); Rt 1.35 min. $^1$H NMR (400 MHz, CD$_3$OD) δ 9.79 (s, 1H), 8.88-8.69 (m, 3H), 8.01 (t, J=9.2 Hz, 1H), 7.83-7.80 (m, 2H), 7.41 (d, J=7.6 Hz, 1H), 7.16-7.08 (m, 2H), 7.04-7.02 (m, 1H), 5.15-5.11 (m, 1H), 4.84 (s, 2H), 4.32-4.28 (m, 1H), 2.96-2.89 (m, 2H), 2.79-2.74 (m, 2H).

Example 33: Synthesis of (1r,3r)-N-((6-fluoroisoquinolin-5-yl)methyl)-3-(3-(pentafluoro-λ$^6$-sulfaneyl)phenoxy)cyclobutan-1-amine, HCl Step 33.1: Synthesis of tert-butyl ((1r,3r)-3-(3-(pentafluoro-λ$^6$-sulfaneyl)phenoxy)cyclobutyl)carbamate [C-07717-111]

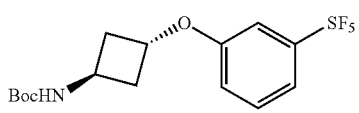

The title compound was synthesized following the procedure as described in Step 1.2, using tert-butyl ((1s,3s)-3-hydroxycyclobutyl)carbamate (120 mg, 0.64 mmol) and 3-(pentafluoro-λ$^6$-sulfaneyl)phenol [CAS No. 672-31-1] (150 g, 0.68 mmol). The crude was purified by flash chromatography (8 g SiliCycle column, 0-8% EtOAc in Hexane elution) to provide tert-butyl ((1r,3r)-3-(3-(pentafluoro-λ$^6$-sulfaneyl)phenoxy)cyclobutyl)carbamate (150 mg, 60%). 1H NMR (300 MHz, CDCl3) δ 7.34-7.32 (m, 2H), 7.15 (s, 1H), 6.90-6.87 (m, 1H), 4.83-4.77 (m, 1H), 4.32-4.27 (m, 1H), 2.59-2.53 (m, 2H), 2.46-2.37 (m, 2H), 1.45 (s, 9H).

Step 33.2: Synthesis of (1r,3r)-3-(3-(pentafluoro-λ$^6$-sulfaneyl)phenoxy)cyclobutan-1-amine, HCl

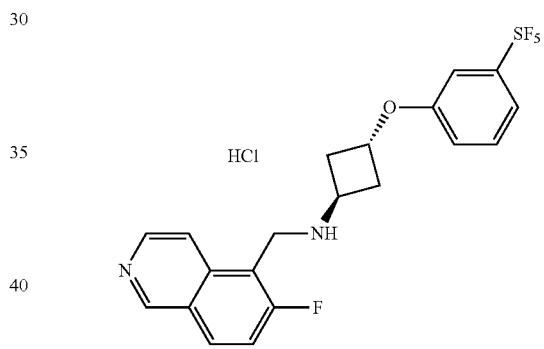

The solution of tert-butyl ((1r,3r)-3-(3-(pentafluoro-λ$^6$-sulfaneyl)phenoxy)cyclobutyl)carbamate (150 mg, 0.39 mmol) and HCl solution (20% in 1,4-dioxane) (2 mL) was stirred at rt for 1 h. Then the reaction mixture was concentrated in vacuo, and triturated with Et$_2$O to yield (1r,3r)-3-(3-(pentafluoro-λ$^6$-sulfaneyl)phenoxy)cyclobutan-1-amine, HCl (100 mg, 91%). $^1$H NMR (400 MHz, DMSO-d6) δ 8.31 (s, 3H), 7.65-7.48 (m, 2H), 7.33 (dd, J=7.2, 2.0 Hz, 1H), 7.13 (dd, J=8.0, 2.0 Hz, 1H), 5.12-5.08 (m, 1H), 3.87-3.81 (m, 1H), 2.64-2.59 (m, 2H), 2.49-2.43 (m, 2H).

Step 33.3: Synthesis of (1r,3r)-N-((6-fluoroisoquinolin-5-yl)methyl)-3-(3-(pentafluoro-λ$^6$-sulfaneyl)phenoxy)cyclobutan-1-amine, HCl The title compound was synthesized following the procedure as described in Step 25.6, using (1r,3r)-3-(3-(pentafluoro-λ$^6$-sulfaneyl)phenoxy)cyclobutan-1-amine, HCl (70 mg, 0.21 mmol) and 6-fluoroisoquinoline-5-carbaldehyde (Step 3.1, 32 mg, 0.18 mmol). Crude product was purified by prep-HPLC (Column: GEMINI-NX (150 mm×21.2 mm), 5.0μ; Mobile Phase: 0.02% NH$_4$OH in water and acetonitrile). The isolated product was stirred with HCl solution (4M in 1,4-dioxane) (1 mL) at rt for 1 h. Then concentrated to provide (1r,3r)-N-((6-fluoroisoquinolin-5-yl)methyl)-3-(3-(pentafluoro-λ$^6$-sulfaneyl)phenoxy)cyclobutan-1-amine, HCl (20 mg, 20%). MS (ESI+) [Method 6A]: m/z 449.1 (M+H); Rt 1.34 min. $^1$H NMR (400 MHz, CD$_3$OD) δ 9.85 (s, 1H), 8.80-8.73 (m, 3H), 8.01 (t, J=9.6 Hz, 1H), 7.51 (t, J=8.4 Hz, 1H), 7.46-7.43 (m, 1H), 7.28-7.27 (m, 1H), 7.10 (dd, J=8.4, 2.0 Hz, 1H), 5.12-5.07 (m, 1H), 4.84 (d, J=2.0 Hz, 2H), 4.32-4.28 (m, 1H), 2.95-2.88 (m, 2H), 2.70-2.67 (m, 2H).

Example 34: Synthesis of ethyl 3-((1r,3r)-3-(((6-fluoroisoquinolin-5-yl)methyl)amino)cyclobutoxy)benzoate, HCl

Step 34.1: Synthesis of ethyl 3-((1r,3r)-3-((tert-butoxycarbonyl)amino)cyclobutoxy)benzoate

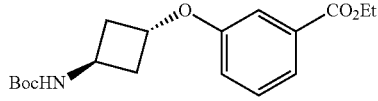 [SMILES: CCOC(=O)c1cccc(O[C@H]2C[C@H](NC(=O)OC(C)(C)C)C2)c1]

The title compound was synthesized following the procedure as described under Step 1.2, using tert-butyl ((1s,3s)-3-hydroxycyclobutyl)carbamate (200 mg, 1.07 mmol) and ethyl 3-hydroxybenzoate [CAS No. 7781-98-8] (195 g, 1.18 mmol). The crude product was purified by flash chromatography (12 g SiliCycle column, 0-40% EtOAc in Hexane elution) to provide ethyl 3-((1r,3r)-3-((tert-butoxycarbonyl)amino)cyclobutoxy)benzoate as off white solid (220 mg, 61%). $^1$H NMR (300 MHz, DMSO-d6) δ 7.54-7.51 (m, 1H), 7.42 (t, J=7.5 Hz, 1H), 7.34-7.30 (m, 2H), 7.12-7.08 (m, 1H), 4.88-4.84 (m, 1H), 4.30 (q, J=6.9 Hz, 2H), 4.12-3.97 (m, 1H), 2.38-2.31 (m, 4H), 1.38 (s, 9H), 1.31 (t, J=6.9 Hz, 3H).

Step 34.2: Synthesis of ethyl 3-((1r,3r)-3-aminocyclobutoxy)benzoate, HCl

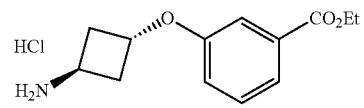 [SMILES: Cl ; CCOC(=O)c1cccc(O[C@H]2C[C@H](N)C2)c1]

The solution of ethyl 3-((1r,3r)-3-((tert-butoxycarbonyl)amino)cyclobutoxy)benzoate (220 mg, 0.66 mmol) and HCl solution (20% in 1,4-dioxane) (5 mL) was stirred at rt for 2 h. Then the reaction mixture was concentrated in vacuo, and triturated with Et$_2$O to yield ethyl 3-((1r,3r)-3-aminocyclobutoxy)benzoate, HCl (120 mg, 67%). MS (ESI+) [Method 6A]: m/z 236.2 (M+H); Rt 1.31 min. $^1$H NMR (300 MHz, DMSO-d6) δ 8.22 (s, 3H), 7.58-7.55 (m, 1H), 7.46 (t, J=8.1 Hz, 1H), 7.31 (s, 1H), 7.11 (dd, J=8.1, 1.8 Hz, 1H), 5.08-5.04 (m, 1H), 4.31 (q, J=6.9 Hz, 2H), 3.87-3.83 (m, 1H), 2.60-2.49 (m, 4H), 1.31 (t, J=6.9 Hz, 3H).

Step 34.3: Synthesis of ethyl 3-((1r,3r)-3-(((6-fluoroisoquinolin-5-yl)methyl)amino)cyclobutoxy)benzoate, HCl

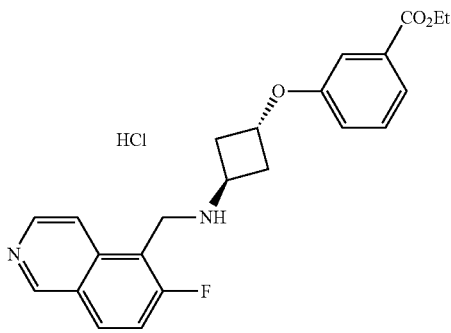 [SMILES: CCOC(=O)c1cccc(O[C@H]2C[C@H](NCc3c(F)ccc4cnccc34)C2)c1 ; Cl]

The title compound was synthesized following the procedure as described in Step 1.4, using ethyl 3-((1r,3r)-3-aminocyclobutoxy)benzoate, HCl (80 mg, 0.30 mmol) and 6-fluoroisoquinoline-5-carbaldehyde (Step 3.1, 46 mg, 0.27 mmol). Crude product was purified by prep-HPLC (Column: LUNA C18 (250 mm×21.0 mm), 5.0µ; Mobile Phase: 0.01% HCO$_2$H in water and acetonitrile). The isolated product was stirred with HCl solution (4M in 1,4-dioxane) (2 mL) at rt for 1 h. Then concentrated and then the residue was triturated with Et$_2$O to provide ethyl 3-((1r,3r)-3-(((6-fluoroisoquinolin-5-yl)methyl)amino)cyclobutoxy)benzoate, HCl (40 mg, 31%). MS (ESI+) [Method 6A]: m/z 395.1 (M+H); Rt 1.32 min. $^1$H NMR (400 MHz, CD$_3$OD) δ 9.85 (s, 1H), 8.81-8.75 (m, 3H), 8.02 (t, J=9.2 Hz, 1H), 7.67 (dt, J=9.2, 1.6 Hz, m, 1H), 7.45-7.41 (m, 2H), 7.12 (ddd, J=8.4, 2.8, 0.8 Hz, 1H), 5.09-5.06 (m, 1H), 4.85 (d, J=2.0 Hz, 2H), 4.38 (q, J=7.2 Hz, 2H), 4.33-4.28 (m, 1H), 2.92-2.87 (m, 2H), 2.77-2.71 (m, 2H), 1.40 (t, J=7.2 Hz, 3H).

Example 35: Synthesis of (1r,3r)-3-(2,3-difluorophenoxy)-N-((6-fluoroisoquinolin-5-yl)methyl)cyclobutan-1-amine

Step 35.1: Synthesis of tert-butyl ((1r,3r)-3-(2,3-difluorophenoxy)cyclobutyl)carbamate

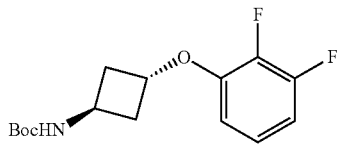 [SMILES: CC(C)(C)OC(=O)N[C@H]1C[C@H](Oc2cccc(F)c2F)C1]

The title compound was synthesized following the procedure as described in Step 1.2, using tert-butyl ((1s,3s)-3-hydroxycyclobutyl)carbamate (100 mg, 0.53 mmol) and 2,3-difluorophenol [6418-38-8] (70 mg, 0.53 mmol). The crude product was purified by flash chromatography (4 g SiliCycle column, 0-10% EtOAc in Hexane elution) to provide tert-butyl ((1r,3r)-3-(2,3-difluorophenoxy)cyclobutyl)carbamate (110 mg, 68%). $^1$H NMR (600 MHz, CDCl$_3$) δ 6.94-6.91 (m, 1H), 6.76-6.73 (m, 1H), 6.52-6.49 (m, 1H), 4.74-4.71 (m, 1H), 4.32-4.28 (m, 1H), 2.63-2.59 (m, 2H), 2.43-2.38 (m, 2H), 1.45 (s, 9H).

Step 35.2: Synthesis of (1r,3r)-3-(2,3-difluorophenoxy)cyclobutan-1-amine, HCl

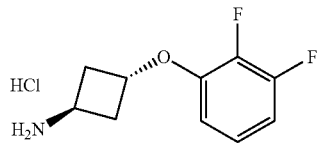 [SMILES: Cl ; N[C@H]1C[C@H](Oc2cccc(F)c2F)C1]

A round bottom flask was charged with tert-butyl ((1r,3r)-3-(2,3-difluorophenoxy)cyclobutyl)carbamate (110 mg, 0.37 mmol) and HCl solution (20% in 1,4-dioxane) (2 mL), and stirred at rt for 16 h. Then the reaction mixture was concentrated in vacuo to yield crude (1r,3r)-3-(2,3-difluorophenoxy)cyclobutan-1-amine, HCl (90 mg, 122%). %). MS (ESI+) [Method 6A]: m/z 200.1 (M+H); Rt 1.25 min.

Step 35.3: Synthesis of (1r,3r)-3-(2,3-difluorophenoxy)-N-((6-fluoroisoquinolin-5-yl)methyl)cyclobutan-1-amine

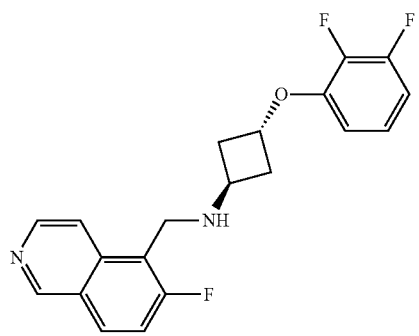 [SMILES: Fc1cccc(O[C@H]2C[C@H](NCc3c(F)ccc4cnccc34)C2)c1F]

The title compound was synthesized following the procedure as described in Step 25.6, using (1r,3r)-3-(2,3-difluorophenoxy)cyclobutan-1-amine, HCl (110 mg, 0.55 mmol) and 6-fluoroisoquinoline-5-carbaldehyde (Step 3.1, 96 mg, 0.55 mmol). Crude product was purified by prep-HPLC (Column: LUNA C18 (250 mm×21.0 mm), 5.0µ; Mobile Phase: 0.01% HCO$_2$H in water and acetonitrile) to provide (1r,3r)-3-(2,3-difluorophenoxy)-N-((6-fluoroisoquinolin-5-yl)methyl)cyclobutan-1-amine (40 mg, 21%). MS (ESI+) [Method 1A]: m/z 359.0 (M+H); Rt 0.13 min. $^1$H NMR (400 MHz, CD$_3$OD) δ 9.33 (s, 1H), 8.61 (s, 1H), 8.29 (dd, J=9.6, 6.0 Hz, 1H), 8.15 (d, J=6.0 Hz, 1H), 7.62 (t, J=9.6 Hz, 1H), 7.09-7.02 (m, 1H), 6.89-6.82 (m, 1H), 6.72-6.68 (m, 1H), 4.98-4.94 (m, 1H), 4.47 (s, 2H), 3.97-3.93 (m, 1H), 2.58 (t, J=5.6 Hz, 4H).

Example 36: Synthesis of (1r,3r)-N-((6-fluoroisoquinolin-5-yl)methyl)-3-(4-(trifluoromethoxy)phenoxy)cyclobutan-1-amine, HCl

Step 36.1: Synthesis of tert-butyl ((1r,3r)-3-(4-(trifluoromethoxy)phenoxy)cyclobutyl)carbamate

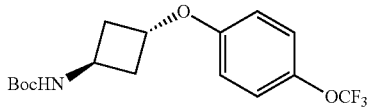 [SMILES: CC(C)(C)OC(=O)N[C@H]1C[C@H](Oc2ccc(OC(F)(F)F)cc2)C1]

The title compound was synthesized following the procedure as described in Step 1.2, using tert-butyl ((1s,3s)-3-hydroxycyclobutyl)carbamate (380 mg, 2.14 mmol) and 4-(trifluoromethoxy)phenol [CAS No. 828-27-3] (400 mg, 2.14 mmol). The crude product was purified by flash chromatography (12 g SiliCycle column, 0-20% EtOAc in Hexane elution) to provide tert-butyl ((1r,3r)-3-(4-(trifluoromethoxy)phenoxy)cyclobutyl)carbamate (330 mg, 44%). $^1$H NMR (600 MHz, CDCl$_3$) δ 7.11 (d, J=7.8 Hz, 2H), 6.74 (d, J=9.0 Hz, 2H), 4.76-4.74 (m, 1H), 4.31-4.27 (m, 1H), 2.57-2.53 (m, 2H), 2.40-2.37 (m, 2H), 1.45 (s, 9H).

Step 36.2: Synthesis of (1r,3r)-3-(4-(trifluoromethoxy)phenoxy)cyclobutan-1-amine, HCl

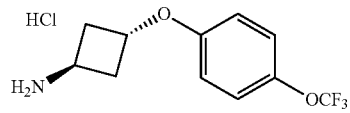 [SMILES: Cl ; N[C@H]1C[C@H](Oc2ccc(OC(F)(F)F)cc2)C1]

A round bottom flask was charged with tert-butyl ((1r,3r)-3-(4-(trifluoromethoxy)phenoxy)cyclobutyl)carbamate (330 mg, 0.95 mmol) and HCl solution (20% in 1,4-dioxane) (5 mL), and stirred at rt for 2 h. Then the reaction mixture was concentrated in vacuo, the residue was triturated with Et$_2$O, solid collected by filtration and dried to provide (1r,3r)-3-(4-(trifluoromethoxy)phenoxy)cyclobutan-1-amine, HCl (210 mg, 77%). MS (ESI+) [Method 6A]: m/z 248.1 (M+H); Rt 1.35 min. $^1$H NMR (400 MHz, DMSO-d6) δ 8.26 (s, 3H), 7.31 (d, J=8.0 Hz, 2H), 6.90 (d, J=8.8 Hz, 2H), 5.01-4.98 (m, 1H), 3.85-3.81 (m, 1H), 2.63-2.57 (m, 2H), 2.46-2.42 (m, 2H).

Step 36.3: Synthesis of (1r,3r)-N-((6-fluoroisoquinolin-5-yl)methyl)-3-(4-(trifluoromethoxy)phenoxy)cyclobutan-1-amine, HCl

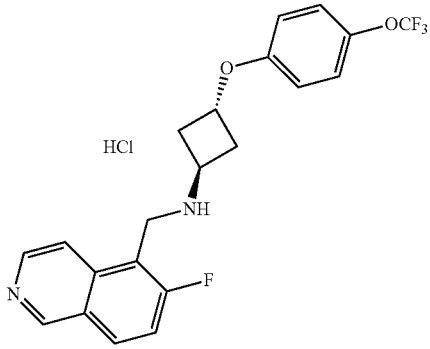 [SMILES: Fc1ccc2cnccc2c1CN[C@H]1C[C@H](Oc2ccc(OC(F)(F)F)cc2)C1 ; Cl]

The title compound was synthesized following the procedure as described in Step 25.6, using (1r,3r)-3-(4-(trifluoromethoxy)phenoxy)cyclobutan-1-amine, HCl (210 mg, 0.74 mmol) and 6-fluoroisoquinoline-5-carbaldehyde (Step 3.1, 110 mg, 0.67 mmol). Crude product was purified by prep-HPLC (Column: LUNA C18 (250 mm×21.0 mm), 5.0μ; Mobile Phase: 0.01% HCO$_2$H in water and acetonitrile). The isolated product was stirred with HCl solution (4M in 1,4-dioxane) (1 mL) at rt for 1 h. Then concentrated in vacuo, residue was triturated with Et$_2$O, solid formed was collected by filtration and dried to provide (1r,3r)-N-((6-fluoroisoquinolin-5-yl)methyl)-3-(4-(trifluoromethoxy)phenoxy)cyclobutan-1-amine, HCl (37 mg, 12%). MS (ESI+) [Method 1A]: m/z 407.1 (M+H); Rt 1.36 min. $^1$H NMR (400 MHz, CD$_3$OD) δ 9.80 (s, 1H), 8.78 (d, J=6.4 Hz, 1H), 8.74-8.66 (m, 2H), 7.98 (d, J=8.8 Hz, 1H), 7.24 (dd, J=8.8, 0.8 Hz, 2H), 6.92 (dd, J=6.8, 2.4 Hz, 2H), 5.03-4.99 (m, 1H), 4.83 (d, J=2.0 Hz, 2H), 4.31-4.27 (m, 1H), 2.90-2.83 (m, 2H), 2.75-2.68 (m, 2H).

Example 37: Synthesis of (1r,3r)-N-((6-fluoroisoquinolin-5-yl)methyl)-3-(3-(trifluoromethoxy)phenoxy)cyclobutan-1-amine, HCl Step 37.1: Synthesis of tert-butyl ((1r,3r)-3-(3-(trifluoromethoxy)phenoxy)cyclobutyl)carbamate

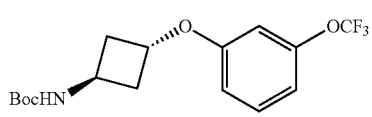 [SMILES: CC(C)(C)OC(=O)N[C@H]1C[C@H](Oc2cccc(OC(F)(F)F)c2)C1]

The title compound was synthesized following the procedure as described in Step 1.2, using tert-butyl ((1s,3s)-3-hydroxycyclobutyl)carbamate (150 mg, 0.80 mmol) and 3-(trifluoromethoxy)phenol [CAS No. 827-99-6] (150 mg, 0.84 mmol). The crude was purified by flash chromatography (8 g SiliCycle column, 0-8% EtOAc in Hexane elution) to provide tert-butyl ((1r,3r)-3-(3-(trifluoromethoxy)phenoxy)cyclobutyl)carbamate (150 mg, 51%). $^1$H NMR (600 MHz, CDCl$_3$) δ 6.80-6.73 (m, 2H), 6.69 (dd, J=7.8, 1.8 Hz, 1H), 6.61 (s, 1H), 4.79-4.75 (m, 1H), 4.32-4.28 (m, 1H), 2.58-2.54 (m, 2H), 2.41-2.37 (m, 2H), 1.44 (s, 9H).

Step 37.2: Synthesis of (1r,3r)-3-(3-(trifluoromethoxy)phenoxy)cyclobutan-1-amine, HCl

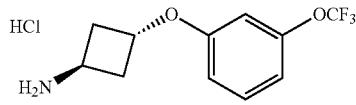

A round bottom flask was charge with tert-butyl ((1r,3r)-3-(3-(trifluoromethoxy)phenoxy)cyclobutyl)carbamate (150 mg, 0.43 mmol) and HCl solution (20% in 1,4-dioxane) (5 mL), and stirred at rt for 1 h. Then the reaction mixture was concentrated in vacuo, the residue was triturated with Et$_2$O, solid collected by filtration and dried to yield (1r,3r)-3-(3-(trifluoromethoxy)phenoxy)cyclobutan-1-amine, HCl (100 mg, 83%). MS (ESI+) [Method 6A]: m/z 247.9 (M+H); Rt 1.31 min.

Step 37.3: Synthesis of (1r,3r)-N-((6-fluoroisoquinolin-5-yl)methyl)-3-(3-(trifluoromethoxy)phenoxy)cyclobutan-1-amine, HCl

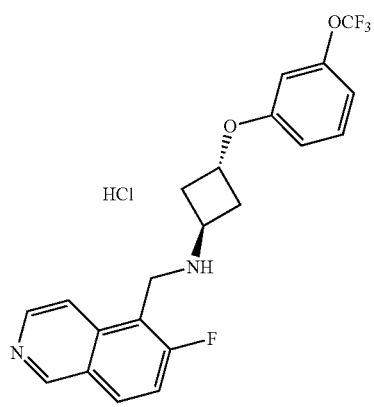 [SMILES: Fc1ccc2cnccc2c1CN[C@H]1C[C@H](Oc2cccc(OC(F)(F)F)c2)C1 ; Cl]

The title compound was synthesized following the procedure as described in Step 1.4, using (1r,3r)-3-(3-(trifluoromethoxy)phenoxy)cyclobutan-1-amine, HCl (70 mg, 0.25 mmol) and 6-fluoroisoquinoline-5-carbaldehyde (Step 3.1, 38 mg, 0.22 mmol). Crude product was purified by prep-HPLC (Column: KINETEX EVO C18 (150 mm×21.2 mm), 5.0μ; Mobile Phase: 0.01% NH$_4$OH in water and acetonitrile). The isolated product was stirred with HCl solution (4M in 1,4-dioxane) (1 mL) at rt for 1 h. Then concentrated in vacuo, and lyophilized to provide (1r,3r)-N-((6-fluoroisoquinolin-5-yl)methyl)-3-(3-(trifluoromethoxy)phenoxy)cyclobutan-1-amine, HCl (40 mg, 37%). MS (ESI+) [Method 6A]: m/z 407.2 (M+H); Rt 1.32 min. $^1$H NMR (400 MHz, CD$_3$OD) 9.91 (s, 1H), 8.86-8.79 (m, 3H), 8.06 (t, J=8.8 Hz, 1H), 8.41 (t, J=8.8 Hz, 1H), 6.93-6.87 (m, 2H), 6.78 (s, 1H), 5.10-5.05 (m, 1H), 4.86 (d, J=2.0 Hz, 2H), 4.33-4.29 (m, 1H), 2.97-2.91 (m, 2H), 2.77-2.71 (m, 2H).

Example 38: Synthesis of (1r,3r)-3-(4-fluoro-3-(trifluoromethoxy)phenoxy)-N-((6-fluoroisoquinolin-5-yl)methyl)cyclobutan-1-amine, HCl

Step 38.1: Synthesis of tert-butyl ((1r,3r)-3-(4-fluoro-3-(trifluoromethoxy)phenoxy)cyclobutyl)carbamate

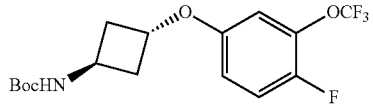 [SMILES: CC(C)(C)OC(=O)N[C@H]1C[C@H](Oc2ccc(F)c(OC(F)(F)F)c2)C1]

The title compound was synthesized following the procedure as described in Step 1.2, using tert-butyl ((1s,3s)-3-hydroxycyclobutyl)carbamate (95 mg, 0.51 mmol) and 4-fluoro-3-(trifluoromethoxy)phenol [CAS No. 886501-26-4] (100 mg, 0.51 mmol). The crude product, tert-butyl ((1r,3r)-3-(4-fluoro-3-(trifluoromethoxy)phenoxy)cyclobutyl)carbamate (170 mg, 91%) was isolated as brown gummy oil. 1H NMR (300 MHz, CDCl3) δ 7.08 (t, J=9.0 Hz, 1H), 6.71-6.61 (m, 2H), 4.74-4.69 (m, 1H), 4.32-4.27 (m, 1H), 2.59-2.50 (m, 2H), 2.42-2.35 (m, 2H), 1.45 (s, 9H).

Step 38.2: Synthesis of (1r,3r)-3-(4-fluoro-3-(trifluoromethoxy)phenoxy)cyclobutan-1-amine, HCl

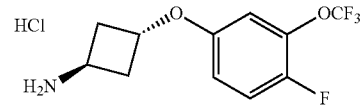

To the crude tert-butyl ((1r,3r)-3-(4-fluoro-3-(trifluoromethoxy)phenoxy)cyclobutyl)carbamate (170 mg, 0.47 mmol), HCl solution (20% in 1,4-dioxane) (5 mL) was added and stirred at rt for 1 h. Then the reaction mixture was concentrated in vacuo, the residue was triturated with Et₂O, filtered and dried to yield (1r,3r)-3-(4-fluoro-3-(trifluoromethoxy)phenoxy)cyclobutan-1-amine, HCl (100 mg, 71%). MS (ESI+) [Method 6A]: m/z 266.1 (M+H); Rt 1.33 min. 1H NMR (400 MHz, DMSO-d6) δ 8.25 (brs, 3H), 7.46 (t, J=9.2 Hz, 1H), 7.02-6.99 (m, 1H), 6.92-6.88 (m, 1H), 5.02-4.97 (m, 1H), 3.85-3.81 (m, 1H), 2.64-2.57 (m, 2H), 2.45-2.38 (m, 2H).

Step 38.3: Synthesis of (1r,3r)-3-(4-fluoro-3-(trifluoromethoxy)phenoxy)-N-((6-fluoroisoquinolin-5-yl)methyl)cyclobutan-1-amine, HCl

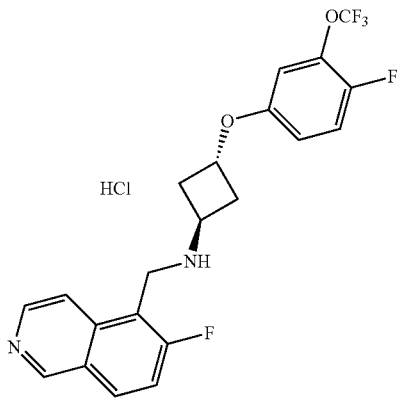 [SMILES: Fc1ccc(O[C@H]2C[C@H](NCc3c(F)ccc4cnccc34)C2)cc1OC(F)(F)F ; Cl]

The title compound was synthesized following the procedure as described in Step 1.4, using (1r,3r)-3-(4-fluoro-3-(trifluoromethoxy)phenoxy)cyclobutan-1-amine, HCl (70 mg, 0.23 mmol) and 6-fluoroisoquinoline-5-carbaldehyde (Step 3.1, 40 mg, 0.23 mmol). The crude product was purified by prep-HPLC (Column: WATERS XBRIDGE C18 (150 mm×21.2 mm), 5.0µ; Mobile Phase: 0.02% NH₄OH in water and acetonitrile). The isolated product was stirred with HCl solution (4M in 1,4-dioxane) (1 mL) at rt for 1 h. Then concentrated in vacuo, and lyophilized to provide (1r,3r)-3-(4-fluoro-3-(trifluoromethoxy)phenoxy)-N-((6-fluoroisoquinolin-5-yl)methyl)cyclobutan-1-amine, HCl (18 mg, 15%). MS (ESI+) [Method 6A]: m/z 425.1 (M+H); Rt 1.33 min. ¹H NMR (400 MHz, CD₃OD) δ 9.88 (s, 1H), 8.80-8.76 (m, 3H), 8.03 (t, J=9.6 Hz, 1H), 7.29 (t, J=9.6 Hz, 1H), 6.93-6.87 (m, 2H), 5.05-4.99 (m, 1H), 4.84 (d, J=2.0 Hz, 2H), 4.32-4.28 (m, 1H), 2.94-2.87 (m, 2H), 2.75-2.68 (m, 2H).

Example 39: Synthesis of (1r,3r)-N-((6-fluoroisoquinolin-5-yl)methyl)-3-((2,2,3,3-tetrafluoro-2,3-dihydrobenzo[b][1,4]dioxin-6-yl)oxy)cyclobutan-1-amine, HCl

Step 39.1: Synthesis of tert-butyl ((1r,3r)-3-((2,2,3,3-tetrafluoro-2,3-dihydrobenzo[b][1,4]dioxin-6-yl)oxy)cyclobutyl)carbamate

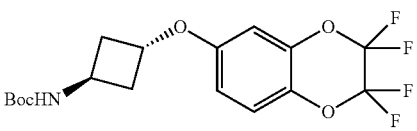 [SMILES: CC(C)(C)OC(=O)N[C@H]1C[C@H](Oc2ccc3c(c2)OC(F)(F)C(F)(F)O3)C1]

The title compound was synthesized following the procedure as described in Step 1.2, using tert-butyl ((1s,3s)-3-hydroxycyclobutyl)carbamate (125 mg, 0.67 mmol) and 2,2,3,3-tetrafluoro-2,3-dihydrobenzo[b][1,4]dioxin-6-ol [CAS No. 103467-50-1] (150 mg, 0.67 mmol). The crude was purified by flash chromatography (12 g SiliCycle column, 0-30% EtOAc in Hexane elution) to provide as tert-butyl ((1r,3r)-3-((2,2,3,3-tetrafluoro-2,3-dihydrobenzo[b][1, 4]dioxin-6-yl)oxy)cyclobutyl)carbamate (200 mg, 76%). $^1$H NMR (300 MHz, CDCl$_3$) δ 7.02 (d, J=9.0 Hz, 2H), 6.60-6.56 (m, 1H), 6.50 (d, J=2.7 Hz, 1H), 4.24-4.69 (m, 1H), 4.32-4.27 (m, 1H), 2.56-2.50 (m, 2H), 2.42-2.37 (m, 2H), 1.45 (s, 9H).

Step 39.2: Synthesis of (1r,3r)-3-((2,2,3,3-tetrafluoro-2,3-dihydrobenzo[b][1,4]dioxin-6-yl)oxy)cyclobutan-1-amine, HCl

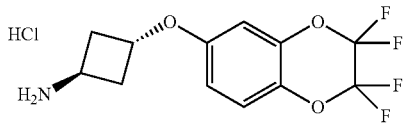 [SMILES: Cl ; N[C@H]1C[C@H](Oc2ccc3c(c2)OC(F)(F)C(F)(F)O3)C1]

The solution of tert-butyl ((1r,3r)-3-((2,2,3,3-tetrafluoro-2,3-dihydrobenzo[b][1,4]dioxin-6-yl)oxy)cyclobutyl)carbamate (200 mg, 0.67 mmol) and HCl solution (20% in 1,4-dioxane) (3 mL) was stirred at rt for 3 h. Then the reaction mixture was concentrated in vacuo, the residue was triturated with Et$_2$O, solid was filtered and dried to yield (1r,3r)-3-((2,2,3,3-tetrafluoro-2,3-dihydrobenzo[b][1,4]dioxin-6-yl)oxy)cyclobutan-1-amine, HCl (150 mg, 68%). MS (ESI+) [Method 6A]: m/z 294.1 (M+H); Rt 1.32 min.

Step 39.3: Synthesis of (1r,3r)-N-((6-fluoroisoquinolin-5-yl)methyl)-3-((2,2,3,3-tetrafluoro-2,3-dihydrobenzo[b][1,4]dioxin-6-yl)oxy)cyclobutan-1-amine, HCl

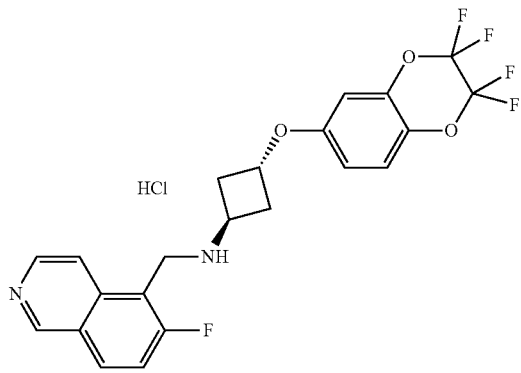 [SMILES: Fc1ccc2cnccc2c1CN[C@H]1C[C@H](Oc2ccc3c(c2)OC(F)(F)C(F)(F)O3)C1 ; Cl]

The title compound was synthesized following the procedure as described in Step 1.4, using (1r,3r)-3-((2,2,3,3-tetrafluoro-2,3-dihydrobenzo[b][1,4]dioxin-6-yl)oxy)cyclobutan-1-amine, HCl (150 mg, 0.45 mmol) and 6-fluoroisoquinoline-5-carbaldehyde (Step 3.1, 80 mg, 0.45 mmol). Crude product was purified by prep-HPLC (Column: ZORBAX (150 mm×21.2 mm), 5.0µ; Mobile Phase: 0.1% HCO$_2$H in water and acetonitrile). The isolated product was stirred with HCl solution (4M in 1,4-dioxane) (2 mL) at rt for 2 h. Then concentrated in vacuo, and lyophilized to provide (1r,3r)-N-((6-fluoroisoquinolin-5-yl)methyl)-3-((2,2,3,3-tetrafluoro-2,3-dihydrobenzo[b][1,4]dioxin-6-yl)oxy)cyclobutan-1-amine, HCl (40 mg, 19%). MS (ESI+) [Method 1A]: m/z 453.3 (M+H); Rt 0.51 min. $^1$H NMR (400 MHz, CD$_3$OD) δ 9.82 (s, 1H), 8.79-8.70 (m, 3H), 7.99 (t, J=9.2 Hz, 1H), 7.23 (t, J=10.0 Hz, 1H), 6.80-6.78 (m, 2H), 5.02-4.97 (m, 1H), 4.82 (d, J=2.0 Hz, 2H), 4.29-4.25 (m, 1H), 2.88-2.83 (m, 2H), 2.73-2.68 (m, 2H).

Example 40: Synthesis of (1r,3r)-3-(3-(1,2-difluoroethyl)-4-fluorophenoxy)-N-((6-fluoroisoquinolin-5-yl)methyl)cyclobutan-1-amine Step 40.1: Synthesis of tert-butyl ((1r,3r)-3-(3-bromo-4-fluorophenoxy)cyclobutyl)carbamate

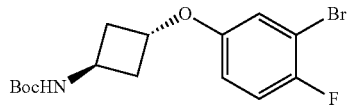 [SMILES: CC(C)(C)OC(=O)N[C@H]1C[C@H](Oc2ccc(F)c(Br)c2)C1]

The title compound was synthesized following the procedure as described in Step 1.2, using tert-butyl ((1s,3s)-3-hydroxycyclobutyl)carbamate (196 mg, 1.05 mmol) and 3-bromo-4-fluorophenol [CAS No. 27407-11-0] (200 mg, 1.05 mmol). The crude product was purified by flash chromatography (4 g SiliCycle column, 0-10% EtOAc in Hexane elution) to provide tert-butyl ((1r,3r)-3-(3-bromo-4-fluorophenoxy)cyclobutyl)carbamate (300 mg, 81%). $^1$H NMR (300 MHz, CDCl$_3$) δ 7.01 (t, J=8.7 Hz, 1H), 6.92 (dd, J=5.7, 3.0 Hz, 1H), 6.70-6.65 (m, 1H), 4.74-4.67 (m, 1H), 4.30-4.25 (m, 1H), 2.57-2.49 (m, 2H), 2.41-2.34 (m, 2H), 1.45 (s, 9H).

Step 40.2: Synthesis of tert-butyl ((1r,3r)-3-(4-fluoro-3-vinylphenoxy)cyclobutyl)carbamate

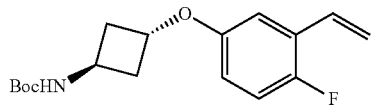 [SMILES: C=Cc1cc(O[C@H]2C[C@H](NC(=O)OC(C)(C)C)C2)ccc1F]

The stirred solution of tert-butyl ((1r,3r)-3-(3-bromo-4-fluorophenoxy)cyclobutyl)carbamate (300 mg, 0.83 mmol), potassium trifluoro(vinyl)borate (223 g, 1.67 mmol) and TEA (0.23 mL, 1.67 mmol) in IPA (10 mL) was degassed with argon for 10 min. Then Pd(dppf)Cl$_2$·CH$_2$Cl$_2$ (54 mg, 0.67 mmol) was added, degassed and heated at 80° C. for 16 h under argon atmosphere. Reaction mixture was cooled to rt, diluted with water and extracted with EtOAc twice. The combined organic portion was washed with brine, dried over anhydrous Na$_2$SO$_4$, filtered and concentrated in vacuo to yield the crude product. The crude was purified by flash chromatography (12 g SiliCycle column, 0-20% EtOAc in Hexane elution) to provide tert-butyl ((1r,3r)-3-(4-fluoro-3-vinylphenoxy)cyclobutyl)carbamate (200 mg, 78%). MS (ESI+) [Method 1A]: m/z 252.2 (M−t-Bu+H); Rt 0.22 min. $^1$H NMR (300 MHz, CDCl$_3$) δ 7.04-6.77 (m, 3H), 6.70-6.58 (m, 1H), 5.65 (dd, J=18.9, 1.2 Hz, 1H), 5.36 (dd, J=11.1, 1.2 Hz, 1H), 4.87-4.68 (M, 1H), 4.31-4.26 (m, 1H), 2.59-2.49 (m, 2H), 2.41-2.33 (m, 2H), 1.45 (s, 9H).

Step 40.3: Synthesis of tert-butyl ((1r,3r)-3-(3-(1,2-dihydroxyethyl)-4-fluorophenoxy)cyclobutyl)carbamate

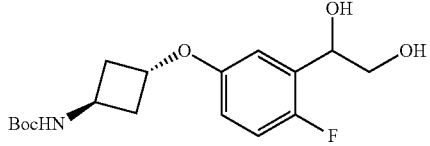 [SMILES: CC(C)(C)OC(=O)N[C@H]1C[C@H](Oc2ccc(F)c(C(O)CO)c2)C1]

To the solution of tert-butyl ((1r,3r)-3-(4-fluoro-3-vinylphenoxy)cyclobutyl)carbamate (200 mg, 0.65 mmol) and N-Methyl morpholine N-oxide monohydride (1.31 g, 9.76 mmol) in acetone-t-BuOH-water (21 mL, 10:10:1), $OsO_4$ (5 mg, 0.02 mmol) was added; and the reaction mixture was stirred at rt for 16 h. The reaction mixture was diluted with water and extracted with EtOAc twice. The combined organic portion was washed with brine, dried over anhydrous $Na_2SO_4$, filtered and concentrated in vacuo. The residue was purified by flash chromatography (24 g SiliCycle column, 0-50% EtOAc in Hexane elution) to provide tert-butyl ((1r,3r)-3-(3-(1,2-dihydroxyethyl)-4-fluorophenoxy)cyclobutyl)carbamate (100 mg, 54%). MS (ESI+) [Method 4A]: m/z 242.0 (M−Boc+H); Rt 1.12 min. $^1$H NMR (400 MHz, DMSO-d6) δ 7.32 (d, J=7.2 Hz, 1H), 7.02 (t, J=9.2 Hz, 1H), 6.89-6.87 (m, 1H), 6.69-6.65 (m, 1H), 5.38 (d, J=4.8 Hz, 1H), 4.82-4.72 (M, 3H), 4.07-4.00 (m, 1H), 3.45-3.36 (m, 2H), 2.35-2.27 (m, 4H), 1.38 (s, 9H).

Step 40.4: Synthesis of tert-butyl ((1r,3r)-3-(3-(1,2-difluoroethyl)-4-fluorophenoxy)cyclobutyl)carbamate

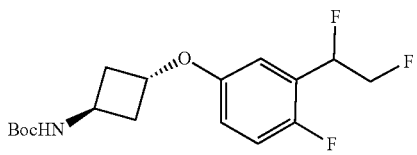 [SMILES: CC(C)(C)OC(=O)N[C@H]1C[C@H](Oc2ccc(F)c(C(F)CF)c2)C1]

To the solution of tert-butyl ((1r,3r)-3-(3-(1,2-dihydroxyethyl)-4-fluorophenoxy)cyclobutyl)carbamate (100 mg, 0.29 mmol) in $CH_2Cl_2$ (4 mL), DAST (0.11 mL, 0.88 mmol) was added drop wise at rt and stirred for 16 h. The reaction mixture was diluted with water and extracted with EtOAc twice. The combined organic portion was washed with brine, dried over anhydrous $Na_2SO_4$, filtered and concentrated in vacuo. The residue was purified by flash chromatography (4 g SiliCycle column, 0-4% EtOAc in Hexane elution) to provide tert-butyl ((1r,3r)-3-(3-(1,2-difluoroethyl)-4-fluorophenoxy)cyclobutyl)carbamate (60 mg, 60%). $^1$H NMR (300 MHz, $CDCl_3$) δ 6.98 (t, J=9.3 Hz, 1H), 6.85-6.82 (m, 1H), 6.76-6.70 (m, 1H), 6.03-5.82 (m, 1H), 4.79-4.69 (m, 2H), 4.67-4.49 (m, 1H), 4.32-4.28 (m, 1H), 2.58-2.50 (m, 2H), 2.42-2.34 (m, 2H), 1.45 (s, 9H).

Step 40.5: Synthesis of (1r,3r)-3-(3-(1,2-difluoroethyl)-4-fluorophenoxy)cyclobutan-1-amine, TFA

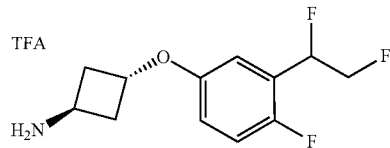 [SMILES: N[C@H]1C[C@H](Oc2ccc(F)c(C(F)CF)c2)C1]

To the solution of tert-butyl ((1r,3r)-3-(3-(1,2-difluoroethyl)-4-fluorophenoxy)cyclobutyl)carbamate (60 mg, 0.17 mmol) in $CH_2Cl_2$ (3 mL), $CF_3CO_2H$ (1 mL) was added at 0° C. and stirred for 4 h under argon. Then the reaction mixture was concentrated in vacuo to afford crude (1r,3r)-3-(3-(1,2-difluoroethyl)-4-fluorophenoxy)cyclobutan-1-amine, TFA (50 mg, 80%). MS (ESI+) [Method 6A]: m/z 246.0 (M+H); Rt 1.29 min.

Step 40.6: Synthesis of (1r,3r)-3-(3-(1,2-difluoroethyl)-4-fluorophenoxy)-N-((6-fluoroisoquinolin-5-yl)methyl)cyclobutan-1-amine

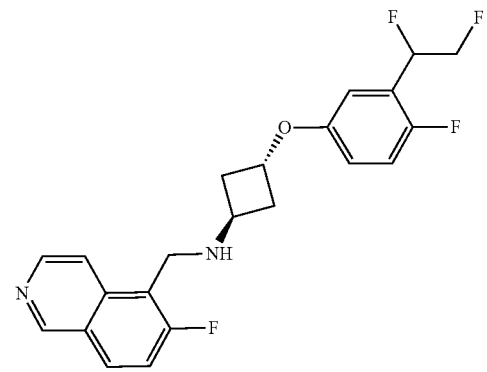 [SMILES: FCC(F)c1cc(O[C@H]2C[C@H](NCc3c(F)ccc4cnccc34)C2)ccc1F]

The title compound was synthesized following the procedure as described in Step 1.4, using (1r,3r)-3-(3-(1,2-difluoroethyl)-4-fluorophenoxy)cyclobutan-1-amine, TFA (50 mg, 0.20 mmol) and 6-fluoroisoquinoline-5-carbaldehyde (Step 3.1, 35 mg, 0.20 mmol). The residue was purified by prep-HPLC (Column: GEMINI NX C18 (150 mm×21.2 mm), 5.0μ; Mobile Phase: 0.02% $NH_4OH$ in water and acetonitrile) to afford (1r,3r)-3-(3-(1,2-difluoroethyl)-4-fluorophenoxy)-N-((6-fluoroisoquinolin-5-yl)methyl)cyclobutan-1-amine (10 mg, 35%). MS (ESI+) [Method 6A]: m/z 405.3 (M+H); Rt 1.32 min. $^1$H NMR (400 MHz, $CD_3OD$) δ 9.24 (d, J=0.8 Hz, 1H), 8.52 (d, J=6.0 Hz, 1H), 8.16 (dd, J=8.4, 5.6 Hz, 1H), 8.11 (d, J=6.0 Hz, 1H), 7.53 (t, J=9.6 Hz, 1H), 7.05 (d, J=8.8 Hz, 1H), 6.88-6.85 (m, 1H), 6.83-6.80 (m, 1H), 6.01-5.83 (m, 1H), 4.82-4.79 (m, 1H), 4.74-4.67 (m, 1H), 4.63-4.55 (m, 1H), 4.19 (d, J=2.0 Hz, 2H), 3.61-3.57 (m, 1H), 2.33 (t, J=6.0 Hz, 4H).

Example 41: Synthesis of (1r,3r)-3-(4-fluoro-3-(fluoromethyl)phenoxy)-N-((6-fluoroisoquinolin-5-yl)methyl)cyclobutan-1-amine, HCl

Step 41.1: Synthesis of 4-fluoro-3-formylphenyl benzoate

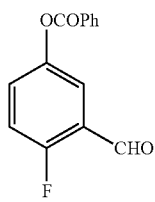

To the solution of 2-fluoro-5-hydroxy benzaldehyde [CAS No. 103438-84-2] (0.75 g, 5.35 mmol), TEA (2.25 mL, 16.05 mmol) and DMAP (65 mg, 0.54 mmol) in anhydrous THF (50 mL), PhCOCl (1.0 g, 5.89 mmol) was added dropwise at rt and stirred for 16 h. The reaction mixture was diluted with EtOAc, then washed with water, aqueous HCl solution (1M) and saturated NaHCO₃ solution. The organic portion was dried over anhydrous Mg₂SO₄, filtered and concentrated in vacuo. The residue was purified by flash chromatography (12 g SiliCycle column, 0-5% EtOAc in Hexane elution) to provide 4-fluoro-3-formylphenyl benzoate (1.0 g, 76%). $^1$H NMR (600 MHz, CDCl₃) δ 10.37 (s, 1H), 8.19 (d, J=7.2 Hz, 2H), 7.72-7.71 (m, 1H), 7.67 (t, J=7.8 Hz, 1H), 7.54-7.52 (m, 2H), 7.49-7.47 (m, 1H), 7.28-7.25 (m, 1H).

Step 41.2: Synthesis of 4-fluoro-3-(hydroxymethyl)phenyl benzoate

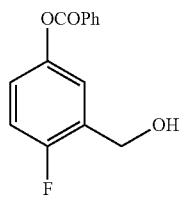

To the solution of 4-fluoro-3-formylphenyl benzoate (600 mg, 2.45 mmol) in THF (50 mL), NaBH₄ (185 mg, 4.90 mmol) and MeOH (3 drops) were added at −78° C. and stirred for 1 h. Then the reaction mixture was diluted with water and extracted with EtOAc twice. The combined organic portion was washed with brine, dried over anhydrous Mg₂SO₄, filtered and concentrated in vacuo. The residue was purified by flash chromatography (12 g SiliCycle column, 0-10% EtOAc in Hexane elution) to provide 4-fluoro-3-(hydroxymethyl)phenyl benzoate (400 mg, 66%). $^1$H NMR (400 MHz, CDCl₃) δ 8.19 (d, J=7.2 Hz, 2H), 7.67-7.63 (m, 1H), 7.52 (t, J=8.0 Hz, 1H), 7.33-7.31 (m, 1H), 7.12-7.09 (m, 2H), 4.79 (s, 2H).

Step 41.3: Synthesis of 4-fluoro-3-(fluoromethyl)phenyl benzoate

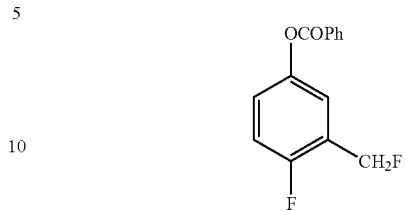

To the solution of 4-fluoro-3-(hydroxymethyl)phenyl benzoate (400 mg, 1.62 mmol) in CH₂Cl₂ (30 mL), DAST (0.52 mL, 3.24 mmol) was added drop wise at 0° C. and stirred at rt for 16 h. The reaction was quenched with saturated NaHCO₃ solution, and extracted with EtOAc 3×'s. The combined organic portion was washed with brine, dried over anhydrous Na₂SO₄, filtered and concentrated in vacuo. The residue was purified by flash chromatography (12 g SiliCycle column, 0-8% EtOAc in Hexane elution) to provide 4-fluoro-3-(fluoromethyl)phenyl benzoate (250 mg, 61%). $^1$H NMR (400 MHz, CDCl₃) δ 8.21-8.17 (m, 2H), 7.68-7.62 (m, 1H), 7.55-7.49 (m, 2H), 7.32-7.29 (m, 1H), 7.25-7.11 (m, 2H), 5.54 (s, 1H), 5.43 (s, 1H).

Step 41.4: Synthesis of 4-fluoro-3-(fluoromethyl)phenol

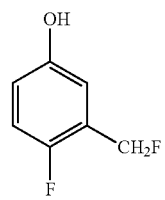

To the solution of 4-fluoro-3-(fluoromethyl)phenyl benzoate (350 mg, 1.41 mmol) in THF-MeOH (17 mL, 15:2 v/v), NaOH solution (3M) (1.4 mL, 4.23 mmol) was added and stirred at rt for 16 h. Reaction mixture was concentrated in vacuo, residue was diluted with water, acidified with HCl solution (2N) and then extracted with EtOAc twice. The combined organic portion was washed with saturated NaHCO₃ solution, dried over anhydrous Na₂SO₄, filtered and concentrated in vacuo to afford crude 4-fluoro-3-(fluoromethyl)phenol (170 mg, 83%). $^1$H NMR (400 MHz, CDCl₃) δ 6.98-6.91 (m, 1H), 6.90-6.87 (m, 1H), 6.82-6.75 (m, 1H), 5.47 (d, J=1.2 Hz, 1H), 5.35 (d, J=1.2 Hz, 1H).

Step 41.5: Synthesis of tert-butyl ((1r,3r)-3-(4-fluoro-3-(fluoromethyl)phenoxy)cyclobutyl)carbamate

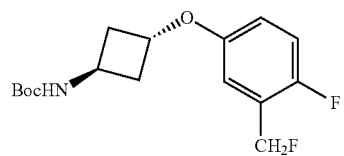

The title compound was synthesized following the procedure as described in Step 1.2, using tert-butyl ((1s,3s)-3-hydroxycyclobutyl)carbamate (221 mg, 1.18 mmol) and 4-fluoro-3-(fluoromethyl)phenol (170 mg, 1.18 mmol). The crude product was purified by flash chromatography (12 g SiliCycle column, 0-8% EtOAc in Hexane elution) to provide tert-butyl ((1r,3r)-3-(4-fluoro-3-(fluoromethyl)phenoxy)cyclobutyl)carbamate (170 mg, 45%). 1H NMR (400 MHz, CDCl3) δ 6.99-6.94 (m, 1H), 6.81-6.77 (m, 1H), 6.74-6.69 (m, 1H), 5.42 (dd, J=47.6, 0.8 Hz, 2H), 4.57-4.52 (m, 1H), 4.32-4.26 (m, 1H), 2.57-2.51 (m, 2H), 2.39-2.33 (m, 2H), 1.45 (s, 9H).

Step 41.6: Synthesis of (1r,3r)-3-(4-fluoro-3-(fluoromethyl)phenoxy)cyclobutan-1-amine, HCl

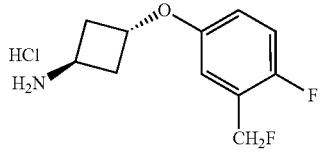

The solution of tert-butyl ((1r,3r)-3-(4-fluoro-3-(fluoromethyl)phenoxy)cyclobutyl)carbamate (170 mg, 0.54 mmol) and HCl solution (4M in 1,4-dioxane) (2 mL) was stirred at rt for 16 h. Then the reaction mixture was concentrated in vacuo, the residue was triturated with Et₂O, solid was filtered and dried to yield (1r,3r)-3-(4-fluoro-3-(fluoromethyl)phenoxy)cyclobutan-1-amine, HCl (140 mg, 100%). ¹H NMR (400 MHz, CD₃OD) δ 7.12-7.05 (m, 1H), 7.08-6.86 (m, 1H), 6.87-6.83 (m, 1H), 5.47 (d, J=0.8 Hz, 1H), 5.35 (d, J=0.8 Hz, 1H), 4.97-4.90 (m, 1H), 4.05-3.45 (m, 1H), 2.70-2.55 (m, 4H).

Step 41.7: Synthesis of (1r,3r)-3-(4-fluoro-3-(fluoromethyl)phenoxy)-N-((6-fluoroisoquinolin-5-yl)methyl)cyclobutan-1-amine, HCl

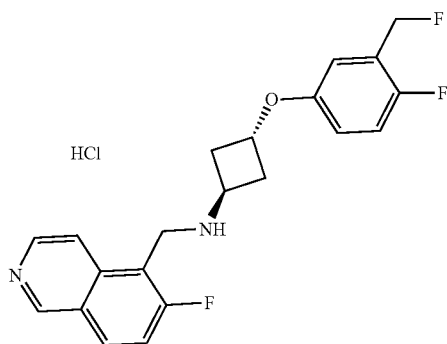 [SMILES: FCc1cc(O[C@H]2C[C@H](NCc3c(F)ccc4cnccc34)C2)ccc1F ; Cl]

The title compound was synthesized following the procedure as described in Step 1.4, using (1r,3r)-3-(4-fluoro-3-(fluoromethyl)phenoxy)cyclobutan-1-amine, HCl (140 mg, 0.54 mmol) and 6-fluoroisoquinoline-5-carbaldehyde (Step 3.1, 94 mg, 0.54 mmol). Crude product was purified by prep-HPLC (Column: KINETEX EVO C18 (150 mm×21.2 mm), 5.0µ; Mobile Phase: 0.1% HCO₂H in water and acetonitrile). The isolated product was stirred with HCl solution (4M in 1,4-dioxane) (2 mL) at rt for 2 h. Then concentrated in vacuo, and lyophilized to afford (1r,3r)-3-(4-fluoro-3-(fluoromethyl)phenoxy)-N-((6-fluoroisoquinolin-5-yl)methyl)cyclobutan-1-amine, HCl (30 mg, 14%). MS (ESI+) [Method 1A]: m/z 373.0 (M+H); Rt 0.17 min. ¹H NMR (400 MHz, CD₃OD) δ 9.85 (s, 1H), 8.80-8.70 (m, 3H), 8.05-7.95 (m, 1H), 7.15-7.05 (m, 1H), 6.95-6.85 (m, 2H), 5.46 (s, 1H), 5.35 (s, 1H), 5.05-4.95 (m, 1H), 4.83 (d, J=1.2 Hz, 2H)), 4.35-4.20 (m, 1H), 2.90-2.85 (m, 2H), 2.22-2.13 (m, 2H).

Example 42: Synthesis of (1r,3r)-3-(4-(2,2-difluorocyclopropyl)phenoxy)-N-((6-fluoroisoquinolin-5-yl)methyl)cyclobutan-1-amine, HCO₂H Step 42.1: Synthesis of 1-methoxy-4-vinylbenzene

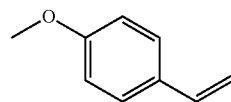

To the solution of methyl triphenylphosphonium bromide (7.87 g, 22.03 mmol) in anhydrous THF (15 mL), n-BuLi (2.5M in THF) (8.8 mL, 22.03 mmol) was added drop wise at 0° C. and stirred for 1 h under argon atmosphere, while temperature was slowly raised to rt. The reaction mixture was cooled to 0° C. and then 4-methoxybenzaldehyde [CAS No. 123-11-5] (2.0 g, 14.69 mmol), dissolved in anhydrous THF (5 mL), was added drop wise. Reaction temperature was allowed to raise slowly to rt while stirring for 3 h. Reaction was quenched with saturated NH₄Cl solution, and extracted with EtOAc twice. The combined organic portion was washed with brine, dried over anhydrous Na₂SO₄, filtered and concentrated in vacuo. The residue was purified by flash chromatography (12 g SiliCycle column, 0-10% EtOAc in Hexane elution) to provide 1-methoxy-4-vinylbenzene (1.4 g, 71%). ¹H NMR (300 MHz, CDCl₃) δ 7.35 (d, J=9 Hz, 2H), 6.87 (d, J=9 Hz, 2H), 6.72-6.62 (m, 1H), 5.61 (d, J=17.4 Hz, 1H), 5.13 (d, J=11.1 Hz, 1H), 3.81 (s, 3H).

Step 42.2: Synthesis of 1-(2,2-difluorocyclopropyl)-4-methoxybenzene

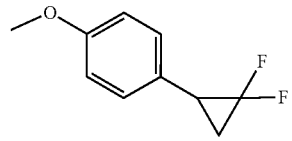

To the stirred solution of 1-methoxy-4-vinylbenzene (500 mg, 3.73 mmol) and NaI (280 mg, 1.86 mmol) in anhydrous THF (5 mL), TMSCF₃ (2.8 mL, 18.63 mmol) was added drop wise at rt, over a period of 10 min. Then the reaction vessel was sealed and stirred at 120° C. (pre-heated oil bath) for 16 h. Reaction was quenched with water, and extracted with EtOAc twice. The combined organic portion was washed with brine, dried over anhydrous Na₂SO₄, filtered and concentrated in vacuo to get crude 1-(2,2-difluorocyclopropyl)-4-methoxybenzene (500 mg, 73%). ¹H NMR (300 MHz, CDCl₃) δ 7.15 (d, J=9 Hz, 2H), 6.85 (d, J=9 Hz, 2H), 3.80 (s, 3H), 2.78-2.60 (m, 1H), 1.82-1.70 (m, 1H), 1.62-1.50 (m, 1H).

Step 42.3: Synthesis of 4-(2,2-difluorocyclopropyl)phenol

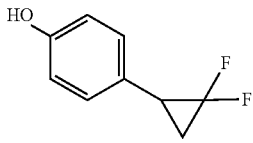 [SMILES: Oc1ccc(C2CC2(F)F)cc1]

To the stirred solution of 1-(2,2-difluorocyclopropyl)-4-methoxybenzene (500 mg, 2.71 mmol) in anhydrous $CH_2Cl_2$ (5 mL), $BBr_3$ (0.31 mL, 3.25 mmol) was added drop wise at 0° C., over a period of 5 min. Then the reaction temperature was allowed to raise to rt, and stirred for 4 h. Reaction was quenched with saturated $NaHCO_3$ solution and extracted with EtOAc twice. The combined organic portion was washed with brine, anhydrous $Na_2SO_4$, filtered and concentrated in vacuo. The residue was purified by flash chromatography (12 g SiliCycle column, 0-20% EtOAc in Hexane elution) to provide 4-(2,2-difluorocyclopropyl)phenol (350 mg, 75%). $^1$H NMR (300 MHz, $CDCl_3$) δ 7.10 (d, J=8.7 Hz, 2H), 6.79 (d, J=8.7 Hz, 2H), 2.78-2.61 (m, 1H), 1.85-1.20 (m, 1H), 1.55-1.49 (m, 1H).

Step 42.4: Synthesis of tert-butyl ((1r,3r)-3-(4-(2,2-difluorocyclopropyl)phenoxy)cyclobutyl)carbamate

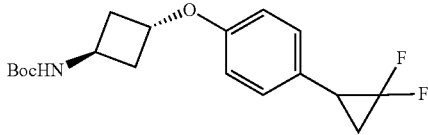 [SMILES: CC(C)(C)OC(=O)N[C@H]1C[C@H](Oc2ccc(C3CC3(F)F)cc2)C1]

The title compound was synthesized following the procedure as described in Step 1.2, using tert-butyl ((1s,3s)-3-hydroxycyclobutyl)carbamate (150 mg, 0.80 mmol) and 4-(2,2-difluorocyclopropyl)phenol (150 mg, 0.88 mmol). The crude product was purified by flash chromatography (12 g SiliCycle column, 0-20% EtOAc in Hexane elution) to provide tert-butyl ((1r,3r)-3-(4-(2,2-difluorocyclopropyl)phenoxy)cyclobutyl)carbamate (180 mg, 54%). $^1$H NMR (300 MHz, $CDCl_3$) δ 7.26-7.15 (m, 2H), 6.83-6.67 (m, 2H), 4.79-4.72 (m, 1H), 4.28 (bs, 1H), 2.74-2.62 (m, 1H), 2.60-2.50 (m, 2H), 2.40-2.30 (m, 2H), 1.83-1.70 (m, 1H), 1.55-1.43 (m, 1H), 1.45 (s, 9H).

Step 42.5: Synthesis of (1r,3r)-3-(4-(2,2-difluorocyclopropyl)phenoxy)cyclobutan-1-amine, HCl

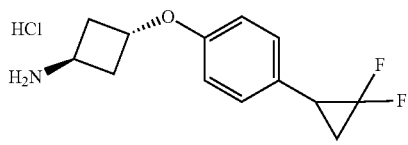 [SMILES: Cl ; N[C@H]1C[C@H](Oc2ccc(C3CC3(F)F)cc2)C1]

The solution of tert-butyl ((1r,3r)-3-(4-(2,2-difluorocyclopropyl)phenoxy)cyclobutyl)carbamate (120 mg, 0.35 mmol) and HCl solution (4M in 1,4-dioxane) (2 mL) was stirred at rt for 16 h. Then the reaction mixture was concentrated in vacuo, the residue was triturated with n-pentane, solid was filtered and dried to yield (1r,3r)-3-(4-(2,2-difluorocyclopropyl)phenoxy)cyclobutan-1-amine, HCl (80 mg, 82%). MS (ESI+) [Method 6A]: m/z 240.1 (M+H); Rt 1.29 min. $^1$H NMR (300 MHz, $CD_3OD$) δ 7.15 (d, J=8.7 Hz, 2H), 6.77 (d, J=8.7 Hz, 2H), 4.95-4.90 (m, 1H), 4.02-3.90 (m, 1H), 2.82-2.70 (m, 1H), 2.63-2.55 (m, 4H), 1.90-1.75 (m, 1H), 1.75-1.55 (m, 1H).

Step 42.6: Synthesis of (1r,3r)-3-(4-(2,2-difluorocyclopropyl)phenoxy)-N-((6-fluoroisoquinolin-5-yl)methyl)cyclobutan-1-amine, $HCO_2H$

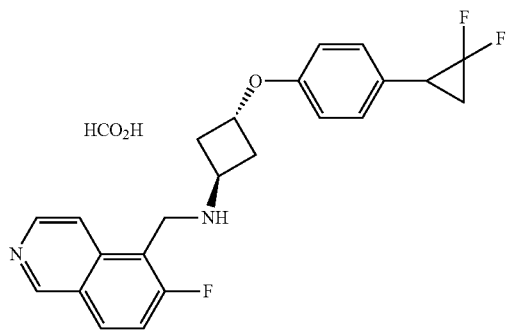 [SMILES: Fc1ccc2cnccc2c1CN[C@H]1C[C@H](Oc2ccc(C3CC3(F)F)cc2)C1 ; "HCO2H"]

The title compound was synthesized following the procedure as described in Step 1.4, using (1r,3r)-3-(4-(2,2-difluorocyclopropyl)phenoxy)cyclobutan-1-amine, HCl (100 mg, 0.36 mmol) and 6-fluoroisoquinoline-5-carbaldehyde (58 mg, 0.33 mmol). Crude product was purified by prep-HPLC (Column: LUNA Phenomenex (250 mm×21.2 mm), 5.0μ; Mobile Phase: 0.1% $HCO_2H$ in water and acetonitrile-MeOH (1:1)) to afford (1r,3r)-3-(4-(2,2-difluorocyclopropyl)phenoxy)-N-((6-fluoroisoquinolin-5-yl)methyl)cyclobutan-1-amine, $HCO_2H$ (30 mg, 23%). MS (ESI+) [Method 1A]: m/z 399.1 (M+H); Rt 0.19 min. $^1$H NMR (400 MHz, $CD_3OD$) δ (400 MHz, $CD_3OD$) δ 9.31 (s, 1H), 8.60 (d, J=6.4 Hz, 1H), 8.34-8.29 (m, 1H), 8.27 (s, 1H), 8.12 (d, J=6.4 Hz, 1H), 7.62 (t, J=9.6 Hz, 1H), 7.15 (d, J=8.4 Hz, 2H), 6.76 (d, J=8.4 Hz, 2H), 4.51 (d, J=2 Hz, 2H), 4.02-3.93 (m, 1H), 2.82-2.70 (m, 1H), 2.62-2.95 (m, 4H), 1.86-1.75 (m, 1H), 1.68-1.55 (m, 1H).

Example 43: Synthesis of (1r,3r)-3-(4-fluoro-3-isopropylphenoxy)-N-(isoquinolin-5-ylmethyl)cyclobutan-1-amine, HCl

Step 43.1: Synthesis of tert-butyl ((1r,3r)-3-(3-bromo-4-fluorophenoxy)cyclobutyl)carbamate

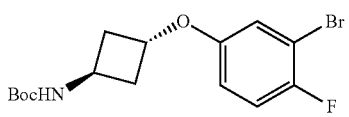 [SMILES: CC(C)(C)OC(=O)N[C@H]1C[C@H](Oc2ccc(F)c(Br)c2)C1]

The title compound was synthesized following the procedure as described in Step 1.2, using tert-butyl ((1s,3s)-3-hydroxycyclobutyl)carbamate (490 mg, 2.62 mmol) and 3-bromo-4-fluorophenol [CAS No. 27407-11-0] (500 mg, 2.62 mmol). The crude was purified by flash chromatography (12 g SiliCycle column, 0-20% EtOAc in Hexane elution) to provide tert-butyl ((1r,3r)-3-(3-bromo-4-fluorophenoxy)cyclobutyl)carbamate (730 mg, 77%). $^1$H NMR (600 MHz, CDCl$_3$) δ 7.02-6.99 (m, 1H), 6.92-6.90 (m, 1H), 6.68-6.66 (m, 1H), 4.80-4.58 (m, 2H), 4.70 (bs, 1H), 2.58-2.49 (m, 2H), 2.40-2.30 (m, 2H), 1.44 (s, 9H).

Step 43.2: Synthesis of tert-butyl ((1r,3r)-3-(4-fluoro-3-(prop-1-en-2-yl)phenoxy)cyclobutyl)carbamate

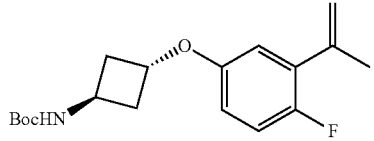 [SMILES: C=C(C)c1cc(O[C@H]2C[C@H](NC(=O)OC(C)(C)C)C2)ccc1F]

The stirred solution of tert-butyl ((1r,3r)-3-(3-bromo-4-fluorophenoxy)cyclobutyl)carbamate (0.63 g, 1.75 mmol), 4,4,5,5-tetramethyl-2-(prop-1-en-2-yl)-1,3,2-dioxaborolane (0.35 g, 2.10 mmol) and K$_3$PO$_4$ (0.91 g, 5.25 mmol) in 1,4-dioxane-water (30 mL, 4:1 v/v) was degassed with argon for 20 min. Then Pd(dppf)Cl$_2$·CH$_2$Cl$_2$ (0.14 g, 0.17 mmol) was added, degassed and heated at 100° C. for 16 h under argon atmosphere. Reaction mixture was cooled to rt, diluted with water and extracted with EtOAc twice. The combined organic portion was washed with brine, dried over anhydrous Na$_2$SO$_4$, filtered and concentrated in vacuo to yield the crude product. The crude product was purified by flash chromatography (12 g SiliCycle column, 0-20% EtOAc in Hexane elution) to provide tert-butyl ((1r,3r)-3-(4-fluoro-3-(prop-1-en-2-yl)phenoxy)cyclobutyl)carbamate (0.6 g, 92%). MS (ESI+) [Method 1A]: m/z 266.1 (M−56+H); Rt 1.68 min. 1H NMR (600 MHz, CDCl3) δ 6.92 (t, J=9.6 Hz, 1H), 6.69-6.68 (m, 1H), 6.60-6.58 (m, 1H), 5.21 (s, 2H), 4.75-4.72 (m, 1H), 4.31-4.26 (m, 1H), 2.57-2.52 (m, 2H), 2.38-2.34 (m, 2H), 2.11 (s, 3H), 1.45 (s, 9H).

Step 43.3: Synthesis of tert-butyl ((1r,3r)-3-(4-fluoro-3-isopropylphenoxy)cyclobutyl)carbamate

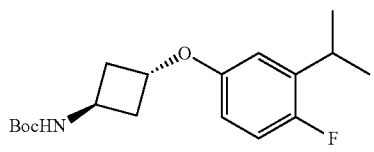 [SMILES: CC(C)c1cc(O[C@H]2C[C@H](NC(=O)OC(C)(C)C)C2)ccc1F]

To the solution of tert-butyl ((1r,3r)-3-(4-fluoro-3-(prop-1-en-2-yl)phenoxy)cyclobutyl)carbamate (0.6 g, 2.02 mmol) in EtOH (10 mL), Pd/C (10% w/w) (0.2 g) was added under N$_2$. Reaction mixture was degassed, connected with H$_2$ balloon and stirred at rt for 4 h. Reaction mixture was filtered through celite bed, the bed was washed with EtOH. The combined filtrate was concentrated in vacuo to afford tert-butyl ((1r,3r)-3-(4-fluoro-3-isopropylphenoxy)cyclobutyl)carbamate (0.55 g, 84%). $^1$H NMR (600 MHz, CDCl3) δ 6.87 (t, J=9.0 Hz, 1H), 6.67-6.65 (m, 1H), 6.49-6.46 (m, 1H), 4.76-4.72 (m, 1H), 4.31-4.27 (m, 1H), 3.20-3.15 (m, 1H), 2.57-2.52 (m, 2H), 2.38-2.32 (m, 2H), 1.45 (s, 9H), 1.22 (s, 6H).

Step 43.4: Synthesis of (1r,3r)-3-(4-fluoro-3-isopropylphenoxy)cyclobutan-1-amine, HCl

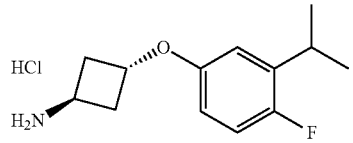 [SMILES: Cl ; CC(C)c1cc(O[C@H]2C[C@H](N)C2)ccc1F]

The solution of tert-butyl ((1r,3r)-3-(4-fluoro-3-isopropylphenoxy)cyclobutyl)carbamate (0.55 g, 0.17 mmol) and HCl solution (4M in 1,4-dioxane) (5 mL) was stirred at rt for 16 h. Then the reaction mixture was concentrated in vacuo, the residue was triturated with Et$_2$O, solid was filtered and dried to yield (1r,3r)-3-(4-fluoro-3-isopropylphenoxy)cyclobutan-1-amine, HCl (0.33 g, 74%). $^1$H NMR (600 MHz, DMSO-d6) δ 8.21 9 (bs, 3H), 7.09-7.00 (m, 1H), 6.75-6.71 (m, 1H), 6.65-6.55 (m, 1H), 5.00-4.90 (m, 1H), 3.88-3.78 (m, 1H), 3.15-3.05 (m, 1H), 2.60-2.55 (m, 2H), 2.45-2.35 (m, 2H), 1.22-1.15 (m, 6H).

Step 43.5: Synthesis of (1r,3r)-3-(4-fluoro-3-isopropylphenoxy)-N-(isoquinolin-5-ylmethyl)cyclobutan-1-amine, HCl

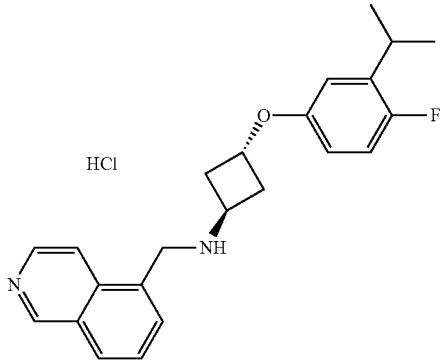 [SMILES: CC(C)c1cc(O[C@H]2C[C@H](NCc3cccc4cnccc34)C2)ccc1F ; Cl]

The title compound was synthesized following the procedure as described in Step 1.4, using (1r,3r)-3-(4-fluoro-3-isopropylphenoxy)cyclobutan-1-amine, HCl (100 mg, 0.39 mmol) and isoquinoline-5-carbaldehyde (54 mg, 0.35 mmol). Crude product was purified by prep-HPLC (Column: KINETEX EVO C18 (150 mm×21.2 mm), 5.0μ; Mobile Phase: 0.02% NH$_4$OH in water and acetonitrile). The isolated product was stirred with HCl solution (4M in 1,4-dioxane) (2 mL) at rt for 1 h. Then concentrated in vacuo, and the residue was triturated with Et$_2$O, and solid was filtered and dried to afford (1r,3r)-3-(4-fluoro-3-isopropylphenoxy)-N-(isoquinolin-5-ylmethyl)cyclobutan-1-amine, HCl (50 mg, 35%). MS (ESI+) [Method 1A]: m/z 364.9 (M+H); Rt 1.35 min. $^1$H NMR (300 MHz, CD$_3$OD) δ 9.85 (s, 1H), 8.78-8.70 (m, 2H), 8.61 (d, J=8.4 Hz, 1H), 8.41 (d, J=6.9 Hz, 1H), 8.14-8.09 (m, 1H), 6.94 (t, J=8.7 Hz, 1H), 6.80-6.70 (m, 1H), 6.65-6.55 (m, 1H), 5.00-4.99 (m, 1H), 4.83 (m, 2H), 4.30-4.20 (m, 1H), 3.25-3.10 (m, 1H), 2.90-2.80 (m, 2H), 2.70-2.60 (m, 2H), 1.30-1.20 (m, 6H).

Example 44: Synthesis of (1r,3r)-N-((6-fluoroisoquinolin-5-yl)methyl)-3-(3-(2-(trifluoromethyl)oxetan-2-yl)phenoxy)cyclobutan-1-amine Step 44.1: Synthesis of 3-(benzyloxy)benzaldehyde

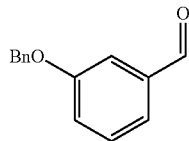

To the solution of 3-hydroxybenzaldehyde [CAS No. 100-83-4] (2.0 g, 16.37 mmol) and $K_2CO_3$ (4.52 g, 24.56 mmol) in anhydrous DMF (20 mL), BnBr (2.91 mL, 24.56 mmol) was added drop wise at rt and stirred for 16 h. The reaction mixture was diluted with water and extracted with EtOAc twice. The combined organic portion was washed with brine, dried over anhydrous $Na_2SO_4$, filtered and concentrated in vacuo. The residue was purified by flash chromatography (24 g SiliCycle column, 0-10% EtOAc in Hexane elution) to provide 3-(benzyloxy)benzaldehyde (3.0 g, 86%). $^1$H NMR (600 MHz, CDCl$_3$) δ 9.98 (s, 1H), 7.50-7.35 (m, 8H), 7.30-7.25 (m, 1H), 5.13 (s, 2H).

Step 44.2: Synthesis of 1-(3-(benzyloxy)phenyl)-2,2,2-trifluoroethan-1-ol

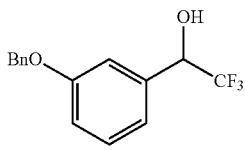

To the stirred solution of 3-(benzyloxy)benzaldehyde (2.5 g, 11.77 mmol) in anhydrous DMF (30 mL), TMSCF$_3$ (2.08 mL, 14.13 mmol) was added drop wise at rt. Then $K_2CO_3$ (0.32 g, 2.36 mmol) was added and stirred at rt for 4 h under $N_2$. The reaction mixture was diluted with water and extracted with EtOAc twice. The combined organic portion was washed with brine, dried over anhydrous $Na_2SO_4$, filtered and concentrated in vacuo. The residue was purified by flash chromatography (12 g SiliCycle column, 0-10% EtOAc in Hexane elution) to afford 1-(3-(benzyloxy)phenyl)-2,2,2-trifluoroethan-1-ol (3.0 g, 90%). $^1$H NMR (600 MHz, CDCl$_3$) δ 7.46-7.44 (m, 2H), 7.40 (t, J=7.8 Hz, 2H), 7.36-7.32 (m, 2H), 7.13 (s, 1H), 7.07 (d, J=7.8 Hz, 1H), 7.03 (dd, J=8.4, 1.8 Hz, 1H), 5.09 (s, 2H), 5.02-4.97 (m, 1H), 2.57 (d, J=4.2 Hz, 1H).

Step 44.3: Synthesis of 1-(3-(benzyloxy)phenyl)-2,2,2-trifluoroethan-1-one

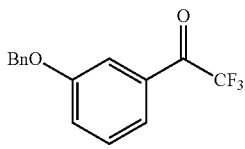

To the solution of 1-(3-(benzyloxy)phenyl)-2,2,2-trifluoroethan-1-ol (1.0 g, 3.54 mmol) in anhydrous $CH_2Cl_2$ (20 mL), Dess-Martin periodinane (1.95 g, 4.61 mmol) was added portion wise at 0° C. and stirred at rt for 16 h. The reaction was quenched with saturated NaHCO$_3$ solution and extracted with $CH_2Cl_2$ twice. The combined organic portion was washed successively with saturated NaHCO$_3$ solution, water and brine, dried over anhydrous $Na_2SO_4$, filtered and concentrated in vacuo. The residue was purified by flash chromatography (12 g SiliCycle column, 0-10% EtOAc in Hexane elution) to provide 1-(3-(benzyloxy)phenyl)-2,2,2-trifluoroethan-1-one (0.8 g, 80%). $^1$H NMR (300 MHz, CDCl$_3$) δ 7.70-7.60 (m, 2H), 7.50-7.30 (m, 7H), 5.13 (s, 2H).

Step 44.4: Synthesis of 2-(3-(benzyloxy)phenyl)-2-(trifluoromethyl)oxetane

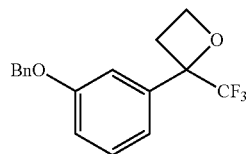

To the solution of KOt-Bu (1.2 g, 1.07 mmol) in anhydrous DMSO (10 mL), trimethylsulfoxonium iodide (2.35 g, 10.70 mmol) was added and stirred at rt for 10 min. Then 1-(3-(benzyloxy)phenyl)-2,2,2-trifluoroethan-1-one (1.0 g, 3.57 mmol), dissolved in DMSO (5 mL), was added drop wise at rt and stirred for 16 h. Reaction was quenched with water and extracted with EtOAc twice. The combined organic portion was washed successively with water and brine, dried over anhydrous $Na_2SO_4$, filtered and concentrated in vacuo. The residue was purified by flash chromatography (12 g SiliCycle column, 0-6% EtOAc in Hexane elution) to provide 2-(3-(benzyloxy)phenyl)-2-(trifluoromethyl)oxetane (0.5 g, 45%). $^1$H NMR (600 MHz, CDCl$_3$) δ 7.45 (d, J=7.2 Hz, 2H), 7.40 (t, J=19.8 Hz, 2H), 7.34 (t, J=8.4 Hz, 2H), 7.08 (s, 1H), 7.00 (t, J=7.2 Hz, 2H), 5.07 (s, 2H), 4.84-4.80 (m, 1H), 4.62-4.57 (m, 1H), 3.28-3.20 (m, 1H), 2.94-2.87 (m, 1H).

Step 44.5: Synthesis of 3-(2-(trifluoromethyl)oxetan-2-yl)phenol

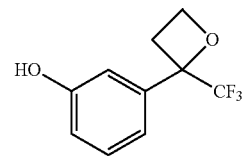 [SMILES: Oc1cccc(C2(C(F)(F)F)CCO2)c1]

To the solution of 2-(3-(benzyloxy)phenyl)-2-(trifluoromethyl)oxetane (450 mg, 1.46 mmol) in EtOAc (3 mL), Pd/C (10% w/w) (10 mg) was added under argon. Reaction mixture was degassed, connected with $H_2$ balloon and stirred at rt for 2 h. Reaction mixture was filtered through celite bed, the bed was washed with EtOAc. The combined filtrate was concentrated in vacuo to afford crude 3-(2-(trifluoromethyl)oxetan-2-yl)phenol (300 mg, 94%). $^1$H NMR (300 MHz, CDCl$_3$) δ 7.30-7.26 (m, 1H), 7.00-6.90 (m, 2H), 6.88-6.70 (m, 1H), 5.10 (bs, 1H), 4.85-4.78 (m, 1H), 4.63-4.56 (m, 1H), 3.28-3.19 (m, 1H), 2.44-2.85 (m, 1H).

Step 44.6: Synthesis of tert-butyl ((1r,3r)-3-(3-(2-(trifluoromethyl)oxetan-2-yl)phenoxy)cyclobutyl)carbamate

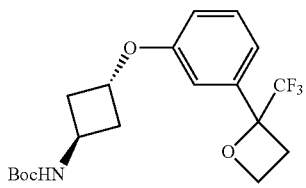 [SMILES: CC(C)(C)OC(=O)N[C@H]1C[C@H](Oc2cccc(C3(C(F)(F)F)CCO3)c2)C1]

The title compound was synthesized following the procedure as described in Step 1.2, using tert-butyl ((1s,3s)-3-hydroxycyclobutyl)carbamate (200 mg, 1.07 mmol) and 3-(2-(trifluoromethyl)oxetan-2-yl)phenol (230 mg, 1.07 mmol). The crude was purified by flash chromatography (12 g SiliCycle column, 0-25% EtOAc in Hexane elution) to provide tert-butyl ((1r,3r)-3-(3-(2-(trifluoromethyl)oxetan-2-yl)phenoxy)cyclobutyl)carbamate (200 mg, 48%). $^1$H NMR (300 MHz, CDCl3) δ 7.33-7.27 (m, 1H), 6.98-6.93 (m, 1H), 6.87-6.84 (m, 1H), 6.78-6.75 (m, 1H), 4.85-4.78 (m, 2H), 4.62-4.55 (m, 1H), 4.32-4.27 (m, 1H), 3.28-3.19 (m, 1H), 2.94-2.85 (m, 1H), 2.61-2.53 (m, 2H), 2.41-2.35 (m, 2H), 1.45 (s, 9H).

Step 44.7: Synthesis of (1r,3r)-3-(3-(2-(trifluoromethyl)oxetan-2-yl)phenoxy)cyclobutan-1-amine

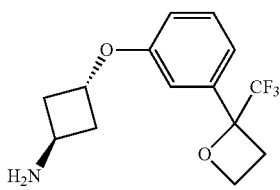 [SMILES: N[C@H]1C[C@H](Oc2cccc(C3(C(F)(F)F)CCO3)c2)C1]

To the solution of tert-butyl ((1r,3r)-3-(3-(2-(trifluoromethyl)oxetan-2-yl)phenoxy)cyclobutyl)carbamate (180 mg, 0.46 mmol) in CH$_2$Cl$_2$ (5 mL), TFA (1.0 mL) was added at 0° C. and stirred for 4 h. Solvent was removed by N$_2$ flush. Then the residue was basified with saturated NaHCO$_3$ solution and extracted with CH$_2$Cl$_2$ twice. The combined organic portion was washed successively with water and brine, dried over anhydrous Na$_2$SO$_4$, filtered and concentrated in vacuo to afford crude (1r,3r)-3-(3-(2-(trifluoromethyl)oxetan-2-yl)phenoxy)cyclobutan-1-amine (120 mg, 90%). MS (ESI+) [Method 6A]: m/z 288.1 (M+H); Rt 1.29 min.

Step 44.8: Synthesis of (1r,3r)-N-((6-fluoroisoquinolin-5-yl)methyl)-3-(3-(2-(trifluoromethyl)oxetan-2-yl)phenoxy)cyclobutan-1-amine

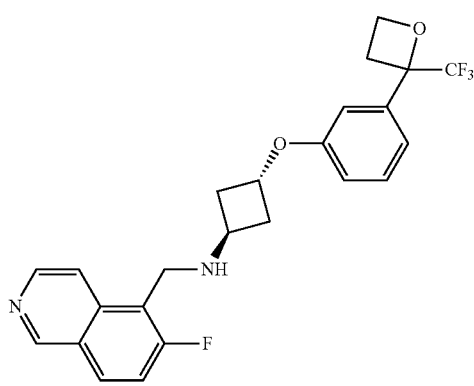 [SMILES: Fc1ccc2cnccc2c1CN[C@H]1C[C@H](Oc2cccc(C3(C(F)(F)F)CCO3)c2)C1]

The title compound was synthesized following the procedure as described in Step 1.4, using (1r,3r)-3-(3-(2-(trifluoromethyl)oxetan-2-yl)phenoxy)cyclobutan-1-amine (80 mg, 0.28 mmol) and 6-fluoroisoquinoline-5-carbaldehyde (44 mg, 0.25 mmol). Crude product was purified by prep-HPLC (Column: XBRIDGE C18 (150 mm×19 mm), 5.0µ; Mobile Phase: 0.01% NH$_4$OH in water and acetonitrile) to afford (1r,3r)-N-((6-fluoroisoquinolin-5-yl)methyl)-3-(3-(2-(trifluoromethyl)oxetan-2-yl)phenoxy)cyclobutan-1-amine (32 mg, 25%). MS (ESI+) [Method 1A]: m/z 447.3 (M+H); Rt 0.23 min. $^1$H NMR (400 MHz, CD$_3$OD) δ 9.27 (s, 1H), 8.60-8.53 (m, 1H), 8.43 (bs, 1H), 8.24-8.20 (m, 1H), 8.12 (d, J=6 Hz, 1H), 7.57 (t, J=9.2 Hz, 1H), 7.32 (t, J=8.0 Hz, 1H), 6.97 (d, J=8.0 Hz, 1H), 6.88-6.80 (m, 2H), 4.82-4.72 (m, 1H), 4.62-4.55 (m, 1H), 4.34 (m, 2H), 3.82-3.73 (m, 1H), 3.33-3.23 (m, 1H), 2.85-2.75 (m, 1H), 2.54 (t, J=5.0 Hz, 4H).

Example 45: Synthesis of (5-((((1r,3r)-3-(4-(tert-butyl)-3,5-difluorophenoxy)cyclobutyl)amino)methyl)-6-fluoroisoquinolin-8-yl)methanol Step 45.1: Synthesis of tert-butyl ((1r,3r)-3-(4-(tert-butyl)-3,5-difluorophenoxy)cyclobutyl)carbamate

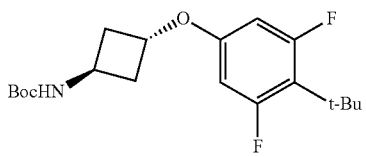 [SMILES: CC(C)(C)OC(=O)N[C@H]1C[C@H](Oc2cc(F)c(C(C)(C)C)c(F)c2)C1]

The title compound was synthesized following the procedure as described in Step 1.2, using tert-butyl ((1s,3s)-3-hydroxycyclobutyl)carbamate (0.18 g, 0.97 mmol) and 4-(tert-butyl)-3,5-difluorophenol [CAS No. 910486-78-1] (0.2 g, 1.07 mmol). Crude was purified by flash chromatography (12 g SiliCycle column, 0-25% EtOAc in Hexane elution) to provide tert-butyl ((1r,3r)-3-(4-(tert-butyl)-3,5-difluorophenoxy)cyclobutyl)carbamate (0.3 g, 78%). $^1$H NMR (300 MHz, CDCl$_3$) δ 6.24 (s, 1H), 6.20 (s, 1H), 4.72-4.66 (m, 1H), 4.16-4.12 (m, 1H), 2.56-2.49 (m, 2H), 2.40-2.35 (m, 2H), 1.45 (s, 9H), 1.41 (s, 9H).

Step 45.2: Synthesis of (1r,3r)-3-(4-(tert-butyl)-3,5-difluorophenoxy)cyclobutan-1-amine, HCl

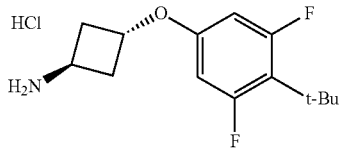 [SMILES: Cl ; CC(C)(C)c1c(F)cc(O[C@H]2C[C@H](N)C2)cc1F]

A round bottom flask was charged with tert-butyl ((1r,3r)-3-(4-(tert-butyl)-3,5-difluorophenoxy)cyclobutyl)carbamate (0.3 g, 0.84 mmol) and HCl solution (4M in 1,4-dioxane) (2 mL), and stirred at rt for 4 h. Then the reaction mixture was concentrated in vacuo. The residue was triturated with Et$_2$O, solid was filtered and dried to yield (1r,3r)-3-(4-(tert-butyl)-3,5-difluorophenoxy)cyclobutan-1-amine, HCl (0.22 g, 89%). MS (ESI+) [Method 1A]: m/z 256.2 (M+H); Rt 1.33 min. $^1$H NMR (300 MHz, DMSO-d6) δ 6.38 (s, 1H), 6.35 (s, 1H), 4.92-4.87 (m, 1H), 3.99-3.95 (m, 1H), 2.64-2.58 (m, 4H), 1.42 (s, 9H).

Step 45.3: Synthesis of (1r,3r)-3-(4-(tert-butyl)-3,5-difluorophenoxy)-N-((8-(((tert-butyldimethylsilyl)oxy)methyl)-6-fluoroisoquinolin-5-yl)methyl)cyclobutan-1-amine

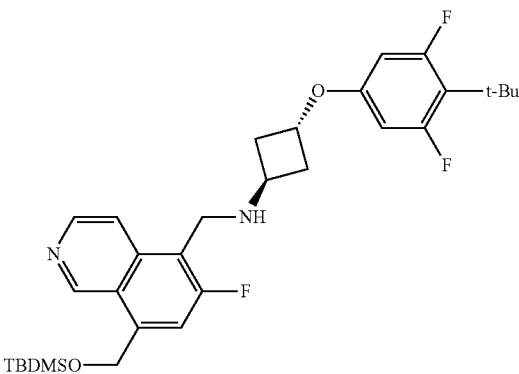 [SMILES: CC(C)(C)c1c(F)cc(O[C@H]2C[C@H](NCc3c(F)cc(CO[Si](C)(C)C(C)(C)C)c4cnccc34)C2)cc1F]

The title compound was synthesized following the procedure as described in Step 1.4, using (1r,3r)-3-(4-(tert-butyl)-3,5-difluorophenoxy)cyclobutan-1-amine, HCl (200 mg, 0.69 mmol) and 8-(((tert-butyldimethylsilyl)oxy)methyl)-6-fluoroisoquinoline-5-carbaldehyde (Step 6.8, 320 mg, 1.03 mmol). The crude was purified by flash chromatography (12 g SiliCycle column, 0-5% MeOH in CH$_2$Cl$_2$ elution) to provide (1r,3r)-3-(4-(tert-butyl)-3,5-difluorophenoxy)-N-((8-(((tert-butyldimethylsilyl)oxy)methyl)-6-fluoroisoquinolin-5-yl)methyl)cyclobutan-1-amine (250 mg, 65%). MS (ESI+) [Method 6A]: m/z 559.2 (M+H); Rt 1.51 min.

Step 45.4: Synthesis of (5-((((1r,3r)-3-(4-(tert-butyl)-3,5-difluorophenoxy)cyclobutyl)amino)methyl)-6-fluoroisoquinolin-8-yl)methanol

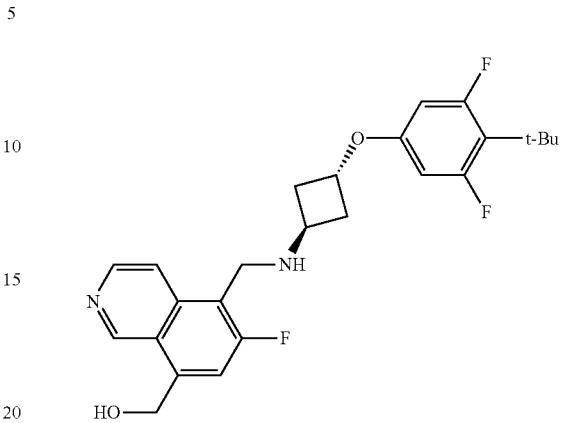

Deprotection was carried out according to Step 6.11. The residue was purified by prep-HPLC (Column: XBRIDGE C18 (150 mm×21.2 mm), 5.0μ; Mobile Phase: 0.02% NH$_4$OH in water and acetonitrile) to afford (5-((((1r,3r)-3-(4-(tert-butyl)-3,5-difluorophenoxy)cyclobutyl)amino)methyl)-6-fluoroisoquinolin-8-yl)methanol (60 mg, 30%). MS (ESI+) [Method 6A]: m/z 445.2 (M+H); Rt 1.35 min. $^1$H NMR (400 MHz, CD$_3$OD) δ 9.45 (s, 1H), 8.55 (d, J=6 Hz, 1H), 8.12 (d, J=6 Hz, 1H), 7.56 (d, J=10.4 Hz, 1H), 6.31 (d, J=13.2 Hz, 2H), 5.18 (s, 2H), 4.80-4.70 (m, 1H), 4.16 (d, J=1.6 Hz, 2H), 3.60-3.50 (m, 1H), 2.38-2.28 (m, 4H), 1.41 (s, 9H).

Example 46: Synthesis of (1r,3r)-3-((2,2-difluorobenzo[d][1,3]dioxol-5-yl)oxy)-N-((6-fluoroisoquinolin-5-yl)methyl)cyclobutan-1-amine, HCl

Step 46.1: Synthesis of 2,2-difluorobenzo[d][1,3]dioxol-5-ol

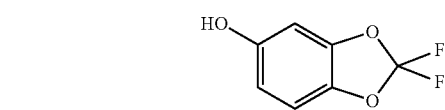 [SMILES: Oc1ccc2c(c1)OC(F)(F)O2]

The sealed tube charged with 5-bromo-2,2-difluorobenzo[d][1,3]dioxole [CAS No. 33070-32-5] (1.0 g, 4.22 mmol), KOH (474 mg, 8.44 mmol), t-BuXPHOS (25 mg, 0.05 mmol) and 1,4-dioxane-water (6 mL, 1:1 v/v), was purged with N$_2$ for 10 min. Then Pd$_2$(dba)$_3$ (194 mg, 0.21 mmol) was added, purged with N$_2$, sealed tube was closed and stirred at 100° C. for 16 h. Reaction was cooled to rt, quenched with HCl solution (1M) and extracted with EtOAc twice. The combined filtrate was concentrated in vacuo. The residue was purified by flash chromatography (12 g SiliCycle column, 0-20% EtOAc in Hexane elution) to afford 2,2-difluorobenzo[d][1,3]dioxol-5-ol (0.41 g, 55%). MS (ESI+) [Method 6A]: m/z 173.1 (M+H); Rt 1.49 min. $^1$H NMR (400 MHz, CDCl$_3$) δ 6.88 (d, J=8.4 Hz, 1H), 6.62 (s, 1H), 6.49-6.46 (m, 1H).

Step 46.2: Synthesis of tert-butyl ((1r,3r)-3-((2,2-difluorobenzo[d][1,3]dioxol-5-yl)oxy)cyclobutyl)carbamate

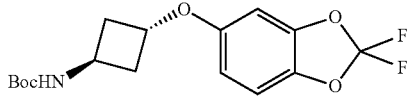 [SMILES: CC(C)(C)OC(=O)N[C@H]1C[C@H](Oc2ccc3c(c2)OC(F)(F)O3)C1]

The title compound was synthesized following the procedure as described in Step 1.2, using tert-butyl ((1s,3s)-3-hydroxycyclobutyl)carbamate (0.40 g, 2.14 mmol) and 2,2-difluorobenzo[d][1,3]dioxol-5-ol (0.41 g, 2.35 mmol). Crude product was purified by flash chromatography (12 g SiliCycle column, 0-30% EtOAc in Hexane elution) to provide tert-butyl ((1r,3r)-3-((2,2-difluorobenzo[d][1,3]dioxol-5-yl)oxy)cyclobutyl)carbamate (0.45 g, 61%). $^1$H NMR (300 MHz, CDCl$_3$) δ 6.91 (d, J=8.4 Hz, 1H), 6.55 (d, J=2.4 Hz, 1H), 6.41 (dd, J=8.4, 2.1 Hz, 1H), 4.74-4.67 (m, 1H), 4.31-4.26 (m, 1H), 2.58-2.50 (m, 2H), 2.40-2.34 (m, 2H), 1.45 (s, 9H).

Step 46.3: Synthesis of (1r,3r)-3-((2,2-difluorobenzo[d][1,3]dioxol-5-yl)oxy)cyclobutan-1-amine, HCl

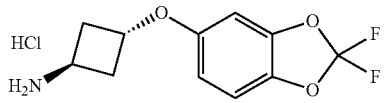 [SMILES: Cl ; N[C@H]1C[C@H](Oc2ccc3c(c2)OC(F)(F)O3)C1]

A solution of tert-butyl ((1r,3r)-3-((2,2-difluorobenzo[d][1,3]dioxol-5-yl)oxy)cyclobutyl)carbamate (110 mg, 0.32 mmol) and HCl solution (4M in 1,4-dioxane) (2 mL) was stirred at rt for 1 h. Then the reaction mixture was concentrated in vacuo. The residue was triturated with Et$_2$O, solid was filtered and dried to yield (1r,3r)-3-((2,2-difluorobenzo[d][1,3]dioxol-5-yl)oxy)cyclobutan-1-amine, HCl (90 mg, 99%). MS (ESI+) [Method 6A]: m/z 244.1 (M+H); Rt 1.29 min. $^1$H NMR (300 MHz, DMSO-d6) δ 8.16 (s, 3H), 7.33 (d, J=8.7 Hz, 1H), 7.00 (d, J=2.7 Hz, 1H), 6.61 (dd, J=9.3, 2.7 Hz, 1H), 4.95-4.91 (m, 1H), 3.85-3.81 (m, 1H), 2.61-2.55 (m, 2H), 2.45-2.38 (m, 2H).

Step 46.4: Synthesis of (1r,3r)-3-((2,2-difluorobenzo[d][1,3]dioxol-5-yl)oxy)-N-((6-fluoroisoquinolin-5-yl)methyl)cyclobutan-1-amine, HCl

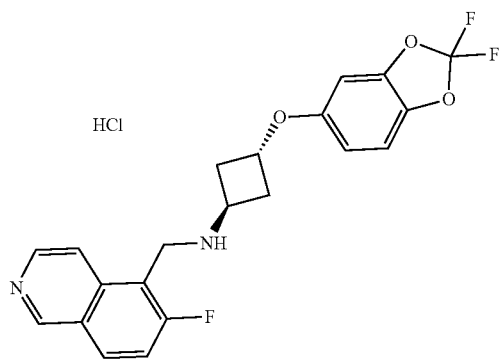 [SMILES: Fc1ccc2cnccc2c1CN[C@H]1C[C@H](Oc2ccc3c(c2)OC(F)(F)O3)C1 ; Cl]

The title compound was synthesized following the procedure as described in Step 1.4, using (1r,3r)-3-((2,2-difluorobenzo[d][1,3]dioxol-5-yl)oxy)cyclobutan-1-amine, HCl (85 mg, 0.31 mmol) and 6-fluoroisoquinoline-5-carbaldehyde (Step 3.1, 175 mg, 0.28 mmol). Crude product was purified by prep-HPLC (Column: LUNA Phenomenex (250 mm×21.2 mm), 5.0μ; Mobile Phase: 0.1% HCO$_2$H in water and acetonitrile). The isolated product was stirred with HCl solution (4M in 1,4-dioxane) (2 mL) at rt for 1 h. Then concentrated in vacuo to afford (1r,3r)-3-((2,2-difluorobenzo[d][1,3]dioxol-5-yl)oxy)-N-((6-fluoroisoquinolin-5-yl)methyl)cyclobutan-1-amine, HCl (30 mg, 22%). MS (ESI+) [Method 1A]: m/z 403.1 (M+H); Rt 1.32 min. $^1$H NMR (400 MHz, CD$_3$OD) δ 9.85 (s, 1H), 8.80-8.70 (m, 3H), 8.01 (t J=8.4 Hz, 1H), 7.10 (d, J=8.8 Hz, 1H), 6.81 (d, J=2.8 Hz, 1H), 6.60 (d, J=8.4 Hz, 1H), 5.00-4.98 (m, 1H), 4.82 (d, J=2.0 Hz, 2H), 4.30-4.20 (m, 1H), 2.89-2.82 (m, 2H), 2.71-2.64 (m, 2H).

Example 47: Synthesis of (5-((((1r,3r)-3-((2,2-difluorobenzo[d][1,3]dioxol-5-yl)oxy)cyclobutyl)amino)methyl)-6-fluoroisoquinolin-8-yl)methanol, HCl

Step 47.1: Synthesis of (1r,3r)-N-((8-(((tert-butyldimethylsilyl)oxy)methyl)-6-fluoroisoquinolin-5-yl)methyl)-3-((2,2-difluorobenzo[d][1,3]dioxol-5-yl)oxy)cyclobutan-1-amine

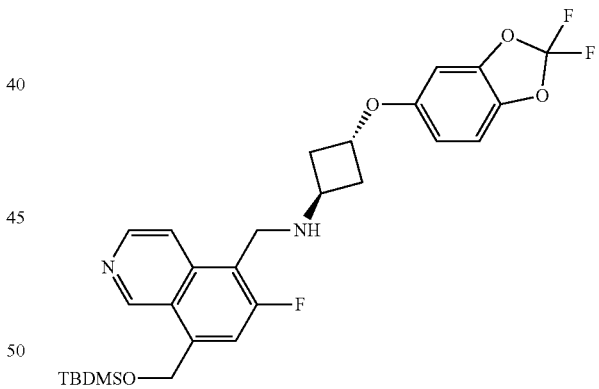

The title compound was synthesized following the procedure as described in Step 1.4, using (1r,3r)-3-((2,2-difluorobenzo[d][1,3]dioxol-5-yl)oxy)cyclobutan-1-amine, HCl (Step 46.3, 180 mg, 0.64 mmol) and 8-(((tert-butyldimethylsilyl)oxy)methyl)-6-fluoroisoquinoline-5-carbaldehyde (Step 6.8, 206 mg, 0.64 mmol). The crude was purified by flash chromatography (12 g SiliCycle column, 0-10% MeOH in CH$_2$Cl$_2$ elution) to provide (1r,3r)-N-((8-(((tert-butyldimethylsilyl)oxy)methyl)-6-fluoroisoquinolin-5-yl)methyl)-3-((2,2-difluorobenzo[d][1,3]dioxol-5-yl)oxy)cyclobutan-1-amine (160 mg, 45%). MS (ESI+) [Method 6A]: m/z 547.3 (M+H); Rt 1.42 min.

Step 47.2: Synthesis of (5-((((1r,3r)-3-((2,2-difluorobenzo[d][1,3]dioxol-5-yl)oxy)cyclobutyl)amino)methyl)-6-fluoroisoquinolin-8-yl)methanol, HCl

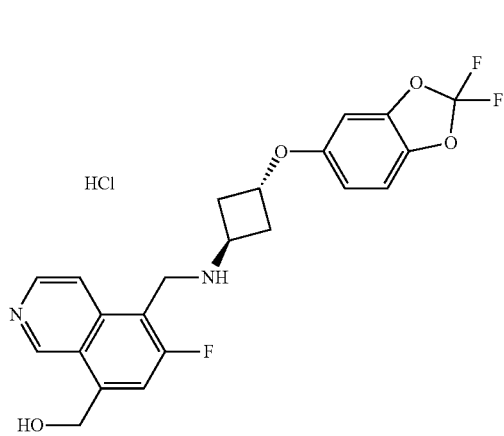 [SMILES: OCc1cc(F)c(CN[C@H]2C[C@H](Oc3ccc4c(c3)OC(F)(F)O4)C2)c2ccncc12 ; Cl]

Deprotection was carried out according to Step 6.11. The residue was purified by prep-HPLC (Column: WATERS X BRIDGE (250 mm×21.2 mm), 5.0µ; Mobile Phase: 0.02% NH₄OH in water and acetonitrile). The isolated product was stirred with HCl solution (4M in 1,4-dioxane) (2 mL) at rt for 1 h. Then concentrated in vacuo and then lyophilized to afford (5-((((1r,3r)-3-((2,2-difluorobenzo[d][1,3]dioxol-5-yl)oxy)cyclobutyl)amino)methyl)-6-fluoroisoquinolin-8-yl)methanol, HCl (20 mg, 14%). MS (ESI+) [Method 6A]: m/z 433.2 (M+H); Rt 1.30 min. $^1$H NMR (400 MHz, CD$_3$OD) δ 9.93 (s, 1H), 8.83-8.78 (m, 2H), 8.01 (d, J=10.4 Hz, 1H), 7.10 (d, J=8.8 Hz, 1H), 6.81 (d, J=2.4 Hz, 1H), 6.60 (dd, J=1.2 & 8.8 Hz, 1H), 5.30 (s, 2H), 5.02-4.96 (m, 1H), 4.80 (s, 2H), 4.28-4.23 (m, 1H), 2.91-2.84 (m, 2H), 2.72-2.64 (m, 2H).

Example 48: Synthesis of (5-((((1r,3r)-3-(3,5-difluoro-4-methoxyphenoxy)cyclobutyl)amino)methyl)-6-fluoroisoquinolin-8-yl)methanol Step 48.1: Synthesis of 3,5-difluoro-4-methoxyphenol

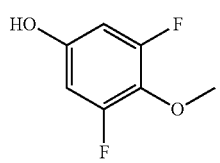

A sealed tube charged with 5-bromo-1,3-difluoro-2-methoxybenzene [CAS No. 104197-14-0](500 mg, 2.24 mmol), KOH (237 mg, 4.48 mmol), t-BuXPHOS (13 mg, 0.03 mmol) and 1,4-dioxane-water (3 mL, 1:1 v/v), was purged with N₂ for 10 min. Then Pd₂(dba)₃ (103 mg, 0.11 mmol) was added, purged with N₂, sealed tube was closed and stirred at 100° C. for 16 h. Reaction was cooled to rt, quenched with HCl solution (1M) and extracted with EtOAc twice. The combined filtrate was concentrated in vacuo. The residue was purified by flash chromatography (12 g SiliCycle column, 0-20% EtOAc in Hexane elution) to afford 3,5-difluoro-4-methoxyphenol (330 g, 91%). MS (ESI+) [Method 6A]: m/z 159.0 (M+H); Rt 1.43 min.

Step 48.2: Synthesis of tert-butyl ((1r,3r)-3-(3,5-difluoro-4-methoxyphenoxy)cyclobutyl)carbamate

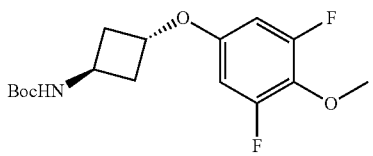 [SMILES: COc1c(F)cc(O[C@H]2C[C@H](NC(=O)OC(C)(C)C)C2)cc1F]

The title compound was synthesized following the procedure as described in Step 1.2, using tert-butyl ((1s,3s)-3-hydroxycyclobutyl)carbamate (0.35 g, 1.87 mmol) and 3,5-difluoro-4-methoxyphenol (0.33 g, 2.06 mmol). Crude was purified by flash chromatography (12 g SiliCycle column, 0-30% EtOAc in Hexane elution) to provide tert-butyl ((1r,3r)-3-(3,5-difluoro-4-methoxyphenoxy)cyclobutyl)carbamate (0.43 g, 69%). 1H NMR (400 MHz, CDCl3) δ 6.32 (d, J=8.0 Hz, 2H), 4.68-4.64 (m, 1H), 4.31-4.27 (m, 1H), 3.88 (s, 3H), 2.56-2.49 (m, 2H), 2.39-2.34 (m, 2H), 1.45 (s, 9H).

Step 48.3: Synthesis of (1r,3r)-3-(3,5-difluoro-4-methoxyphenoxy)cyclobutan-1-amine, HCl

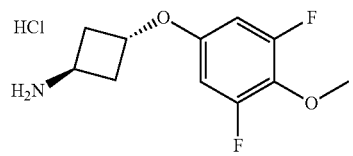 [SMILES: Cl ; COc1c(F)cc(O[C@H]2C[C@H](N)C2)cc1F]

A solution of tert-butyl ((1r,3r)-3-(3,5-difluoro-4-methoxyphenoxy)cyclobutyl)carbamate (430 mg, 1.31 mmol) and HCl solution (4M in 1,4-dioxane) (5 mL) was stirred at rt for 16 h. Then the reaction mixture was concentrated in vacuo. The residue was triturated with Et₂O, solid was filtered and dried to yield (1r,3r)-3-(3,5-difluoro-4-methoxyphenoxy)cyclobutan-1-amine, HCl (300 mg, 86%). MS (ESI+) [Method 6A]: m/z 230.1 (M+H); Rt 1.26 min.

Step 48.4: Synthesis of (1r,3r)-N-((8-(((tert-butyldimethylsilyl)oxy)methyl)-6-fluoroisoquinolin-5-yl)methyl)-3-(3,5-difluoro-4-methoxyphenoxy)cyclobutan-1-amine

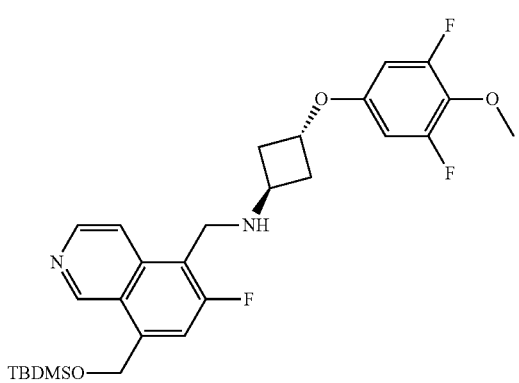 [SMILES: COc1c(F)cc(O[C@H]2C[C@H](NCc3c(F)cc(CO[Si](C)(C)C(C)(C)C)c4cnccc34)C2)cc1F]

The title compound was synthesized following the procedure as described in Step 1.4, using (1r,3r)-3-(3,5-difluoro-4-methoxyphenoxy)cyclobutan-1-amine, HCl (100 mg, 0.38 mmol) and 8-(((tert-butyldimethylsilyl)oxy)methyl)-6-fluoroisoquinoline-5-carbaldehyde (Step 6.8, 121 mg, 0.38 mmol). The crude product was purified by flash chromatography (12 g SiliCycle column, 0-10% MeOH in CH$_2$Cl$_2$ elution) to provide (1r,3r)-N-((8-(((tert-butyldimethylsilyl)oxy)methyl)-6-fluoroisoquinolin-5-yl)methyl)-3-(3,5-difluoro-4-methoxyphenoxy)cyclobutan-1-amine (170 mg, 84%). MS (ESI+) [Method 6A]: m/z 533.4 (M+H); Rt 1.41 min.

Step 48.5: Synthesis of (5-((((1r,3r)-3-(3,5-difluoro-4-methoxyphenoxy)cyclobutyl)amino)methyl)-6-fluoroisoquinolin-8-yl)methanol

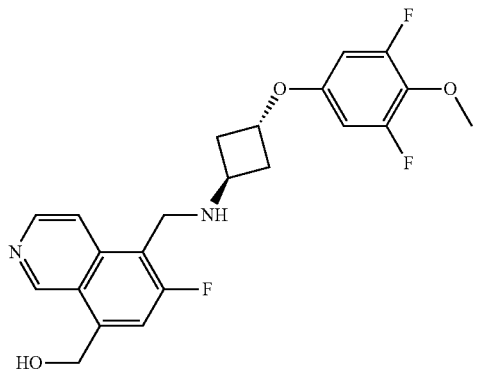 [SMILES: COc1c(F)cc(O[C@H]2C[C@H](NCc3c(F)cc(CO)c4cnccc34)C2)cc1F]

Deprotection was carried out according to Step 6.11. The residue was purified by prep-HPLC (Column: KINETEX EVO (250 mm×21.2 mm), 5.0μ; Mobile Phase: 0.02% NH$_4$OH in water and acetonitrile) to afford (5-((((1r,3r)-3-(3,5-difluoro-4-methoxyphenoxy)cyclobutyl)amino)methyl)-6-fluoroisoquinolin-8-yl)methanol (35 mg, 26%). MS (ESI+) [Method 6A]: m/z 419.2 (M+H); Rt 1.26 min. $^1$H NMR (400 MHz, CD$_3$OD) δ 9.47 (s, 1H), 8.57 (d, J=6.0 Hz, 1H), 8.14 (d, J=6.0 Hz, 1H), 7.59 (d, J=10.4 Hz, 1H), 6.47-6.43 (m, 2H), 5.21 (s, 2H), 4.78-4.75 (m, 1H), 4.18 (d, J=2.0 Hz, 2H), 3.86 (s, 3H), 3.61-3.57 (m, 1H), 2.36-2.33 (m, 4H).

Example 49: Synthesis of (1r,3r)-3-(3,5-difluoro-4-methoxyphenoxy)-N-((6-fluoroisoquinolin-5-yl)methyl)cyclobutan-1-amine, HCl

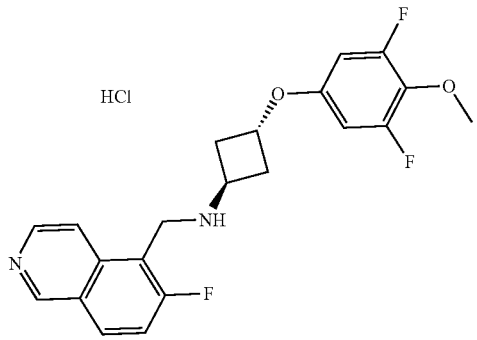 [SMILES: COc1c(F)cc(O[C@H]2C[C@H](NCc3c(F)ccc4cnccc34)C2)cc1F ; Cl]

The title compound was synthesized following the procedure as described in Step 1.4, using (1r,3r)-3-(3,5-difluoro-4-methoxyphenoxy)cyclobutan-1-amine, HCl (Step 48.3, 150 mg, 0.56 mmol) and 6-fluoroisoquinoline-5-carbaldehyde (Step 3.1, 79 mg, 0.45 mmol). Crude product was purified by prep-HPLC (Column: LUNA Phenomenex (250 mm×21.2 mm), 5.0μ; Mobile Phase: 0.1% HCO$_2$H in water and acetonitrile). The isolated product was stirred with HCl solution (4M in 1,4-dioxane) (2 mL) at rt for 1 h. Then concentrated in vacuo to afford (1r,3r)-3-(3,5-difluoro-4-methoxyphenoxy)-N-((6-fluoroisoquinolin-5-yl)methyl)cyclobutan-1-amine, HCl (70 mg, 29%). MS (ESI+) [Method 1A]: m/z 389.1 (M+H); Rt 0.19 min. $^1$H NMR (400 MHz, CD$_3$OD) δ 9.84 (s, 1H), 8.80-8.72 (m, 3H), 8.00 (t, J=9.2 Hz, 1H), 6.55-6.50 (m, 2H), 4.95-4.90 (m, 1H), 4.81 (d, J=2.0 Hz, 2H), 4.27-4.20 (m, 1H), 3.85 (s, 3H), 2.89-2.81 (m, 2H), 2.71-2.64 (m, 2H).

Example 50: Synthesis of (1r,3r)-3-(3-(difluoromethoxy)-4-fluorophenoxy)-N-((6-fluoroisoquinolin-5-yl)methyl)cyclobutan-1-amine, HCl Step 50.1: Synthesis of 4-bromo-2-(difluoromethoxy)-1-fluorobenzene

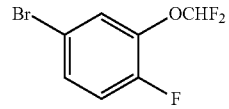

To the solution of 5-bromo-2-fluorophenol [CAS No. 112204-58-7] (3.0 g, 15.69 mmol) in DMF (50 mL), sodium 2-chloro-2,2-difluoroacetate (5.9 g, 39.71 mmol) and Cs$_2$CO$_3$ (7.6 g, 23.37 mmol) were added at rt. Then water (5.0 mL) was added and the reaction mixture was stirred at 70° C. for 16 h. Reaction was cooled to rt, diluted with water and extracted with EtOAc 3×'s. The combined filtrate was concentrated in vacuo. The residue was to purified by flash chromatography (8 g SiliCycle column, 0-10% EtOAc in Hexane elution) to afford 4-bromo-2-(difluoromethoxy)-1-fluorobenzene (1.0 g, 26%). $^1$H NMR (400 MHz, CDCl$_3$) δ 7.42-7.40 (m, 1H), 7.35-7.31 (m, 1H), 7.07 (t, J=9.2 Hz, 1H), 6.55 (t, J=72.8 Hz, 1H).

Step 50.2: Synthesis of 3-(difluoromethoxy)-4-fluorophenol

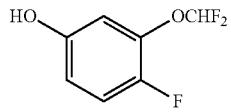

The sealed tube charged with 4-bromo-2-(difluoromethoxy)-1-fluorobenzene (1.0 g, 4.14 mmol), bis(pinacolato)diboron (2.3 g, 9.05 mmol), KOAc (1.8 g, 18.34 mmol) and 1,4-dioxane (50 mL) was purged with N$_2$ for 10 min. Then Pd(dppf)Cl$_2$·CH$_2$Cl$_2$ (0.45 g, 0.62 mmol) was added, vessel was closed and stirred at 80° C. for 16 h. Reaction mixture was cooled, acetone (20 mL) and oxone (5.7 g, 9.28 mmol) dissolved in water (10 mL) were added, and stirred at rt for 1 h. Reaction mixture was then diluted with water and extracted with EtOAc 3×'s. The combined filtrate was concentrated in vacuo. The residue was purified by flash chromatography (24 g SiliCycle column, 0-10% EtOAc in Hexane elution) to afford 3-(difluoromethoxy)-4-fluorophenol (0.15 g, 21%). $^1$H NMR (400 MHz, DMSO-d6) δ 9.77 (s, 1H), 7.20 (t, J=71.6 Hz, 1H), 7.19-7.15 (m, 1H), 6.70 (dd, J=6.8, 2.8 Hz, 1H), 6.65-6.61 (m, 1H).

Step 50.3: Synthesis of tert-butyl ((1r,3r)-3-(3-(difluoromethoxy)-4-fluorophenoxy)cyclobutyl)carbamate

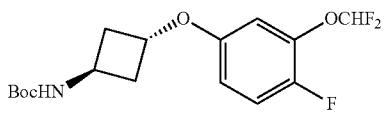 [SMILES: CC(C)(C)OC(=O)N[C@H]1C[C@H](Oc2ccc(F)c(OC(F)F)c2)C1]

The title compound was synthesized following the procedure as described in Step 1.2, using tert-butyl ((1s,3s)-3-hydroxycyclobutyl)carbamate (0.15 g, 0.80 mmol) and 3-(difluoromethoxy)-4-fluorophenol (0.15 g, 0.84 mmol). Crude product was purified by flash chromatography (12 g SiliCycle column, 0-20% EtOAc in Hexane elution) to provide tert-butyl ((1r,3r)-3-(3-(difluoromethoxy)-4-fluorophenoxy)cyclobutyl)carbamate (0.3 g, 102%). $^1$H NMR (600 MHz, CDCl$_3$) δ 7.05 (t, J=9.0 Hz, 1H), 6.65-6.63 (m, 1H), 6.57-6.54 (m, 1H), 6.53 (t, J=73.8 Hz, 1H), 4.73-4.69 (m, 1H), 4.31-4.27 (m, 1H), 2.56-2.51 (m, 2H), 2.39-2.35 (m, 2H), 1.44 (s, 9H).

Step 50.4: Synthesis of (1r,3r)-3-(3-(difluoromethoxy)-4-fluorophenoxy)cyclobutan-1-amine, HCl

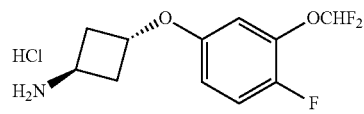

A solution of tert-butyl ((1r,3r)-3-(3-(difluoromethoxy)-4-fluorophenoxy)cyclobutyl)carbamate (300 mg, 0.86 mmol) and HCl solution (4M in 1,4-dioxane) (2 mL) was stirred at rt for 1 h. Then the reaction mixture was concentrated in vacuo. The residue was triturated with Et$_2$O, solid was filtered and dried to yield (1r,3r)-3-(3-(difluoromethoxy)-4-fluorophenoxy)cyclobutan-1-amine, HCl (200 mg, 87%). $^1$H NMR (300 MHz, CD$_3$OD) δ 7.19-7.15 (m, 1H), 6.83 (t, J=72.4 Hz, 1H), 6.75-6.66 (m, 2H), 4.92-4.87 (m, 1H), 3.97-3.93 (m, 1H), 2.61-2.54 (m, 4H).

Step 50.5: Synthesis of (1r,3r)-3-(3-(difluoromethoxy)-4-fluorophenoxy)-N-((6-fluoroisoquinolin-5-yl)methyl)cyclobutan-1-amine, HCl

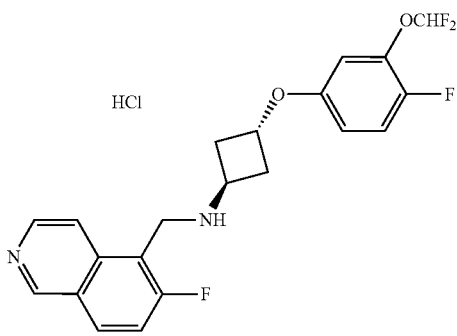 [SMILES: Fc1ccc(O[C@H]2C[C@H](NCc3c(F)ccc4cnccc34)C2)cc1OC(F)F ; Cl]

The title compound was synthesized following the procedure as described in Step 1.4, using (1r,3r)-3-(3-(difluoromethoxy)-4-fluorophenoxy)cyclobutan-1-amine, HCl (200 mg, 0.71 mmol) and 6-fluoroisoquinoline-5-carbaldehyde (Step 3.1, 110 mg, 0.63 mmol). Crude product was purified by prep-HPLC (Column: YMC-ACTUS TRIART C-18 (150 mm×21.2 mm), 5.0μ; Mobile Phase: 0.01% NH$_4$OH in water and acetonitrile). The isolated product was stirred with HCl solution (4M in 1,4-dioxane) (1 mL) at rt for 1 h. Then concentrated in vacuo and lyophilized to afford (1r,3r)-3-(3-(difluoromethoxy)-4-fluorophenoxy)-N-((6-fluoroisoquinolin-5-yl)methyl)cyclobutan-1-amine, HCl (85 mg, 29%). MS (ESI+) [Method 6A]: m/z 407.1 (M+H); Rt 1.30 min. $^1$H NMR (400 MHz, CD$_3$OD) δ 9.85 (s, 1H), 8.76-8.72 (m, 3H), 7.99 (t, J=9.2 Hz, 1H), 7.21-7.16 (m, 1H), 6.84 (t, J=73.6 Hz, 1H), 6.79-6.76 (m, 1H), 7.74-7.70 (m, 1H), 4.99-4.95 (m, 1H), 4.82 (d, J=2.0 Hz, 2H), 4.29-4.24 (m, 1H), 2.90-2.82 (m, 2H), 2.72-2.65 (m, 2H).

Example 51: Synthesis of (1r,3r)-3-(4-(difluoromethoxy)-3-fluorophenoxy)-N-((6-fluoroisoquinolin-5-yl)methyl)cyclobutan-1-amine, HCl Step 51.1: Synthesis of 4-bromo-1-(difluoromethoxy)-2-fluorobenzene

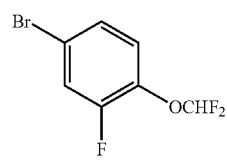

To the solution of 4-bromo-2-fluorophenol [CAS No. 2105-94-4] (5.0 g, 26.31 mmol) in DMF (40 mL), sodium 2-chloro-2,2-difluoroacetate (10.03 g, 65.78 mmol) and Cs$_2$CO$_3$ (12.86 g, 39.47 mmol) were added at rt. Then water (4.0 mL) was added and reaction mixture was stirred at 70° C. for 16 h. Reaction was cooled to rt, diluted with water and extracted with EtOAc twice. The combined filtrate was concentrated in vacuo. The residue was purified by flash chromatography (24 g SiliCycle column, Hexane elution) to afford 4-bromo-1-(difluoromethoxy)-2-fluorobenzene (4.0 g, 63%). $^1$H NMR (300 MHz, CDCl$_3$) δ 7.38-7.28 (m, 2H), 7.14 (t, J=8.7 Hz, 1H), 6.53 (t, J=73.2 Hz, 1H).

Step 51.2: Synthesis of 2-(4-(difluoromethoxy)-3-fluorophenyl)-4,4,5,5-tetramethyl-1,3,2-dioxaborolane]

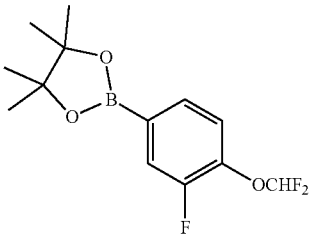 [SMILES: CC1(C)OB(c2ccc(OC(F)F)c(F)c2)OC1(C)C]

The sealed tube charged with 4-bromo-1-(difluoromethoxy)-2-fluorobenzene (3.5 g, 14.52 mmol), bis(pinacolato)diboron (5.53 g, 21.78 mmol), KOAc (4.27 g, 43.56 mmol) and 1,4-dioxane (50 mL) was purged with $N_2$ for 10 min. Then Pd(dppf)$Cl_2 \cdot CH_2Cl_2$ (0.45 g, 0.62 mmol) was added, vessel was closed and stirred at 80° C. for 16 h. Reaction mixture was cooled, filtered through celite bed and the bed was washed with EtOAc. The filtrate was concentrated in vacuo and the residue was purified by flash chromatography (24 g SiliCycle column, 0-10% EtOAc in Hexane elution) to afford 2-(4-(difluoromethoxy)-3-fluorophenyl)-4,4,5,5-tetramethyl-1,3,2-dioxaborolane (4.0 g, 93%). $^1$H NMR (300 MHz, CDCl$_3$) δ 7.61-7.54 (m, 2H), 7.23-7.99 (m, 1H), 6.58 (t, J=73.5 Hz, 1H), 1.34 (s, 12H).

Step 51.3: Synthesis of 4-(difluoromethoxy)-3-fluorophenol

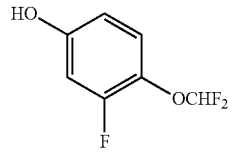 [SMILES: Oc1ccc(OC(F)F)c(F)c1]

To the solution of 2-(4-(difluoromethoxy)-3-fluorophenyl)-4,4,5,5-tetramethyl-1,3,2-dioxaborolane (1.0 g, 3.47 mmol) in acetone (10 mL), oxone (1.28 g, 4.17 mmol) dissolved in water (10 mL) was added dropwise at 0° C. and stirred for 1 h. Reaction mixture was then diluted with water and extracted with EtOAc twice. The combined filtrate was concentrated in vacuo. The residue was purified by flash chromatography (12 g SiliCycle column, 0-10% EtOAc in Hexane elution) to afford 4-(difluoromethoxy)-3-fluorophenol (0.5 g, 80%). $^1$H NMR (400 MHz, DMSO-d6) δ 9.99 (s, 1H), 7.16 (t, J=9.3 Hz, 1H), 7.04 (t, J=74.4 Hz, 1H), 6.74-6.69 (m, 1H), 6.62-6.58 (m, 1H).

Step 51.4: Synthesis of tert-butyl ((1r,3r)-3-(4-(difluoromethoxy)-3-fluorophenoxy)cyclobutyl)carbamate

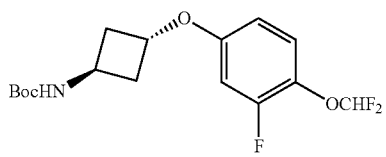 [SMILES: CC(C)(C)OC(=O)N[C@H]1C[C@H](Oc2ccc(OC(F)F)c(F)c2)C1]

The title compound was synthesized following the procedure as described in Step 1.2, using tert-butyl ((1s,3s)-3-hydroxycyclobutyl)carbamate (0.4 g, 2.14 mmol) and 4-(difluoromethoxy)-3-fluorophenol (0.46 g, 2.56 mmol). Crude product was purified by flash chromatography (12 g SiliCycle column, 0-10% EtOAc in Hexane elution) to provide tert-butyl ((1r,3r)-3-(4-(difluoromethoxy)-3-fluorophenoxy)cyclobutyl)carbamate (0.4 g, 53%). $^1$H NMR (300 MHz, CDCl$_3$) δ 7.12 (t, J=9.3 Hz, 1H), 6.60-6.49 (m, 2H), 6.45 (t, J=74.1 Hz, 1H), 4.75-4.69 (m, 1H), 4.32-4.27 (m, 1H), 2.59-2.50 (m, 2H). 2.42-2.35 (m, 2H), 1.45 (s, 9H).

Step 51.5: Synthesis of (1r,3r)-3-(4-(difluoromethoxy)-3-fluorophenoxy)cyclobutan-1-amine, HCl

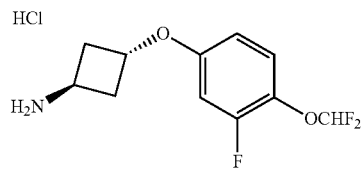 [SMILES: Cl ; N[C@H]1C[C@H](Oc2ccc(OC(F)F)c(F)c2)C1]

A solution of tert-butyl ((1r,3r)-3-(4-(difluoromethoxy)-3-fluorophenoxy)cyclobutyl)carbamate (0.6 g, 1.73 mmol) and HCl solution (4M in 1,4-dioxane) (10 mL) was stirred at rt for 4 h. Then the reaction mixture was concentrated in vacuo. The residue was triturated with Et$_2$O, solid was filtered and dried to yield (1r,3r)-3-(4-(difluoromethoxy)-3-fluorophenoxy)cyclobutan-1-amine, HCl (0.45 g, 91%). MS (ESI+) [Method 6A]: m/z 248.1 (M+H); Rt 1.29 min. $^1$H NMR (300 MHz, DMSO-d6) δ 7.19-7.15 (m, 1H), 6.83 (t, J=72.4 Hz, 1H), 6.75-6.66 (m, 2H), 4.92-4.87 (m, 1H), 3.97-3.93 (m, 1H), 2.61-2.54 (m, 4H).

Step 51.6: Synthesis of (1r,3r)-3-(4-(difluoromethoxy)-3-fluorophenoxy)-N-((6-fluoroisoquinolin-5-yl)methyl)cyclobutan-1-amine, HCl

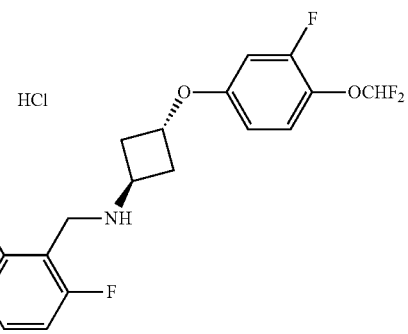

The title compound was synthesized following the procedure as described in Step 1.4, using (1r,3r)-3-(4-(difluoromethoxy)-3-fluorophenoxy)cyclobutan-1-amine, HCl (450 mg, 1.59 mmol) and 6-fluoroisoquinoline-5-carbaldehyde (Step 3.1, 250 mg, 1.43 mmol). Crude product was purified by prep-HPLC (Column: ZORBAX (150 mm×21.2 mm), 5.0μ; Mobile Phase: 0.1% HCO$_2$H in water and acetonitrile-MeOH). The isolated product was stirred with HCl solution (4M in 1,4-dioxane) (2 mL) at rt for 1 h. Then concentrated in vacuo to afford (1r,3r)-3-(4-(difluoromethoxy)-3-fluorophenoxy)-N-((6-fluoroisoquinolin-5-yl)methyl)cyclobutan-1-amine, HCl (280 mg, 39%). MS (ESI+) [Method 1A]: m/z 407.1 (M+H); Rt 1.30 min. ¹H NMR (400 MHz, CD₃OD) δ 9.88 (s, 1H), 8.82-8.75 (m, 3H), 8.02 (t, J=9.6 Hz, 1H), 7.23 (t, J=8.8 Hz, 1H), 6.78 (dd, J=8.0, 2.8 Hz, 1H), 6.72 (t, J=74.0 Hz, 1H), 6.68 (dq, J=9.2, 1.6 Hz, 1H), 5.02-4.97 (m, 1H), 4.83 (d, J=2.0 Hz, 2H), 4.29-4.25 (m, 1H), 2.92-2.85 (m, 2H), 2.73-2.65 (m, 2H).

Example 52: Synthesis of (1r,3r)-3-(3,5-difluoro-4-methylphenoxy)-N-((6-fluoroisoquinolin-5-yl)methyl)cyclobutan-1-amine, HCO₂H Step 52.1: Synthesis of 2-(3,5-difluoro-4-methylphenyl)-4,4,5,5-tetramethyl-1,3,2-dioxaborolane

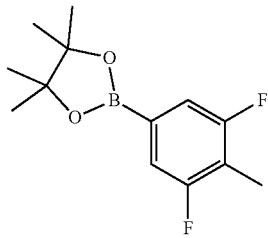

The sealed tube charged with 5-bromo-1,3-difluoro-2-methylbenzene [CAS No. 179617-08-4] (500 mg, 2.42 mmol), bis(pinacolato)diboron (675 mg, 2.66 mmol), KOAc (474 mg, 4.83 mmol) and 1,4-dioxane (15 mL) was purged with N₂ for 10 min. Then Pd(dppf)Cl₂·CH₂Cl₂ (88 mg, 0.12 mmol) was added, vessel was closed and stirred at 100° C. for 16 h. Reaction mixture was cooled, filtered through celite bed and the bed was washed with EtOAc. The filtrate was concentrated in vacuo and the residue was purified by flash chromatography (12 g SiliCycle column, 0-5% EtOAc in Hexane elution) to afford 2-(3,5-difluoro-4-methylphenyl)-4,4,5,5-tetramethyl-1,3,2-dioxaborolane (380 mg, 68%). ¹H NMR (300 MHz, CDCl₃) δ 7.27-7.21 (m, 2H), 2.06 (t, J=1.8 Hz, 3H), 1.33 (s, 12H).

Step 52.2: Synthesis of 3,5-difluoro-4-methylphenol

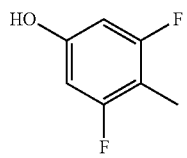

To the solution of 2-(3,5-difluoro-4-methylphenyl)-4,4,5,5-tetramethyl-1,3,2-dioxaborolane (0.28 g, 1.10 mmol) in acetone (5 mL), oxone (1.01 g, 1.65 mmol) dissolved in water (5 mL) was added dropwise at 0° C. and stirred for 1 h. Reaction mixture was then diluted with water and extracted with EtOAc twice. The combined filtrate was concentrated in vacuo. The residue was purified by flash chromatography (12 g SiliCycle column, 0-8% EtOAc in Hexane elution) to afford 3,5-difluoro-4-methylphenol (0.13 g, 81%). ¹H NMR (400 MHz, DMSO-d6) δ 10.08 (s, 1H), 6.41 (d, J=9.3 Hz, 2H), 2.06 (s, 3H).

Step 52.3: Synthesis of tert-butyl ((1r,3r)-3-(3,5-difluoro-4-methylphenoxy)cyclobutyl)carbamate

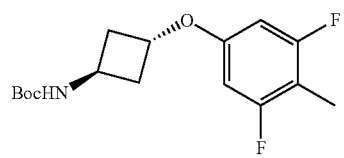 [SMILES: Cc1c(F)cc(O[C@H]2C[C@H](NC(=O)OC(C)(C)C)C2)cc1F]

The title compound was synthesized following the procedure as described in Step 1.2, using tert-butyl ((1s,3s)-3-hydroxycyclobutyl)carbamate (104 mg, 0.56 mmol) and 3,5-difluoro-4-methylphenol (80 mg, 0.56 mmol). Crude product was purified by flash chromatography (12 g SiliCycle column, 0-10% EtOAc in Hexane elution) to provide tert-butyl ((1r,3r)-3-(3,5-difluoro-4-methylphenoxy)cyclobutyl)carbamate (70 mg, 40%). 1H NMR (300 MHz, CDCl3) δ 6.27 (d, J=8.7 Hz, 2H), 4.73-4.66 (m, 1H), 4.31-4.26 (m, 1H), 2.57-2.49 (m, 2H), 2.40-2.32 (m, 2H), 2.09 (s, 3H), 1.45 (s, 9H).

Step 52.4: Synthesis of (1r,3r)-3-(3,5-difluoro-4-methylphenoxy)cyclobutan-1-amine, HCl

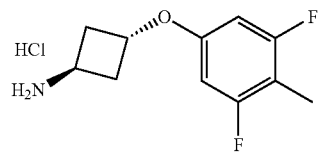

To the solution of tert-butyl ((1r,3r)-3-(3,5-difluoro-4-methylphenoxy)cyclobutyl)carbamate (170 mg, 0.69 mmol) in 1,4-dioxane (0.5 mL), HCl solution (4M in 1,4-dioxane) (2 mL) was added dropwise at 0° C. and stirred at rt for 4 h. Then the reaction mixture was concentrated in vacuo. The residue was triturated with Et₂O, solid was filtered and dried to yield (1r,3r)-3-(3,5-difluoro-4-methylphenoxy)cyclobutan-1-amine, HCl (120 mg, 88%). MS (ESI+) [Method 6A]: m/z 214.2 (M+H); Rt 1.31 min. ¹H NMR (300 MHz, DMSO-d6) δ 8.32 (brs, 3H), 6.57 (d, J=8.4 Hz, 2H), 5.03-4.96 (m, 1H), 3.84-3.78 (m, 1H), 2.66-2.57 (m, 2H), 2.43-2.34 (m, 2H), 2.05 (s, 3H).

Step 52.5: Synthesis of (1r,3r)-3-(3,5-difluoro-4-methylphenoxy)-N-((6-fluoroisoquinolin-5-yl)methyl)cyclobutan-1-amine, HCO₂H

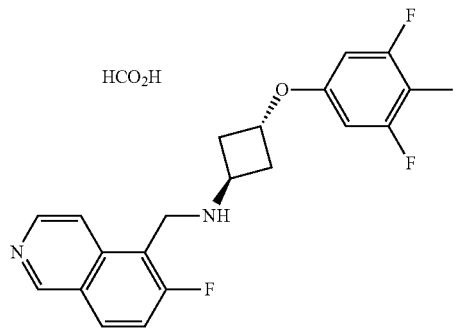 [SMILES: Cc1c(F)cc(O[C@H]2C[C@H](NCc3c(F)ccc4cnccc34)C2)cc1F ; "HCO2H"]

The title compound was synthesized following the procedure as described in Step 1.4, using (1r,3r)-3-(3,5-difluoro-4-methylphenoxy)cyclobutan-1-amine, HCl (120 mg, 0.48 mmol) and 6-fluoroisoquinoline-5-carbaldehyde (Step 3.1, 76 mg, 0.43 mmol). Crude product was purified by prep-HPLC (Column: WATERS X BRIDGE C18 (150 mm×19.0 mm), 5.0µ; Mobile Phase: 0.1% HCO$_2$H in water and acetonitrile) to afford (1r,3r)-3-(3,5-difluoro-4-methylphenoxy)-N-((6-fluoroisoquinolin-5-yl)methyl)cyclobutan-1-amine, HCO$_2$H (50 mg, 28%). MS (ESI+) [Method 1A]: m/z 373.2 (M+H); Rt 1.30 min. $^1$H NMR (400 MHz, DMSO-d6) δ 9.32 (s, 1H), 8.56-8.53 (m, 1H), 8.18-8.15 (m, 2H), 8.09-8.07 (m, 1H), 7.58 (t, J=8.8 Hz, 1H), 6.53 (d, J=8.8 Hz, 1H), 4.82-4.77 (m, 1H), 4.06 (d, J=2.0 Hz, 2H), 3.44-3.39 (m, 1H), 2.30-2.23 (m, 2H), 2.20-2.15 (m, 2H), 2.04 (m, 3H).

Example 53: Synthesis of (5-((((1r,3r)-3-(3,5-difluoro-4-methylphenoxy)cyclobutyl)amino)methyl)-6-fluoroisoquinolin-8-yl)methanol, HCl Step 53.1: Synthesis of (1r,3r)-N-((8-(((tert-butyldimethylsilyl)oxy)methyl)-6-fluoroisoquinolin-5-yl)methyl)-3-(3,5-difluoro-4-methylphenoxy)cyclobutan-1-amine

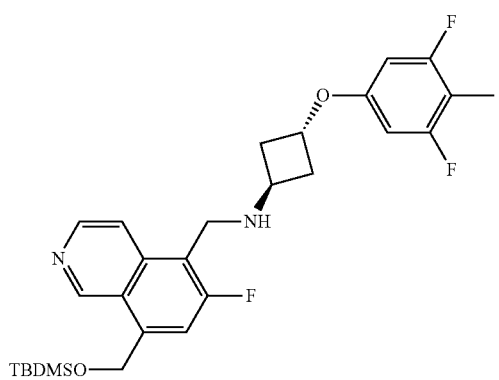 [SMILES: Cc1c(F)cc(O[C@H]2C[C@H](NCc3c(F)cc(CO[Si](C)(C)C(C)(C)C)c4cnccc34)C2)cc1F]

The title compound was synthesized following the procedure as described in Step 1.4, using (1r,3r)-3-(3,5-difluoro-4-methylphenoxy)cyclobutan-1-amine, HCl (Step 52.4, 100 mg, 0.40 mmol) and 8-(((tert-butyldimethylsilyl)oxy)methyl)-6-fluoroisoquinoline-5-carbaldehyde (Step 6.8, 128 mg, 0.40 mmol). The crude (1r,3r)-N-((8-(((tert-butyldimethylsilyl)oxy)methyl)-6-fluoroisoquinolin-5-yl)methyl)-3-(3,5-difluoro-4-methylphenoxy)cyclobutan-1-amine was obtained (250 mg, 120% crude). MS (ESI+) [Method 6A]: m/z 517.2 (M+H); Rt 1.45.

Step 53.2: Synthesis of (5-((((1r,3r)-3-(3,5-difluoro-4-methylphenoxy)cyclobutyl)amino)methyl)-6-fluoroisoquinolin-8-yl)methanol, HCl

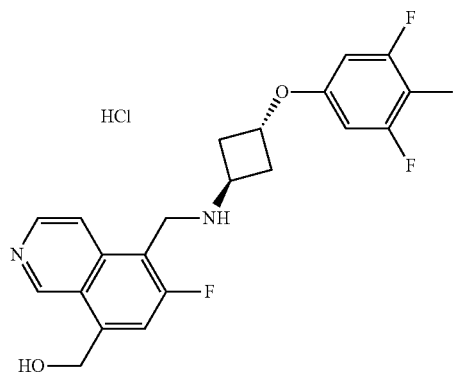 [SMILES: Cc1c(F)cc(O[C@H]2C[C@H](NCc3c(F)cc(CO)c4cnccc34)C2)cc1F ; Cl]

Deprotection was carried out according to Step 6.11. The residue was purified by flash chromatography (12 g SiliCycle column, 0-20% MeOH in CH$_2$Cl$_2$ elution), followed by prep-HPLC (Column: LUNA Phenomenex (150 mm×21.2 mm), 5.0µ; Mobile Phase: 0.1% HCO$_2$H in water and acetonitrile). The isolated product was stirred with HCl solution (4M in 1,4-dioxane) (2 mL) at rt for 1 h, then concentrated in vacuo and lyophilized to afford (5-((((1r,3r)-3-(3,5-difluoro-4-methylphenoxy)cyclobutyl)amino)methyl)-6-fluoroisoquinolin-8-yl)methanol, HCl (20 mg, 9%). MS (ESI+) [Method 6A]: m/z 403.1 (M+H); Rt 1.32 min. $^1$H NMR (400 MHz, CD$_3$OD) δ 9.88 (s, 1H), 8.79-8.76 (m, 1H), 8.70-8.68 (m, 1H), 7.98 (d, J=10.8 Hz, 1H), 6.45 (d, J=8.8 Hz, 2H), 5.29 (s, 2H), 4.96-4.92 (m, 1H), 4.78 (d, J=1.6 Hz, 2H), 4.26-4.22 (m, 1H), 2.89-2.81 (m, 2H), 2.71-2.64 (m, 2H), 2.08 (s, 3H).

Example 54: Synthesis of (1r,3r)-3-(3,4-difluoro-5-methylphenoxy)-N-((6-fluoroisoquinolin-5-yl)methyl)cyclobutan-1-amine, HCl Step 54.1: Synthesis of 5-bromo-2,3-difluorobenzaldehyde

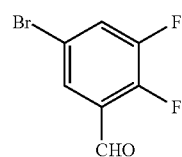

To the solution of 2,3-difluorobenzaldehyde [CAS No. 2646-91-5] (5.0 g, 35.19 mmol) in concentrated H$_2$SO$_4$ (38 mL), NBS (7.51 g, 42.23 mmol) was added portion wise at 60° C., and stirred for 16 h. The reaction mixture was cooled, poured dropwise onto ice-water, extracted with Et$_2$O 3×'s. The combined organic portion was washed with brine, dried over anhydrous Na$_2$SO$_4$, filtered and concentrated in vacuo to yield the crude product. The crude was purified by flash chromatography (40 g SiliCycle column, 0-5% EtOAc in Hexane elution) to provide 5-bromo-2,3-difluorobenzaldehyde (2.04 g, 26%). $^1$H NMR (300 MHz, CDCl$_3$) δ 10.29 (s, 1H), 7.78-7.75 (m, 1H), 7.62-7.56 (m, 1H).

Step 54.2: Synthesis of (5-bromo-2,3-difluorophenyl)methanol

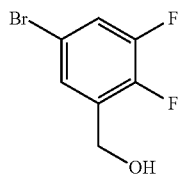

To the stirred solution of 5-bromo-2,3-difluorobenzaldehyde (2.04 g, 9.23 mmol) in MeOH (10 mL), NaBH$_4$ (0.69 g, 18.46 mmol) was added portion wise at 0° C. The reaction mixture was stirred at rt for 2 h. Then the reaction mixture was diluted with water and extracted with EtOAc 3×'s. The combined organic portion was washed with brine, dried over anhydrous Na$_2$SO$_4$, filtered and concentrated in vacuo to afford crude (5-bromo-2,3-difluorophenyl)methanol (1.7 g, 82%). $^1$H NMR (600 MHz, CDCl$_3$) δ 7.39-7.38 (m, 1H), 7.29-7.25 (m, 1H), 4.77 (s, 2H).

Step 54.3: Synthesis of 5-bromo-2,3-difluorobenzyl methanesulfonate

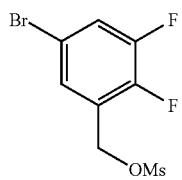

To the stirred solution of (5-bromo-2,3-difluorophenyl)methanol (1.7 g, 2.62 mmol) and TEA (2.12 mL, 15.25 mmol) in CH$_2$Cl$_2$ (25 mL), MsCl (0.71 mL, 9.15 mmol) was added drop wise at 0° C. and stirred for 1 h under N$_2$. Then the reaction mixture was diluted with water and extracted with CH$_2$Cl$_2$ 3×'s. The combined organic portion was washed with 1N HCl solution, saturated NaHCO$_3$ solution and brine successively, dried over anhydrous Na$_2$SO$_4$, filtered and concentrated in vacuo to afford crude 5-bromo-2,3-difluorobenzyl methanesulfonate (2.2 g, 95%) which was used as is in the next reaction.

Step 54.4: Synthesis of 5-bromo-1,2-difluoro-3-methylbenzene

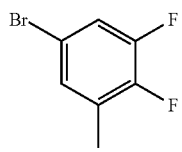

To the stirred solution of 5-bromo-2,3-difluorobenzyl methanesulfonate (2.2 g, 7.31 mmol) in anhydrous THF (20 mL), LiEt$_3$BH (1M in THF) (15.34 mL, 15.34 mmol) was added drop wise at 0° C. and stirred for 5 min; then at rt for 1 h under N$_2$. The reaction mixture was cooled to 0° C., diluted with water and extracted with Et$_2$O 3×'s. The combined organic portion was washed with brine, dried over anhydrous Na$_2$SO$_4$, filtered and concentrated in vacuo. The crude product was purified by flash chromatography (24 g SiliCycle column, Hexane elution) to afford 5-bromo-1,2-difluoro-3-methylbenzene (1.4 g, 92%). $^1$H NMR (600 MHz, CDCl$_3$) δ 7.17-7.14 (m, 1H), 7.11-7.09 (m, 1H), 2.28 (s, 3H).

Step 54.5: Synthesis of 2-(3,4-difluoro-5-methylphenyl)-4,4,5,5-tetramethyl-1,3,2-dioxaborolane

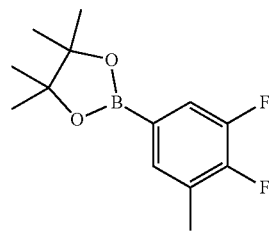 [SMILES: Cc1cc(B2OC(C)(C)C(C)(C)O2)cc(F)c1F]

The sealed tube charged with 5-bromo-1,2-difluoro-3-methylbenzene (1.4 g, 6.76 mmol), bis(pinacolato)diboron (2.06 g, 8.12 mmol), KOAc (1.32 g, 13.53 mmol) and 1,4-dioxane (20 mL) was purged with N$_2$ for 10 min. Then Pd(dppf)Cl$_2$·CH$_2$Cl$_2$ (0.25 g, 0.34 mmol) was added, vessel was closed and stirred at 100° C. for 16 h. Reaction mixture was cooled, filtered through celite bed and the bed was washed with Et$_2$O. The filtrate was concentrated in vacuo and the residue was purified by flash chromatography (24 g SiliCycle column, Hexane elution) to afford 2-(3,4-difluoro-5-methylphenyl)-4,4,5,5-tetramethyl-1,3,2-dioxaborolane (1.17 g, 68%). $^1$H NMR (300 MHz, CDCl3) δ 7.42-7.37 (m, 2H), 2.30 (d, J=2.4 Hz, 3H), 1.33 (s, 12H).

Step 54.6: Synthesis of 3,4-difluoro-5-methylphenol

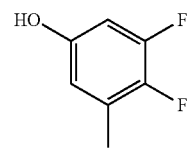

To the solution of 2-(3,4-difluoro-5-methylphenyl)-4,4,5,5-tetramethyl-1,3,2-dioxaborolane (0.57 g, 2.24 mmol) in acetone (10 mL), oxone (2.06 g, 3.37 mmol) dissolved in water (10 mL) was added dropwise at 0° C. and stirred for 1 h. Reaction mixture was then diluted with water and extracted with Et$_2$O twice. The combined organic portion was washed with brine, dried over anhydrous Na$_2$SO$_4$, filtered and concentrated in vacuo. The residue was to purified by flash chromatography (12 g SiliCycle column, 0-10% EtOAc in Hexane elution) to afford 3,4-difluoro-5-methylphenol (0.23 g, 71%). $^1$H NMR (400 MHz, DMSO-d6) δ 9.68 (s, 1H), 6.57-6.52 (m, 1H), 6.47-6.44 (m, 1H), 2.19 (d, J=2.4 Hz, 3H).

Step 54.7: Synthesis of tert-butyl ((1r,3r)-3-(3,4-difluoro-5-methylphenoxy)cyclobutyl)carbamate

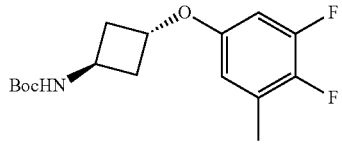 [SMILES: Cc1cc(O[C@H]2C[C@H](NC(=O)OC(C)(C)C)C2)cc(F)c1F]

To the stirred solution of 3,4-difluoro-5-methylphenol (100 mg, 0.69 mmol) and $Cs_2CO_3$ (452 mg, 1.39 mmol) in anhydrous DMF (3 mL), (1s,3s)-3-((tert-butoxycarbonyl)amino)cyclobutyl methanesulfonate (Step 99.1, 184 mg, 0.69 mmol) was added at rt and heated at 70° C. for 16 h under $N_2$. Reaction mixture was diluted with water and extracted with EtOAc twice. The combined organic portion was concentrated in vacuo. The residue was to purified by flash chromatography (12 g SiliCycle column, 0-10% EtOAc in Hexane elution) to afford tert-butyl ((1r,3r)-3-(3,4-difluoro-5-methylphenoxy)cyclobutyl)carbamate (100 mg, 46%). $^1$H NMR (300 MHz, $CDCl_3$) δ 6.43-6.32 (m, 2H), 4.70-4.65 (m, 1H), 4.27-4.23 (m, 1H), 2.54-2.47 (m, 2H), 2.39-2.33 (m, 2H), 2.26 (d, J=2.4 Hz, 3H), 1.45 (s, 9H).

Step 54.8: Synthesis of (1r,3r)-3-(3,4-difluoro-5-methylphenoxy)cyclobutan-1-amine, HCl

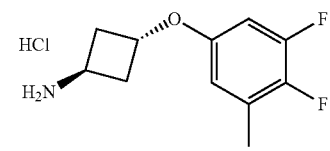

To the solution of tert-butyl ((1r,3r)-3-(3,4-difluoro-5-methylphenoxy)cyclobutyl)carbamate (180 mg, 0.57 mmol) in 1,4-dioxane (0.5 mL), HCl solution (4M in 1,4-dioxane) (2 mL) was added dropwise at 0° C. and stirred at rt for 4 h. Then the reaction mixture was concentrated in vacuo. The residue was triturated with $Et_2O$, solid was filtered and dried to yield to afford (1r,3r)-3-(3,4-difluoro-5-methylphenoxy)cyclobutan-1-amine, HCl (120 mg, 83%). MS (ESI+) [Method 1A]: m/z 214.1 (M+H); Rt 0.14 min. $^1$H NMR (300 MHz, DMSO-d6) δ 8.28 (brs, 3H), 6.77-6.70 (m, 1H), 6.58-6.55 (m, 1H), 4.97-4.91 (m, 1H), 3.85-3.78 (m, 1H), 2.65-2.56 (m, 2H), 2.44-2.33 (m, 2H), 2.25 (d, J=1.2 Hz, 3H).

Step 54.9: Synthesis of (1r,3r)-3-(3,4-difluoro-5-methylphenoxy)-N-((6-fluoroisoquinolin-5-yl)methyl)cyclobutan-1-amine, HCl

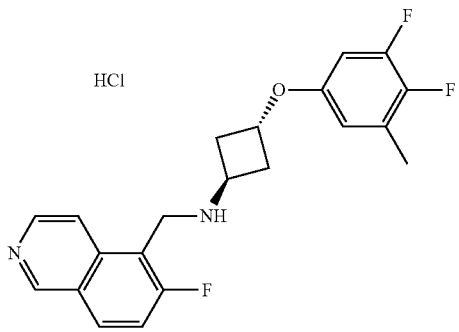 [SMILES: Cc1cc(O[C@H]2C[C@H](NCc3c(F)ccc4cnccc34)C2)cc(F)c1F ; Cl]

The title compound was synthesized following the procedure as described in Step 1.4, using (1r,3r)-3-(3,4-difluoro-5-methylphenoxy)cyclobutan-1-amine, HCl (120 mg, 0.48 mmol) and 6-fluoroisoquinoline-5-carbaldehyde (Step 3.1, 76 mg, 0.43 mmol). Crude product was purified by prep-HPLC (Column: KINETEX EVO (150 mm×19.0 mm), 5.0µ; Mobile Phase: 0.1% $HCO_2H$ in water and acetonitrile). The isolated product was stirred with HCl solution (4M in 1,4-dioxane) (2 mL) at rt for 1 h, then concentrated in vacuo and lyophilized to afford (1r,3r)-3-(3,4-difluoro-5-methylphenoxy)-N-((6-fluoroisoquinolin-5-yl)methyl)cyclobutan-1-amine, HCl (85 mg, 47%). MS (ESI+) [Method 1A]: m/z 373.1 (M+H); Rt 0.19 min. $^1$H NMR (400 MHz, DMSO-d6) δ 9.82 (s, 1H), 8.80-8.78 (m, 1H), 8.75-8.69 (m, 2H), 7.99 (t, J=8.8 Hz, 1H), 6.64-6.58 (m, 1H), 6.55-6.53 (m, 1H), 4.97-4.93 (m, 1H), 4.82 (d, J=2.0 Hz, 2H), 4.29-4.24 (m, 1H), 2.90-2.82 (m, 2H), 2.72-2.65 (m, 2H), 2.29 (d, J=2.4 Hz, 3H).

Example 55: Synthesis of (1r,3r)-3-((2,6-difluoropyridin-3-yl)oxy)-N-((6-fluoroisoquinolin-5-yl)methyl)cyclobutan-1-amine, HCl

Step 55.1: Synthesis of tert-butyl ((1r,3r)-3-((2,6-difluoropyridin-3-yl)oxy)cyclobutyl)carbamate

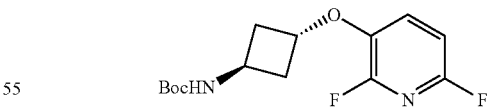

The title compound was synthesized following the procedure as described in Step 1.2, using tert-butyl ((1s,3s)-3-hydroxycyclobutyl)carbamate (0.40 g, 2.14 mmol) and 2,6-difluoropyridin-3-ol [CAS No. 209328-85-8] (0.30 g, 2.35 mmol). Crude product was purified by flash chromatography (12 g SiliCycle column, 0-20% EtOAc in Hexane elution) to provide tert-butyl ((1r,3r)-3-((2,6-difluoropyridin-3-yl)oxy)cyclobutyl)carbamate (0.40 g, 60%). MS (ESI+) [Method 6A]: m/z 244.9 (M−t-Bu+H); Rt 1.58 min.

211

Step 55.2: Synthesis of (1r,3r)-3-((2,6-difluoropyridin-3-yl)oxy)cyclobutan-1-amine, HCl

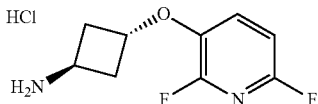

A solution of tert-butyl ((1r,3r)-3-((2,6-difluoropyridin-3-yl)oxy)cyclobutyl)carbamate (0.40 g, 1.33 mmol) and HCl solution (4M in 1,4-dioxane) (10 mL) was stirred at rt for 16 h. Then the reaction mixture was concentrated in vacuo. The residue was triturated with Et$_2$O, solid was filtered and dried to afford (1r,3r)-3-((2,6-difluoropyridin-3-yl)oxy)cyclobutan-1-amine, HCl (0.20 g, 63%). MS (ESI+) [Method 6A]: m/z 200.9 (M+H); Rt 4.84 min. $^1$H NMR (300 MHz, DMSO-d6) δ 8.46 (brs, 3H), 7.70-7.61 (m, 1H), 7.14-7.10 (m, 1H), 5.15-5.07 (m, 1H), 3.89-3.80 (m, 1H), 2.69-2.60 (m, 2H), 2.50-2.41 (m, 2H).

Step 55.3: Synthesis of (1r,3r)-3-((2,6-difluoropyridin-3-yl)oxy)-N-((6-fluoroisoquinolin-5-yl)methyl)cyclobutan-1-amine, HCl

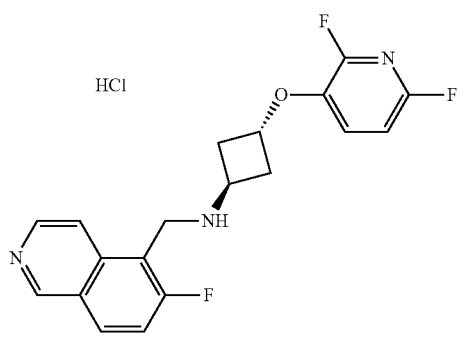 [SMILES: Fc1ccc(O[C@H]2C[C@H](NCc3c(F)ccc4cnccc34)C2)c(F)n1 ; Cl]

A round bottom flask fitted with Dean-Stark apparatus was charged with (1r,3r)-3-((2,6-difluoropyridin-3-yl)oxy)cyclobutan-1-amine, HCl (0.20 g, 0.85 mmol), 6-fluoroisoquinoline-5-carbaldehyde (Step 3.1, 0.15 g, 0.85 mmol), TEA (0.12 mL, 0.85 mmol) and benzene (50 mL), and then refluxed for 4 h. Reaction mixture was concentrated in vacuo to remove solvent, residue was dissolved in MeOH (10 mL), cooled to 0° C., NaBH$_4$ (0.16 g, 4.23 mmol) was added portion wise and stirred at rt for 2 h. Then the reaction mixture was diluted with water and extracted with EtOAc twice. The combined organic portion was washed with brine, dried over anhydrous Na$_2$SO$_4$, filtered and concentrated in vacuo. The crude product was purified by prep-HPLC (Column: LUNA Phenomenex (250 mm×21.2 mm), 5.0μ; Mobile Phase: 0.1% HCO$_2$H in water and acetonitrile). The isolated product was stirred with HCl solution (4M in 1,4-dioxane) (5 mL) at rt for 1 h, and then concentrated in vacuo. The residue was triturated with Et$_2$O, solid was collected and dried in vacuo to afford (1r,3r)-3-((2,6-difluoropyridin-3-yl)oxy)-N-((6-fluoroisoquinolin-5-yl)methyl)cyclobutan-1-amine, HCl (0.19 g, 56%). MS (ESI+) [Method 1A]: m/z 360.2 (M+H); Rt 0.13 min. $^1$H NMR (400 MHz, DMSO-d6) δ 9.90 (brs, 1H), 8.86-8.84 (m, 1H), 8.85-8.76 (m, 2H), 8.03 (t, J=9.6 Hz, 1H), 7.62-7.56 (m, 1H), 6.91 (dd, J=8.4, 2.8 Hz, 1H), 5.11-5.07 (m, 1H), 4.84 (d, J=2.0 Hz, 2H), 4.33-4.28 (m, 1H), 2.96-2.88 (m, 2H), 2.78-2.70 (m, 2H).

Example 56: Synthesis of (1r,3r)-N-((6-fluoroisoquinolin-5-yl)methyl)-3-((2-(trifluoromethyl)pyridin-4-yl)oxy)cyclobutan-1-amine, HCl

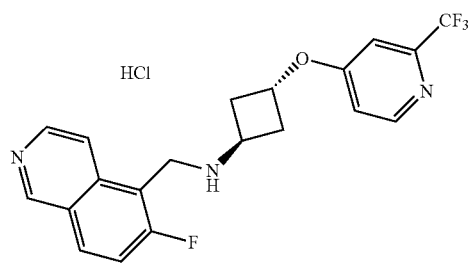 [SMILES: Fc1ccc2cnccc2c1CN[C@H]1C[C@H](Oc2ccnc(C(F)(F)F)c2)C1 ; Cl]

The title compound was synthesized following the procedure as described in Step 1.4, using (1r,3r)-3-((2-(trifluoromethyl)pyridin-4-yl)oxy)cyclobutan-1-amine, HCl (Step 16.2, 306 mg, 1.14 mmol) and 6-fluoroisoquinoline-5-carbaldehyde (Step 3.1, 200 mg, 1.14 mmol). The crude product was purified by prep-HPLC (Column: WATERS X BRIDGE (150 mm×21.2 mm), 5.0μ; Mobile Phase: 0.02% NH$_4$OH in water and acetonitrile). The isolated product was stirred with HCl solution (4M in 1,4-dioxane) (5 mL) at rt for 1 h, then concentrated in vacuo, and lyophilized to afford (1r,3r)-N-((6-fluoroisoquinolin-5-yl)methyl)-3-((2-(trifluoromethyl)pyridin-4-yl)oxy)cyclobutan-1-amine, HCl (120 mg, 24%). MS (ESI+) [Method 6A]: m/z 392.1 (M+H); Rt 1.25 min. $^1$H NMR (400 MHz, CD$_3$OD) δ 9.92 (s, 1H), 8.89 (d, J=6.8 Hz, 1H), 8.83-8.79 (m, 2H), 8.56 (d, J=5.6 Hz, 1H), 8.05 (t, J=9.2 Hz, 1H), 7.33 (d, J=2.4 Hz, 1H), 7.16-7.14 (m, 1H), 5.27-5.23 (m, 1H), 4.86 (d, J=1.5 Hz, 2H), 4.35-4.31 (m, 1H), 3.05-2.98 (m, 2H), 2.81-2.74 (m, 2H).

Example 57: Synthesis of (1r,3r)-3-((5,6-difluoropyridin-3-yl)oxy)-N-((6-fluoroisoquinolin-5-yl)methyl)cyclobutan-1-amine, HCl

Step 57.1: Synthesis of 2,3-difluoro-5-(4,4,5,5-tetramethyl-1,3,2-dioxaborolan-2-yl)pyridine

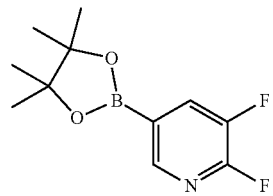 [SMILES: CC1(C)OB(c2cnc(F)c(F)c2)OC1(C)C]

The sealed tube charged with 5-chloro-2,3-difluoropyridine [CAS No. 89402-43-7] (1.0 g, 6.69 mmol), bis(pinacolato)diboron (1.89 g, 8.03 mmol), KOAc (0.98 g, 10.03 mmol), tri-cyclohexyl phosphine (131 mg, 0.47 mmol) and 1,4-dioxane (15 mL) was purged with argon for 15 min. Then Pd$_2$(dba)$_3$ (123 mg, 0.34 mmol) was added and the reaction mixture was stirred at 85° C. for 16 h. Reaction mixture was cooled, filtered through celite bed and the bed was washed with EtOAc. The filtrate was washed with water 3×'s, dried over anhydrous Na₂SO₄, filtered and concentrated in vacuo. The residue was purified by flash chromatography (12 g SiliCycle column, 30% EtOAc in Hexane elution) to afford 2,3-difluoro-5-(4,4,5,5-tetramethyl-1,3,2-dioxaborolan-2-yl)pyridine (1.29 g, 80%). $^1$H NMR (300 MHz, CDCl₃) δ 8.31 (s, 1H), 7.88 (t, J=9.9 Hz, 1H), 1.35 (s, 12H).

Step 57.2: Synthesis of 5,6-difluoropyridin-3-ol

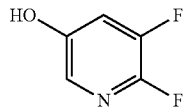

The title compound was prepared according to Step 51.3. The combined organic portion was further washed with brine, dried over anhydrous Na₂SO₄, filtered and concentrated in vacuo. The residue was purified by flash chromatography (12 g SiliCycle column, 20% EtOAc in Hexane elution) to afford 5,6-difluoropyridin-3-ol (415 mg, 64%). MS (ESI+) [Method 6A]: m/z 132.1 (M+H); Rt 0.31 min. $^1$H NMR (300 MHz, CDCl₃) δ 7.58 (t, J=2.4 Hz, 1H), 7.20-7.13 (m, 1H).

Step 57.3: Synthesis of tert-butyl ((1r,3r)-3-((5,6-difluoropyridin-3-yl)oxy)cyclobutyl)carbamate

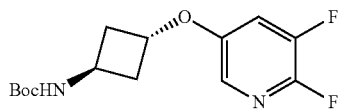 [SMILES: CC(C)(C)OC(=O)N[C@H]1C[C@H](Oc2cnc(F)c(F)c2)C1]

The title compound was synthesized following the procedure as described in Step 1.2, using tert-butyl ((1s,3s)-3-hydroxycyclobutyl)carbamate (593 mg, 3.17 mmol) and 5,6-difluoropyridin-3-ol (415 mg, 3.17 mmol). Crude product was purified by flash chromatography (24 g SiliCycle column, 0-40% EtOAc in Hexane elution) to provide tert-butyl ((1r,3r)-3-((5,6-difluoropyridin-3-yl)oxy)cyclobutyl)carbamate (400 mg, 42%). MS (ESI+) [Method 6A]: m/z 245.1 (M−t-Bu+H); Rt 1.57 min. (600 MHz, CDCl₃) δ 7.44 (d, J=1.8 Hz, 1H), 7.07-7.03 (m, 1H), 4.79-4.76 (m, 1H), 4.33-4.29 (m, 1H), 2.58-2.53 (m, 2H), 2.44-2.39 (m, 2H), 1.45 (s, 9H).

Step 57.4: Synthesis of (1r,3r)-3-((5,6-difluoropyridin-3-yl)oxy)cyclobutan-1-amine, HCl

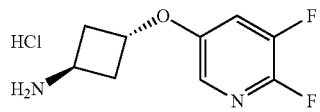 [SMILES: Cl ; N[C@H]1C[C@H](Oc2cnc(F)c(F)c2)C1]

The solution of tert-butyl ((1r,3r)-3-((5,6-difluoropyridin-3-yl)oxy)cyclobutyl)carbamate (200 mg, 0.67 mmol) and HCl solution (4M in 1,4-dioxane) (4 mL) was stirred at rt for 1 h. Then the reaction mixture was concentrated in vacuo. The residue was triturated with Et₂O, solid was filtered and dried to yield (1r,3r)-3-((5,6-difluoropyridin-3-yl)oxy)cy-clobutan-1-amine, HCl (130 mg, 83%). MS (ESI+) [Method 1A]: m/z 201.1 (M+H); Rt 0.58 min. $^1$H NMR (300 MHz, CDCl₃) δ 7.57-7.53 (m, 1H), 7.32-7.26 (m, 1H), 5.06-4.98 (m, 1H), 4.53-4.48 (m, 1H), 2.85-2.78 (m, 2H), 2.63-2.57 (m, 2H).

Step 57.5: Synthesis of (1r,3r)-3-((5,6-difluoropyridin-3-yl)oxy)-N-((6-fluoroisoquinolin-5-yl)methyl)cyclobutan-1-amine, HCl

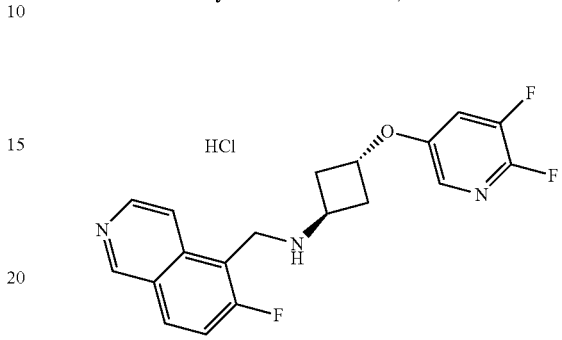

The title compound was synthesized following the procedure as described in Step 1.4, using (1r,3r)-3-((5,6-difluoropyridin-3-yl)oxy)cyclobutan-1-amine, HCl (130 mg, 0.55 mmol) and 6-fluoroisoquinoline-5-carbaldehyde (Step 3.1, 87 mg, 0.49 mmol). The crude product was purified by prep-HPLC (Column: LUNA Phenomenex (250 mm×21.2 mm), 5.0μ; Mobile Phase: 0.02% NH₄OH in water and acetonitrile-MeOH (1:1)). The isolated product was stirred with HCl solution (4M in 1,4-dioxane) (2 mL) at rt for 2 h, then concentrated in vacuo. Residue was triturated with n-pentane. The solid was collected, dried and lyophilized to afford (1r,3r)-3-((5,6-difluoropyridin-3-yl)oxy)-N-((6-fluoroisoquinolin-5-yl)methyl)cyclobutan-1-amine, HCl (50 mg, 25%). MS (ESI+) [Method 6A]: m/z 360.2 (M+H); Rt 1.24 min. $^1$H NMR (400 MHz, CD₃OD) 9.83 (brs, 1H), 8.81-8.71 (m, 3H), 8.00 (t, J=9.2 Hz, 1H), 7.61-7.60 (m, 1H), 7.50-7.45 (m, 1H), 5.10-5.04 (m, 1H), 4.84 (d, J=2.0 Hz, 2H), 4.35-4.27 (m, 1H), 2.94-2.87 (m, 2H), 2.78-2.71 (m, 2H).

Example 58: Synthesis of (1r,3r)-3-((2-fluoro-6-(trifluoromethyl)pyridin-3-yl)oxy)-N-((6-fluoroisoquinolin-5-yl)methyl)cyclobutan-1-amine, HCl Step 58.1: Synthesis of 2-fluoro-3-iodo-6-(trifluoromethyl)pyridine

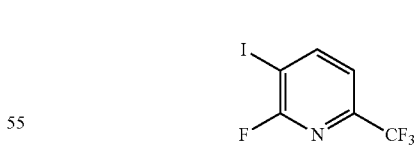

To the solution of 2-fluoro-6-(trifluoromethyl)pyridine [CAS No. 94239-04-0] (0.5 g, 3.02 mmol), in anhydrous THF (10 mL), LDA (2M in THF) (2.2 mL, 4.40 mmol) was added dropwise at −65° C. and stirred for 10 min under N₂. Then I₂ (0.76 g, 3.02 mmol) dissolved in THF (2 mL) was added dropwise, temperature was raised slowly to rt and stirred for 2 h. The reaction was quenched with saturated NH₄Cl solution, then basified with 10% NaOH solution and extracted with EtOAc twice. Then the combined organic portion was washed with brine, dried over Na₂SO₄, filtered and concentrated in vacuo to afford crude 2-fluoro-3-iodo-6-(trifluoromethyl)pyridine (0.7 g, 80%). ¹H NMR (600 MHz, CDCl₃) δ 8.37 (t, J=7.8 Hz, 1H), 7.35 (dd, J=7.8, 1.2 Hz, 1H).

Step 58.2: Synthesis of 2-fluoro-6-(trifluoromethyl)pyridin-3-ol

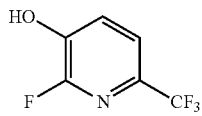

The sealed tube charged with 2-fluoro-3-iodo-6-(trifluoromethyl)pyridine (0.5 g, 1.72 mmol), bis(pinacolato)diboron (0.65 g, 2.56 mmol), KOAc (0.49 g, 4.99 mmol) and 1,4-dioxane (5 mL) was purged with N₂ for 10 min. Then Pd(dppf)Cl₂·CH₂Cl₂ (0.13 g, 0.18 mmol) was added, vessel was closed and stirred at 80° C. After 16 h, the reaction mixture was cooled, acetone (2 mL) and oxone (1.5 g, 2.44 mmol), dissolved in water (2 mL) were added, and stirred at rt for 1 h. Reaction mixture was then diluted with water and extracted with EtOAc 3×'s. The combined filtrate was concentrated in vacuo. The residue was purified by flash chromatography (24 g SiliCycle column, 0-20% EtOAc in Hexane elution) to afford 2-fluoro-6-(trifluoromethyl)pyridin-3-ol (0.1 g, 28%). ¹H NMR (300 MHz, DMSO-d6) δ 11.55 (brs, 1H), 7.69 (t, J=8.4 Hz, 1H), 7.54 (t, J=9.9 Hz, 1H).

Step 58.3: Synthesis of tert-butyl ((1r,3r)-3-((2-fluoro-6-(trifluoromethyl)pyridin-3-yl)oxy)cyclobutyl)carbamate

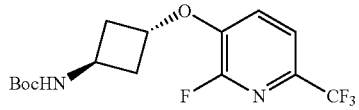 [SMILES: CC(C)(C)OC(=O)N[C@H]1C[C@H](Oc2ccc(C(F)(F)F)nc2F)C1]

The title compound was synthesized following the procedure as described in Step 1.2, using tert-butyl ((1s,3s)-3-hydroxycyclobutyl)carbamate (103 mg, 0.55 mmol) and 2-fluoro-6-(trifluoromethyl)pyridin-3-ol (100 mg, 0.55 mmol). Crude product was purified by flash chromatography (12 g SiliCycle column, 0-10% EtOAc in Hexane elution) to provide tert-butyl ((1r,3r)-3-((2-fluoro-6-(trifluoromethyl)pyridin-3-yl)oxy)cyclobutyl)carbamate (150 mg, 85%). ¹H NMR (300 MHz, CDCl₃) δ 7.48 (d, J=7.8 Hz, 1H), 7.11 (t, J=7.5 Hz, 1H), 4.93-4.87 (m, 1H), 4.32-4.27 (m, 1H), 2.66-2.59 (m, 2H), 2.54-2.48 (m, 2H), 1.45 (s, 9H).

Step 58.4: Synthesis of (1r,3r)-3-((2-fluoro-6-(trifluoromethyl)pyridin-3-yl)oxy)cyclobutan-1-amine, HCl

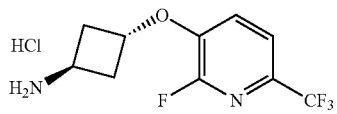 [SMILES: Cl ; N[C@H]1C[C@H](Oc2ccc(C(F)(F)F)nc2F)C1]

The solution of tert-butyl ((1r,3r)-3-((2-fluoro-6-(trifluoromethyl)pyridin-3-yl)oxy)cyclobutyl)carbamate (150 mg, 0.42 mmol) and HCl solution (4M in 1,4-dioxane) (4 mL) was stirred at rt for 1 h. Then the reaction mixture was concentrated in vacuo. The residue was triturated with Et₂O, solid was filtered and dried to afford (1r,3r)-3-((2-fluoro-6-(trifluoromethyl)pyridin-3-yl)oxy)cyclobutan-1-amine, HCl (100 mg, 57%). ¹H NMR (300 MHz, CD₃OD) δ 7.67 (d, J=8.4 Hz, 1H), 7.46 (t, J=8.7 Hz, 1H), 5.13-5.09 (m, 1H), 4.06-4.00 (m, 1H), 2.73-2.68 (m, 4H).

Step 58.5: Synthesis of (1r,3r)-3-((2-fluoro-6-(trifluoromethyl)pyridin-3-yl)oxy)-N-((6-fluoroisoquinolin-5-yl)methyl)cyclobutan-1-amine, HCl

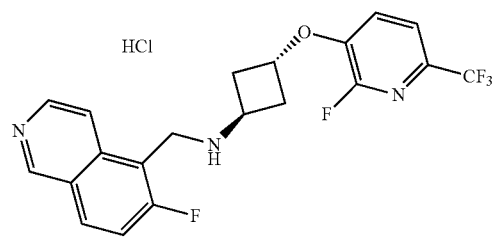 [SMILES: Fc1ccc2cnccc2c1CN[C@H]1C[C@H](Oc2ccc(C(F)(F)F)nc2F)C1 ; Cl]

The title compound was synthesized following the procedure as described in Step 1.4, using (1r,3r)-3-((2-fluoro-6-(trifluoromethyl)pyridin-3-yl)oxy)cyclobutan-1-amine, HCl (50 mg, 0.17 mmol) and 6-fluoroisoquinoline-5-carbaldehyde (Step 3.1, 25 mg, 0.15 mmol). The crude product was purified by prep-HPLC (Column: YMC-ACTUS TRIART C-18 (150 mm×21.2 mm), 5.0μ; Mobile Phase: 0.01% NH₄OH in water and acetonitrile). The isolated product was stirred with HCl solution (4M in 1,4-dioxane) (1 mL) at rt for 1 h, then concentrated in vacuo. Residue was triturated with n-pentane. The solid was collected, dried and lyophilized to afford (1r,3r)-3-((2-fluoro-6-(trifluoromethyl)pyridin-3-yl)oxy)-N-((6-fluoroisoquinolin-5-yl)methyl)cyclobutan-1-amine, HCl (12 mg, 16%). MS (ESI+) [Method 6A]: m/z 410.1 (M+H); Rt 1.28 min. ¹H NMR (400 MHz, CD₃OD) δ 9.86 (brs, 1H), 8.79-8.74 (m, 3H), 8.02 (t, J=9.2 Hz, 1H), 7.70 (d, J=8.4 Hz, 1H), 7.54 (t, J=9.2 Hz, 1H), 5.24-4.99 (m, 1H), 4.85 (d, J=2.0 Hz, 2H), 4.37-4.32 (m, 1H), 3.01-2.96 (m, 2H), 2.85-2.78 (m, 2H).

Example 59: Synthesis of 5-((1r,3r)-3-(((6-fluoroisoquinolin-5-yl)methyl)amino)cyclobutoxy)-2-(trifluoromethyl)benzonitrile, HCl Step 59.1: Synthesis of tert-butyl ((1r,3r)-3-(3-cyano-4-(trifluoromethyl)phenoxy)cyclobutyl)carbamate

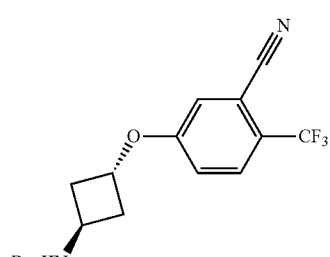

To the solution of tert-butyl ((1r,3r)-3-hydroxycyclobutyl) carbamate (150 mg, 0.80 mmol) in DMF (2 mL), NaH (60% on mineral oil) (48 mg, 2.00 mmol) was added at 0° C., stirred for 5 min. Then and 5-fluoro-2-(trifluoromethyl) benzonitrile [CAS No. 240800-45-7] (182 mg, 0.96 mmol) was added at 0° C. and the reaction mixture was stirred at rt for 16 h under N₂. The reaction mixture was quenched with saturated NH₄Cl solution and stirred for 10 minutes. The solid separated was filtered, washed with water and dried in vacuo to afford crude tert-butyl ((1r,3r)-3-(3-cyano-4-(trifluoromethyl)phenoxy)cyclobutyl)carbamate (25 mg, 87%). MS (ESI+) [Method 6A]: m/z 357.2 (M+H); Rt 1.63 min. ¹H NMR (300 MHz, CDCl₃) δ 7.67 (d, J=8.7 Hz, 1H), 7.16-7.14 (m, 1H), 7.04 (dd, J=9.0, 1.8 Hz, 1H), 4.87-4.79 (m, 1H), 4.33-4.28 (m, 1H), 2.61-2.53 (m, 2H), 2.52-2.43 (m, 2H), 1.45 (s, 9H).

Step 59.2: Synthesis of 5-((1r,3r)-3-aminocyclobutoxy)-2-(trifluoromethyl)benzonitrile, HCl

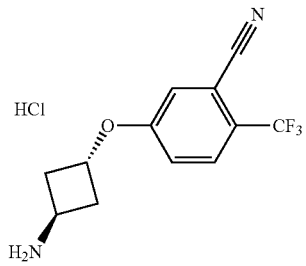 [SMILES: Cl ; N#Cc1cc(O[C@H]2C[C@H](N)C2)ccc1C(F)(F)F]

A round bottom flask was charged with tert-butyl ((1r,3r)-3-(3-cyano-4-(trifluoromethyl)phenoxy)cyclobutyl)carbamate (250 mg, 0.70 mmol) and HCl solution (4M in 1,4-dioxane) (5 mL), and stirred at rt for 2 h. Then the reaction mixture was concentrated in vacuo. The residue was triturated with pentane, the solid appeared was filtered and dried to yield 5-((1r,3r)-3-aminocyclobutoxy)-2-(trifluoromethyl)benzonitrile, HCl (200 mg, 97%). MS (ESI+) [Method 6A]: m/z 256.9 (M+H); Rt 1.31 min.

Step 59.3: Synthesis of 5-((1r,3r)-3-(((6-fluoroisoquinolin-5-yl)methyl)amino)cyclobutoxy)-2-(trifluoromethyl)benzonitrile, HCl

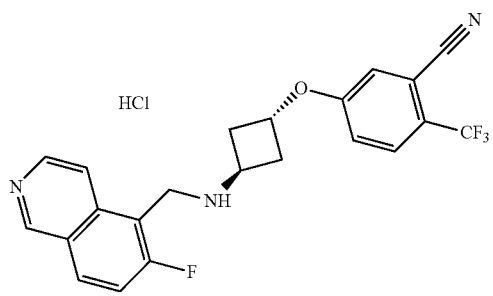 [SMILES: N#Cc1cc(O[C@H]2C[C@H](NCc3c(F)ccc4cnccc34)C2)ccc1C(F)(F)F ; Cl]

The title compound was synthesized following the procedure as described in Step 1.4, using 5-((1r,3r)-3-aminocyclobutoxy)-2-(trifluoromethyl)benzonitrile, HCl (100 mg, 0.34 mmol) and 6-fluoroisoquinoline-5-carbaldehyde (Step 3.1, 54 mg, 0.31 mmol). The crude product was purified by prep-HPLC (Column: XBRIDGE (150 mm×19.0 mm), 5.0μ; Mobile Phase: 0.02% NH₄OH in water and acetonitrile). The isolated product was stirred with HCl solution (4M in 1,4-dioxane) (2 mL) at rt for 2 h, then concentrated in vacuo. Residue was triturated with n-pentane. The solid was collected, dried and lyophilized to afford 5-((1r,3r)-3-(((6-fluoroisoquinolin-5-yl)methyl)amino)cyclobutoxy)-2-(trifluoromethyl)benzonitrile, HCl (40 mg, 26%). MS (ESI+) [Method 6A]: m/z 416.1 (M+H); Rt 1.34 min. ¹H NMR (400 MHz, CD₃OD) δ 9.81 (brs, 1H), 8.85-8.78 (m, 3H), 8.04 (t, J=9.2 Hz, 1H), 7.78 (d, J=8.7 Hz, 1H), 7.51-7.50 (m, 1H), 7.33-7.30 (m, 1H), 5.22-5.17 (m, 1H), 4.87 (d, J=1.6 Hz, 2H), 4.37-4.31 (m, 1H), 3.03-2.97 (m, 2H), 2.81-2.73 (m, 2H).

Example 60: Synthesis of ethyl 5-((1r,3r)-3-(((6-fluoroisoquinolin-5-yl)methyl)amino)cyclobutoxy)-2-(trifluoromethyl)benzoate Step 60.1: Synthesis of ethyl 5-fluoro-2-(trifluoromethyl)benzoate

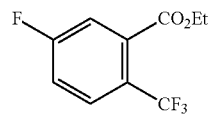

The stirred solution of 5-fluoro-2-(trifluoromethyl) benzoic acid [CAS No. 654-99-9] (3.0 g, 14.42 mmol) and SOCl₂ (3.5 g, 28.84 mmol) in EtOH (100 mL) was heated at 70° C. for 5 h. Reaction mixture was concentrated, basified with saturated NaHCO₃ solution, and then extracted with EtOAc twice. Then the combined organic portion was washed with brine, dried over Na₂SO₄, filtered and concentrated in vacuo. The residue was purified by flash chromatography (40 g SiliCycle column, 15% EtOAc in Hexane elution) to afford ethyl 5-fluoro-2-(trifluoromethyl)benzoate (3.0 g, 88%). ¹H NMR (300 MHz, CDCl₃) δ 7.77-7.73 (m, 1H), 7.50-7.47 (m, 1H), 7.29-7.25 (m, 1H), 4.40 (q, J=7.2 Hz, 2H), 1.39 (t, J=7.2 Hz, 3H).

Step 60.2: Synthesis of ethyl 5-((1r,3r)-3-((tert-butoxycarbonyl)amino)cyclobutoxy)-2-(trifluoromethyl)benzoate

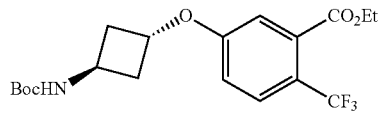 [SMILES: CCOC(=O)c1cc(O[C@H]2C[C@H](NC(=O)OC(C)(C)C)C2)ccc1C(F)(F)F]

To the solution of tert-butyl ((1r,3r)-3-hydroxycyclobutyl) carbamate (1.18 g, 6.35 mmol) in anhydrous DMF (20 mL), NaH (60% on mineral oil) (0.26 g, 6.35 mmol) was added at 0° C. and stirred for 5 min. Then ethyl 5-fluoro-2-(trifluoromethyl)benzoate (1.5 g, 6.35 mmol) was added at 0° C. and stirred for 10 min under N₂. Reaction mixture was poured in ice-water and extracted with EtOAc 3×'s. The combined organic portion was washed with brine, dried over Na₂SO₄, filtered and concentrated in vacuo. The residue was purified by flash chromatography (12 g SiliCycle column, 25% EtOAc in Hexane elution) to afford ethyl 5-((1r,3r)-3-((tert-butoxycarbonyl)amino)cyclobutoxy)-2-(trifluoromethyl)benzoate (500 mg, 18%). ¹H NMR (400 MHz, CDCl₃) δ 7.62 (d, J=8.4 Hz, 1H), 7.12-7.11 (m, 1H), 6.92-6.88 (m, 1H), 4.87-4.82 (m, 1H), 4.38 (q, J=7.2 Hz, 2H), 4.33-4.27 (m, 1H), 2.58-2.52 (m, 2H), 2.47-2.39 (m, 2H), 1.45 (s, 9H), 1.38 (t, J=7.2 Hz, 3H).

Step 60.3: Synthesis of ethyl 5-((1r,3r)-3-aminocyclobutoxy)-2-(trifluoromethyl)benzoate, HCl
[C-07619-021]

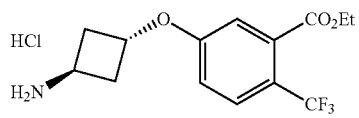

A round bottom flask was charged with ethyl 5-((1r,3r)-3-((tert-butoxycarbonyl)amino)cyclobutoxy)-2-(trifluoromethyl)benzoate (500 mg, 1.24 mmol) and HCl solution (4M in 1,4-dioxane) (10 mL), and stirred at rt for 16 h. Then the reaction mixture was concentrated in vacuo. The residue was triturated with pentane, the solid appeared was filtered and dried to yield ethyl 5-((1r,3r)-3-aminocyclobutoxy)-2-(trifluoromethyl)benzoate, HCl (350 mg, 83%). MS (ESI+) [Method 1A]: m/z 304.6 (M+H); Rt 0.24 min. ¹H NMR (400 MHz, CD₃OD) δ 7.73 (d, J=9.6 Hz, 1H), 7.18-7.17 (m, 1H), 7.08 (dd, J=8.8, 2.0 Hz, 1H), 5.07-5.04 (m, 1H), 4.36 (q, J=7.2 Hz, 2H), 4.03-3.97 (m, 1H), 2.70-2.62 (m, 4H), 1.36 (t, J=7.2 Hz, 3H).

Step 60.4: Synthesis of ethyl 5-((1r,3r)-3-(((6-fluoroisoquinolin-5-yl)methyl)amino)cyclobutoxy)-2-(trifluoromethyl)benzoate [C-08247-017]

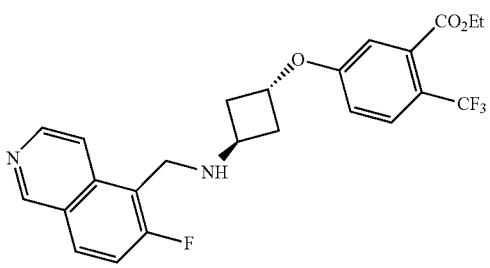 [SMILES: CCOC(=O)c1cc(O[C@H]2C[C@H](NCc3c(F)ccc4cnccc34)C2)ccc1C(F)(F)F]

The round bottom flask fitted with Dean-Stark apparatus, was charged with ethyl 5-((1r,3r)-3-aminocyclobutoxy)-2-(trifluoromethyl)benzoate (150 mg, 0.44 mmol) and benzene (10 mL). Then 6-fluoroisoquinoline-5-carbaldehyde (77 mg, 0.44 mmol) and TEA (45 mg, 0.44 mmol) were added and then refluxed for 16 h. Reaction mixture was concentrated in vacuo, residue was dissolved in MeOH (5 mL), and Na(CN)BH₃ (55 mg, 0.88 mmol) was added at rt and stirred for 3 h. Reaction mixture was concentrated, residue was diluted with EtOAc and washed with saturated NaHCO₃ solution. The organic portion was dried over anhydrous Na₂SO₄, filtered and concentrated in vacuo. The crude product was purified by prep-HPLC (Column: UNA Phenomenex (250 mm×21.2 mm), 5.0µ; Mobile Phase: 0.1% HCO₂H in water and acetonitrile) to afford ethyl 5-((1r,3r)-3-(((6-fluoroisoquinolin-5-yl)methyl)amino)cyclobutoxy)-2-(trifluoromethyl)benzoate (20 mg, 9%). MS (ESI+) [Method 5A]: m/z 463.2 (M+H); Rt 1.17 min. ¹H NMR (400 MHz, CD₃OD) δ 9.88 (brs, 1H), 8.83-8.74 (m, 3H), 8.03 (t, J=8.4 Hz, 1H), 7.74 (d, J=8.8 Hz, 1H), 7.21-7.20 (m, 1H), 7.13-7.99 (m, 1H), 5.16-5.12 (m, 1H), 4.84 (s, 2H), 4.37 (q, J=7.2 Hz, 2H), 4.33-4.27 (m, 1H), 2.98-2.92 (m, 2H), 2.77-2.70 (m, 2H), 1.36 (t, J=7.2 Hz, 3H).

Example 61: Synthesis of 2-((1r,3r)-3-(((6-fluoroisoquinolin-5-yl)methyl)amino)cyclobutoxy)-6-(trifluoromethyl)benzonitrile, HCl Step 61.1: Synthesis of tert-butyl ((1r,3r)-3-(2-cyano-3-(trifluoromethyl)phenoxy)cyclobutyl)carbamate

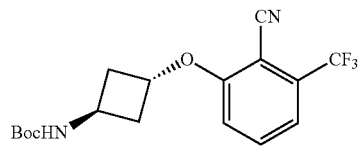 [SMILES: CC(C)(C)OC(=O)N[C@H]1C[C@H](Oc2cccc(C(F)(F)F)c2C#N)C1]

To the solution of tert-butyl ((1r,3r)-3-hydroxycyclobutyl)carbamate (800 mg, 4.27 mmol) in DMF (15 mL), NaH (60% on mineral oil) (154 mg, 6.41 mmol) was added at 0° C., stirred for 1 h. Then 2-fluoro-6-(trifluoromethyl)benzonitrile [CAS No. 133116-83-3] (1.2 g, 6.41 mmol) was added at 0° C. and reaction mixture was stirred at rt for 16 h under N₂. The reaction mixture was diluted with water, and extracted with EtOAc twice. The combined organic portion was washed with a brine solution, dried over anhydrous Na₂SO₄, filtered and concentrated in vacuo. The residue was purified by flash chromatography (12 g SiliCycle column, 0-35% EtOAc in Hexane elution) to provide tert-butyl ((1r,3r)-3-(2-cyano-3-(trifluoromethyl)phenoxy)cyclobutyl)carbamate (485 mg, 31%). ¹H NMR (400 MHz, CDCl₃) δ 7.59 (t, J=8.0 Hz, 1H), 7.33 (d, J=8.0 Hz, 1H), 6.94 (dd, J=8.8 Hz, 1H), 4.97-4.92 (m, 1H), 4.32-4.27 (m, 1H), 2.69-2.63 (m, 2H), 2.59-2.52 (m, 2H), 1.45 (s, 9H).

Step 61.2: Synthesis of 2-((1r,3r)-3-aminocyclobutoxy)-6-(trifluoromethyl)benzonitrile, HCl

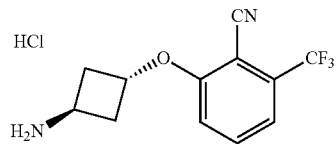 [SMILES: Cl ; N#Cc1c(O[C@H]2C[C@H](N)C2)cccc1C(F)(F)F]

A round bottom flask was charge with tert-butyl ((1r,3r)-3-(2-cyano-3-(trifluoromethyl)phenoxy)cyclobutyl)carbamate (250 mg, 0.70 mmol) and HCl solution (4M in 1,4-dioxane) (2.5 mL), and stirred at rt for 3 h. Then the reaction mixture was concentrated in vacuo. The residue was triturated with pentane, the solid appeared was filtered and dried to yield 2-((1r,3r)-3-aminocyclobutoxy)-6-(trifluoromethyl)benzonitrile, HCl (175 mg, 85%). ¹H NMR (300 MHz, DMSO-d6) δ 8.27 (brs, 3H), 7.88 (t, J=8.7 Hz, 1H), 7.57 (d, J=8.1 Hz, 1H), 7.35 (d, J=8.4 Hz, 1H), 5.25-5.19 (m, 1H), 3.92-3.86 (m, 1H), 2.73-2.65 (m, 2H), 2.59-2.52 (m, 2H).

Step 61.3: Synthesis of 2-((1r,3r)-3-(((6-fluoroisoquinolin-5-yl)methyl)amino)cyclobutoxy)-6-(trifluoromethyl)benzonitrile, HCl

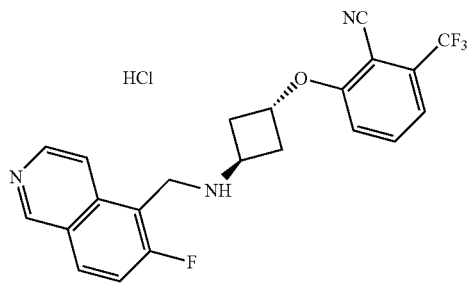 [SMILES: N#Cc1c(O[C@H]2C[C@H](NCc3c(F)ccc4cnccc34)C2)cccc1C(F)(F)F ; Cl]

The title compound was synthesized following the procedure as described in Step 1.4, using 2-((1r,3r)-3-aminocyclobutoxy)-6-(trifluoromethyl)benzonitrile, HCl (175 mg, 0.6 mmol) and 6-fluoroisoquinoline-5-carbaldehyde (Step 3.1, 95 mg, 0.54 mmol). The crude product was purified by flash chromatography (12 g SiliCycle column, 0-10% MeOH in CH$_2$Cl$_2$ elution), followed by prep-HPLC (Column: LUNA Phenomenex (150 mm×21.2 mm), 5.0µ; Mobile Phase: 0.1% HCO$_2$H in water and acetonitrile). The isolated product was stirred with HCl solution (4M in 1,4-dioxane) (2 mL) at rt for 2 h, then concentrated in vacuo and lyophilized to afford 2-((1r,3r)-3-(((6-fluoroisoquinolin-5-yl)methyl)amino)cyclobutoxy)-6-(trifluoromethyl)benzonitrile, HCl (5 mg, 2%). MS (ESI+) [Method 6A]: m/z 416.2 (M+H); Rt 1.31 min. $^1$H NMR (400 MHz, DMSO-d6) δ 9.92 (brs, 2H), 8.70 (brs, 1H), 8.59-8.55 (m, 1H), 7.94-7.88 (m, 2H), 7.58 (d, J=8.0 Hz, 1H), 7.38 (d, J=8.8 Hz, 1H), 5.28-5.24 (m, 1H), 4.63 (s, 2H), 4.18-4.13 (m, 1H), 2.94-2.88 (m, 2H), 2.60-2.53 (m, 2H).

Example 62: Synthesis of (1r,3r)-3-((6-chloro-5-(trifluoromethyl)pyridin-3-yl)oxy)-N-((6-fluoroisoquinolin-5-yl)methyl)cyclobutan-1-amine, HCl

Step 62.1: Synthesis of tert-butyl ((1r,3r)-3-((6-chloro-5-(trifluoromethyl)pyridin-3-yl)oxy)cyclobutyl)carbamate

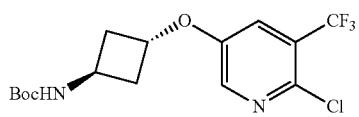 [SMILES: CC(C)(C)OC(=O)N[C@H]1C[C@H](Oc2cnc(Cl)c(C(F)(F)F)c2)C1]

A sealed tube was charged with 2-chloro-5-iodo-3-(trifluoromethyl)pyridine [CAS No. 887707-25-7] (1.0 g, 3.25 mmol), tert-butyl ((1r,3r)-3-hydroxycyclobutyl)carbamate (0.91 g, 4.88 mmol), Cs$_2$CO$_3$ (1.58 g, 4.88 mmol) and toluene (15 mL), and purged with N$_2$ for 10 min. Then CuI (31 mg, 0.16 mmol) and 3,4,7,8-tetramethyl-1,10-phenanthroline were added, purged with N$_2$, sealed tube was closed and stirred at 110° C. for 16 h. Reaction was cooled to rt, filtered through celite bed and the bed was washed with EtOAc. The filtrate was concentrated in vacuo and the residue was purified by flash chromatography (12 g SiliCycle column, 0-20% EtOAc in Hexane elution) to afford tert-butyl ((1r,3r)-3-((6-chloro-5-(trifluoromethyl)pyridin-3-yl)oxy)cyclobutyl)carbamate (0.2 g, 17%). MS (ESI+) [Method 6A]: m/z 366.8 (M+H); Rt 1.63 min. $^1$H NMR (300 MHz, CDCl$_3$) δ 8.08 (d, J=3.0 Hz, 1H), 7.40 (d, J=3.0 Hz, 1H), 4.88-4.81 (m, 1H), 4.35-4.28 (m, 1H), 2.62-2.53 (m, 2H), 2.51-2.42 (m, 2H), 1.45 (s, 9H).

Step 62.2: Synthesis of (1r,3r)-3-((6-chloro-5-(trifluoromethyl)pyridin-3-yl)oxy)cyclobutan-1-amine, HCl

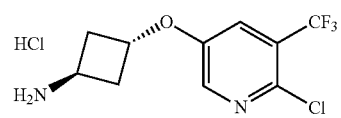 [SMILES: Cl ; N[C@H]1C[C@H](Oc2cnc(Cl)c(C(F)(F)F)c2)C1]

A round bottom flask was charge with tert-butyl ((1r,3r)-3-((6-chloro-5-(trifluoromethyl)pyridin-3-yl)oxy)cyclobutyl)carbamate (100 mg, 0.27 mmol) and HCl solution (4M in 1,4-dioxane) (4 mL), and stirred at rt for 4 h. Then the reaction mixture was concentrated in vacuo to yield (1r,3r)-3-((6-chloro-5-(trifluoromethyl)pyridin-3-yl)oxy)cyclobutan-1-amine, HCl (70 mg, 85%). MS (ESI+) [Method 6A]: m/z 308.0 (M+MeCN+H); Rt 1.28 min.

Step 62.3: Synthesis of (1r,3r)-3-((6-chloro-5-(trifluoromethyl)pyridin-3-yl)oxy)-N-((6-fluoroisoquinolin-5-yl)methyl)cyclobutan-1-amine, HCl

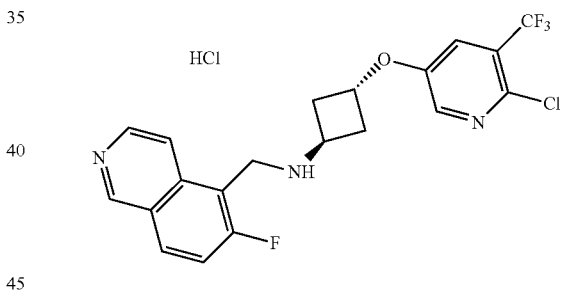

The title compound was synthesized following the procedure as described in Step 1.4, using (1r,3r)-3-((6-chloro-5-(trifluoromethyl)pyridin-3-yl)oxy)cyclobutan-1-amine, HCl (70 mg, 0.23 mmol) and 6-fluoroisoquinoline-5-carbaldehyde (Step 3.1, 37 mg, 0.21 mmol). The crude product was purified by prep-HPLC (Column: XBRIDGE C18 (150 mm×19.0 mm), 5.0µ; Mobile Phase: 0.01% NH$_4$OH in water and acetonitrile-MeOH (1:1). The isolated product was stirred with HCl solution (4M in 1,4-dioxane) (1 mL) at rt for 2 h, then concentrated in vacuo and triturated with Et$_2$O. The solid was collected and dried to afford (1r,3r)-3-((6-chloro-5-(trifluoromethyl)pyridin-3-yl)oxy)-N-((6-fluoroisoquinolin-5-yl)methyl)cyclobutan-1-amine, HCl (13 mg, 13%). MS (ESI+) [Method 6A]: m/z 426.0 (M+H); Rt 1.31 min. $^1$H NMR (400 MHz, CD$_3$OD) δ 9.31 (s, 1H), 8.60 (d, J=6.0 Hz, 1H), 8.30-8.26 (m, 1H), 8.20 (d, J=2.8 Hz, 1H), 8.14 (d, J=6.4 Hz, 1H), 7.66-7.59 (m, 2H), 5.07-5.01 (m, 1H), 4.43 (d, J=2.0 Hz, 2H), 3.93-3.87 (m, 1H), 2.60-2.54 (m, 4H).

Example 63: Synthesis of N-(4-fluoro-3-(trifluoromethyl)phenyl)-N³-((6-fluoroisoquinolin-5-yl)methyl)cyclobutane-1,3-diamine

Step 63.1: Synthesis of tert-butyl (3-((4-fluoro-3-(trifluoromethyl)phenyl)amino)cyclobutyl)carbamate

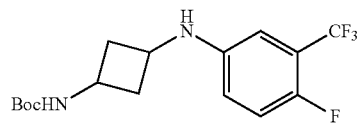 [SMILES: CC(C)(C)OC(=O)NC1CC(Nc2ccc(F)c(C(F)(F)F)c2)C1]

To the stirred solution of tert-butyl (3-oxocyclobutyl)carbamate [CAS No. 154748-49-9] (0.5 g, 2.70 mmol) and 4-fluoro-3-(trifluoromethyl)aniline [CAS No. 2357-47-3] (1.4 g, 8.10 mmol) in MeOH (10 mL), AcOH (0.2 mL, 3.78 mmol) and NaCNBH$_3$ (0.25 g, 4.05 mmol) were added at rt.

The reaction mixture was stirred at rt for 3 h. Reaction mixture was diluted with water and extracted with EtOAc twice. The combined organic portion was washed with brine solution, dried over anhydrous Na$_2$SO$_4$, filtered and concentrated in vacuo. The residue was purified by flash chromatography (4 g SiliCycle column, 0-15% EtOAc in Hexane elution) to provide tert-butyl (3-((4-fluoro-3-(trifluoromethyl)phenyl)amino)cyclobutyl)carbamate (0.6 g, 64%) MS (ESI+) [Method 6A]: m/z 349.1 (M+H); Rt 1.63 min. $^1$H NMR (300 MHz, CDCl$_3$) δ 6.99 (t, J=9.3 Hz, 1H), 6.68-6.59 (m, 2H), 3.87-3.83 (m, 1H), 3.56-3.50 (m, 1H), 2.92-2.87 (m, 2H), 1.75-1.66 (m, 2H), 1.44 (s, 9H).

Step 63.2: Synthesis of N¹-(4-fluoro-3-(trifluoromethyl)phenyl)cyclobutane-1,3-diamine, HCl

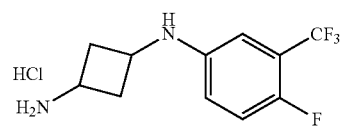 [SMILES: Cl ; NC1CC(Nc2ccc(F)c(C(F)(F)F)c2)C1]

A round bottom flask was charged with tert-butyl (3-((4-fluoro-3-(trifluoromethyl)phenyl)amino)cyclobutyl)carbamate (300 mg, 0.86 mmol) and HCl solution (4M in 1,4-dioxane) (2 mL), and stirred at rt for 4 h. Then the reaction mixture was concentrated in vacuo to yield N¹-(4-fluoro-3-(trifluoromethyl)phenyl)cyclobutane-1,3-diamine, HCl (240 mg, 97%). MS (ESI+) [Method 6A]: m/z 249.1 (M+H); Rt 1.30 min. $^1$H NMR (300 MHz, DMSO-d6) δ 8.30 (brs, 1H), 7.26-7.18 (m, 1H), 6.79-6.70 (m, 2H), 3.64-3.59 (m, 1H), 3.45-3.39 (m, 1H), 2.73-2.64 (m, 2H), 2.00-1.90 (m, 2H).

Step 63.3: Synthesis of N¹-(4-fluoro-3-(trifluoromethyl)phenyl)-N³-((6-fluoroisoquinolin-5-yl)methyl)cyclobutane-1,3-diamine

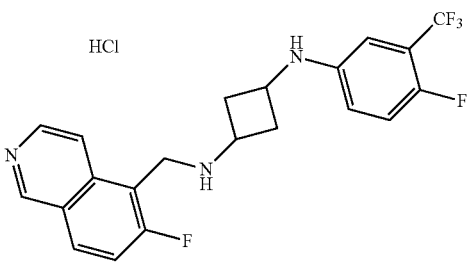 [SMILES: Fc1ccc(NC2CC(NCc3c(F)ccc4cnccc34)C2)cc1C(F)(F)F ; Cl]

The title compound was synthesized following the procedure as described in Step 1.4, using N¹-(4-fluoro-3-(trifluoromethyl)phenyl)cyclobutane-1,3-diamine, HCl (240 mg, 0.84 mmol) and 6-fluoroisoquinoline-5-carbaldehyde (Step 3.1, 132 mg, 0.76 mmol) and AcOH (0.01 mL). Prep-HPLC of the crude (Column: LUNA Phenomenex (250 mm×21.2 mm), 5.0μ; Mobile Phase: 0.1% HCO$_2$H in water and acetonitrile) afforded two peaks of N¹-(4-fluoro-3-(trifluoromethyl)phenyl)-N³-((6-fluoroisoquinolin-5-yl)methyl)cyclobutane-1,3-diamine. Peak-1: (15 mg, 4%). MS (ESI+) [Method 6A]: m/z 408.2 (M+H); Rt 1.30 min. $^1$H NMR (400 MHz, CD$_3$OD) δ 9.91 (s, 1H), 8.93-8.90 (m, 1H), 8.67 (d, J=6.4 Hz, 1H), 8.53 (d, J=6.8 Hz, 1H), 8.21 (d, J=10.4 Hz, 1H), 7.17 (t, J=9.6 Hz, 1H), 7.02-6.94 (m, 2H), 4.57 (s, 2H), 3.91-3.81 (m, 2H), 2.99-2.92 (m, 2H), 2.39-2.33 (m, 2H). Peak-2: (40 mg, 11%). MS (ESI+) [Method 6A]: m/z 408.1 (M+H); Rt 1.31 min. $^1$H NMR (400 MHz, DMSO-d6) δ 10.08 (brs, 2H, exchangeable with D$_2$O), 9.90 (s, 1H), 8.85-8.83 (m, 1H), 8.79-8.77 (m, 1H), 8.74-8.70 (m, 1H), 8.03 (t, J=9.2 Hz, 1H), 7.22 (t, J=9.6 Hz, 1H), 6.81-6.72 (m, 2H), 4.62 (s, 2H), 3.71-3.64 (m, 2H), 2.79-2.71 (m, 2H), 2.21-2.13 (m, 2H).

Example 64: Synthesis of (1r,3r)-3-((3-fluoro-4-(trifluoromethyl)benzyl)oxy)-N-((6-fluoroisoquinolin-5-yl)methyl)cyclobutan-1-amine, HCl

Step 64.1: Synthesis of (3-fluoro-4-(trifluoromethyl)phenyl)methanol

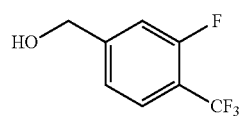

To the solution of 3-fluoro-4-(trifluoromethyl)benzaldehyde [204339-72-0] (1.0 g, 5.21 mmol) in MeOH (10 mL), NaBH$_4$ (295 mg, 7.81 mmol) was added at 0° C. and stirred for 2 h. Then the reaction mixture was diluted with water and extracted with EtOAc 3×'s. The combined organic portion was washed with brine, dried over anhydrous Na$_2$SO$_4$, filtered and concentrated in vacuo to provide crude (3-fluoro-4-(trifluoromethyl)phenyl)methanol (1.2 g, 118%). $^1$H NMR (300 MHz, CDCl$_3$) δ 7.58 (t, J=7.5 Hz, 1H), 7.26-7.20 (m, 2H), 4.78 (s, 2H).

Step 64.2: Synthesis of 4-(bromomethyl)-2-fluoro-1-(trifluoromethyl)benzene

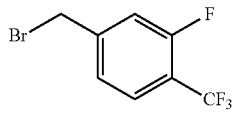

To the solution of (3-fluoro-4-(trifluoromethyl)phenyl)methanol (1.8 g, 9.27 mmol) in Et$_2$O (20 mL), PBr$_3$ (1M in CH$_2$Cl$_2$) (6.5 mL, 6.50 mmol) was added drop wise at 0° C. and then stirred at rt for 2 h. Then the reaction mixture was diluted with ice-water and extracted with EtOAc 3×'s. The combined organic portion was washed with brine, dried over anhydrous Na$_2$SO$_4$, filtered and concentrated in vacuo. The residue was purified by flash chromatography (12 g SiliCycle column, 0-10% EtOAc in Hexane elution) to provide 4-(bromomethyl)-2-fluoro-1-(trifluoromethyl)benzene (0.8 g, 33%). $^1$H NMR (600 MHz, CDCl$_3$) δ 7.58 (t, J=7.8 Hz, 1H), 7.27-7.24 (m, 2H), 4.45 (s, 2H).

Step 64.3: Synthesis of tert-butyl ((1r,3r)-3-((3-fluoro-4-(trifluoromethyl)benzyl)oxy)cyclobutyl)carbamate

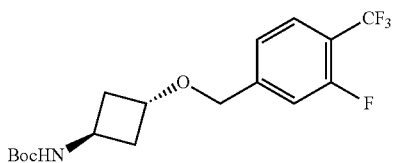 [SMILES: CC(C)(C)OC(=O)N[C@H]1C[C@H](OCc2ccc(C(F)(F)F)c(F)c2)C1]

To the solution of tert-butyl ((1r,3r)-3-hydroxycyclobutyl)carbamate (200 mg, 1.07 mmol) in DMF (5 mL), NaH (60% on mineral oil) (39 mg, 0.44 mmol) was added at 0° C., stirred for 30 min. Then 4-(bromomethyl)-2-fluoro-1-(trifluoromethyl)benzene (358 mg, 1.39 mmol) was added and the reaction mixture was stirred at rt for 16 h under N$_2$. The reaction mixture was diluted with ice-water, and extracted with EtOAc 3×'s. The combined organic portion was washed with brine solution, dried over anhydrous Na$_2$SO$_4$, filtered and concentrated in vacuo. The residue was purified by flash chromatography (12 g SiliCycle column, 0-15% EtOAc in Hexane elution) to provide tert-butyl ((1r,3r)-3-((3-fluoro-4-(trifluoromethyl)benzyl)oxy)cyclobutyl)carbamate (275 mg, 71%). $^1$H NMR (400 MHz, DMSO-d6) δ 7.77 (t, J=8.0 Hz, 1H), 7.43 (d, J=12.0 Hz, 1H), 7.37 (d, J=8.0 Hz, 1H), 7.22 (d, J=7.6 Hz, 1H), 4.46 (s, 2H), 4.14-4.10 (m, 1H), 4.03-3.98 (m, 1H), 2.25-2.19 (m, 2H), 2.14-2.07 (m, 2H), 1.37 (s, 9H).

Step 64.4: Synthesis of (1r,3r)-3-((3-fluoro-4-(trifluoromethyl)benzyl)oxy)cyclobutan-1-amine, HCl

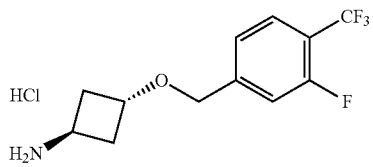 [SMILES: Cl ; N[C@H]1C[C@H](OCc2ccc(C(F)(F)F)c(F)c2)C1]

A solution of tert-butyl ((1r,3r)-3-((3-fluoro-4-(trifluoromethyl)benzyl)oxy)cyclobutyl)carbamate (275 mg, 0.76 mmol) and HCl solution (4M in 1,4-dioxane) (3 mL), was stirred at rt for 3 h. Then the reaction mixture was concentrated in vacuo to yield crude (1r,3r)-3-((3-fluoro-4-(trifluoromethyl)benzyl)oxy)cyclobutan-1-amine, HCl (170 mg, 75%). $^1$H NMR (300 MHz, DMSO-d6) δ 8.15 (brs, 3H), 7.78 (t, J=8.4 Hz, 1H), 7.45 (d, J=8.7 Hz, 1H), 7.37 (d, J=8.4 Hz, 1H), 4.49 (s, 2H), 4.33-4.28 (m, 1H), 3.77-3.73 (m, 1H), 2.33 (t, J=6.6 Hz, 4H).

Step 64.5: Synthesis of (1r,3r)-3-((3-fluoro-4-(trifluoromethyl)benzyl)oxy)-N-((6-fluoroisoquinolin-5-yl)methyl)cyclobutan-1-amine, HCl

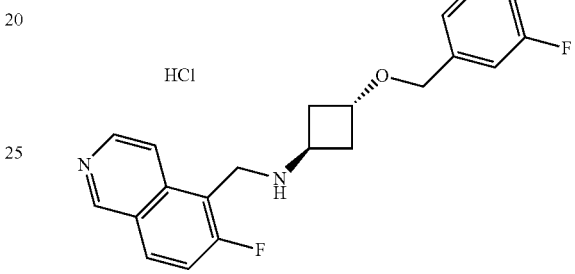

The title compound was synthesized following the procedure as described in Step 25.6, using (1r,3r)-3-((3-fluoro-4-(trifluoromethyl)benzyl)oxy)cyclobutan-1-amine, HCl (100 mg, 0.33 mmol) and 6-fluoroisoquinoline-5-carbaldehyde (Step 3.1, 53 mg, 0.30 mmol). Prep-HPLC (Column: LUNA Phenomenex (250 mm×21.2 mm), 5.0μ; Mobile Phase: 0.1% HCO$_2$H in water and acetonitrile-MeOH (1:1)) of the crude, followed by treatment with HCl solution (4M in 1,4-dioxane) afforded (1r,3r)-3-((3-fluoro-4-(trifluoromethyl)benzyl)oxy)-N-((6-fluoroisoquinolin-5-yl)methyl)cyclobutan-1-amine, HCl (70 mg, 45%). MS (ESI+) [Method 4B]: m/z 423.2 (M+H); Rt 1.01 min. $^1$H NMR (400 MHz, CD$_3$OD) δ 9.85 (s, 1H), 8.80-8.74 (m, 3H), 8.01 (t, J=9.6 Hz, 1H), 7.69 (t, J=8.0 Hz, 1H), 7.39-7.35 (m, 2H), 4.81 (d, J=2.0 Hz, 2H), 4.59 (s, 2H), 4.42-4.38 (m, 1H), 4.25-4.20 (m, 1H), 2.64 (t, J=7.2 Hz, 4H).

Example 65: Synthesis of N-((1r,3r)-3-(4-fluoro-3-(trifluoromethyl)phenoxy)cyclobutyl)-2-(isoquinolin-5-yl)acetamide

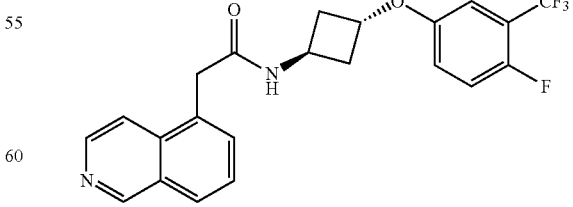

To the stirred solution of 2-(isoquinolin-5-yl)acetic acid [CAS No. 395074-85-8] (300 mg, 1.60 mmol) in DMF (10 mL), HATU (913 mg, 2.40 mmol) was added. After 15 min, DIPEA (0.57 mL, 3.21 mmol) and (1r,3r)-3-(4-fluoro-3-

(trifluoromethyl)phenoxy)cyclobutan-1-amine, HCl (Step 1.3, 455 mg, 1.60 mmol) were added and stirred at rt for 16 h. Reaction mixture was diluted with water and extracted with EtOAc twice. The combined organic portion was washed with brine solution, dried over anhydrous Na₂SO₄, filtered and concentrated in vacuo. The residue was purified by flash chromatography (4 g SiliCycle column, 3% MeOH in CHCl₃ elution) and the isolated product was re-purified by prep-HPLC (Column: KINETEX EVO C18 (150 mm×19.0 mm), 5.0μ; Mobile Phase: 0.02% NH₄OH in water and acetonitrile) to afford N-((1r,3r)-3-(4-fluoro-3-(trifluoromethyl)phenoxy)cyclobutyl)-2-(isoquinolin-5-yl)acetamide. MS (ESI+) [Method 4B]: m/z 419.4 (M+H); Rt 1.38 min. $^1$H NMR (400 MHz, CD₃OD) δ 9.23 (s, 1H), 8.47 (d, J=6.8 Hz, 1H), 8.04 (d, J=8.4 Hz, 1H), 7.99 (d, J=6.0 Hz, 1H), 7.74 (d, J=6.4 Hz, 1H), 7.66 (dd, J=8.0, 6.8 Hz, 1H), 7.23 (t, J=9.6 Hz, 1H), 7.07-7.02 (m, 2H), 4.89-4.84 (m, 1H), 4.47-4.40 (m, 1H), 4.02 (s, 2H), 2.51-2.47 (m, 4H).

Example 66: Synthesis of N-(2-(6-fluoro-5-((((1r, 3r)-3-(4-fluoro-3-(trifluoromethyl)phenoxy)cyclobutyl)amino)methyl)isoquinolin-8-yl)-2-hydroxyethyl)methanesulfonamide Step 66.1: Synthesis of 8-(((tert-butyldimethylsilyl)oxy)methyl)-5-(1,3-dioxolan-2-yl)-6-fluoroisoquinoline

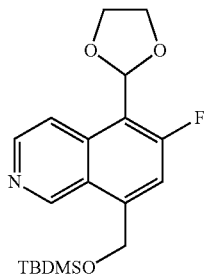 [SMILES: CC(C)(C)[Si](C)(C)OCc1cc(F)c(C2OCCO2)c2ccncc12]

To the stirred solution of 8-(((tert-butyldimethylsilyl)oxy)methyl)-6-fluoroisoquinoline-5-carbaldehyde (Step 6.9, 7.0 g, 21.91 mmol) and PTSA (0.83 g, 4.38 mmol) in EtOH-C₆H₆ (150 mL, 1:4 v/v), in a round bottom fitted with Dean-Stark apparatus, ethylene glycol (4.9 mL, 87.65 mmol) was added at rt. Then the reaction mixture was heated at 100° C. for 24 h. Reaction mixture was cooled to rt, quenched with saturated NaHCO₃ solution and extracted with EtOAc twice. The combined organic portion was washed with water, brine, dried over anhydrous Na₂SO₄, filtered and concentrated in vacuo to yield the crude product. The crude was purified by flash chromatography (40 g SiliCycle column, 0-10% EtOAc in Hexane elution, followed by 0-10% MeOH in CH₂Cl₂ elution) to provide 8-(((tert-butyldimethylsilyl)oxy)methyl)-5-(1,3-dioxolan-2-yl)-6-fluoroisoquinoline (3.0 g, 37%). MS (ESI+) [Method 6A]: m/z 364.2 (M+H); Rt 1.66 min.

Step 66.2: Synthesis of (5-(1,3-dioxolan-2-yl)-6-fluoroisoquinolin-8-yl)methanol

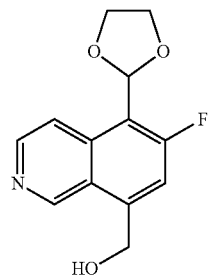 [SMILES: OCc1cc(F)c(C2OCCO2)c2ccncc12]

To the solution of 8-(((tert-butyldimethylsilyl)oxy)methyl)-5-(1,3-dioxolan-2-yl)-6-fluoroisoquinoline (3.0 g, 8.25 mmol) in THF (50 mL), TBAF solution (1M in THF) (9.9 mL, 9.90 mmol) was added dropwise at 0° C. and stirred for 1 h. Reaction mixture was diluted with water and extracted with EtOAc twice. The combined organic portion was washed with brine solution, dried over anhydrous Na₂SO₄, filtered and concentrated in vacuo. The residue was triturated with pentane and dried to provide (5-(1,3-dioxolan-2-yl)-6-fluoroisoquinolin-8-yl)methanol (2.0 g, 97%). MS (ESI+) [Method 1A]: m/z 250.3 (M+H); Rt 0.12 min.

Step 66.3: Synthesis of 5-(1,3-dioxolan-2-yl)-6-fluoroisoquinoline-8-carbaldehyde

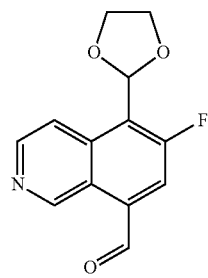 [SMILES: O=Cc1cc(F)c(C2OCCO2)c2ccncc12]

To the stirred solution of (5-(1,3-dioxolan-2-yl)-6-fluoroisoquinolin-8-yl)methanol (2.0 g, 8.02 mmol) in CHCl₃ (40 mL), activated MnO₂ (6.97 g, 80.24 mmol) was added and heated at 70° C. for 2 h, under N₂. The reaction mixture was cooled to rt, filtered through celite bed and the bed was washed with chloroform. The combined filtrate was concentrated in vacuo to get crude compound. The crude was purified by flash chromatography (24 g SiliCycle column, 0-70% EtOAc in hexane elution) to provide 5-(1,3-dioxolan-2-yl)-6-fluoroisoquinoline-8-carbaldehyde (1.3 g, 65%). MS (ESI+) [Method 6A]: m/z 248.2 (M+H); Rt 1.29 min.

Step 66.4: Synthesis of 1-(5-(1,3-dioxolan-2-yl)-6-fluoroisoquinolin-8-yl)-2-nitroethan-1-ol

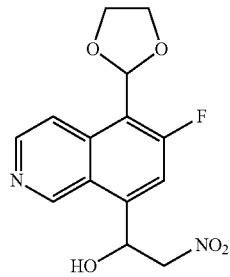 [SMILES: O=[N+]([O-])CC(O)c1cc(F)c(C2OCCO2)c2ccncc12]

To the solution of 5-(1,3-dioxolan-2-yl)-6-fluoroisoquinoline-8-carbaldehyde (1.3 g, 5.26 mmol) in anhydrous THF (15 mL), MeNO$_2$ (0.56 mL, 10.51 mmol) and K$_2$CO$_3$ (0.14 g, 1.05 mmol) were added, and stirred at rt for 16 h under N$_2$. Reaction mixture was diluted with water and extracted with EtOAc twice. The combined organic portion was washed with brine solution, dried over anhydrous Na$_2$SO$_4$, filtered and concentrated in vacuo to provide crude 1-(5-(1,3-dioxolan-2-yl)-6-fluoroisoquinolin-8-yl)-2-nitroethan-1-ol (1.2 g, 74%). MS (ESI+) [Method 1A]: m/z 309.1 (M+H); Rt 0.19 min.

Example 66.5: Synthesis of 8-(1-((tert-butyldimethylsilyl)oxy)-2-nitroethyl)-5-(1,3-dioxolan-2-yl)-6-fluoroisoquinoline

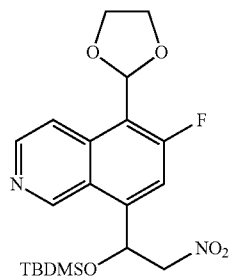 [SMILES: CC(C)(C)[Si](C)(C)OC(C[N+](=O)[O-])c1cc(F)c(C2OCCO2)c2ccncc12]

To the stirred solution of 1-(5-(1,3-dioxolan-2-yl)-6-fluoroisoquinolin-8-yl)-2-nitroethan-1-ol (1.2 g, 3.89 mmol) and imidazole (1.32 g, 19.46 mmol) in DMF (15 mL), TBDMS-Cl (1.76 g, 11.67 mmol) was added portion wise at 0° C. The reaction mixture was stirred at rt for 16 h under N$_2$. Then the reaction mixture was diluted with water and extracted with EtOAc twice. The combined organic portion was washed with brine, dried over anhydrous Na$_2$SO$_4$, filtered and concentrated in vacuo. The residue was purified by flash chromatography (12 g SiliCycle column, 0-10% EtOAc in hexane elution) to afford 8-(1-((tert-butyldimethylsilyl)oxy)-2-nitroethyl)-5-(1,3-dioxolan-2-yl)-6-fluoroisoquinoline (1.1 g, 67%). MS (ESI+) [Method 1A]: m/z 423.4 (M+H); Rt 1.90 min.

Step 66.6: Synthesis of 2-(5-(1,3-dioxolan-2-yl)-6-fluoroisoquinolin-8-yl)-2-((tert-butyldimethylsilyl)oxy)ethan-1-amine

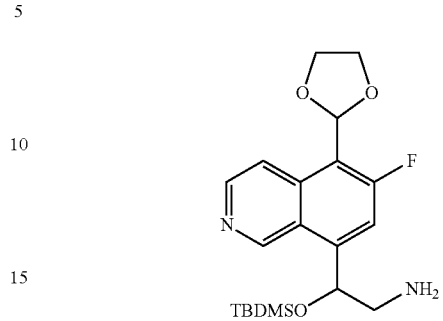

To the stirred solution of 8-(1-((tert-butyldimethylsilyl)oxy)-2-nitroethyl)-5-(1,3-dioxolan-2-yl)-6-fluoroisoquinoline (1.1 g, 2.60 mmol) in MeOH—H$_2$O (90 mL, 8:1 v/v), NH$_4$Cl (2.08 g, 39.05 mmol) was added. The reaction mixture was cooled to 0° C. and Zn-dust (2.55 g, 39.05 mmol) was added portion wise. The reaction mixture was stirred at rt for 16 h. The reaction mixture was filtered through a celite bed, which was washed with MeOH. The combined filtrate was concentrated in vacuo. The residue was diluted with CH$_2$Cl$_2$, washed with saturated NaHCO$_3$ solution, brine, dried over anhydrous Na$_2$SO$_4$, filtered and concentrated in vacuo to yield crude 2-(5-(1,3-dioxolan-2-yl)-6-fluoroisoquinolin-8-yl)-2-((tert-butyldimethylsilyl)oxy)ethan-1-amine (0.9 g, 88%). MS (ESI+) [Method 3A]: m/z 393.0 (M+H); Rt 1.31 min.

Step 66.7: Synthesis of N-(2-(5-(1,3-dioxolan-2-yl)-6-fluoroisoquinolin-8-yl)-2-((tert-butyldimethylsilyl)oxy)ethyl)methanesulfonamide

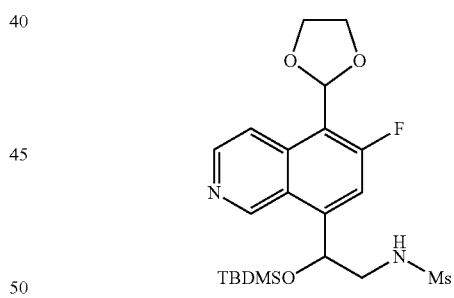

The stirred solution of 2-(5-(1,3-dioxolan-2-yl)-6-fluoroisoquinolin-8-yl)-2-((tert-butyldimethylsilyl)oxy)ethan-1-amine (0.22 g, 0.56 mmol) and TEA (0.31 mL, 2.24 mmol) in anhydrous CH$_2$Cl$_2$ (4 mL) was cooled to 0° C. Then Ms$_2$O (0.19 g, 1.12 mmol) dissolved in CH$_2$Cl$_2$ (2 mL) was added dropwise and the reaction mixture was stirred at rt for 16 h under N$_2$. Reaction mixture was diluted with water and extracted with CH$_2$Cl$_2$ twice. The combined organic portion was washed with brine, dried over anhydrous Na$_2$SO$_4$, filtered and concentrated in vacuo to yield the crude product. The crude was purified by flash chromatography (12 g SiliCycle column, 0-5% MeOH in CH$_2$Cl$_2$ elution) to provide N-(2-(5-(1,3-dioxolan-2-yl)-6-fluoroisoquinolin-8-yl)-2-((tert-butyldimethylsilyl)oxy)ethyl)methanesulfonamide (0.15 g, 57%). MS (ESI+) [Method 3A]: m/z 471.2 (M+H); Rt 1.78 min.

231

Step 66.8: Synthesis of N-(2-((tert-butyldimethylsilyl)oxy)-2-(6-fluoro-5-formylisoquinolin-8-yl)ethyl)methanesulfonamide

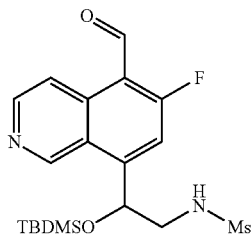 [SMILES: CC(C)(C)[Si](C)(C)OC(CNS(C)(=O)=O)c1cc(F)c(C=O)c2ccncc12]

To the solution of N-(2-(5-(1,3-dioxolan-2-yl)-6-fluoroisoquinolin-8-yl)-2-((tert-butyldimethylsilyl)oxy)ethyl)methanesulfonamide (150 mg, 0.32 mmol) in acetone (4 mL), PTSA (61 mg, 0.32 mmol) was added and stirred at rt. After 16 h, again PTSA (61 mg, 0.32 mmol) was added and stirred at rt for further 16 h. The reaction mixture was diluted with saturated NaHCO₃ solution and extracted with EtOAc twice. The combined organic portion was washed with brine, dried over anhydrous Na₂SO₄, filtered and concentrated in vacuo to yield crude N-(2-((tert-butyldimethylsilyl)oxy)-2-(6-fluoro-5-formylisoquinolin-8-yl)ethyl)methanesulfonamide (0.1 g, 74%). MS (ESI+) [Method 3A]: m/z 427.3 (M+H); Rt 1.92 min.

Step 66.9: Synthesis of N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl)methanesulfonamide

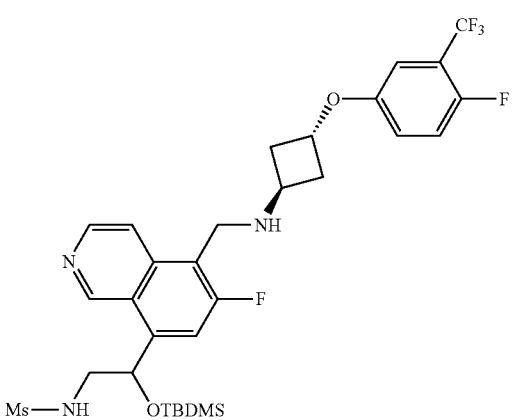 [SMILES: CC(C)(C)[Si](C)(C)OC(CNS(C)(=O)=O)c1cc(F)c(CN[C@H]2C[C@H](Oc3ccc(F)c(C(F)(F)F)c3)C2)c2ccncc12]

The title compound was synthesized following the procedure as described in Step 1.4, using (1r,3r)-3-(4-fluoro-3-(trifluoromethyl)phenoxy)cyclobutan-1-amine, HCl (Step 1.3, 90 mg, 0.32 mmol) and N-(2-((tert-butyldimethylsilyl)oxy)-2-(6-fluoro-5-formylisoquinolin-8-yl)ethyl)methanesulfonamide (94 mg, 0.22 mmol). The crude product was obtained (200 mg, 96%). MS (ESI+) [Method 5A]: m/z 658.2 (M+H); Rt 1.22 min.

232

Example 66.10: Synthesis of N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl)methanesulfonamide

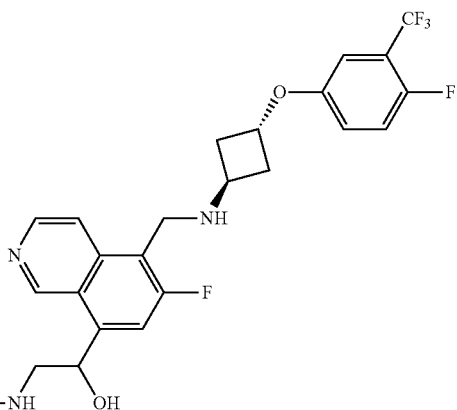

To the solution of N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl)methanesulfonamide (200 mg, 0.30 mmol) in THF (5 mL), TBAF solution (1M in THF) (0.36 mL, 0.36 mmol) was added dropwise as 0° C. and stirred for 1 h. Reaction mixture was diluted with water and extracted with EtOAc twice. The combined organic portion was washed with a brine solution, dried over anhydrous Na₂SO₄, filtered and concentrated in vacuo. The residue was purified by prep-HPLC (Column: WATERS XBRIDGE (150 mm×21.2 mm), 5.0μ; Mobile Phase: 0.02% NH₄OH in in water and acetonitrile) to afford N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl)methanesulfonamide (27 mg, 16%). MS (ESI+) [Method 1A]: m/z 546.2 (M+H); Rt 0.27 min. ¹H NMR (400 MHz, CD₃OD) δ 9.60 (s, 1H), 8.54 (d, J=6.0 Hz, 1H), 8.13 (d, J=6.0 Hz, 1H), 7.70 (d, J=10.4 Hz, 1H), 7.24-7.19 (m, 1H), 7.06-7.00 (m, 2H), 5.67-5.64 (m, 1H), 4.85-4.82 (m, 2H), 4.89 (d, J=1.6 Hz, 2H), 3.62-3.57 (m, 1H), 3.52 (dd, J=14.0, 4.0 Hz, 1H), 2.93 (s, 3H), 2.36 (t, J=6.0 Hz, 4H).

Example 67: Synthesis of N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl) sulfuric diamide Step 67.1: Synthesis of tert-butyl (N-(2-(5-(1,3-dioxolan-2-yl)-6-fluoroisoquinolin-8-yl)-2-((tert-butyldimethylsilyl)oxy)ethyl)sulfamoyl)carbamate

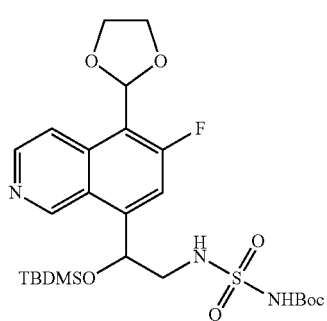 [SMILES: CC(C)(C)OC(=O)NS(=O)(=O)NCC(O[Si](C)(C)C(C)(C)C)c1cc(F)c(C2OCCO2)c2ccncc12]

To the solution of chlorosulfonyl isocyanate (54 mg, 0.38 mmol) in anhydrous CH$_2$Cl$_2$ (3 mL), t-BuOH (0.4 mL, 0.38 mmol) was added dropwise at 0° C. and stirred for 20 min under argon atmosphere. This solution was added dropwise at 0° C. to a stirred solution of 2-(5-(1,3-dioxolan-2-yl)-6-fluoroisoquinolin-8-yl)-2-((tert-butyldimethylsilyl)oxy)ethan-1-amine (Step 66.6, 100 mg, 0.25 mmol) and DIPEA (0.22 mL, 1.27 mmol) in anhydrous CH$_2$Cl$_2$ (3 mL). Then the reaction mixture was allowed to stir at rt for 2 h. The reaction was diluted with water and extracted with CH$_2$Cl$_2$ twice. The combined organic portion was washed with brine, dried over anhydrous Na$_2$SO$_4$, filtered and concentrated in vacuo to yield the crude product. The crude was purified by flash chromatography (12 g SiliCycle column, 0-5% MeOH in CH$_2$Cl$_2$ elution) to provide crude tert-butyl (N-(2-(5-(1,3-dioxolan-2-yl)-6-fluoroisoquinolin-8-yl)-2-((tert-butyldimethylsilyl)oxy)ethyl)sulfamoyl)carbamate (0.25 g, 172%). MS (ESI+) [Method 5A]: m/z 570.3 (M+H); Rt 1.65 min.

Step 67.2: Synthesis of tert-butyl (N-(2-((tert-butyldimethylsilyl)oxy)-2-(6-fluoro-5-formylisoquinolin-8-yl)ethyl)sulfamoyl)carbamate

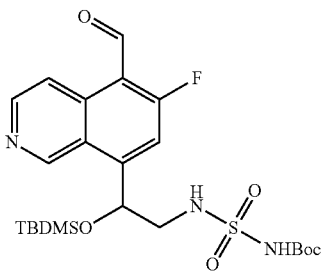 [SMILES: CC(C)(C)OC(=O)NS(=O)(=O)NCC(O[Si](C)(C)C(C)(C)C)c1cc(F)c(C=O)c2ccncc12]

The title compound was prepared according to Step 66.8, except that after 4 h a second lot of PTSA (84 mg, 0.44 mmol) was added and stirred at rt for further 12 h. tert-Butyl (N-(2-((tert-butyldimethylsilyl)oxy)-2-(6-fluoro-5-formylisoquinolin-8-yl)ethyl)sulfamoyl)carbamate was obtained as crude material (180 mg, 78%). MS (ESI+) [Method 3A]: m/z 528.0 (M+H); Rt 2.10 min.

Step 67.3: Synthesis of tert-butyl (N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl)sulfamoyl)carbamate

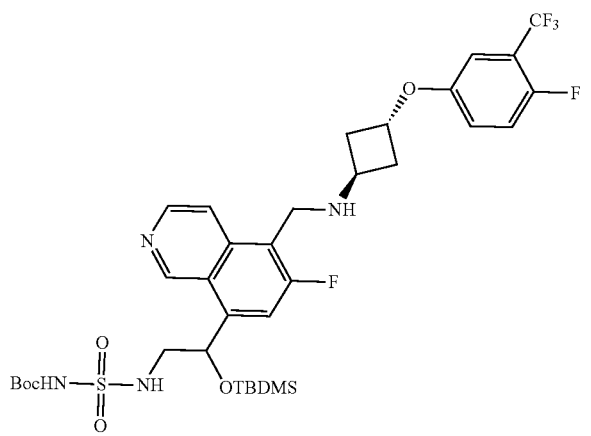 [SMILES: CC(C)(C)OC(=O)NS(=O)(=O)NCC(O[Si](C)(C)C(C)(C)C)c1cc(F)c(CN[C@H]2C[C@H](Oc3ccc(F)c(C(F)(F)F)c3)C2)c2ccncc12]

The title compound was synthesized following the procedure as described in Step 1.4, using (1r,3r)-3-(4-fluoro-3-(trifluoromethyl)phenoxy)cyclobutan-1-amine, HCl (Step 1.3, 140 mg, 0.49 mmol) and tert-butyl (N-(2-((tert-butyldimethylsilyl)oxy)-2-(6-fluoro-5-formylisoquinolin-8-yl)ethyl)sulfamoyl)carbamate (180 mg, 0.34 mmol). The crude tert-butyl (N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl)sulfamoyl)carbamate was obtained (300 mg crude, 80%). MS (ESI+) [Method 6A]: m/z 659.1 (M−Boc+H); Rt 1.33 min.

Step 67.4: Synthesis of N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl) sulfuric diamide, HCl

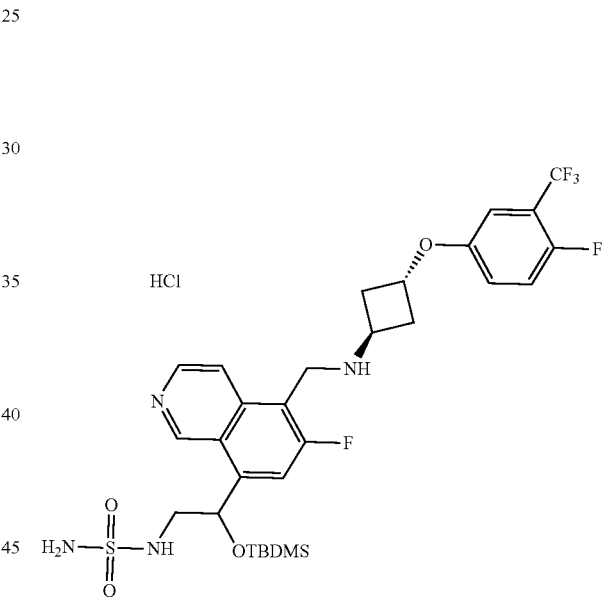

The solution of tert-butyl (N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl)sulfamoyl)carbamate (300 mg, 0.39 mmol) and HCl solution (4M in 1,4-dioxane) (4 mL) was stirred at rt for 4 h. Then the reaction mixture was concentrated in vacuo to provide crude N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl) sulfuric diamide, HCl (250 mg crude, 91%). MS (ESI+) [Method 6A]: m/z 659.1 (M−H); Rt 1.34 min.

Step 67.5: Synthesis of N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl)sulfuric diamide

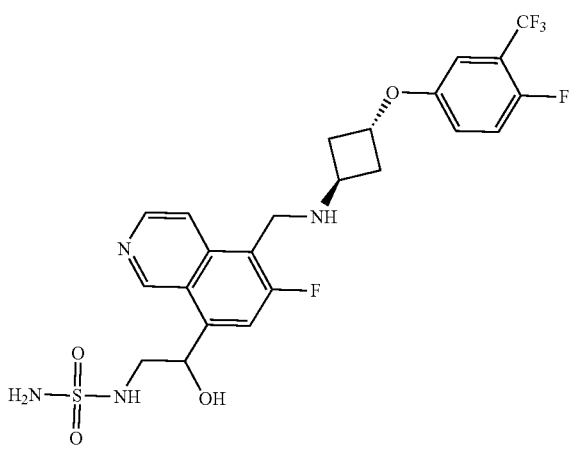 [SMILES: NS(=O)(=O)NCC(O)c1cc(F)c(CN[C@H]2C[C@H](Oc3ccc(F)c(C(F)(F)F)c3)C2)c2ccncc12]

To the solution of N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl) sulfuric diamide, HCl (250 mg, 0.36 mmol) in THF (5 mL), TBAF solution (1M in THF) (0.67 mL, 0.67 mmol) was added dropwise as 0° C. and stirred at rt for 2 h. Reaction mixture was diluted with water and extracted with EtOAc twice. The combined organic portion was washed with brine solution, dried over anhydrous $Na_2SO_4$, filtered and concentrated in vacuo. The residue was purified by prep-HPLC (Column: YMC-ACTUS TRIART (150 mm×20.0 mm), 5.0μ; Mobile Phase: 0.02% $NH_4OH$ in in water and acetonitrile) to afford N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl) sulfuric diamide (3 mg, 1.5%). MS (ESI+) [Method 3A]: m/z 547.2 (M+H); Rt 0.98 min. $^1H$ NMR (400 MHz, $CD_3OD$) δ 9.63 (s, 1H), 8.54 (d, J=6.4 Hz, 1H), 8.13 (d, J=6.4 Hz, 1H), 7.70 (d, J=10.8 Hz, 1H), 7.24-7.19 (m, 1H), 7.06-7.01 (m, 2H), 5.77-5.73 (m, 1H), 4.85-4.82 (m, 1H), 4.63-4.58 (m, 1H), 4.17 (d, J=1.6 Hz, 2H), 3.62-3.57 (m, 1H), 3.50 (dd, J=13.6, 3.2 Hz, 1H), 2.35 (t, J=6.4 Hz, 4H).

Example 68: Synthesis of (1r,3r)-3-(4-fluoro-3-(trifluoromethyl)phenoxy)-N-((6-fluoroisoquinolin-5-yl)methyl)-1-methylcyclobutan-1-amine and (1s,3s)-3-(4-fluoro-3-(trifluoromethyl)phenoxy)-N-((6-fluoroisoquinolin-5-yl)methyl)-1-methylcyclobutan-1-amine Step 68.1: Synthesis of tert-butyl (3-hydroxy-1-methylcyclobutyl)carbamate

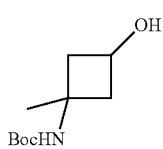

To the stirred solution of 3-amino-3-methylcyclobutan-1-ol, HCl [1403766-64-2] (200 mg, 1.45 mmol) and TEA (1.0 mL, 7.27 mmol) in anhydrous DMF (5 mL), $(Boc)_2O$ (950 mg, 4.36 mmol) was added at 0° C. Then the reaction was continued at rt for 16 h under $N_2$. Reaction mixture was diluted with water and extracted with extracted with EtOAc 3×'s. The combined organic portion was washed with brine solution, dried over anhydrous $Na_2SO_4$, filtered and concentrated in vacuo. The residue was purified by flash chromatography (12 g SiliCycle column, 0-20% EtOAc in Hexane elution) to provide tert-butyl (3-hydroxy-1-methylcyclobutyl)carbamate (230 mg, 78%). $^1H$ NMR (300 MHz, $CDCl_3$) δ 4.62-4.57 (m, 1H), 4.13-4.08 (m, 1H), 2.60-2.45 (m, 4H), 1.44 (s, 9H), 1.31 (s, 3H).

Step 68.2: Synthesis of 3-((tert-butoxycarbonyl)amino)-3-methylcyclobutyl methanesulfonate

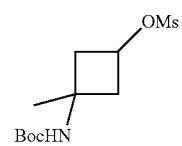

To the stirred solution of tert-butyl (3-hydroxy-1-methylcyclobutyl)carbamate (230 mg, 1.14 mmol) and TEA (0.5 mL, 1.49 mmol) in anhydrous $CH_2Cl_2$ (5 mL), MsCl (0.1 mL, 1.49 mmol) was added at 0° C. Then the reaction mixture was stirred at rt for 2 h under $N_2$. Reaction mixture was diluted with water and extracted with $CH_2Cl_2$ 3×'s. The combined organic portion was washed with brine solution, dried over anhydrous $Na_2SO_4$, filtered and concentrated in vacuo. The residue was purified by flash chromatography (12 g SiliCycle column, 0-15% EtOAc in Hexane elution) to provide 3-((tert-butoxycarbonyl)amino)-3-methylcyclobutyl methanesulfonate (240 mg, 75%). $^1H$ NMR (300 MHz, $CDCl_3$) δ 4.91-4.83 (m, 1H), 2.99 (s, 3H), 2.74-2.68 (m, 2H), 2.60-2.54 (m, 2H), 1.44 (s, 9H), 1.38 (s, 3H).

Step 68.3: Synthesis of tert-butyl (3-(4-fluoro-3-(trifluoromethyl)phenoxy)-1-methylcyclobutyl)carbamate

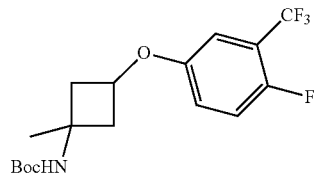 [SMILES: CC1(NC(=O)OC(C)(C)C)CC(Oc2ccc(F)c(C(F)(F)F)c2)C1]

To the stirred solution of 4-fluoro-3-(trifluoromethyl)phenol [CAS No. 61721-07-1] (185 g, 1.03 mmol) and 3-((tert-butoxycarbonyl)amino)-3-methylcyclobutyl methanesulfonate (240 mg, 0.86 mmol) in anhydrous DMF (5 mL), $Cs_2CO_3$ (840 mg, 2.58 mmol) was added at rt. The reaction mixture was heated at 70° C. for 16 h under $N_2$. Reaction mixture was cooled to rt, diluted with EtOAc and washed with water, followed by brine. The organic portion was dried over anhydrous $Na_2SO_4$, filtered and concentrated in vacuo. The residue was purified by flash chromatography (12 g SiliCycle column, 0-25% EtOAc in Hexane elution) to provide tert-butyl (3-(4-fluoro-3-(trifluoromethyl)phenoxy)-1-methylcyclobutyl)carbamate (140 mg, 45%). ¹H NMR (300 MHz, CDCl₃) δ 7.11-6.86 (m, 3H), 4.80-4.65 (m, 1H), 2.65-2.58 (m, 2H), 2.51-2.43 (m, 2H), 1.46 (s, 9H), 1.44 (s, 3H).

Step 68.4: Synthesis of 3-(4-fluoro-3-(trifluoromethyl)phenoxy)-1-methylcyclobutan-1-amine hydrochloride, HCl

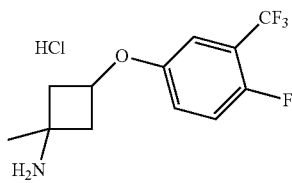 [SMILES: CC1(N)CC(Oc2ccc(F)c(C(F)(F)F)c2)C1 ; Cl]

The solution of tert-butyl (3-(4-fluoro-3-(trifluoromethyl)phenoxy)-1-methylcyclobutyl)carbamate (140 mg, 0.39 mmol) and HCl solution (4M in 1,4-dioxane) (1.0 mL) was stirred at rt for 4 h. The reaction mixture was concentrated in vacuo to provide 3-(4-fluoro-3-(trifluoromethyl)phenoxy)-1-methylcyclobutan-1-amine, HCl (80 mg, 69%). MS (ESI+) [Method 6A]: m/z 264.1 (M+H); Rt 1.30 min. ¹H NMR (400 MHz, DMSO-d6) δ 8.33 (brs, 3H), 7.46-7.41 (m, 1H), 7.15-7.12 (m, 1H), 7.08-7.06 (m, 1H), 5.01-4.96 (m, 1H), 2.77-2.73 (m, 2H), 2.18-2.13 (m, 2H), 1.43 (s, 3H).

Step 68.5: Synthesis of (1r,3r)-3-(4-fluoro-3-(trifluoromethyl)phenoxy)-N-((6-fluoroisoquinolin-5-yl)methyl)-1-methylcyclobutan-1-amine and (1s,3s)-3-(4-fluoro-3-(trifluoromethyl)phenoxy)-N-((6-fluoroisoquinolin-5-yl)methyl)-1-methylcyclobutan-1-amine

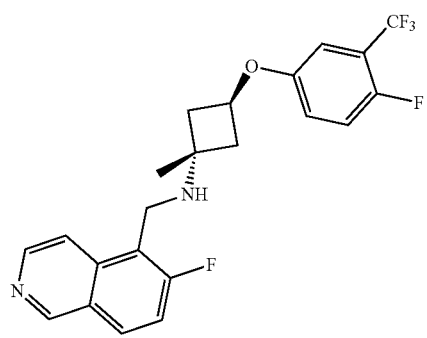

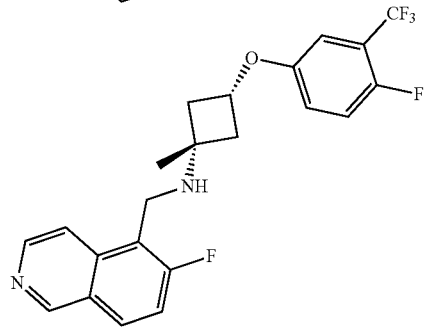

A round bottom flask fitted with Dean-Stark apparatus was charged with 3-(4-fluoro-3-(trifluoromethyl)phenoxy)-1-methylcyclobutan-1-amine hydrochloride, HCl (70 mg, 0.23 mmol), 6-fluoroisoquinoline-5-carbaldehyde (Step 3.1, 36 mg, 0.21 mmol), TEA (0.05 mL, 0.23 mmol) and benzene (10 mL) and the reaction mixture heated at 100° C. for 16 h. Then the reaction mixture was concentrated in vacuo, the residue was dissolved in MeOH (5 mL), cooled to 0° C., NaBH₄ (35 mg, 0.93 mmol) was added and stirred at rt for 3 h. Reaction mixture was diluted with water and extracted with EtOAc twice. The combined organic portion was washed with brine solution, dried over anhydrous Na₂SO₄, filtered and concentrated in vacuo. Prep-HPLC purification of the crude (Column: X SELECT (250 mm×19 mm), 5.0μ; Mobile Phase: 0.1% HCO₂H in water and acetonitrile; followed by GEMINI (150 mm×21.2 mm), 5.0p; Mobile Phase: 0.02% NH₄OH in water and acetonitrile) afforded two peaks. Peak 1, (1r,3r)-3-(4-fluoro-3-(trifluoromethyl)phenoxy)-N-((6-fluoroisoquinolin-5-yl)methyl)-1-methylcyclobutan-1-amine was obtained as off white solid (45 mg, 46%). MS (ESI+) [Method 6A]: m/z 423.1 (M+H); Rt 1.36 min. ¹H NMR (400 MHz, CD₃OD) δ 9.82 (s, 1H), 8.79-8.71 (m, 3H), 8.01 (t, J=9.6 Hz, 1H), 7.30 (t, J=9.2 Hz, 1H), 7.16-7.11 (m, 2H), 5.02-4.97 (m, 1H), 4.82 (s, 2H), 3.15-3.09 (m, 2H), 2.52-2.47 (m, 2H), 1.89 (s, 3H). Peak 2, (1s,3s)-3-(4-fluoro-3-(trifluoromethyl)phenoxy)-N-((6-fluoroisoquinolin-5-yl)methyl)-1-methylcyclobutan-1-amine (3 mg, 3%). MS (ESI+) [Method 6A]: m/z 423.15 (M+H); Rt 1.33 min. ¹H NMR (400 MHz, CD₃OD) δ 9.23 (s, 1H), 8.50 (d, J=5.6 Hz, 1H), 8.15-8.12 (m, 1H), 8.09-8.07 (m, 1H), 7.52 (t, J=9.6 Hz, 1H), 7.22 (t, J=9.2 Hz, 1H), 7.12-7.06 (m, 2H), 5.02-4.97 (m, 1H), 4.82 (s, 2H), 3.15-3.09 (m, 2H), 2.51-2.47 (m, 2H), 1.89 (s, 3H).

Example 69: Synthesis of 2-(3-amino-6-fluoroisoquinolin-5-yl)-N-((1r,3r)-3-(4-fluoro-3-(trifluoromethyl)phenoxy)cyclobutyl)acetamide Step 69.1: Synthesis of ethyl 2-(3-(bis(tert-butoxycarbonyl)amino)-6-fluoroisoquinolin-5-yl)-2-oxoacetate

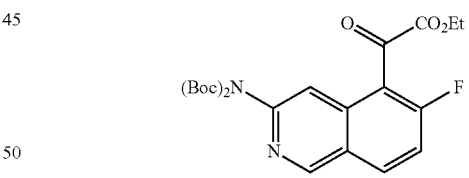

To the stirred solution of tert-butyl (tert-butoxycarbonyl)(6-fluoroisoquinolin-3-yl)carbamate (Step 14.3, 10.0 g, 27.59 mmol) in anhydrous THF (100 mL), LDA (2.0M in THF) (34.5 mL, 68.98 mmol) was added dropwise at −78° C. under N₂. After stirring for 2.5 h, diethyl oxalate (12.1 g, 82.78 mmol) dissolved in anhydrous THF (50 mL) was added dropwise at −78° C., and the reaction mixture was stirred for 1 h under N₂. The reaction mixture was quenched with saturated NH₄Cl solution and extracted with EtOAc twice. The combined organic portion was washed with brine, dried over anhydrous Na₂SO₄, filtered and concentrated in vacuo. The residue was purified by flash chromatography (80 g SiliCycle column, 0-20% EtOAc in hexane elution) to provide ethyl 2-(3-(bis(tert-butoxycarbonyl)amino)-6-fluoroisoquinolin-5-yl)-2-oxoacetate (7.0 g, 55%). MS (ESI+)

[Method 5A]: m/z 363.1 (M−Boc+H); Rt 1.58 min. $^1$H NMR (300 MHz, CDCl$_3$) δ 9.17 (s, 1H), 8.39 (s, 1H), 8.28-8.23 (m, 1H), 7.40 (t, J=9.9 Hz, 1H), 4.46 (q, J=7.2 Hz, 2H), 1.46 (s, 18H), 1.42 (t, J=7.2 Hz, 3H).

Step 69.2: Synthesis of ethyl 2-(3-(bis(tert-butoxycarbonyl)amino)-6-fluoroisoquinolin-5-yl)-2-hydroxyacetate

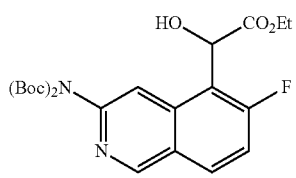

To the stirred solution of ethyl 2-(3-(bis(tert-butoxycarbonyl)amino)-6-fluoroisoquinolin-5-yl)-2-oxoacetate (7.0 g, 15.13 mmol) in EtOH-H$_2$O mixture (124 mL, 55:7 v/v), AcOH (3.5 mL) and NaCNBH$_3$ (1.14 g, 18.16 mmol) were added portion wise at rt. After stirring for 16 h, the reaction was quenched with saturated NaHCO$_3$ solution and extracted with EtOAc twice. The combined organic portion was washed with brine, dried over anhydrous Na$_2$SO$_4$, filtered and concentrated in vacuo to provide crude ethyl 2-(3-(bis(tert-butoxycarbonyl)amino)-6-fluoroisoquinolin-5-yl)-2-hydroxyacetate (6.0 g, 85%). MS (ESI+) [Method 1A]: m/z 465.4 (M+H); Rt 1.67 min.

Step 69.3: Synthesis of ethyl 2-acetoxy-2-(3-(bis(tert-butoxycarbonyl)amino)-6-fluoroisoquinolin-5-yl)acetate

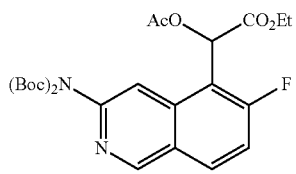

To the stirred solution of ethyl 2-(3-(bis(tert-butoxycarbonyl)amino)-6-fluoroisoquinolin-5-yl)-2-hydroxyacetate (6.0 g, 12.91 mmol) in anhydrous CH$_2$Cl$_2$ (80 mL), TEA (4.53 mL, 32.29 mmol) and DMAP (100 mg, 0.82 mmol) were added at rt. Then Ac$_2$O (1.7 mL, 18.08 mmol) was added drop wise at 0° C. and the reaction mixture was stirred at rt for 3 h under argon. The reaction mixture was diluted with water and extracted with CH$_2$Cl$_2$ twice. The combined organic portion was washed with brine, dried over anhydrous Na$_2$SO$_4$, filtered and concentrated in vacuo to provide crude ethyl 2-acetoxy-2-(3-(bis(tert-butoxycarbonyl)amino)-6-fluoroisoquinolin-5-yl)acetate (7.0 g, 107%). MS (ESI+) [Method 1A]: m/z 507.2 (M+H); Rt 1.87 min.

Step 69.4: Synthesis of ethyl 2-(3-(bis(tert-butoxycarbonyl)amino)-6-fluoroisoquinolin-5-yl)acetate

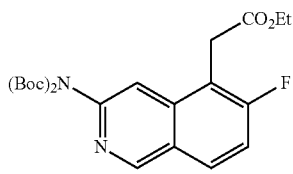

The rock shaker vessel was charged with ethyl 2-acetoxy-2-(3-(bis(tert-butoxycarbonyl)amino)-6-fluoroisoquinolin-5-yl)acetate (7.0 g, 13.81 mmol) and EtOH (250 mL). Pd/C (10% w/w, 50% wet) (3.5 g) was added under argon and degassed. Then the reaction mixture agitated under H$_2$ (70 psi) at 60° C. for 16 h. Reaction mixture was filtered through celite bed, the bed was washed with EtOAc. The combined filtrate was concentrated in vacuo to afford ethyl 2-(3-(bis(tert-butoxycarbonyl)amino)-6-fluoroisoquinolin-5-yl)acetate (6.0 g, 97%). MS (ESI+) [Method 5A]: m/z 449.1 (M+H); Rt 2.37 min.

Step 69.5: Synthesis of 2-(3-((tert-butoxycarbonyl)amino)-6-fluoroisoquinolin-5-yl)acetic acid

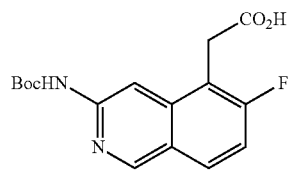 [SMILES: CC(C)(C)OC(=O)Nc1cc2c(CC(=O)O)c(F)ccc2cn1]

To the solution of ethyl 2-(3-(bis(tert-butoxycarbonyl)amino)-6-fluoroisoquinolin-5-yl)acetate (7.3 g, 16.27 mmol) in THF-MeOH-water (120 mL, 5:3:2 v/v/v), LiOH·H$_2$O (1.7 g, 40.69 mmol) was added at rt and stirred for 4 h. Then the solvent was evaporated, residue was diluted with water and acidified with a citric acid solution. The solid appeared was filtered, washed with water and dried in vacuo to afford crude 2-(3-((tert-butoxycarbonyl)amino)-6-fluoroisoquinolin-5-yl)acetic acid (4.0 g, 76%). MS (ESI+) [Method 5A]: m/z 321.1 (M+H); Rt 1.33 min.

Step 69.6: Synthesis of tert-butyl (6-fluoro-5-(2-(((1r,3r)-3-(4-fluoro-3-(trifluoromethyl)phenoxy)cyclobutyl)amino)-2-oxoethyl)isoquinolin-3-yl)carbamate

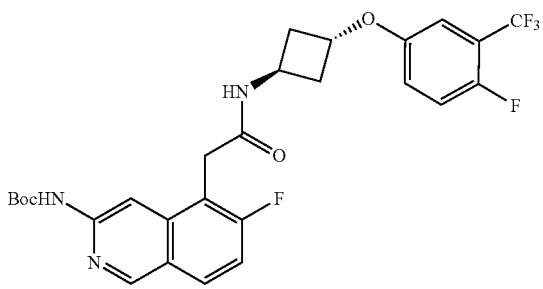 [SMILES: CC(C)(C)OC(=O)Nc1cc2c(CC(=O)N[C@H]3C[C@H](Oc4ccc(F)c(C(F)(F)F)c4)C3)c(F)ccc2cn1]

To the stirred solution of 2-(3-((tert-butoxycarbonyl)amino)-6-fluoroisoquinolin-5-yl)acetic acid (2.0 g, 6.24 mmol) and (1r,3r)-3-(4-fluoro-3-(trifluoromethyl)phenoxy)cyclobutan-1-amine, HCl (Step 1.3, 1.78 g, 6.24 mmol) in DMF (30 mL), HATU (3.56 g, 9.37 mmol) was added. Then DIPEA (5.43 mL, 31.21 mmol) were added dropwise at 0° C. and the reaction mixture was stirred at rt for 2 h. The reaction mixture was diluted with cold water. The precipitated solid was filtered, washed with water and dried in vacuo to afford tert-butyl (6-fluoro-5-(2-(((1r,3r)-3-(4-fluoro-3-(trifluoromethyl)phenoxy)cyclobutyl)amino)-2-oxoethyl)isoquinolin-3-yl)carbamate (3.5 g crude, 101%). MS (ESI+) [Method 1A]: m/z 552.2 (M+H); Rt 1.89 min.

Step 69.7: Synthesis of 2-(3-amino-6-fluoroisoquinolin-5-yl)-N-((1r,3r)-3-(4-fluoro-3-(trifluoromethyl)phenoxy)cyclobutyl)acetamide

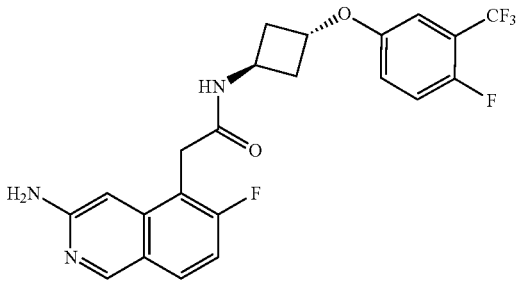 [SMILES: Nc1cc2c(CC(=O)N[C@H]3C[C@H](Oc4ccc(F)c(C(F)(F)F)c4)C3)c(F)ccc2cn1]

The solution of tert-butyl (6-fluoro-5-(2-(((1r,3r)-3-(4-fluoro-3-(trifluoromethyl)phenoxy)cyclobutyl)amino)-2-oxoethyl)isoquinolin-3-yl)carbamate (3.5 g, 6.35 mmol) in HCl (4M in 1,4-dioxane) (50 mL) was stirred at rt for 16 h. The reaction mixture was concentrated in vacuo and the residue was triturated with Et₂O. The crude product was purified by prep-HPLC (Column: X BRIDGE (150 mm×21.2 mm), 5.0μ; Mobile phase: 0.02% NH₄OH in water and acetonitrile). The isolated product was stirred with Et₂O (30 mL) for 30 min, solid was filtered and dried in vacuo to afford 2-(3-amino-6-fluoroisoquinolin-5-yl)-N-((1r,3r)-3-(4-fluoro-3-(trifluoromethyl)phenoxy)cyclobutyl)acetamide (1.41 g, 45%). MS (ESI+) [Method 1A]: m/z 452.2 (M+H); Rt 1.34 min. ¹H NMR (400 MHz, CD₃OD) δ 8.75 (s, 1H), 7.85-7.81 (m, 1H), 7.24 (t, J=9.2 Hz, 1H), 7.09-7.02 (m, 3H), 6.82 (s, 1H), 4.88-4.83 (m, 1H), 4.48-4.44 (m, 1H), 3.87 (s, 2H), 2.51 (dd, J=6.8, 5.6 Hz, 4H).

Example 70: Synthesis of N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl)acetamide Step 70.1: Synthesis of 1-(6-fluoroisoquinolin-8-yl)-2-nitroethan-1-ol

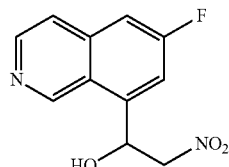

To the solution of 6-fluoroisoquinoline-8-carbaldehyde (Step 6.5, 4.0 g, 22.83 mmol) in anhydrous THF (40 mL), MeNO₂ (4.89 mL, 91.34 mmol) and K₂CO₃ (1.26 g, 9.13 mmol) were added, and stirred at rt for 16 h under N₂. Reaction mixture was diluted with water and extracted with EtOAc twice. The combined organic portion was washed with brine solution, dried over anhydrous Na₂SO₄, filtered and concentrated in vacuo to provide crude 1-(6-fluoroisoquinolin-8-yl)-2-nitroethan-1-ol (5.0 g, 93%). MS (ESI+) [Method 1A]: m/z 237.3 (M+H); Rt 0.14 min.

Step 70.2: Synthesis of 8-(1-((tert-butyldimethylsilyl)oxy)-2-nitroethyl)-6-fluoroisoquinoline

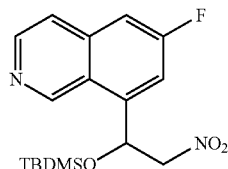

To the stirred solution of 1-(6-fluoroisoquinolin-8-yl)-2-nitroethan-1-ol (5.0 g, 21.16 mmol) and imidazole (7.2 g, 105.77 mmol) in DMF (50 mL), TBDMS-Cl (9.57 g, 63.50 mmol) was added portion wise at 0° C. Then the reaction mixture was stirred at rt for 16 h. The reaction mixture was diluted with water and extracted with CH₂Cl₂ twice. The combined organic portion was washed with brine, dried over anhydrous Na₂SO₄, filtered and concentrated in vacuo. The residue was purified by flash chromatography (40 g Sili-Cycle column, 0-15% EtOAc in Hexane elution) to afford 8-(1-((tert-butyldimethylsilyl)oxy)-2-nitroethyl)-6-fluoroisoquinoline (5.0 g, 67%). MS (ESI+) [Method 5A]: m/z 351.2 (M+H); Rt 1.61 min.

Step 70.3: Synthesis of 2-((tert-butyldimethylsilyl)oxy)-2-(6-fluoroisoquinolin-8-yl)ethan-1-amine

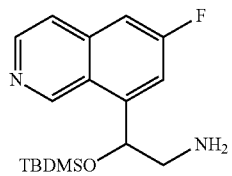 [SMILES: CC(C)(C)[Si](C)(C)OC(CN)c1cc(F)cc2ccncc12]

To the stirred solution of 8-(1-((tert-butyldimethylsilyl)oxy)-2-nitroethyl)-6-fluoroisoquinoline (5.0 g, 14.26 mmol) in MeOH—H₂O (100 mL, 4:1 v/v), NH₄Cl (7.63 g, 142.64 mmol) was added. The reaction mixture was cooled to 0° C. and Zn-dust (9.32 g, 142.64 mmol) was added portion wise. The reaction mixture was stirred at rt for 16 h. The reaction mixture was filtered through celite bed, which was washed with MeOH. The combined filtrate was concentrated in vacuo. The residue was diluted with CH₂Cl₂, washed with saturated NaHCO₃ solution, brine, dried over anhydrous Na₂SO₄, filtered and concentrated in vacuo to yield crude 2-((tert-butyldimethylsilyl)oxy)-2-(6-fluoroisoquinolin-8-yl)ethan-1-amine (3.8 g, 83%). MS (ESI+) [Method 5A]: m/z 321.2 (M+H); Rt 1.03 min.

243

Step 70.4: Synthesis of N-(2-((tert-butyldimethylsilyl)oxy)-2-(6-fluoroisoquinolin-8-yl)ethyl)acetamide

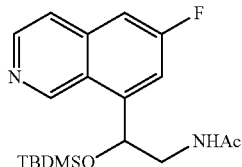

To the stirred solution of 2-((tert-butyldimethylsilyl)oxy)-2-(6-fluoroisoquinolin-8-yl)ethan-1-amine (300 mg, 0.94 mmol) in anhydrous $CH_2Cl_2$ (10 mL), TEA (0.52 mL, 3.74 mmol) and DMAP (23 mg, 0.19 mmol) were added at rt. Then $Ac_2O$ (0.17 mL, 1.87 mmol) was added drop wise at 0° C. and the reaction mixture was stirred at rt for 16 h under $N_2$. The reaction mixture was diluted with water and extracted with $CH_2Cl_2$ twice. The combined organic portion was washed with brine, dried over anhydrous $Na_2SO_4$, filtered and concentrated in vacuo. The residue was purified by flash chromatography (12 g SiliCycle column, 0-100% EtOAc in Hexane elution) to provide N-(2-((tert-butyldimethylsilyl)oxy)-2-(6-fluoroisoquinolin-8-yl)ethyl)acetamide (150 mg, 44%). MS (ESI+) [Method 5A]: m/z 363.2 (M+H); Rt 1.31 min.

Step 70.5: Synthesis of N-(2-((tert-butyldimethylsilyl)oxy)-2-(6-fluoro-5-formylisoquinolin-8-yl)ethyl)acetamide

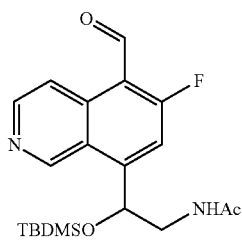 [SMILES: CC(=O)NCC(O[Si](C)(C)C(C)(C)C)c1cc(F)c(C=O)c2ccncc12]

To the stirred solution of N-(2-((tert-butyldimethylsilyl)oxy)-2-(6-fluoroisoquinolin-8-yl)ethyl)acetamide (150 mg, 0.41 mmol) in anhydrous THF (2 mL), LDA (2M in THF) (0.62 mL, 1.24 mmol) was added dropwise at –78° C. under $N_2$ atmosphere. After 2.5 h, ethyl formate (91 mg, 1.24 mmol) dissolved in THF (1 mL) was added dropwise at –78° C., and stirred for further 1 h. The reaction was quenched with saturated $NH_4Cl$ solution and extracted with EtOAc twice. The combined organic portion was washed with brine, dried over anhydrous $Na_2SO_4$, filtered and concentrated in vacuo. The residue was purified by flash chromatography (12 g SiliCycle column, 0-10% MeOH in $CH_2Cl_2$ elution) to provide N-(2-((tert-butyldimethylsilyl)oxy)-2-(6-fluoro-5-formylisoquinolin-8-yl)ethyl)acetamide (100 mg, 62%). MS (ESI+) [Method 5A]: m/z 391.2 (M+H); Rt 1.29 min.

244

Step 70.6: Synthesis of N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl)acetamide

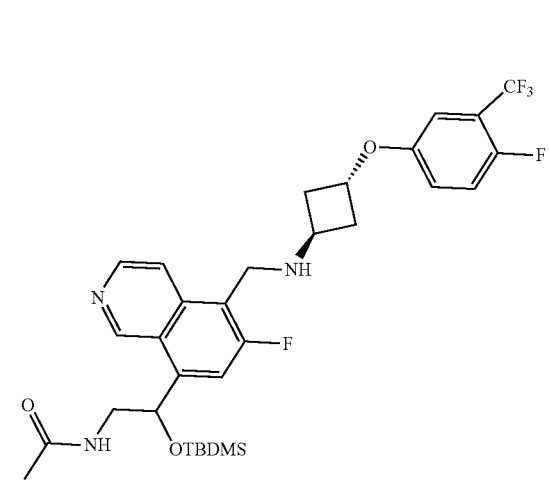 [SMILES: CC(=O)NCC(O[Si](C)(C)C(C)(C)C)c1cc(F)c(CN[C@H]2C[C@H](Oc3ccc(F)c(C(F)(F)F)c3)C2)c2ccncc12]

The title compound was synthesized following the procedure as described in Step 1.4, using (1r,3r)-3-(4-fluoro-3-(trifluoromethyl)phenoxy)cyclobutan-1-amine, HCl (Step 1.3, 70 mg, 0.25 mmol) and N-(2-((tert-butyldimethylsilyl)oxy)-2-(6-fluoro-5-formylisoquinolin-8-yl)ethyl)acetamide (86 mg, 0.22 mmol). Purification of the crude by flash chromatography (4 g SiliCycle column, 0-5% MeOH in $CHCl_3$ elution) afforded N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl)acetamide (20 mg, 13%). MS (ESI+) [Method 1A]: m/z 624.1 (M+H); Rt 1.46 min.

Step 70.7: Synthesis of N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl)acetamide, HCl

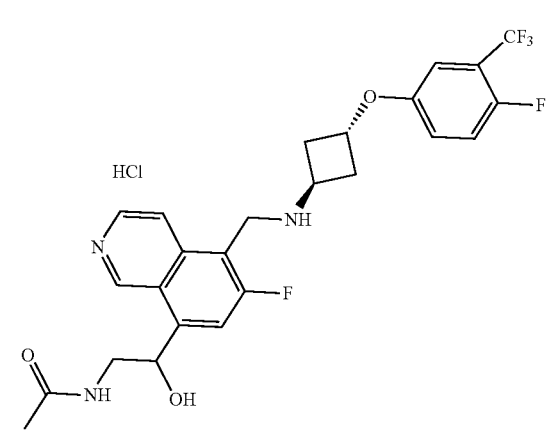 [SMILES: CC(=O)NCC(O)c1cc(F)c(CN[C@H]2C[C@H](Oc3ccc(F)c(C(F)(F)F)c3)C2)c2ccncc12 ; Cl]

To the solution of N-(2-((tert-butyldimethylsilyl)oxy)-2-(6-fluoro-5-((((1r,3r)-3-(4-fluoro-3-(trifluoromethyl)phenoxy)cyclobutyl)amino)methyl)isoquinolin-8-yl)ethyl)acetamide (20 mg, 0.03 mmol) in THF (1 mL), TBAF solution (1M in THF) (0.04 mL, 0.04 mmol) was added dropwise as 0° C. and stirred for 2 h under argon. Reaction mixture was diluted with water and extracted with EtOAc twice. The combined organic portion was washed with brine solution, dried over anhydrous Na$_2$SO$_4$, filtered and concentrated in vacuo. The residue was purified by prep-HPLC (Column: LUNA Phenomenex (250 mm×21.2 mm), 5.0μ; Mobile Phase: 0.1% HCO$_2$H in in water and acetonitrile). To the isolated product, HCl solution (20% in 1,4-dioxane) (1 mL) was added, stirred at rt for 1 h, and then concentrated in vacuo. The residue was triturated with Et$_2$O, solid precipitated was filtered and dried to afford N-(2-(6-fluoro-5-((((1r,3r)-3-(4-fluoro-3-(trifluoromethyl)phenoxy)cyclobutyl) amino)methyl)isoquinolin-8-yl)-2-hydroxyethyl)acetamide, HCl (12 mg, 71%). MS (ESI+) [Method 1A]: m/z 510.2 (M+H); Rt 0.12 min. $^1$H NMR (400 MHz, CD$_3$OD) δ 10.37 (s, 1H), 8.89 (d, J=6.8 Hz, 1H), 8.81 (d, J=7.2 Hz, 1H), 8.09 (d, J=10.4 Hz, 1H), 7.28 (t, J=9.6 Hz, 1H), 7.15-7.09 (m, 2H), 5.69-5.66 (m, 1H), 5.09-5.04 (m, 1H), 4.82 (s, 2H), 4.31-4.25 (m, 1H), 3.73 (dd, J=14.0, 3.6 Hz, 1H), 3.35 (dd, J=14.0, 7.6 Hz, 1H), 2.96-2.89 (m, 2H), 2.73-2.67 (m, 2H), 1.95 (s, 3H).

Example 71: Synthesis of (1r,3r)-N-((6-fluoroisoquinolin-5-yl)methyl)-3-(3-(trifluoromethyl)phenoxy)cyclobutan-1-amine, HCl Step 71.1: Synthesis of tert-butyl ((1r,3r)-3-(3-(trifluoromethyl)phenoxy)cyclobutyl)carbamate

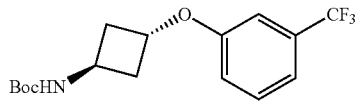 [SMILES: CC(C)(C)OC(=O)N[C@H]1C[C@H](Oc2cccc(C(F)(F)F)c2)C1]

To the solution of tert-butyl ((1s,3s)-3-hydroxycyclobutyl)carbamate (300 mg, 1.60 mmol), 3-(trifluoromethyl)phenol [CAS No. 98-17-9] (260 mg, 1.60 mmol) and diisopropyl azodicarboxylate (0.47 mL, 2.40 mmol) in THF (10 mL), PPh$_3$ (630 mg, 2.40 mmol) was added at rt. The reaction mixture was stirred at 50° C. for 16 h under N$_2$ atmosphere. Reaction mixture was diluted with water and extracted with EtOAc 3×'s. The combined organic portion was washed with brine solution, dried over anhydrous Na$_2$SO$_4$, filtered and concentrated in vacuo. The residue was purified by flash chromatography (12 g SiliCycle column, 0-20% EtOAc in Hexane elution) to provide tert-butyl ((1r,3r)-3-(3-(trifluoromethyl)phenoxy)cyclobutyl)carbamate (350 mg, 66%). $^1$H NMR (300 MHz, CDCl$_3$) δ 7.37 (t, J=8.1 Hz, 1H), 7.19 (d, J=8.1 Hz, 1H), 6.98 (s, 1H), (d, J=8.1 Hz, 1H), 6.94 (d, J=8.1 Hz, 1H), 4.85-4.77 (m, 1H), 4.33-4.27 (m, 1H), 2.61-2.52 (m, 2H), 2.44-2.37 (m, 2H), 1.45 (s, 9H).

Step 71.2: Synthesis of (1r,3r)-3-(3-(trifluoromethyl)phenoxy)cyclobutan-1-amine, HCl

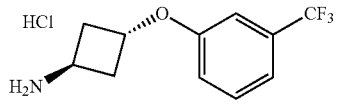 [SMILES: Cl ; N[C@H]1C[C@H](Oc2cccc(C(F)(F)F)c2)C1]

The solution of tert-butyl ((1r,3r)-3-(3-(trifluoromethyl)phenoxy)cyclobutyl)carbamate (350 mg, 1.05 mmol) and HCl solution (4M in 1,4-dioxane) (5.0 mL) was stirred at rt for 16 h. The reaction mixture was concentrated in vacuo and the residue was triturated with pentane, the solid appeared was filtered and dried to yield (1r,3r)-3-(3-(trifluoromethyl)phenoxy)cyclobutan-1-amine, HCl (270 g, 96%). MS (ESI+) [Method 6A]: m/z 231.90 (M+H); Rt 1.29 min.

Step 71.3: Synthesis of (1r,3r)-N-((6-fluoroisoquinolin-5-yl)methyl)-3-(3-(trifluoromethyl)phenoxy)cyclobutan-1-amine, HCl

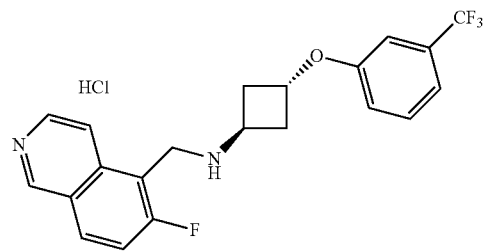 [SMILES: Fc1ccc2cnccc2c1CN[C@H]1C[C@H](Oc2cccc(C(F)(F)F)c2)C1 ; Cl]

The title compound was synthesized following the procedure as described in Step 1.4, using (1r,3r)-3-(3-(trifluoromethyl)phenoxy)cyclobutan-1-amine, HCl (60 mg, 0.22 mmol) and 6-fluoroisoquinoline-5-carbaldehyde (Step 3.1, 36 mg, 0.20 mmol). The crude product was purified by prep-HPLC (Column: WATERS X BRIDGE C18 (150 mm×21.2 mm), 5.0μ; Mobile Phase: 0.02% NH$_4$OH in in water and acetonitrile). To the isolated product, HCl solution (4M in 1,4-dioxane) (2 mL) was added, stirred at rt for 2 h, and then concentrated in vacuo. The residue was triturated with pentane and then lyophilized to provide (1r,3r)-N-((6-fluoroisoquinolin-5-yl)methyl)-3-(3-(trifluoromethyl)phenoxy)cyclobutan-1-amine, HCl (50 mg, 52%). MS (ESI+) [Method 6A]: m/z 391.2 (M+H); Rt 1.32 min. $^1$H NMR (400 MHz, CD$_3$OD) δ 9.88 (s, 1H), 8.83-8.75 (m, 3H), 8.02 (t, J=8.4 Hz, 1H), 7.50 (t, J=6.8 Hz, 1H), 7.77 (d, J=6.8 Hz, 1H), 7.12-7.09 (m, 2H), 5.11-5.07 (m, 1H), 4.84 (d, J=2.0 Hz, 2H), 4.33-4.26 (m, 1H), 2.95-2.48 (m, 2H), 2.75-2.68 (m, 2H).

Example 72: Synthesis of 2-(6-fluoro-5-((((1r,3r)-3-(4-fluoro-3-(trifluoromethyl)phenoxy)cyclobutyl) amino)methyl)isoquinolin-8-yl)-2-hydroxyacetic acid Step 72.1: Synthesis of 6-fluoro-5-((((1r,3r)-3-(4-fluoro-3-(trifluoromethyl)phenoxy)cyclobutyl) amino)methyl)isoquinoline-8-carbaldehyde

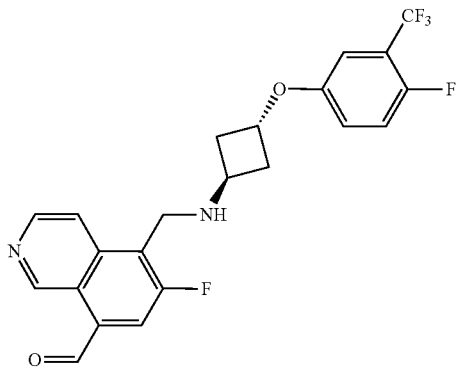 [SMILES: O=Cc1cc(F)c(CN[C@H]2C[C@H](Oc3ccc(F)c(C(F)(F)F)c3)C2)c2ccncc12]

To the stirred solution of (6-fluoro-5-((((1r,3r)-3-(4-fluoro-3-(trifluoromethyl)phenoxy)cyclobutyl)amino)methyl)isoquinolin-8-yl)methanol (Step 6.11, 0.95 g, 2.17 mmol) in CHCl$_3$ (25 mL), activated MnO$_2$ (1.88 g, 21.66 mmol) was added at rt and heated at 70° C. for 2 h, under argon. The reaction mixture was cooled to rt, filtered through celite bed and the bed was washed with chloroform. The combined filtrate was concentrated in vacuo to get crude compound. The crude was purified by flash chromatography (12 g SiliCycle column, 0-5% MeOH in CHCl$_3$ elution) to provide 6-fluoro-5-((((1r,3r)-3-(4-fluoro-3-(trifluoromethyl)phenoxy)cyclobutyl)amino)methyl)isoquinoline-8-carbaldehyde (0.5 g, 53%). MS (ESI+) [Method 6A]: m/z 437.1 (M+H); Rt 1.33 min.

Step 72.2: Synthesis of 2-(6-fluoro-5-((((1r,3r)-3-(4-fluoro-3-(trifluoromethyl)phenoxy)cyclobutyl)amino)methyl)isoquinolin-8-yl)-2-hydroxyacetonitrile

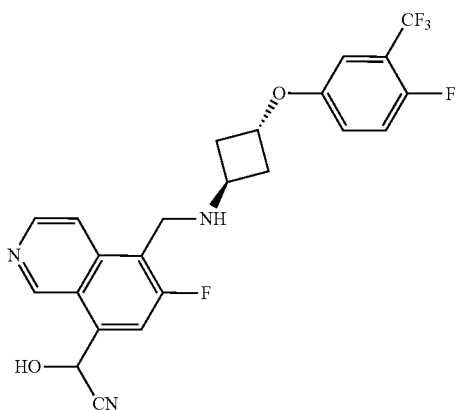 [SMILES: N#CC(O)c1cc(F)c(CN[C@H]2C[C@H](Oc3ccc(F)c(C(F)(F)F)c3)C2)c2ccncc12]

To the solution of 6-fluoro-5-((((1r,3r)-3-(4-fluoro-3-(trifluoromethyl)phenoxy)cyclobutyl)amino)methyl)isoquinoline-8-carbaldehyde (250 mg, 0.57 mmol) in anhydrous CH$_2$Cl$_2$ (4 mL), Cu(OTf)$_2$ (10 mg, 0.03 mmol) was added at rt and stirred for 15 min. Then TMSCN (73 mg, 0.74 mmol) was added and the reaction mixture was stirred at rt for 16 h under argon. The reaction mixture was concentrated in vacuo. To the residue MeCN (1.0 mL) and 1M HCl (1.0 mL) were added at 0° C. and stirred for 30 minutes. The solution was diluted with water and extracted with EtOAc 3×'s. The combined organic portion was washed with brine solution, dried over anhydrous Na$_2$SO$_4$, filtered and concentrated in vacuo to provide crude 2-(6-fluoro-5-((((1r,3r)-3-(4-fluoro-3-(trifluoromethyl)phenoxy)cyclobutyl)amino)methyl)isoquinolin-8-yl)-2-hydroxyacetonitrile (200 mg, 75%). MS (ESI+) [Method 6A]: m/z 464.2 (M+H); Rt 1.36 min.

Step 72.3: Synthesis of 2-(6-fluoro-5-((((1r,3r)-3-(4-fluoro-3-(trifluoromethyl)phenoxy)cyclobutyl)amino)methyl)isoquinolin-8-yl)-2-hydroxyacetic acid

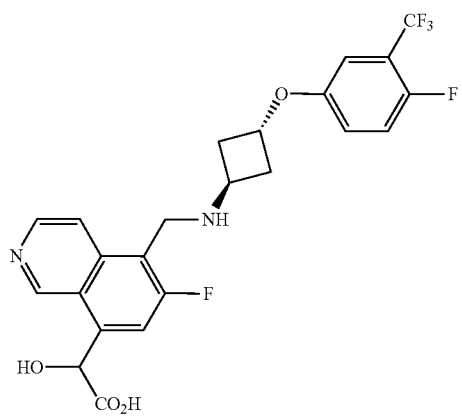 [SMILES: O=C(O)C(O)c1cc(F)c(CN[C@H]2C[C@H](Oc3ccc(F)c(C(F)(F)F)c3)C2)c2ccncc12]

To the stirred solution of 2-(6-fluoro-5-((((1r,3r)-3-(4-fluoro-3-(trifluoromethyl)phenoxy)cyclobutyl)amino)methyl)isoquinolin-8-yl)-2-hydroxyacetonitrile (200 mg, 0.43 mmol) in CH$_2$Cl$_2$ (1 mL), concentrated HCl (2.0 mL) was added at rt, and heated at 40° C. for 16 h. The reaction mixture was concentrated in vacuo, residue was dissolved in water and washed with Et$_2$O 3×'s. Then the aqueous portion was concentrated. Prep-HPLC purification of the crude (Column: LUNA (250 mm×21.2 mm), 5.0μ; Mobile Phase: 0.1% HCO$_2$H in water and acetonitrile) afforded 2-(6-fluoro-5-((((1r,3r)-3-(4-fluoro-3-(trifluoromethyl)phenoxy)cyclobutyl)amino)methyl)isoquinolin-8-yl)-2-hydroxyacetic acid (10 mg, 4%). MS (ESI+) [Method 6A]: m/z 483.1 (M+H); Rt 1.34 min. $^1$H NMR (600 MHz, CD$_3$OD) δ 9.84 (s, 1H), 9.73 (brs, 2H), 8.66-8.63 (m, 1H), 8.43-8.40 (m, 1H), 7.88 (d, J=8.4 Hz, 1H), 7.47 (t, J=8.0 Hz, 1H), 7.21-7.18 (m, 1H), 7.03-7.01 (m, 1H), 5.09-5.05 (m, 1H), 4.60 (s, 2H), 4.10-4.06 (m, 1H), 2.84-2.76 (m, 2H), 2.48-2.41 (m, 2H).

Example 73: Synthesis of 6-fluoro-5-((((1r,3r)-3-(4-fluoro-3-(trifluoromethyl)phenoxy)cyclobutyl)amino)methyl)isoquinoline 2-oxide

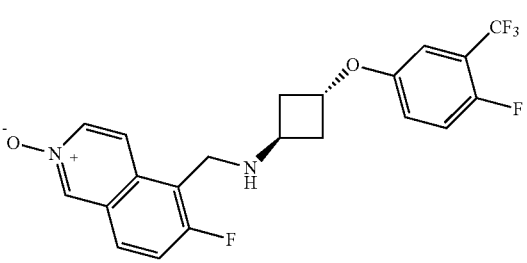

To the solution of (1r,3r)-3-(4-fluoro-3-(trifluoromethyl)phenoxy)-N-((6-fluoroisoquinolin-5-yl)methyl)cyclobutan-1-amine (Step 3.2, 60 mg, 0.15 mmol) in CH$_2$Cl$_2$ (4 mL), m-CPBA (50 mg, 0.29 mmol) was added and stirred at rt, for 16 h under argon. The reaction mixture was concentrated and the residue was dissolved in EtOAc, washed with saturated NaHCO$_3$ solution, followed by brine. Then the organic portion was dried over anhydrous Na$_2$SO$_4$, filtered and concentrated in vacuo. The crude was purified by prep-HPLC (Column: GEMINI NX C18 (150 mm×21.0 mm), 5.0µ; Mobile Phase: 0.02% NH₄OH in water and acetonitrile) to afford 6-fluoro-5-(((((1r,3r)-3-(4-fluoro-3-(trifluoromethyl)phenoxy)cyclobutyl)amino)methyl)isoquinoline 2-oxide (30 mg, 48%). MS (ESI+) [Method 6A]: m/z 425.1 (M+H); Rt 1.45 min. ¹H NMR (400 MHz, CD₃OD) δ 9.21 (s, 1H), 8.47 (d, J=6.4 Hz, 1H), 8.26 (d, J=5.6 Hz, 1H), 8.14 (dd, J=8.4, 5.2 Hz, 1H), 7.50 (t, J=9.6 Hz, 1H), 7.23 (t, J=9.2 Hz, 1H), 7.10-7.03 (m, 2H), 4.86-4.82 (m, 1H), 4.24 (s, 2H), 3.70-3.66 (m, 1H), 2.77-2.72 (m, 2H), 2.36-2.30 (m, 2H).

Example 74: Synthesis of 5-(((((1r,3r)-3-((6-(trifluoromethyl)pyridin-3-yl)oxy)cyclobutyl)amino)methyl)isoquinolin-3-amine Step 74.1: Synthesis of tert-butyl (tert-butoxycarbonyl)(5-(((((1r,3r)-3-((6-(trifluoromethyl)pyridin-3-yl)oxy)cyclobutyl)amino)methyl)isoquinolin-3-yl)carbamate

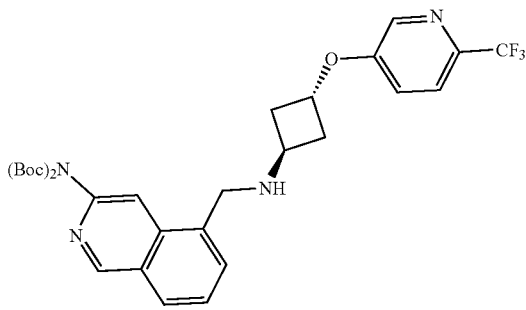

The title compound was synthesized following the procedure as described in Step 25.6, using (1r,3r)-3-((6-(trifluoromethyl)pyridin-3-yl)oxy)cyclobutan-1-amine, HCl (Step 2.2, 50 mg, 0.19 mmol) and tert-butyl (tert-butoxycarbonyl)(5-formylisoquinolin-3-yl)carbamate (Step 13.3, 70 mg, 0.19 mmol). The combined organic portion was washed with brine solution, dried over anhydrous Na₂SO₄, filtered and concentrated in vacuo to afford crude tert-butyl (tert-butoxycarbonyl)(5-(((((1r,3r)-3-((6-(trifluoromethyl)pyridin-3-yl)oxy)cyclobutyl)amino)methyl)isoquinolin-3-yl)carbamate (70 mg, 64%). MS (ESI+) [Method 6A]: m/z 456.3 (M−Boc−tBu+Na+H); Rt 1.38 min Step 74.2: Synthesis of 5-(((((1r,3r)-3-((6-(trifluoromethyl)pyridin-3-yl)oxy)cyclobutyl)amino)methyl)isoquinolin-3-amine

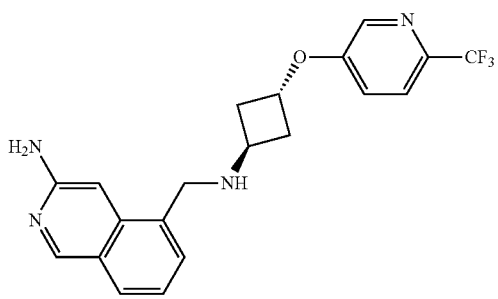 [SMILES: Nc1cc2c(CN[C@H]3C[C@H](Oc4ccc(C(F)(F)F)nc4)C3)cccc2cn1]

Deprotection was carried out according to Step 13.5. The reaction mixture was stirred at rt for 4 h. Then the reaction mixture was concentrated in vacuo and purified by prep-HPLC (Column: KINETEX EVO C18 (150 mm×21.0 mm), 5.0µ; Mobile Phase: 0.02% NH₄OH in water and acetonitrile) to provide 5-(((((1r,3r)-3-((6-(trifluoromethyl)pyridin-3-yl)oxy)cyclobutyl)amino)methyl)isoquinolin-3-amine (15 mg, 59%). MS (ESI+) [Method 6A]: m/z 389.2 (M+H); Rt 1.26 min. ¹H NMR (400 MHz, CD₃OD) δ 8.79 (d, J=0.8 Hz, 1H), 8.28 (d, J=2.8 Hz, 1H), 7.75 (dd, J=10.4, 8.4 Hz, 2H), 7.75 (d, J=6.0 Hz, 1H), 7.40-7.38 (m, 1H), 7.22 (dd, J=8.4, 6.8 Hz, 1H), 7.01 (s, 1H), 5.03-4.99 (m, 1H), 4.03 (s, 2H), 3.70-3.66 (m, 1H), 2.45 (t, J=5.6 Hz, 4H).

Example 75: Synthesis of 6-fluoro-5-((1r,3r)-3-(((6-fluoroisoquinolin-5-yl)methyl)amino)cyclobutoxy)picolinonitrile, HCl Step 75.1: Synthesis of 6-bromo-2-fluoropyridin-3-ol

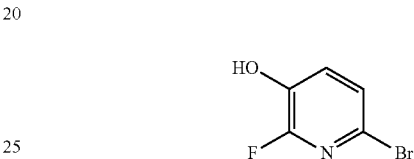

The stirred solution of 2-fluoropyridin-3-ol [CAS No. 174669-74-0] (2.0 g, 17.56 mmol) in AcOH (25 mL) was cooled to 0° C.; then Br₂ (2.82 g, 17.56 mmol) and NaOAc (1.59 g, 19.32 mmol) were added successively. The reaction mixture was stirred at rt for 1 h under argon. The reaction mixture was poured into ice water, neutralized with 2N NaOH solution, and extracted with EtOAc 3×'s. The combined organic portion was washed with brine solution, dried over anhydrous Na₂SO₄, filtered and concentrated in vacuo. The residue was purified by flash chromatography (12 g SiliCycle column, 0-30% EtOAc in Hexane elution) to provide 6-bromo-2-fluoropyridin-3-ol (3.4 g, 99%). ¹H NMR (300 MHz, CDCl₃) δ 7.31-7.27 (m, 2H).

Step 75.2: Synthesis of tert-butyl ((1r,3r)-3-((6-bromo-2-fluoropyridin-3-yl)oxy)cyclobutyl)carbamate

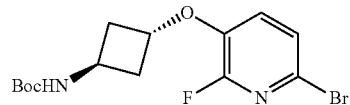 [SMILES: CC(C)(C)OC(=O)N[C@H]1C[C@H](Oc2ccc(Br)nc2F)C1]

To the stirred solution of 6-bromo-2-fluoropyridin-3-ol (250 mg, 1.31 mmol) in anhydrous THF (5 mL), tert-butyl ((1s,3s)-3-hydroxycyclobutyl)carbamate (160 mg, 1.31 mmol) and TPP (340 mg, 1.96 mmol) were added at rt. The reaction mixture was cooled to 0° C., DIAD (0.26 mL, 1.96 mmol) was added and then heated at 50° C. for 16 h under argon. Reaction mixture was diluted with water and extracted with EtOAc 3×'s. The combined organic portion was washed with brine solution, dried over anhydrous Na₂SO₄, filtered and concentrated in vacuo. The residue was purified by flash chromatography (12 g SiliCycle column, 0-30% EtOAc in Hexane elution) to provide tert-butyl ((1r,3r)-3-((6-bromo-2-fluoropyridin-3-yl)oxy)cyclobutyl)carbamate (350 mg, 90%). MS (ESI+) [Method 6A]: m/z 304.5, 306.5 (M−tBu+H); Rt 1.61 min. ¹H NMR (600 MHz, CDCl₃) δ 7.26-7.24 (m, 1H), 6.98-6.95 (m, 1H), 6.33 (brs, 1H), 4.81-4.77 (m, 1H), 4.32-4.27 (m, 1H), 2.62-2.56 (m, 2H), 2.48-2.42 (m, 2H), 1.45 (s, 9H).

Step 75.3: Synthesis of tert-butyl ((1r,3r)-3-((6-cyano-2-fluoropyridin-3-yl)oxy)cyclobutyl)carbamate

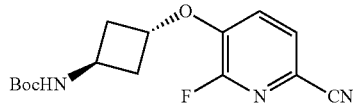 [SMILES: CC(C)(C)OC(=O)N[C@H]1C[C@H](Oc2ccc(C#N)nc2F)C1]

The stirred solution of tert-butyl ((1r,3r)-3-((6-bromo-2-fluoropyridin-3-yl)oxy)cyclobutyl)carbamate (250 mg, 0.69 mmol), Zn-dust (4 mg, 0.07 mmol), Zn(CN)₂ (40 mg, 0.34 mmol), dppf (7 mg, 0.01 mmol) and Pd₂(dba)₃ (12 mg, 0.001 mmol) in DMA (3 mL) was purged with argon for 15 min. The reaction mixture was heated at 100° C. for 5 h under argon. Reaction mixture was cooled rt, filtered through celite bed, then the bed was washed with EtOAc. The collected filtrate was washed with water 3×'s, dried over anhydrous Na₂SO₄, filtered and concentrated in vacuo. The residue was purified by flash chromatography (12 g SiliCycle column, 0-30% EtOAc in Hexane elution) to provide tert-butyl ((1r,3r)-3-((6-cyano-2-fluoropyridin-3-yl)oxy)cyclobutyl) carbamate (115 mg, 54%). $^1$H NMR (400 MHz, CDCl₃) δ 7.54 (d, J=8.4 Hz, 1H), 7.08-7.05 (m, 1H), 4.93-4.87 (m, 1H), 4.32-4.27 (m, 1H), 2.65-2.53 (m, 4H), 1.45 (s, 9H).

Step 75.4: Synthesis of 5-((1r,3r)-3-aminocyclobutoxy)-6-fluoropicolinonitrile, HCl

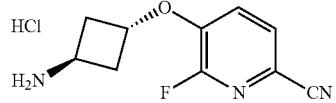 [SMILES: Cl ; N#Cc1ccc(O[C@H]2C[C@H](N)C2)c(F)n1]

Deprotection was carried out according to Step 13.5. The reaction was stirred at rt for 2 h, then concentrated in vacuo. The residue was triturated with pentane, the solid appeared was filtered and dried to yield 5-((1r,3r)-3-aminocyclobutoxy)-6-fluoropicolinonitrile, HCl (60 mg, 69%). $^1$H NMR (400 MHz, DMSO-d6) δ 8.23 (brs, 2H), 8.03 (d, J=10.4 Hz, 1H), 7.57 (t, J=9.6 Hz, 1H), 5.19-5.14 (m, 1H), 3.91-3.85 (m, 1H), 2.70-2.54 (m, 2H), 2.56-2.51 (m, 2H).

Step 75.5: Synthesis of 6-fluoro-5-((1r,3r)-3-(((6-fluoroisoquinolin-5-yl)methyl)amino)cyclobutoxy) picolinonitrile, HCl

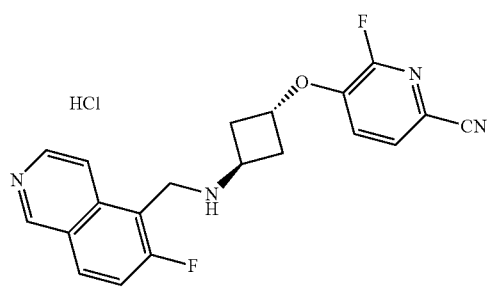 [SMILES: N#Cc1ccc(O[C@H]2C[C@H](NCc3c(F)ccc4cnccc34)C2)c(F)n1 ; Cl]

The title compound was synthesized following the procedure as described in Step 1.4, using 5-((1r,3r)-3-aminocyclobutoxy)-6-fluoropicolinonitrile, HCl (60 mg, 0.25 mmol) and 6-fluoroisoquinoline-5-carbaldehyde (Step 3.1, 39 mg, 0.22 mmol). The crude product was purified by prep-HPLC (Column: LUNA Phenomenex (250 mm×21.2 mm), 5.0μ; Mobile Phase: 0.1% HCO₂H in in water and acetonitrile). To the isolated product, HCl solution (4M in 1,4-dioxane) (2 mL) was added, stirred at rt for 2 h, and then concentrated in vacuo. The residue was triturated with n-pentane and then lyophilized to provide 6-fluoro-5-((1r,3r)-3-(((6-fluoroisoquinolin-5-yl)methyl)amino)cyclobutoxy)picolinonitrile, HCl (30 mg, 30%). MS (ESI+) [Method 6A]: m/z 367.2 (M+H); Rt 1.25 min. $^1$H NMR (400 MHz, CD₃OD) δ 9.84 (s, 1H), 8.78-8.73 (m, 3H), 8.00 (t, J=8.4 Hz, 1H), 7.77 (d, J=8.0 Hz, 1H), 7.49 (t, J=8.0 Hz, 1H), 5.23-5.17 (m, 1H), 4.83 (d, J=1.6 Hz, 2H), 4.33-4.28 (m, 1H), 3.02-2.94 (m, 2H), 2.82-2.75 (m, 2H).

Example 76: Synthesis of (1r,3r)-N-((6-fluoroisoquinolin-5-yl)methyl)-3-(4-(trifluoromethyl)phenoxy)cyclobutan-1-amine, HCl Step 76.1: Synthesis of tert-butyl ((1r,3r)-3-(4-(trifluoromethyl)phenoxy)cyclobutyl)carbamate

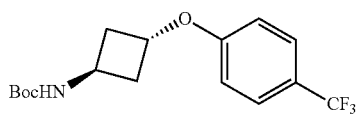 [SMILES: CC(C)(C)OC(=O)N[C@H]1C[C@H](Oc2ccc(C(F)(F)F)cc2)C1]

The title compound was synthesized following the procedure as described in Step 1.2, using tert-butyl ((1s,3s)-3-hydroxycyclobutyl)carbamate (300 mg, 1.60 mmol) and 4-(trifluoromethyl)phenol [CAS No. 402-45-9] (260 mg, 1.60 mmol). The residue was purified by flash chromatography (12 g SiliCycle column, 0-20% EtOAc in Hexane elution) to provide tert-butyl ((1r,3r)-3-(4-(trifluoromethyl)phenoxy)cyclobutyl)carbamate 380 mg, 71%). $^1$H NMR (300 MHz, CDCl₃) δ 7.52 (d, J=8.1 Hz, 2H), 6.82 (d, J=8.1 Hz, 2H), 4.85-4.78 (m, 1H), 4.33-4.27 (m, 1H), 2.61-2.52 (m, 2H), 2.44-2.37 (m, 2H), 1.45 (s, 9H).

Step 76.2: Synthesis of (1r,3r)-3-(4-(trifluoromethyl)phenoxy)cyclobutan-1-amine, HCl

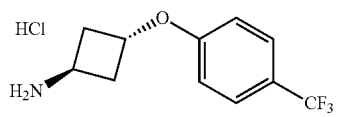 [SMILES: Cl ; N[C@H]1C[C@H](Oc2ccc(C(F)(F)F)cc2)C1]

Deprotection was carried out according to Step 13.5. The reaction mixture was concentrated in vacuo and the residue was triturated with n-pentane, the solid appeared was filtered and dried to yield (1r,3r)-3-(4-(trifluoromethyl)phenoxy)cyclobutan-1-amine, HCl (300 g, 97%). MS (ESI+) [Method 6A]: m/z 231.9 (M+H); Rt 1.3 min.

Step 76.3: Synthesis of (1r,3r)-N-((6-fluoroisoquinolin-5-yl)methyl)-3-(4-(trifluoromethyl)phenoxy)cyclobutan-1-amine, HCl [C-07664-106]

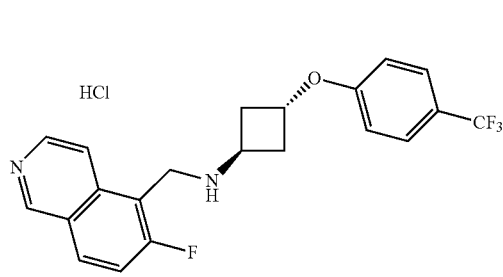 [SMILES: Fc1ccc2cnccc2c1CN[C@H]1C[C@H](Oc2ccc(C(F)(F)F)cc2)C1 ; Cl]

The title compound was synthesized following the procedure as described in Step 1.4, using (1r,3r)-3-(4-(trifluoromethyl)phenoxy)cyclobutan-1-amine, HCl (60 mg, 0.22 mmol) and 6-fluoroisoquinoline-5-carbaldehyde (Step 3.1, 36 mg, 0.20 mmol). The crude product was purified by prep-HPLC (Column: WATERS X BRIDGE C18 (150 mm×21.2 mm), 5.0μ; Mobile Phase: 0.02% NH₄OH in in water and acetonitrile). To the isolated product, HCl solution (4M in 1,4-dioxane) (2 mL) was added, stirred at rt for 2 h, and then concentrated in vacuo. The residue was triturated with n-pentane and then lyophilized to provide (1r,3r)-N-((6-fluoroisoquinolin-5-yl)methyl)-3-(4-(trifluoromethyl)phenoxy)cyclobutan-1-amine, HCl (40 mg, 42%). MS (ESI+) [Method 6A]: m/z 391.2 (M+H); Rt 1.31 min. $^1$H NMR (400 MHz, CD$_3$OD) δ 9.80 (s, 1H), 8.77 (d, J=6.0 Hz, 1H), 8.72-8.68 (m, 2H), 7.98 (t, J=8.4 Hz, 1H), 7.61 (d, J=8.4 Hz, 2H), 6.99 (d, J=8.8 Hz, 2H), 5.09-5.04 (m, 1H), 4.82 (d, J=2.0 Hz, 2H), 4.30-4.25 (m, 1H), 2.91-2.84 (m, 2H), 2.75-2.68 (m, 2H).

Example 77: Synthesis of 2-(6-fluoro-5-((((1r,3r)-3-(4-fluoro-3-(trifluoromethyl)phenoxy)cyclobutyl)amino)methyl)isoquinolin-8-yl)butane-1,4-diol

Step 77.1: Synthesis of 2-(6-fluoroisoquinolin-8-yl)malononitrile

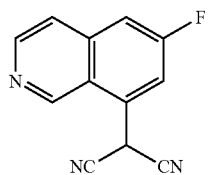 [SMILES: N#CC(C#N)c1cc(F)cc2ccncc12]

The suspension of NaH (60% on mineral oil) (4.25 g, 106.16 mmol) in anhydrous DME (350 mL) was cooled to 0° C., malononitrile (8.78 g, 132.71 mmol) was added and stirred for 30 min at 0° C. under N₂. Then 8-bromo-6-fluoroisoquinoline (Step 6.4, 20.0 g, 88.47 mmol) dissolved in DME (50 mL) was added drop wise, followed by Pd(PPh₃)₄ (10.2 g, 8.85 mmol) and the reaction mixture was stirred at 85° C. for 16 h under N₂. The reaction mixture was concentrated in vacuo, residue was washed with pentane, diluted with water and then neutralized with 3N HCl solution. The red solid precipitate was collected by filtration and dried to afford crude 2-(6-fluoroisoquinolin-8-yl)malononitrile (28.0 g, 150%). MS (ESI+) [Method 6A]: m/z 210.1 (M-H), 212.1 (M+1); Rt 1.37 min.

Step 77.2: Synthesis of dimethyl 2-(6-fluoroisoquinolin-8-yl)malonate

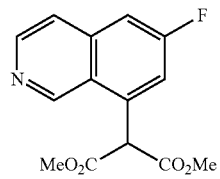

To the stirred solution of 2-(6-fluoroisoquinolin-8-yl)malononitrile (28.0 g, 132.58 mmol) in anhydrous MeOH (420 mL), SOCl₂ (280 mL) was added drop wise at 0° C. and stirred at rt for 16 h under N₂. The reaction mixture concentrated in vacuo. The residue was basified with saturated NaHCO₃ solution, extracted with EtOAc 3×'s. The combined organic layer was washed with brine, dried over anhydrous Na₂SO₄, filtered and concentrated in vacuo. The crude was purified by flash chromatography (80 g SiliCycle column, 0-30% EtOAc in Hexane elution) to provide dimethyl 2-(6-fluoroisoquinolin-8-yl)malonate (13.0 g, 41%). MS (ESI+) [Method 6A]: m/z 276.1 (M-H), 278.1 (M+1); Rt 1.36 min.

Step 77.3: Synthesis of methyl 2-(6-fluoroisoquinolin-8-yl)acetate

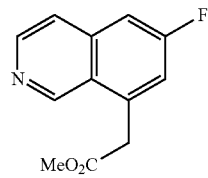 [SMILES: COC(=O)Cc1cc(F)cc2ccncc12]

To the stirred solution of dimethyl 2-(6-fluoroisoquinolin-8-yl)malonate (6.0 g, 21.64 mmol) in DMSO-H₂O (66 mL, 10:1 v/v), LiCl (1.37 g, 32.46 mmol) was added at rt and then heated at 100° C. for 16 h. Reaction mixture was cooled to rt, diluted with water and extracted with EtOAc twice. The combined organic layer was washed with brine, dried over anhydrous Na₂SO₄, filtered and concentrated in vacuo. The crude was purified by flash chromatography (40 g SiliCycle column, 0-20% EtOAc in Hexane elution) to provide methyl 2-(6-fluoroisoquinolin-8-yl)acetate (2.5 g, 53%). MS (ESI+) [Method 6A]: m/z 220.1 (M+1); Rt 0.84 min. $^1$H NMR (600 MHz, CDCl₃) 59.39 (s, 1H), 8.55 (d, J=5.4 Hz, 1H), 7.63 (d, J=6.0 Hz, 1H), 7.38 (d, J=9.0 Hz, 1H), 7.30 (d, J=8.4 Hz, 1H), 4.17 (s, 2H), 3.73 (s, 3H).

Step 77.4: Synthesis of 4-ethyl 1-methyl 2-(6-fluoroisoquinolin-8-yl)succinate

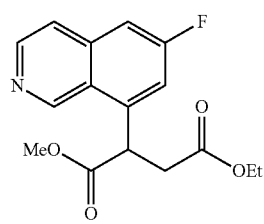 [SMILES: CCOC(=O)CC(C(=O)OC)c1cc(F)cc2ccncc12]

To the stirred solution of methyl 2-(6-fluoroisoquinolin-8-yl)acetate (2.40 g, 10.94 mmol) in anhydrous THF (25 mL), LIHMDS (1.0M in THF) (14.23 mL, 14.23 mmol) was added dropwise at −78° C. and stirred for 1 h under N$_2$. Then ethyl 2-bromoacetate (2.0 g, 12.04 mmol), dissolved in THF (10 mL), was added drop wise at −78° C. and stirred for 2 h. Reaction was quenched with saturated NH$_4$Cl solution, and extracted with EtOAc twice. The combined organic layer was washed with brine dried over anhydrous Na$_2$SO$_4$, filtered and concentrated in vacuo. The crude was purified by flash chromatography (24 g SiliCycle column, 0-20% EtOAc in Hexane elution) to provide 4-ethyl 1-methyl 2-(6-fluoroisoquinolin-8-yl)succinate (3.1 g, 93%). MS (ESI+) [Method 1A]: m/z 306.3 (M+1); Rt 0.31 min. $^1$H NMR (300 MHz, CDCl$_3$) (59.56 (s, 1H), 8.55 (d, J=5.4 Hz, 1H), 7.63 (d, J=5.4 Hz, 1H), 7.37 (dd, J=9.3, 2.1 Hz, 1H), 7.30 (dd, J=9.9, 2.1 Hz, 1H), 5.04 (dd, J=9.0, 5.1 Hz, 1H), 4.14 (q, J=7.2 Hz, 2H), 3.70 (s, 3H), 3.37 (dd, J=17.1, 9.9 Hz, 1H), 2.82 (dd, J=17.1, 5.1 Hz, 1H), 1.21 (t, J=7.2 Hz, 3H).

Step 77.5: Synthesis of 2-(6-fluoroisoquinolin-8-yl)butane-1,4-diol

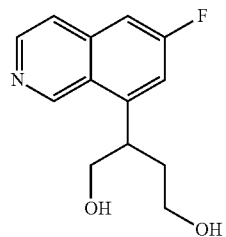 [SMILES: OCCC(CO)c1cc(F)cc2ccncc12]

To the stirred solution of 4-ethyl 1-methyl 2-(6-fluoroisoquinolin-8-yl)succinate (250 mg, 0.82 mmol) in anhydrous THF (4 mL), LAH (62 mg, 1.64 mmol) was added portion wise at 0° C. Reaction mixture was stirred at rt for 3 h under argon. The reaction was quenched with ice cold water and extracted with EtOAc. The combined organic layer was washed with brine dried over anhydrous Na$_2$SO$_4$, filtered and concentrated in vacuo. The crude was purified by flash chromatography (24 g SiliCycle column, 0-25% EtOAc in Hexane elution) to provide 2-(6-fluoroisoquinolin-8-yl)butane-1,4-diol (80 mg, 41%). MS (ESI+) [Method 6A]: m/z 236.2 (M+1); Rt 0.16 min.

Step 77.6: Synthesis of 6-fluoro-8-(2,2,3,3,10,10,11,11-octamethyl-4,9-dioxa-3,10-disiladodecan-6-yl)isoquinoline

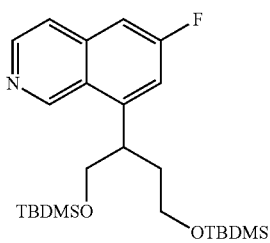 [SMILES: CC(C)(C)[Si](C)(C)OCCC(CO[Si](C)(C)C(C)(C)C)c1cc(F)cc2ccncc12]

To the stirred solution of 2-(6-fluoroisoquinolin-8-yl)butane-1,4-diol (80 mg, 0.34 mmol) and imidazole (162 mg, 2.38 mmol) in DMF (2 mL), TBDMS-Cl (256 mg, 1.70 mmol) was added portion wise at 0° C. The reaction mixture was stirred at rt for 16 h under N$_2$. Then the reaction mixture was diluted with water and extracted with EtOAc twice. The combined organic portion was washed with brine, dried over anhydrous Na$_2$SO$_4$, filtered and concentrated in vacuo. The residue was purified by flash chromatography (12 g SiliCycle column, 0-20% EtOAc in Hexane elution) to provide 6-fluoro-8-(2,2,3,3,10,10,11,11-octamethyl-4,9-dioxa-3,10-disiladodecan-6-yl)isoquinoline (130 mg, 83%). MS (ESI+) [Method 1A]: m/z 464.6 (M+H); Rt 2.52 min.

Step 77.7: Synthesis of 6-fluoro-8-(2,2,3,3,10,10,11,11-octamethyl-4,9-dioxa-3,10-disiladodecan-6-yl)isoquinoline-5-carbaldehyde

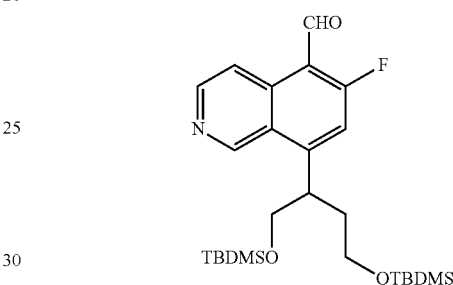

The title compound was prepared according to Step 6.8. The residue was purified by flash chromatography (12 g SiliCycle column, 0-10% EtOAc in Hexane elution) to provide 6-fluoro-8-(2,2,3,3,10,10,11,11-octamethyl-4,9-dioxa-3,10-disiladodecan-6-yl)isoquinoline-5-carbaldehyde (80 mg, 75%). MS (ESI+) [Method 5A]: m/z 493.5 (M+H); Rt 3.09 min.

Step 77.8: Synthesis of (1r,3r)-3-(4-fluoro-3-(trifluoromethyl)phenoxy)-N-((6-fluoro-8-(2,2,3,3,10,10,11,11-octamethyl-4,9-dioxa-3,10-disiladodecan-6-yl)isoquinolin-5-yl)methyl)cyclobutan-1-amine

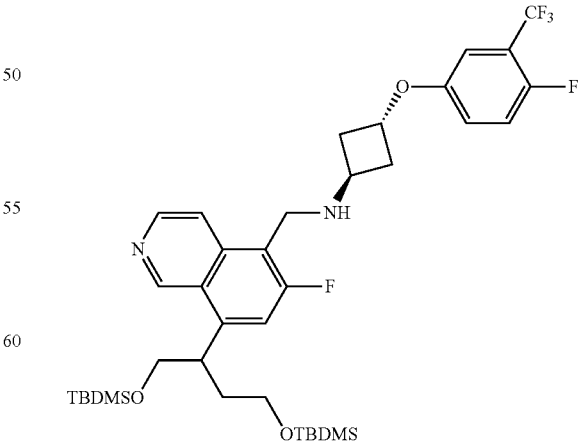

The title compound was synthesized following the procedure as described in Step 1.4, using (1r,3r)-3-(4-fluoro-3-

(trifluoromethyl)phenoxy)cyclobutan-1-amine, HCl (Step 1.3, 55 mg, 0.19 mmol) and 6-fluoro-8-(2,2,3,3,10,10,11,11-octamethyl-4,9-dioxa-3,10-disiladodecan-6-yl)isoquinoline-5-carbaldehyde (76 mg, 0.15 mmol). The crude product was purified by flash chromatography (4 g SiliCycle column, 0-10% MeOH in CHCl$_3$ elution) to provide (1r,3r)-3-(4-fluoro-3-(trifluoromethyl)phenoxy)-N-((6-fluoro-8-(2,2,3,3,10,10,11,11-octamethyl-4,9-dioxa-3,10-disiladodecan-6-yl)isoquinolin-5-yl)methyl)cyclobutan-1-amine (100 mg, 72%). MS (ESI+) [Method 5A]: m/z 725.4 (M+H); Rt 2.44 min.

Example 77.9: Synthesis of 2-(6-fluoro-5-((((1r,3r)-3-(4-fluoro-3-(trifluoromethyl)phenoxy)cyclobutyl)amino)methyl)isoquinolin-8-yl)butane-1,4-diol

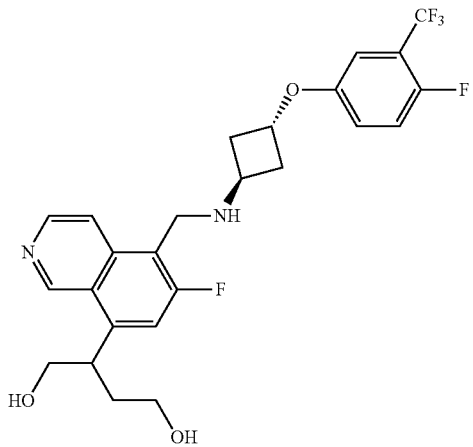 [SMILES: OCCC(CO)c1cc(F)c(CN[C@H]2C[C@H](Oc3ccc(F)c(C(F)(F)F)c3)C2)c2ccncc12]

Deprotection was carried out according to Step 7.6. The residue was purified by prep-HPLC (Column: X SELECT (250 mm×21.2 mm), 5.0μ; Mobile Phase: 0.02% NH$_4$OH in in water and acetonitrile) to afford 2-(6-fluoro-5-((((1r,3r)-3-(4-fluoro-3-(trifluoromethyl)phenoxy)cyclobutyl)amino)methyl)isoquinolin-8-yl)butane-1,4-diol (23 mg, 34%). MS (ESI+) [Method 1A]: m/z 497.2 (M+H); Rt 0.18 min. $^1$H NMR (400 MHz, CD$_3$OD) δ 9.64 (s, 1H), 8.54 (d, J=6.0 Hz, 1H), 8.13 (d, J=6.4 Hz, 1H), 7.54 (d, J=8.4 Hz, 1H), 7.24 (t, J=6.8 Hz, 1H), 7.08-7.02 (m, 3H), 4.90-4.85 (m, 1H), 4.20 (s, 2H), 4.13-4.07 (m, 1H), 3.89 (d, J=6.0 Hz, 2H), 3.64-3.57 (m, 2H), 3.48-3.42 (m, 1H), 2.39-2.35 (m, 4H), 2.26-2.18 (m, 1H), 2.03-1.97 (m, 1H).

Example 78: Synthesis of (1r,3r)-3-((3,4-difluorobenzyl)oxy)-N-((6-fluoroisoquinolin-5-yl)methyl)cyclobutan-1-amine Step 78.1: Synthesis of tert-butyl ((1r,3r)-3-((3,4-difluorobenzyl)oxy)cyclobutyl)carbamate

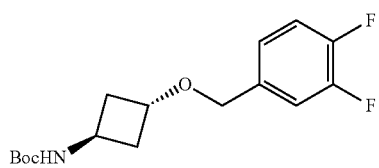 [SMILES: CC(C)(C)OC(=O)N[C@H]1C[C@H](OCc2ccc(F)c(F)c2)C1]

To the solution of tert-butyl ((1r,3r)-3-hydroxycyclobutyl)carbamate (200 mg, 1.07 mmol) in THF (3 mL), NaH (60% on mineral oil) (51 mg, 1.28 mmol) was added at 0° C., stirred for 15 min. Then 4-(bromomethyl)-1,2-difluorobenzene [CAS No. 85118-01-0] (243 mg, 1.18 mmol) was added dropwise and the reaction mixture was stirred at rt for 2 h under N$_2$. The reaction mixture was diluted with ice-water, and stirred for 15 min. The white solid that precipitated was filtered and dried to provide tert-butyl ((1r,3r)-3-((3,4-difluorobenzyl)oxy)cyclobutyl)carbamate (240 mg, 72%). $^1$H NMR (300 MHz, CDCl$_3$) δ 7.18-7.04 (m, 3H), 4.69-4.65 (m, 1H), 4.34 (s, 2H), 4.20-4.14 (m, 1H), 2.45-2.37 (m, 2H), 2.18-2.11 (m, 2H), 1.44 (s, 9H).

Step 78.2: Synthesis of (1r,3r)-3-((3,4-difluorobenzyl)oxy)cyclobutan-1-amine, HCl

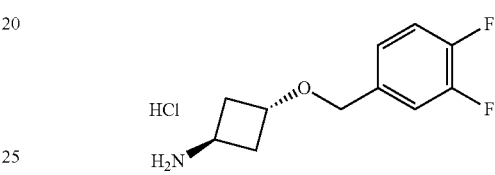

A solution of tert-butyl ((1r,3r)-3-((3,4-difluorobenzyl)oxy)cyclobutyl)carbamate (240 mg, 0.77 mmol) and HCl solution (4M in 1,4-dioxane) (5 mL) was stirred at rt for 2 h. Then the reaction mixture was concentrated in vacuo and the residue was triturated with Et$_2$O. The solid that precipitated was filtered and dried to yield crude (1r,3r)-3-((3,4-difluorobenzyl)oxy)cyclobutan-1-amine, HCl (210 mg, 109%). MS (ESI+) [Method 6A]: m/z 214.1 (M+H); Rt 1.25 min.

Step 78.3: Synthesis of (1r,3r)-3-((3,4-difluorobenzyl)oxy)-N-((6-fluoroisoquinolin-5-yl)methyl)cyclobutan-1-amine

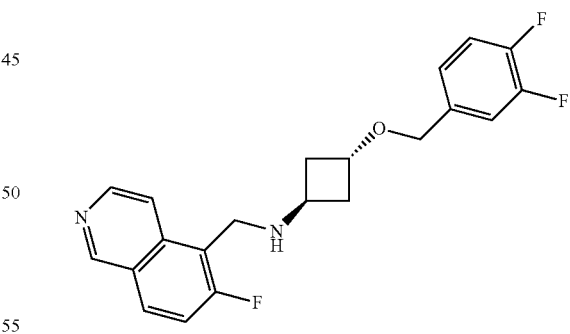

The title compound was synthesized following the procedure as described in Step 1.4, using (1r,3r)-3-((3,4-difluorobenzyl)oxy)cyclobutan-1-amine, HCl (100 mg, 0.40 mmol) and 6-fluoroisoquinoline-5-carbaldehyde (Step 3.1, 63 mg, 0.36 mmol). The crude product was purified by prep-HPLC (Column: LUNA Phenomenex (250 mm×21.2 mm), 5.0μ; Mobile Phase: 0.1% HCO$_2$H in water and acetonitrile-MeOH (1:1)) to afford (1r,3r)-3-((3,4-difluorobenzyl)oxy)-N-((6-fluoroisoquinolin-5-yl)methyl)cyclobutan-1-amine (60 mg, 40%). MS (ESI+) [Method 6A]: m/z 373.1 (M+H); Rt 1.30 min. $^1$H NMR (400 MHz, CD$_3$OD) δ 9.28 (brs, 1H), 8.57 (brs, 1H), 8.24 (dd, J=8.8, 5.2 Hz, 1H), 8.10 (d, J=6.0 Hz, 1H), 7.58 (t, J=8.8 Hz, 1H), 7.27-7.18 (m, 2H), 7.13-7.19 (m, 1H), 4.39 (s, 2H), 4.36 (s, 2H), 4.26-4.01 (m, 1H), 3.77-3.72 (m, 1H), 2.38-2.32 (m, 2H), 2.30-2.24 (m, 2H).

Example 79: Synthesis of (1r,3r)-3-(3,4-dimethylphenoxy)-N-((6-fluoroisoquinolin-5-yl)methyl)cyclobutan-1-amine, HCl Step 79.1: Synthesis of tert-butyl ((1r,3r)-3-(3,4-dimethylphenoxy)cyclobutyl)carbamate

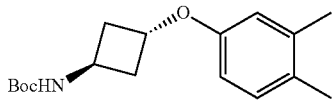 [SMILES: Cc1ccc(O[C@H]2C[C@H](NC(=O)OC(C)(C)C)C2)cc1C]

The title compound was synthesized following the procedure as described in Step 1.2, using tert-butyl ((1s,3s)-3-hydroxycyclobutyl)carbamate (200 mg, 1.07 mmol) and 3,4-dimethylphenol [CAS No. 95-65-8] (144 mg, 1.18 mmol). The crude was purified by flash chromatography (12 g SiliCycle column, 0-20% EtOAc in Hexane elution) to provide tert-butyl ((1r,3r)-3-(3,4-dimethylphenoxy)cyclobutyl)carbamate (270 mg, 87%). $^1$H NMR (300 MHz, CDCl$_3$) δ 6.99 (t, J=7.8 Hz, 1H), 6.65-6.48 (m, 2H), 5.27-5.22 (m, 1H), 4.77-4.73 (m, 1H), 2.59-2.50 (m, 2H), 2.38-2.31 (m, 2H), 2.21 (s, 3H), 2.18 (s, 3H), 1.45 (s, 9H).

Step 79.2: Synthesis of (1r,3r)-3-(3,4-dimethylphenoxy)cyclobutan-1-amine, HCl

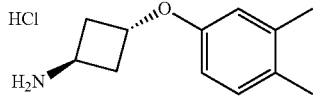

The solution of tert-butyl ((1r,3r)-3-(3,4-dimethylphenoxy)cyclobutyl)carbamate (270 mg, 0.93 mmol) and HCl (4M in 1,4-dioxane) (3 mL) was stirred at rt for 16 h. Then the reaction mixture was concentrated in vacuo, the residue was triturated with Et$_2$O, the solid was filtered and dried to yield (1r,3r)-3-(3,4-dimethylphenoxy)cyclobutan-1-amine, HCl (80 mg, 38%). MS (ESI+) [Method 6A]: m/z 192.2 (M+H); Rt 1.28 min.

Step 79.3: Synthesis of (1r,3r)-3-(3,4-dimethylphenoxy)-N-((6-fluoroisoquinolin-5-yl)methyl)cyclobutan-1-amine, HCl

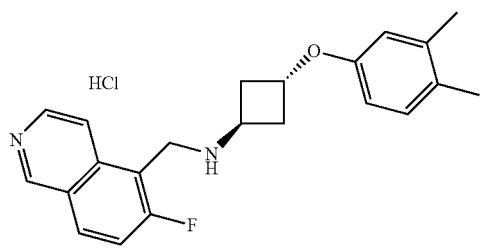 [SMILES: Cc1ccc(O[C@H]2C[C@H](NCc3c(F)ccc4cnccc34)C2)cc1C ; Cl]

The title compound was synthesized following the procedure as described in Step 1.4, using (1r,3r)-3-(3,4-dimethylphenoxy)cyclobutan-1-amine, HCl (80 mg, 0.35 mmol) and 6-fluoroisoquinoline-5-carbaldehyde (Step 3.1, 56 mg, 0.32 mmol). The crude product was purified by prep-HPLC (Column: LUNA C18 (250 mm×21.0 mm), 5.0µ; Mobile Phase: 0.1% HCO$_2$H in water and acetonitrile). The isolated product was stirred with HCl solution (20% in 1,4-dioxane) (2 mL) at rt for 2 h, then concentrated in vacuo to afford (1r,3r)-3-(3,4-dimethylphenoxy)-N-((6-fluoroisoquinolin-5-yl)methyl)cyclobutan-1-amine, HCl (30 mg, 22%). MS (ESI+) [Method 1A]: m/z 351.0 (M+H); Rt 0.18 min. $^1$H NMR (400 MHz, CD$_3$OD) δ 9.87 (brs, 1H), 8.81 (brs, 1H), 8.78-8.74 (m, 2H), 8.02 (t, J=9.2 Hz, 1H), 7.03 (d, J=8.4 Hz, 1H), 6.64 (d, J=2.4 Hz, 1H), 6.54 (dd, J=8.0, 2.8 Hz, 1H), 4.97-4.93 (m, 1H), 4.83 (d, J=1.6 Hz, 2H), 4.27-4.23 (m, 1H), 2.86-2.79 (m, 2H), 2.71-2.64 (m, 2H), 2.24 (s, 3H), 2.14 (s, 3H).

Example 80: Synthesis of ethyl 4-((1r,3r)-3-(((6-fluoroisoquinolin-5-yl)methyl)amino)cyclobutoxy)benzoate Step 80.1: Synthesis of ethyl 4-((1r,3r)-3-((tert-butoxycarbonyl)amino)cyclobutoxy)benzoate

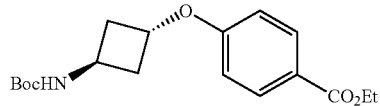

The title compound was synthesized following the procedure as described in Step 1.2, using tert-butyl ((1s,3s)-3-hydroxycyclobutyl)carbamate (200 mg, 1.07 mmol) and ethyl 4-hydroxybenzoate [CAS No. 120-47-8] (195 g, 1.18 mmol). The crude product was purified by flash chromatography (12 g SiliCycle column, 0-40% EtOAc in Hexane elution) to provide ethyl 4-((1r,3r)-3-((tert-butoxycarbonyl)amino)cyclobutoxy)benzoate (250 mg, 70%). $^1$H NMR (300 MHz, DMSO-d6) δ 7.97 (d, J=8.7 Hz, 2H), 6.77 (d, J=9.3 Hz, 2H), 5.08-4.99 (m, 1H), 4.87-4.81 (m, 1H), 4.34 (q, J=7.2 Hz, 2H), 2.61-2.53 (m, 2H), 2.45-2.38 (m, 2H), 1.45 (s, 9H), 1.37 (t, J=7.2 Hz, 3H).

Step 80.2: Synthesis of ethyl 4-((1r,3r)-3-aminocyclobutoxy)benzoate, HCl

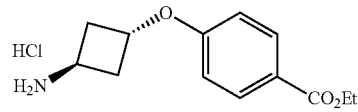 [SMILES: Cl ; CCOC(=O)c1ccc(O[C@H]2C[C@H](N)C2)cc1]

The solution of ethyl 4-((1r,3r)-3-((tert-butoxycarbonyl)amino)cyclobutoxy)benzoate (250 mg, 0.75 mmol) and HCl (4M in 1,4-dioxane) (3 mL) was stirred at rt for 2 h. Then the reaction mixture was concentrated in vacuo, and triturated with Et$_2$O to yield ethyl 4-((1r,3r)-3-aminocyclobutoxy)benzoate, HCl (110 mg, 54%). MS (ESI+) [Method 6A]: m/z 236.1 (M+H); Rt 1.28 min. $^1$H NMR (400 MHz, CD$_3$OD) δ 7.98 (d, J=8.8 Hz, 2H), 6.90 (d, J=9.2 Hz, 2H), 5.06-5.00 (m, 1H), 4.34 (q, J=7.2 Hz, 2H), 4.03-3.97 (m, 1H), 2.70-2.59 (m, 4H), 1.38 (t, J=7.2 Hz, 3H).

Step 80.3: Synthesis of ethyl 4-((1r,3r)-3-(((6-fluoroisoquinolin-5-yl)methyl)amino)cyclobutoxy)benzoate

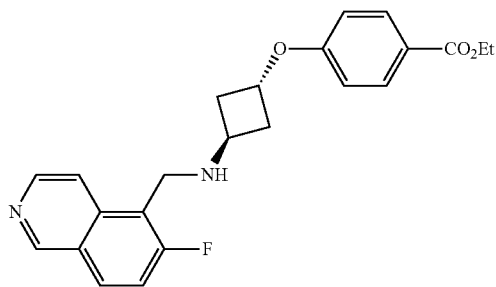 [SMILES: CCOC(=O)c1ccc(O[C@H]2C[C@H](NCc3c(F)ccc4cnccc34)C2)cc1]

The title compound was synthesized following the procedure as described in Step 1.4, using ethyl 4-((1r,3r)-3-aminocyclobutoxy)benzoate, HCl (80 mg, 0.30 mmol) and 6-fluoroisoquinoline-5-carbaldehyde (Step 3.1, 46 mg, 0.27 mmol). Crude product was purified by prep-HPLC (Column: LUNA C18 (250 mm×21.0 mm), 5.0µ; Mobile Phase: 0.1% HCO$_2$H in water and acetonitrile) to provide ethyl 4-((1r,3r)-3-(((6-fluoroisoquinolin-5-yl)methyl)amino)cyclobutoxy)benzoate (30 mg, 24%). MS (ESI+) [Method 6A]: m/z 395.1 (M+H); Rt 1.32 min. $^1$H NMR (400 MHz, CD$_3$OD) δ 9.26 (s, 1H), 8.54 (d, J=6.0 Hz, 1H), 8.18 (dd, J=9.2, 5.6 Hz, 1H), 8.13 (d, J=6.4 Hz, 1H), 7.95 (dd, J=7.2, 2.0 Hz, 2H), 7.54 (t, J=9.2 Hz, 1H), 6.86 (dd, J=7.2, 2.0 Hz, 2H), 4.93-4.89 (m, 1H), 4.33 (q, J=7.2 Hz, 2H), 4.22 (d, J=1.6 Hz, 2H), 3.65-3.60 (m, 1H), 2.39 (dd, J=6.4, 5.6 Hz, 4H), 1.38 (t, J=7.2 Hz, 3H).

Example 81: Synthesis of 5-((((1r,3r)-3-(4-fluoro-3-(trifluoromethyl)phenoxy)cyclobutyl)amino)methyl)-N,N-dimethylisoquinolin-6-amine, HCl Step 81.1: Synthesis of 6-(dimethylamino)isoquinoline-5-carbaldehyde

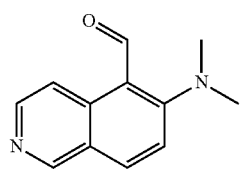

To the solution of 6-fluoroisoquinoline [CAS No. 1075-11-2] (0.5 g, 3.40 mmol) in anhydrous THF (10 mL), LDA (2M in THF) (4.25 mL, 8.49 mmol) was added dropwise at −78° C. and stirred for 2.5 h under N$_2$ atmosphere. Then anhydrous DMF (0.78 mL, 10.19 mmol) was added dropwise at −78° C., stirred for 30 min and temperature was raised to 0° C. slowly over a period of 1 h while stirring. The reaction was quenched with saturated NH$_4$Cl solution and extracted with EtOAc twice. The combined organic portion was washed with brine, dried over anhydrous Na$_2$SO$_4$, filtered and concentrated in vacuo to yield the crude product. The crude was purified by flash chromatography (12 g SiliCycle column, 0-20% EtOAc in Hexane elution) to elute 6-fluoroisoquinoline-5-carbaldehyde (pale brown solid, 30 mg, 5%), followed by 6-(dimethylamino)isoquinoline-5-carbaldehyde (pale brown gummy liquid, 70 mg, 10%). Peak 1: 6-fluoroisoquinoline-5-carbaldehyde: MS (ESI+) [Method 6A]: m/z 175.8 (M+H); Rt 0.84 min. Peak 2: 6-(dimethylamino)isoquinoline-5-carbaldehyde: MS (ESI+) [Method 6A]: m/z 200.9 (M+H); Rt 0.44 min. $^1$H NMR (300 MHz, CDCl$_3$) δ 10.30 (s, 1H), 9.01 (s, 1H), 8.76 (d, J=6.6 Hz, 1H), 8.52 (d, J=6.3 Hz, 1H), 7.93 (d, J=9.6 Hz, 1H), 7.35 (d, J=9.3 Hz, 1H), 3.24 (s, 6H).

Step 81.2: Synthesis of 5-((((1r,3r)-3-(4-fluoro-3-(trifluoromethyl)phenoxy)cyclobutyl)amino)methyl)-N,N-dimethylisoquinolin-6-amine, HCl

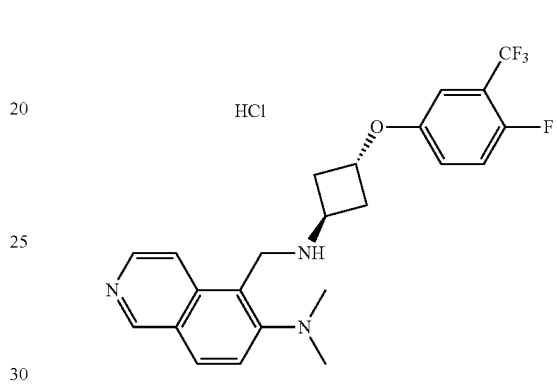

The title compound was synthesized following the procedure as described in Step 1.4, using (1r,3r)-3-(4-fluoro-3-(trifluoromethyl)phenoxy)cyclobutan-1-amine, HCl (Step 1.3, 80 mg, 0.28 mmol) and 6-(dimethylamino)isoquinoline-5-carbaldehyde (50 mg, 0.25 mmol). The crude product was purified by prep-HPLC (Column: KINETEX (150 mm×21.2 mm), 5.0µ; Mobile Phase: 0.02% NH$_4$OH in water and acetonitrile). The isolated product was stirred with HCl solution (4M in 1,4-dioxane) (2 mL) at rt for 2 h, then concentrated in vacuo. The residue was triturated with Et$_2$O, filtered and dried to afford 5-((((1r,3r)-3-(4-fluoro-3-(trifluoromethyl)phenoxy)cyclobutyl)amino)methyl)-N,N-dimethylisoquinolin-6-amine, HCl (20 mg, 15%). MS (ESI+) [Method 6A]: m/z 434.4 (M+H); Rt 1.31 min. $^1$H NMR (400 MHz, CD$_3$OD) δ 9.48 (s, 1H), 8.51 (d, J=7.2 Hz, 1H), 8.44 (d, J=5.2 Hz, 1H), 8.41 (s, 1H), 7.96 (d, J=9.2 Hz, 1H), 7.29 (t, J=9.2 Hz, 1H), 7.13-7.07 (m, 2H), 4.99-4.96 (m, 1H), 4.83 (s, 2H), 4.16-4.10 (m, 1H), 3.15 (s, 6H), 2.83-2.76 (m, 2H), 2.65-2.59 (m, 2H).

Example 82: Synthesis of (1r,3r)-3-(3,5-difluorophenoxy)-N-((6-fluoroisoquinolin-5-yl)methyl)cyclobutan-1-amine, HCl Step 82.1: Synthesis of tert-butyl ((1r,3r)-3-(3,5-difluorophenoxy)cyclobutyl)carbamate

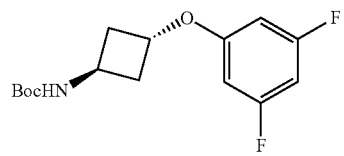 [SMILES: CC(C)(C)OC(=O)N[C@H]1C[C@H](Oc2cc(F)cc(F)c2)C1]

The title compound was synthesized following the procedure as described in Step 1.2, using tert-butyl ((1s,3s)-3-hydroxycyclobutyl)carbamate (150 mg, 0.80 mmol) and 3,5-difluorophenol [CAS No. 2713-34-0] (100 mg, 0.80 mmol). Crude product was purified by flash chromatography (8 g SiliCycle column, 0-10% EtOAc in Hexane elution) to provide tert-butyl ((1r,3r)-3-(3,5-difluorophenoxy)cyclobutyl)carbamate (120 mg, 50%). $^1$H NMR (300 MHz, CDCl$_3$) δ 6.42-6.38 (m, 1H), 6.28 (dd, J=9.0, 2.4 Hz, 2H), 4.73-4.69 (m, 1H), 4.32-4.26 (m, 1H), 2.58-2.51 (m, 2H), 2.41-2.34 (m, 2H), 1.45 (s, 9H).

Step 82.2: Synthesis of (1r,3r)-3-(3,5-difluorophenoxy)cyclobutan-1-amine, HCl

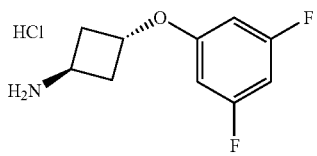 [SMILES: Cl ; N[C@H]1C[C@H](Oc2cc(F)cc(F)c2)C1]

A round bottom flask was charge with tert-butyl ((1r,3r)-3-(3,5-difluorophenoxy)cyclobutyl)carbamate (120 mg, 0.40 mmol) and HCl solution (4M in 1,4-dioxane) (2 mL), and stirred at rt for 1 h. Then the reaction mixture was concentrated in vacuo. The residue was triturated with Et$_2$O, solid was filtered and dried to yield (1r,3r)-3-(3,5-difluorophenoxy)cyclobutan-1-amine, HCl (90 mg, 84%). $^1$H NMR (300 MHz, DMSO-d6) δ 8.19 (brs, 3H), 6.86-6.79 (m, 1H), 6.59 (dd, J=9.3, 2.4 Hz, 2H), 5.01-4.96 (m, 1H), 3.86-3.81 (m, 1H), 2.64-2.57 (m, 2H), 2.49-2.37 (m, 2H).

Step 82.3: Synthesis of (1r,3r)-3-(3,5-difluorophenoxy)-N-((6-fluoroisoquinolin-5-yl)methyl)cyclobutan-1-amine, HCl

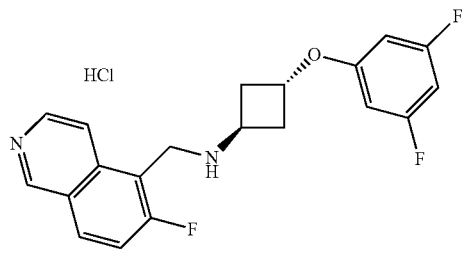 [SMILES: Fc1cc(F)cc(O[C@H]2C[C@H](NCc3c(F)ccc4cnccc34)C2)c1 ; Cl]

The title compound was synthesized following the procedure as described in Step 1.4, using (1r,3r)-3-(3,5-difluorophenoxy)cyclobutan-1-amine, HCl (70 mg, 0.29 mmol) and 6-fluoroisoquinoline-5-carbaldehyde (Step 3.1, 46 mg, 0.26 mmol). The crude product was purified by prep-HPLC (Column: XBRIDGE C18 (150 mm×19 mm), 5.0µ; Mobile Phase: 0.1% HCO$_2$H in water and acetonitrile). To the isolated product, HCl solution (4M in 1,4-dioxane) (1 mL) was added, stirred at rt for 1 h, and then concentrated in vacuo. The residue was triturated with pentane and then lyophilized to provide (1r,3r)-3-(3,5-difluorophenoxy)-N-((6-fluoroisoquinolin-5-yl)methyl)cyclobutan-1-amine, HCl (7 mg, 6%). MS (ESI+) [Method 6A]: m/z 359.1 (M+H); Rt 1.29 min. $^1$H NMR (400 MHz, CD$_3$OD) δ 9.83 (s, 1H), 8.80-8.78 (m, 1H), 8.76-8.72 (m, 2H), 8.01 (t, J=8.8 Hz, 1H), 6.61-6.56 (m, 1H), 6.52-6.49 (m, 2H), 5.03-4.99 (m, 1H), 4.83 (d, J=2.0 Hz, 2H), 4.31-4.26 (m, 1H), 2.92-2.85 (m, 2H), 2.75-2.68 (m, 2H).

Example 83: Synthesis of (1r,3r)-N-((6-fluoroisoquinolin-5-yl)methyl)-3-(4-(pentafluoro-λ$^6$-sulfaneyl)phenoxy)cyclobutan-1-amine, HCl Step 83.1: Synthesis of tert-butyl ((1r,3r)-3-(4-(pentafluoro-λ$^6$-sulfaneyl)phenoxy)cyclobutyl)carbamate

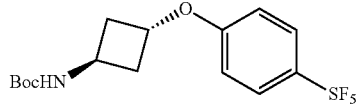

The title compound was synthesized following the procedure as described in Step 1.2, using tert-butyl ((1s,3s)-3-hydroxycyclobutyl)carbamate (120 mg, 0.64 mmol) and 4-(pentafluorosulfaneyl)phenol [CAS No. 774-94-7] (150 mg, 0.68 mmol). Crude product was purified by flash chromatography (8 g SiliCycle column, 0-10% EtOAc in Hexane elution) to provide tert-butyl ((1r,3r)-3-(4-(pentafluoro-λ$^6$-sulfaneyl)phenoxy)cyclobutyl)carbamate as a yellowish gummy oil (150 mg, 67%). $^1$H NMR (600 MHz, CDCl$_3$) δ 7.65 (d, J=8.4 Hz, 2H), 6.77 (d, J=8.4 Hz, 2H), 4.82-4.78 (m, 1H), 4.33-4.28 (m, 1H), 2.58-2.53 (m, 2H), 2.43-2.38 (m, 2H), 1.45 (s, 9H).

Step 83.2: Synthesis of (1r,3r)-3-(4-(pentafluoro-λ$^6$-sulfaneyl)phenoxy)cyclobutan-1-amine, HCl

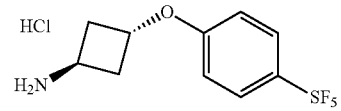

A round bottom flask was charge with tert-butyl ((1r,3r)-3-(4-(pentafluoro-λ$^6$-sulfaneyl)phenoxy)cyclobutyl)carbamate (150 mg, 0.39 mmol) and HCl solution (4M in 1,4-dioxane) (2 mL), and stirred at rt for 1 h. Then the reaction mixture was concentrated in vacuo. The residue was triturated with Et$_2$O, solid was filtered and dried to yield (1r,3r)-3-(4-(pentafluoro-λ$^6$-sulfaneyl)phenoxy)cyclobutan-1-amine, HCl (110 mg, 96%). $^1$H NMR (300 MHz, DMSO-d6) δ 8.20 (brs, 3H), 7.84 (d, J=9.3 Hz, 2H), 6.97 (d, J=9.0 Hz, 2H), 5.08-5.03 (m, 1H), 3.88-3.82 (m, 1H), 2.65-2.57 (m, 2H), 2.49-2.43 (m, 2H).

Step 83.3: Synthesis of (1r,3r)-N-((6-fluoroisoquinolin-5-yl)methyl)-3-(4-(pentafluoro-λ⁶-sulfaneyl)phenoxy)cyclobutan-1-amine, HCl

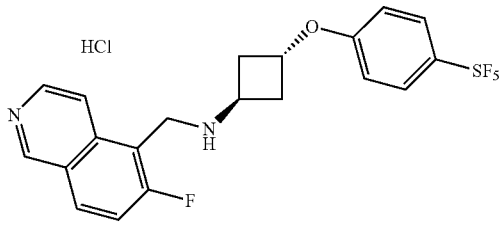

The title compound was synthesized following the procedure as described in step 1.4, using (1r,3r)-3-(4-(pentafluoro-λ⁶-sulfaneyl)phenoxy)cyclobutan-1-amine, HCl (70 mg, 0.21 mmol) and 6-fluoroisoquinoline-5-carbaldehyde (Step 3.1, 32 mg, 0.18 mmol). The crude product was purified by prep-HPLC (Column: GEMINI-NX (150 mm×21.2 mm), 5.0μ; Mobile Phase: 0.02% NH$_4$OH in water and acetonitrile). To the isolated product, HCl solution (4M in 1,4-dioxane) (1 mL) was added, stirred at rt for 1 h, and then concentrated in vacuo. The residue was triturated with pentane and then lyophilized to provide (1r,3r)-N-((6-fluoroisoquinolin-5-yl)methyl)-3-(4-(pentafluoro-λ⁶-sulfaneyl)phenoxy)cyclobutan-1-amine, HCl (30 mg, 28%). MS (ESI+) [Method 6A]: m/z 449.1 (M+H); Rt 1.34 min. $^1$H NMR (400 MHz, CD$_3$OD) δ 9.78 (s, 1H), 8.77 (d, J=6.8 Hz, 1H), 8.73-8.66 (m, 2H), 7.97 (t, J=8.8 Hz, 1H), 7.78 (d, J=9.6 Hz, 2H), 6.98 (d, J=8.8 Hz, 2H), 5.11-5.06 (m, 1H), 4.82 (d, J=1.6 Hz, 2H), 4.33-4.25 (m, 1H), 2.93-2.86 (m, 2H), 2.76-2.69 (m, 2H).

Example 84: Synthesis of (1r,3r)-3-(3,5-dimethylphenoxy)-N-((6-fluoroisoquinolin-5-yl)methyl)cyclobutan-1-amine, HCl

Step 84.1: Synthesis of tert-butyl ((1r,3r)-3-(3,5-dimethylphenoxy)cyclobutyl)carbamate

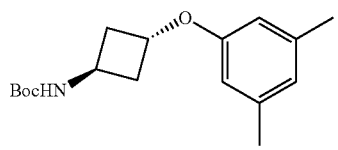 [SMILES: Cc1cc(C)cc(O[C@H]2C[C@H](NC(=O)OC(C)(C)C)C2)c1]

The title compound was synthesized following the procedure as described in Step 1.2, using tert-butyl ((1s,3s)-3-hydroxycyclobutyl)carbamate (150 mg, 0.80 mmol) and 3,5-dimethylphenol [CAS No. 108-68-9] (108 mg, 0.88 mmol). Crude product was purified by flash chromatography (12 g SiliCycle column, 0-10% EtOAc in Hexane elution) to provide tert-butyl ((1r,3r)-3-(3,5-dimethylphenoxy)cyclobutyl)carbamate (140 mg, 60%). $^1$H NMR (400 MHz, CDCl$_3$) δ 6.59 (s, 1H), 6.46 (s, 1H), 6.39 (s, 1H), 4.77-4.72 (m, 1H), 4.39-4.33 (m, 1H), 2.57-2.51 (m, 2H), 2.38-2.31 (m, 2H), 2.27 (s, 6H), 1.45 (s, 9H).

Step 84.2: Synthesis of (1r,3r)-3-(3,5-dimethylphenoxy)cyclobutan-1-amine, HCl

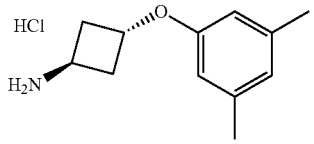

A round bottom flask was charged with tert-butyl ((1r,3r)-3-(3,5-dimethylphenoxy)cyclobutyl)carbamate (140 mg, 0.48 mmol) and HCl solution (4M in 1,4-dioxane) (3 mL), and stirred at rt for 16 h. Then the reaction mixture was concentrated in vacuo. The residue was triturated with Et$_2$O, solid was filtered and dried to yield (1r,3r)-3-(3,5-dimethylphenoxy)cyclobutan-1-amine, HCl (72 mg, 66%). $^1$H NMR (600 MHz, CDCl3) δ 8.65 (brs, 3H), 6.57 (s, 1H), 6.38 (s, 2H), 5.03-5.00 (m, 1H), 4.09-4.04 (m, 1H), 2.87-2.82 (m, 2H), 2.67-2.62 (m, 2H), 2.24 (s, 6H).

Step 84.3: Synthesis of (1r,3r)-3-(3,5-dimethylphenoxy)-N-((6-fluoroisoquinolin-5-yl)methyl)cyclobutan-1-amine, HCl

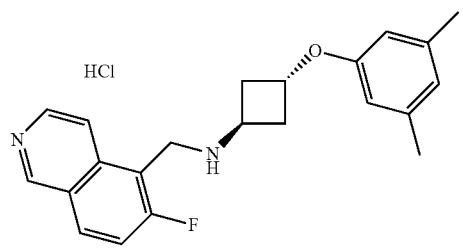 [SMILES: Cc1cc(C)cc(O[C@H]2C[C@H](NCc3c(F)ccc4cnccc34)C2)c1 ; Cl]

The title compound was synthesized following the procedure as described in Step 1.4, using (1r,3r)-3-(3,5-dimethylphenoxy)cyclobutan-1-amine, HCl (75 mg, 0.31 mmol) and 6-fluoroisoquinoline-5-carbaldehyde (Step 3.1, 49 mg, 0.28 mmol). The crude product was purified by prep-HPLC (Column: LUNA C18 (250 mm×21.2 mm), 5.0μ; Mobile Phase: 0.1% HCO$_2$H in water and acetonitrile). To the isolated product, HCl solution (4M in 1,4-dioxane) (1 mL) was added, stirred at rt for 1 h, and then concentrated to provide (1r,3r)-3-(3,5-dimethylphenoxy)-N-((6-fluoroisoquinolin-5-yl)methyl)cyclobutan-1-amine, HCl (25 mg, 23%). MS (ESI+) [Method 1A]: m/z 351.1 (M+H); Rt 0.21 min. $^1$H NMR (400 MHz, CD$_3$OD) δ 9.74 (s, 1H), 8.77 (d, J=6.0 Hz, 1H), 8.79-8.75 (m, 1H), 8.59 (d, J=6.8 Hz, 1H), 7.95 (t, J=9.2 Hz, 1H), 6.34 (s, 1H), 6.45 (s, 2H), 4.97-4.93 (m, 1H), 4.81 (d, J=2.0 Hz, 2H), 4.27-4.23 (m, 1H), 2.82-2.77 (m, 2H), 2.71-2.66 (m, 2H), 2.27 (s, 6H).

Example 85: Synthesis of (1r,3r)-3-(4-cyclopropylphenoxy)-N-((6-fluoroisoquinolin-5-yl)methyl)cyclobutan-1-amine, HCl

Step 85.1: Synthesis of tert-butyl ((1r,3r)-3-(4-cyclopropylphenoxy)cyclobutyl)carbamate

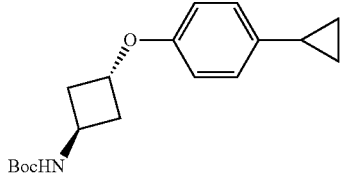 [SMILES: CC(C)(C)OC(=O)N[C@H]1C[C@H](Oc2ccc(C3CC3)cc2)C1]

The title compound was synthesized following the procedure as described in Step 1.2, using tert-butyl ((1s,3s)-3-hydroxycyclobutyl)carbamate (300 mg, 1.60 mmol) 4-cyclopropylphenol [CAS No. 10292-61-2] (200 mg, 1.49 mmol). Crude product was purified by flash chromatography (12 g SiliCycle column, 0-10% EtOAc in Hexane elution) to provide tert-butyl ((1r,3r)-3-(4-cyclopropylphenoxy)cyclobutyl)carbamate (80 mg, 17%). $^1$H NMR (400 MHz, CDCl$_3$) δ 6.97 (d, J=9.0 Hz, 2H), 6.67 (d, J=9.0 Hz, 2H), 4.76-4.71 (m, 1H), 4.28-4.22 (m, 1H), 2.57-2.49 (m, 2H), 2.37-2.31 (m, 2H), 1.85-1.82 (m, 1H), 1.45 (s, 9H), 0.90-0.86 (m, 2H), 0.61-0.58 (m, 2H).

Step 85.2: Synthesis of (1r,3r)-3-(4-cyclopropylphenoxy)cyclobutan-1-amine

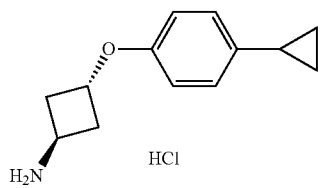 [SMILES: N[C@H]1C[C@H](Oc2ccc(C3CC3)cc2)C1 ; Cl]

A round bottom flask was charged with tert-butyl ((1r,3r)-3-(4-cyclopropylphenoxy)cyclobutyl)carbamate (80 mg, 0.34 mmol) and HCl solution (4M in 1,4-dioxane) (2 mL), and stirred at rt for 1 h. Then the reaction mixture was concentrated in vacuo. The residue was triturated with Et$_2$O, solid was filtered and dried to yield (1r,3r)-3-(4-cyclopropylphenoxy)cyclobutan-1-amine, HCl (60 mg, 96%). $^1$H NMR (400 MHz, CDCl$_3$) δ 8.28 (brs, 3H), 6.99 (d, J=8.4 Hz, 2H), 6.68 (d, J=8.4 Hz, 2H), 4.97-4.93 (m, 1H), 3.82-3.77 (m, 1H), 2.59-2.50 (m, 2H), 2.41-2.35 (m, 2H), 1.87-1.80 (m, 1H), 0.88-0.85 (m, 2H), 0.57-0.55 (m, 2H).

Step 85.3: Synthesis of (1r,3r)-3-(4-cyclopropylphenoxy)-N-((6-fluoroisoquinolin-5-yl)methyl)cyclobutan-1-amine, HCl

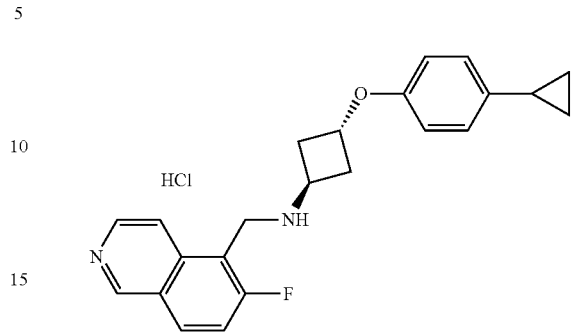

The title compound was synthesized following the procedure as described in Step 1.4, using (1r,3r)-3-(4-cyclopropylphenoxy)cyclobutan-1-amine, HCl (60 mg, 0.25 mmol) and 6-fluoroisoquinoline-5-carbaldehyde (Step 3.1, 39 mg, 0.22 mmol). The crude product was purified by prep-HPLC (Column: GEMINI-NX (150 mm×21.2 mm), 5.0µ; Mobile Phase: 0.02% NH$_4$OH in water and acetonitrile). To the isolated product, HCl solution (4M in 1,4-dioxane) (1 mL) was added, stirred at rt for 1 h, concentrated and then lyophilized to provide (1r,3r)-3-(4-cyclopropylphenoxy)-N-((6-fluoroisoquinolin-5-yl)methyl)cyclobutan-1-amine, HCl (12 mg, 15%). MS (ESI+) [Method 1A]: m/z 363.2 (M+H); Rt 1.31 min. $^1$H NMR (400 MHz, CD$_3$OD) δ 9.88 (brs, 1H), 8.77-8.74 (m, 3H), 8.01 (t, J=9.2 Hz, 1H), 7.01 (d, J=8.4 Hz, 2H), 6.72 (d, J=8.4 Hz, 2H), 4.97-4.93 (m, 1H), 4.83 (s, 2H), 4.27-4.23 (m, 1H), 2.86-2.79 (m, 2H), 2.70-2.64 (m, 2H), 1.89-1.82 (m, 1H), 0.92-0.88 (m, 2H), 0.60-0.56 (m, 2H).

Example 86: Synthesis of 4-((1r,3r)-3-(((6-fluoroisoquinolin-5-yl)methyl)amino)cyclobutoxy)-2-(trifluoromethyl)benzonitrile, HCl

Step 86.1: Synthesis of tert-butyl ((1r,3r)-3-(4-cyano-3-(trifluoromethyl)phenoxy)cyclobutyl)carbamate

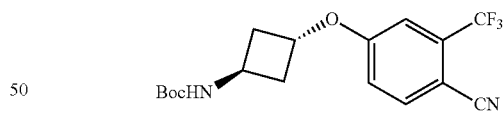

To the stirred solution of tert-butyl ((1r,3r)-3-hydroxycyclobutyl)carbamate (200 mg, 1.07 mmol) in anhydrous DMF (2 mL), NaH (60% on oil) (39 mg, 1.60 mmol) was added at 0° C., followed by 4-fluoro-2-(trifluoromethyl)benzonitrile [CAS No. 194853-86-6] (303 mg, 1.60 mmol). The reaction mixture was stirred at rt for 16 h under N2. The reaction was quenched with water and extracted with EtOAc twice. The combined organic portion was washed with brine solution, dried over anhydrous Na$_2$SO$_4$, filtered and concentrated in vacuo. The residue was purified by flash chromatography (12 g SiliCycle column, 0-20% EtOAc in Hexane elution) to afford tert-butyl ((1r,3r)-3-(4-cyano-3-(trifluoromethyl)phenoxy)cyclobutyl)carbamate as white solid (413 mg, 108%). 1H NMR (300 MHz, CDCl3) δ 7.73 (d, J=8.1 Hz, 1H), 7.15 (d, J=3.0 Hz, 1H), 6.96 (dd, J=9.0, 2.4 Hz, 1H), 4.89-4.85 (m, 1H), 4.33-4.28 (m, 1H), 2.62-2.54 (m, 2H), 2.53-2.45 (m, 2H), 1.45 (s, 9H).

Step 86.2: Synthesis of 4-((1r,3r)-3-aminocyclobutoxy)-2-(trifluoromethyl)benzonitrile, HCl [C-07711-069]

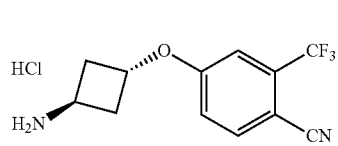 [SMILES: Cl ; N#Cc1ccc(O[C@H]2C[C@H](N)C2)cc1C(F)(F)F]

The solution of tert-butyl ((1r,3r)-3-(4-cyano-3-(trifluoromethyl)phenoxy)cyclobutyl)carbamate (413 mg, 1.16 mmol) and HCl (4M in 1,4-dioxane) (5 mL) was stirred at rt for 16 h. Then the reaction mixture was concentrated in vacuo. The residue was triturated with Et₂O, solid was filtered and dried to yield 4-((1r,3r)-3-aminocyclobutoxy)-2-(trifluoromethyl)benzonitrile, HCl as white solid (330 mg, 97%). MS (ESI+) [Method 6A]: m/z 257.1 (M+H); Rt 1.27 min.

Step 86.3: Synthesis of 4-((1r,3r)-3-(((6-fluoroisoquinolin-5-yl)methyl)amino)cyclobutoxy)-2-(trifluoromethyl)benzonitrile, HCl

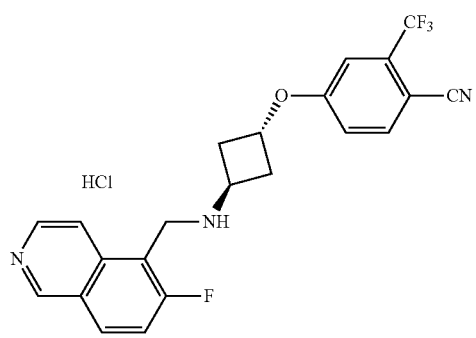 [SMILES: N#Cc1ccc(O[C@H]2C[C@H](NCc3c(F)ccc4cnccc34)C2)cc1C(F)(F)F ; Cl]

The title compound was synthesized following the procedure as described in Step 25.6, using 4-((1r,3r)-3-aminocyclobutoxy)-2-(trifluoromethyl)benzonitrile, HCl (70 mg, 0.24 mmol) and 6-fluoroisoquinoline-5-carbaldehyde (Step 3.1, 39 mg, 0.22 mmol). The crude product was purified by prep-HPLC (Column: ZORBAX C18 (150 mm×21.2 mm), 5.0μ; Mobile Phase: 10 mM NH₄OAc in water and acetonitrile). To the isolated product, HCl solution (4M in 1,4-dioxane) (1 mL) was added, stirred at rt for 1 h, concentrated to provide 4-((1r,3r)-3-(((6-fluoroisoquinolin-5-yl)methyl)amino)cyclobutoxy)-2-(trifluoromethyl)benzonitrile, HCl (38 mg, 35%). MS (ESI+) [Method 6A]: m/z 416.2 (M+H); Rt 1.31 min. ¹H NMR (400 MHz, CD₃OD) δ 9.80 (brs, 1H), 8.79 (d, J=6.8 Hz, 1H), 8.75-8.68 (m, 2H), 8.01-7.96 (m, 2H), 7.37 (s, 1H), 7.25 (d, J=8.0 Hz, 1H), 5.21-5.17 (m, 1H), 4.84 (s, 2H), 4.34-4.30 (m, 1H), 2.97-2.92 (m, 2H), 2.81-2.75 (m, 2H).

Example 87: Synthesis of (1r,3r)-3-(4-fluoro-3-(trifluoromethyl)phenoxy)-N-(quinazolin-8-ylmethyl)cyclobutan-1-amine, HCl

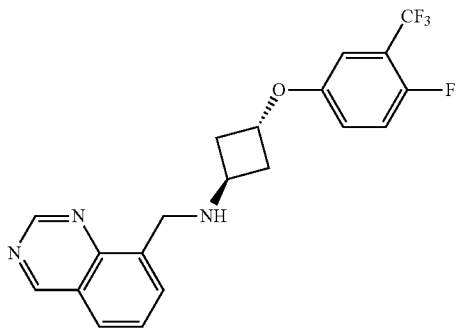 [SMILES: Fc1ccc(O[C@H]2C[C@H](NCc3cccc4cncnc34)C2)cc1C(F)(F)F]

The title compound was synthesized following the procedure as described in Step 1.4, using (1r,3r)-3-(4-fluoro-3-(trifluoromethyl)phenoxy)cyclobutan-1-amine, HCl (Step 1.3, 60 mg, 0.21 mmol) and quinazoline-8-carbaldehyde [CAS No. 1823899-37-1] (39 mg, 0.22 mmol). The crude product was purified by prep-HPLC (Column: Gemini-NX (150 mm×21.2 mm), 5.0μ; Mobile Phase: 0.01% NH₄OH in water and acetonitrile). To the isolated product, HCl solution (20% in 1,4-dioxane) (0.5 mL) was added, stirred at rt for 1 h. The solution was concentrated, residue was triturated with Et₂O, the solid was collected and dried to provide (1r,3r)-3-(4-fluoro-3-(trifluoromethyl)phenoxy)-N-(quinazolin-8-ylmethyl)cyclobutan-1-amine, HCl (28 mg, 31%). MS (ESI+) [Method 6A]: m/z 392.3 (M+H); Rt 1.33 min. ¹H NMR (400 MHz, CD₃OD) δ 9.54 (s, 1H), 9.32 (s, 1H), 8.08 (dd, J=8.0, 1.6 Hz, 1H), 8.04 (d, J=6.8 Hz, 1H), 7.56 (dd, J=8.0, 7.2 Hz, 1H), 7.24 (t, J=9.6 Hz, 1H), 7.08-7.03 (m, 2H), 4.89-4.85 (m, 1H), 4.32 (s, 2H), 3.64-3.59 (m, 1H), 2.39-2.34 (m, 4H).

Example 88: Synthesis of (1r,3r)-3-(3-cyclopropylphenoxy)-N-((6-fluoroisoquinolin-5-yl)methyl)cyclobutan-1-amine, HCl Step 88.1: Synthesis of (3-bromophenoxy)(tert-butyl)dimethylsilane

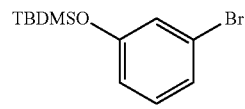 [SMILES: CC(C)(C)[Si](C)(C)Oc1cccc(Br)c1]

To the stirred solution of 3-bromophenol [CAS No. 591-20-8] (1.0 g, 5.82 mmol) in CH₂Cl₂ (20 mL), imidazole (1.2 g, 17.44 mmol) was added at rt and stirred for 15 min. Reaction mixture was cooled to 0° C., TBDMS-Cl (2.0 g, 14.53 mmol) was added and stirred at rt for 16 h under N₂. Reaction mixture was diluted with water and extracted with ethyl acetate 3×'s. The combined organic portion was washed with brine solution, dried over anhydrous Na₂SO₄, filtered and concentrated in vacuo. The residue was purified by flash chromatography (12 g SiliCycle column, 0-20% EtOAc in Hexane elution) to afford (3-bromophenoxy)(tert-butyl)dimethylsilane (1.6 g, 96%). ¹H NMR (300 MHz, CD$_3$OD) δ 7.18-7.08 (m, 2H), 6.99 (s, 1H), 6.83-6.80 (m, 1H), 0.99 (s, 9H), 0.21 (s, 6H).

Step 88.2: Synthesis of tert-butyl(3-cyclopropylphenoxy)dimethylsilane

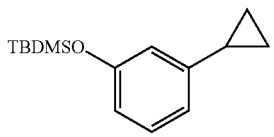 [SMILES: CC(C)(C)[Si](C)(C)Oc1cccc(C2CC2)c1]

The stirred solution of (3-bromophenoxy)(tert-butyl)dimethylsilane (1.6 g, 5.59 mmol), cyclopropyl boronic acid (0.96 g, 11.18 mmol) and K$_3$PO$_4$ (2.4 g, 11.18 mmol) in toluene (20 mL) was purged with N$_2$ for 10 min. Then Pd(OAc)$_2$ (120 mg, 0.56 mmol) and tricyclohexylphosphine (156 mg, 0.56 mmol) were added, and the reaction mixture was heated at 120° C. for 16 h under N$_2$. The reaction mixture was cooled to rt, filtered through a celite bed and the bed was thoroughly washed with EtOAc. The combined filtrate was concentrated in vacuo to afford crude tert-butyl (3-cyclopropylphenoxy)dimethylsilane (1.2 g, 86%). $^1$H NMR (400 MHz, CD$_3$OD) δ 7.10 (t, J=8.0 Hz, 1H), 6.69 (d, J=7.2 Hz, 1H), 6.63-6.60 (m, 1H), 6.54 (t, J=2.0 Hz, 1H), 1.88-1.83 (m, 1H), 1.01 (s, 9H), 0.98-0.93 (m, 2H), 0.66-0.62 (m, 2H), 0.20 (s, 6H).

Step 88.3: Synthesis of 3-cyclopropylphenol

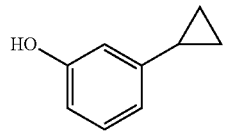

To the solution of tert-butyl(3-cyclopropylphenoxy)dimethylsilane (1.2 g, 4.84 mmol), in THF (8 mL), TBAF (1M in THF) (4.8 mL, 4.84 mmol) was added drop wise at 0° C. and the stirred at rt for 1 h. Reaction was quenched with saturated NH$_4$Cl solution and extracted with EtOAc 3x's. The combined organic portion was washed with brine solution and dried over anhydrous Na$_2$SO$_4$, filtered and then concentrated in vacuo. The residue was purified by flash chromatography (12 g SiliCycle column, 0-20% EtOAc in Hexane elution) to afford 3-cyclopropylphenol (0.6 g, 92%). $^1$H NMR (300 MHz, CD$_3$OD) δ 7.01 (t, J=8.1 Hz, 1H), 6.55-6.47 (m, 2H), 6.47-6.46 (m, 1H), 1.83-1.77 (m, 1H), 0.92-0.88 (m, 2H), 0.64-0.58 (m, 2H).

Step 88.4: Synthesis of tert-butyl ((1r,3r)-3-(3-cyclopropylphenoxy)cyclobutyl)carbamate

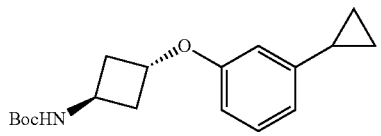 [SMILES: CC(C)(C)OC(=O)N[C@H]1C[C@H](Oc2cccc(C3CC3)c2)C1]

The title compound was synthesized following the procedure as described in Step 1.2, using tert-butyl ((1s,3s)-3-hydroxycyclobutyl)carbamate (500 mg, 2.67 mmol) 3-cyclopropylphenol (360 mg, 2.67 mmol). Crude product was purified by flash chromatography (12 g SiliCycle column, 0-35% EtOAc in Hexane elution) to provide tert-butyl ((1r,3r)-3-(3-cyclopropylphenoxy)cyclobutyl)carbamate (200 mg, 25%). $^1$H NMR (300 MHz, CDCl$_3$) δ 7.02-6.99 (m, 1H), 6.54-6.47 (m, 3H), 4.88-4.84 (m, 1H), 4.20-4.15 (m, 1H), 2.43-2.35 (m, 4H), 1.44 (s, 9H), 1.83-1.77 (m, 1H), 0.93-0.88 (m, 2H), 0.64-0.60 (m, 2H).

Step 88.5: Synthesis of (1r,3r)-3-(3-cyclopropylphenoxy)cyclobutan-1-amine, HCl

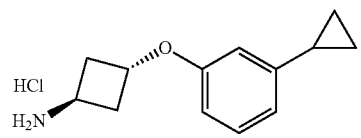 [SMILES: Cl ; N[C@H]1C[C@H](Oc2cccc(C3CC3)c2)C1]

The solution of tert-butyl ((1r,3r)-3-(3-cyclopropylphenoxy)cyclobutyl)carbamate (200 mg, 0.66 mmol) and HCl (4M in 1,4-dioxane) (3 mL) was stirred at rt for 2 h. Then the reaction mixture was concentrated in vacuo. The residue was triturated with Et$_2$O, solid was filtered and dried to yield (1r,3r)-3-(3-cyclopropylphenoxy)cyclobutan-1-amine, HCl (70 mg, 44%). $^1$H NMR (300 MHz, DMSO-d$_6$) δ 8.32 (brs, 3H), 7.14 (t, J=8.1 Hz, 1H), 6.66 (d, J=8.1 Hz, 1H), 6.54 (d, J=8.1 Hz, 1H), 6.49 (s, 1H), 5.01-4.96 (m, 1H), 3.82-3.78 (m, 1H), 2.62-2.51 (m, 2H), 2.44-2.36 (m, 2H), 1.90-1.84 (m, 1H), 0.94-0.91 (m, 2H), 0.66-0.63 (m, 2H).

Step 88.6: Synthesis of (1r,3r)-3-(3-cyclopropylphenox)-N-((6-fluoroisoquinolin-5-yl)methyl)cyclobutan-1-amine, HCl

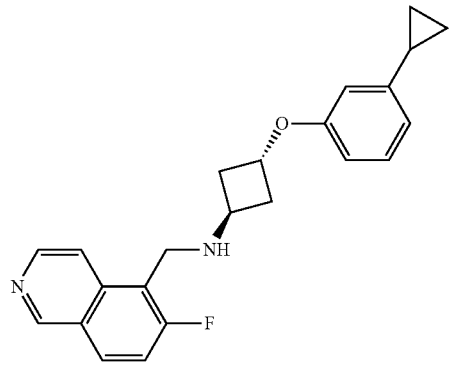 [SMILES: Fc1ccc2cnccc2c1CN[C@H]1C[C@H](Oc2cccc(C3CC3)c2)C1]

The title compound was synthesized following the procedure as described in Step 1.4, using (1r,3r)-3-(3-cyclopropylphenoxy)cyclobutan-1-amine, HCl (60 mg, 0.25 mmol) and 6-fluoroisoquinoline-5-carbaldehyde (Step 3.1, 40 mg, 0.23 mmol). The crude product was purified by prep-HPLC (Column: KINETEX EVO C18 (150 mm×21.2 mm), 5.0μ; Mobile Phase: 0.02% NH$_4$OH in water and acetonitrile). To the isolated product, HCl solution (20% in 1,4-dioxane) (2 mL) was added, stirred at rt for 1 h. The solution was concentrated, the residue was triturated with Et$_2$O, the solid was collected and dried to provide (1r,3r)-3-(3-cyclopropylphenoxy)-N-((6-fluoroisoquinolin-5-yl)methyl)cyclobutan-1-amine, HCl (30 mg, 33%). MS (ESI+) [Method 6A]: m/z 363.2 (M+H); Rt 1.30 min. $^1$H NMR (400 MHz, CD$_3$OD) δ 9.87 (s, 1H), 8.79-8.74 (m, 3H), 8.02 (t, J=9.6 Hz, 1H), 7.14 (t, J=8.0 Hz, 1H), 6.68 (d, J=7.6 Hz, 1H), 6.60-6.57 (m, 1H), 6.55-6.54 (m, 1H), 5.00-4.96 (m, 1H), 4.83 (d, J=2.0 Hz, 2H), 4.28-4.24 (m, 1H), 2.88-2.81 (m, 2H), 2.71-2.64 (m, 2H), 1.90-1.85 (m, 1H), 0.98-0.94 (m, 2H), 0.67-0.63 (m, 2H).

Example 89: Synthesis of (6-fluoro-5-((((1s,3s)-3-(4-fluoro-3-(trifluoromethyl)phenoxy)cyclobutyl)amino)methyl)isoquinolin-8-yl)methanol, HCl Step 89.1: Synthesis of tert-butyl ((1s,3s)-3-(4-fluoro-3-(trifluoromethyl)phenoxy)cyclobutyl)carbamate

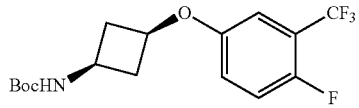 [SMILES: CC(C)(C)OC(=O)N[C@H]1C[C@@H](Oc2ccc(F)c(C(F)(F)F)c2)C1]

The title compound was synthesized following the procedure as described in Step 1.2, using tert-butyl ((1r,3r)-3-hydroxycyclobutyl)carbamate [CAS No. 389890-42-0] (0.5 g, 2.67 mmol) and 4-fluoro-3-(trifluoromethyl)phenol [CAS No. 61721-07-1] (0.52 g, 2.94 mmol). The reaction mixture was concentrated and the residue was purified by flash chromatography (12 g SiliCycle column, 0-10% EtOAc in Hexane elution) to provide tert-butyl ((1s,3s)-3-(4-fluoro-3-(trifluoromethyl)phenoxy)cyclobutyl)carbamate as pale yellow gummy mass (0.6 g, 64%). $^1$H NMR (300 MHz, CDCl$_3$) δ 7.09 (t, J=9.3 Hz, 1H), 6.99-6.96 (m, 1H), 6.94-6.89 (m, 1H), 4.74-4.69 (m, 1H), 3.93-3.87 (m, 1H), 2.99-2.92 (m, 2H), 2.05-1.96 (m, 2H), 1.44 (s, 9H).

Step 89.2: Synthesis of (1s,3s)-3-(4-fluoro-3-(trifluoromethyl)phenoxy)cyclobutan-1-amine, HCl

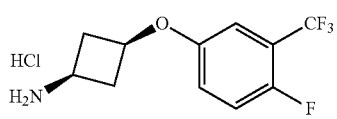 [SMILES: Cl ; N[C@H]1C[C@@H](Oc2ccc(F)c(C(F)(F)F)c2)C1]

A round bottom flask was charge with tert-butyl ((1s,3s)-3-(4-fluoro-3-(trifluoromethyl)phenoxy)cyclobutyl)carbamate (0.6 g, 1.72 mmol) and HCl solution (4M in 1,4-dioxane) (10 mL), and stirred at rt for 16 h. Then the reaction mixture was concentrated in vacuo. The residue was triturated with pentane, the solid appeared was filtered and dried to yield (1s,3s)-3-(4-fluoro-3-(trifluoromethyl)phenoxy)cyclobutan-1-amine, HCl as pale yellow solid (0.45 g, 92%). LCMS [Method 4A]: m/z 250.0 [M+H]$^+$; Rt 0.98 min. $^1$H NMR (300 MHz, DMSO-d6) δ 8.35 (brs, 3H), 7.46 (t, J=9.0 Hz, 1H), 7.25-7.20 (m, 1H), 7.16-7.13 (m, 1H), 4.62-4.56 (m, 1H), 3.42-3.37 (m, 1H), 2.88-2.79 (m, 2H), 2.28-2.18 (m, 2H).

Step 89.3: Synthesis of (1s,3s)-N-((8-(((tert-butyldimethylsilyl)oxy)methyl)-6-fluoroisoquinolin-5-yl)methyl)-3-(4-fluoro-3-(trifluoromethyl)phenoxy)cyclobutan-1-amine

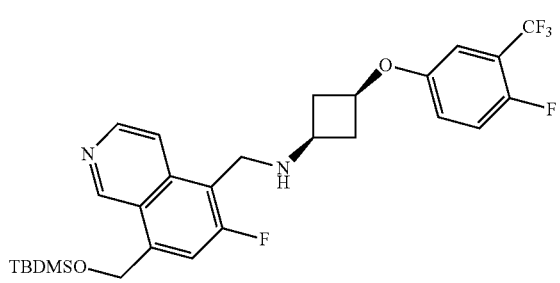 [SMILES: CC(C)(C)[Si](C)(C)OCc1cc(F)c(CN[C@H]2C[C@@H](Oc3ccc(F)c(C(F)(F)F)c3)C2)c2ccncc12]

The title compound was synthesized following the procedure as described in Step 1.4, using (1s,3s)-3-(4-fluoro-3-(trifluoromethyl)phenoxy)cyclobutan-1-amine, HCl (150 mg, 0.53 mmol) and 8-(((tert-butyldimethylsilyl)oxy)methyl)-6-fluoroisoquinoline-5-carbaldehyde (150 mg, 0.47 mmol). The crude product was purified by flash chromatography (12 g SiliCycle column, 0-5% MeOH in CHCl$_3$ elution) to provide (1s,3s)-N-((8-(((tert-butyldimethylsilyl)oxy)methyl)-6-fluoroisoquinolin-5-yl)methyl)-3-(4-fluoro-3-(trifluoromethyl)phenoxy)cyclobutan-1-amine as yellowish gummy mass (200 mg, 69%). MS (ESI+) [Method 6A]: m/z 553.3 (M+H); Rt 1.42 min.

Step 89.4: Synthesis of (6-fluoro-5-((((1s,3s)-3-(4-fluoro-3-(trifluoromethyl)phenoxy)cyclobutyl)amino)methyl)isoquinolin-8-yl)methanol, HCl

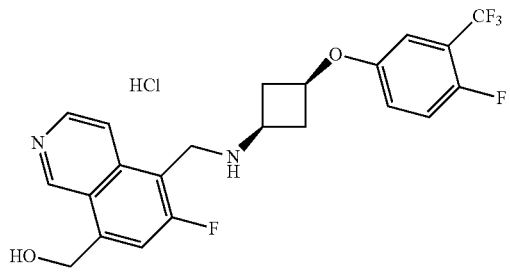 [SMILES: OCc1cc(F)c(CN[C@H]2C[C@@H](Oc3ccc(F)c(C(F)(F)F)c3)C2)c2ccncc12 ; Cl]

Deprotection was carried out according to Step 8.5. The residue was purified by prep-HPLC (Column: KINETEX EVO (150 mm×21.2 mm), 5.0μ; Mobile Phase: 0.02% NH$_4$OH in water and acetonitrile). To the isolated product, HCl solution (20% in 1,4-dioxane) (4 mL) was added and stirred at rt for 1 h, concentrated in vacuo, triturated with Et$_2$O-Pentane, collected solid was dried to provide (6-fluoro-5-((((1s,3s)-3-(4-fluoro-3-(trifluoromethyl)phenoxy)cyclobutyl)amino)methyl)isoquinolin-8-yl)methanol, HCl as white solid (50 mg, 29%). MS (ESI+) [Method 4A]: m/z 439.2 (M+H); Rt 1.46 min. $^1$H NMR (400 MHz, CD$_3$OD) 9.95 (s, 1H), 8.84 (d, J=6.8 Hz, 1H), 8.79 (d, J=7.2 Hz, 1H), 8.03 (d, J=10.4 Hz, 1H), 7.27 (t, J=9.2 Hz, 1H), 7.17-7.11 (m, 2H), 5.31 (d, J=0.4 Hz, 2H), 4.82 (d, J=1.6 Hz, 2H), 4.73-4.68 (m, 1H), 3.89-3.83 (m, 1H), 3.15-3.10 (m, 2H), 2.49-2.43 (m, 2H).

Example 90: Synthesis of (6-fluoro-5-((((1r,3r)-3-((2-(trifluoromethyl)pyridin-4-yl)oxy)cyclobutyl)amino)methyl)isoquinolin-8-yl)methanol Step 90.1: Synthesis of (1r,3r)-N-((8-(((tert-butyldimethylsilyl)oxy)methyl)-6-fluoroisoquinolin-5-yl)methyl)-3-((2-(trifluoromethyl)pyridin-4-yl)oxy)cyclobutan-1-amine

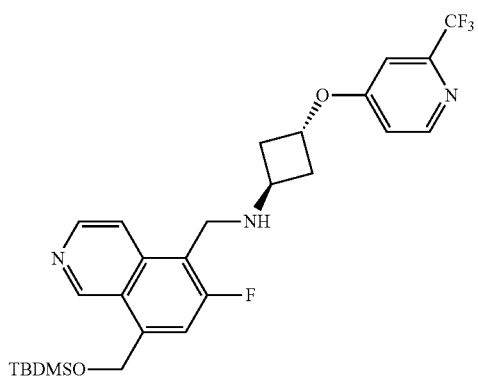 [SMILES: CC(C)(C)[Si](C)(C)OCc1cc(F)c(CN[C@H]2C[C@H](Oc3ccnc(C(F)(F)F)c3)C2)c2ccncc12]

The title compound was synthesized following the procedure as described in Step 1.4, using (1r,3r)-3-((2-(trifluoromethyl)pyridin-4-yl)oxy)cyclobutan-1-amine, HCl (Step 16.2, 150 mg, 0.56 mmol) and 8-(((tert-butyldimethylsilyl)oxy)methyl)-6-fluoroisoquinoline-5-carbaldehyde (Step 6.8, 140 mg, 0.45 mmol). The crude product was purified by flash chromatography (12 g SiliCycle column, 0-5% MeOH in CHCl₃ elution) to provide (1r,3r)-N-((8-(((tert-butyldimethylsilyl)oxy)methyl)-6-fluoroisoquinolin-5-yl)methyl)-3-((2-(trifluoromethyl)pyridin-4-yl)oxy)cyclobutan-1-amine (120 mg, 40%). MS (ESI+) [Method 6A]: m/z 536.23 (M+H); Rt 1.38 min.

Step 90.2: Synthesis of (6-fluoro-5-((((1r,3r)-3-((2-(trifluoromethyl)pyridin-4-yl)oxy)cyclobutyl)amino)methyl)isoquinolin-8-yl)methanol, HCl

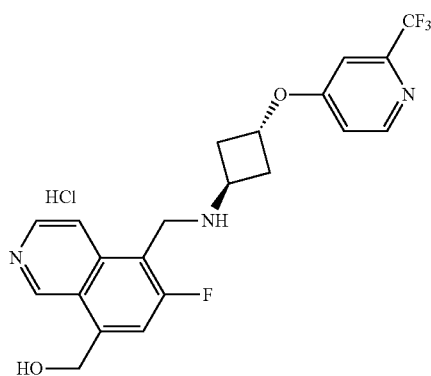 [SMILES: OCc1cc(F)c(CN[C@H]2C[C@H](Oc3ccnc(C(F)(F)F)c3)C2)c2ccncc12 ; Cl]

Deprotection was carried out according to Step 8.5. The residue was purified by flash chromatography (12 g SiliCycle column, 0-5% MeOH in CH₂Cl₂ elution), and then re-purified by prep-HPLC (Column: XBRIDGE (150 mm×21.2 mm), 5.0µ; Mobile Phase: 0.02% NH₄OH in water and acetonitrile). To the isolated product, HCl solution (20% in 1,4-dioxane) (0.5 mL) was added, and stirred at rt for 1 h; then concentrated. The residue was triturated with Et2O, solid was collected and dried to afford (6-fluoro-5-((((1r,3r)-3-((2-(trifluoromethyl)pyridin-4-yl)oxy)cyclobutyl)amino)methyl)isoquinolin-8-yl)methanol, HCl (32 mg, 31%). MS (ESI+) [Method 6A]: m/z 422.1 (M+H); Rt 1.24 min. ¹H NMR (400 MHz, CD₃OD) δ 9.98 (s, 1H), 8.88 (d, J=7.2 Hz, 1H), 8.81 (d, J=7.2 Hz, 1H), 8.56 (d, J=5.6 Hz, 1H), 8.06 (d, J=10.4 Hz, 1H), 7.33 (d, J=2.4 Hz, 1H), 7.15 (dd, J=6.0, 2.8 Hz, 1H), 5.32 (s, 2H), 5.27-5.21 (m, 1H), 4.83 (s, 2H), 4.34-4.29 (m, 1H), 3.03-2.96 (m, 2H), 2.81-2.74 (m, 2H).

Example 91: Synthesis of (1r,3r)-3-(3-(difluoromethyl)-4-fluorophenoxy)-N-((6-fluoroisoquinolin-5-yl)methyl)cyclobutan-1-amine, HCl Step 91.1: Synthesis of 4-fluoro-3-formylphenyl benzoate

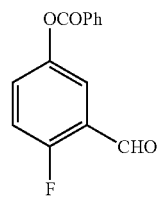

To the solution of 2-fluoro-5-hydroxy benzaldehyde [CAS No. 103438-84-2] (750 mg, 5.35 mmol), TEA (1.62 g, 16.05 mmol) and DMAP (65 mg, 0.54 mmol) in anhydrous THF (50 mL), PhCOCl (1.0 g, 5.89 mmol) was added at rt and stirred for 16 h under N₂. Then the reaction mixture was diluted with EtOAc and washed with water, aqueous 1M HCl solution and saturated NHCO₃ solution successively. The organic portion was collected, dried over anhydrous MgSO₄, filtered and then concentrated in vacuo. The residue was purified by flash chromatography (12 g SiliCycle column, 0-5% EtOAc in Hexane elution) to afford 4-fluoro-3-formylphenyl benzoate (1.0 g, 77%). ¹H NMR (600 MHz, CDCl₃) δ 10.37 (s, 1H), 8.19 (d, J=7.2 Hz, 2H), 7.72 (dd, J=6.0, 3.0 Hz, 1H), 7.67 (t, J=7.8 Hz, 1H), 7.53 (t, J=8.4 Hz, 2H), 7.49-7.47 (m, 1H), 7.26 (t, J=7.8 Hz, 1H).

Step 91.2: Synthesis of 3-(difluoromethyl)-4-fluorophenyl benzoate

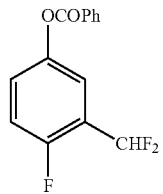

To the solution of 4-fluoro-3-formylphenyl benzoate (400 mg, 1.63 mmol) in anhydrous CH₂Cl₂ (50 mL), DAST (530 mg, 3.27 mmol) was added at 0° C. and stirred at rt for 16 h under N₂. Then the reaction was quenched with saturated NaHCO₃ solution and extracted with EtOAc 3×'s. The combined organic portion was washed with brine solution and dried over anhydrous Na₂SO₄, filtered and then concentrated in vacuo. The residue was purified by flash chromatography (12 g SiliCycle column, 0-5% EtOAc in Hexane elution) to afford 3-(difluoromethyl)-4-fluorophenyl benzoate (300 mg, 69%). MS (ESI+) [Method 6A]: m/z 265.0 (M−H); Rt 1.61 min. $^1$H NMR (600 MHz, CDCl$_3$) δ 8.20 (d, J=7.8 Hz, 2H), 7.67 (d, J=7.8 Hz, 1H), 7.53 (t, J=8.4 Hz, 2H), 7.47-7.45 (m, 1H), 7.35-7.33 (m, 1H), 7.21 (t, J=9.0 Hz, 1H), 6.91 (t, J=54.6 Hz, 1H).

Step 91.3: Synthesis of 3-(difluoromethyl)-4-fluorophenol

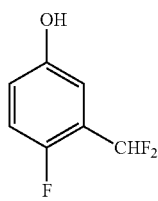

To the solution of 3-(difluoromethyl)-4-fluorophenyl benzoate (300 mg, 1.12 mmol) in THF-MeOH (12 mL, 5:1 v/v), 3N NaOH solution (1.12 mL, 3.36 mmol) was added at rt and stirred for 6 h. Reaction mixture was concentrated to dryness, the residue was diluted with water and acidified with 2N HCl solution, and then extracted with EtOAc twice. The combined organic portion was washed with saturated NaHCO$_3$ solution and dried over anhydrous Na$_2$SO$_4$, filtered and then concentrated in vacuo to afford crude 3-(difluoromethyl)-4-fluorophenol (150 mg, 82%). $^1$H NMR (400 MHz, CDCl$_3$) δ 7.04-6.99 (m, 2H), 6.92-6.88 (m, 1H), 6.83 (t, J=55.6 Hz, 1H).

Step 91.4: Synthesis of tert-butyl ((1r,3r)-3-(3-(difluoromethyl)-4-fluorophenoxy)cyclobutyl)carbamate

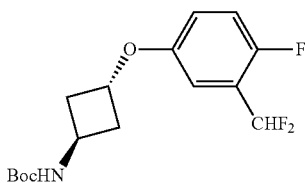 [SMILES: CC(C)(C)OC(=O)N[C@H]1C[C@H](Oc2ccc(F)c(C(F)F)c2)C1]

To the solution of tert-butyl ((1s,3s)-3-hydroxycyclobutyl)carbamate (172 mg, 0.92 mmol) in THF (0.5 M), 3-(difluoromethyl)-4-fluorophenol (150 mg, 0.92 mmol), PPh$_3$ (1.5 eq) and diisopropyl azodicarboxylate (1.5 eq) were added at rt. The reaction mixture was stirred at 50-60° C. for 16 h under N$_2$ atmosphere. Reaction mixture was diluted with water and extracted with EtOAc 3×'s. The combined organic portion was washed with brine solution, dried over anhydrous Na$_2$SO$_4$, filtered and concentrated in vacuo. Crude was purified by flash chromatography (8 g SiliCycle column, 0-8% EtOAc in Hexane elution) to provide tert-butyl ((1r,3r)-3-(3-(difluoromethyl)-4-fluorophenoxy)cyclobutyl)carbamate (100 mg, 33%). $^1$H NMR (400 MHz, CDCl$_3$) δ 7.03 (t, J=9.2 Hz, 1H), 6.93-6.90 (m, 1H), 6.87-6.83 (m, 1H), 6.85 (t, J=55.2 Hz, 1H), 4.79-4.73 (m, 1H), 4.32-4.27 (m, 1H), 2.58-2.51 (m, 2H), 2.41-2.35 (m, 2H), 1.45 (s, 9H).

Step 91.5: Synthesis of (1r,3r)-3-(3-(difluoromethyl)-4-fluorophenoxy)cyclobutan-1-amine, HCl

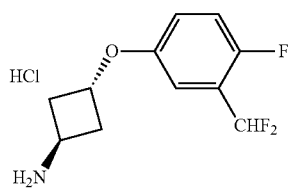 [SMILES: Cl ; N[C@H]1C[C@H](Oc2ccc(F)c(C(F)F)c2)C1]

To the solution of tert-butyl ((1r,3r)-3-(3-(difluoromethyl)-4-fluorophenoxy)cyclobutyl)carbamate (100 mg, 0.30 mmol) in 1,4-dioxane (2 mL), 4M HCl solution (in 1,4-dioxane) (0.75 mL) was stirred at rt for 16 h. Then the reaction mixture was concentrated in vacuo. The residue was triturated with Et$_2$O, solid was filtered and dried to yield (1r,3r)-3-(3-(difluoromethyl)-4-fluorophenoxy)cyclobutan-1-amine, HCl (80 mg, 100%). MS (ESI+) [Method 6A]: m/z 232.1 (M+H); Rt 1.27 min. $^1$H NMR (300 MHz, DMSO-d$_6$) δ7.18 (t, J=8.0 Hz, 1H), 7.01-6.98 (m, 2H), 6.96 (t, J=55.6 Hz, 1H), 4.98-4.92 (m, 1H), 4.01-3.97 (m, 1H), 2.66-2.61 (m, 4H).

Step 91.6: Synthesis of (1r,3r)-3-(3-(difluoromethyl)-4-fluorophenoxy)-N-((6-fluoroisoquinolin-5-yl)methyl)cyclobutan-1-amine, HCl

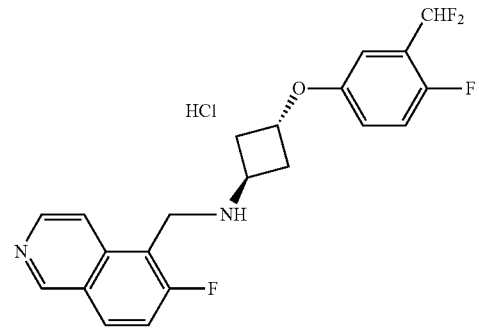 [SMILES: Fc1ccc(O[C@H]2C[C@H](NCc3c(F)ccc4cnccc34)C2)cc1C(F)F ; Cl]

The title compound was synthesized following the procedure as described in Step 1.4, using (1r,3r)-3-(3-(difluoromethyl)-4-fluorophenoxy)cyclobutan-1-amine, HCl (80 mg, 0.30 mmol) and 6-fluoroisoquinoline-5-carbaldehyde (Step 3.1, 53 mg, 0.30 mmol). The crude product was purified by prep-HPLC (Column: LUNA (250 mm×21.2 mm), 5.0µ; Mobile Phase: 0.1% HCO$_2$H in water and acetonitrile). To the isolated product, HCl solution (20% in 1,4-dioxane) (2 mL) was added, stirred at rt for 1 h. The solution was concentrated, residue was triturated with Et$_2$O, the solid was collected and dried to provide (1r,3r)-3-(3-(difluoromethyl)-4-fluorophenoxy)-N-((6-fluoroisoquinolin-5-yl)methyl)cyclobutan-1-amine, HCl (40 mg, 33%). MS (ESI+) [Method 1A]: m/z 391.0 (M+H); Rt 0.18 min. $^1$H NMR (400 MHz, CD$_3$OD) δ 9.82 (s, 1H), 8.78-8.72 (m, 3H), 7.99 (t, J=9.2 Hz, 1H), 7.18 (t, J=10.0 Hz, 1H), 7.03-7.00 (m, 2H), 6.95 (t, J=54.8 Hz, 1H), 5.03-4.99 (m, 1H), 4.82 (d, J=2.0 Hz, 2H), 4.31-4.24 (m, 1H), 2.90-2.85 (m, 2H), 2.73-2.66 (m, 2H).

Example 92: Synthesis of (1r,3r)-N-((6-fluoroisoquinolin-5-yl)methyl)-3-((6-methoxy-5-(trifluoromethyl)pyridin-3-yl)oxy)cyclobutan-1-amine, HCl Step 92.1: Synthesis of tert-butyl ((1r,3r)-3-((6-chloro-5-(trifluoromethyl)pyridin-3-yl)oxy)cyclobutyl)carbamate

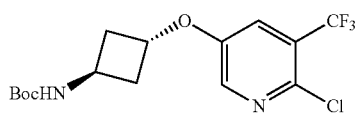

A sealed tube was charged with 2-chloro-5-iodo-3-(trifluoromethyl)pyridine [CAS No. 887707-25-7] (1.0 g, 3.25 mmol), tert-butyl ((1r,3r)-3-hydroxycyclobutyl)carbamate (0.91 g, 4.88 mmol), Cs$_2$CO$_3$ (1.58 g, 4.88 mmol) and toluene (15 mL), and purged with N$_2$ for 10 min. Then CuI (31 mg, 0.16 mmol) and 3,4,7,8-tetramethyl-1,10-phenanthroline were added, purged with N$_2$, sealed tube was closed and stirred at 110° C. for 16 h. Reaction was cooled to rt, filtered through celite bed and the bed was washed with EtOAc. The filtrate was concentrated in vacuo and the residue was purified by flash chromatography (12 g SiliCycle column, 0-20% EtOAc in Hexane elution) to afford tert-butyl ((1r,3r)-3-((6-chloro-5-(trifluoromethyl)pyridin-3-yl)oxy)cyclobutyl)carbamate as white liquid (0.2 g, 17%). MS (ESI+) [Method 6A]: m/z 366.8 (M+H); Rt 1.63 min. $^1$H NMR (300 MHz, CDCl$_3$) δ 8.08 (d, J=3.0 Hz, 1H), 7.40 (d, J=3.0 Hz, 1H), 4.88-4.81 (m, 1H), 4.35-4.28 (m, 1H), 2.62-2.53 (m, 2H), 2.51-2.42 (m, 2H), 1.45 (s, 9H).

Step 92.2: Synthesis of (1r,3r)-3-((6-methoxy-5-(trifluoromethyl)pyridin-3-yl)oxy)cyclobutan-1-amine

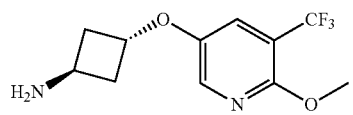 [SMILES: COc1ncc(O[C@H]2C[C@H](N)C2)cc1C(F)(F)F]

To the stirred solution of tert-butyl ((1r,3r)-3-((6-chloro-5-(trifluoromethyl)pyridin-3-yl)oxy)cyclobutyl)carbamate (80 mg, 0.22 mmol) in anhydrous MeOH (5 mL), NaOMe (59 mg, 1.09 mmol) was added and heated at 70° C. for 16 h. The reaction mixture was concentrated in vacuo. Then the residue was diluted water and extracted 3× with EtOAc. The combined organic portion was washed with brine solution and dried over anhydrous Na$_2$SO$_4$, filtered and then concentrated in vacuo. The residue was purified by flash chromatography (12 g SiliCycle column, 0-10% MeOH in CH$_2$Cl$_2$ elution) to afford (1r,3r)-3-((6-methoxy-5-(trifluoromethyl)pyridin-3-yl)oxy)cyclobutan-1-amine (50 mg, 88%). MS (ESI+) [Method 6A]: m/z 263.1 (M+H); Rt 1.33 min.

Step 92.3: Synthesis of (1r,3r)-N-((6-fluoroisoquinolin-5-yl)methyl)-3-((6-methoxy-5-(trifluoromethyl)pyridin-3-yl)oxy)cyclobutan-1-amine, HCl

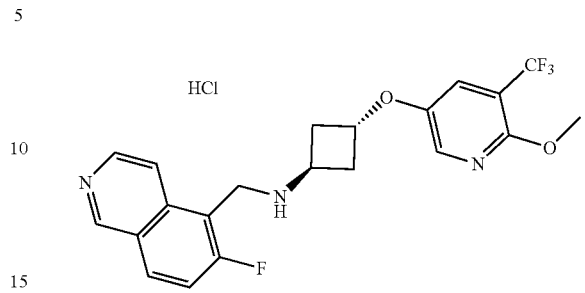

The solution of (1r,3r)-3-((6-methoxy-5-(trifluoromethyl)pyridin-3-yl)oxy)cyclobutan-1-amine (50 mg, 0.19 mmol) and 6-fluoroisoquinoline-5-carbaldehyde (step 3.1, 30 mg, 0.17 mmol), catalytic AcOH was added, and stirred at rt for 16 h under argon. Then the reaction mixture was cooled to 0° C., NaBH$_4$ (14 mg, 0.38 mmol) was added and stirred at rt for 2 h. Reaction mixture was diluted with water and extracted with EtOAc twice. The combined organic portion was washed with brine solution, dried over anhydrous Na$_2$SO$_4$, filtered and concentrated in vacuo. The residue was purified by prep-HPLC (Column: LUNA, (250 mm×21.2 mm), 5.0μ; Mobile Phase: 0.1% HCO$_2$H in water and acetonitrile). To the isolated product HCl solution (20% in 1,4-dioxane) (0.5 mL) was added, stirred for 1 h and then concentrated. The residue was triturated with Et$_2$O, solid was collected and dried to afford (1r,3r)-N-((6-fluoroisoquinolin-5-yl)methyl)-3-((6-methoxy-5-(trifluoromethyl)pyridin-3-yl)oxy)cyclobutan-1-amine, HCl (16 mg, 19%). MS (ESI+) [Method 6A]: m/z 422.2 (M+H); Rt 1.31 min. $^1$H NMR (400 MHz, CD$_3$OD) δ 9.78 (s, 1H), 8.80 (s, 2H), 8.78 (dd, J=9.2, 5.2 Hz, 1H), 8.03 (t, J=9.2 Hz, 1H), 7.98-7.97 (m, 1H), 7.57 (d, J=2.4 Hz, 1H), 5.03-4.99 (m, 1H), 4.85 (d, J=2.0 Hz, 2H), 4.33-4.27 (m, 1H), 3.98 (s, 3H), 2.92-2.87 (m, 2H), 2.77-2.71 (m, 2H).

Example 93: Synthesis of (1r,3r)-3-(3-fluoro-4-(trifluoromethoxy)phenoxy)-N-((6-fluoroisoquinolin-5-yl)methyl)cyclobutan-1-amine, HCl Step 93.1: Synthesis of tert-butyl ((1r,3r)-3-(3-fluoro-4-(trifluoromethoxy)phenoxy)cyclobutyl)carbamate

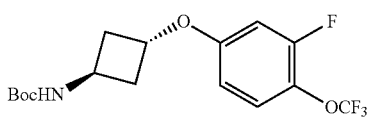 [SMILES: CC(C)(C)OC(=O)N[C@H]1C[C@H](Oc2ccc(OC(F)(F)F)c(F)c2)C1]

To the solution of tert-butyl ((1s,3s)-3-hydroxycyclobutyl)carbamate (100 mg, 0.53 mmol) in THF (0.5 M), 3-fluoro-4-(trifluoromethoxy)phenol [CAS No. 177596-38-2] (100 mg, 0.53 mmol), PPh$_3$ (1.5 eq) and diisopropyl azodicarboxylate (1.5 eq) were added at rt. The reaction mixture was stirred at 50-60° C. for 16 h under N$_2$ atmosphere. Reaction mixture was diluted with water and extracted with EtOAc (3×'s). The combined organic portion was washed with brine solution, dried over anhydrous Na$_2$SO$_4$, filtered and concentrated in vacuo. The crude product was purified by flash chromatography (12 g Sili-Cycle column, 0-20% EtOAc in Hexane elution) to provide tert-butyl ((1r,3r)-3-(3-fluoro-4-(trifluoromethoxy)phenoxy)cyclobutyl)carbamate (100 mg, 51%). ¹H NMR (300 MHz, CDCl₃) δ 7.15 (t, J=8.7 Hz, 1H), 7.69 (dd, J=11.1, 3.0 Hz, 1H), 6.62-6.58 (m, 1H), 4.77-4.69 (m, 1H), 4.33-4.27 (m, 1H), 2.60-2.51 (m, 2H), 2.43-2.35 (m, 2H), 1.45 (s, 9H).

Step 93.2: Synthesis of (1r,3r)-3-(3-fluoro-4-(trifluoromethoxy)phenoxy)cyclobutan-1-amine, HCl

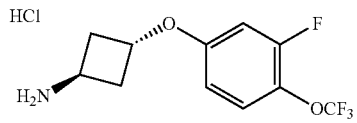 [SMILES: Cl ; N[C@H]1C[C@H](Oc2ccc(OC(F)(F)F)c(F)c2)C1]

A round bottom flask was charged with tert-butyl ((1r,3r)-3-(3-fluoro-4-(trifluoromethoxy)phenoxy)cyclobutyl)carbamate (100 mg, 0.27 mmol) and HCl solution (4M in 1,4-dioxane) (2 mL); and the solution was stirred rt for 4 h. Then the reaction mixture was concentrated in vacuo. The residue was triturated with Et₂O, solid was filtered and dried to yield (1r,3r)-3-(3-fluoro-4-(trifluoromethoxy)phenoxy)cyclobutan-1-amine, HCl (70 mg, 85%). MS (ESI+) [Method 6A]: m/z 265.9 (M+H); Rt 1.35 min. ¹H NMR (300 MHz, DMSO-d6) δ 8.12 (brs, 3H), 7.51 (t, J=9.0 Hz, 1H), 7.00 (dd, J=12.0, 3.0 Hz, 1H), 6.78-6.73 (m, 1H), 5.00-4.95 (m, 1H), 3.89-3.82 (m, 1H), 2.64-2.44 (m, 4H).

Step 93.3: Synthesis of (1r,3r)-3-(3-fluoro-4-(trifluoromethoxy)phenoxy)-N-((6-fluoroisoquinolin-5-yl)methyl)cyclobutan-1-amine, HCl

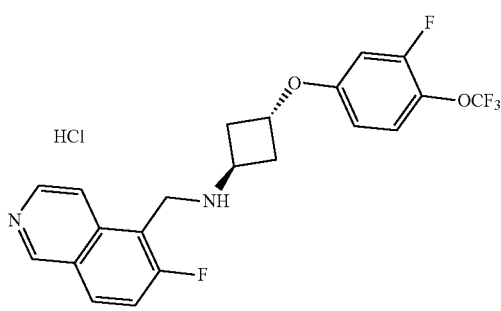 [SMILES: Fc1cc(O[C@H]2C[C@H](NCc3c(F)ccc4cnccc34)C2)ccc1OC(F)(F)F ; Cl]

The title compound was synthesized following the procedure as described in Step 1.4, using (1r,3r)-3-(3-fluoro-4-(trifluoromethoxy)phenoxy)cyclobutan-1-amine, HCl (70 mg, 0.23 mmol) and 6-fluoroisoquinoline-5-carbaldehyde (Step 3.1, 36 mg, 0.21 mmol). The crude product was purified by prep-HPLC (Column: WATERS X BRIDGE (150 mm×21.2 mm), 5.0µ; Mobile Phase: 0.02% NH₄OH in water and acetonitrile). To the isolated product, HCl solution (4M in 1,4-dioxane) (1 mL) was added, stirred at rt for 1 h. The solution was concentrated, residue was triturated with Et₂O, the solid was collected and dried to provide (1r,3r)-3-(3-fluoro-4-(trifluoromethoxy)phenoxy)-N-((6-fluoroisoquinolin-5-yl)methyl)cyclobutan-1-amine, HCl (8 mg, 8%). MS (ESI+) [Method 6A]: m/z 425.1 (M+H); Rt 1.36 min. ¹H NMR (600 MHz, CD₃OD) δ 9.58 (s, 1H), 8.71 (d, J=6.0 Hz, 1H), 8.56 (dd, J=9.6, 5.4 Hz, 1H), 8.39 (d, J=6.6 Hz, 1H), 7.83 (t, J=9.6 Hz, 1H), 7.35 (t, J=9.0 Hz, 1H), 6.84 (dd, J=12.0, 2.4 Hz, 1H), 6.72 (dq, J=9.0, 1.2 Hz, 1H), 4.99-4.95 (m, 1H), 4.76 (s, 2H), 4.28-4.24 (m, 1H), 2.85-2.80 (m, 2H), 2.72-2.67 (m, 2H).

Example 94: Synthesis of (1r,3r)-N-((6-fluoroisoquinolin-5-yl)methyl)-3-((6-(trifluoromethyl)pyridin-3-yl)oxy)cyclobutan-1-amine, HCl

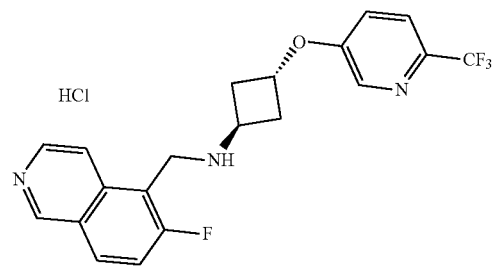 [SMILES: Fc1ccc2cnccc2c1CN[C@H]1C[C@H](Oc2ccc(C(F)(F)F)nc2)C1 ; Cl]

The title compound was synthesized following the procedure as described in Step 1.4, using (1r,3r)-3-((6-(trifluoromethyl)pyridin-3-yl)oxy)cyclobutan-1-amine, HCl (Step 2.2, 300 mg, 1.12 mmol) and 6-fluoroisoquinoline-5-carbaldehyde (Step 3.1, 230 mg, 1.31 mmol). The crude product was purified by prep-HPLC (Column: GEMINI-NX (150 mm×21.2 mm), 5.0µ; Mobile Phase: 0.02% NH₄OH in water and acetonitrile). To the isolated product, HCl solution (4M in 1,4-dioxane) (1 mL) was added, stirred at rt for 1 h. The solution was concentrated, and then lyophilized to provide (1r,3r)-N-((6-fluoroisoquinolin-5-yl)methyl)-3-((6-(trifluoromethyl)pyridin-3-yl)oxy)cyclobutan-1-amine, HCl (180 mg, 17%). MS (ESI+) [Method 6A]: m/z 392.2 (M+H); Rt 1.27 min. ¹H NMR (600 MHz, CD₃OD) δ 9.88 (s, 1H), 8.83-8.75 (m, 3H), 8.33 (d, J=2.8 Hz, 1H), 8.03 (t, J=9.6 Hz, 1H), 7.77 (d, J=9.2 Hz, 1H), 7.45 (dd, J=9.2, 2.8 Hz, 1H), 5.20-5.16 (m, 1H), 4.84 (d, J=2.0 Hz, 2H), 4.34-4.29 (m, 1H), 2.98-2.93 (m, 2H), 2.80-2.73 (m, 2H).

Example 95: Synthesis of (1r,3r)-N-((6-fluoroisoquinolin-5-yl)methyl)-3-((5-(trifluoromethyl)pyridin-3-yl)oxy)cyclobutan-1-amine, HCl Step 95.1: Synthesis of 3-(benzyloxy)-5-(trifluoromethyl)pyridine

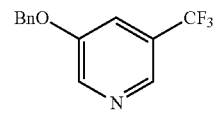

The stirred solution of benzyl alcohol (2.0 g, 18.49 mmol) and 3-chloro-5-(trifluoromethyl)pyridine [CAS No. 85148-26-1] (3.69 g, 20.34 mmol) in DMF (40 mL) was cooled to 0° C. Then NaH (60% on mineral oil) (0.96 g, 24.04 mmol) was added portion wise and the reaction mixture was heated at 40° C. for 2 h under argon atmosphere. The reaction was quenched with saturated NH₄Cl solution and extracted with EtOAc twice. The combined organic layer was washed with water, then with brine, dried over anhydrous Na₂SO₄, filtered and concentrated in vacuo. The residue was purified by flash chromatography (12 g SiliCycle column, 0-30%

EtOAc in Hexane elution) to afford 3-(benzyloxy)-5-(trifluoromethyl)pyridine (1.3 g, 28%). MS (ESI+) [Method 1A]: m/z 254.2 (M+H); Rt 2.56 min. $^1$H NMR (300 MHz, CDCl$_3$) δ 8.59-8.51 (m, 1H), 7.46-7.28 (m, 7H), 4.53 (s, 2H).

Step 95.2: Synthesis of 5-(trifluoromethyl)pyridin-3-ol

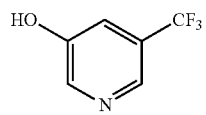

To the stirred solution of 3-(benzyloxy)-5-(trifluoromethyl)pyridine (900 mg, 3.55 mmol) in EtOH (12 mL), Pd/C (10% w/w) (150 mg) was added under N$_2$. The flask was connected with H$_2$ balloon and the reaction mixture was stirred at rt for 2 h under H$_2$ atmosphere. The reaction mixture was filtered through celite bed, and the bed was thoroughly washed with EtOAc. The combined filtrate was concentrated in vacuo to provide crude 5-(trifluoromethyl)pyridin-3-ol (400 mg, 69%). MS (ESI+) [Method 6A]: m/z 163.9 (M+H); Rt 1.37 min.

Step 95.3: Synthesis of tert-butyl ((1r,3r)-3-((5-(trifluoromethyl)pyridin-3-yl)oxy)cyclobutyl)carbamate

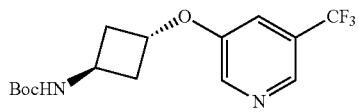 [SMILES: CC(C)(C)OC(=O)N[C@H]1C[C@H](Oc2cncc(C(F)(F)F)c2)C1]

To the solution of tert-butyl ((1s,3s)-3-hydroxycyclobutyl)carbamate (300 mg, 1.60 mmol) in THF (0.5 M), 5-(trifluoromethyl)pyridin-3-ol (261 mg, 1.60 mmol), PPh$_3$ (1.5 eq) and diisopropyl azodicarboxylate (1.5 eq) were added at rt. The reaction mixture was stirred at 50-60° C. for 16 h under N$_2$ atmosphere. Reaction mixture was diluted with water and extracted with EtOAc (3×'s). The combined organic portion was washed with brine solution, dried over anhydrous Na$_2$SO$_4$, filtered and concentrated in vacuo. The crude product was purified by flash chromatography (12 g SiliCycle column, 0-20% EtOAc in Hexane elution) to provide tert-butyl ((1r,3r)-3-((5-(trifluoromethyl)pyridin-3-yl)oxy)cyclobutyl)carbamate (300 mg, 56%). MS (ESI+) [Method 6A]: m/z 332.9 (M+H); Rt 1.57 min.

Step 95.4: Synthesis of (1r,3r)-3-((5-(trifluoromethyl)pyridin-3-yl)oxy)cyclobutan-1-amine, HCl

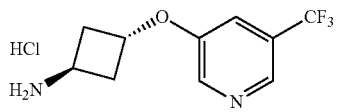

A round bottom flask was charged with tert-butyl ((1r,3r)-3-((5-(trifluoromethyl)pyridin-3-yl)oxy)cyclobutyl)carbamate (100 mg, 0.30 mmol) and HCl solution (4M in 1,4-dioxane) (5 mL) and the solution was stirred rt for 16 h. Then the reaction mixture was concentrated in vacuo. The residue was triturated with n-pentane, solid was filtered and dried to yield (1r,3r)-3-((5-(trifluoromethyl)pyridin-3-yl)oxy)cyclobutan-1-amine, HCl (80 mg, 99%). MS (ESI+) [Method 6A]: m/z 232.9 (M+H); Rt 1.22 min.

Step 95.5: Synthesis of (1r,3r)-N-((6-fluoroisoquinolin-5-yl)methyl)-3-((5-(trifluoromethyl)pyridin-3-yl)oxy)cyclobutan-1-amine, HCl

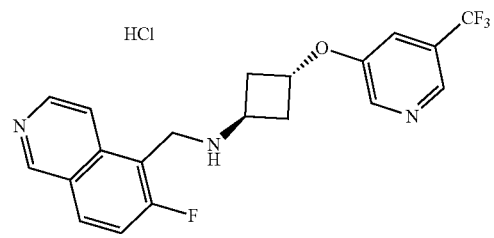 [SMILES: Fc1ccc2cnccc2c1CN[C@H]1C[C@H](Oc2cncc(C(F)(F)F)c2)C1 ; Cl]

The title compound was synthesized following the procedure as described in Step 1.4, using (1r,3r)-3-((5-(trifluoromethyl)pyridin-3-yl)oxy)cyclobutan-1-amine, HCl (80 mg, 0.3 mmol) and 6-fluoroisoquinoline-5-carbaldehyde (Step 3.1, 47 mg, 0.27 mmol). The crude product was purified by prep-HPLC (Column: YMC-ACUTUS-TRIART C18 (150 mm×21.2 mm), 5.0µ; Mobile Phase: 0.02% NH$_4$OH in water and acetonitrile). To the isolated product, HCl solution (4M in 1,4-dioxane) (2 mL) was added, stirred at rt for 2 h. The solution was concentrated, residue was triturated with n-pentane, the solid was collected, dried and lyophilized to provide (1r,3r)-N-((6-fluoroisoquinolin-5-yl)methyl)-3-((5-(trifluoromethyl)pyridin-3-yl)oxy)cyclobutan-1-amine, HCl (40 mg, 31%). MS (ESI+) [Method 6A]: m/z 392.1 (M+H); Rt 1.29 min. $^1$H NMR (600 MHz, CD$_3$OD) δ 9.93 (s, 1H), 8.89-8.80 (m, 3H), 8.61 (s, 1H), 8.54 (s, 1H), 8.07 (t, J=9.6 Hz, 1H), 7.71 (s, 1H), 5.26-5.22 (m, 1H), 4.67 (s, 2H), 4.38-4.32 (m, 1H), 4.36 (p, J=8.0 Hz, 1H), 3.02-2.96 (m, 2H), 2.83-2.76 (m, 2H).

Example 96: Synthesis of (1r,3r)-3-(benzo[d]thiazol-2-yloxy)-N-((6-fluoroisoquinolin-5-yl)methyl)cyclobutan-1-amine, HCl Step 96.1: Synthesis of tert-butyl ((1r,3r)-3-(benzo[d]thiazol-2-yloxy)cyclobutyl)carbamate

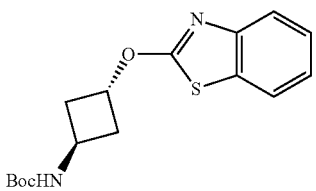 [SMILES: CC(C)(C)OC(=O)N[C@H]1C[C@H](Oc2nc3ccccc3s2)C1]

To the solution of tert-butyl ((1s,3s)-3-hydroxycyclobutyl)carbamate (200 mg, 1.07 mmol) in THF (0.5 M), benzo[d]thiazol-2-ol [CAS No. 934-34-9] (160 mg, 1.07 mmol), PPh$_3$ (1.5 eq) and diisopropyl azodicarboxylate (1.5 eq) were added at rt. The reaction mixture was stirred at 50-60° C. for 16 h under N$_2$ atmosphere. Reaction mixture was diluted with water and extracted with EtOAc 3×'s. The combined organic portion was washed with brine solution, dried over anhydrous Na$_2$SO$_4$, filtered and concentrated in vacuo. The crude product was purified by flash chromatography (12 g SiliCycle column, 0-25% EtOAc in Hexane elution) to provide tert-butyl ((1r,3r)-3-(benzo[d]thiazol-2-yloxy)cyclobutyl)carbamate (200 mg, 58%). MS (ESI+) [Method 6A]: m/z 321.1 (M+H); Rt 1.61 min. $^1$H NMR (300 MHz, CDCl$_3$) δ 7.65 (t, J=8.1 Hz, 2H), 7.35 (dt, J=6.9, 1.2 Hz, 1H), 7.25-7.19 (m, 1H), 5.51-5.45 (m, 1H), 4.37-4.31 (m, 1H), 2.73-2.63 (m, 2H), 2.52-2.43 (m, 2H), 1.45 (s, 9H).

Step 96.2: Synthesis of (1r,3r)-3-(benzo[d]thiazol-2-yloxy)cyclobutan-1-amine, HCl

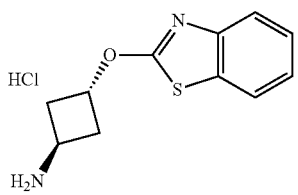 [SMILES: Cl ; N[C@H]1C[C@H](Oc2nc3ccccc3s2)C1]

A round bottom flask was charged with tert-butyl ((1r, 3r)-3-(benzo[d]thiazol-2-yloxy)cyclobutyl)carbamate (200 mg, 0.62 mmol) and HCl solution (4M in 1,4-dioxane) (10 mL) and the solution was stirred rt for 16 h. Then the reaction mixture was concentrated in vacuo to yield (1r,3r)-3-(benzo[d]thiazol-2-yloxy)cyclobutan-1-amine, HCl (130 mg, 81%). MS (ESI+) [Method 6A]: m/z 220.9 (M+H); Rt 1.28 min. $^1$H NMR (400 MHz, DMSO-d$_6$) δ 8.41 (brs, 3H), 7.90 (d, J=7.6 Hz, 1H), 7.67 (d, J=7.6 Hz, 1H), 7.40 (t, J=8.4 Hz, 1H), 7.31 (t, J=8.4 Hz, 1H), 5.63-5.58 (m, 1H), 3.91-3.86 (m, 1H), 2.70-2.62 (m, 4H).

Step 96.3: Synthesis of (1r,3r)-3-(benzo[d]thiazol-2-yloxy)-N-((6-fluoroisoquinolin-5-yl)methyl)cyclobutan-1-amine, HCl

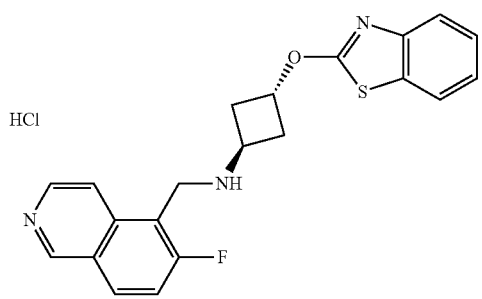 [SMILES: Cl ; Fc1ccc2cnccc2c1CN[C@H]1C[C@H](Oc2nc3ccccc3s2)C1]

The title compound was synthesized following the procedure as described in Step 1.4, using (1r,3r)-3-(benzo[d]thiazol-2-yloxy)cyclobutan-1-amine, HCl (70 mg, 0.27 mmol) and 6-fluoroisoquinoline-5-carbaldehyde (Step 3.1, 43 mg, 0.25 mmol). The crude product was purified by prep-HPLC (Column: YMC-ACUTUS-TRIART C18 (150 mm×21.2 mm), 5.0µ; Mobile Phase: 0.02% NH$_4$OH in water and acetonitrile). To the isolated product, HCl solution (20% in 1,4-dioxane) (0.5 mL) was added, stirred at rt for 1 h. The solution was concentrated, residue was triturated with Et$_2$O, the solid was collected, dried in vacuo to provide (1r,3r)-3-(benzo[d]thiazol-2-yloxy)-N-((6-fluoroisoquinolin-5-yl)methyl)cyclobutan-1-amine, HCl (26 mg, 25%). MS (ESI+) [Method 6A]: m/z 380.1 (M+H); Rt 1.29 min. $^1$H NMR (600 MHz, CD$_3$OD) δ 9.26 (s, 1H), 8.55 (d, J=6.4 Hz, 1H), 8.19-8.14 (m, 2H), 7.74 (d, J=8.0 Hz, 1H), 6.62 (d, J=8.0 Hz, 1H), 7.55 (t, J=9.6 Hz, 1H), 7.38 (t, J=8.0 Hz, 1H), 7.26 (t, J=7.2 Hz, 1H), 5.47-5.43 (m, 1H), 4.22 (d, J=1.6 Hz, 2H), 3.70-3.64 (m, 1H), 2.53-2.44 (m, 4H).

Example 97: Synthesis of (1r,3r)-N-((6-ethylisoquinolin-5-yl)methyl)-3-(4-fluoro-3-(trifluoromethyl)phenoxy)cyclobutan-1-amine, HCl Step 97.1: Synthesis of 6-vinylisoquinoline

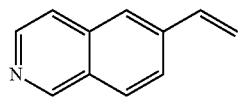

The stirred solution of 6-bromoisoquinoline [CAS No. 34784-05-9] (2.0 g, 9.70 mmol), tributyl(vinyl)stannane (3.5 g, 11.01 mmol) in 1,4-dioxane (20 mL) was degassed with N$_2$ for 10 min. Then Pd(PPh$_3$)$_4$ (0.8 g, 0.69 mmol) was added, degassed, reaction vessel was closed and heated at 100° C. for 16 h. Reaction mixture was cooled to rt, diluted with water and extracted with EtOAc 3×'s. The combined organic portion was washed with brine, dried over anhydrous Na$_2$SO$_4$, filtered and concentrated in vacuo. The crude product was purified by flash chromatography (24 g Sili-Cycle column, 0-30% EtOAc in Hexane elution) to provide 6-vinylisoquinoline (1.5 g, 99%). MS (ESI+) [Method 6A]: m/z 155.8 (M+H); Rt 1.12 min.

Step 97.2: Synthesis of 6-ethylisoquinoline

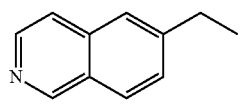

A round bottom flask charged with 6-vinylisoquinoline (500 mg, 3.22 mmol) and EtOAc (5 mL). The solution was purged with N$_2$ for 10 min. Then Pd/C (10% w/w) (50 mg) was added, H$_2$ balloon was connected and the reaction mixture was stirred at rt for 1 h. Reaction mixture was filtered through celite bed, the bed was washed with EtOAc. The combined filtrate was concentrated in vacuo to afford crude 6-ethylisoquinoline (500 mg, 99%). $^1$H NMR (600 MHz, CdCl$_3$) δ 9.19 (s, 1H), 8.48 (d, J=6.0 Hz, 1H), 7.88 (d, J=8.4 Hz, 1H), 7.60-7.58 (m, 2H), 7.47 (d, J=8.4 Hz, 1H), 2.85 (q, J=7.8 Hz, 2H), 1.34 (t, J=7.8 Hz, 3H).

Step 97.3: Synthesis of 5-bromo-6-ethylisoquinoline

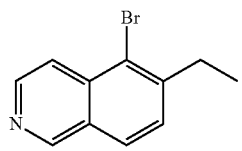

A round bottom flask charged with 6-ethylisoquinoline (460 mg, 2.93 mmol) and AlCl$_3$ (780 mg, 5.85 mmol) was heated to 75° C. Then Br$_2$ (0.1 mL, 5.85 mmol) was added drop wise over a period of 10 min and the resulting mixture was stirred at 75° C. for 2 h. The nearly black reaction mixture was poured into vigorously stirred ice-water. The cold mixture was treated with NH$_4$OH solution and extracted with EtOAc twice. The combined organic layer was washed with brine solution, dried over anhydrous Na$_2$SO$_4$, filtered and concentrated in vacuo. The residue was purified by flash chromatography (8 g SiliCycle column, 0-30% EtOAc in Hexane elution) to provide 5-bromo-6-ethylisoquinoline (180 mg, 26%). MS (ESI+) [Method 6A]: m/z 235.9, 237.90 (M+H); Rt 1.48 min.

Step 97.4: Synthesis of 6-ethyl-5-vinylisoquinoline

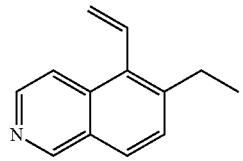

The stirred solution of 5-bromo-6-ethylisoquinoline (180 mg, 0.76 mmol), potassium trifluoro(vinyl)borate (204 mg, 1.52 mmol) and TEA (0.21 mL, 1.52 mmol) in IPA (5 mL) was degassed with argon for 5 min. Then Pd(dppf)Cl$_2$·CH$_2$Cl$_2$ (100 mg, 0.13 mmol) was added, degassed and heated at 90° C. for 16 h under argon atmosphere. Reaction mixture was cooled to rt, filtered through celite bed and the bed was thoroughly washed with EtOAc. The combined filtrate was concentrated in vacuo and the residue was purified by flash chromatography (4 g SiliCycle column, 0-30% EtOAc in Hexane elution) to provide 6-ethyl-5-vinylisoquinoline (120 mg, 86%. MS (ESI+) [Method 6A]: m/z 184.0 (M+H); Rt 1.31 min.

Step 97.5: Synthesis of 6-ethylisoquinoline-5-carbaldehyde

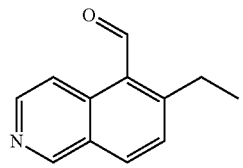

To the solution of 6-ethyl-5-vinylisoquinoline (120 mg, 0.65 mmol) in t-BuOH-1,4-dioxane (8 mL, 1:3 v/v), OsO$_4$ (5 mg, 0.02 mmol) was added at rt and stirred for 15 min. Then NaIC$_4$ (700 mg, 3.27 mmol) dissolved in water (2 mL) was added drop wise at rt and stirred for 16 h. Reaction mixture was diluted with water and extracted with EtOAc 3x's. The combined organic portion was washed with brine, dried over anhydrous Na$_2$SO$_4$, filtered and concentrated in vacuo to yield the crude product. The crude was purified by flash chromatography (12 g SiliCycle column, 0-35% EtOAc in Hexane elution) to provide 6-ethylisoquinoline-5-carbaldehyde (120 mg, 59%). MS (ESI+) [Method 6A]: m/z 186.0 (M+H); Rt 1.24 min Step 97.6: Synthesis of (1r,3r)-N-((6-ethylisoquinolin-5-yl)methyl)-3-(4-fluoro-3-(trifluoromethyl)phenoxy)cyclobutan-1-amine, HCl

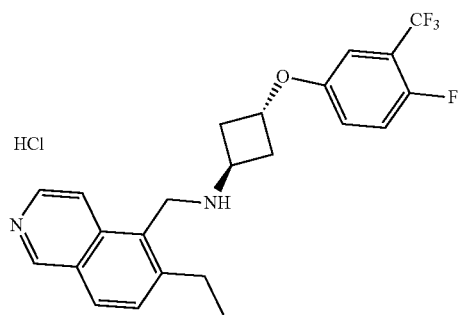 [SMILES: CCc1ccc2cnccc2c1CN[C@H]1C[C@H](Oc2ccc(F)c(C(F)(F)F)c2)C1 ; Cl]

The title compound was synthesized following the procedure as described in Step 1.4, using (1r,3r)-3-(4-fluoro-3-(trifluoromethyl)phenoxy)cyclobutan-1-amine, HCl (Step 1.3, 100 mg, 0.35 mmol) and 6-ethylisoquinoline-5-carbaldehyde (58 mg, 0.32 mmol). The crude product was purified by prep-HPLC (Column: GEMINI-NX (150 mm×21.2 mm), 5.0μ; Mobile Phase: 0.02% NH$_4$OH in water and acetonitrile). To the isolated product, HCl solution (20% in 1,4-dioxane) (2 mL) was added, stirred at rt for 2 h. The solution was concentrated and the residue was triturated with n-Pentane, the solid was collected, and dried in vacuo to provide (1r,3r)-N-((6-ethylisoquinolin-5-yl)methyl)-3-(4-fluoro-3-(trifluoromethyl)phenoxy)cyclobutan-1-amine, HCl (70 mg, 44%). MS (ESI+) [Method 6A]: m/z 419.2 (M+H); Rt 1.34 min. $^1$H NMR (400 MHz, CD$_3$OD) δ 9.83 (s, 1H), 8.77 (dd, J=17.4, 6.4 Hz, 2H), 8.61 (d, J=8.8 Hz, 1H), 8.13 (d, J=8.4 Hz, 1H), 7.32 (t, J=9.6 Hz, 1H), 7.19-7.13 (m, 2H), 5.11-5.06 (m, 1H), 4.86 (s, 2H), 4.46-4.40 (m, 1H), 3.20 (q, J=7.2 Hz, 2H), 3.00-2.93 (m, 2H), 2.79-2.73 (m, 2H), 1.43 (t, J=7.2 Hz, 3H).

Example 98: Synthesis of (1r,3r)-N-((3-chloroisoquinolin-5-yl)methyl)-3-(4-fluoro-3-(trifluoromethyl)phenoxy)cyclobutan-1-amine, HCl Step 98.1: Synthesis of 5-bromo-3-chloroisoquinoline

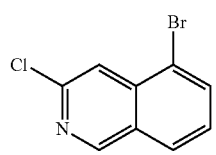 [SMILES: Clc1cc2c(Br)cccc2cn1]

The stirred solution of 3-chloroisoquinoline [CAS No. 19493-45-9] (1.0 g, 6.11 mmol) in H$_2$SO$_4$ (10.0 mL) was cooled to 0° C. Then NBS (1.6 g, 9.17 mmol) was added portion wise and stirred for 4 h. The reaction was poured into ice-water, basified with aqueous NH$_4$OH solution and then extracted with EtOAc twice. The combined organic layer was washed with brine solution, dried over anhydrous Na$_2$SO$_4$, filtered and concentrated in vacuo. The residue was purified by flash chromatography (12 g SiliCycle column, 0-10% EtOAc in Hexane elution) to provide 5-bromo-3- chloroisoquinoline (1.0 g, 67%). MS (ESI+) [Method 1A]: m/z 244.0 (M+H); Rt 1.88 min.

Step 98.2: Synthesis of 3-chloro-5-vinylisoquinoline

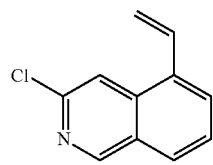

The title compound was prepared according to Step 97.4. The reaction mixture was heated at 90° C. for 3 h under $N_2$. Reaction mixture was cooled to rt, diluted with water and extracted with EtOAc 3×'s. The combined organic portion was washed with brine, dried over anhydrous $Na_2SO_4$, filtered and concentrated in vacuo to yield the crude product. The crude was purified by flash chromatography (12 g SiliCycle column, 0-30% EtOAc in Hexane elution) to provide 3-chloro-5-vinylisoquinoline (233 mg, 60%). MS (ESI+) [Method 1A]: m/z 190.0 (M+H); Rt 1.83 min.

Step 98.3: Synthesis of 3-chloroisoquinoline-5-carbaldehyde

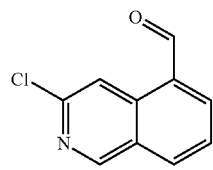 [SMILES: O=Cc1cccc2cnc(Cl)cc12]

To the solution of 3-chloro-5-vinylisoquinoline (233 mg, 1.23 mmol) in t-BuOH-1,4-dioxane (8 mL, 3:5 v/v), $OsO_4$ (10 mg, 0.04 mmol) was added at rt and stirred for 15 min. Then $NaIO_4$ (1.3 g, 6.14 mmol) dissolved in water (3 mL) was added drop wise at rt and stirred for 16 h. Reaction mixture was diluted with water and extracted with EtOAc 3×'s. The combined organic portion was washed with brine, dried over anhydrous $Na_2SO_4$, filtered and concentrated in vacuo to yield the crude product. The crude was purified by flash chromatography (12 g SiliCycle column, 0-30% EtOAc in Hexane elution) to provide 3-chloroisoquinoline-5-carbaldehyde (97 mg, 41%). MS (ESI+) [Method 6A]: m/z 191.8 (M+H); Rt 1.46 min Step 98.4: Synthesis of (1r,3r)-N-((3-chloroisoquinolin-5-yl)methyl)-3-(4-fluoro-3-(trifluoromethyl)phenoxy)cyclobutan-1-amine, HCl

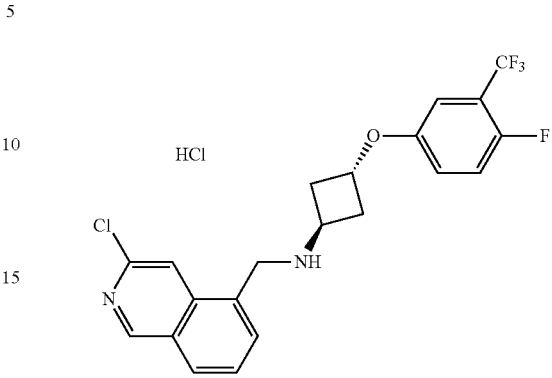

The title compound was synthesized following the procedure as described in Step 1.4, using (1r,3r)-3-(4-fluoro-3-(trifluoromethyl)phenoxy)cyclobutan-1-amine, HCl (Step 1.3, 80 mg, 0.28 mmol) and 3-chloroisoquinoline-5-carbaldehyde (42 mg, 0.25 mmol). The crude product was purified by prep-HPLC (Column: KINETEX EVO C18 (150 mm×21.2 mm), 5.0μ; Mobile Phase: 0.02% $NH_4OH$ in water and acetonitrile). To the isolated product, HCl solution (20% in 1,4-dioxane) (0.5 mL) was added, stirred at rt for 1 h. Then the solution was concentrated, residue was triturated with $Et_2O$, the solid was collected, dried in vacuo to provide (1r,3r)-N-((3-chloroisoquinolin-5-yl)methyl)-3-(4-fluoro-3-(trifluoromethyl)phenoxy)cyclobutan-1-amine, HCl (37 mg, 29%). MS (ESI+) [Method 6A]: m/z 424.8 (M+H); Rt 1.36 min. $^1$H NMR (400 MHz, $CD_3OD$) δ 9.23 (s, 1H), 8.27 (d, J=21.4 Hz, 1H), 8.23 (s, 1H), 8.03 (d, J=7.6 Hz, 1H), 7.79 (dd, J=8.0, 6.0 Hz, 1H), 7.28 (t, J=9.2 Hz, 1H), 7.14-7.07 (m, 2H), 5.02-4.96 (m, 1H), 4.68 (s, 2H), 4.25-4.20 (m, 1H), 2.85-2.79 (m, 2H), 2.70-2.63 (m, 2H).

Example 99: Synthesis of (1r,3r)-3-((4-fluoro-3-(trifluoromethyl)phenyl)thio)-N-(isoquinolin-5-ylmethyl)cyclobutan-1-amine, HCl Step 99.1: Synthesis of (1s,3s)-3-((tert-butoxycarbonyl)amino)cyclobutyl methanesulfonate

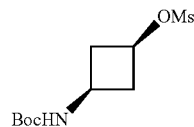

To the stirred solution of tert-butyl ((1s,3s)-3-hydroxycyclobutyl)carbamate (1.0 g, 5.34 mmol) in $CH_2Cl_2$ (10 mL), TEA (2.2 mL, 16.02 mmol) was added drop wise at rt. The reaction mixture was cooled to −10° C., then MsCl (0.54 mL, 6.94 mmol) was added drop wise and stirred at rt for 1 h under $N_2$. Reaction mixture was diluted with water and extracted with $CH_2Cl_2$ thrice. The combined organic portion was washed with brine solution, dried over anhydrous $Na_2SO_4$, filtered and concentrated in vacuo to provide crude (1s,3s)-3-((tert-butoxycarbonyl)amino)cyclobutyl methanesulfonate (1.4 g, 99%). $^1$H NMR (300 MHz, $CDCl_3$) δ

4.73-4.69 (m, 1H), 3.84-3.78 (m, 1H), 2.98 (s, 3H), 2.95-2.86 (m, 2H), 2.24-2.12 (m, 2H), 1.43 (s, 9H).

Step 99.2: Synthesis of S-((1r,3r)-3-((tert-butoxycarbonyl)amino)cyclobutyl) ethanethioate

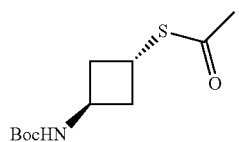 [SMILES: CC(=O)S[C@H]1C[C@H](NC(=O)OC(C)(C)C)C1]

A sealed tube was charged with (1s,3s)-3-((tert-butoxycarbonyl)amino)cyclobutyl methanesulfonate (700 mg, 2.64 mmol) and DMF (15 mL). Then potassium ethanethioate (603 mg, 5.28 mmol) was added and the reaction mixture was degassed with argon. The vessel was closed and stirred at 90° C. for 18 h. Reaction mixture was cooled to rt, diluted with water and extracted with EtOAc twice. The combined organic portion was washed with brine solution, dried over anhydrous $Na_2SO_4$, filtered and concentrated in vacuo. The residue was purified by flash chromatography (12 g SiliCycle column, 0-20% EtOAc in Hexane elution) to provide S-((1r,3r)-3-((tert-butoxycarbonyl)amino)cyclobutyl) ethanethioate (470 mg, 73%). $^1$H NMR (300 MHz, $CDCl_3$) δ 4.78 (brs, 1H), 4.31 (brs, 1H), 3.94-3.90 (m, 1H), 2.48-2.32 (m, 4H), 2.30 (s, 3H), 1.43 (s, 9H).

Step 99.3: Synthesis of tert-butyl ((1r,3r)-3-mercaptocyclobutyl)carbamate

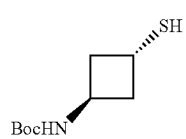

To the stirred solution of S-((1r,3r)-3-((tert-butoxycarbonyl)amino)cyclobutyl) ethanethioate (470 mg, 1.92 mmol) in THF-MeOH (9 mL, 2:2 v/v), 1N NaOH solution (11.5 mL, 11.49 mmol) was added. The reaction mixture was stirred at rt for 20 min, then diluted with water and extracted with EtOAc twice. The combined organic portion was washed with brine solution, dried over anhydrous $Na_2SO_4$, filtered and concentrated in vacuo to provide crude tert-butyl ((1r,3r)-3-mercaptocyclobutyl)carbamate (350 mg, 90%). $^1$H NMR (300 MHz, $CDCl_3$) δ 4.70 (brs, 1H), 4.43 (brs, 1H), 3.54-3.47 (m, 1H), 2.42-2.27 (m, 4H), 1.43 (s, 9H).

Step 99.4: Synthesis of tert-butyl ((1r,3r)-3-((4-fluoro-3-(trifluoromethyl)phenyl)thio)cyclobutyl)carbamate

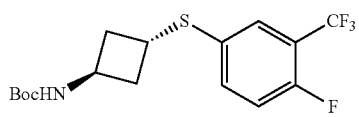 [SMILES: CC(C)(C)OC(=O)N[C@H]1C[C@H](Sc2ccc(F)c(C(F)(F)F)c2)C1]

The stirred solution of tert-butyl ((1r,3r)-3-mercaptocyclobutyl)carbamate (330 mg, 1.62 mmol), 4-bromo-1-fluoro-2-(trifluoromethyl)benzene [CAS No. 393-37-3] (0.3 mL, 2.44 mmol) and DIPEA (0.6 mL, 0.19 mmol) in 1,4-dioxane was degassed with argon. Then Xantphos (94 mg, 0.16 mmol) and $Pd_2(dba)_3$ (75 mg, 0.08 mmol) were added, and the reaction mixture was heated at 110° C. for 18 h under argon. The reaction mixture was concentrated in vacuo and the residue was purified by flash chromatography (12 g SiliCycle column, 0-20% EtOAc in Hexane elution) to provide tert-butyl ((1r,3r)-3-((4-fluoro-3-(trifluoromethyl)phenyl)thio)cyclobutyl)carbamate (750 mg, 120%). $^1$H NMR (600 MHz, $CDCl_3$) δ 7.45-7.43 (m, 1H), 7.40-7.38 (m, 1H), 7.12 (t, J=9.6 Hz, 1H), 4.76 (brs, 1H), 4.42 (brs, 1H), 3.80-3.76 (m, 1H), 2.42-2.33 (m, 4H), 1.43 (s, 9H).

Step 99.5: Synthesis of (1r,3r)-3-((4-fluoro-3-(trifluoromethyl)phenyl)thio)cyclobutan-1-amine, HCl

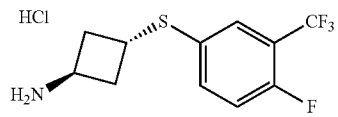 [SMILES: Cl ; N[C@H]1C[C@H](Sc2ccc(F)c(C(F)(F)F)c2)C1]

A round bottom flask was charged with tert-butyl ((1r,3r)-3-((4-fluoro-3-(trifluoromethyl)phenyl)thio)cyclobutyl)carbamate (710 mg, 1.94 mmol) and HCl solution (20% in 1,4-dioxane) (10 mL); and the solution was stirred rt for 16 h. Then the reaction mixture was concentrated in vacuo to afford (1r,3r)-3-((4-fluoro-3-(trifluoromethyl)phenyl)thio)cyclobutan-1-amine, HCl (410 mg, 80%). MS (ESI+) [Method 6A]: m/z 266.0 (M+H); Rt 1.31 min.

Step 99.6: Synthesis of (1r,3r)-3-((4-fluoro-3-(trifluoromethyl)phenyl)thio)-N-(isoquinolin-5-ylmethyl)cyclobutan-1-amine, HCl

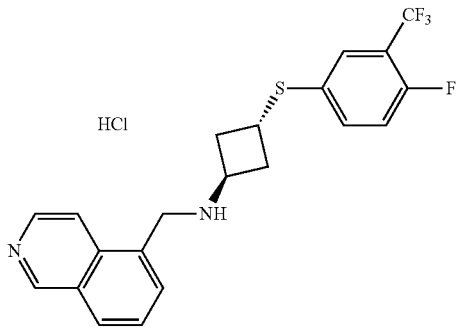 [SMILES: Fc1ccc(S[C@H]2C[C@H](NCc3cccc4cnccc34)C2)cc1C(F)(F)F ; Cl]

The title compound was synthesized following the procedure as described in Step 25.6, using (1r,3r)-3-((4-fluoro-3-(trifluoromethyl)phenyl)thio)cyclobutan-1-amine, HCl (80 mg, 0.27 mmol) and isoquinoline-5-carbaldehyde [CAS No. 80278-67-7] (38 mg, 0.24 mmol). The crude product was purified by prep-HPLC (Column: GEMINI-NX (150 mm×21.2 mm), 5.0μ; Mobile Phase: 0.02% $NH_4OH$ in water and acetonitrile). The isolated product was stirred with HCl solution (20% in 1,4-dioxane), then concentrated and dried to afford (1r,3r)-3-((4-fluoro-3-(trifluoromethyl)phenyl)thio)-N-(isoquinolin-5-ylmethyl)cyclobutan-1-amine, HCl (45 mg, 38%). MS (ESI+) [Method 1A]: m/z 406.8 (M+H); Rt 0.22 min. $^1$H NMR (400 MHz, $CD_3OD$) δ 9.86 (s, 1H), 8.75-8.72 (m, 2H), 8.61 (d, J=8.8 Hz, 1H), 8.41 (d, J=7.2 Hz, 1H), 8.12 (dd, J=8.0, 7.2 Hz, 1H), 7.35-7.61 (m, 2H), 7.36 (t, J=8.8 Hz, 1H), 4.80 (s, 2H), 4.33-4.28 (m, 1H), 4.19-4.13 (m, 1H), 2.98-2.90 (m, 2H), 2.52-2.46 (m, 2H).

Example 100: Synthesis of (1r,3r)-3-((4-fluoro-3-(trifluoromethyl)phenyl)thio)-N-((6-fluoroisoquinolin-5-yl)methyl)cyclobutan-1-amine, HCl

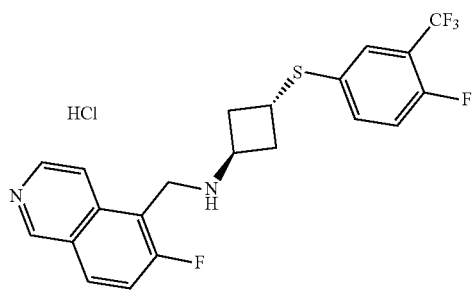 [SMILES: Fc1ccc(S[C@H]2C[C@H](NCc3c(F)ccc4cnccc34)C2)cc1C(F)(F)F ; Cl]

The title compound was synthesized following the procedure as described in Step 25.6, using (1r,3r)-3-((4-fluoro-3-(trifluoromethyl)phenyl)thio)cyclobutan-1-amine, HCl (Step 99.5, 80 mg, 0.27 mmol) and 6-fluoroisoquinoline-5-carbaldehyde (Step 3.1, 42 mg, 0.24 mmol). The crude product was purified by prep-HPLC (Column: GEMINI-NX (150 mm×21.2 mm), 5.0µ; Mobile Phase: 0.02% NH$_4$OH in water and acetonitrile). The isolated product was stirred with HCl solution (20% in 1,4-dioxane), then concentrated and dried to afford (1r,3r)-3-((4-fluoro-3-(trifluoromethyl)phenyl)thio)-N-((6-fluoroisoquinolin-5-yl)methyl)cyclobutan-1-amine, HCl (16 mg, 14%). MS (ESI+) [Method 1A]: m/z 425.2 (M+H); Rt 0.29 min. $^1$H NMR (400 MHz, CD$_3$OD) δ 9.89 (s, 1H), 8.82-8.76 (m, 3H), 8.02 (t, J=9.6 Hz, 1H), 7.67-7.61 (m, 2H), 7.35 (t, J=9.6 Hz, 1H), 4.80 (s, 2H), 4.33-4.28 (m, 1H), 4.19-4.13 (m, 1H), 2.98-2.91 (m, 2H), 2.54-2.48 (m, 2H).

Example 101: Synthesis of (1r,3r)-3-(4-(difluoromethyl)-3-fluorophenoxy)-N-((6-fluoroisoquinolin-5-yl)methyl)cyclobutan-1-amine Step 101.1: Synthesis of 4-(difluoromethyl)-3-fluorophenol

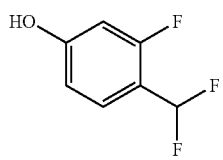

To the solution of 2-fluoro-4-hydroxybenzaldehyde [CAS No. 348-27-6] (500 mg, 3.57 mmol) in CH$_2$Cl$_2$ (5 mL), bis(2-methoxyethyl)aminosulfur trifluoride (50% in THF) (4.8 mL, 10.71 mmol) was added drop wise for 5 min at 0° C. and the reaction mixture was stirred at rt for 60 h under argon. The reaction was quenched with saturated aqueous NaHCO$_3$ solution and extracted with CH$_2$Cl$_2$ 3×'s. The combined organic portion was washed with brine solution, dried over anhydrous Na$_2$SO$_4$, filtered and concentrated in vacuo. The residue was purified by flash chromatography (12 g SiliCycle column, 0-7% EtOAc in Hexane elution) to provide 4-(difluoromethyl)-3-fluorophenol (200 mg, 35%). MS (ESI+) [Method 6A]: m/z 160.9 (M–H); Rt 1.44 min.

Step 101.2: Synthesis of (1s,3s)-3-aminocyclobutan-1-ol, HCl

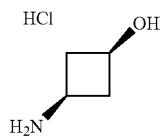

The solution of tert-butyl ((1s,3s)-3-hydroxycyclobutyl)carbamate [CAS No. 389890-43-1] (300 mg, 1.60 mmol) and HCl (20% solution in 1,4-dioxane) (3 mL) was stirred at rt for 16 h. Then the reaction mixture was concentrated in vacuo. The residue was triturated with Et$_2$O, the brick red solid was collected and dried to yield (1s,3s)-3-aminocyclobutan-1-ol, HCl (160 mg, 81%). $^1$H NMR (400 MHz, DMSO-d6) δ 8.21 (brs, 3H), 3.90-3.84 (m, 1H), 3.15-3.09 (m, 1H), 2.51-2.46 (m, 2H), 1.96-1.90 (m, 2H).

Step 101.3: Synthesis of (1s,3s)-3-(((6-fluoroisoquinolin-5-yl)methyl)amino)cyclobutan-1-ol

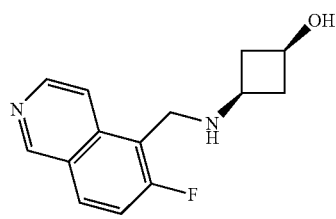 [SMILES: O[C@H]1C[C@@H](NCc2c(F)ccc3cnccc23)C1]

The title compound was synthesized using (1s,3s)-3-aminocyclobutan-1-ol, HCl (80 mg, 0.65 mmol) and 6-fluoroisoquinoline-5-carbaldehyde (Step 3.1, 102 mg, 1.17 mmol), following the procedure as described in step 1.4. The crude product was purified by flash chromatography (4 g SiliCycle column, 0-8% MeOH in CH$_2$Cl$_2$ elution) to provide (1s,3s)-3-(((6-fluoroisoquinolin-5-yl)methyl)amino)cyclobutan-1-ol (70 mg, 44%). MS (ESI+) [Method 6A]: m/z 247.0 (M+H); Rt 0.13 min.

Step 101.4: Synthesis of (1r,3r)-3-(4-(difluoromethyl)-3-fluorophenoxy)-N-((6-fluoroisoquinolin-5-yl)methyl)cyclobutan-1-amine

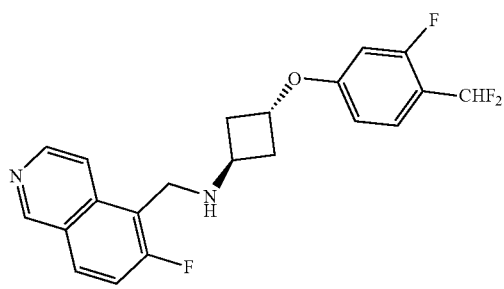 [SMILES: Fc1cc(O[C@H]2C[C@H](NCc3c(F)ccc4cnccc34)C2)ccc1C(F)F]

To the solution (1s,3s)-3-(((6-fluoroisoquinolin-5-yl)methyl)amino)cyclobutan-1-ol (50 mg, 0.31 mmol) in THF (0.5 M), 4-(difluoromethyl)-3-fluorophenol (70 mg, 0.31 mmol), PPh$_3$ (1.5 eq) and diisopropyl azodicarboxylate (1.5 eq) were added at rt. The reaction mixture was stirred at 50-60° C. for 16 h under N$_2$ atmosphere. Reaction mixture was diluted with water and extracted with EtOAc (3×'s). The combined organic portion was washed with brine solution, dried over anhydrous Na$_2$SO$_4$, filtered and concentrated in vacuo. The crude product was purified by flash chromatography (4 g SiliCycle column, 0-8% MeOH in CH$_2$Cl$_2$ elution). The isolated compound (90 mg) was re-purified by prep-HPLC (Column: XBRIDGE (150 mm×21.2 mm), 5.0μ; Mobile Phase: 0.02% NH$_4$OH in water and acetonitrile) to afford (1r,3r)-3-(4-(difluoromethyl)-3-fluorophenoxy)-N-((6-fluoroisoquinolin-5-yl)methyl)cyclobutan-1-amine (4 mg, 3%). MS (ESI+) [Method 6A]: m/z 391.1 (M+H); Rt 1.31 min. $^1$H NMR (400 MHz, CD$_3$OD) δ 9.26 (s, 1H), 8.54 (d, J=6.0 Hz, 1H), 8.20-8.16 (m, 1H), 8.13 (d, J=6.4 Hz, 1H), 7.55 (t, J=8.8 Hz, 1H), 7.48 (t, J=8.8 Hz, 1H), 6.88 (t, J=55.2 Hz, 1H), 6.74-6.72 (m, 1H), 6.66 (d, J=12.4 Hz, 1H), 4.91-4.86 (m, 1H), 4.22 (d, J=2.0 Hz, 2H), 3.65-3.59 (m, 1H), 2.40-2.36 (m, 4H).

Example 102: Synthesis of (1r,3r)-3-(4-fluoro-3-(trifluoromethyl)phenoxy)-N-((7-fluoroquinazolin-8-yl)methyl)cyclobutan-1-amine Step 102.1: Synthesis of (Z)—N-(3-fluoro-2-methylphenyl)-2-(hydroxyimino)acetamide

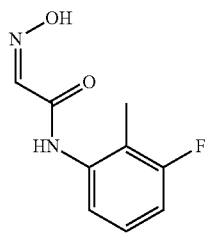

In a 1000 mL four necked RB flask fitted with reflux condenser, thermometer pocket and nitrogen inlet, hydroxyl amine hydrochloride (36 g, 0.52 mol) and anhydrous Na$_2$SO$_4$ (137 g) was added to a boiling solution of 3-fluoro-2-methylaniline [443-86-7] (20 g, 0.160 mol), 1 N HCl (145 mL), and H$_2$O (450 mL). A boiling solution of chloral hydrate (31.7 g, 0.194 mol) in H$_2$O was added. The resulting reaction mixture was boiled at 80° C. for 4 h and the reaction progress was monitored by TLC and LC-MS. After completion, the reaction mixture was cooled to rt and extracted with Diethyl ether (3×200 mL). The combined organic layers were dried over anhydrous Na$_2$SO$_4$ and filtered. The filtrate was evaporated under reduced pressure to provide (Z)—N-(3-fluoro-2-methylphenyl)-2-(hydroxyimino)acetamide (27.0 g) as a white yellow solid. MS (ESI−) [Method 7A]: m/z 195 (M−H); Rt 1.82 min. $^1$H NMR NMR-400-c (400 MHz, DMSO-d$_6$) δ 12.26 (s, 1H), 9.73 (s, 1H), 7.70 (s, 1H), 7.33 (d, J=8.0 Hz, 1H), 7.24 (q, J=7.6 Hz, 1H), 7.06 (t, J=8.9 Hz, 1H), 2.11 (d, J=2.1 Hz, 3H).

Step 102.2: Synthesis 6-fluoro-7-methylindoline-2,3-dione

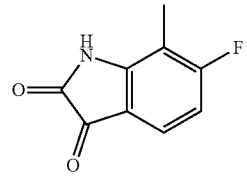

In a 500 mL four necked RB flask fitted with reflux condenser, thermometer pocket and nitrogen inlet, (Z)—N-(3-fluoro-2-methylphenyl)-2-(hydroxyimino)acetamide (27 g, 0.137 mol) was added portion-wise to a stirred solution of conc. H$_2$SO$_4$ (140 mL) at 80° C. for 2 h. After completion, the reaction mixture was cooled to rt and poured over crushed ice. The resulting solid was collected by filtration and dried in a rotating flask under vacuum at 50° C. to provide 6-fluoro-7-methylindoline-2,3-dione (16.0 g) as brown solid. MS (ESI−) [Method 7A]: m/z 178 (M−H)$^+$; Rt 1.81 min. $^1$H NMR NMR-400-c (400 MHz, DMSO-d$_6$): δ 11.32 (s, 1H), 7.46 (dd, J=8.3, 5.5 Hz, 1H), 6.87 (dd, J=10.3, 8.3 Hz, 1H), 2.12 (d, J=1.8 Hz, 3H).

Step 102.3: Synthesis of 7-fluoro-8-methyl-2H-benzo[d][1,3]oxazine-2,4(1H)-dione

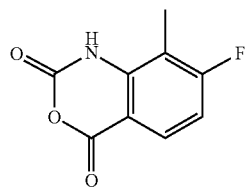

In a 500 mL four necked RB flask fitted with reflux condenser, thermometer pocket and nitrogen inlet, Hydrogen peroxide (13 mL) was added drop-wise to a stirred solution of 6-fluoro-7-methylindoline-2,3-dione (16 g, 0.089 mol) and sulfuric acid (0.5 mL) in acetic acid (150 mL) at 70° C. for 4 h. Progress of the reaction was monitored by TLC. After completion of the reaction, the reaction mixture was cooled to rt, diluted with water (100 mL) and extracted the reaction mixture with ethyl acetate (3×100 mL). The combined organic layers were dried over anhydrous Na$_2$SO$_4$ and filtered. The filtrate was concentrated under reduced pressure to provide 7-fluoro-8-methyl-2H-benzo[d][1,3]oxazine-2,4 (1)-dione (16.0 g) as a black brown solid. MS (ESI−) [Method 7A]: m/z 194 (M−H)$^+$; Rt 1.80 min.

Step 102.4: Synthesis of 2-amino-4-fluoro-3-methylbenzamide

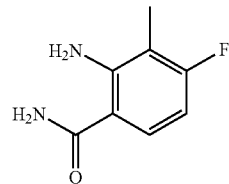

In a 250 mL single neck RB flask, ammonia (35 mL) was added to a stirred solution of 7-fluoro-8-methyl-2H-benzo[d][1,3]oxazine-2,4(1H)-dione (16 g, 0.082 mol) in water (70 mL). The reaction mixture was stirred at rt for 72 h, progress of reaction was monitored by TLC. After completion of reaction, the reaction mixture was diluted with water (100 mL) and extracted with ethyl acetate (3 5×100 mL). The combined organic layers were dried over anhydrous $Na_2SO_4$ and filtered. The filtrate was concentrated under reduced pressure to provide 2-amino-4-fluoro-3-methylbenzamide (7.5 g) as a brown solid. MS (ESI+) [Method 7A]: m/z 169 (M+H)$^+$; Rt 1.73 min. $^1$H NMR NMR-400-c (400 MHz, DMSO-d$_6$): δ 7.75 (s, 1H), 7.49 (dd, J=8.9, 6.5 Hz, 1H), 7.11 (s, 1H), 6.81 (s, 2H), 6.33 (t, J=9.0 Hz, 1H), 2.08-1.88 (m, 3H).

Step 102.5: Synthesis of
7-fluoro-8-methylquinazolin-4(3H)-one

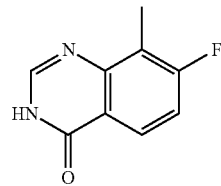

p-Toluenesulfonic acid monohydrate (0.85 g, 0.004 mol) was added portions to a stirred mixture of 2-amino-4-fluoro-3-methylbenzamide (7.5 g, 0.045 mol) in triethyl orthoformate (26 mL). The resulting reaction mixture was refluxed for 1 h. Progress of reaction was monitored by TLC. After completion of the reaction the solvent was evaporated on the rotovap and the crude material was purified by flash column chromatography using 0-40% EtOAc in n-hexane to provide 7-fluoro-8-methylquinazolin-4(3H)-one (5.6 g) as a white solid. MS (ESI+) [Method 7A]: m/z 179 (M+H); Rt 1.75 min. $^1$H NMR NMR-400-c (400 MHz, DMSO-d$_6$):12.36 (s, 1H), 9.17 (d, J=3.5 Hz, 1H), 8.10 (t, 1H), 7.34 (t, J=9.1 Hz, 1H), 2.50 (s, 3H).

Step 102.6: Synthesis of
4-chloro-7-fluoro-8-methylquinazoline

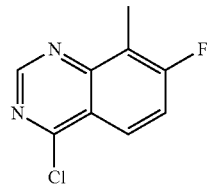

In a 100 mL three necked RB flask fitted with thermometer pocket, reflux condenser, DIPEA (21 mL, 0.123 mol) was added drop-wise to a stirred solution of 7-fluoro-8-methylquinazolin-4(3H)-one (5.5 g, 0.031 mol), POCl$_3$ (5.7 mL, 0.0061 mol) in toluene (55 mL) at 0° C. The resulting reaction mixture was stirred at 100° C. for 12 h. Progress of the reaction was monitored by TLC. The reaction mixture was cooled to rt and poured over a mixture of ice and water. Extracted the reaction mixture with EtOAc (3×70 mL). The combined organic layers were dried over anhydrous $Na_2SO_4$ and filtered. Evaporated the filtrate under reduced pressure and the crude product was purified by flash column chromatography using 0-15% EtOAc in n-hexane to provide 4-chloro-7-fluoro-8-methylquinazoline (2.7 g) as an off-white solid. MS (ESI+) [Method 7A]: m/z 196.6 (M)$^+$; Rt 2.18 min. $^1$H NMR NMR-400-c (400 MHz, DMSO-d$_6$): δ 8.22 (s, 1H), 8.02 (t, J=8.8, 6.3 Hz, 1H), 7.36 (t, J=9.1 Hz, 1H), 2.42 (s, J=2.4 Hz, 3H).

Step 102.7: Synthesis of
7-fluoro-8-methylquinazoline

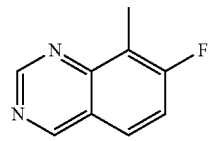

In a 30 mL sealed tube, Pd(dppf)Cl$_2$ (0.19 g, 0.00026 mol) and TMEDA (2.1 mL g, 0.0138 mol) were added to a stirred solution of 4-chloro-7-fluoro-8-methylquinazoline (1.6 g, 0.0081 mol) in THF (20 mL) and degassed and placed under argon. Sodium borohydride (0.52 g, 0.0138 mol) was then added and the resulting reaction mixture was stirred at rt for 4 h. Progress of reaction was monitored by TLC. After completion, the reaction mixture was diluted with water (70 mL), and extracted with EtOAc (3×50 mL). The combined organic layers were dried over anhydrous $Na_2SO_4$ and filtered. Evaporated filtrate under reduced pressure to get crude product which was purified by flash column chromatography by using 0-20% EtOAc in n-hexane to provide 7-fluoro-8-methylquinazoline (0.80 g) as an off-white solid. MS (ESI+) [Method 7A]: m/z 163.2 (M+H); Rt 1.85 min. $^1$H NMR NMR-400-c (400 MHz, DMSO-d$_6$): δ 9.59 (s, 1H), 9.34 (s, 1H), 8.12 (dd, J=9.0, 6.2 Hz, 1H), 7.68 (t, J=9.3 Hz, 1H), 2.58 (d, J=2.4 Hz, 3H).

Step 102.8: Synthesis of
8-(bromomethyl)-7-fluoroquinazoline

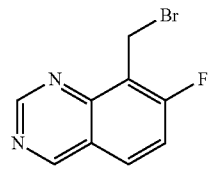 [SMILES: Fc1ccc2cncnc2c1CBr]

In a 25 mL three necked RB flask, fitted with reflux condenser, thermometer pocket and nitrogen inlet, N-Bromosuccinimide (0.82 g, 0.0046 mol) and benzoyl peroxide (0.074 g, 0.0003 mol) were added to a stirred solution of 7-fluoro-8-methylquinazoline (0.5 g, 0.0030 mol) in CCl$_4$ (6 mL). The resulting reaction mixture was stirred 76° C. for 4 h. Progress of reaction was monitored by TLC. Upon completion of the reaction, the reaction mixture was cooled to rt and diluted with CCl$_4$ (30 mL). Filtered the reaction mixture and the filtrate was evaporated on a rotovap to provide 8-(bromomethyl)-7-fluoroquinazoline (0.67 g) as a pale yellow solid. MS (ESI+) [Method 7B]: m/z 241 (M+2H)$^+$; Rt 1.57 min.

Step 102.9: Synthesis of (1r,3r)-3-(4-fluoro-3-(trifluoromethyl)phenoxy)-N-((7-fluoroquinazolin-8-yl)methyl)cyclobutan-1-amine

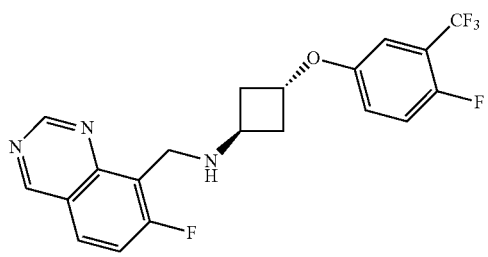 [SMILES: Fc1ccc(O[C@H]2C[C@H](NCc3c(F)ccc4cncnc34)C2)cc1C(F)(F)F]

To (1r,3r)-3-(4-fluoro-3-(trifluoromethyl)phenoxy)cyclobutan-1-amine, HCl salt (0.252 g, 0.883 mmol) was added dioxane (6 mL) and DMF (1 mL) and 5 eq of TEA. The mixture was stirred and then sonicated for 5 minutes and then concentrated to a clear solution (DMF remaining). Then added Dioxane (6 mL) and TEA (0.308 mL, 2.208 mmol). 8-(bromomethyl)-7-fluoroquinazoline (0.212 g, 0.883 mmol) was then added in dioxane (3.00 mL) and the light yellow cloudy reaction was stirred at room temperature for 2 h. Then added another 1 mL of DMF and 2.5 eq of TEA and continued stirring. After an additional 30 minutes, the reaction was diluted with EtOAc (50 mL) and water and extracted. This was done 3×'s. The combined organics were washed with water (50 mL), dried over sodium sulfate and concentrated to an oil that was purified by flash column chromatography (0-10% MeOH:DCM) to obtain an oil that was then purified via basic HPLC (50-70%-Acetonitrile (ACN/H$_2$O+5 mM NH$_4$OH) at 30 ml/min) Column: XBridge C18 OBD 19×150 mm) to obtain a semi-solid that was dissolved in dioxane and treated with 4 N HCl in dioxane (0.5 mL) at 0° C. and then stirred at room temperature for 2 hours. The white mixture reaction was concentrated, dissolved in 4:1 ACN:Water and placed on the lyophilizer to provide (1r,3r)-3-(4-fluoro-3-(trifluoromethyl)phenoxy)-N-((7-fluoroquinazolin-8-yl)methyl)cyclobutan-1-amine as an HCl salt (0.030 g, 7.24%). MS (ESI+) [Method 7C]: m/z 410.3 (M+H); Rt 1.52 min. $^1$H NMR (NMR-400-b) (400 MHz, DMSO-d$_6$): δ 9.73 (s, 1H), 9.67 (d, J=6.0 Hz, 1H), 9.48 (s, 1H), 8.44 (dd, J=9.1, 6.0 Hz, 1H), 7.86 (t, J=9.3 Hz, 1H), 7.47 (t, J=9.7 Hz, 1H), 7.19 (dt, J=9.1, 3.6 Hz, 1H), 7.12 (dd, J=5.8, 3.1 Hz, 1H), 5.06 (tt, J=7.2, 3.7 Hz, 1H), 4.67-4.55 (m, 2H), 4.01 (tt, J=8.2, 5.7 Hz, 1H), 2.87-2.74 (m, 2H), 2.48-2.42 (m, 2H).

Example 103: Synthesis of N-((1r,3r)-3-(4-fluoro-3-(trifluoromethyl)phenoxy)cyclobutyl)-2-(6-fluoro-8-(hydroxymethyl)isoquinolin-5-yl)acetamide Step 103.1: Synthesis of ethyl 2-(8-(((tert-butyldimethylsilyl)oxy)methyl)-6-fluoroisoquinolin-5-yl)-2-oxoacetate

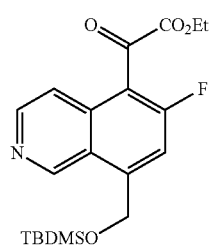 [SMILES: CCOC(=O)C(=O)c1c(F)cc(CO[Si](C)(C)C(C)(C)C)c2cnccc12]

To the stirred solution of 8-(((tert-butyldimethylsilyl)oxy)methyl)-6-fluoroisoquinoline (Step 6.7, 6.0 g, 20.58 mmol) in dry THF (90 mL), LDA (2M in THF) (20.5 mL, 41.17 mmol) was added dropwise at −78° C. and stirred for 2.5 h, under N$_2$. Then diethyl oxalate (8.3 mL, 61.76 mmol) dissolved in dry THF (30 mL) was added dropwise at −78° C. and stirred for further 1 h. The reaction mixture was quenched with saturated NH$_4$Cl solution and extracted with EtOAc twice. The combined organic portion was washed with brine, dried over anhydrous Na$_2$SO$_4$, filtered and concentrated in vacuo. The crude was purified by flash chromatography (24 g SiliCycle column, 0-15% EtOAc in Hexane elution) to provide ethyl 2-(8-(((tert-butyldimethylsilyl)oxy)methyl)-6-fluoroisoquinolin-5-yl)-2-oxoacetate (6.0 g). MS (ESI+) [Method 5A]: m/z 390.1 (M−H); Rt 1.73 min.

Step 103.2: Synthesis of ethyl 2-(8-(((tert-butyldimethylsilyl)oxy)methyl)-6-fluoroisoquinolin-5-yl)-2-hydroxyacetate

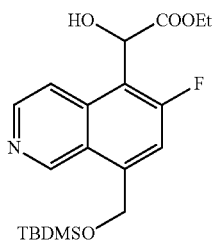 [SMILES: CCOC(=O)C(O)c1c(F)cc(CO[Si](C)(C)C(C)(C)C)c2cnccc12]

To the solution of ethyl 2-(8-(((tert-butyldimethylsilyl)oxy)methyl)-6-fluoroisoquinolin-5-yl)-2-oxoacetate (1.8 g, 4.59 mmol) in EtOH-AcOH—H$_2$O (45 mL, 40:1:4 v/v/v), NaCNBH$_3$ (0.35 g, 5.52 mmol) was added at rt and stirred for 16 h under argon. The reaction was quenched with saturated NaHCO$_3$ solution and extracted with EtOAc twice. The combined organic portion was washed with brine, dried over anhydrous Na$_2$SO$_4$, filtered and concentrated in vacuo. The crude product was purified by flash chromatography (24 g SiliCycle column, 0-20% EtOAc in Hexane elution) to provide ethyl 2-(8-(((tert-butyldimethylsilyl)oxy)methyl)-6-fluoroisoquinolin-5-yl)-2-hydroxyacetate (1.4 g). MS (ESI+) [Method 1A]: m/z 394.2 (M+H); Rt 1.72 min.

Step 103.3: Synthesis of ethyl 2-acetoxy-2-(8-(((tert-butyldimethylsilyl)oxy)methyl)-6-fluoroisoquinolin-5-yl)acetate

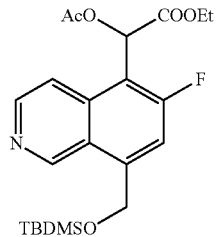

To the solution of ethyl 2-(8-(((tert-butyldimethylsilyl)oxy)methyl)-6-fluoroisoquinolin-5-yl)-2-hydroxyacetate (2.5 g, 6.35 mmol) in CH$_2$Cl$_2$ (20 mL), TEA (4.4 mL, 31.76 mmol) and DMAP (100 mg) were added at rt. Then Ac$_2$O (1.2 mL, 12.71 mmol) was added dropwise at 0° C. and the reaction mixture was stirred at rt for 2 h. The reaction mixture was diluted with water and extracted with CH$_2$Cl$_2$ twice. The combined organic portion was washed with brine, dried over anhydrous Na$_2$SO$_4$, filtered and concentrated in vacuo. The crude product was purified by flash chromatography (24 g SiliCycle column, 0-20% EtOAc in Hexane elution) to provide ethyl 2-acetoxy-2-(8-(((tert-butyldimethylsilyl)oxy)methyl)-6-fluoroisoquinolin-5-yl)acetate as (2.6 g). MS (ESI+) [Method 1A]: m/z 436.2 (M+H); Rt 2.02 min.

Step 103.4: Synthesis of ethyl 2-(8-(((tert-butyldimethylsilyl)oxy)methyl)-6-fluoroisoquinolin-5-yl)acetate

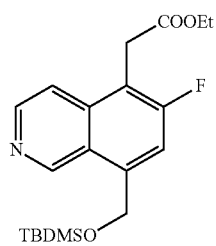 [SMILES: CCOC(=O)Cc1c(F)cc(CO[Si](C)(C)C(C)(C)C)c2cnccc12]

To the solution of ethyl 2-acetoxy-2-(8-(((tert-butyldimethylsilyl)oxy)methyl)-6-fluoroisoquinolin-5-yl)acetate (2.6 g, 5.97 mmol), HMPA (8.3 mL, 47.75 mmol) and MeOH (0.23 g, 7.16 mmol), SmI$_2$ (0.1M in THF) (179 mL, 17.91 mmol) was added dropwise and stirred at rt for 16 h, under argon. The reaction was quenched with saturated K$_2$CO$_3$ solution, and extracted with EtOAc twice. The combined organic portion was washed with brine, dried over anhydrous Na$_2$SO$_4$, filtered and concentrated in vacuo to provide crude ethyl 2-(8-(((tert-butyldimethylsilyl)oxy)methyl)-6-fluoroisoquinolin-5-yl)acetate (2.6 g). MS (ESI+) [Method 6A]: m/z 378.4 (M+H); Rt 1.68 min.

Step 103.5: Synthesis of methyl 2-(8-(((tert-butyldimethylsilyl)oxy)methyl)-6-fluoroisoquinolin-5-yl)acetate

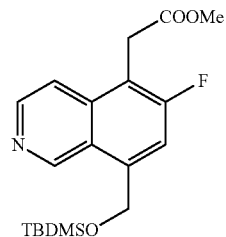

The crude ethyl 2-(8-(((tert-butyldimethylsilyl)oxy)methyl)-6-fluoroisoquinolin-5-yl)acetate (2.6 g, 5.97 mmol) was dissolved in MeOH (20 mL). Then K$_2$CO$_3$ (412 mg, 2.94 mmol) was added and stirred at rt for 1 h. The reaction mixture was diluted with water and extracted with EtOAc twice. The combined organic portion was washed with brine, dried over anhydrous Na$_2$SO$_4$, filtered and concentrated in vacuo. The residue was purified by flash chromatography (12 g SiliCycle column, 0-30% EtOAc in Hexane elution) to provide methyl 2-(8-(((tert-butyldimethylsilyl)oxy)methyl)-6-fluoroisoquinolin-5-yl)acetate (1.3 g). MS (ESI+) [Method 6A]: m/z 364.1 (M+H); Rt 1.62 min.

Step 103.6: Synthesis of 2-(8-(((tert-butyldimethylsilyl)oxy)methyl)-6-fluoroisoquinolin-5-yl)acetic acid

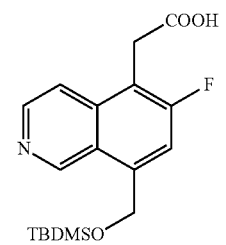

To the solution of methyl 2-(8-(((tert-butyldimethylsilyl)oxy)methyl)-6-fluoroisoquinolin-5-yl)acetate (1.3 g, 3.58 mmol) in THF-MeOH—H$_2$O (20 mL, 7:2:1 v/v/v), LiOH·H$_2$O (0.3 g, 7.15 mmol) was added and the reaction mixture was stirred at rt for 2 h. The reaction mixture was concentrated under reduced pressure, residue was acidified with citric acid solution and the solid formed was filtered and dried in vacuo to afford 2-(8-(((tert-butyldimethylsilyl)oxy)methyl)-6-fluoroisoquinolin-5-yl)acetic acid (1.17 g). MS (ESI+) [Method 5A]: m/z 350.2 (M+H); Rt 1.40 min.

Step 103.7: Synthesis of 2-(8-(((tert-butyldimethyl-silyl)oxy)methyl)-6-fluoroisoquinolin-5-yl)-N-((1r,3r)-3-(4-fluoro-3-(trifluoromethyl)phenoxy)cyclobutyl)acetamide

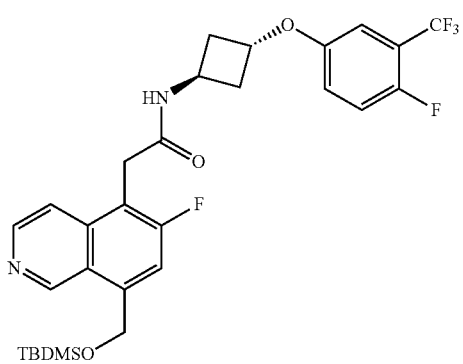 [SMILES: CC(C)(C)[Si](C)(C)OCc1cc(F)c(CC(=O)N[C@H]2C[C@H](Oc3ccc(F)c(C(F)(F)F)c3)C2)c2ccncc12]

To the stirred solution of 2-(8-(((tert-butyldimethylsilyl)oxy)methyl)-6-fluoroisoquinolin-5-yl)acetic acid (1.17 g, 3.35 mmol) in DMF (20 mL), (1r,3r)-3-(4-fluoro-3-(trifluoromethyl)phenoxy)cyclobutan-1-amine (1.14 g, 4.02 mmol) and HATU (1.9 g, 5.02 mmol) were added. Then DIPEA (2.9 mL, 16.74 mmol) was added drop wise at 0° C. and the reaction mixture was stirred a rt for 3 h. The reaction mixture was diluted with water and extracted with EtOAc 3×'s. The combined organic portion was washed with brine, dried over anhydrous Na$_2$SO$_4$, filtered and concentrated in vacuo to provide crude 2-(8-(((tert-butyldimethylsilyl)oxy)methyl)-6-fluoroisoquinolin-5-yl)-N-((1r,3r)-3-(4-fluoro-3-(trifluoromethyl)phenoxy)cyclobutyl)acetamide (2.0 g). MS (ESI+) [Method 6A]: m/z 581.3 (M+H); Rt 1.71 min.

Step 103.8: Synthesis of N-((1r,3r)-3-(4-fluoro-3-(trifluoromethyl)phenoxy)cyclobutyl)-2-(6-fluoro-8-(hydroxymethyl)isoquinolin-5-yl)acetamide

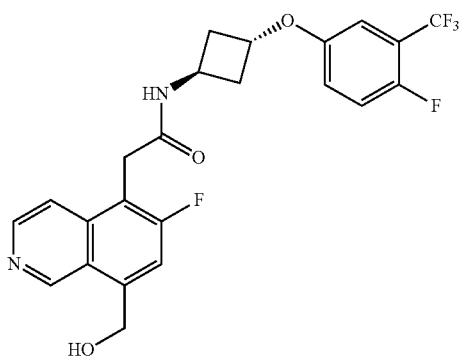 [SMILES: O=C(Cc1c(F)cc(CO)c2cnccc12)N[C@H]1C[C@H](Oc2ccc(F)c(C(F)(F)F)c2)C1]

Deprotection was carried out according to Step 8.5. The residue was purified by prep-HPLC (Column: EPIC C18 (150 mm×21.2 mm), 5.0μ; Mobile Phase: 0.02% NH$_4$OH in in water and acetonitrile) to afford N-((1r,3r)-3-(4-fluoro-3-(trifluoromethyl)phenoxy)cyclobutyl)-2-(6-fluoro-8-(hydroxymethyl)isoquinolin-5-yl)acetamide as white solid (1.0 g, 52%). MS (ESI+) [Method 1A]: m/z 467.2 (M+H); Rt 0.68 min. $^1$H NMR (400 MHz, CD$_3$OD) δ 9.45 (s, 1H), 8.50 (d, J=6.0 Hz, 1H), 7.94 (d, J=6.0 Hz, 1H), 7.56 (d, J=10.4 Hz, 1H), 7.22 (t, J=9.6 Hz, 1H), 7.07-7.03 (m, 2H), 5.18 (s, 2H), 4.89-4.86 (m, 1H), 4.46-4.41 (m, 1H), 4.03 (s, 2H), 2.50 (dd, J=7.2, 6.4 Hz, 4H).

The following compounds were made in an analogous manner to the examples described herein.

Example 104: 2-amino-1-(6-fluoro-5-((((1r,3r)-3-(4-fluoro-3-(trifluoromethyl)phenoxy)cyclobutyl)amino)methyl)isoquinolin-8-yl)ethan-1-ol

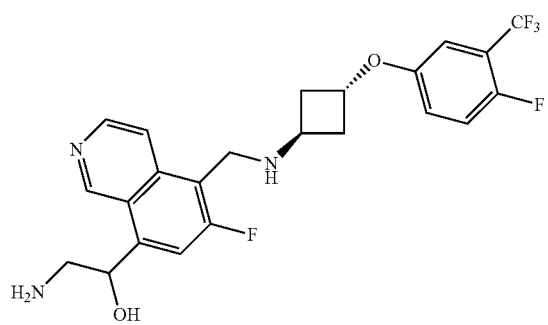 [SMILES: NCC(O)c1cc(F)c(CN[C@H]2C[C@H](Oc3ccc(F)c(C(F)(F)F)c3)C2)c2ccncc12]

Example 105: (1r,3r)-3-((2,4-difluorobenzyl)oxy)-N-((6-fluoroisoquinolin-5-yl)methyl)cyclobutan-1-amine

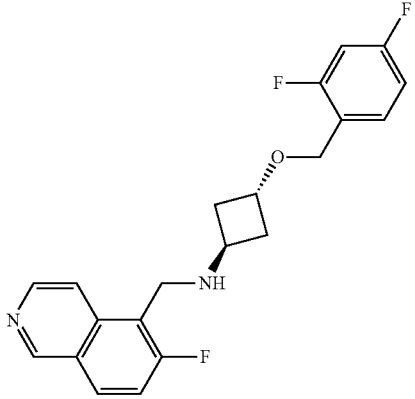 [SMILES: Fc1ccc(CO[C@H]2C[C@H](NCc3c(F)ccc4cnccc34)C2)c(F)c1]

Example 106: (1r,3r)-N-((6-fluoroisoquinolin-5-yl)methyl)-3-((2-methyl-6-(trifluoromethyl)pyridin-4-yl)oxy)cyclobutan-1-amine

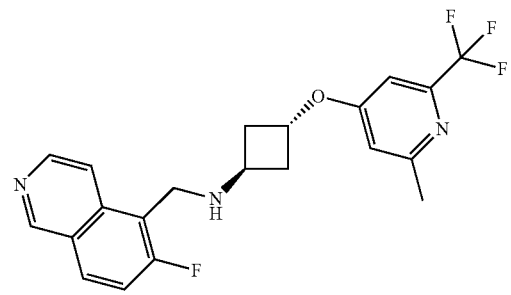 [SMILES: Cc1cc(O[C@H]2C[C@H](NCc3c(F)ccc4cnccc34)C2)cc(C(F)(F)F)n1]

Example 107: (1r,3r)-N-((6-fluoroisoquinolin-5-yl)methyl)-3-((4-(trifluoromethyl)thiazol-2-yl)oxy)cyclobutan-1-amine

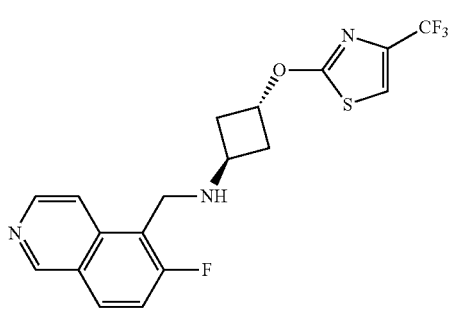 [SMILES: Fc1ccc2cnccc2c1CN[C@H]1C[C@H](Oc2nc(C(F)(F)F)cs2)C1]

Example 108: 5-(((1r,3r)-3-(((6-fluoroisoquinolin-5-yl)methyl)amino)cyclobutoxy)pyrimidine-2-carbonitrile

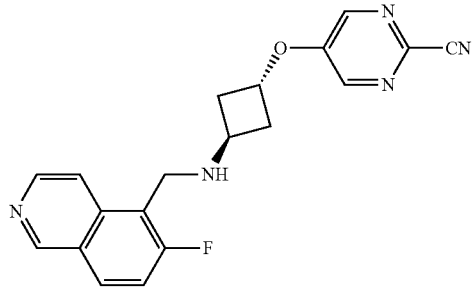 [SMILES: N#Cc1ncc(O[C@H]2C[C@H](NCc3c(F)ccc4cnccc34)C2)cn1]

Example 109: 5-((((1r,3r)-3-(4-fluoro-3-(trifluoromethyl)phenoxy)cyclobutyl)amino)methyl)isoquinolin-1-amine

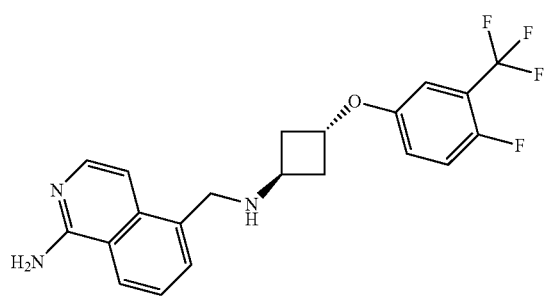 [SMILES: Nc1nccc2c(CN[C@H]3C[C@H](Oc4ccc(F)c(C(F)(F)F)c4)C3)cccc12]

Example 110: (1r,3r)-3-((6-(difluoromethyl)pyridin-3-yl)oxy)-N-((6-fluoroisoquinolin-5-yl)methyl)cyclobutan-1-amine

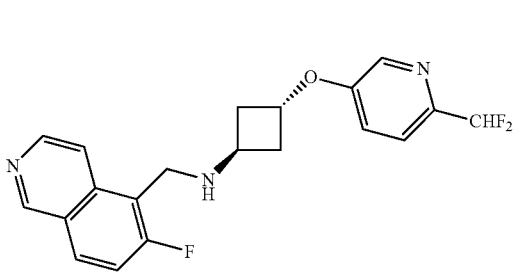 [SMILES: Fc1ccc2cnccc2c1CN[C@H]1C[C@H](Oc2ccc(C(F)F)nc2)C1]

Example 111: (1r,3r)-3-((2-(difluoromethyl)pyridin-4-yl)oxy)-N-((6-fluoroisoquinolin-5-yl)methyl)cyclobutan-1-amine

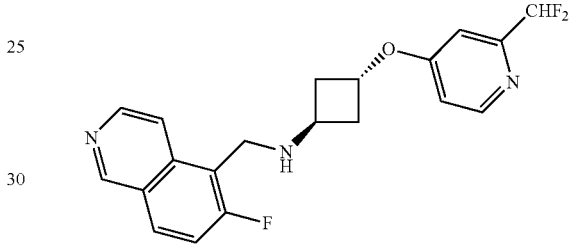

Example 112: (1r,3r)-N-(isoquinolin-5-ylmethyl)-3-((6-(trifluoromethyl)pyridin-3-yl)oxy)cyclobutan-1-amine

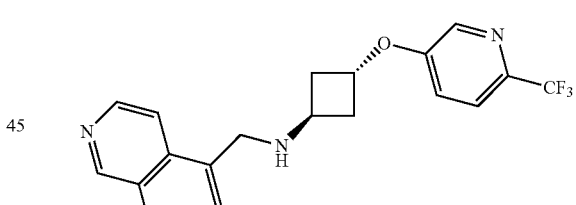

Biological Data
Determination of TRPV1 Inhibition

Chinese Hamster Ovary (CHO) cells transfected to express human TrpV1 receptor (which are herein referred to as CHO-huTrpV1 cells), were grown in F-12 Ham's Nutrient Mixture media (HyClone SH30026.01) supplemented with 10% Fetal Bovine Serum (Invitrogen #26140-079), 1% Antibiotic/antimycotic (Invitrogen #15240-062) and 500 ug/mL geneticin (ThermoFisher scientific #1031035). Cells were grown in T-75 flasks at 37° C. incubator with 5% $CO_2$. The cells were passaged twice a week at a ratio of 1:10 to 1:20 to maintain steady growth. For experimentation, cells were harvested at approximately 80% confluency and plated onto 384 well black cell culture plates (cat #781091, Greinier Bio-One Inc.) at 15,000 cells per well in 20 μl media and grown overnight.

FLIPR Calcium Assay to Detect Calcium Influx in CHO-Hu TrpV1 Cells

The loading dye was prepared following instruction of Calcium 6 assay kit (Molecular Probes, #R8190): 10 ml buffer from bottle B was added to 1 vial of bottle A (adapted to room temperature from −20° C.) and mixed well, then 2.5 mM of fresh prepared probenecid, was added and mixed well. 20 µl/well of loading dye was added on top of the cells, and incubated at 37° C. for 1 hour 30 min.

Assay buffer preparation: 1×HBSS, 2 mM HEPES, 0.1% BSA plus 2.5 mM freshly prepared probenecid (Invitrogen, #P36400). 25 µl/well assay buffer in 384 well clear plate (cat #782281, Greiner Bio-one) was dispensed with buffer distributor (Multidrop ComB1 from Thermo Scientific). The compounds were in 384 Echo plate (cat #LPL0200, Labcyte) and the starting concentration of compound was 10 mM, then 1 to 3 serial dilution in 100% DMSO, 8 ul/well). 125 nl compounds was transferred to the 384 well plate containing 25 µl/well buffer with Echo® 555 Liquid Handler (Labcyte), such that the compound concentration was 5 fold of final concentration. The plate was shook slowly at 40 rpm/min for 10 min to mix. 10 µl of 5 fold compound in the buffer was transferred to the cell plate (containing 20 µl cells and 20 µl dye) using Vertical Pipetting Station 384ST (Agilent Technologies). Six fold of final concentration of NADA (N-arachidonyl dopamine, cat #A8848, Sigma) in the assay buffer was prepared and 30 µl/well was distributed in 384 well clear plate.

After compounds were added to the cell plate with loading dye, within 10-15 minutes, cell plate and plate containing NADA was placed into the FLIPR (Fluorescent Imaging Plate Reader) instrument (Tetra System, Molecular device). The TRPV1 receptor was stimulated by application of 10 µl per well of NADA. For testing the effect of compounds for possible antagonism, 2.5 µM NADA was used at the EC80 concentration.

For determination of antagonist $IC_{50}$ values (concentration of antagonist that inhibits response to NADA by 50%), at least 10 antagonist concentration were measured in triplicate. The response in the presence of the antagonist was calculated as a percentage of the control response to NADA and was plotted against the concentration of the antagonist. The $IC_{50}$ was estimated by non-linear regression analysis to sigmoidal-logistic curves by HELIOS (PROD 2) system. These values were averaged (means and standard error of the mean) for at least three independent experiments. The $IC_{50}$ values are shown in Table 1 below.

TABLE 1

Antagonist effect of compounds of the discloure against human TRPV1

| Example No. | $IC_{50}$ (µM) |
|---|---|
| 1 | 0.0208 |
| 2 | 0.711 |
| 3 | 0.00344 |
| 4 | 0.0268 |
| 5 | 0.259 |
| 6 | 0.00725 |
| 7 peak 1 | 0.00062 |
| 7 peak 2 | 0.0063 |
| 7 racemic | 0.0104 |
| 8 | 0.165 |
| 9 peak 1 | 0.00009 |
| 9 peak 2 | 0.0137 |
| 9 racemic | 0.00058 |
| 10 | 0.166 |
| 11 | 0.395 |

TABLE 1-continued

Antagonist effect of compounds of the discloure against human TRPV1

| Example No. | $IC_{50}$ (µM) |
|---|---|
| 12 | 0.0578 |
| 13 | 0.0637 |
| 14 | 0.00404 |
| 15 | 0.0510 |
| 16 | 0.0310 |
| 17 | 0.130 |
| 18 | 0.00163 |
| 19 | 0.0162 |
| 20 | 0.0872 |
| 21 peak 1 | 0.00442 |
| 21 peak 2 | 0.0113 |
| 22 | 0.436 |
| 23 | 0.232 |
| 24 | 0.906 |
| 25 | 0.100 |
| 26 | 0.108 |
| 27 | 0.0230 |
| 28 | 0.280 |
| 29 | 0.0623 |
| 30 | 0.186 |
| 31 | 0.264 |
| 32 | 0.102 |
| 33 | 0.0154 |
| 34 | 0.0836 |
| 35 | 0.128 |
| 36 | 0.0989 |
| 37 | 0.0813 |
| 38 | 0.0514 |
| 39 | 0.0108 |
| 40 | 0.124 |
| 41 | 0.0900 |
| 42 | 0.173 |
| 43 | 0.528 |
| 44 | 0.0326 |
| 45 | 0.0188 |
| 46 | 0.0402 |
| 47 | 0.0238 |
| 48 | 0.0345 |
| 49 | 0.0163 |
| 50 | 0.0806 |
| 51 | 0.117 |
| 52 | 0.0271 |
| 53 | 0.0769 |
| 54 | 0.0595 |
| 55 | 0.352 |
| 56 | 0.119 |
| 57 | 0.656 |
| 58 | 0.0829 |
| 59 | 0.0758 |
| 60 | 0.320 |
| 61 | 0.194 |
| 62 | 0.336 |
| 63 | 0.0986 |
| 64 | 0.163 |
| 65 | 0.00098 |
| 66 | 1.11 |
| 67 | 0.00377 |
| 68 cis | 0.333 |
| 68 trans | 0.0129 |
| 69 | 0.00015 |
| 70 | 0.402 |
| 71 | 0.0316 |
| 72 | 0.0521 |
| 73 | 0.193 |
| 74 | 0.995 |
| 75 | 0.269 |
| 76 | 0.0277 |
| 77 | 0.691 |
| 78 | 0.770 |
| 79 | 0.147 |
| 80 | 0.980 |
| 81 | 0.255 |
| 82 | 0.169 |
| 83 | 0.207 |
| 84 | 0.722 |

TABLE 1-continued

Antagonist effect of compounds of the discloure against human TRPV1

| Example No. | IC$_{50}$ (μM) |
|---|---|
| 85 | 0.155 |
| 86 | 0.0693 |
| 87 | 0.321 |
| 88 | 0.0952 |
| 89 | 0.440 |
| 90 | 0.874 |
| 91 | 0.0399 |
| 92 | 0.580 |
| 93 | 0.0826 |
| 94 | 0.193 |
| 95 | 0.323 |
| 96 | 0.747 |
| 97 | 0.280 |
| 98 | 0.418 |
| 99 | 0.362 |
| 100 | 0.0740 |
| 101 | 0.0147 |
| 102 | 0.0603 |
| 103 | 0.00044 |
| 104 | 2.15 |
| 105 | 1.28 |
| 106 | 1.65 |
| 107 | 1.91 |
| 108 | 2.51 |
| 109 | 1.46 |
| 110 | 1.38 |
| 111 | 1.65 |
| 112 | 2.69 |

The compounds of the disclosure inhibit NADA-mediated cellular TRPV1 activity with IC$_{50}$ down to sub-nanomolar level. As such, the compounds of the disclosure may be useful in treating the diseases and/or disorders described herein, e.g., a disease/disorder mediated by TRPV1.

All publications and patent documents cited herein are incorporated herein by reference as if each such publication or document was specifically and individually indicated to be incorporated herein by reference. The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the invention that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

The invention claimed is:
1. A compound of Formula (I) or a pharmaceutically acceptable salt thereof,

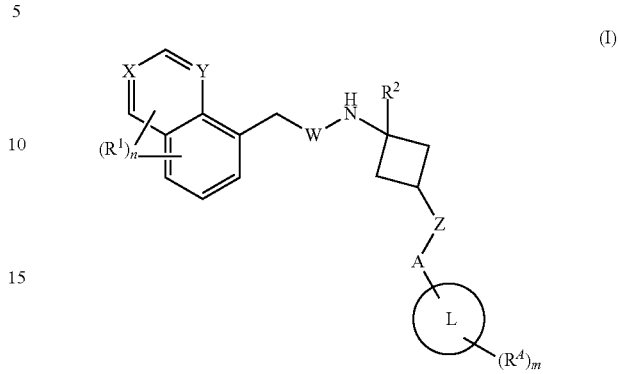

wherein:
W is C(=O) or absent;
X is N or N oxide;
Y is N or CH;
Z is NH, O or S;
A is CH$_2$ or absent;
L is selected from 5- to 10-membered heteroaryl having 1-3 heteroatoms independently selected from N, O, and S, C$_6$-C$_{10}$aryl, and 6- to 10-membered partially saturated heterocyclyl having 1-3 heteroatoms independently selected from N, O, and S;
R$^A$ is at each occurrence independently selected from halo, —CN, C$_1$-C$_6$haloalkyl, C$_1$-C$_6$alkyl, SF$_5$, C$_3$-C$_6$cycloalkyl, C$_1$-C$_6$alkoxyl, C$_1$-C$_6$haloalkoxyl, 4- to 6-membered heterocyclyl having 1-2 heteroatoms independently selected from N, O, and S, —(CH$_2$)$_p$—NR$^3$R$^4$ and —C(=O)—O—(C$_1$-C$_6$alkyl),
wherein the C$_3$-C$_6$cycloalkyl and 4- to 6-membered heterocyclyl are each independently substituted with 0-4 R$^{A1}$;
R$^{A1}$ is at each occurrence independently selected from halo and C$_1$-C$_6$haloalkyl;
R$^1$ is at each occurrence independently selected from hydroxyl, C$_1$-C$_6$alkyl, C$_1$-C$_6$alkoxyl, halo, C$_1$-C$_6$haloalkyl and NR$^3$R$^4$,
wherein the C$_1$-C$_6$alkyl and C$_1$-C$_6$haloalkyl are each independently substituted with 0-4 R$^{1a}$;
R$^{1a}$ is at each occurrence independently selected from hydroxyl, NR$^3$R$^4$ and —C(=O)—OH;
R$^2$ is selected from hydrogen and C$_1$-C$_6$alkyl;
R$^3$ is at each occurrence independently selected from hydrogen and C$_1$-C$_6$alkyl;
R$^4$ is at each occurrence independently selected from —SO$_2$R$^5$, hydrogen, —C(=O)—(C$_1$-C$_6$alkyl) and C$_1$-C$_6$alkyl;
R$^5$ is at each occurrence independently selected from NH$_2$ and C$_1$-C$_6$alkyl;
n is 0, 1, 2, 3 or 4;
m is 0, 1, 2, 3, 4 or 5;
p is 0, 1 or 2.
2. The compound of claim 1 or a pharmaceutically acceptable salt thereof, wherein
W is C(=O) or absent;
X is N or N oxide;
Y is CH;
Z is NH, O or S;
A is CH$_2$ or absent;

L is selected from 5- to 10-membered heteroaryl having 1-3 heteroatoms independently selected from N, O, and S, $C_6$-$C_{10}$aryl and 6- to 10-membered partially saturated heterocyclyl having 1-3 heteroatoms independently selected from N, O, and S;

$R^A$ is at each occurrence independently selected from halo, —CN, $C_1$-$C_6$haloalkyl, $C_1$-$C_6$alkyl, $SF_5$, $C_3$-$C_6$cycloalkyl, $C_1$-$C_6$alkoxyl, $C_1$-$C_6$haloalkoxyl, 4- to 6-membered heterocyclyl having 1-2 heteroatoms independently selected from N, O, and S and —$(CH_2)_p$—$NR^3R^4$, wherein the $C_3$-$C_6$cycloalkyl and 4- to 6-membered heterocyclyl are each independently substituted with 0-4 $R^{A1}$;

$R^{A1}$ is at each occurrence independently selected from halo and $C_1$-$C_6$haloalkyl;

$R^1$ is at each occurrence independently selected from $C_1$-$C_6$alkyl, halo, $C_1$-$C_6$haloalkyl and $NR^3R^4$, wherein the $C_1$-$C_6$alkyl and $C_1$-$C_6$haloalkyl are each independently substituted with 0-4 $R^{1a}$;

$R^{1a}$ is at each occurrence independently selected from hydroxyl, $NR^3R^4$ and —C(=O)—OH;

$R^2$ is selected from hydrogen and $C_1$-$C_6$alkyl;

$R^3$ is at each occurrence independently selected from hydrogen and $C_1$-$C_6$alkyl;

$R^4$ is at each occurrence independently selected from —$SO_2R^5$, hydrogen, —C(=O)—($C_1$-$C_6$alkyl) and $C_1$-$C_6$alkyl;

$R^5$ is at each occurrence independently selected from $NH_2$ and $C_1$-$C_6$alkyl;

n is 0, 1, 2, 3, 4;

m is 0, 1, 2, 3, 4 or 5;

p is 0, 1 or 2.

3. The compound of claim 1 or a pharmaceutically acceptable salt thereof,
wherein
W is C(=O) or absent;
X is N or N oxide;
Y is CH;
Z is NH, O or S;
A is $CH_2$ or absent;
L is selected from 5- to 10-membered heteroaryl having 1-3 heteroatoms independently selected from N, O, and S, $C_6$-$C_{10}$aryl and 6- to 10-membered partially saturated heterocyclyl having 1-3 heteroatoms independently selected from N, O, and S;

$R^A$ is at each occurrence independently selected from halo, —CN, $C_1$-$C_6$haloalkyl, $C_1$-$C_6$alkyl, $C_3$-$C_6$cycloalkyl, $C_1$-$C_6$alkoxyl, $C_1$-$C_6$haloalkoxyl, 4- to 6-membered heterocyclyl having 1-2 heteroatoms independently selected from N, O, and S and —$(CH_2)_p$—$NR^3R^4$, wherein the $C_3$-$C_6$cycloalkyl and 4- to 6-membered heterocyclyl are each independently substituted with 0-4 $R^{A1}$;

$R^{A1}$ is at each occurrence independently selected from halo and $C_1$-$C_6$haloalkyl;

$R^1$ is at each occurrence independently selected from $C_1$-$C_6$alkyl, halo, $C_1$-$C_6$haloalkyl and $NH_2$, wherein the $C_1$-$C_6$alkyl and $C_1$-$C_6$haloalkyl are each independently substituted with 0-4 $R^{1a}$;

$R^{1a}$ is at each occurrence independently selected from hydroxyl, $NR^3R^4$ and —C(=O)—OH;

$R^2$ is selected from hydrogen and $C_1$-$C_3$alkyl;

$R^3$ is at each occurrence independently selected from hydrogen and $C_1$-$C_6$alkyl;

$R^4$ is at each occurrence independently selected from —$SO_2R^5$, hydrogen, —C(=O)—($C_1$-$C_6$alkyl) and $C_1$-$C_6$alkyl;

$R^5$ is at each occurrence independently selected from $NH_2$ and $C_1$-$C_6$alkyl;

n is 0, 1, 2 or 3;

m is 0, 1, 2, 3 or 4;

p is 0, 1 or 2.

4. The compound of claim 1 or a pharmaceutically acceptable salt thereof,
wherein
W is absent;
X is N;
Y is CH;
Z is NH, O or S;
A is absent;
L is selected from 5- to 10-membered heteroaryl having 1-3 heteroatoms independently selected from N, O, and S, $C_6$-$C_{10}$aryl, and 6- to 10-membered partially saturated heterocyclyl having 1-3 heteroatoms independently selected from N, O, and S;

$R^A$ is at each occurrence independently selected from halo, —CN, $C_1$-$C_6$haloalkyl, $C_1$-$C_6$alkyl, $C_3$-$C_6$cycloalkyl, $C_1$-$C_6$haloalkoxyl, 4- to 6-membered heterocyclyl having 1-2 heteroatoms independently selected from N, O, and S and —$(CH_2)_p$—$NR^3R^4$, wherein the $C_3$-$C_6$cycloalkyl and 4- to 6-membered heterocyclyl are each independently substituted with 0-4 $R^{A1}$;

$R^{A1}$ is at each occurrence independently selected from halo and $C_1$-$C_6$haloalkyl;

$R^1$ is at each occurrence independently selected from $C_1$-$C_6$alkyl, halo, $C_1$-$C_6$haloalkyl, wherein the $C_1$-$C_6$alkyl and $C_1$-$C_6$haloalkyl are each independently substituted with 0-4 $R^{1a}$;

$R^{1a}$ is at each occurrence independently selected from hydroxyl, $NR^3R^4$ and —C(=O)—OH;

$R^2$ is selected from hydrogen and $C_1$-$C_3$alkyl;

$R^3$ is at each occurrence independently selected from hydrogen and $C_1$-$C_6$alkyl;

$R^4$ is at each occurrence independently selected from —$SO_2R^5$, hydrogen, —C(=O)—($C_1$-$C_6$alkyl) and $C_1$-$C_6$alkyl;

$R^5$ is at each occurrence independently selected from $NH_2$ and $C_1$-$C_6$alkyl;

n is 0, 1, 2 or 3;

m is 0, 1, 2, 3 or 4;

p is 0, 1 or 2.

5. The compound of claim 1 or a pharmaceutically acceptable salt thereof,
wherein $R^A$ is selected from fluoro, chloro, —CN, $C_1$-$C_6$fluoroalkyl (e.g., $C_1$-$C_3$fluoroalkyl), $C_1$-$C_6$alkyl, $C_3$-$C_6$cycloalkyl, $C_1$-$C_6$fluoroalkoxyl and 4-membered heterocyclyl having 1 oxygen atom,
wherein the $C_3$-$C_6$cycloalkyl and the 4-membered oxygen containing heterocyclyl are each independently substituted with 0-3 $R^{A1}$, and wherein $R^{A1}$ is at each occurrence independently selected from halo and $C_1$-$C_6$haloalkyl.

6. The compound of claim 1 or a pharmaceutically acceptable salt thereof,
wherein L is selected from $C_6$-$C_{10}$aryl, 6- to 10-membered partially saturated heterocyclyl having 1-3 heteroatoms independently selected from N, O, and S, 5- to 10-membered heteroaryl having 1-3 heteroatoms independently selected from N, O, and S selected from

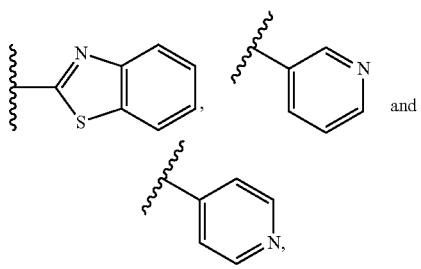

and wherein the $C_6$-$C_{10}$aryl, 6- to 10-membered partially saturated heterocyclyl and 5- to 10-membered heteroaryl are each independently substituted with 0-4 $R^A$, and wherein $R^A$ is defined according to claim 1.

7. The compound of claim 1, or a pharmaceutically acceptable salt thereof,
wherein L is selected from 6- to 10-membered partially saturated heterocyclyl having 1-3 heteroatoms independently selected from N, O, and S, 5- to 10-membered heteroaryl having 1-3 heteroatoms independently selected from N, O, and S, and $C_6$-$C_{10}$aryl selected from phenyl and naphthyl,
wherein the 6- to 10-membered partially saturated heterocyclyl, 5- to 10-membered heteroaryl, phenyl and naphthyl are each independently substituted with 0-4 $R^A$, and wherein $R^A$ is defined according to claim 1.

8. The compound of claim 1, or a pharmaceutically acceptable salt thereof, wherein L is selected from 5- to 10-membered heteroaryl having 1-3 heteroatoms independently selected from N, O, and S, $C_6$-$C_{10}$aryl and 6- to 10-membered partially saturated heterocyclyl selected from

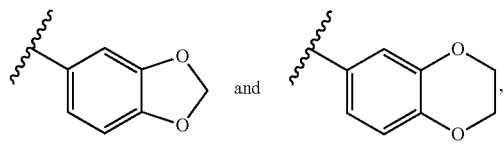 [SMILES: *c1ccc2c(c1)OCO2 ; *c1ccc2c(c1)OCCO2]

and wherein the 5- to 10-membered heteroaryl, $C_6$-$C_{10}$aryl and 6- to 10-membered partially saturated heterocyclyl are each independently substituted with 0-4 $R^A$, and wherein $R^A$ is defined according to claim 1.

9. The compound of claim 1 or a pharmaceutically acceptable salt thereof,
wherein $R^1$ is at each occurrence independently selected from $C_1$-$C_6$alkyl, halo, $C_1$-$C_6$haloalkyl and $NH_2$,
wherein the $C_1$-$C_6$alkyl and $C_1$-$C_6$haloalkyl are each independently substituted with 0-4 $R^{1a}$,
wherein $R^{1a}$ is at each occurrence independently selected from hydroxyl and $NR^3R^4$.

10. The compound of claim 1 or a pharmaceutically acceptable salt thereof,
wherein
W is absent;
X is N;
Y is CH;
Z is O;
A is absent;
L is $C_6$-$C_{10}$aryl;
$R^A$ is at each occurrence independently selected from halo, —CN, $C_1$-$C_6$haloalkyl, $C_1$-$C_6$alkyl;
$R^1$ is at each occurrence independently selected from $C_1$-$C_6$alkyl, halo and $C_1$-$C_6$haloalkyl,
wherein the $C_1$-$C_6$alkyl and $C_1$-$C_6$haloalkyl are each independently substituted with 0-4 $R^{1a}$;
$R^{1a}$ is at each occurrence independently selected from hydroxyl and $NR^3R^4$;
$R^2$ is selected from hydrogen and $C_1$-$C_3$alkyl;
$R^3$ is at each occurrence independently selected from hydrogen and $C_1$-$C_6$alkyl;
$R^4$ is at each occurrence independently selected from —$SO_2R^5$, hydrogen and $C_1$-$C_6$alkyl;
$R^5$ is at each occurrence independently selected from $NH_2$ and $C_1$-$C_6$alkyl;
n is 1, 2 or 3;
m is 0, 1, 2 or 3.

11. The compound of claim 1 or a pharmaceutically acceptable salt thereof, wherein $R^1$ is at each occurrence independently selected from

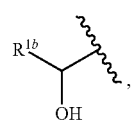

fluoro and $NH_2$,
wherein $R^{1b}$ is hydrogen or $C_1$-$C_5$alkyl,
wherein the $C_1$-$C_5$alkyl is substituted with 0-3 hydroxyl.

12. The compound of claim 1 or a pharmaceutically acceptable salt thereof, of Formula (Ia), Formula (Ib), Formula (Ic), Formula (Id), Formula (Ie), or Formula (If):

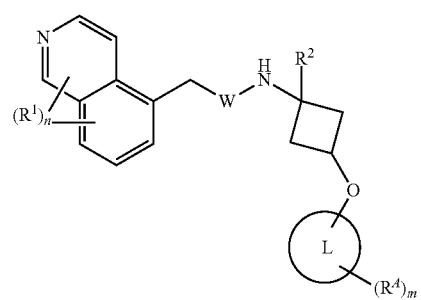

(Ia)

wherein W, L, $R^1$, $R^2$, $R^A$, n and m are defined according to claim 1;

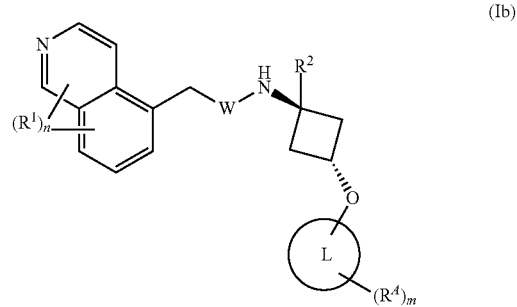

(Ib)

wherein W, L, $R^1$, $R^2$, $R^A$, n and m are defined according to claim 1;

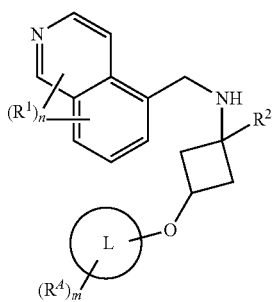

(Ic)

wherein L, $R^1$, $R^2$, $R^A$, n and m are defined according to claim 1;

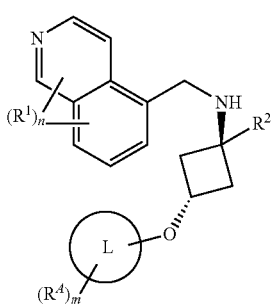

(Id)

wherein L, $R^1$, $R^2$, $R^A$, n and m are defined according to claim 1;

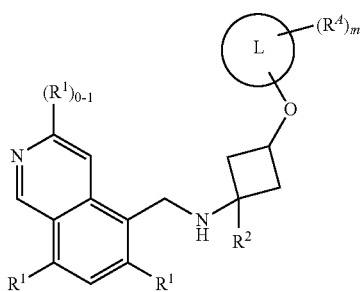

(Ie)

wherein L, $R^1$, $R^2$, $R^A$ and m are defined according to claim 1;

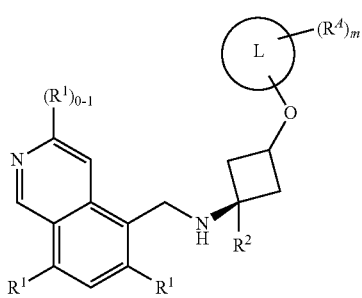

(If)

wherein L, $R^1$, $R^2$, $R^A$ and m are defined according to claim 1.

13. A compound or a pharmaceutically acceptable salt thereof, selected from:

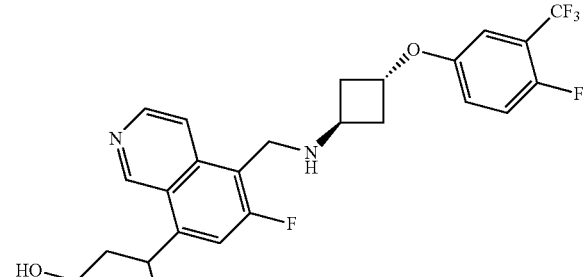

1-(6-fluoro-5-((((1r,3r)-3-(4-fluoro-3-(trifluoromethyl)phenoxy)cyclobutyl)amino)methyl)isoquinolin-8-yl)propane-1,3-diol

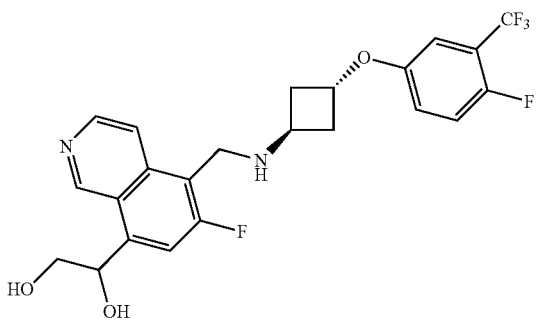

(S)-1-(6-fluoro-5-((((1r,3S)-3-(4-fluoro-3-(trifluoromethyl)phenoxy)cyclobutyl)amino)methyl)isoquinolin-8-yl)ethane-1,2-diol

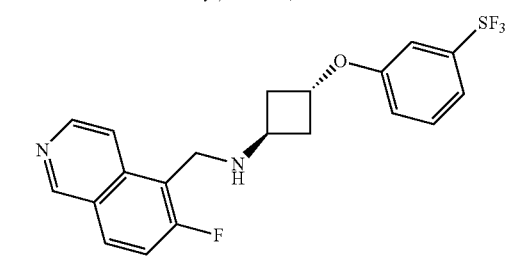

(1r,3r)-N-((6-fluoroisoquinolin-5-yl)methyl)-3-(3-(pentafluoro-$\lambda^6$-sulfaneyl)phenoxy)cyclobutan-1-amine

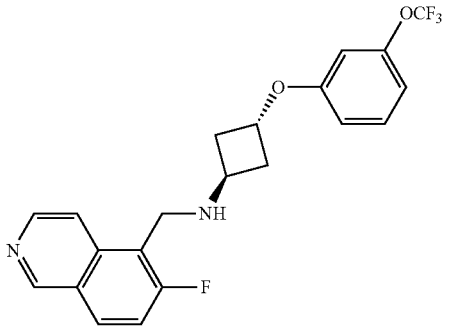

(1r,3r)-N-((6-fluoroisoquinolin-5-yl)methyl)-3-(3-(trifluoromethoxy)phenoxy)cyclobutan-1-amine 317
-continued

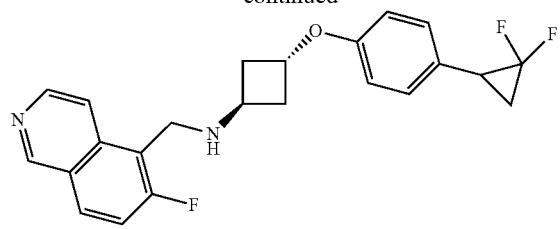

(1r,3r)-3-(4-(2,2-difluorocyclopropyl)phenoxy)-N-((6-fluoroisoquinolin-5-yl)methyl)cyclobutan-1-amine

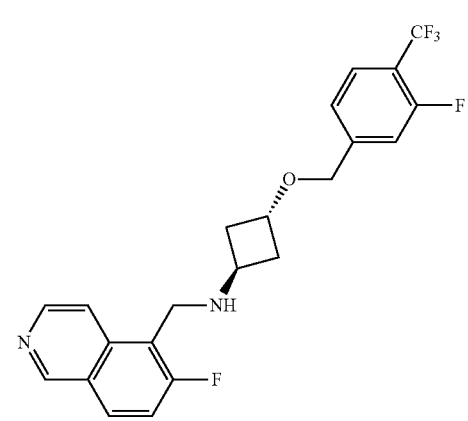

(1r,3r)-3-((3-fluoro-4-(trifluoromethyl)benzyl)oxy)-N-((6-fluoroisoquinolin-5-yl)methyl)cyclobutan-1-amine

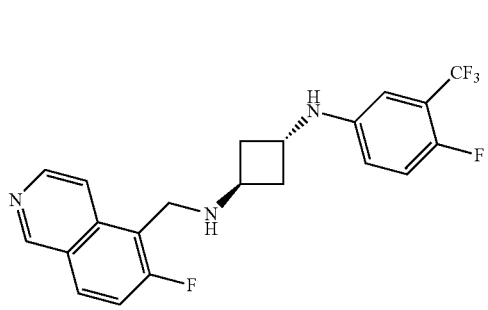

(1r,3r)-N1-(4-fluoro-3-(trifluoromethyl)phenyl)-N3-((6-fluoroisoquinolin-5-yl)methyl)cyclobutane-1,3-diamine

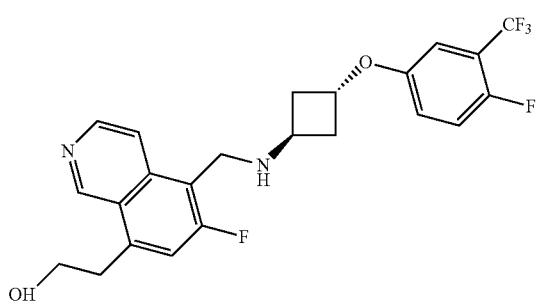

2-(6-fluoro-5-((((1r,3r)-3-(4-fluoro-3-(trifluoromethyl)phenoxy)cyclobutyl)amino)methyl)isoquinolin-8-yl)ethan-1-ol 318
-continued

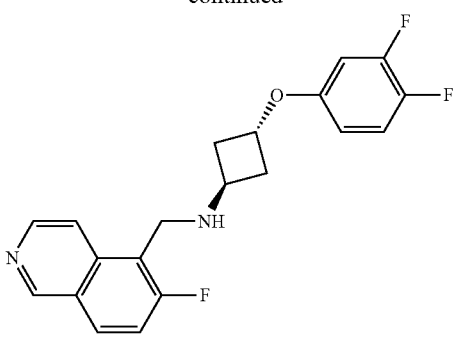

(1r,3r)-3-(3,4-difluorophenoxy)-N-((6-fluoroisoquinolin-5-yl)methyl)cyclobutan-1-amine

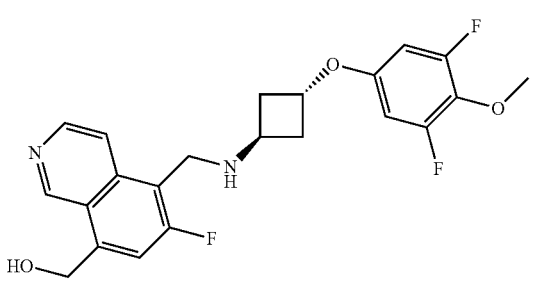

(5-((((1r,3r)-3-(3,5-difluoro-4-methoxyphenoxy)cyclobutyl)amino)methyl)-6-fluoroisoquinolin-8-yl)methanol

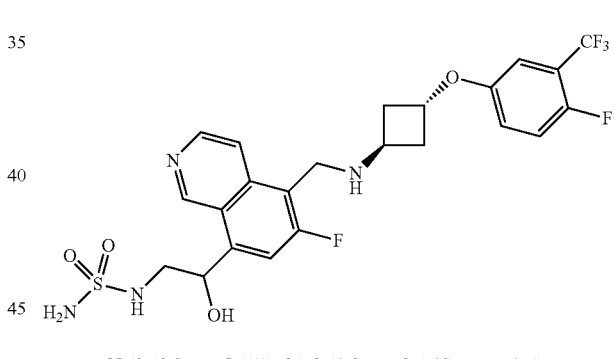

N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl)sulfuric diamide

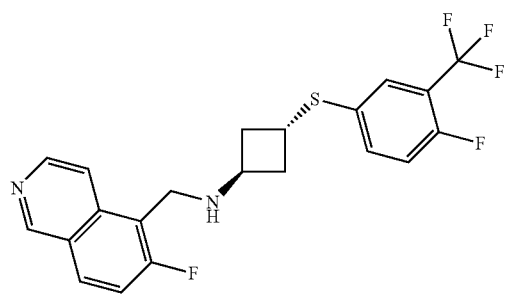

(1r,3r)-3-((4-fluoro-3-(trifluoromethyl)phenyl)thio)-N-((6-fluoroisoquinolin-5-yl)methyl)cyclobutan-1-amine

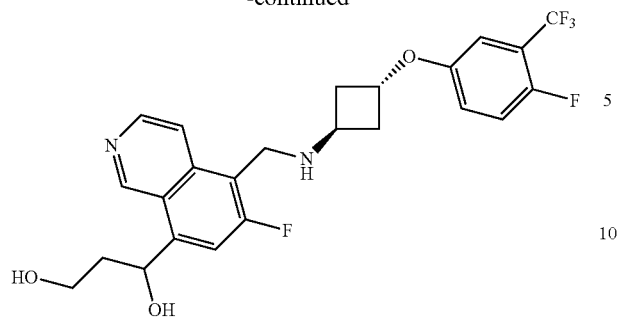

1-(6-fluoro-5-((((1r,3r)-3-(4-fluoro-3-(trifluoromethyl)phenoxy)cyclobutyl)amino)methyl)isoquinolin-8-yl)propane-1,3-diol

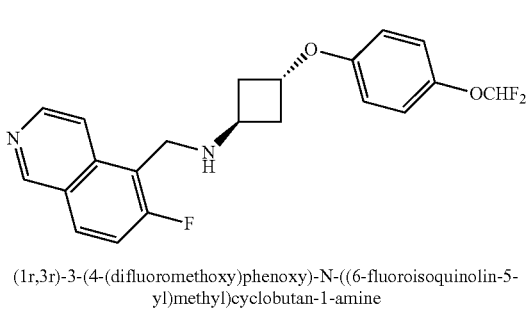

(1r,3r)-3-(4-(difluoromethoxy)phenoxy)-N-((6-fluoroisoquinolin-5-yl)methyl)cyclobutan-1-amine

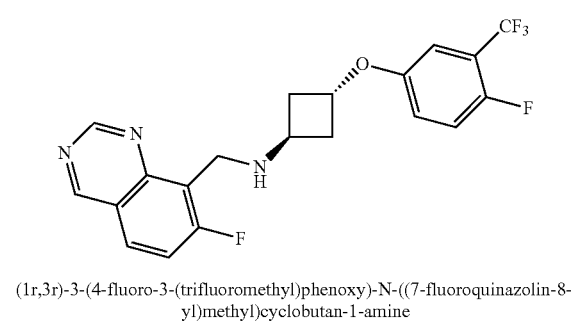

(1r,3r)-3-(4-fluoro-3-(trifluoromethyl)phenoxy)-N-((7-fluoroquinazolin-8-yl)methyl)cyclobutan-1-amine

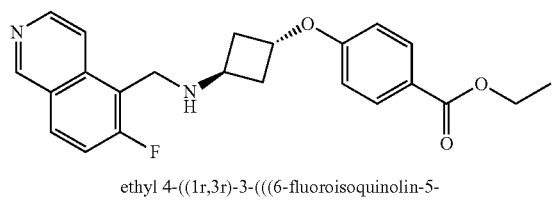

ethyl 4-((1r,3r)-3-(((6-fluoroisoquinolin-5-yl)methyl)amino)cyclobutoxy)benzoate

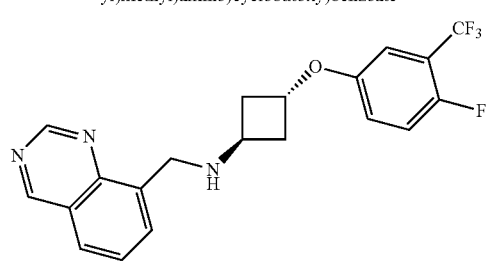

(1r,3r)-3-(4-fluoro-3-(trifluoromethyl)phenoxy)-N-(quinazolin-8-ylmethyl)cyclobutan-1-amine

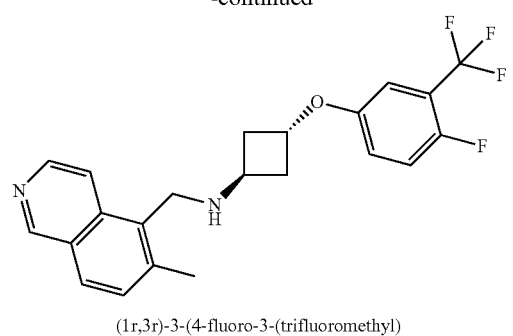

(1r,3r)-3-(4-fluoro-3-(trifluoromethyl)phenoxy)-N-((6-methylisoquinolin-5-yl)methyl)cyclobutan-1-amine

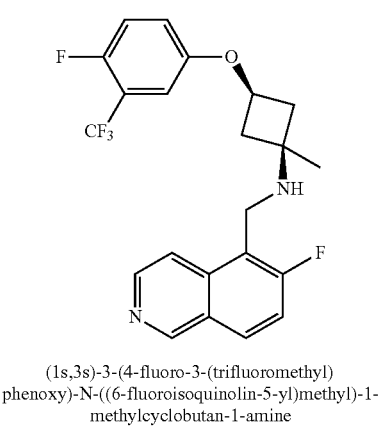

(1s,3s)-3-(4-fluoro-3-(trifluoromethyl)phenoxy)-N-((6-fluoroisoquinolin-5-yl)methyl)-1-methylcyclobutan-1-amine

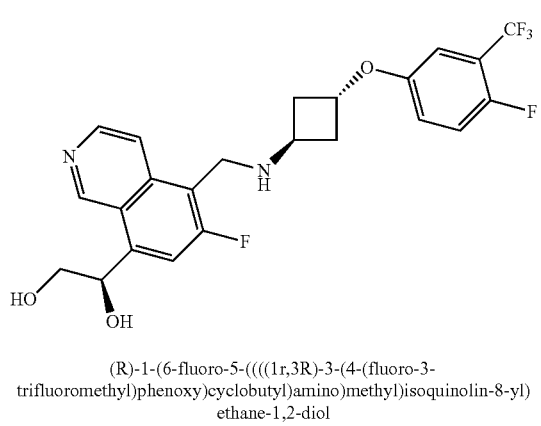

(R)-1-(6-fluoro-5-(((((1r,3R)-3-(4-(fluoro-3-trifluoromethyl)phenoxy)cyclobutyl)amino)methyl)isoquinolin-8-yl)ethane-1,2-diol

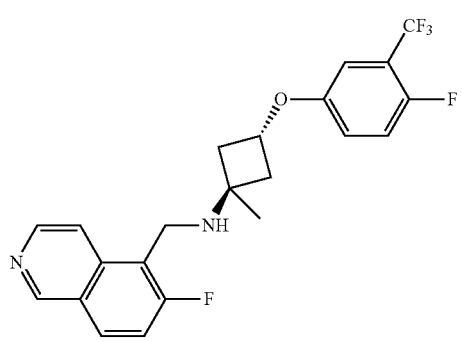

(1r,3r)-3-(4-fluoro-3-(trifluoromethyl)phenoxy)-N-((6-fluoroisoquinolin-5-yl)methyl)-1-methylcyclobutan-1-amine

321

-continued

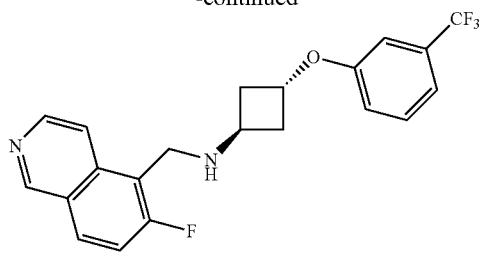

(1r,3r)-N-((6-fluoroisoquinolin-5-yl)methyl)-3-(3-
(trifluoromethyl)phenoxy)cyclobutan-1-amine

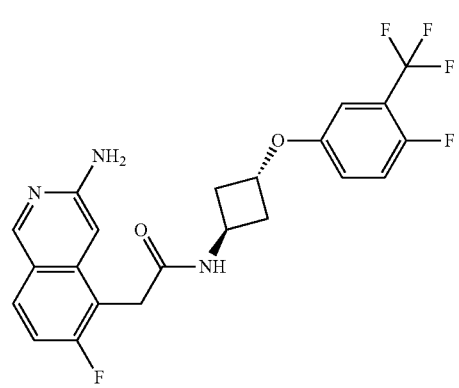

2-(3-amino-6-fluoroisoquinolin-5-yl)-N-((1r,3r)-3-(4-fluoro-3-
(trifluoromethyl)phenoxy)cyclobutyl)acetamide

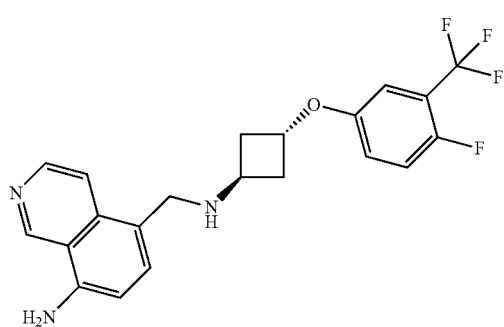

5-((((1r,3r)-3-(4-fluoro-3-
(trifluoromethyl)phenoxy)cyclobutyl)amino)methyl)isoquinolin-8-amine

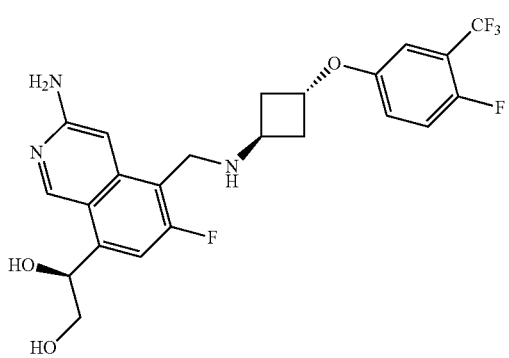

(S)-1-(3-amino-6-fluoro-5-((((1r,3S)-3-(4-fluoro-3-
(trifluoromethyl)phenoxy)cyclobutyl)amino)methyl)isoquinolin-8-
yl)ethane-1,2-diol

322

-continued

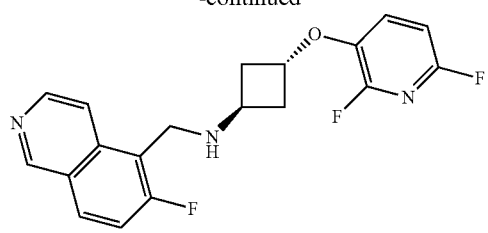

(1r,3r)-3-((2,6-difluoropyridin-3-yl)oxy)-N-((6-fluoroisoquinolin-5-
yl)methyl)cyclobutan-1-amine

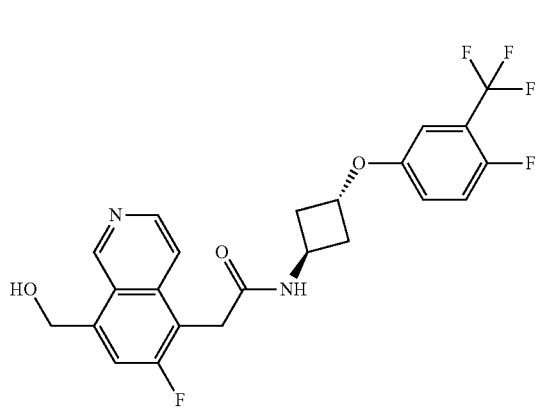

N-((1r,3r)-3-(4-fluoro-3-(trifluoromethyl)phenoxy)cyclobutyl)-
2-(6-fluoro-8-(hydroxymethyl)isoquinolin-5-yl)acetamide

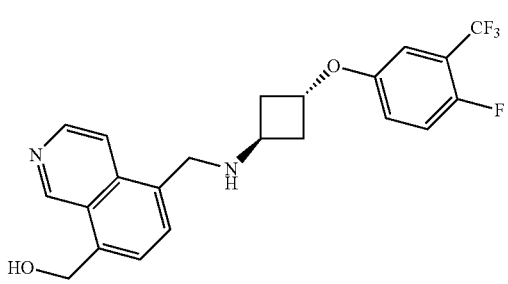

5-((((1r,3r)-3-(4-fluoro-3-
trifluoromethyl)phenoxy)cyclobutyl)amino)methyl)isoquinolin-8-yl)
methanol

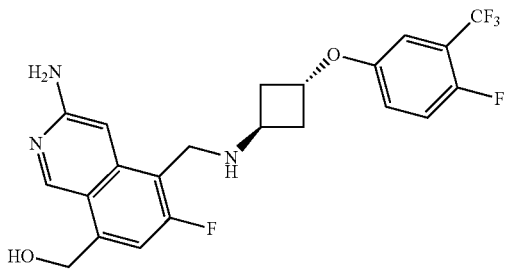

(3-amino-6-fluoro-5-((((1r,3r)-3-(4-fluoro-3-
trifluoromethyl)phenoxy)cyclobutyl)amino)methyl)isoquinolin-8-yl)
methanol

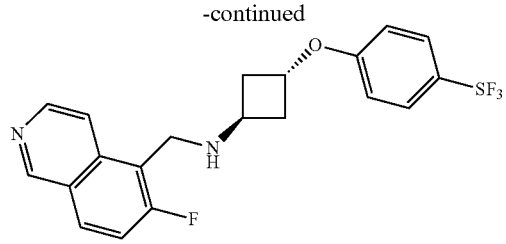

(1r,3r)-N-((6-fluoroisoquinolin-5-yl)methyl)-3-(4(pentafluoro-λ6-sulfaneyl)phenoxy)cyclobutan-1-amine

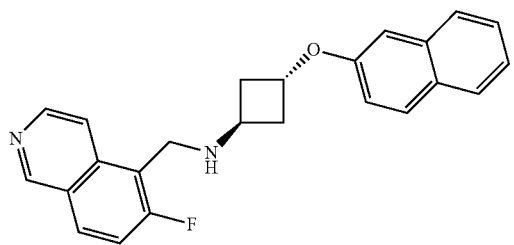

(1r,3r)-N-((6-fluoroisoquinolin-5-yl)methyl)-3-(naphthalen-2-yloxy)cyclobutan-1-amine

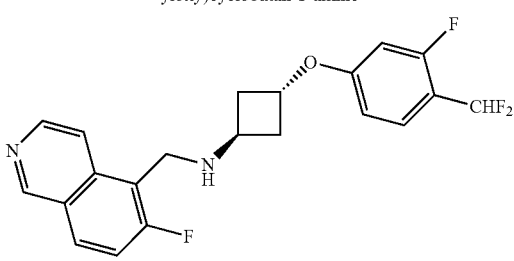

(1r,3r)-3-(4-(difluoromethyl)-3-fluorophenoxy-N-((6-fluoroisoquinolin-5-yl)cyclobutan-1-amine

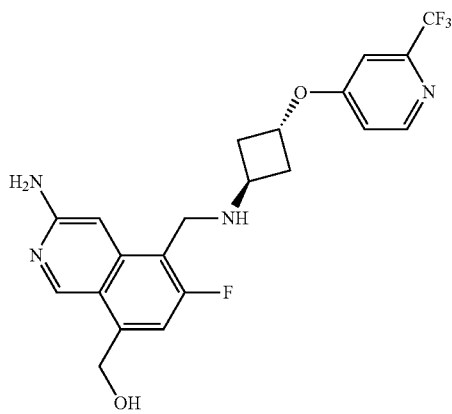

(3-amino-6-fluoro-5-((((1r,3r)-3-((2-trifluoromethyl)pyridin-4-yl)oxy)cyclobutan)amino)methyl)isoquinolin-8-yl)methanol

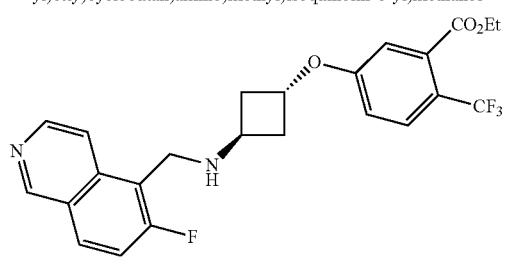

ethyl 5-((1r,3r)-3-(((6-fluoroisoquinolin-5-yl)methly)amino)cyclobutoxy)-2-(trifluoromethyl)benzoate

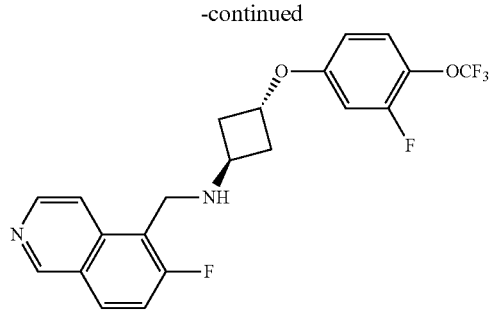

(1r,3r)-3-(3-fluoro-4-(trifluoromethoxy)phenoxy)-N-((6-fluoroisoquinolin-5-yl)methyl)cyclobutan-1-amine

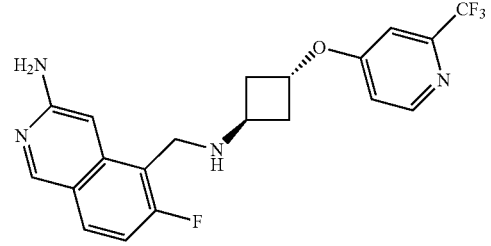

6-fluoro-5-((((1r,3r)-3-((2-trifluoromethyl)pyridin-4-yl)oxy)cyclobutan)amino)methyl)isoquinolin-3-amine

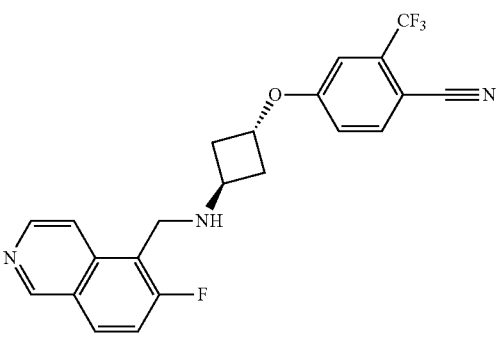

4-((1r,3r)-3-(((6-fluoroisoquinolin-5-yl)methyl)amino)cyclobutoxy)-2-(trifluoromethyl)benzonitrile

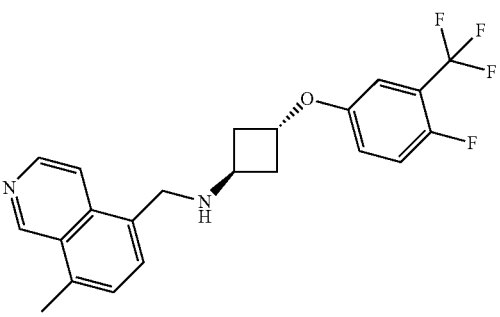

(1r,3r)-3-(4-fluoro-3-(trifluoromethyl)phenoxy)-N-((8-methylisoquinolin-5-yl)methyl)cyclobutan-1-amine -continued

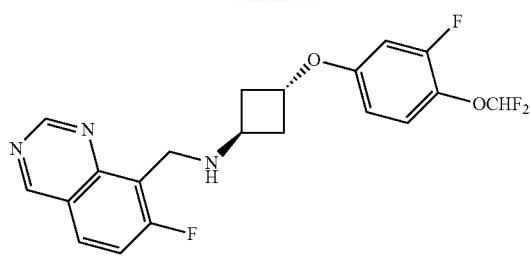

(1r,3r)-3-(4-(difluoromethoxy)-3-fluorophenoxy)-N-((6-fluoroisoquinolin-5-yl)methyl)cyclobutan-1-amine

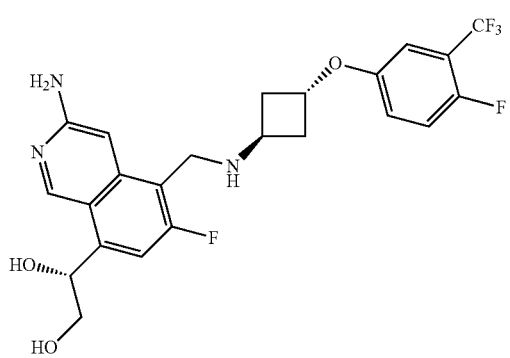

(R)-1-(3-amino-6-fluoro-5-((((1r,3R)-3-(4-fluoro-3-(trifluoromethyl)phenoxy)cyclobutyl)amino)methyl)isoqinolin-8-yl)ethane-1,2-diol

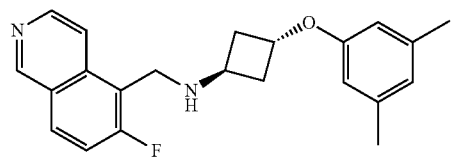

(1r,3r)-3-(3,5-dimethylphenoxy)-N-((6-fluoroisoquinolin-5-yl)methyl)cyclobutan-1-amine

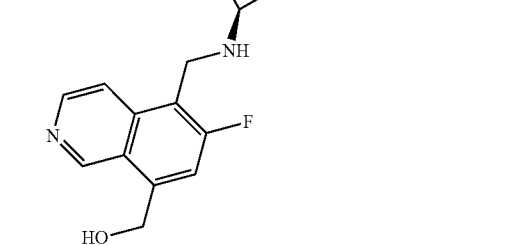

(5-((((1r,3r)-3-(4-(tert-butyl)-3,5-difluorophenoxy)cyclobutyl)amino)methyl)-6-fluoroisoquinolin-8-yl)methanol -continued

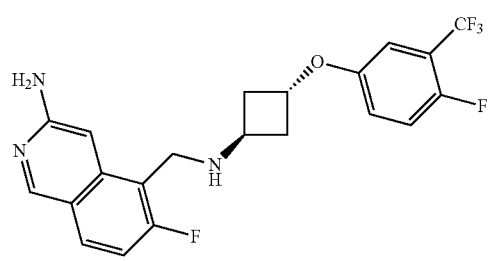

6-fluoro-5-((((1r,3r)-3-(4-(fluoro-3-trifluoromethyl)phenoxy)cyclobutyl)amino)methyl)isoquinolin-3-amine

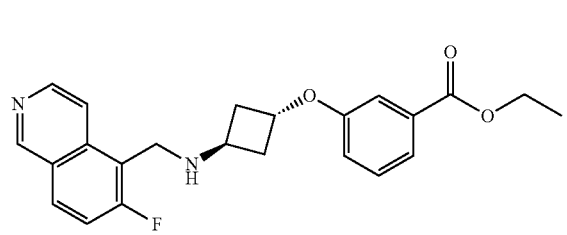

ethyl 3-((1r,3r)-3-(((6-fluoroisoquinolin-5-yl)methyl)amino)cyclobutoxy)benzoate

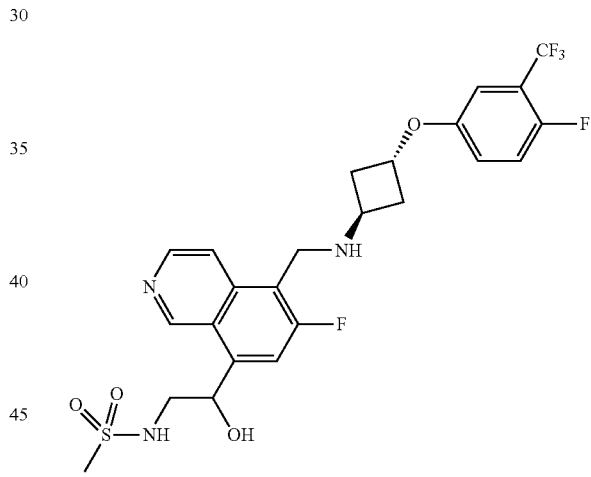

N-(2-(6-fluoro-5-((((1r,3r)-3-(4-fluoro-3-(trifluoromethyl)phenoxy)cyclobutyl)amino)methyl)isoquinolin-8-yl)-2-hydroxyethyl)methanesulfonamide

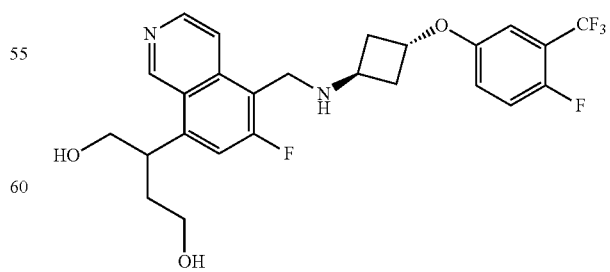

2-(6-fluoro-5-((((1r,3r)-3-(4-fluoro-3-(trifluoromethyl)phenoxy)cyclobutyl)amino)methyl)isoquinolin-8-yl)butane-1,4-diol -continued

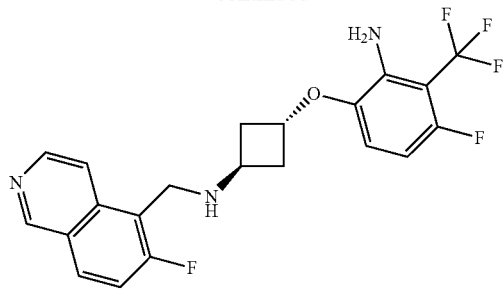

3-fluoro-6-(((1r,3r)-3-(((6-fluoroisoquinolin-5-yl)methyl)amino)cyclobutoxy)-2-(trifluoromethyl)aniline

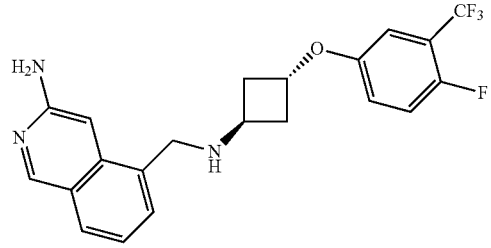

5-(((((1r,3r)-3-(4-fluoro-3-(trifluoromethyl)phenoxy)cyclobutyl)amino)methyl)isoquinolin-3-amine

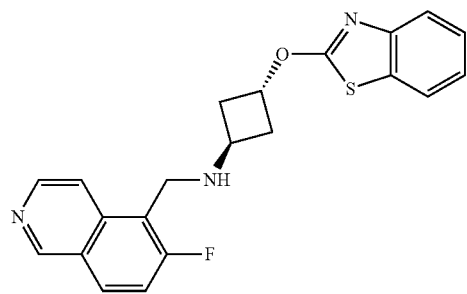

(1r,3r)-3-(benzo[d]thiazol-2-yloxy)-N-((6-fluoroisoquinolin-5-yl)methyl)cyclobutan-1-amine

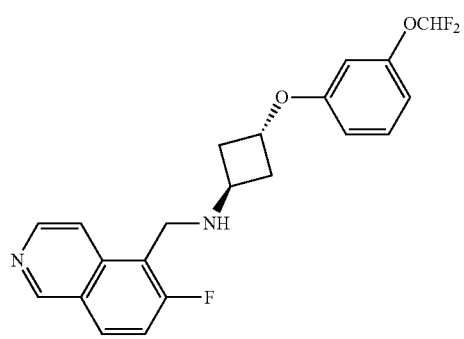

(1r,3r)-3-(3-(difluoromethoxy)phenoxy)-N-((6-fluoroisoquinolin-5-yl)methyl)cyclobutan-1-amine -continued

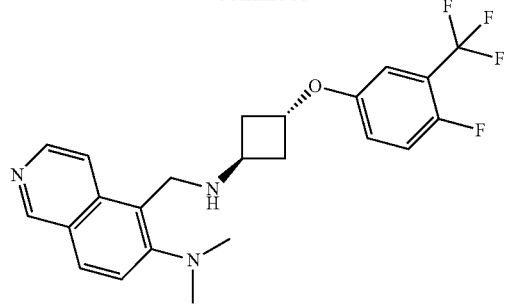

5-(((((1r,3r)-3-(4-fluoro-3-trifluoromethyl)phenoxy)cyclobutyl)amino)methyl)-N,N-dimethylisoquinolin-6-amine

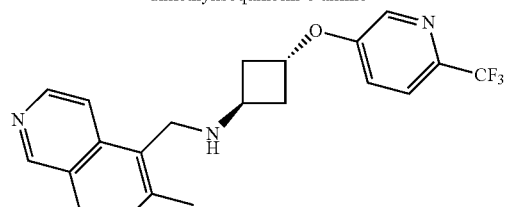

(1r,3r)-N-((6-methylisoquinolin-5-yl)methyl)-3-((6-(trifluoromethyl)pyridin-3-yl)oxy)cyclobutan-1-amine

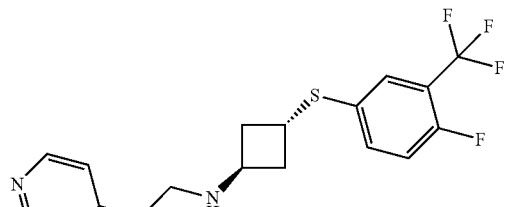

(1r,3r)-3-((4-fluoro-3-(trifluoromethyl)phenyl)thio)-N-(isoquinolin-5-ylmethyl)cyclobutan-1-amine

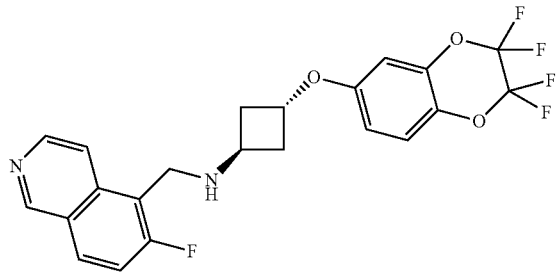

(1r,3r)-N-((6-fluoroisoquinolin-5-yl)methyl)-3-((2,2,3,4-tetrafluoro-2,3-dihydrobenzo[b][1,4]dioxin-6-yl)oxy)cyclobutan-1-amine

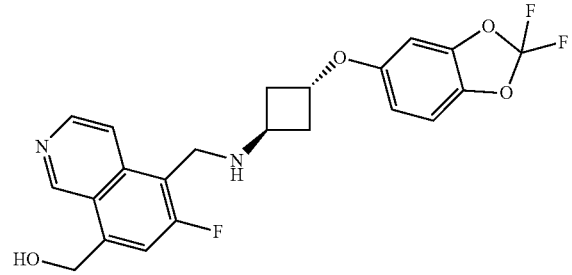

(5-(((((1r,3r)-3-((2,2-difluorobenzo[d][1,3]dioxol-5-yl)oxy)cyclobutyl)amino)methyl)-6-fluoroisoquinolin-8-yl)methanol

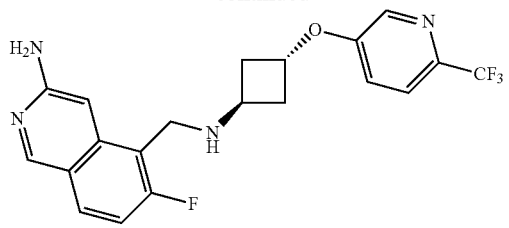

6-fluoro-5-((((1r,3r)-3-((6-trifluoromethyl)pyridin-3-yl)oxy)cyclobutyl)amino)methyl)isoquinolin-3-amine

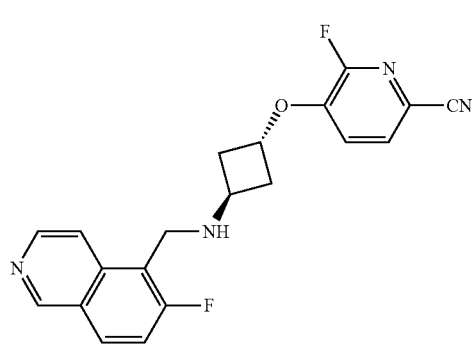

6-fluoro-5-(((1r,3r)-3-(((6-fluoroisoquinolin-5-yl)methyl)amino)cyclobutoxy)picolinonitrile

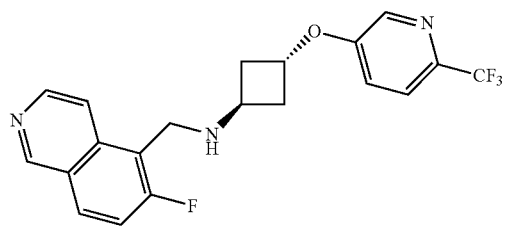

(1r,3r)-N-((6-fluoroisoquinolin-5-yl)methyl)-3-((6-(trifluoromethyl)pyridin-3-yl)oxy)cyclobutan-1-amine

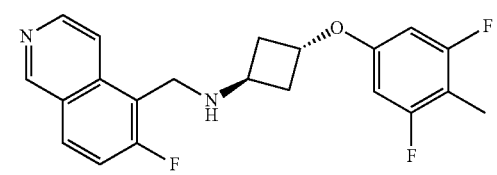

(1r,3r)-3-(3,5-difluoro-4-methylphenoxy)-N-((6-fluoroisoquinolin-5-yl)methyl)cyclobutan-1-amine

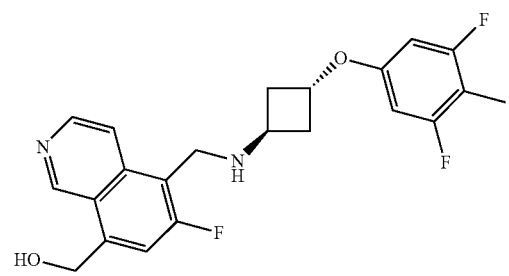

(5-((((1r,3r)-3-(3,5-difluoro-4-methylphenoxy)cyclobutyl)amino)methyl)-6-fluoroisoquinolin-8-yl)methanol

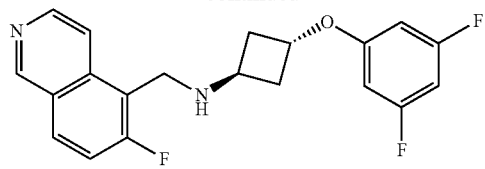

(1r,3r)-3-(3,5-difluorophenoxy)-N-((6-fluoroisoquinolin-5-yl)methyl)cyclobutan-1-amine

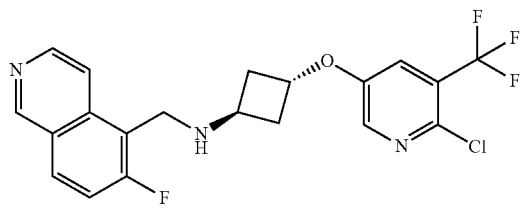

(1r,3r)-3-((6-chloro-5-(trifluoromethyl)pyridin-3-yl)oxy)-N-((6-fluoroisoquinolin-5-yl)methyl)cyclobutan-1-amine

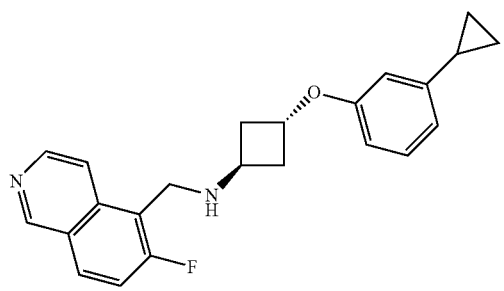

(1r,3r)-3-(3-cyclopropylphenoxy)-N-((6-fluoroisoquinolin-5-yl)methyl)cyclobutan-1-amine

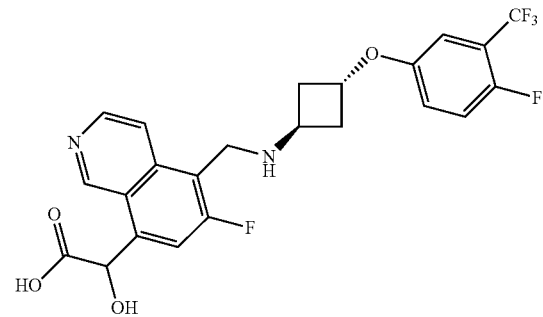

2-(6-fluoro-5-((((1r,3r)-3-(4-fluoro-3-(trifluoromethyl)phenoxy)cyclobutyl)amino)methyl)isoquinolin-8-yl)-2-hydroxyacetic acid

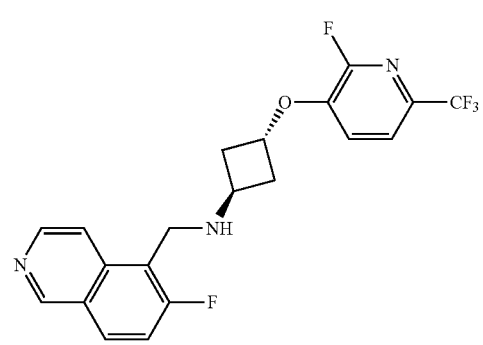

(1r,3r)-3-((2-fluoro-6-(trifluoromethyl)pyridin-3-yl)oxy)-N-((6-fluoroisoquinolin-5-yl)methyl)cyclobutan-1-amine -continued

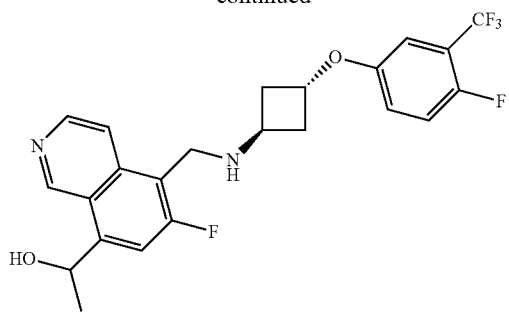

1-(6-fluoro-5-((((1r,3r)-3-(4-fluoro-3-(trifluoromethyl)phenoxy)cyclobutyl)amino)methyl)isoquinolin-8-yl)ethan-1-ol

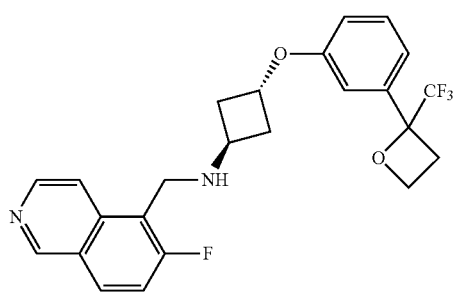

(1r,3r)-N-((6-fluoroisoquinolin-5-yl)methyl)-3-(3-(2-(trifluoromethyl)oxetan-2-yl)phenoxy)cyclobutan-1-amine

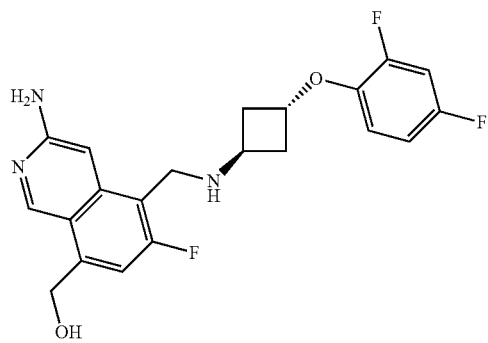

(3-amino-5-((((1r,3r)-3-(2,4-difluorophenoxy)cyclobutyl)amino)methyl)-6-fluoroisoquinolin-8-yl)methanol

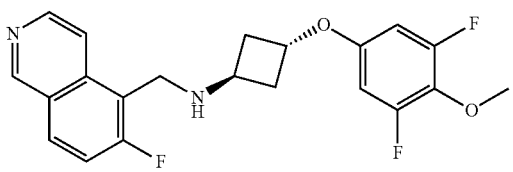

(1r,3r)-3-(3,5-difluoro-4-methoxyphenoxy)-N-((6-fluoroisoquinolin-5-yl)methyl)cyclobutan-1-amine

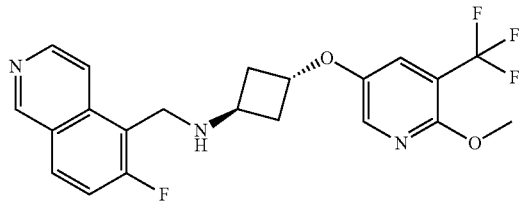

(1r,3r)-N-((6-fluoroisoquinolin-5-yl)methyl)-3-((6-methoxy-5-(trifluoromethyl)pyridin-3-yl)oxy)cyclobutan-1-amine -continued

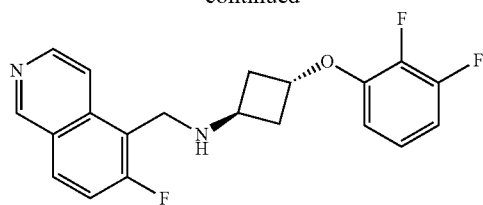

(1r,3r)-3-(2,3-difluorophenoxy)-N-((6-fluoroisoquinolin-5-yl)methyl)cyclobutan-1-amine

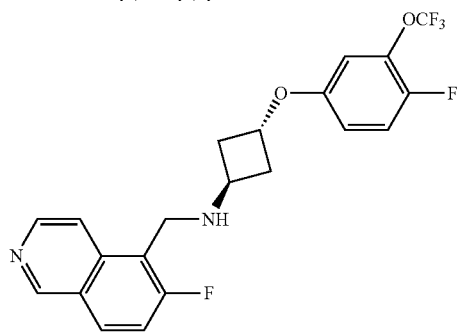

(1r,3r)-3-(4-fluoro-3-(trifluoromethoxy)phenoxy)-N-((6-fluoroisoquinolin-5-yl)methyl)cyclobutan-1-amine

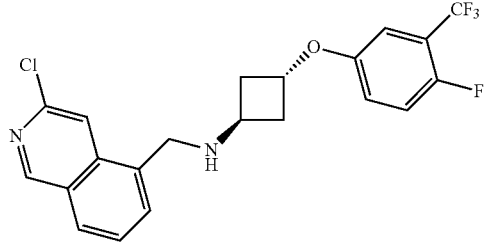

(1r,3r)-N-((3-chloroisoquinolin-5-yl)methyl)-3-(4-fluoro-3-(trifluoromethyl)phenoxy)cyclobutan-1-amine

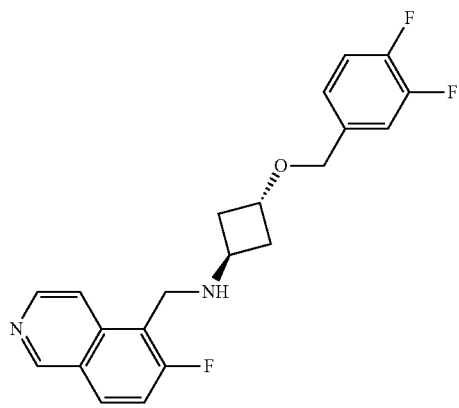

(1r,3r)-3-((3,4-difluorobenzyl)oxy)-N-((6-fluoroisoquinolin-5-yl)methyl)cyclobutan-1-amine

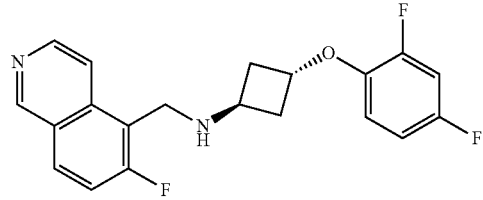

(1r,3r)-3-(2,4-difluorophenoxy)-N-((6-fluoroisoquinolin-5-yl)methyl)cyclobutan-1-amine

333

-continued

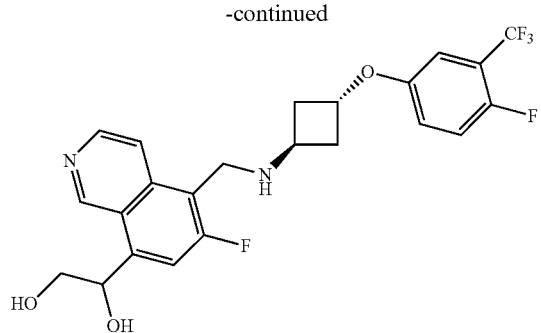

1-(6-fluoro-5-((((1r,3r)-3-(4-fluoro-3-(trifluoromethyl)phenoxy)cyclobutyl)amino)methyl)isoquinolin-8-yl)ethane-1,2-diol

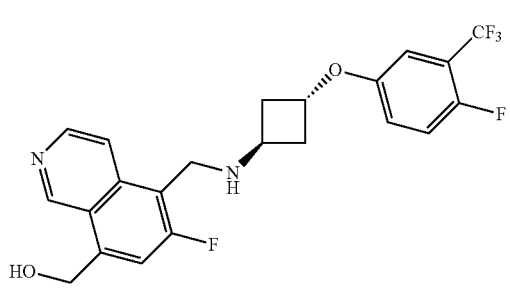

(6-fluoro-5-((((1r,3r)-3-(4-fluoro-3-(trifluoromethyl)phenoxy)cyclobutyl)amino)methyl)isoquinolin-8-yl)methanol

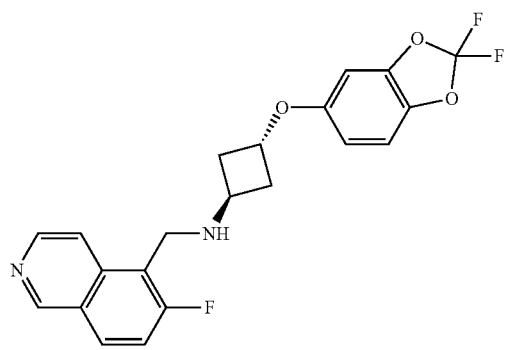

(1r,3r)-3-((2,2-difluorobenzo[d][1,3]dioxol-5-yl)oxy)-N-((6-fluoroisoquinolin-5-yl)methyl)cyclobutan-1-amine

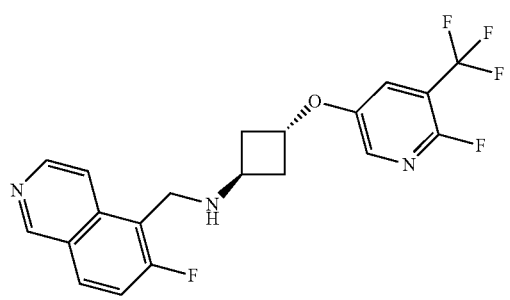

(1r,3r)-N-((6-fluoroisoquinolin-5-yl)methyl)-3-((5-(trifluoromethyl)pyridin-3-yl)oxy)cyclobutan-1-amine

334

-continued

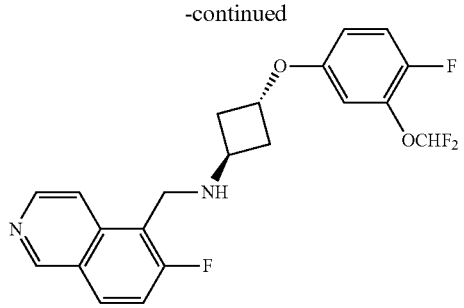

(1r,3r)-3-(3-(difluoromethoxy)-4-fluorophenoxy)-N-((6-fluoroisoquinolin-5-yl)methyl)cyclobutan-1-amine

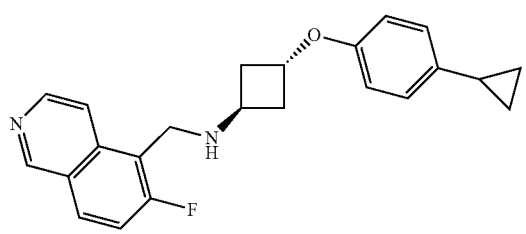

(1r,3r)-3-(4-cyclopropylphenoxy)-N-((6-fluoroisoquinolin-5-yl)methyl)cyclobutan-1-amine

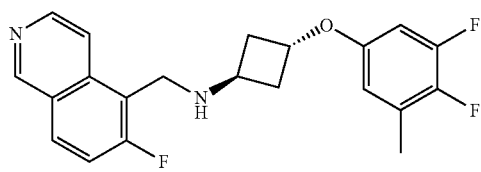

(1r,3r)-3-(3,4-difluoro-5-methylphenoxy)-N-((6-fluoroisoquinolin-5-yl)methyl)cyclobutan-1-amine

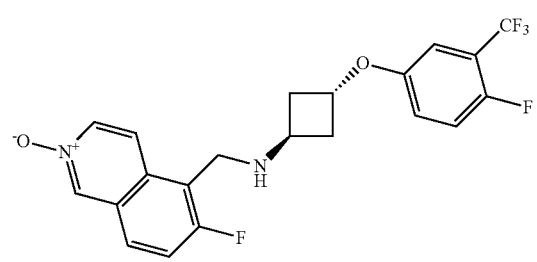

6-fluoro-5-((((1r,3r)-3-(4-fluoro-3-(trifluoromethyl)phenoxy)cyclobutyl)amino)methyl)isoquinoline 2-oxide

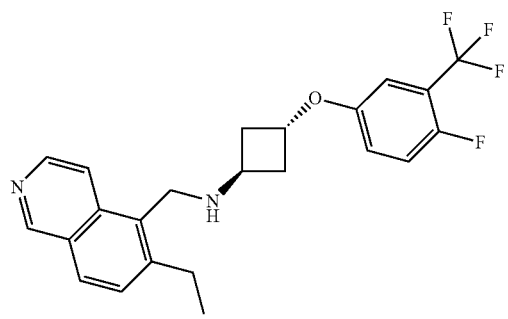

(1r,3r)-N-((6-ethylisoquinolin-5-yl)methyl)-3-(4-fluoro-3-(trifluoromethyl)phenoxy)cyclobutan-1-amine

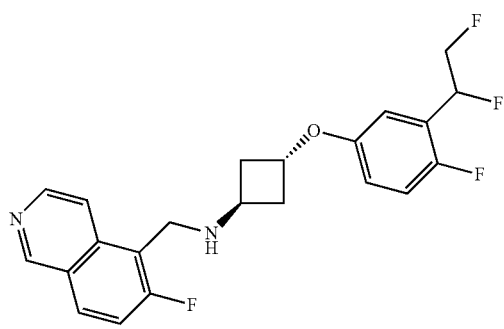

(1r,3r)-3-(3-(1,2-difluoroethyl)-4-fluorophenoxy)-N-
((6-fluoroisoquinolin-5-yl)methyl)cyclobutan-1-amine

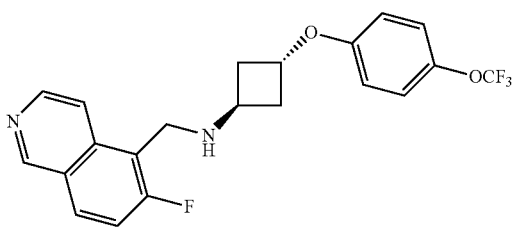

(1r,3r)-N-((6-fluoroisoquinolin-5-yl)methyl)-3-(4-
(trifluoromethoxy)phenoxy)cyclobutan-1-amine

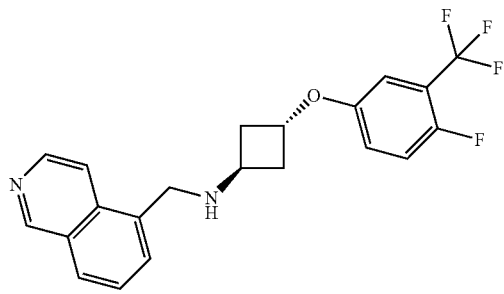

(1r,3r)-3-(4-fluoro-3-(trifluoromethyl)phenoxy)-N-(isoquinolin-5-
ylmethyl)cyclobutan-1-amine

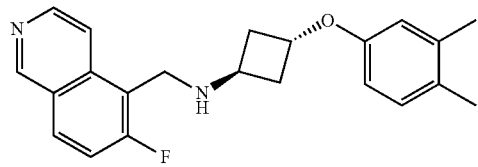

(1r,3r)-3-(3,4-dimethylphenoxy)-N-((6-
fluoroisoquinolin-5-yl)methyl)cyclobutan-1-amine

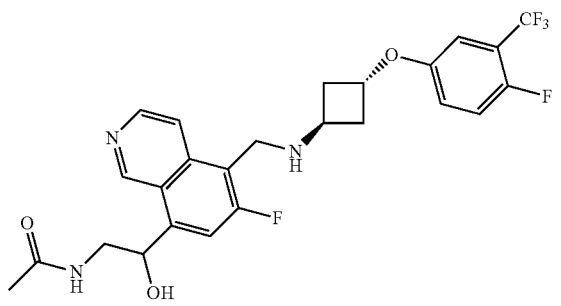

N-(2-(6-fluoro-5-((((1r,3r)-3-(4-fluoro-3-
(trifluoromethyl)phenoxy)cyclobutyl)amino)
methyl)isoquinolin-8-yl)-2-hydroxyethyl)acetamide

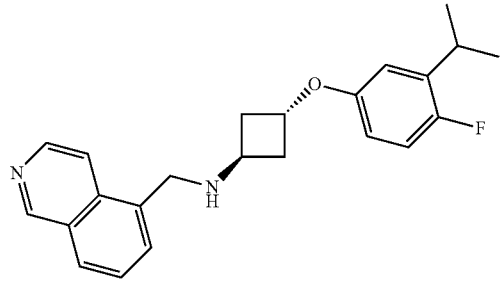

(1r,3r)-3-(4-fluoro-3-isopropylphenoxy)-N-(isoquinolin-5-
ylmethyl)cyclobutan-1-amine

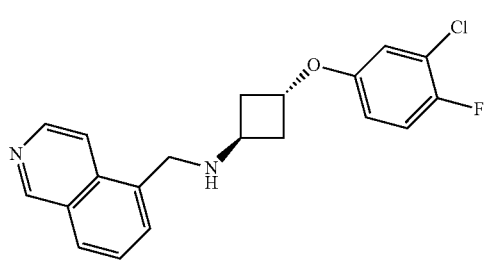

(1r,3r)-3-(3-chloro-4-fluorophenoxy)-N-(isoquinolin-5-
ylmethyl)cyclobutan-1-amine

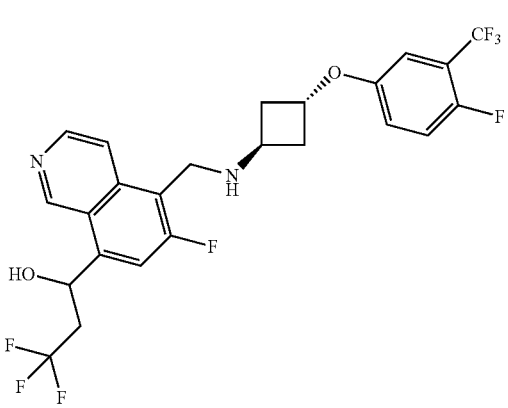

3,3,3-trifluoro-1-(6-fluoro-5-((((1r,3r)-3-(4-fluoro-3-
(trifluoromethyl)phenoxy)cyclobutyl)amino)methyl)isoquinolin-8-
yl)propan-1-ol

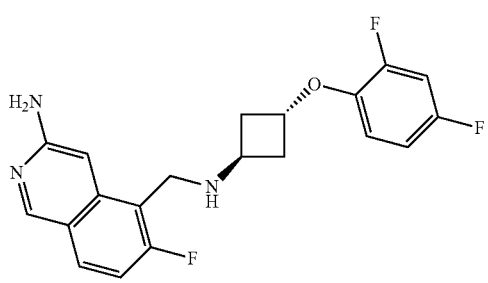

5-((((1r,3r)-3-(2,4-difluorophenoxy)cyclobutyl)amino)methyl)-6-
fluoroisoquinolin-3-amine

337

-continued

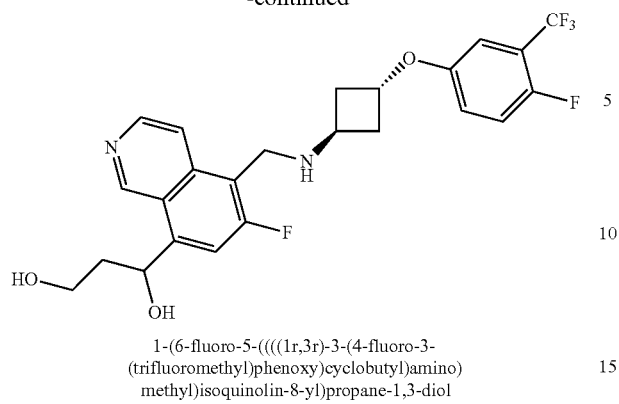

1-(6-fluoro-5-((((1r,3r)-3-(4-fluoro-3-
(trifluoromethyl)phenoxy)cyclobutyl)amino)
methyl)isoquinolin-8-yl)propane-1,3-diol

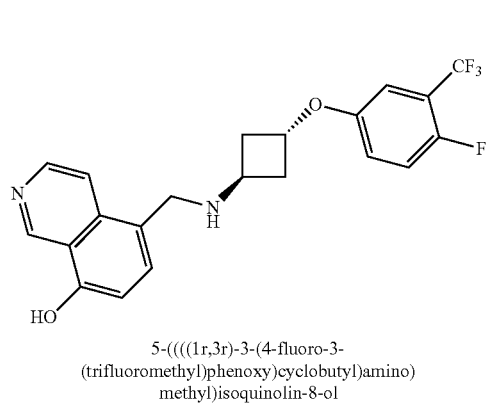

5-(((((1r,3r)-3-(4-fluoro-3-
(trifluoromethyl)phenoxy)cyclobutyl)amino)
methyl)isoquinolin-8-ol

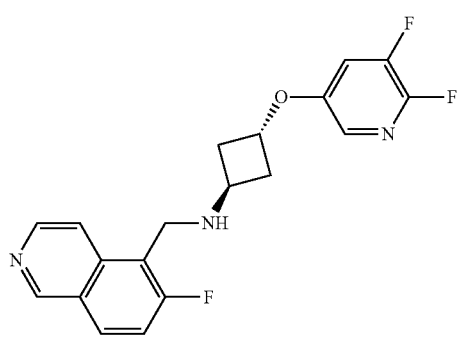

(1r,3r)-3-((5,6-difluoropyridin-3yl)oxy)-N-((6-
fluoroisoquinolin-5-yl)methyl)cyclobutan-1-amine

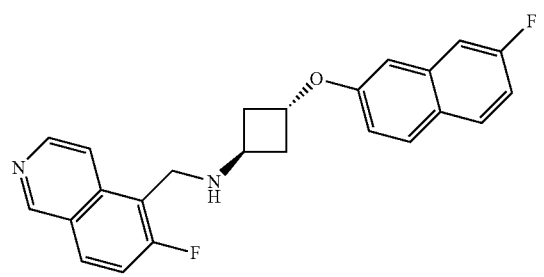

(1r,3r)-N-((6-fluoroisoquinolin-5-yl)methyl)-3-((7-fluoronaphthalen-2-
yl)oxy)cyclobutan-1-amine

338

-continued

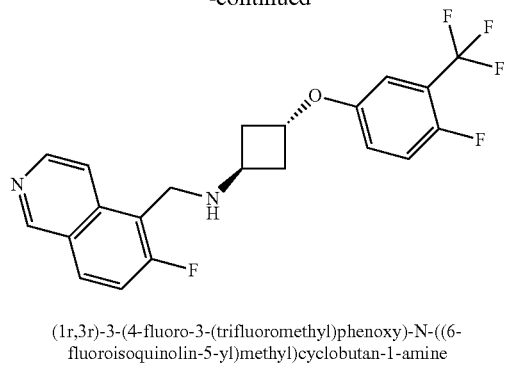

(1r,3r)-3-(4-fluoro-3-(trifluoromethyl)phenoxy)-N-((6-
fluoroisoquinolin-5-yl)methyl)cyclobutan-1-amine

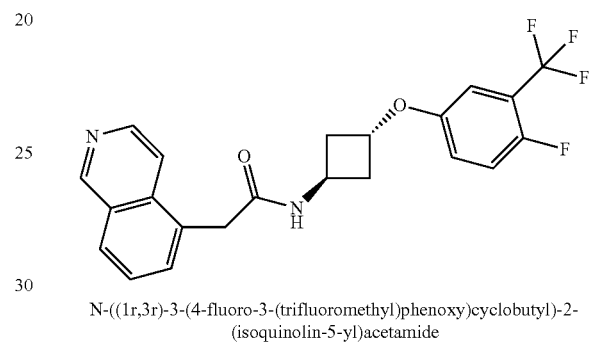

N-((1r,3r)-3-(4-fluoro-3-(trifluoromethyl)phenoxy)cyclobutyl)-2-
(isoquinolin-5-yl)acetamide

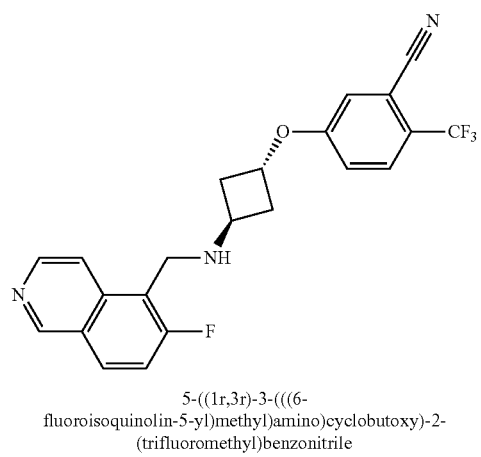

5-((1r,3r)-3-(((6-
fluoroisoquinolin-5-yl)methyl)amino)cyclobutoxy)-2-
(trifluoromethyl)benzonitrile

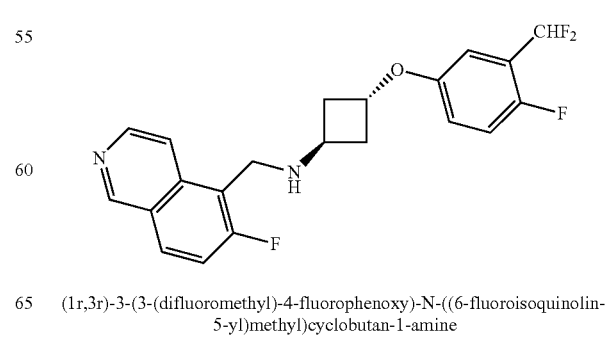

(1r,3r)-3-(3-(difluoromethyl)-4-fluorophenoxy)-N-((6-fluoroisoquinolin-
5-yl)methyl)cyclobutan-1-amine 339
-continued

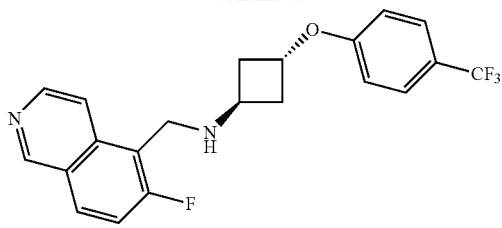

(1r,3r)-N-((6-fluoroisoquinolin-5-yl)methyl)-3-(4-(trifluoromethyl)phenoxy)cyclobutan-1-amine

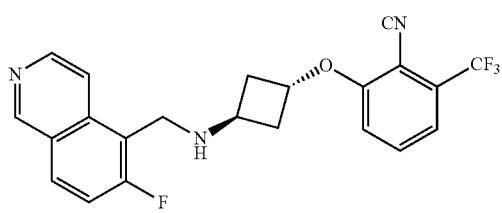

2-((1r,3r)-3-(((6-fluoroisoquinolin-5-yl)methyl)amino)cyclobutoxy)-6-(trifluoromethyl)benzonitrile

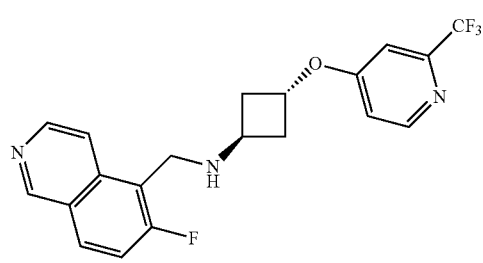

(1r,3r)-N-((6-fluoroisoquinolin-5-yl)methyl)-3-((2-(trifluoromethyl)pyridin-4-yl)oxy)cyclobutan-1-amine

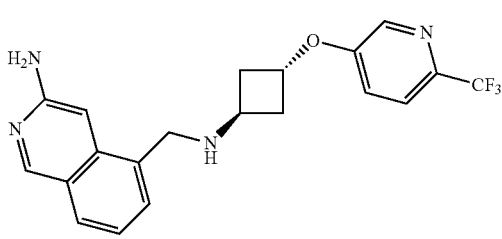

5-((((1r,3r)-3-((6-(trifluoromethyl)pyridin-3-yl)oxy)cyclobutyl)amino)methyl)isoquinolin-3-amine

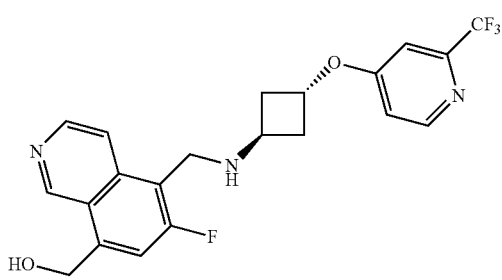

(6-fluoro-5-((((1r,3r)-3-((2-(trifluoromethyl)pyridin-4-yl)oxy)cyclobutyl)amino)methyl)isoquinolin-8-yl)methanol 340
-continued

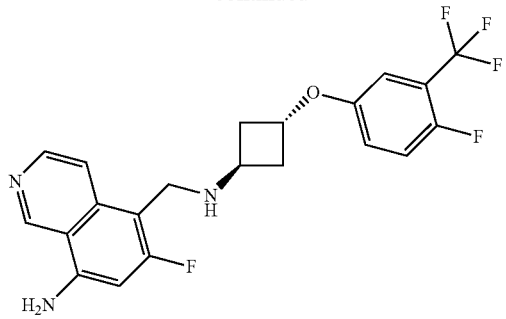

6-fluoro-5-((((1r,3r)-3-(4-fluoro-3-(trifluoromethyl)phenoxy)cyclobutyl)amino)methyl)isoquinolin-8-amine

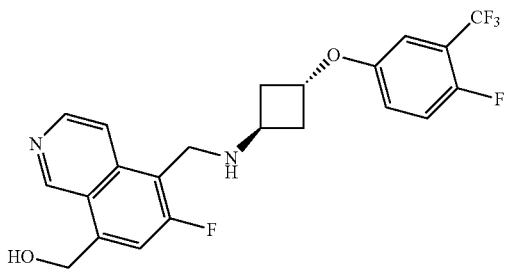

(6-fluoro-5-((((1s,3s)-3-(4-fluoro-(trifluoromethyl)phenoxy)cyclobutyl)amino)methyl)isoquinolin-8-yl)methanol

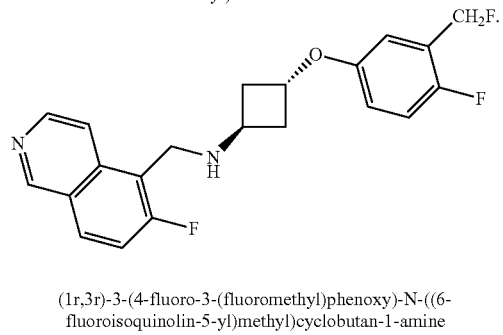

(1r,3r)-3-(4-fluoro-3-(fluoromethyl)phenoxy)-N-((6-fluoroisoquinolin-5-yl)methyl)cyclobutan-1-amine 14. A pharmaceutical composition comprising a therapeutically effective amount of a compound of claim 1, or a pharmaceutically acceptable salt thereof, and a pharmaceutically acceptable carrier or excipient.

15. A method of treating an ocular surface disorder in a subject in need thereof, the method comprising administering to the subject a therapeutically effective amount of a compound of claim 1, or a pharmaceutically acceptable salt thereof.

16. The method of claim 15, wherein the ocular surface disorder is selected from chronic ocular surface pain (COSP), dry eye disease, conjunctivitis, keratoconjuctivitis, vernal keratoconjunctivitis, allergic conjunctivitis, Meibomian gland dysfunction, thyroid eye disease, keratoconus, ocular pain syndrome, Steven-Johnson's syndrome, corneal epitheliopathies, corneal neuropathies, LASIK induced corneal neuropathies, corneal dystrophies, epithelial basement membrane dystrophy, corneal erosions or abrasions, ocular surface diseases, blepharitis, meibomitis, glaucoma, conjunctivochalasis, keratopathis, keratitis, iritis, episclentis, corneal surgery, trichiasis, pterygium, xerophthalmia, and patients recovering from neurotrophic keratitis.

17. A method of treating ocular surface pain or ocular hyperemia in a subject in need thereof, the method comprising administering to the subject a therapeutically effective amount of a compound of claim 1, or a pharmaceutically acceptable salt thereof.

18. The method according to claim 17, wherein the patient is suffering from one or more of dry eye disease, conjunctivitis, keratoconjuctivitis, vernal keratoconjunctivitis, allergic conjunctivitis, Meibomian gland dysfunction, thyroid eye disease, keratoconus, ocular pain syndrome, Steven-Johnson's syndrome, corneal epitheliopathies, corneal neuropathies, LASIK induced corneal neuropathies, corneal dystrophies, epithelial basement membrane dystrophy, corneal erosions or abrasions, ocular surface diseases, blepharitis, meibomitis, glaucoma, conjunctivochalasis, keratopathis keratitis, iritis, episclentis, corneal surgery, trichiasis, pterygium, xerophthalmia, or patients recovering from neurotrophic keratitis.

19. A method of treating corneal induced pain in a subject in need thereof, the method comprising administering to the subject a therapeutically effective amount of a compound of claim 1, or a pharmaceutically acceptable salt thereof.

20. A pharmaceutical composition comprising a therapeutically effective amount of a compound of claim 13, or a pharmaceutically acceptable salt thereof, and a pharmaceutically acceptable carrier or excipient.

21. A method of treating ocular surface pain or ocular hyperemia in a subject in need thereof, the method comprising administering to the subject a therapeutically effective amount of a compound of claim 13, or a pharmaceutically acceptable salt thereof.

22. A method of treating corneal induced pain in a subject in need thereof, the method comprising administering to the subject a therapeutically effective amount of a compound of claim 13, or a pharmaceutically acceptable salt thereof.

23. A method of treating an ocular surface disorder in a subject in need thereof, the method comprising administering to the subject a therapeutically effective amount of a compound of claim 13, or a pharmaceutically acceptable salt thereof.

24. The method of claim 23, wherein the ocular surface disorder is selected from chronic ocular surface pain (COSP), dry eye disease, conjunctivitis, keratoconjuctivitis, vernal keratoconjunctivitis, allergic conjunctivitis, Meibomian gland dysfunction, thyroid eye disease, keratoconus, ocular pain syndrome, Steven-Johnson's syndrome, corneal epitheliopathies, corneal neuropathies, LASIK induced corneal neuropathies, corneal dystrophies, epithelial basement membrane dystrophy, corneal erosions or abrasions, ocular surface diseases, blepharitis, meibomitis, glaucoma, conjunctivochalasis, keratopathis, keratitis, iritis, episclentis, corneal surgery, trichiasis, pterygium, xerophthalmia, and patients recovering from neurotrophic keratitis.

25. A compound or a pharmaceutically acceptable salt thereof selected from:

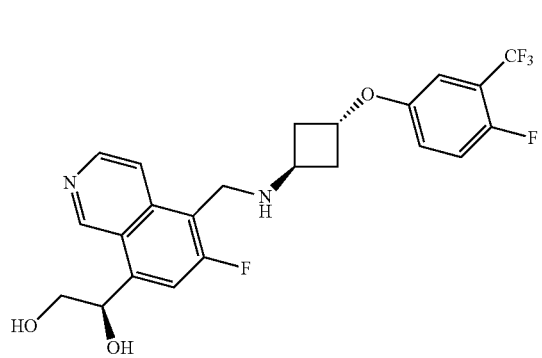

(i)

(R)-1-(6-fluoro-5-((((1r,3R)-3-(4-fluoro-3-(trifluoromethyl)phenoxy)cyclobutyl)amino)methyl)isoquinolin-8-yl)ethane-1,2-diol; or

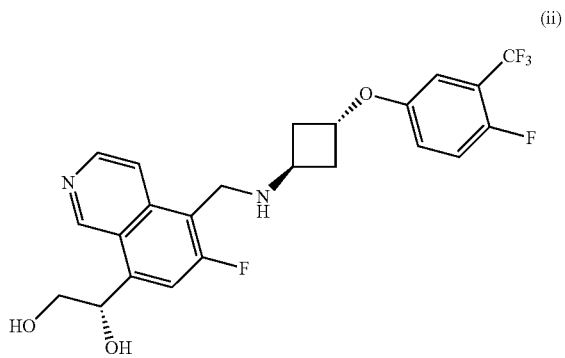 [SMILES: OC[C@@H](O)c1cc(F)c(CN[C@H]2C[C@H](Oc3ccc(F)c(C(F)(F)F)c3)C2)c2ccncc12]

(ii)

(S)-1-(6-fluoro-5-((((1r,3S)-3-(4-fluoro-3-(trifluoromethyl)phenoxy)cyclobutyl)amino)methyl)isoquinolin-8-yl)ethane-1,2-diol.

26. A pharmaceutical composition comprising a therapeutically effective amount of a compound of claim 25, or a pharmaceutically acceptable salt thereof, and a pharmaceutically acceptable carrier or excipient.

27. A method of treating ocular surface pain or ocular hyperemia in a subject in need thereof, the method comprising administering to the subject a therapeutically effective amount of a compound of claim 25, or a pharmaceutically acceptable salt thereof.

28. A method of treating corneal induced pain in a subject in need thereof, the method comprising administering to the subject a therapeutically effective amount of a compound of claim 25, or a pharmaceutically acceptable salt thereof.

29. A method of treating an ocular surface disorder in a subject in need thereof, the method comprising administering to the subject a therapeutically effective amount of a compound of claim 25, or a pharmaceutically acceptable salt thereof.

30. The method of claim 29, wherein the ocular surface disorder is selected from chronic ocular surface pain (COSP), dry eye disease, conjunctivitis, keratoconjuctivitis, vernal keratoconjunctivitis, allergic conjunctivitis, Meibomian gland dysfunction, thyroid eye disease, keratoconus, ocular pain syndrome, Steven-Johnson's syndrome, corneal epitheliopathies, corneal neuropathies, LASIK induced corneal neuropathies, corneal dystrophies, epithelial basement membrane dystrophy, corneal erosions or abrasions, ocular surface diseases, blepharitis, meibomitis, glaucoma, conjunctivochalasis, keratopathis, keratitis, iritis, episclentis, corneal surgery, trichiasis, pterygium, xerophthalmia, and patients recovering from neurotrophic keratitis.

* * * * *